US012674180B2

(12) United States Patent
Cruite et al.

(10) Patent No.: US 12,674,180 B2
(45) Date of Patent: *Jul. 7, 2026

(54) CD8-SPECIFIC ANTIBODY CONSTRUCTS AND COMPOSITIONS THEREOF

(71) Applicant: Sana Biotechnology, Inc., Seattle, WA (US)

(72) Inventors: Patricia Ann Cruite, Medford, MA (US); Shirisha Amatya, Cambridge, MA (US); Hugh Harding, Framingham, MA (US); Lauren Pepper MacKenzie, Belmont, MA (US)

(73) Assignee: Sana Biotechnology, Inc., Seattle, WA (US)

( * ) Notice: Subject to any disclaimer, the term of this patent is extended or adjusted under 35 U.S.C. 154(b) by 9 days.

This patent is subject to a terminal disclaimer.

(21) Appl. No.: 18/056,572

(22) Filed: Nov. 17, 2022

(65) Prior Publication Data

US 2023/0257773 A1      Aug. 17, 2023

Related U.S. Application Data

(63) Continuation of application No. 17/715,253, filed on Apr. 7, 2022, now Pat. No. 11,535,869.

(60) Provisional application No. 63/299,254, filed on Jan. 13, 2022, provisional application No. 63/172,518, filed on Apr. 8, 2021.

(51) Int. Cl.
| | |
|---|---|
| *C12N 15/86* | (2006.01) |
| *A61K 38/00* | (2006.01) |
| *A61K 39/00* | (2006.01) |
| *A61P 35/00* | (2006.01) |
| *A61P 35/04* | (2006.01) |
| *C07K 14/005* | (2006.01) |
| *C07K 14/705* | (2006.01) |
| *C07K 14/725* | (2006.01) |
| *C07K 16/28* | (2006.01) |

(52) U.S. Cl.
CPC .............. *C12N 15/86* (2013.01); *A61P 35/00* (2018.01); *A61P 35/04* (2018.01); *C07K 14/005* (2013.01); *C07K 14/7051* (2013.01); *C07K 14/70517* (2013.01); *C07K 14/70521* (2013.01); *C07K 14/70578* (2013.01); *C07K 16/2803* (2013.01); *C07K 16/2815* (2013.01); *A61K 38/00* (2013.01); *A61K 2039/505* (2013.01); *A61K 2039/545* (2013.01); *C07K 2317/569* (2013.01); *C07K 2317/622* (2013.01); *C07K 2317/76* (2013.01); *C07K 2317/92* (2013.01); *C07K 2319/02* (2013.01); *C07K 2319/33* (2013.01); *C12N 2740/15043* (2013.01); *C12N 2760/18222* (2013.01); *C12N 2760/18233* (2013.01); *C12N 2760/18271* (2013.01)

(58) Field of Classification Search
CPC .................................................. C07K 16/2815
See application file for complete search history.

(56) References Cited

U.S. PATENT DOCUMENTS

| | | | |
|---|---|---|---|
| 6,790,641 | B2 | 9/2004 | Schauber et al. |
| 6,896,881 | B1 | 5/2005 | Russell et al. |
| 7,094,398 | B1 | 8/2006 | Lieber et al. |
| 9,486,539 | B2 | 11/2016 | Lee et al. |
| 10,040,830 | B2 | 8/2018 | Chatterjee et al. |
| 10,064,958 | B2 | 9/2018 | Lee et al. |
| 11,535,869 | B2 * | 12/2022 | Cruite ..................... A61P 35/00 |
| 11,576,872 | B2 | 2/2023 | Von Maltzahn et al. |
| 11,576,982 | B2 | 2/2023 | Lee et al. |
| 11,608,509 | B2 | 3/2023 | Fejoz et al. |
| 2002/0150556 | A1 | 10/2002 | Vile et al. |
| 2003/0072773 | A1 | 4/2003 | Wertz et al. |
| 2003/0207445 | A1 | 11/2003 | Schauber et al. |
| 2005/0070493 | A1 | 3/2005 | Fawell et al. |
| 2006/0045910 | A1 | 3/2006 | Ehringer |
| 2006/0104950 | A1 | 5/2006 | Okano et al. |
| 2007/0031455 | A1 | 2/2007 | Audonnet |
| 2007/0154481 | A1 * | 7/2007 | Gelinas ................... A61P 31/00 |
| | | | 536/23.53 |
| 2009/0041724 | A1 | 2/2009 | Steen et al. |
| 2010/0316570 | A1 | 12/2010 | Discher et al. |
| 2011/0184049 | A1 | 7/2011 | Chuah et al. |
| 2012/0322147 | A1 | 12/2012 | Mangeot et al. |
| 2013/0273549 | A1 | 10/2013 | Sullivan et al. |
| 2014/0079774 | A1 | 3/2014 | Brinker |
| 2015/0050242 | A1 | 2/2015 | Lee et al. |

(Continued)

FOREIGN PATENT DOCUMENTS

| | | |
|---|---|---|
| EP | 1 115 879 | 7/2001 |
| EP | 2615176 | 7/2013 |

(Continued)

OTHER PUBLICATIONS

Holliger and Hudson (Nature Biotechnology Sep. 2005, 23(9): 1126-1136) (Year: 2005).*

(Continued)

*Primary Examiner* — Peter J Reddig
(74) *Attorney, Agent, or Firm* — Morrison & Foerster LLP

(57) ABSTRACT

Disclosed herein are antibodies or antigen binding fragments thereof that specifically bind human CD8. Also disclosed are fusion proteins comprising a Henipavirus glycoprotein G and CD8 antibodies for targeting and transducing cells expressing CD8. Viral vectors and other compositions containing the fusion proteins, as well as methods of using the fusion proteins, are also disclosed.

21 Claims, 17 Drawing Sheets

Specification includes a Sequence Listing.

(56) References Cited

U.S. PATENT DOCUMENTS

| | | |
|---|---|---|
| 2015/0133420 A1 | 5/2015 | Cheng et al. |
| 2015/0216903 A1 | 8/2015 | Heffner et al. |
| 2016/0011197 A1 | 1/2016 | Walfish et al. |
| 2016/0354313 A1 | 12/2016 | Beer et al. |
| 2017/0087087 A1 | 3/2017 | Leonard et al. |
| 2017/0165348 A1 | 6/2017 | Cantore et al. |
| 2017/0183686 A1 | 6/2017 | Khorova et al. |
| 2017/0189449 A1 | 7/2017 | Lim |
| 2017/0296677 A1 | 10/2017 | Lee et al. |
| 2017/0368098 A1 | 12/2017 | Chen et al. |
| 2018/0028600 A1 | 2/2018 | Hong et al. |
| 2018/0028687 A1 | 2/2018 | Selaru et al. |
| 2018/0312824 A1 | 11/2018 | Zhang et al. |
| 2019/0023790 A1 | 1/2019 | Regeneron |
| 2019/0125898 A1 | 5/2019 | Lee et al. |
| 2019/0144885 A1 | 5/2019 | Costa Fejoz et al. |
| 2019/0271006 A1 | 9/2019 | Nakaishi et al. |
| 2019/0351047 A1 | 11/2019 | Jasny et al. |
| 2020/0060980 A1 | 2/2020 | Von Maltzahn et al. |
| 2021/0030467 A1 | 2/2021 | Mee et al. |
| 2021/0032589 A1 | 2/2021 | Mee et al. |
| 2021/0137839 A1 | 5/2021 | Von Maltzahn et al. |
| 2021/0187018 A1 | 6/2021 | Von Maltzahn et al. |
| 2021/0198698 A1 | 7/2021 | Von Maltzahn et al. |
| 2021/0228627 A1 | 7/2021 | Von Maltzahn et al. |
| 2021/0353543 A1 | 11/2021 | Trudeau et al. |
| 2021/0393736 A1 | 12/2021 | Hong et al. |
| 2022/0008557 A1 | 1/2022 | Von Maltzahn et al. |
| 2022/0241328 A1 | 8/2022 | Bandoro et al. |
| 2023/0043255 A1 | 2/2023 | Von Maltzahn et al. |
| 2023/0048166 A1 | 2/2023 | Von Maltzahn et al. |
| 2023/0068547 A1 | 3/2023 | Von Maltzahn et al. |
| 2023/0285591 A1 | 9/2023 | Lee et al. |
| 2023/0348934 A1 | 11/2023 | Fejoz et al. |
| 2024/0033227 A1 | 2/2024 | von Maltzahn et al. |
| 2024/0279685 A1 | 8/2024 | Lee et al. |
| 2024/0408192 A1 | 12/2024 | Bandoro et al. |
| 2025/0082777 A1 | 3/2025 | Foster et al. |
| 2025/0144235 A1 | 5/2025 | Jain |
| 2025/0152709 A1 | 5/2025 | Bandoro et al. |
| 2025/0333469 A1 | 10/2025 | Bandoro et al. |
| 2025/0369018 A1 | 12/2025 | Von Maltzahn et al. |

FOREIGN PATENT DOCUMENTS

| | | |
|---|---|---|
| EP | 3235908 | 10/2017 |
| EP | 3964585 | 3/2022 |
| JP | H 10313865 | 12/1998 |
| JP | 2013-034401 | 2/2013 |
| WO | WO 1995/023846 | 9/1995 |
| WO | WO 1995/032706 | 12/1995 |
| WO | WO 1997/004748 | 2/1997 |
| WO | WO 2000/009730 | 2/2000 |
| WO | WO 2000/017374 | 3/2000 |
| WO | WO 2001/074861 | 10/2001 |
| WO | WO 2001/075135 | 10/2001 |
| WO | WO 2002/002765 | 1/2002 |
| WO | WO 2002/044206 | 6/2002 |
| WO | WO 2006/027202 | 3/2006 |
| WO | WO 2006/028786 | 3/2006 |
| WO | WO 2006/059141 | 6/2006 |
| WO | WO 2006/078221 | 7/2006 |
| WO | WO 2007/005244 | 1/2007 |
| WO | WO 2008/037458 | 4/2008 |
| WO | WO 2008/071959 | 6/2008 |
| WO | WO 2008/081008 A1 | 7/2008 |
| WO | WO 2008/115199 | 9/2008 |
| WO | WO 2009/130208 | 10/2009 |
| WO | WO 2010/053489 | 5/2010 |
| WO | WO 2010/075061 | 7/2010 |
| WO | WO 2011/011584 | 1/2011 |
| WO | WO 2011/058052 | 5/2011 |
| WO | WO 2012/095535 | 7/2012 |
| WO | WO 2012/149376 | 11/2012 |
| WO | WO 2012/158643 | 11/2012 |
| WO | WO 2012/170911 | 12/2012 |
| WO | WO 2013/045639 | 4/2013 |
| WO | WO 2013/084000 | 6/2013 |
| WO | WO 2013/148327 | 10/2013 |
| WO | WO 2014/076137 | 5/2014 |
| WO | WO 2014/164553 | 10/2014 |
| WO | WO 2015/011478 | 1/2015 |
| WO | WO 2015/110957 | 7/2015 |
| WO | WO 2016/009326 | 1/2016 |
| WO | WO 2016/124781 | 8/2016 |
| WO | WO 2016/138525 | 9/2016 |
| WO | WO 2016/183482 | 11/2016 |
| WO | WO 2016/196350 | 12/2016 |
| WO | WO 2017/005923 | 1/2017 |
| WO | WO 2017/011519 | 1/2017 |
| WO | WO 2017/151717 | 9/2017 |
| WO | WO 2017/165245 | 9/2017 |
| WO | WO 2017/173034 | 10/2017 |
| WO | WO 2017/182585 | 10/2017 |
| WO | WO 2017/211945 | 12/2017 |
| WO | WO 2017/218850 | 12/2017 |
| WO | WO 2018/009923 | 1/2018 |
| WO | WO 2018/022749 | 2/2018 |
| WO | WO 2018/106732 | 6/2018 |
| WO | WO 2018/115507 | 6/2018 |
| WO | WO 2018/129563 | 7/2018 |
| WO | WO 2018/132479 | 7/2018 |
| WO | WO 2018/208728 | 11/2018 |
| WO | WO 2019/086351 | 5/2019 |
| WO | WO 2019/113512 | 6/2019 |
| WO | WO 2019/152692 | 8/2019 |
| WO | WO 2019/157316 | 8/2019 |
| WO | WO 2019/157319 | 8/2019 |
| WO | WO 2019/161281 | 8/2019 |
| WO | WO 2019/217964 | 11/2019 |
| WO | WO 2019/222403 | 11/2019 |
| WO | WO 2020/014209 | 1/2020 |
| WO | WO 2020/092554 A1 | 5/2020 |
| WO | WO 2020/102485 | 5/2020 |
| WO | WO 2020/102499 | 5/2020 |
| WO | WO 2020/102503 | 5/2020 |
| WO | WO 2020/102578 | 5/2020 |
| WO | WO 2020/121273 | 6/2020 |
| WO | WO 2020/210003 | 10/2020 |
| WO | WO 2021/046143 | 3/2021 |
| WO | WO 2021/168355 | 8/2021 |
| WO | WO 2021/202604 | 10/2021 |
| WO | WO 2021/207801 | 10/2021 |
| WO | WO 2022/010889 | 1/2022 |
| WO | WO 2022/150731 | 7/2022 |
| WO | WO 2022/165262 | 8/2022 |
| WO | WO 2022/216915 | 10/2022 |
| WO | WO 2022/251712 | 12/2022 |
| WO | WO 2023/115041 | 6/2023 |
| WO | WO 2023/133595 | 7/2023 |
| WO | WO 2023/150518 | 8/2023 |
| WO | WO 2023/150647 | 8/2023 |
| WO | WO 2023/193015 | 10/2023 |
| WO | WO 2024/026377 | 2/2024 |
| WO | WO 2024/044655 | 2/2024 |
| WO | WO 2024/064838 | 3/2024 |
| WO | WO 2024/119157 | 6/2024 |
| WO | WO 2024/220560 | 10/2024 |
| WO | WO 2024/243340 | 11/2024 |

OTHER PUBLICATIONS

Dianova (Antibody structure—what is a secondary antibody? https://www.dianova.com/en/faq/antibody-structure-what-is-a-secondary-antibody/, downloaded Aug. 14, 2024) (Year: 2024).*

Abengozar et al., "Blocking ephrinB2 with highly specific antibodies inhibits angiogenesis, lymphangiogenesis, and tumor growth". Blood 119(19):4565-76, 2012.

Aguilar et al. "N-glycans on nipah virus fusion protein protect against neutrilization but reduce membrane fusion and viral entry", Virol. (80) 4878-4889, 2006.

(56)         References Cited

OTHER PUBLICATIONS

Aguilar et al., "Polybasic KKR Motif in the Cytoplasmic Tail of Nipah Virus Fusion Protein Modulates Membrane Fusion by Inside-Out Signaling," J Viral (2007) 81:4520-4532.

Alam et al., "Coexpression of EphB4 and ephrinB2 in tumor advancement of uterine cervical cancers", Gynecologic Oncology 114(1):84-88, 2009.

Anliker et al., Specific gene transfer to neurons, endothelial cells and hematopoietic progenitors with lentiviral vectors, 7(11) Nature Methods 929-937 (Nov. 2010).

Barile et al., "Exosomes: Therapy delivery tools and biomarkers of diseases," Pharmacol Ther. (2017) 174: 63-78.

Bender et al., "Developing an Engineered Nipah Virus Glycoprotein Based Lentiviral Vector System Retargeted to Cell Surface Receptors of Choice," Mol. Ther. (2015) 23(1); S2.

Bender et al., "Receptor-Targeted Nipah Virus Glycoproteins Improve Cell-Type Selective Gene Delivery and Reveal a Preference for Membrane-Proximal Cell Attachment," PLOS Pathogens 12(6):e1005641.

Biering et al. "N-glycans on the nipah virus attachment glycoprotein modulate fusion and viral entry as they protect against antibody neutrilization" J Virol. (2012) 86(22): 11991-12002.

Bishop et al., "Identification of Hendra Virus G Glycoprotein Residues That Are Critical for Receptor Binding," J Viral (2007) 81:5893-5901.

Bowden et al., "Structural basis of Nipah and Hendra virus attachment to their cell-surface receptor ephrin-B2," Nature Structural & Molecular Biology (2008) 15(6):567-572.

Chiriaco et al., "Dual-regulated lentiviral vector for gene therapy of X linked chronic granulomatosis." Molecular Therapy (2014) 22(8): 1472-1483.

Enkirch et al., *Targeted lentiviral vectors pseudotyped with the Tupaia paramyxovirus glycoproteins*, 20(1) Gene Therapy 16-23 (2013).

Field et al., "Comparison of lentiviral and sleeping beauty mediated alpha&bgr T cell receptor gene transfer." PLOS ONE (2013) 8(6): e68201.

Frecha et al., *Stable transduction of quiescent T cells without induction of cycle progression by a novel lentiviral vector pseudotyped with measles virus glycoproteins*, 112(13) Blood 4843-4852 (Dec. 15, 2008).

Friedel et al., "Receptor-targeted lentiviral vectors are exceptionally sensitive toward the biophysical properties of the displayed single-chain Fv," Protein Eng Des Sel. (2015) 28(4): 93-106. doi: 10.1093/protein/gzv005.

Funke et al., *Targeted Cell Entry of Lentiviral Vectors*, 16(8) Molecular Therapy 1427-1436 (Aug. 2008).

Guillaume et al., "Evidence of a Potential Receptor-Binding Site on the Nipah Virus G Protein (NiV-G): Identification of Globular Head Residues with a Role in Fusion Promotion and Their Localization on an NiV-G Structural Model," J Viral (2006) 80:7546-7554.

Haga et al.,"Permanent, lowered HLA class I expression using lentivirus vectors with shRNA constructs: averting cytotoxicity by alloreactive T lymphocytes." Transplantation Proceedings (2006) 38(10):3184-3188.

Imamura et al., *Autonomous growth and increased cytotoxicity of natural killer cells expressing membrane-bound interleukin-15*, 124(7) Blood 1081-1088 (Aug. 2014).

Khetawat et al., "A Functional Henipavirus Envelope Glycoprotein Pseudotyped Lentivirus Assay System," Khetawat and Broder Virology Journal (2010) 7:312.

Kneissl et al., *Measles Virus Glycoprotein-Based Lentiviral Targeting Vectors That Avoid Neutralizing Antibodies*, 7(10) PLOS ONE 1-8 (Oct. 2012).

Lattanzi et al "A Strategy of antigen incoperation into exosomes: Comparing cross-presentation levels of antigens delivered by engineered exosomes and by lentiviral virus-like particles", Vaccine (2012) col. 20, No. 50; 7229.

Leavitt et al., "Concordant modulation of neutrilization resistance and high infectivity of the primary human immunodeficiency virus type 1 MN strain and definition of a potential gp41 binding site in gp120". Journal of Virology 560-570, 2003.

Lee et al. "Modes of paramyxovirus fusion: a Henipavirus perspective" 2011. Trends in Microbiology.Aug;19(8):389-99.

Lentz et al. "Review, viral vectors for gene delivery to the central nervous system" Neurobiology of Disease 48:179-188, 2012.

Levy et al., "Surface engineering of lentiviral vectors for gene transfer into gene therapy target cells," Current Opinion in Pharmacology (2015) 24:79-85.

Milani et al., "Genome editing for scalable produciton of alloantigen free lentiviral vectors for in vivo gene therapy." EMBO Molecular Medicine (2017) 9(11): 1558-1573.

Montagna et al., "VSV-G-Enveloped Vesicles for Traceless Delivery of CRISPR-Cas9" Mol Ther Nucleic Acids. (2018) 12:453-462.

Morizono et al., "Redirecting lentiviral vectors pseudotyped with sinbis virus-derived envelope proteins to DC-SIGN by modificiation of N-linked glycans of envelope proteins," J Virol. (2010) 84(14): 6923-34.

Munch et al., DARPins: An Efficient Targeting Domain for Lentiviral Vectors, 19(4) Molecular Therapy 686-693 (2011).

Munch et al., "Off-target-free gene delivery by affinity-purified receptor-targeted viral vectors," Nature Communications (2015) 6:6246.

Nakamura et al., "Antibody-targeted cell fusion," Nat Biotechnol. (2004) 22(3): 331-336.

Needleman et al., A General Method Applicable to the Search for Similarities in the Amino Acid Sequence of Two Proteins, 48 J. Mol. Biol. 443-453 (1970).

Negrete et al., "EphrinB2 is the entry receptor for Nipah virus, an emergent deadly paramyxovirus", Nature (436)401-405, 2005.

Negrete et al., "Single Amino Acid Changes in the Nipah and Hendra Virus Attachment Glycoproteins Distinguish EphrinB2 from EphrinB3 Usage," J Viral (2007) 81(19):10804-10814.

Nordlund et al., "SNARE-fusion mediated insertion of membrane proteins into native and artificial membranes." Nat Commun. (2014) 5: 4303.

Palomares et al., "Nipah Virus Envelope-Pseudotyped Lentiviruses Efficiently Target ephrinB2-Positive Stem Cell Populations In Vitro and Bypass the Liver Sink When Administered In Vivo," J Viral (2013) 87:2094-2108.

Pichard et al., "Specific Micro-RNA regulated TetR-KRAB Transcriptional control of transgene expression in viral vector transduced cells," PLOS ONE (2012) 7(12):e51952.

Riazifar et al., "Stem Cell Extracellular Vesicles: Extended Messages of Regeneration," Annu Rev Pharmacol Toxicol. (2017) 57: 125-154.

Schauber-Plewa et al., "Complement regulatory proteins are incorporated into lentiviral vectors and protect particles against complement inactivation." Gene Therapy. (2004) 12(3): 238-245.

Single Domain Antibodies, Single-Domain Antibodies—MeSH—NCBI (nih.gov), 2013.

Sosale et al., "Marker of self: CD47 on lentiviral vectors decreases macrophage-mediated clearance and increases delivery to SIRPA-expressing lung carcinoma tumors." Molecular Therapy (2016) 3(7): 16080.

Stefan et al., "DARPins recognizing the tumor-associated antigen EpCAM selected by phage and ribosome display and engineered for multivalency," J Mol Biol. (2011) 413(4): 826-43.

Steffen et al., "Henipavirus mediated membrane fusion, virus entry and targeted therapeutics," Viruses (2012) 4:280-309.

Tang et al., "Therapeutic potential of CAR-T cell-derived exosomes: a cell-free modality for targeted cancer therapy." Oncotarget (2015) 6(42); 44179-44190.

Tomas et al., "Improved GaLV-TR glycoproteins to pseudotype lentiviral vectors: impact of viral protease activity in the production of LV pseudotypes." Molecular Therapy (2019) 15: 1-8.

Verhoeyen et al., "Lentiviral vector gene transfer into human T cells," Methods in Mal Biol (2009) 506:97-114.

Verhoeyen et al., *IL-7 surface-engineered lentiviral vectors promote survival and efficient gene transfer in resting primary T lymphocytes*, 101 (6) Blood 2167-2174 (Mar. 15, 2003).

(56) References Cited

OTHER PUBLICATIONS

Weiss et al., "Review, The blood-brain barrier in brain homeostasis and neurological diseases" Biochimica Biophys Acta. (2009) 1788: 841-857.

White et al., "Structures and mechanisms of viral membrane fusion proteins: multiple variations on a common theme," Crit Rev Biochem Mol Biol. (2008) 43(3): 189-219.

Witting S.R. et al., Characterization of a 3rd Generation Lentiviral Vector Pseudotyped With Nipah Virus Envelope Proteins for Endothelial Cell Transduction. Gene Ther, May 23, 2013, vol. 20, No. 10.

Xu et al., "Host cell recognition by the henipaviruses: Crystal structures of the Nipah G attachment glycoprotein and its complex with ephrin-B3," PNAS (2008) 105(29):9953-9958.

Xu et al., "New Insights into the Hendra Virus Attachment and Entry Process from Structures of the Virus G Glycoprotein and Its Complex with Ephrin-B2," PLOS One (2012) 7(11):e48742.

Yang et al., "Virus-mimetic fusogenic exosomes for direct delivery of integral membrane proteins to target cell membranes." Advanced Materials (2017) 29(13): 1605604.

Zakaria et al., "Combination of hepatocyte specific delivery and transformation dependent expression of shRNA inducing transcriptional gene silencing of c-Myc promoter in hepatocellular carcinoma cells", BMC Cancer, Biomed Central, London (2014) 14(1): 582.

Zhang et al., "Cell specific targeting of lentiviral vector mediated by fusion proteins derived from Sindbis virus, vesicular stomatitis virus, or avian sarcoma/leukosis virus", Retrovirology 7(3) 1-15, 2010.

Zhou et al., "Cell type specific gene delivery by lentiviral vectors," Onco Immunolgy (2013) 2:e22566.

Zhou Q et al. T cell receptor gene transfer exclusively to human CD8 cells enhances tumor killing. Blood Aug. 16, 2012, vol. 120 No 22:4334.

Zhou et al., Exclusive Transduction of Human CD4+ T Cells upon Systemic Delivery of CD4-Targeted Lentiviral Vectors, 195(5) J. Immunol. 2493-2501 (2015).

International Search Report issued on Jun. 13, 2017, in corresponding PCT Application No. PCT/EP2017/059435.

Abe et al. (Jul. 1, 1998), "Enhanced Gene Transfer with Fusogenic Liposomes Containing Vesicular Stomatitis Virus G Glycoprotein," Journal of Virology, 72(7), 6159-6163.

Adlakha-Hutcheon et al. (Aug. 1999), "Controlled destabilization of a liposome drug delivery system enhances mitoxantrone antitumor activity," Nature Biotechnology, 17, 775-779.

Agarwal et al., "In vivo generated human CAR T cells eradicate tumor cells," OncoImmunology (2019) 8(12): e1671761, 7 pages.

Agarwal et al., "In Vivo Generation of CAR T Cells Selectively in Human CD4+ Lymphocytes," Mol Ther. (2020) 28(8):1783-1794.

Agrawal et al., "Complement Evasion Strategies of Viruses: An Overview," Front Microbiol. (2017) Jun. 16; 8:1117.

Ali et al., " Virosome: An engineered virus for vaccine delivery," Saudi Pharmaceuticals Journal (2023), vol. 31, p. 752-764.

Alvarez-Erviti et al., "Delivery of siRNA to the mouse brain by systemic injection of targeted exosomes." Nature Biotechnology (2011) 29(4): 341-345.

Bagai et al., " Targeted Delivery of Hygromycin B Using Reconstituted Sendai Viral Envelopes Lacking Hemagglutinin-neuraminidase," FEBS (1993), vol. 277, p. 183-188.

Bakshi et al., "Engineering Single Domain Antibodies Into Antivirals and Vaccine Delivery Vehicles to Combat Infectious Diseases," Diss. Ghent University (2019).

Bannas et al. (Nov. 22, 2017), "Nanobodies and Nanobody-Based Human Heavy Chain Antibodies As Antitumor Therapeutics," Frontiers in Immunology, 8(1603), in 13 pages.

Blechacz et al. (Jun. 2008), "Measles Virus as An Oncolytic Vector Platform," Current Gene Therapy, 8(3), 162-175.

Brown et al., "A microRNA-regulated lentiviral vector mediates stable correction of hemophilia B mice," Blood. (2007) 110(13): 4144-4152.

Carter et al., "Versatile in vivo genome editing with the prototypical Streptococcus thermophilus CRISPR1-Cas9 system," BioRxiv. (2018); 10 pages.

Cattaneo, "Paramyxovirus entry and targeted vectors for cancer therapy," PLoS Pathog. (2010) 6(6): e1000973.

Challener, "Advances in In Vivo CAR T-cell Therapies," BioPharm International (Mar. 7, 2023) 2(3):4 pages.

Chen et al., "Development of T cells carrying two complementary chimeric antigen receptors against glypican-3 and asialoglycoprotein receptor 1 for the treatment of hepatocellular carcinoma," Cancer Immunol. Immunother. (2017) 66(4):475-89.

Costello et al., "Gene transfer into stimulated and unstimulated T lymphocytes by HIV-1-derived lentiviral vectors" Gene Ther. (2000) 7(7):596-604.

David et al., "Viral Vectors: The Road to Reducing Genotoxicity," Toxicol Sci. (2017) 155(2):315-325.

Eisenstein et al. (2020), "Nature Biotechnology's academic spinouts of 2019," Nature Biotechnology (2020) 38:546-547.

Escors et al., "Cell and Tissue Gene Targeting with Lentiviral Vectors," Lentiviral Vectors and Gene Therapy. (2012) 29-50.

Ezigbo et al. (Sep. 30, 2014), "Hepatocellular carcinoma in a patient with chronic lymphocytic leukaemia involving the liver," BMJ Case Report, 1-3.

Felt et al., "Recent Advances in Vesicular Stomatitis Virus-Based Oncolytuc Virotherapy: a 5-year Update," Journal of General Virology (2017), vol. 98, p. 2895-2911.

Field et al. (Jan. 12, 2017), "Interleukin-2 receptor-a proximal promoter hypothylation is associated with multiple sclerosis," Genes and Immunity, 18, 59-66.

Frank et al., "Surface-Engineered Lentiviral Vectors for Selective Gene Transfer into Subtypes of Lymphocytes," Mol Ther Methods Clin Dev. (2019) 12:19-31.

Funke et al., "Targeted cell entry of lentiviral vectors," Mol. Ther. (2008) 16(8):1427-1436.

Galimi et al., "Development of Ecdysone-Regulated Lentiviral Vectors," Molecular Therapy (2005) 11(1):142-148.

Ghassemi et al., "Rapid manufacturing of non-activated potent CAR T cells," Nat Biomed Eng. (2022) 6(2):118-128.

Girard-Gagnepain (Nov. 11, 2014), "Evaluation of new lentiviral vector pseudotypes for gene transfer into hematopoietic cells," Virology, Ecole normale supérieure de lyon-ENSLYON, NNT: 2014ENSL0939. tel-01084864, in 393 pages.

Girard-Gagnepain et al., "Baboon envelope pseudotyped LVs outperform VSV-G-LVs for gene transfer into early-cytokine-stimulated and resting HSCs," Blood (2014) 124(8):1221-1231.

Gonzales-Aseguinolaza et al. (Sep. 2010), "Durable Correction of Inherited Metabolic Liver Disorders Requires Preventing Transgene Off-Targeting From Gene Therapy Vectors: The Value of MicroRNAs," Gastroenterology, 139(3), in 4 pages.

Gorelik et al. (Jan. 2002), "Transforming Growth Factor-B in T-Cell Biology," Nature Reviews Immunology, 2, 46-53.

Gori et al., "Protection of mice from methotrexate toxicity by ex vivo transduction using lentivirus vectors expressing drug-resistant dihydrofolate reductase," J Pharmacol Exp Ther (2007) 322(3):989-97.

Greenberg et al., "Targeted transgene expression in muller glia of normal and diseased retinas using lentiviral vectors," IOVS (2007) 48(4):1844-1852.

Hafid et al., "Phenylketonuria: a review of current and future treatments," Transl Pediatr. (2015) (4):304-17.

Hassett et al. (Apr. 15, 2019), "Optimization of Lipid Nanoparticles for Intramuscular Administration of mRNA Vaccine," Molecular Therapy-Nucleic Acids, in 11 pages.

International PCT Application PCT/US2025/017875, filed Feb. 28, 2025, by Sana Biotechnology, Inc., in 487 pages.

Joglekar et al. (Dec. 1, 2017), "Pseudotyped Lentiviral Vectors: One Vectors, Many Guises," Human Gene Therapy Methods, 2017, 28(6), 11 pages.

Juzenas et al., "A comprehensive, cell specific microRNA catalogue of human peripheral blood," Nucleic Acids Research (2017), vol. 45 (16), p. 9290-9301.

Kanvinde et al., "Non-Viral Vectors for Delivery of Nucleic Acid Therapies for Cancer," BioTech (Basel) (2022) 11(1):6, 4 pages.

(56) References Cited

OTHER PUBLICATIONS

Kasaraneni et al. (Dec. 12, 2017), "Retargeting Lentiviruses via SpyCatcher-SpyTag Chemistry for Gene Delivery into Specific Cell Types," mBio, 8(6), in 12 pages.

Kaur et al. (2014), "CD47 Signaling Regulates the Immunosuppressive Activity of VEGF in T Cells," The Journal of Immunology, 193(8), 3914-3924.

Kells et al., "Efficient gene therapy-based method for the delivery of therapeutics to primate cortex". PNAS (106):2407-2411, 2009.

Kneissl et al., "Measles Virus Glycoprotein-Based Lentiviral Targeting Vectors That Avoid Neutralizing Antibodies," PLOS One (2012) 7(10): e46667.

Lam et al., "Efficient and Safe Herpes Simplex Virus Type 1 Amplicon Vector for Transpictionally Targeted Therapy for Human Hepatocellular Carcinomas," The American Society of Gene Therapy (2007), vol. 15, No. 6, p. 1129-1136.

Levy et al. (Oct. 24, 2017), "Measles virus envelope pseudotyped lentiviral vectors transduce quiescent human HSCs at an efficiency without precedent," Blood Advances, 1(23), in 17 pages.

Li, "Enhancing HSP70-ShRNA Transfection in 22RV1 Prostate Cancer Cells by Combination of Sonoporation, Liposomes and HTERTA-CMV Chimeric Promoter," International Journal of Oncology (2013), vol. 43, p. 151-158.

Mhaidly et al. (Apr. 1, 2019), "The Future: In Vivo CAR T Cell Gene Therapy", Molecular Therapy, 2019, 27(4), 3 pages.

Miao et al., "Inclusion of the hepatic locus control region, an intron, and untranslated region increases and stabilizes hepatic factor IX gene expression in vivo but not in vitro," Mol Ther. (2000) 1(6):522-32.

Milani et al., "Phagocytosis-shielded lentiviral vectors improve liver gene therapy in nonhuman primates," Sci Transl Med. (2019) 11(493): eaav7325.

Moll et al., "Importance of the cytoplasmic tails of the measles virus glycoproteins for fusogenic activity and the generation of recombinant measles viruses," J Virol. (2002) 76(14): 7174-86.

Nakamura et al., "Oncolytic Measles Viruses for Cancer Therapy," Expert Opinion on Biological Therapy (2004), vol. 4, No. 10, p. 1685-1692.

Nomura et al. (Feb. 26, 2004), "Microscopic observations reveal that fusogenic peptides induce liposome shrinkage prior to membrane fusion," PNAS 101(10), 3420-3425.

Organism—Wikipedia p. 1 of 10 downloaded Nov. 6, 2017 Cited as: Organism—Wikipedia. Retrieved on Sep. 14, 2023. 7 pages.

Pager et al., "A mature and fusogenic form of the Nipah virus fusion protein requires proteolytic processing by cathepsin L," Virology. (2006) 346(2): 251-257.

Pfeiffer et al., "In vivo generation of human CD19-CAR T cells results in B-cell depletion and signs of cytokine release syndrome," EMBO Mol Med. (2018) 10(11):e9158.

Plemper et al., "Structural and mechanistic studies of measles virus illuminate paramyxovirus entry," PLoS Pathog. (2011) 7(6): e1002058.

Rockx et al. (Aug. 2012), "Recent progress in henipavirus research: molecular biology, genetic diversity, animal models," Antiviral Research, 95(2), 135-149.

Schneider et al., "A Tandem CD19/CD20 Lentiviral Vector Drives On-Target and Off-Target Antigen Modulation in Leukemia Cell Lines," Journal of Immunotherapy (2017), vol. 98, p. 2895-2911.

Sequences cited by the USPTO in the Office Action dated Mar. 7, 2024, in U.S. Appl. No. 17/572,611: SEQ ID No. 17 of U.S. Appl. No. 17/572,611 vs EP3235908 SEQ ID No. 4 (Year: 2017) SEQ ID No. 17 of U.S. Appl. No. 17/572,611 vs U.S. Appl. No. 17/218,025, SEQ ID No. 16 (Year: 2024); SEQ ID No. 21 of U.S. Appl. No. 17/572,611 vs EP3235908, SEQ ID No. 16 (Year: 2017); SEQ ID No. 21 of U.S. Appl. No. 17/572,611 vs U.S. Pat. No. 11,535,869 SEQ ID No. 1092 (Year: 2024); SEQ ID No. 17 of U.S. Appl. 17/572,611 vs U.S. Pat. No. 11,535,869 SEQ ID No. 607 or 635 (Year: 2024); SEQ ID No. 21 of U.S. Appl. No. 17/572,611 vs U.S. Appl. No. 17/218,025, SEQ ID No. 23 (Year: 2024).

Shim et al., "Efficient and Targeted Delivery of siRNA in Vivo," FEBS (2010), vol. 277, p. 4814-4827.

Smith et al., "Viral entry mechanisms: the increasing diversity of paramyxovirus entry," FEBS J. (2009) 276(24): 7217-27.

Sun, W., "Henipavirus Assembly And Budding," Doctoral Dissertation (online). Pennsylvania 4-6, 7/4-6, 8/4-6 State University. 2015 [retrieved on Sep. 30, 2021]. Retrieved from the Internet: [URL: https://etda.libraries.psu.edu/files/final_submissions/10659]; abstract.

Suvanasuthi et al., "Rapid transport of plasmid DNA into the nucleolus via actin depolymerization using the HVJ envelope vector," J Gene Med. (2007) 9(1):55-62.

Vairy et al., "CTL019 (tisagenlecleucel): CAR-T therapy for relapsed and refractory B-cell acute lymphoblastic leukemia," Drug Des Devel Ther. (2018) 12:3885-3898.

Valastyan et al. (2010), "miR-31: A crucial overseer of tumor metastasis and other emerging roles," Cell Cycle, 9(11), 2124-2129.

Verhoeyen et al. (2008), "Production of Lentiviruses Displaying "Early-Acting" Cytokines for Selective Gene Transfer into Hematopoietic Stem Cells," Gene Therapy Protocols, 434(2), 99-112.

Wang et al., "AAV Gene Therapy Corrects OTC Deficiency and Prevents Liver Fibrosis in Aged OTC-Knock Out Heterozygous Mice," Molecular Genetics and Metabolism (Apr. 2017), vol. 120, p. 299-305.

Wu et al., "Combinatorial control of suicide gene expression by tissue-specific promoter and microRNA regulation for cancer therapy," Mol Ther. (2009) Dec.;17(12):2058-66.

Zhang et al. (Dec. 9, 2021), "A multiclade env-gag VLP mRNA vaccine elicits tier-2 HIV-1-neutralizing antibodies and reduces the risk of heterologous SHIV infection in macaques," Nature Medicine, 27(12), in 31 pages.

Diederich et al., "Activation of the Nipah Virus Fusion Protein in MDCK Cells Is Mediated by Cathepsin B within the Endosome-Recycling Compartment," Journal of Virology (2012) 86(7):3736-3745.

Follenzi et al. (2002), "Efficient Gene Delivery and Targeted Expression to Hepatocytes In Vivo by Improved Lentiviral Vectors," Human Gene Therapy, 13(2), 243-260.

Transfiguracion et al. (Sep. 18, 2020), "Rapid In-Process Monitoring of Lentiviral Vector Particles by High-Performance Liquid Chromatography.," Molecular Therapy: Methods & Clinicial Development, 18, 803-810.

* cited by examiner

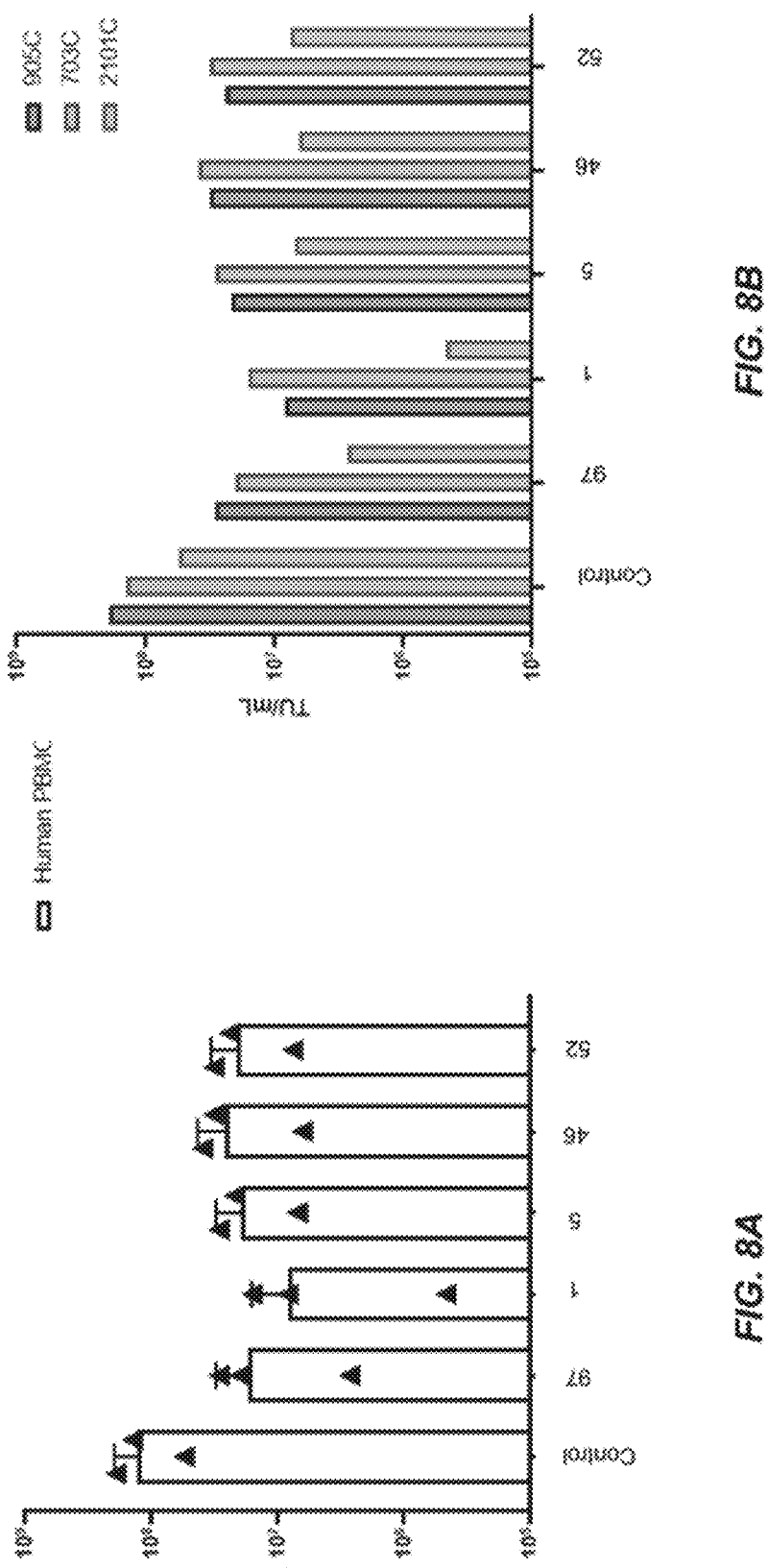

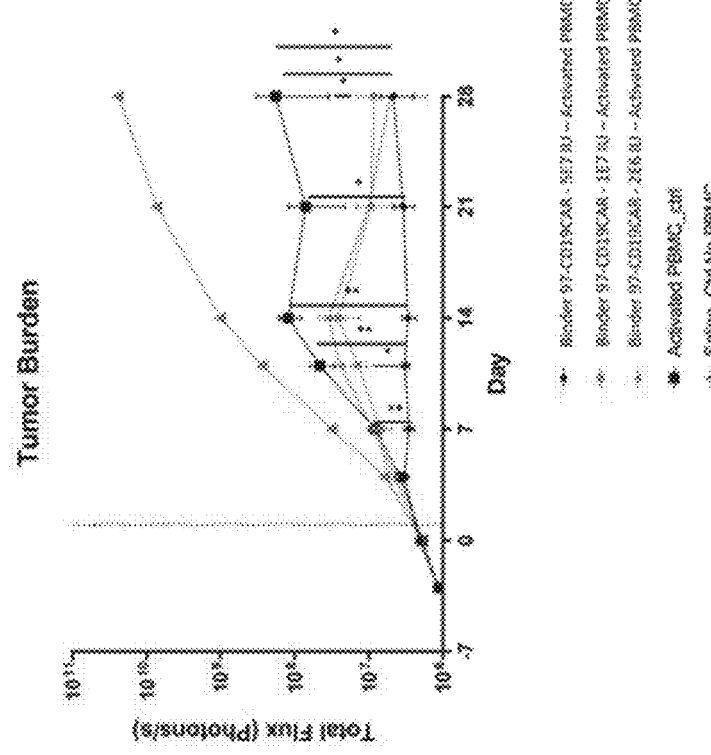
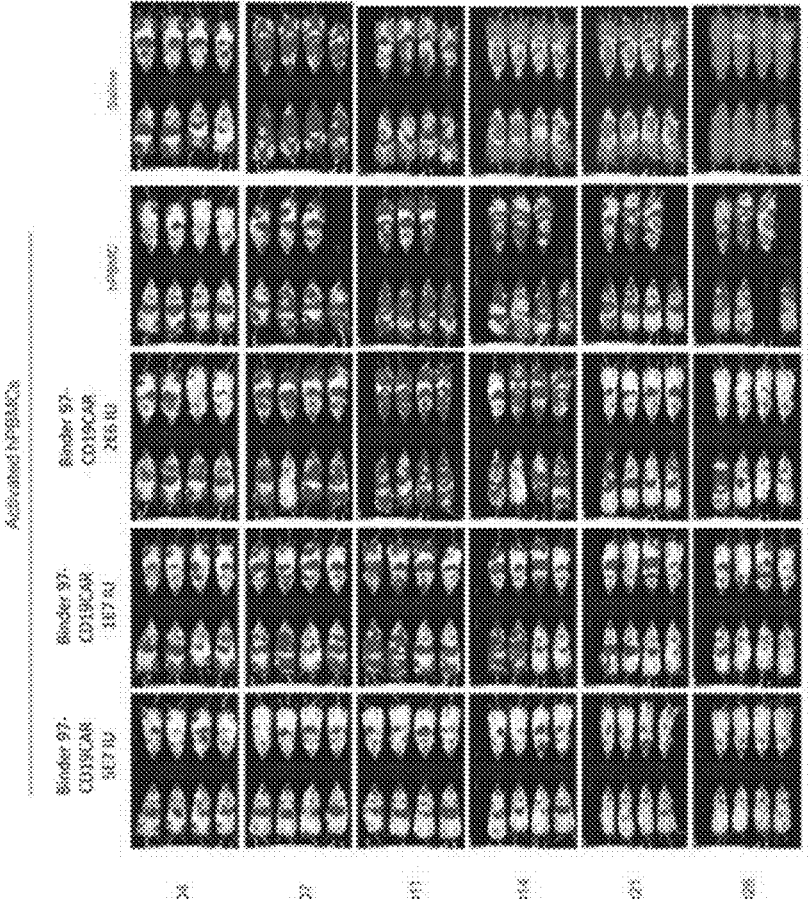
FIG. 11A

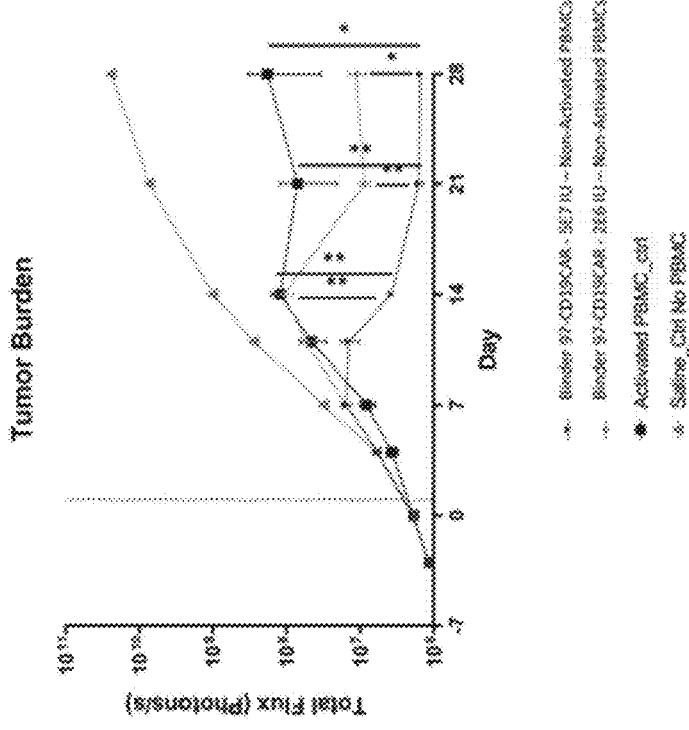
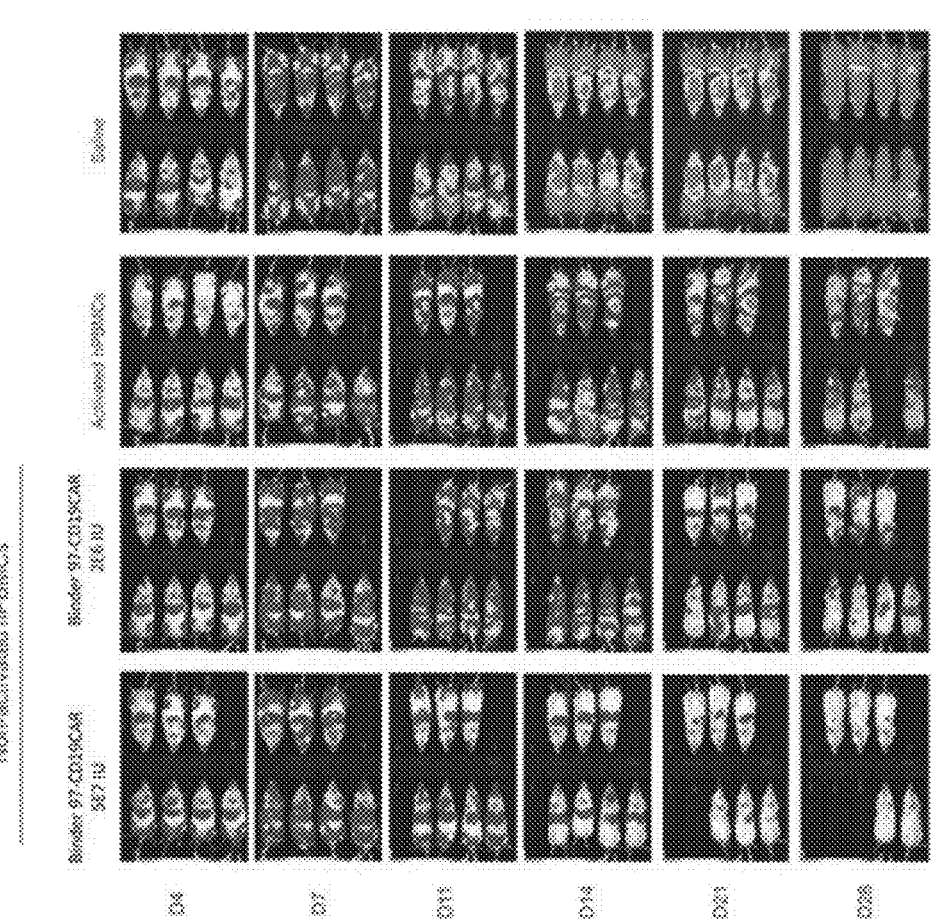
FIG. 11B

SEQUENCE LISTING

Sequence total quantity: 1231
SEQ ID NO: 1                moltype = AA   length = 5
FEATURE                     Location/Qualifiers
source                      1..5
                            mol_type = protein
                            organism = Homo sapiens
SEQUENCE: 1
SYAIS                                                            5

SEQ ID NO: 2                moltype = AA   length = 5
FEATURE                     Location/Qualifiers
source                      1..5
                            mol_type = protein
                            organism = Homo sapiens
SEQUENCE: 2
TYAIN                                                            5

SEQ ID NO: 3                moltype = AA   length = 5
FEATURE                     Location/Qualifiers
source                      1..5
                            mol_type = protein
                            organism = Homo sapiens
SEQUENCE: 3
SYAIN                                                            5

SEQ ID NO: 4                moltype = AA   length = 5
FEATURE                     Location/Qualifiers
source                      1..5
                            mol_type = protein
                            organism = Homo sapiens
SEQUENCE: 4
GYYMH                                                            5

SEQ ID NO: 5                moltype = AA   length = 5
FEATURE                     Location/Qualifiers
source                      1..5
                            mol_type = protein
                            organism = Homo sapiens
SEQUENCE: 5
DYYIQ                                                            5

SEQ ID NO: 6                moltype = AA   length = 5
FEATURE                     Location/Qualifiers
source                      1..5
                            mol_type = protein
                            organism = Homo sapiens
SEQUENCE: 6
RYDIH                                                            5

SEQ ID NO: 7                moltype = AA   length = 5
FEATURE                     Location/Qualifiers
source                      1..5
                            mol_type = protein
                            organism = Homo sapiens

```
SEQUENCE: 7
SYAMN                                                                    5

SEQ ID NO: 8            moltype = AA   length = 5
FEATURE                 Location/Qualifiers
source                  1..5
                        mol_type = protein
                        organism = Homo sapiens SEQUENCE: 8
SYYIH                                                                    5

SEQ ID NO: 9            moltype = AA   length = 5
FEATURE                 Location/Qualifiers
source                  1..5
                        mol_type = protein
                        organism = Homo sapiens SEQUENCE: 9
RHYIH                                                                    5

SEQ ID NO: 10           moltype = AA   length = 5
FEATURE                 Location/Qualifiers
source                  1..5
                        mol_type = protein
                        organism = Homo sapiens SEQUENCE: 10
SYGIS                                                                    5

SEQ ID NO: 11           moltype = AA   length = 5
FEATURE                 Location/Qualifiers
source                  1..5
                        mol_type = protein
                        organism = Homo sapiens SEQUENCE: 11
NTDIN                                                                    5

SEQ ID NO: 12           moltype = AA   length = 5
FEATURE                 Location/Qualifiers
source                  1..5
                        mol_type = protein
                        organism = Homo sapiens SEQUENCE: 12
RSYVH                                                                    5

SEQ ID NO: 13           moltype = AA   length = 5
FEATURE                 Location/Qualifiers
source                  1..5
                        mol_type = protein
                        organism = Homo sapiens SEQUENCE: 13
GYYMH                                                                    5

SEQ ID NO: 14           moltype = AA   length = 5
FEATURE                 Location/Qualifiers
source                  1..5
                        mol_type = protein
                        organism = Homo sapiens SEQUENCE: 14
RYYMH                                                                    5

SEQ ID NO: 15           moltype = AA   length = 5
FEATURE                 Location/Qualifiers
source                  1..5
                        mol_type = protein
                        organism = Homo sapiens SEQUENCE: 15
NYDIN                                                                    5

SEQ ID NO: 16           moltype = AA   length = 5
FEATURE                 Location/Qualifiers
source                  1..5
                        mol_type = protein
                        organism = Homo sapiens SEQUENCE: 16
NYYLH                                                                    5

SEQ ID NO: 17           moltype = AA   length = 5
FEATURE                 Location/Qualifiers
source                  1..5
                        mol_type = protein
```

-continued

```
                         organism = Homo sapiens
SEQUENCE: 17
RYSIH                                                            5

SEQ ID NO: 18           moltype = AA  length = 5
FEATURE                 Location/Qualifiers
source                  1..5
                        mol_type = protein
                        organism = Homo sapiens
SEQUENCE: 18
SRDIS                                                            5

SEQ ID NO: 19           moltype = AA  length = 5
FEATURE                 Location/Qualifiers
source                  1..5
                        mol_type = protein
                        organism = Homo sapiens
SEQUENCE: 19
SYDIN                                                            5

SEQ ID NO: 20           moltype = AA  length = 5
FEATURE                 Location/Qualifiers
source                  1..5
                        mol_type = protein
                        organism = Homo sapiens
SEQUENCE: 20
NSDMN                                                            5

SEQ ID NO: 21           moltype = AA  length = 5
FEATURE                 Location/Qualifiers
source                  1..5
                        mol_type = protein
                        organism = Homo sapiens
SEQUENCE: 21
TYDIN                                                            5

SEQ ID NO: 22           moltype = AA  length = 5
FEATURE                 Location/Qualifiers
source                  1..5
                        mol_type = protein
                        organism = Homo sapiens
SEQUENCE: 22
SYTMD                                                           5

SEQ ID NO: 23           moltype = AA  length = 5
FEATURE                 Location/Qualifiers
source                  1..5
                        mol_type = protein
                        organism = Homo sapiens
SEQUENCE: 23
RYDIN                                                           5

SEQ ID NO: 24           moltype = AA  length = 5
FEATURE                 Location/Qualifiers
source                  1..5
                        mol_type = protein
                        organism = Homo sapiens
SEQUENCE: 24
SYYMH                                                           5

SEQ ID NO: 25           moltype = AA  length = 5
FEATURE                 Location/Qualifiers
source                  1..5
                        mol_type = protein
                        organism = Homo sapiens
SEQUENCE: 25
RYAVS                                                           5

SEQ ID NO: 26           moltype = AA  length = 5
FEATURE                 Location/Qualifiers
source                  1..5
                        mol_type = protein
                        organism = Homo sapiens
SEQUENCE: 26
NYAIS                                                           5

SEQ ID NO: 27           moltype = AA  length = 36
FEATURE                 Location/Qualifiers
source                  1..36
```

-continued

```
                          mol_type = protein
                          organism = synthetic construct
                          note = Description of Artificial Sequence: Synthetic
                           polypeptide
VARIANT                   1..36
                          note = SITE - This sequence may encompass 1-6 GGGGGS
                           repeating units
SEQUENCE: 27
GGGGGSGGGG GSGGGGGSGG GGGSGGGGGS GGGGGS                                       36

SEQ ID NO: 28             moltype = AA  length = 5
FEATURE                   Location/Qualifiers
source                    1..5
                          mol_type = protein
                          organism = Homo sapiens
SEQUENCE: 28
RFDIN                                                                         5

SEQ ID NO: 29             moltype = AA  length = 5
FEATURE                   Location/Qualifiers
source                    1..5
                          mol_type = protein
                          organism = Homo sapiens
SEQUENCE: 29
SHAIS                                                                         5

SEQ ID NO: 30             moltype = AA  length = 5
FEATURE                   Location/Qualifiers
source                    1..5
                          mol_type = protein
                          organism = Homo sapiens
SEQUENCE: 30
SYGIN                                                                         5

SEQ ID NO: 31             moltype = AA  length = 5
FEATURE                   Location/Qualifiers
source                    1..5
                          mol_type = protein
                          organism = Homo sapiens
SEQUENCE: 31
DYDIY                                                                         5

SEQ ID NO: 32             moltype = AA  length = 5
FEATURE                   Location/Qualifiers
source                    1..5
                          mol_type = protein
                          organism = Homo sapiens
SEQUENCE: 32
SYHMH                                                                         5

SEQ ID NO: 33             moltype = AA  length = 5
FEATURE                   Location/Qualifiers
source                    1..5
                          mol_type = protein
                          organism = Homo sapiens
SEQUENCE: 33
SYPMN                                                                         5

SEQ ID NO: 34             moltype = AA  length = 5
FEATURE                   Location/Qualifiers
source                    1..5
                          mol_type = protein
                          organism = Homo sapiens
SEQUENCE: 34
DYYIH                                                                         5

SEQ ID NO: 35             moltype = AA  length = 5
FEATURE                   Location/Qualifiers
source                    1..5
                          mol_type = protein
                          organism = Homo sapiens
SEQUENCE: 35
SFEMN                                                                         5

SEQ ID NO: 36             moltype = AA  length = 5
FEATURE                   Location/Qualifiers
source                    1..5
                          mol_type = protein
                          organism = Homo sapiens
```

-continued

```
SEQUENCE: 36
DYAMH                                                                                          5

SEQ ID NO: 37          moltype = AA  length = 5
FEATURE                Location/Qualifiers
source                 1..5
                       mol_type = protein
                       organism = Homo sapiens SEQUENCE: 37
DSYMH                                                                                          5

SEQ ID NO: 38          moltype = AA  length = 5
FEATURE                Location/Qualifiers
source                 1..5
                       mol_type = protein
                       organism = Homo sapiens SEQUENCE: 38
NYYMH                                                                                          5

SEQ ID NO: 39          moltype = AA  length = 5
FEATURE                Location/Qualifiers
source                 1..5
                       mol_type = protein
                       organism = Homo sapiens SEQUENCE: 39
NYYIH                                                                                          5

SEQ ID NO: 40          moltype = AA  length = 5
FEATURE                Location/Qualifiers
source                 1..5
                       mol_type = protein
                       organism = Homo sapiens SEQUENCE: 40
SYMH                                                                                           5

SEQ ID NO: 41          moltype = AA  length = 5
FEATURE                Location/Qualifiers
source                 1..5
                       mol_type = protein
                       organism = Homo sapiens SEQUENCE: 41
DYYIH                                                                                          5

SEQ ID NO: 42          moltype = AA  length = 5
FEATURE                Location/Qualifiers
source                 1..5
                       mol_type = protein
                       organism = Homo sapiens SEQUENCE: 42
GYYLH                                                                                          5

SEQ ID NO: 43          moltype = AA  length = 5
FEATURE                Location/Qualifiers
source                 1..5
                       mol_type = protein
                       organism = Homo sapiens SEQUENCE: 43
NHYMH                                                                                          5

SEQ ID NO: 44          moltype = AA  length = 5
FEATURE                Location/Qualifiers
source                 1..5
                       mol_type = protein
                       organism = Homo sapiens SEQUENCE: 44
NYYIH                                                                                          5

SEQ ID NO: 45          moltype = AA  length = 5
FEATURE                Location/Qualifiers
source                 1..5
                       mol_type = protein
                       organism = Homo sapiens SEQUENCE: 45
DYYMH                                                                                          5

SEQ ID NO: 46          moltype = AA  length = 5
FEATURE                Location/Qualifiers
source                 1..5
                       mol_type = protein
```

-continued

```
                              organism = Homo sapiens
SEQUENCE: 46
ENEMH                                                             5

SEQ ID NO: 47        moltype = AA  length = 5
FEATURE              Location/Qualifiers
source               1..5
                     mol_type = protein
                     organism = Homo sapiens
SEQUENCE: 47
SYDMH                                                             5

SEQ ID NO: 48        moltype = AA  length = 5
FEATURE              Location/Qualifiers
source               1..5
                     mol_type = protein
                     organism = Homo sapiens
SEQUENCE: 48
NSDMH                                                             5

SEQ ID NO: 49        moltype = AA  length = 5
FEATURE              Location/Qualifiers
source               1..5
                     mol_type = protein
                     organism = Homo sapiens
SEQUENCE: 49
AYYMH                                                             5

SEQ ID NO: 50        moltype = AA  length = 5
FEATURE              Location/Qualifiers
source               1..5
                     mol_type = protein
                     organism = Homo sapiens
SEQUENCE: 50
DYHMH                                                             5

SEQ ID NO: 51        moltype = AA  length = 5
FEATURE              Location/Qualifiers
source               1..5
                     mol_type = protein
                     organism = Homo sapiens
SEQUENCE: 51
DYYMH                                                             5

SEQ ID NO: 52        moltype = AA  length = 5
FEATURE              Location/Qualifiers
source               1..5
                     mol_type = protein
                     organism = Homo sapiens
SEQUENCE: 52
DYYMH                                                             5

SEQ ID NO: 53        moltype = AA  length = 5
FEATURE              Location/Qualifiers
source               1..5
                     mol_type = protein
                     organism = Homo sapiens
SEQUENCE: 53
THDIN                                                             5

SEQ ID NO: 54        moltype = AA  length = 5
FEATURE              Location/Qualifiers
source               1..5
                     mol_type = protein
                     organism = Homo sapiens
SEQUENCE: 54
NYYIH                                                             5

SEQ ID NO: 55        moltype = AA  length = 5
FEATURE              Location/Qualifiers
source               1..5
                     mol_type = protein
                     organism = Homo sapiens
SEQUENCE: 55
DNYMH                                                             5

SEQ ID NO: 56        moltype = AA  length = 5
FEATURE              Location/Qualifiers
source               1..5
```

-continued

```
                              mol_type = protein
                              organism = Homo sapiens
SEQUENCE: 56
SYAIS                                                              5

SEQ ID NO: 57                 moltype = AA   length = 5
FEATURE                       Location/Qualifiers
source                        1..5
                              mol_type = protein
                              organism = Homo sapiens
SEQUENCE: 57
TYDIS                                                              5

SEQ ID NO: 58                 moltype = AA   length = 5
FEATURE                       Location/Qualifiers
source                        1..5
                              mol_type = protein
                              organism = Homo sapiens
SEQUENCE: 58
SYDIN                                                              5

SEQ ID NO: 59                 moltype = AA   length = 5
FEATURE                       Location/Qualifiers
source                        1..5
                              mol_type = protein
                              organism = Homo sapiens
SEQUENCE: 59
SHWIH                                                              5

SEQ ID NO: 60                 moltype = AA   length = 5
FEATURE                       Location/Qualifiers
source                        1..5
                              mol_type = protein
                              organism = Homo sapiens
SEQUENCE: 60
DYDIV                                                             5

SEQ ID NO: 61                 moltype = AA   length = 5
FEATURE                       Location/Qualifiers
source                        1..5
                              mol_type = protein
                              organism = Homo sapiens
SEQUENCE: 61
GHDMH                                                             5

SEQ ID NO: 62                 moltype = AA   length = 5
FEATURE                       Location/Qualifiers
source                        1..5
                              mol_type = protein
                              organism = Homo sapiens
SEQUENCE: 62
NYDMH                                                             5

SEQ ID NO: 63                 moltype = AA   length = 5
FEATURE                       Location/Qualifiers
source                        1..5
                              mol_type = protein
                              organism = Homo sapiens
SEQUENCE: 63
SYAMT                                                             5

SEQ ID NO: 64                 moltype = AA   length = 5
FEATURE                       Location/Qualifiers
source                        1..5
                              mol_type = protein
                              organism = Homo sapiens
SEQUENCE: 64
TYYMH                                                             5

SEQ ID NO: 65                 moltype = AA   length = 5
FEATURE                       Location/Qualifiers
source                        1..5
                              mol_type = protein
                              organism = Homo sapiens
SEQUENCE: 65
NYQIH                                                             5

SEQ ID NO: 66                 moltype = AA   length = 5
FEATURE                       Location/Qualifiers
```

-continued

```
source                  1..5
                        mol_type = protein
                        organism = Homo sapiens
SEQUENCE: 66
SYDIV                                                                    5

SEQ ID NO: 67           moltype = AA  length = 5
FEATURE                 Location/Qualifiers
source                  1..5
                        mol_type = protein
                        organism = Homo sapiens
SEQUENCE: 67
SYDIN                                                                    5

SEQ ID NO: 68           moltype = AA  length = 5
FEATURE                 Location/Qualifiers
source                  1..5
                        mol_type = protein
                        organism = Homo sapiens
SEQUENCE: 68
SHAIH                                                                    5

SEQ ID NO: 69           moltype = AA  length = 5
FEATURE                 Location/Qualifiers
source                  1..5
                        mol_type = protein
                        organism = Homo sapiens
SEQUENCE: 69
SYGIN                                                                    5

SEQ ID NO: 70           moltype = AA  length = 17
FEATURE                 Location/Qualifiers
source                  1..17
                        mol_type = protein
                        organism = Homo sapiens
SEQUENCE: 70
IIDPSDGNTN YAQNFQG                                                       17

SEQ ID NO: 71           moltype = AA  length = 17
FEATURE                 Location/Qualifiers
source                  1..17
                        mol_type = protein
                        organism = Homo sapiens
SEQUENCE: 71
RIDPSSGGTK YAQNFQG                                                       17

SEQ ID NO: 72           moltype = AA  length = 17
FEATURE                 Location/Qualifiers
source                  1..17
                        mol_type = protein
                        organism = Homo sapiens
SEQUENCE: 72
IIDPSGGNTN YAQNFQG                                                       17

SEQ ID NO: 73           moltype = AA  length = 17
FEATURE                 Location/Qualifiers
source                  1..17
                        mol_type = protein
                        organism = Homo sapiens
SEQUENCE: 73
HINPNNGDTN YAQNFQG                                                       17

SEQ ID NO: 74           moltype = AA  length = 17
FEATURE                 Location/Qualifiers
source                  1..17
                        mol_type = protein
                        organism = Homo sapiens
SEQUENCE: 74
WINPNSGGTS YAQKFQG                                                       17

SEQ ID NO: 75           moltype = AA  length = 17
FEATURE                 Location/Qualifiers
source                  1..17
                        mol_type = protein
                        organism = Homo sapiens
SEQUENCE: 75
VINPNDGSTR YAQNFQG                                                       17

SEQ ID NO: 76           moltype = AA  length = 17
```

-continued

```
FEATURE              Location/Qualifiers
source               1..17
                     mol_type = protein
                     organism = Homo sapiens
SEQUENCE: 76
RINPNSGGTN YAQKFQG                                                      17

SEQ ID NO: 77        moltype = AA  length = 17
FEATURE              Location/Qualifiers
source               1..17
                     mol_type = protein
                     organism = Homo sapiens
SEQUENCE: 77
WMNPNSGNTG YAQKFQG                                                      17

SEQ ID NO: 78        moltype = AA  length = 17
FEATURE              Location/Qualifiers
source               1..17
                     mol_type = protein
                     organism = Homo sapiens
SEQUENCE: 78
WISAHNGVTQ YAQKFQG                                                      17

SEQ ID NO: 79        moltype = AA  length = 17
FEATURE              Location/Qualifiers
source               1..17
                     mol_type = protein
                     organism = Homo sapiens
SEQUENCE: 79
IINPSGGSTS YAQKFQG                                                      17

SEQ ID NO: 80        moltype = AA  length = 17
FEATURE              Location/Qualifiers
source               1..17
                     mol_type = protein
                     organism = Homo sapiens
SEQUENCE: 80
WISPYNGNTK YAQKFQG                                                      17

SEQ ID NO: 81        moltype = AA  length = 17
FEATURE              Location/Qualifiers
source               1..17
                     mol_type = protein
                     organism = Homo sapiens
SEQUENCE: 81
IINPNSGDTK YAHQFQG                                                      17

SEQ ID NO: 82        moltype = AA  length = 17
FEATURE              Location/Qualifiers
source               1..17
                     mol_type = protein
                     organism = Homo sapiens
SEQUENCE: 82
IINPSDGDTK YAQEFQG                                                      17

SEQ ID NO: 83        moltype = AA  length = 17
FEATURE              Location/Qualifiers
source               1..17
                     mol_type = protein
                     organism = Homo sapiens
SEQUENCE: 83
WINPNSGDTK YAQKFQG                                                      17

SEQ ID NO: 84        moltype = AA  length = 17
FEATURE              Location/Qualifiers
source               1..17
                     mol_type = protein
                     organism = Homo sapiens
SEQUENCE: 84
VIDPSGGSTS YAQKFQG                                                      17

SEQ ID NO: 85        moltype = AA  length = 17
FEATURE              Location/Qualifiers
source               1..17
                     mol_type = protein
                     organism = Homo sapiens
SEQUENCE: 85
WIDPKSGDTT YAQKFQG                                                      17
```

-continued

```
SEQ ID NO: 86          moltype = AA  length = 17
FEATURE                Location/Qualifiers
source                 1..17
                       mol_type = protein
                       organism = Homo sapiens
SEQUENCE: 86
MINPGAGSST YAQKFQG                                                17

SEQ ID NO: 87          moltype = AA  length = 17
FEATURE                Location/Qualifiers
source                 1..17
                       mol_type = protein
                       organism = Homo sapiens
SEQUENCE: 87
LISGDGGTTY YADSVKG                                                17

SEQ ID NO: 88          moltype = AA  length = 17
FEATURE                Location/Qualifiers
source                 1..17
                       mol_type = protein
                       organism = Homo sapiens
SEQUENCE: 88
SINPNSGDTG YAQKFQG                                                17

SEQ ID NO: 89          moltype = AA  length = 17
FEATURE                Location/Qualifiers
source                 1..17
                       mol_type = protein
                       organism = Homo sapiens
SEQUENCE: 89
RIIPIFGTAN YAQKFQG                                                17

SEQ ID NO: 90          moltype = AA  length = 16
FEATURE                Location/Qualifiers
source                 1..16
                       mol_type = protein
                       organism = Homo sapiens
SEQUENCE: 90
AIGTGGGIYY ADSVKG                                                 16

SEQ ID NO: 91          moltype = AA  length = 17
FEATURE                Location/Qualifiers
source                 1..17
                       mol_type = protein
                       organism = Homo sapiens
SEQUENCE: 91
RINPNSGDTN YAQKFQG                                                17

SEQ ID NO: 92          moltype = AA  length = 17
FEATURE                Location/Qualifiers
source                 1..17
                       mol_type = protein
                       organism = Homo sapiens
SEQUENCE: 92
MINPSDGSTR YAQKFQG                                                17

SEQ ID NO: 93          moltype = AA  length = 17
FEATURE                Location/Qualifiers
source                 1..17
                       mol_type = protein
                       organism = Homo sapiens
SEQUENCE: 93
IINPSDGSTT YAQKFQG                                                17

SEQ ID NO: 94          moltype = AA  length = 17
FEATURE                Location/Qualifiers
source                 1..17
                       mol_type = protein
                       organism = Homo sapiens
SEQUENCE: 94
IINPNGGSPS YAQKFQG                                                17

SEQ ID NO: 95          moltype = AA  length = 17
FEATURE                Location/Qualifiers
source                 1..17
                       mol_type = protein
                       organism = Homo sapiens
SEQUENCE: 95
IINPSDGSTD YAQNFQG                                                17
```

-continued

```
SEQ ID NO: 96           moltype = AA   length = 17
FEATURE                 Location/Qualifiers
source                  1..17
                        mol_type = protein
                        organism = Homo sapiens
SEQUENCE: 96
RINPNTGGTN HAQKFQG                                                17

SEQ ID NO: 97           moltype = AA   length = 17
FEATURE                 Location/Qualifiers
source                  1..17
                        mol_type = protein
                        organism = Homo sapiens
SEQUENCE: 97
AISGSGGSTY YADSVKG                                                17

SEQ ID NO: 98           moltype = AA   length = 17
FEATURE                 Location/Qualifiers
source                  1..17
                        mol_type = protein
                        organism = Homo sapiens
SEQUENCE: 98
WISGYNGDTD YARKLQG                                                17

SEQ ID NO: 99           moltype = AA   length = 17
FEATURE                 Location/Qualifiers
source                  1..17
                        mol_type = protein
                        organism = Homo sapiens
SEQUENCE: 99
WISADNGNTN YEQKVQG                                                17

SEQ ID NO: 100          moltype = AA   length = 17
FEATURE                 Location/Qualifiers
source                  1..17
                        mol_type = protein
                        organism = Homo sapiens
SEQUENCE: 100
WISPNSGATH YAQKFQG                                                17

SEQ ID NO: 101          moltype = AA   length = 17
FEATURE                 Location/Qualifiers
source                  1..17
                        mol_type = protein
                        organism = Homo sapiens
SEQUENCE: 101
WINPNSGNTG YAKKFQG                                                17

SEQ ID NO: 102          moltype = AA   length = 17
FEATURE                 Location/Qualifiers
source                  1..17
                        mol_type = protein
                        organism = Homo sapiens
SEQUENCE: 102
IINPSGGSTR YAQKFQG                                                17

SEQ ID NO: 103          moltype = AA   length = 17
FEATURE                 Location/Qualifiers
source                  1..17
                        mol_type = protein
                        organism = Homo sapiens
SEQUENCE: 103
WINPKSGATN YAQKFQG                                                17

SEQ ID NO: 104          moltype = AA   length = 17
FEATURE                 Location/Qualifiers
source                  1..17
                        mol_type = protein
                        organism = Homo sapiens
SEQUENCE: 104
RISESGDSSF YADSVKG                                                17

SEQ ID NO: 105          moltype = AA   length = 16
FEATURE                 Location/Qualifiers
source                  1..16
                        mol_type = protein
                        organism = Homo sapiens
SEQUENCE: 105
```

-continued

```
AIGTGGGTYY ADSVKG                                                    16

SEQ ID NO: 106        moltype = AA  length = 17
FEATURE               Location/Qualifiers
source                1..17
                      mol_type = protein
                      organism = Homo sapiens SEQUENCE: 106
WMNPSNGDTG YARKFQG                                                   17

SEQ ID NO: 107        moltype = AA  length = 17
FEATURE               Location/Qualifiers
source                1..17
                      mol_type = protein
                      organism = Homo sapiens SEQUENCE: 107
TISPSDGSTT YAQRFQG                                                   17

SEQ ID NO: 108        moltype = AA  length = 17
FEATURE               Location/Qualifiers
source                1..17
                      mol_type = protein
                      organism = Homo sapiens SEQUENCE: 108
IINPSGGSTT YAQKFQG                                                   17

SEQ ID NO: 109        moltype = AA  length = 17
FEATURE               Location/Qualifiers
source                1..17
                      mol_type = protein
                      organism = Homo sapiens SEQUENCE: 109
GFDPEDGETI YAQKFQG                                                   17

SEQ ID NO: 110        moltype = AA  length = 17
FEATURE               Location/Qualifiers
source                1..17
                      mol_type = protein
                      organism = Homo sapiens SEQUENCE: 110
RINPKSGRTY YAQNFQG                                                   17

SEQ ID NO: 111        moltype = AA  length = 17
FEATURE               Location/Qualifiers
source                1..17
                      mol_type = protein
                      organism = Homo sapiens SEQUENCE: 111
VINPGGGSTT YAQTFQG                                                   17

SEQ ID NO: 112        moltype = AA  length = 17
FEATURE               Location/Qualifiers
source                1..17
                      mol_type = protein
                      organism = Homo sapiens SEQUENCE: 112
LMNPKTGDTN YAEKFQG                                                   17

SEQ ID NO: 113        moltype = AA  length = 17
FEATURE               Location/Qualifiers
source                1..17
                      mol_type = protein
                      organism = Homo sapiens SEQUENCE: 113
IIDPSDGYTS YAQKFQG                                                   17

SEQ ID NO: 114        moltype = AA  length = 17
FEATURE               Location/Qualifiers
source                1..17
                      mol_type = protein
                      organism = Homo sapiens SEQUENCE: 114
WINPNSGGTN YAQKFQG                                                   17

SEQ ID NO: 115        moltype = AA  length = 17
FEATURE               Location/Qualifiers
source                1..17
                      mol_type = protein
                      organism = Homo sapiens
```

-continued

```
SEQUENCE: 115
GIMPISGTTI YAQKFQG                                              17

SEQ ID NO: 116           moltype = AA  length = 17
FEATURE                  Location/Qualifiers
source                   1..17
                         mol_type = protein
                         organism = Homo sapiens
SEQUENCE: 116
WMSPTSGDTG YAQKFQG                                              17

SEQ ID NO: 117           moltype = AA  length = 17
FEATURE                  Location/Qualifiers
source                   1..17
                         mol_type = protein
                         organism = Homo sapiens
SEQUENCE: 117
WINPNSGDTS YAQKFQG                                              17

SEQ ID NO: 118           moltype = AA  length = 17
FEATURE                  Location/Qualifiers
source                   1..17
                         mol_type = protein
                         organism = Homo sapiens
SEQUENCE: 118
IIDPSGDITS YAQKFQG                                              17

SEQ ID NO: 119           moltype = AA  length = 17
FEATURE                  Location/Qualifiers
source                   1..17
                         mol_type = protein
                         organism = Homo sapiens
SEQUENCE: 119
IIETSGGSTD YAQKFQG                                              17

SEQ ID NO: 120           moltype = AA  length = 17
FEATURE                  Location/Qualifiers
source                   1..17
                         mol_type = protein
                         organism = Homo sapiens
SEQUENCE: 120
IINPNSGGTN YAQKLQG                                              17

SEQ ID NO: 121           moltype = AA  length = 17
FEATURE                  Location/Qualifiers
source                   1..17
                         mol_type = protein
                         organism = Homo sapiens
SEQUENCE: 121
VISGSGVTTY YADSVKG                                              17

SEQ ID NO: 122           moltype = AA  length = 17
FEATURE                  Location/Qualifiers
source                   1..17
                         mol_type = protein
                         organism = Homo sapiens
SEQUENCE: 122
WINPNSGGTD YAQKFQG                                              17

SEQ ID NO: 123           moltype = AA  length = 17
FEATURE                  Location/Qualifiers
source                   1..17
                         mol_type = protein
                         organism = Homo sapiens
SEQUENCE: 123
MINPSGGSTT YAQKFQG                                              17

SEQ ID NO: 124           moltype = AA  length = 17
FEATURE                  Location/Qualifiers
source                   1..17
                         mol_type = protein
                         organism = Homo sapiens
SEQUENCE: 124
WINPDSGGTN YEQKFQG                                              17

SEQ ID NO: 125           moltype = AA  length = 17
FEATURE                  Location/Qualifiers
source                   1..17
                         mol_type = protein
```

-continued

```
                                organism = Homo sapiens
SEQUENCE: 125
WINPNSGGTN SAQKFQG                                                        17

SEQ ID NO: 126          moltype = AA  length = 17
FEATURE                 Location/Qualifiers
source                  1..17
                        mol_type = protein
                        organism = Homo sapiens
SEQUENCE: 126
IINPSGGSAS YAQKFQG                                                        17

SEQ ID NO: 127          moltype = AA  length = 17
FEATURE                 Location/Qualifiers
source                  1..17
                        mol_type = protein
                        organism = Homo sapiens
SEQUENCE: 127
IISPSDGSTS YAQKLQG                                                        17

SEQ ID NO: 128          moltype = AA  length = 17
FEATURE                 Location/Qualifiers
source                  1..17
                        mol_type = protein
                        organism = Homo sapiens
SEQUENCE: 128
WINPISGGTH YAQKFQG                                                        17

SEQ ID NO: 129          moltype = AA  length = 17
FEATURE                 Location/Qualifiers
source                  1..17
                        mol_type = protein
                        organism = Homo sapiens
SEQUENCE: 129
WISADNGDTS FAQKFQG                                                        17

SEQ ID NO: 130          moltype = AA  length = 17
FEATURE                 Location/Qualifiers
source                  1..17
                        mol_type = protein
                        organism = Homo sapiens
SEQUENCE: 130
GISPIYGTPA YAQKFQG                                                        17

SEQ ID NO: 131          moltype = AA  length = 17
FEATURE                 Location/Qualifiers
source                  1..17
                        mol_type = protein
                        organism = Homo sapiens
SEQUENCE: 131
IINPSDGDTS YAQKFQG                                                        17

SEQ ID NO: 132          moltype = AA  length = 17
FEATURE                 Location/Qualifiers
source                  1..17
                        mol_type = protein
                        organism = Homo sapiens
SEQUENCE: 132
TINPSGGTTT YAQKFQG                                                        17

SEQ ID NO: 133          moltype = AA  length = 17
FEATURE                 Location/Qualifiers
source                  1..17
                        mol_type = protein
                        organism = Homo sapiens
SEQUENCE: 133
WMNPKSGNTG YAQKFQG                                                        17

SEQ ID NO: 134          moltype = AA  length = 17
FEATURE                 Location/Qualifiers
source                  1..17
                        mol_type = protein
                        organism = Homo sapiens
SEQUENCE: 134
IINPGGGNAR HTQKFQG                                                        17

SEQ ID NO: 135          moltype = AA  length = 17
FEATURE                 Location/Qualifiers
source                  1..17
```

-continued

```
                                mol_type = protein
                                organism = Homo sapiens
SEQUENCE: 135
GFDPEDGETV YAQNFQG                                                         17

SEQ ID NO: 136        moltype = AA  length = 17
FEATURE               Location/Qualifiers
source                1..17
                      mol_type = protein
                      organism = Homo sapiens
SEQUENCE: 136
GITPVFGIAN YAQKFQG                                                         17

SEQ ID NO: 137        moltype = AA  length = 17
FEATURE               Location/Qualifiers
source                1..17
                      mol_type = protein
                      organism = Homo sapiens
SEQUENCE: 137
IINPRGGSTN YAQKFQG                                                         17

SEQ ID NO: 138        moltype = AA  length = 17
FEATURE               Location/Qualifiers
source                1..17
                      mol_type = protein
                      organism = Homo sapiens
SEQUENCE: 138
WMNPNNGDTD YAQKFQG                                                         17

SEQ ID NO: 139        moltype = AA  length = 17
FEATURE               Location/Qualifiers
source                1..17
                      mol_type = protein
                      organism = Homo sapiens
SEQUENCE: 139
IINPSGGGTS YAQKFQG                                                         17

SEQ ID NO: 140        moltype = AA  length = 17
FEATURE               Location/Qualifiers
source                1..17
                      mol_type = protein
                      organism = Homo sapiens
SEQUENCE: 140
LINPGSGNTN YAQKFQG                                                         17

SEQ ID NO: 141        moltype = AA  length = 17
FEATURE               Location/Qualifiers
source                1..17
                      mol_type = protein
                      organism = Homo sapiens
SEQUENCE: 141
GIIPIFGTPN YAQKFQG                                                         17

SEQ ID NO: 142        moltype = AA  length = 17
FEATURE               Location/Qualifiers
source                1..17
                      mol_type = protein
                      organism = Homo sapiens
SEQUENCE: 142
TINGDGDDTD YADSVKG                                                         17

SEQ ID NO: 143        moltype = AA  length = 17
FEATURE               Location/Qualifiers
source                1..17
                      mol_type = protein
                      organism = Homo sapiens
SEQUENCE: 143
QIDPNSGDTI YPQKFQG                                                         17

SEQ ID NO: 144        moltype = AA  length = 17
FEATURE               Location/Qualifiers
source                1..17
                      mol_type = protein
                      organism = Homo sapiens
SEQUENCE: 144
IVNPSDGNTN YAQKFQG                                                         17

SEQ ID NO: 145        moltype = AA  length = 17
FEATURE               Location/Qualifiers
```

-continued

```
source                     1..17
                           mol_type = protein
                           organism = Homo sapiens
SEQUENCE: 145
WINTYNGNTY YAQKLQG                                              17

SEQ ID NO: 146             moltype = AA   length = 17
FEATURE                    Location/Qualifiers
source                     1..17
                           mol_type = protein
                           organism = Homo sapiens
SEQUENCE: 146
IINPSDGITD YAQRFQG                                              17

SEQ ID NO: 147             moltype = AA   length = 17
FEATURE                    Location/Qualifiers
source                     1..17
                           mol_type = protein
                           organism = Homo sapiens
SEQUENCE: 147
IINPRDGDTV YAQKFQG                                              17

SEQ ID NO: 148             moltype = AA   length = 13
FEATURE                    Location/Qualifiers
source                     1..13
                           mol_type = protein
                           organism = Homo sapiens
SEQUENCE: 148
ERAAAGYYYY MDV                                                  13

SEQ ID NO: 149             moltype = AA   length = 13
FEATURE                    Location/Qualifiers
source                     1..13
                           mol_type = protein
                           organism = Homo sapiens
SEQUENCE: 149
EHAAGTYYYY MDV                                                  13

SEQ ID NO: 150             moltype = AA   length = 10
FEATURE                    Location/Qualifiers
source                     1..10
                           mol_type = protein
                           organism = Homo sapiens
SEQUENCE: 150
EGDYYYGMDA                                                      10

SEQ ID NO: 151             moltype = AA   length = 8
FEATURE                    Location/Qualifiers
source                     1..8
                           mol_type = protein
                           organism = Homo sapiens
SEQUENCE: 151
ERGGMPDY                                                        8

SEQ ID NO: 152             moltype = AA   length = 7
FEATURE                    Location/Qualifiers
source                     1..7
                           mol_type = protein
                           organism = Homo sapiens
SEQUENCE: 152
GHGIPKY                                                         7

SEQ ID NO: 153             moltype = AA   length = 8
FEATURE                    Location/Qualifiers
source                     1..8
                           mol_type = protein
                           organism = Homo sapiens
SEQUENCE: 153
VRSGSPQH                                                        8

SEQ ID NO: 154             moltype = AA   length = 11
FEATURE                    Location/Qualifiers
source                     1..11
                           mol_type = protein
                           organism = Homo sapiens
SEQUENCE: 154
GGPWIVDAFD I                                                    11

SEQ ID NO: 155             moltype = AA   length = 13
```

-continued

| FEATURE | Location/Qualifiers |
|---|---|
| source | 1..13 |
| | mol_type = protein |
| | organism = Homo sapiens |

SEQUENCE: 155
EATWGPYYYY MDV                                                    13

| SEQ ID NO: 156 | moltype = AA  length = 7 |
|---|---|
| FEATURE | Location/Qualifiers |
| source | 1..7 |
| | mol_type = protein |
| | organism = Homo sapiens |

SEQUENCE: 156
NKDGLQH                                                           7

| SEQ ID NO: 157 | moltype = AA  length = 13 |
|---|---|
| FEATURE | Location/Qualifiers |
| source | 1..13 |
| | mol_type = protein |
| | organism = Homo sapiens |

SEQUENCE: 157
DAKRVGYYYY MDV                                                    13

| SEQ ID NO: 158 | moltype = AA  length = 8 |
|---|---|
| FEATURE | Location/Qualifiers |
| source | 1..8 |
| | mol_type = protein |
| | organism = Homo sapiens |

SEQUENCE: 158
LVGGSPDY                                                          8

| SEQ ID NO: 159 | moltype = AA  length = 6 |
|---|---|
| FEATURE | Location/Qualifiers |
| source | 1..6 |
| | mol_type = protein |
| | organism = Homo sapiens |

SEQUENCE: 159
GAMVDY                                                            6

| SEQ ID NO: 160 | moltype = AA  length = 13 |
|---|---|
| FEATURE | Location/Qualifiers |
| source | 1..13 |
| | mol_type = protein |
| | organism = Homo sapiens |

SEQUENCE: 160
GNYVGSYYYG MDV                                                    13

| SEQ ID NO: 161 | moltype = AA  length = 10 |
|---|---|
| FEATURE | Location/Qualifiers |
| source | 1..10 |
| | mol_type = protein |
| | organism = Homo sapiens |

SEQUENCE: 161
DSRGDWYFDL                                                        10

| SEQ ID NO: 162 | moltype = AA  length = 9 |
|---|---|
| FEATURE | Location/Qualifiers |
| source | 1..9 |
| | mol_type = protein |
| | organism = Homo sapiens |

SEQUENCE: 162
HGGRGLADY                                                         9

| SEQ ID NO: 163 | moltype = AA  length = 13 |
|---|---|
| FEATURE | Location/Qualifiers |
| source | 1..13 |
| | mol_type = protein |
| | organism = Homo sapiens |

SEQUENCE: 163
LKELSSILDA FDI                                                    13

| SEQ ID NO: 164 | moltype = AA  length = 13 |
|---|---|
| FEATURE | Location/Qualifiers |
| source | 1..13 |
| | mol_type = protein |
| | organism = Homo sapiens |

SEQUENCE: 164
ERFGTGYYYY MDV                                                    13

-continued

```
SEQ ID NO: 165           moltype = AA  length = 12
FEATURE                  Location/Qualifiers
source                   1..12
                         mol_type = protein
                         organism = Homo sapiens SEQUENCE: 165
VIGEMVDDAF DL                                                      12

SEQ ID NO: 166           moltype = AA  length = 13
FEATURE                  Location/Qualifiers
source                   1..13
                         mol_type = protein
                         organism = Homo sapiens SEQUENCE: 166
ERLFGTYYYY MDV                                                     13

SEQ ID NO: 167           moltype = AA  length = 8
FEATURE                  Location/Qualifiers
source                   1..8
                         mol_type = protein
                         organism = Homo sapiens SEQUENCE: 167
ADGELTDY                                                           8

SEQ ID NO: 168           moltype = AA  length = 13
FEATURE                  Location/Qualifiers
source                   1..13
                         mol_type = protein
                         organism = Homo sapiens SEQUENCE: 168
HHLPAHYYYY MDV                                                     13

SEQ ID NO: 169           moltype = AA  length = 13
FEATURE                  Location/Qualifiers
source                   1..13
                         mol_type = protein
                         organism = Homo sapiens SEQUENCE: 169
DVPAGRYYYY MDV                                                     13

SEQ ID NO: 170           moltype = AA  length = 13
FEATURE                  Location/Qualifiers
source                   1..13
                         mol_type = protein
                         organism = Homo sapiens SEQUENCE: 170
DRGVGRYYYY MDV                                                     13

SEQ ID NO: 171           moltype = AA  length = 13
FEATURE                  Location/Qualifiers
source                   1..13
                         mol_type = protein
                         organism = Homo sapiens SEQUENCE: 171
DSRYGRYYYY MDV                                                     13

SEQ ID NO: 172           moltype = AA  length = 13
FEATURE                  Location/Qualifiers
source                   1..13
                         mol_type = protein
                         organism = Homo sapiens SEQUENCE: 172
EIVVGPYYYY MDV                                                     13

SEQ ID NO: 173           moltype = AA  length = 13
FEATURE                  Location/Qualifiers
source                   1..13
                         mol_type = protein
                         organism = Homo sapiens SEQUENCE: 173
GMVRGPYYYY MDV                                                     13

SEQ ID NO: 174           moltype = AA  length = 13
FEATURE                  Location/Qualifiers
source                   1..13
                         mol_type = protein
                         organism = Homo sapiens SEQUENCE: 174
EGVTGPYYYY MDV                                                     13
```

-continued

```
SEQ ID NO: 175          moltype = AA   length = 16
FEATURE                 Location/Qualifiers
source                  1..16
                        mol_type = protein
                        organism = Homo sapiens SEQUENCE: 175
DAAAGTRYYY YYGMDV                                                   16

SEQ ID NO: 176          moltype = AA   length = 13
FEATURE                 Location/Qualifiers
source                  1..13
                        mol_type = protein
                        organism = Homo sapiens SEQUENCE: 176
ELYSSTYYYY MDV                                                      13

SEQ ID NO: 177          moltype = AA   length = 13
FEATURE                 Location/Qualifiers
source                  1..13
                        mol_type = protein
                        organism = Homo sapiens SEQUENCE: 177
ALYSGPYYYY MDV                                                      13

SEQ ID NO: 178          moltype = AA   length = 13
FEATURE                 Location/Qualifiers
source                  1..13
                        mol_type = protein
                        organism = Homo sapiens SEQUENCE: 178
DSLVGRYYYY MDV                                                      13

SEQ ID NO: 179          moltype = AA   length = 6
FEATURE                 Location/Qualifiers
source                  1..6
                        mol_type = protein
                        organism = Homo sapiens SEQUENCE: 179
RSELDY                                                              6

SEQ ID NO: 180          moltype = AA   length = 6
FEATURE                 Location/Qualifiers
source                  1..6
                        mol_type = protein
                        organism = Homo sapiens SEQUENCE: 180
GDDNDY                                                              6

SEQ ID NO: 181          moltype = AA   length = 6
FEATURE                 Location/Qualifiers
source                  1..6
                        mol_type = protein
                        organism = Homo sapiens SEQUENCE: 181
GEEVDY                                                              6

SEQ ID NO: 182          moltype = AA   length = 7
FEATURE                 Location/Qualifiers
source                  1..7
                        mol_type = protein
                        organism = Homo sapiens SEQUENCE: 182
GRRVPDY                                                             7

SEQ ID NO: 183          moltype = AA   length = 7
FEATURE                 Location/Qualifiers
source                  1..7
                        mol_type = protein
                        organism = Homo sapiens SEQUENCE: 183
GKVTTDY                                                             7

SEQ ID NO: 184          moltype = AA   length = 7
FEATURE                 Location/Qualifiers
source                  1..7
                        mol_type = protein
                        organism = Homo sapiens

SEQUENCE: 184
```

-continued

```
GRELIEY                                                              7

SEQ ID NO: 185            moltype = AA   length = 7
FEATURE                   Location/Qualifiers
source                    1..7
                          mol_type = protein
                          organism = Homo sapiens SEQUENCE: 185
VYDFPDV                                                              7

SEQ ID NO: 186            moltype = AA   length = 8
FEATURE                   Location/Qualifiers
source                    1..8
                          mol_type = protein
                          organism = Homo sapiens SEQUENCE: 186
STYSHIDY                                                             8

SEQ ID NO: 187            moltype = AA   length = 8
FEATURE                   Location/Qualifiers
source                    1..8
                          mol_type = protein
                          organism = Homo sapiens SEQUENCE: 187
EDSSGFDY                                                             8

SEQ ID NO: 188            moltype = AA   length = 8
FEATURE                   Location/Qualifiers
source                    1..8
                          mol_type = protein
                          organism = Homo sapiens SEQUENCE: 188
DQGGGFDY                                                             8

SEQ ID NO: 189            moltype = AA   length = 8
FEATURE                   Location/Qualifiers
source                    1..8
                          mol_type = protein
                          organism = Homo sapiens SEQUENCE: 189
DQGWGMDV                                                             8

SEQ ID NO: 190            moltype = AA   length = 8
FEATURE                   Location/Qualifiers
source                    1..8
                          mol_type = protein
                          organism = Homo sapiens SEQUENCE: 190
LTEGIPDY                                                             8

SEQ ID NO: 191            moltype = AA   length = 8
FEATURE                   Location/Qualifiers
source                    1..8
                          mol_type = protein
                          organism = Homo sapiens SEQUENCE: 191
DRYGPFDY                                                             8

SEQ ID NO: 192            moltype = AA   length = 9
FEATURE                   Location/Qualifiers
source                    1..9
                          mol_type = protein
                          organism = Homo sapiens SEQUENCE: 192
LVAGGAPDY                                                            9

SEQ ID NO: 193            moltype = AA   length = 9
FEATURE                   Location/Qualifiers
source                    1..9
                          mol_type = protein
                          organism = Homo sapiens SEQUENCE: 193
DGFTGDIAY                                                            9

SEQ ID NO: 194            moltype = AA   length = 9
FEATURE                   Location/Qualifiers
source                    1..9
                          mol_type = protein
                          organism = Homo sapiens
```

-continued

```
SEQUENCE: 194
VDDSSSPDY                                                                          9

SEQ ID NO: 195            moltype = AA   length = 9
FEATURE                   Location/Qualifiers
source                    1..9
                          mol_type = protein
                          organism = Homo sapiens
SEQUENCE: 195
GPDGTEVDY                                                                          9

SEQ ID NO: 196            moltype = AA   length = 9
FEATURE                   Location/Qualifiers
source                    1..9
                          mol_type = protein
                          organism = Homo sapiens
SEQUENCE: 196
SESGSDLDY                                                                          9

SEQ ID NO: 197            moltype = AA   length = 10
FEATURE                   Location/Qualifiers
source                    1..10
                          mol_type = protein
                          organism = Homo sapiens
SEQUENCE: 197
EVEIEGYMDV                                                                         10

SEQ ID NO: 198            moltype = AA   length = 10
FEATURE                   Location/Qualifiers
source                    1..10
                          mol_type = protein
                          organism = Homo sapiens
SEQUENCE: 198
DLDDDWYMDV                                                                         10

SEQ ID NO: 199            moltype = AA   length = 10
FEATURE                   Location/Qualifiers
source                    1..10
                          mol_type = protein
                          organism = Homo sapiens
SEQUENCE: 199
DSTTWDAFDI                                                                         10

SEQ ID NO: 200            moltype = AA   length = 10
FEATURE                   Location/Qualifiers
source                    1..10
                          mol_type = protein
                          organism = Homo sapiens
SEQUENCE: 200
VLVGSGSPDY                                                                         10

SEQ ID NO: 201            moltype = AA   length = 10
FEATURE                   Location/Qualifiers
source                    1..10
                          mol_type = protein
                          organism = Homo sapiens
SEQUENCE: 201
EAAAGLDFQH                                                                         10

SEQ ID NO: 202            moltype = AA   length = 8
FEATURE                   Location/Qualifiers
source                    1..8
                          mol_type = protein
                          organism = Homo sapiens
SEQUENCE: 202
ANSWDADY                                                                           8

SEQ ID NO: 203            moltype = AA   length = 11
FEATURE                   Location/Qualifiers
source                    1..11
                          mol_type = protein
                          organism = Homo sapiens
SEQUENCE: 203
EHSSSWYTFD Y                                                                       11

SEQ ID NO: 204            moltype = AA   length = 11
FEATURE                   Location/Qualifiers
source                    1..11
                          mol_type = protein
```

-continued

```
                         organism = Homo sapiens
SEQUENCE: 204
DDDSSGYYLD Y                                                            11

SEQ ID NO: 205           moltype = AA  length = 14
FEATURE                  Location/Qualifiers
source                   1..14
                         mol_type = protein
                         organism = Homo sapiens
SEQUENCE: 205
ASGDYMDLID YMDY                                                         14

SEQ ID NO: 206           moltype = AA  length = 11
FEATURE                  Location/Qualifiers
source                   1..11
                         mol_type = protein
                         organism = Homo sapiens
SEQUENCE: 206
VGSSGYLAPT H                                                            11

SEQ ID NO: 207           moltype = AA  length = 11
FEATURE                  Location/Qualifiers
source                   1..11
                         mol_type = protein
                         organism = Homo sapiens
SEQUENCE: 207
VRGDGYNLGD Y                                                            11

SEQ ID NO: 208           moltype = AA  length = 11
FEATURE                  Location/Qualifiers
source                   1..11
                         mol_type = protein
                         organism = Homo sapiens
SEQUENCE: 208
DVDTAMGAGD Y                                                            11

SEQ ID NO: 209           moltype = AA  length = 12
FEATURE                  Location/Qualifiers
source                   1..12
                         mol_type = protein
                         organism = Homo sapiens
SEQUENCE: 209
VARWGYGDYP DY                                                           12

SEQ ID NO: 210           moltype = AA  length = 12
FEATURE                  Location/Qualifiers
source                   1..12
                         mol_type = protein
                         organism = Homo sapiens
SEQUENCE: 210
DRNGDYYYGM DV                                                           12

SEQ ID NO: 211           moltype = AA  length = 12
FEATURE                  Location/Qualifiers
source                   1..12
                         mol_type = protein
                         organism = Homo sapiens
SEQUENCE: 211
EGLGSSWYVL DY                                                           12

SEQ ID NO: 212           moltype = AA  length = 12
FEATURE                  Location/Qualifiers
source                   1..12
                         mol_type = protein
                         organism = Homo sapiens
SEQUENCE: 212
DGSHYGYYGM DV                                                           12

SEQ ID NO: 213           moltype = AA  length = 12
FEATURE                  Location/Qualifiers
source                   1..12
                         mol_type = protein
                         organism = Homo sapiens
SEQUENCE: 213
PGPEGYYYGM DV                                                           12

SEQ ID NO: 214           moltype = AA  length = 12
FEATURE                  Location/Qualifiers
source                   1..12
```

-continued

```
                           mol_type = protein
                           organism = Homo sapiens
SEQUENCE: 214
YHWDYGDYRF DY                                                        12

SEQ ID NO: 215             moltype = AA  length = 12
FEATURE                    Location/Qualifiers
source                     1..12
                           mol_type = protein
                           organism = Homo sapiens
SEQUENCE: 215
VEIDYGDSPP DY                                                        12

SEQ ID NO: 216             moltype = AA  length = 12
FEATURE                    Location/Qualifiers
source                     1..12
                           mol_type = protein
                           organism = Homo sapiens
SEQUENCE: 216
GAEWELRYAF DI                                                        12

SEQ ID NO: 217             moltype = AA  length = 13
FEATURE                    Location/Qualifiers
source                     1..13
                           mol_type = protein
                           organism = Homo sapiens
SEQUENCE: 217
ETYYGLYYYG MDV                                                       13

SEQ ID NO: 218             moltype = AA  length = 13
FEATURE                    Location/Qualifiers
source                     1..13
                           mol_type = protein
                           organism = Homo sapiens
SEQUENCE: 218
APSLRGYSYG PDY                                                       13

SEQ ID NO: 219             moltype = AA  length = 13
FEATURE                    Location/Qualifiers
source                     1..13
                           mol_type = protein
                           organism = Homo sapiens
SEQUENCE: 219
DRQERYYYYY MDV                                                       13

SEQ ID NO: 220             moltype = AA  length = 13
FEATURE                    Location/Qualifiers
source                     1..13
                           mol_type = protein
                           organism = Homo sapiens
SEQUENCE: 220
DRSYGDYYYG MDV                                                       13

SEQ ID NO: 221             moltype = AA  length = 13
FEATURE                    Location/Qualifiers
source                     1..13
                           mol_type = protein
                           organism = Homo sapiens
SEQUENCE: 221
EVFSENYYYY MDV                                                       13

SEQ ID NO: 222             moltype = AA  length = 13
FEATURE                    Location/Qualifiers
source                     1..13
                           mol_type = protein
                           organism = Homo sapiens
SEQUENCE: 222
EWDYTHYYYG MDV                                                       13

SEQ ID NO: 223             moltype = AA  length = 13
FEATURE                    Location/Qualifiers
source                     1..13
                           mol_type = protein
                           organism = Homo sapiens
SEQUENCE: 223
GDSSGYYQYY FDY                                                       13

SEQ ID NO: 224             moltype = AA  length = 13
FEATURE                    Location/Qualifiers
```

-continued

```
source                   1..13
                         mol_type = protein
                         organism = Homo sapiens
SEQUENCE: 224
GSWDSSSWYI PEY                                                13

SEQ ID NO: 225           moltype = AA  length = 13
FEATURE                  Location/Qualifiers
source                   1..13
                         mol_type = protein
                         organism = Homo sapiens
SEQUENCE: 225
LVWGGAYYYY MDV                                                13

SEQ ID NO: 226           moltype = AA  length = 13
FEATURE                  Location/Qualifiers
source                   1..13
                         mol_type = protein
                         organism = Homo sapiens
SEQUENCE: 226
PVFSGSYYWY FDP                                                13

SEQ ID NO: 227           moltype = AA  length = 14
FEATURE                  Location/Qualifiers
source                   1..14
                         mol_type = protein
                         organism = Homo sapiens
SEQUENCE: 227
DQAVAGPYYY GMDV                                               14

SEQ ID NO: 228           moltype = AA  length = 14
FEATURE                  Location/Qualifiers
source                   1..14
                         mol_type = protein
                         organism = Homo sapiens
SEQUENCE: 228
DRWLAGPYYY GMDV                                               14

SEQ ID NO: 229           moltype = AA  length = 14
FEATURE                  Location/Qualifiers
source                   1..14
                         mol_type = protein
                         organism = Homo sapiens
SEQUENCE: 229
VMGPVDYYYY GMDV                                               14

SEQ ID NO: 230           moltype = AA  length = 14
FEATURE                  Location/Qualifiers
source                   1..14
                         mol_type = protein
                         organism = Homo sapiens
SEQUENCE: 230
DLGPFGSYYY YMDV                                               14

SEQ ID NO: 231           moltype = AA  length = 14
FEATURE                  Location/Qualifiers
source                   1..14
                         mol_type = protein
                         organism = Homo sapiens
SEQUENCE: 231
EGVVVPPYYY YMDV                                               14

SEQ ID NO: 232           moltype = AA  length = 14
FEATURE                  Location/Qualifiers
source                   1..14
                         mol_type = protein
                         organism = Homo sapiens
SEQUENCE: 232
SSGWSRYYYY YMDV                                               14

SEQ ID NO: 233           moltype = AA  length = 14
FEATURE                  Location/Qualifiers
source                   1..14
                         mol_type = protein
                         organism = Homo sapiens
SEQUENCE: 233
DNGMTTGYYY YMDV                                               14

SEQ ID NO: 234           moltype = AA  length = 14
```

-continued

```
FEATURE              Location/Qualifiers
source               1..14
                     mol_type = protein
                     organism = Homo sapiens SEQUENCE: 234
DRAMVTGYYY GMDV                                                        14

SEQ ID NO: 235       moltype = AA  length = 15
FEATURE              Location/Qualifiers
source               1..15
                     mol_type = protein
                     organism = Homo sapiens SEQUENCE: 235
DRGYGDRGYY YGMDV                                                       15

SEQ ID NO: 236       moltype = AA  length = 15
FEATURE              Location/Qualifiers
source               1..15
                     mol_type = protein
                     organism = Homo sapiens SEQUENCE: 236
SPKATADYYY YYMDV                                                       15

SEQ ID NO: 237       moltype = AA  length = 15
FEATURE              Location/Qualifiers
source               1..15
                     mol_type = protein
                     organism = Homo sapiens SEQUENCE: 237
STVTPSYYYY YGMDV                                                       15

SEQ ID NO: 238       moltype = AA  length = 16
FEATURE              Location/Qualifiers
source               1..16
                     mol_type = protein
                     organism = Homo sapiens SEQUENCE: 238
EPVAGTGYYY YYGMDV                                                      16

SEQ ID NO: 239       moltype = AA  length = 17
FEATURE              Location/Qualifiers
source               1..17
                     mol_type = protein
                     organism = Homo sapiens SEQUENCE: 239
DNLAGFWSDY YYYGMDV                                                     17

SEQ ID NO: 240       moltype = AA  length = 11
FEATURE              Location/Qualifiers
source               1..11
                     mol_type = protein
                     organism = Homo sapiens SEQUENCE: 240
RASQSISSYL N                                                           11

SEQ ID NO: 241       moltype = AA  length = 11
FEATURE              Location/Qualifiers
source               1..11
                     mol_type = protein
                     organism = Homo sapiens SEQUENCE: 241
QASQDISNYL N                                                           11

SEQ ID NO: 242       moltype = AA  length = 16
FEATURE              Location/Qualifiers
source               1..16
                     mol_type = protein
                     organism = Homo sapiens SEQUENCE: 242
RSSQSLLHSN GYNYLD                                                      16

SEQ ID NO: 243       moltype = AA  length = 11
FEATURE              Location/Qualifiers
source               1..11
                     mol_type = protein
                     organism = Homo sapiens SEQUENCE: 243
RASQSISRNL N                                                           11
```

```
SEQ ID NO: 244          moltype = AA  length = 12
FEATURE                 Location/Qualifiers
source                  1..12
                        mol_type = protein
                        organism = Homo sapiens
SEQUENCE: 244
RASQSVSASD LA                                                    12

SEQ ID NO: 245          moltype = AA  length = 11
FEATURE                 Location/Qualifiers
source                  1..11
                        mol_type = protein
                        organism = Homo sapiens
SEQUENCE: 245
QASQDIGNYL N                                                     11

SEQ ID NO: 246          moltype = AA  length = 11
FEATURE                 Location/Qualifiers
source                  1..11
                        mol_type = protein
                        organism = Homo sapiens
SEQUENCE: 246
RASQSISTHL A                                                     11

SEQ ID NO: 247          moltype = AA  length = 11
FEATURE                 Location/Qualifiers
source                  1..11
                        mol_type = protein
                        organism = Homo sapiens
SEQUENCE: 247
RASQTISNYL N                                                     11

SEQ ID NO: 248          moltype = AA  length = 11
FEATURE                 Location/Qualifiers
source                  1..11
                        mol_type = protein
                        organism = Homo sapiens
SEQUENCE: 248
RASQGIRNDL G                                                     11

SEQ ID NO: 249          moltype = AA  length = 11
FEATURE                 Location/Qualifiers
source                  1..11
                        mol_type = protein
                        organism = Homo sapiens
SEQUENCE: 249
RASQSISNYL N                                                     11

SEQ ID NO: 250          moltype = AA  length = 11
FEATURE                 Location/Qualifiers
source                  1..11
                        mol_type = protein
                        organism = Homo sapiens
SEQUENCE: 250
RASQGISDSL A                                                     11

SEQ ID NO: 251          moltype = AA  length = 11
FEATURE                 Location/Qualifiers
source                  1..11
                        mol_type = protein
                        organism = Homo sapiens
SEQUENCE: 251
QASQDIHNYL N                                                     11

SEQ ID NO: 252          moltype = AA  length = 11
FEATURE                 Location/Qualifiers
source                  1..11
                        mol_type = protein
                        organism = Homo sapiens
SEQUENCE: 252
RASQSISDWL A                                                     11

SEQ ID NO: 253          moltype = AA  length = 11
FEATURE                 Location/Qualifiers
source                  1..11
                        mol_type = protein
                        organism = Homo sapiens
SEQUENCE: 253
RASQSISTWL A                                                     11
```

```
SEQ ID NO: 254                 moltype = AA  length = 11
FEATURE                        Location/Qualifiers
source                         1..11
                               mol_type = protein
                               organism = Homo sapiens SEQUENCE: 254
RASQSINRFL N                                                      11

SEQ ID NO: 255                 moltype = AA  length = 11
FEATURE                        Location/Qualifiers
source                         1..11
                               mol_type = protein
                               organism = Homo sapiens SEQUENCE: 255
RASQSVSTYL N                                                      11

SEQ ID NO: 256                 moltype = AA  length = 11
FEATURE                        Location/Qualifiers
source                         1..11
                               mol_type = protein
                               organism = Homo sapiens SEQUENCE: 256
QASQDIAKYL N                                                      11

SEQ ID NO: 257                 moltype = AA  length = 11
FEATURE                        Location/Qualifiers
source                         1..11
                               mol_type = protein
                               organism = Homo sapiens SEQUENCE: 257
QASQGITNYL N                                                      11

SEQ ID NO: 258                 moltype = AA  length = 11
FEATURE                        Location/Qualifiers
source                         1..11
                               mol_type = protein
                               organism = Homo sapiens SEQUENCE: 258
QANQDISNFL E                                                      11

SEQ ID NO: 259                 moltype = AA  length = 11
FEATURE                        Location/Qualifiers
source                         1..11
                               mol_type = protein
                               organism = Homo sapiens SEQUENCE: 259
RASQGISNNL N                                                      11

SEQ ID NO: 260                 moltype = AA  length = 11
FEATURE                        Location/Qualifiers
source                         1..11
                               mol_type = protein
                               organism = Homo sapiens SEQUENCE: 260
RASQSISRSL V                                                      11

SEQ ID NO: 261                 moltype = AA  length = 11
FEATURE                        Location/Qualifiers
source                         1..11
                               mol_type = protein
                               organism = Homo sapiens SEQUENCE: 261
QASHDISKSL N                                                      11

SEQ ID NO: 262                 moltype = AA  length = 11
FEATURE                        Location/Qualifiers
source                         1..11
                               mol_type = protein
                               organism = Homo sapiens SEQUENCE: 262
RASQDIGAYL A                                                      11

SEQ ID NO: 263                 moltype = AA  length = 11
FEATURE                        Location/Qualifiers
source                         1..11
                               mol_type = protein
                               organism = Homo sapiens

SEQUENCE: 263
```

-continued

```
RASQSISSYL A                                                            11

SEQ ID NO: 264          moltype = AA  length = 11
FEATURE                 Location/Qualifiers
source                  1..11
                        mol_type = protein
                        organism = Homo sapiens SEQUENCE: 264
RASQGIRSYL A                                                            11

SEQ ID NO: 265          moltype = AA  length = 11
FEATURE                 Location/Qualifiers
source                  1..11
                        mol_type = protein
                        organism = Homo sapiens SEQUENCE: 265
RASQNIGTWL A                                                            11

SEQ ID NO: 266          moltype = AA  length = 11
FEATURE                 Location/Qualifiers
source                  1..11
                        mol_type = protein
                        organism = Homo sapiens SEQUENCE: 266
RASQTISYYL N                                                            11

SEQ ID NO: 267          moltype = AA  length = 11
FEATURE                 Location/Qualifiers
source                  1..11
                        mol_type = protein
                        organism = Homo sapiens SEQUENCE: 267
RASQNINNYL N                                                            11

SEQ ID NO: 268          moltype = AA  length = 11
FEATURE                 Location/Qualifiers
source                  1..11
                        mol_type = protein
                        organism = Homo sapiens SEQUENCE: 268
RASQTISTYL N                                                            11

SEQ ID NO: 269          moltype = AA  length = 11
FEATURE                 Location/Qualifiers
source                  1..11
                        mol_type = protein
                        organism = Homo sapiens SEQUENCE: 269
RASRGIGNDL A                                                            11

SEQ ID NO: 270          moltype = AA  length = 11
FEATURE                 Location/Qualifiers
source                  1..11
                        mol_type = protein
                        organism = Homo sapiens SEQUENCE: 270
RASQTIGNYV N                                                            11

SEQ ID NO: 271          moltype = AA  length = 11
FEATURE                 Location/Qualifiers
source                  1..11
                        mol_type = protein
                        organism = Homo sapiens SEQUENCE: 271
RASQFIGSWL A                                                            11

SEQ ID NO: 272          moltype = AA  length = 11
FEATURE                 Location/Qualifiers
source                  1..11
                        mol_type = protein
                        organism = Homo sapiens SEQUENCE: 272
RASQSISSWM A                                                            11

SEQ ID NO: 273          moltype = AA  length = 17
FEATURE                 Location/Qualifiers
source                  1..17
                        mol_type = protein
                        organism = Homo sapiens
```

-continued

```
SEQUENCE: 273
KSSQSVLYSS NNKNYLA                                                        17

SEQ ID NO: 274        moltype = AA   length = 11
FEATURE               Location/Qualifiers
source                1..11
                      mol_type = protein
                      organism = Homo sapiens
SEQUENCE: 274
RVSQGISSYL N                                                              11

SEQ ID NO: 275        moltype = AA   length = 11
FEATURE               Location/Qualifiers
source                1..11
                      mol_type = protein
                      organism = Homo sapiens
SEQUENCE: 275
RASQGISNYL A                                                              11

SEQ ID NO: 276        moltype = AA   length = 11
FEATURE               Location/Qualifiers
source                1..11
                      mol_type = protein
                      organism = Homo sapiens
SEQUENCE: 276
RASQSIRNYL T                                                              11

SEQ ID NO: 277        moltype = AA   length = 11
FEATURE               Location/Qualifiers
source                1..11
                      mol_type = protein
                      organism = Homo sapiens
SEQUENCE: 277
RASQNIRLYL N                                                              11

SEQ ID NO: 278        moltype = AA   length = 11
FEATURE               Location/Qualifiers
source                1..11
                      mol_type = protein
                      organism = Homo sapiens
SEQUENCE: 278
QASQDIRKFL N                                                              11

SEQ ID NO: 279        moltype = AA   length = 11
FEATURE               Location/Qualifiers
source                1..11
                      mol_type = protein
                      organism = Homo sapiens
SEQUENCE: 279
QASQDISNYL S                                                              11

SEQ ID NO: 280        moltype = AA   length = 11
FEATURE               Location/Qualifiers
source                1..11
                      mol_type = protein
                      organism = Homo sapiens
SEQUENCE: 280
RASQNVRSWL A                                                              11

SEQ ID NO: 281        moltype = AA   length = 11
FEATURE               Location/Qualifiers
source                1..11
                      mol_type = protein
                      organism = Homo sapiens
SEQUENCE: 281
RASQGIGNDL G                                                              11

SEQ ID NO: 282        moltype = AA   length = 11
FEATURE               Location/Qualifiers
source                1..11
                      mol_type = protein
                      organism = Homo sapiens
SEQUENCE: 282
RASQSISNWL A                                                              11

SEQ ID NO: 283        moltype = AA   length = 11
FEATURE               Location/Qualifiers
source                1..11
                      mol_type = protein
```

-continued

```
                            organism = Homo sapiens
SEQUENCE: 283
RASESIGSWL A                                                    11

SEQ ID NO: 284              moltype = AA  length = 12
FEATURE                     Location/Qualifiers
source                      1..12
                            mol_type = protein
                            organism = Homo sapiens
SEQUENCE: 284
RASQSVTSNY LA                                                   12

SEQ ID NO: 285              moltype = AA  length = 11
FEATURE                     Location/Qualifiers
source                      1..11
                            mol_type = protein
                            organism = Homo sapiens
SEQUENCE: 285
RASQGISSYL A                                                    11

SEQ ID NO: 286              moltype = AA  length = 11
FEATURE                     Location/Qualifiers
source                      1..11
                            mol_type = protein
                            organism = Homo sapiens
SEQUENCE: 286
RASQDIGNYL N                                                    11

SEQ ID NO: 287              moltype = AA  length = 11
FEATURE                     Location/Qualifiers
source                      1..11
                            mol_type = protein
                            organism = Homo sapiens
SEQUENCE: 287
RASQGISNGL S                                                    11

SEQ ID NO: 288              moltype = AA  length = 11
FEATURE                     Location/Qualifiers
source                      1..11
                            mol_type = protein
                            organism = Homo sapiens
SEQUENCE: 288
RASQNIRNYL N                                                    11

SEQ ID NO: 289              moltype = AA  length = 11
FEATURE                     Location/Qualifiers
source                      1..11
                            mol_type = protein
                            organism = Homo sapiens
SEQUENCE: 289
QASLDINNYL N                                                    11

SEQ ID NO: 290              moltype = AA  length = 11
FEATURE                     Location/Qualifiers
source                      1..11
                            mol_type = protein
                            organism = Homo sapiens
SEQUENCE: 290
RASQNIGNYL N                                                    11

SEQ ID NO: 291              moltype = AA  length = 11
FEATURE                     Location/Qualifiers
source                      1..11
                            mol_type = protein
                            organism = Homo sapiens
SEQUENCE: 291
RASQGIRNDL N                                                    11

SEQ ID NO: 292              moltype = AA  length = 11
FEATURE                     Location/Qualifiers
source                      1..11
                            mol_type = protein
                            organism = Homo sapiens
SEQUENCE: 292
RASQGINTWL A                                                    11

SEQ ID NO: 293              moltype = AA  length = 11
FEATURE                     Location/Qualifiers
source                      1..11
```

-continued

```
                            mol_type = protein
                            organism = Homo sapiens
SEQUENCE: 293
RASQFIGSWL A                                                      11

SEQ ID NO: 294         moltype = AA   length = 7
FEATURE                Location/Qualifiers
source                 1..7
                       mol_type = protein
                       organism = Homo sapiens
SEQUENCE: 294
AASSLQS                                                            7

SEQ ID NO: 295         moltype = AA   length = 7
FEATURE                Location/Qualifiers
source                 1..7
                       mol_type = protein
                       organism = Homo sapiens
SEQUENCE: 295
LGSNRAS                                                            7

SEQ ID NO: 296         moltype = AA   length = 7
FEATURE                Location/Qualifiers
source                 1..7
                       mol_type = protein
                       organism = Homo sapiens
SEQUENCE: 296
KASNLKG                                                            7

SEQ ID NO: 297         moltype = AA   length = 7
FEATURE                Location/Qualifiers
source                 1..7
                       mol_type = protein
                       organism = Homo sapiens
SEQUENCE: 297
GASTRAT                                                            7

SEQ ID NO: 298         moltype = AA   length = 7
FEATURE                Location/Qualifiers
source                 1..7
                       mol_type = protein
                       organism = Homo sapiens
SEQUENCE: 298
AASTLQR                                                            7

SEQ ID NO: 299         moltype = AA   length = 7
FEATURE                Location/Qualifiers
source                 1..7
                       mol_type = protein
                       organism = Homo sapiens
SEQUENCE: 299
AASTLQS                                                            7

SEQ ID NO: 300         moltype = AA   length = 7
FEATURE                Location/Qualifiers
source                 1..7
                       mol_type = protein
                       organism = Homo sapiens
SEQUENCE: 300
DASTLQS                                                            7

SEQ ID NO: 301         moltype = AA   length = 7
FEATURE                Location/Qualifiers
source                 1..7
                       mol_type = protein
                       organism = Homo sapiens
SEQUENCE: 301
GASSLRS                                                            7

SEQ ID NO: 302         moltype = AA   length = 7
FEATURE                Location/Qualifiers
source                 1..7
                       mol_type = protein
                       organism = Homo sapiens
SEQUENCE: 302
DASNLET                                                            7

SEQ ID NO: 303         moltype = AA   length = 7
FEATURE                Location/Qualifiers
```

-continued

```
source                  1..7
                        mol_type = protein
                        organism = Homo sapiens
SEQUENCE: 303
SASSLQS                                                                 7

SEQ ID NO: 304          moltype = AA  length = 7
FEATURE                 Location/Qualifiers
source                  1..7
                        mol_type = protein
                        organism = Homo sapiens
SEQUENCE: 304
AASSLQT                                                                 7

SEQ ID NO: 305          moltype = AA  length = 7
FEATURE                 Location/Qualifiers
source                  1..7
                        mol_type = protein
                        organism = Homo sapiens
SEQUENCE: 305
SASTLQS                                                                 7

SEQ ID NO: 306          moltype = AA  length = 7
FEATURE                 Location/Qualifiers
source                  1..7
                        mol_type = protein
                        organism = Homo sapiens
SEQUENCE: 306
DASHLET                                                                 7

SEQ ID NO: 307          moltype = AA  length = 7
FEATURE                 Location/Qualifiers
source                  1..7
                        mol_type = protein
                        organism = Homo sapiens
SEQUENCE: 307
AASTLHS                                                                 7

SEQ ID NO: 308          moltype = AA  length = 7
FEATURE                 Location/Qualifiers
source                  1..7
                        mol_type = protein
                        organism = Homo sapiens
SEQUENCE: 308
AASSLQN                                                                 7

SEQ ID NO: 309          moltype = AA  length = 7
FEATURE                 Location/Qualifiers
source                  1..7
                        mol_type = protein
                        organism = Homo sapiens
SEQUENCE: 309
GASSLQS                                                                 7

SEQ ID NO: 310          moltype = AA  length = 7
FEATURE                 Location/Qualifiers
source                  1..7
                        mol_type = protein
                        organism = Homo sapiens
SEQUENCE: 310
SAFSLQS                                                                 7

SEQ ID NO: 311          moltype = AA  length = 7
FEATURE                 Location/Qualifiers
source                  1..7
                        mol_type = protein
                        organism = Homo sapiens
SEQUENCE: 311
SASNLQS                                                                 7

SEQ ID NO: 312          moltype = AA  length = 7
FEATURE                 Location/Qualifiers
source                  1..7
                        mol_type = protein
                        organism = Homo sapiens
SEQUENCE: 312
DASSLES                                                                 7

SEQ ID NO: 313          moltype = AA  length = 7
```

-continued

```
FEATURE              Location/Qualifiers
source               1..7
                     mol_type = protein
                     organism = Homo sapiens
SEQUENCE: 313
EASTLES                                                                    7

SEQ ID NO: 314       moltype = AA  length = 7
FEATURE              Location/Qualifiers
source               1..7
                     mol_type = protein
                     organism = Homo sapiens
SEQUENCE: 314
GASTLET                                                                    7

SEQ ID NO: 315       moltype = AA  length = 7
FEATURE              Location/Qualifiers
source               1..7
                     mol_type = protein
                     organism = Homo sapiens
SEQUENCE: 315
AASTLQT                                                                    7

SEQ ID NO: 316       moltype = AA  length = 7
FEATURE              Location/Qualifiers
source               1..7
                     mol_type = protein
                     organism = Homo sapiens
SEQUENCE: 316
GASTLQS                                                                    7

SEQ ID NO: 317       moltype = AA  length = 7
FEATURE              Location/Qualifiers
source               1..7
                     mol_type = protein
                     organism = Homo sapiens
SEQUENCE: 317
GASNLET                                                                    7

SEQ ID NO: 318       moltype = AA  length = 7
FEATURE              Location/Qualifiers
source               1..7
                     mol_type = protein
                     organism = Homo sapiens
SEQUENCE: 318
MGSNRAS                                                                    7

SEQ ID NO: 319       moltype = AA  length = 7
FEATURE              Location/Qualifiers
source               1..7
                     mol_type = protein
                     organism = Homo sapiens
SEQUENCE: 319
DASTLET                                                                    7

SEQ ID NO: 320       moltype = AA  length = 7
FEATURE              Location/Qualifiers
source               1..7
                     mol_type = protein
                     organism = Homo sapiens
SEQUENCE: 320
GASNLHT                                                                    7

SEQ ID NO: 321       moltype = AA  length = 7
FEATURE              Location/Qualifiers
source               1..7
                     mol_type = protein
                     organism = Homo sapiens
SEQUENCE: 321
WASTRES                                                                    7

SEQ ID NO: 322       moltype = AA  length = 7
FEATURE              Location/Qualifiers
source               1..7
                     mol_type = protein
                     organism = Homo sapiens
SEQUENCE: 322
KTSSLES                                                                    7
```

```
SEQ ID NO: 323            moltype = AA  length = 7
FEATURE                   Location/Qualifiers
source                    1..7
                          mol_type = protein
                          organism = Homo sapiens SEQUENCE: 323
TASNLQS                                                                    7

SEQ ID NO: 324            moltype = AA  length = 7
FEATURE                   Location/Qualifiers
source                    1..7
                          mol_type = protein
                          organism = Homo sapiens SEQUENCE: 324
DASNLQS                                                                    7

SEQ ID NO: 325            moltype = AA  length = 7
FEATURE                   Location/Qualifiers
source                    1..7
                          mol_type = protein
                          organism = Homo sapiens SEQUENCE: 325
LASSLQS                                                                    7

SEQ ID NO: 326            moltype = AA  length = 7
FEATURE                   Location/Qualifiers
source                    1..7
                          mol_type = protein
                          organism = Homo sapiens SEQUENCE: 326
STSSLQS                                                                    7

SEQ ID NO: 327            moltype = AA  length = 7
FEATURE                   Location/Qualifiers
source                    1..7
                          mol_type = protein
                          organism = Homo sapiens SEQUENCE: 327
AASSLQR                                                                    7

SEQ ID NO: 328            moltype = AA  length = 7
FEATURE                   Location/Qualifiers
source                    1..7
                          mol_type = protein
                          organism = Homo sapiens SEQUENCE: 328
KASSLES                                                                    7

SEQ ID NO: 329            moltype = AA  length = 7
FEATURE                   Location/Qualifiers
source                    1..7
                          mol_type = protein
                          organism = Homo sapiens SEQUENCE: 329
AASSLQG                                                                    7

SEQ ID NO: 330            moltype = AA  length = 7
FEATURE                   Location/Qualifiers
source                    1..7
                          mol_type = protein
                          organism = Homo sapiens SEQUENCE: 330
AASNLQS                                                                    7

SEQ ID NO: 331            moltype = AA  length = 7
FEATURE                   Location/Qualifiers
source                    1..7
                          mol_type = protein
                          organism = Homo sapiens SEQUENCE: 331
AASTLRS                                                                    7

SEQ ID NO: 332            moltype = AA  length = 7
FEATURE                   Location/Qualifiers
source                    1..7
                          mol_type = protein
                          organism = Homo sapiens SEQUENCE: 332
AASSLHS                                                                    7
```

-continued

```
SEQ ID NO: 333            moltype = AA   length = 9
FEATURE                   Location/Qualifiers
source                    1..9
                          mol_type = protein
                          organism = Homo sapiens

SEQUENCE: 333
QQSYSTPLT                                                        9

SEQ ID NO: 334            moltype = AA   length = 9
FEATURE                   Location/Qualifiers
source                    1..9
                          mol_type = protein
                          organism = Homo sapiens

SEQUENCE: 334
QQSYSNLVS                                                        9

SEQ ID NO: 335            moltype = AA   length = 9
FEATURE                   Location/Qualifiers
source                    1..9
                          mol_type = protein
                          organism = Homo sapiens

SEQUENCE: 335
MQALQTPFT                                                        9

SEQ ID NO: 336            moltype = AA   length = 9
FEATURE                   Location/Qualifiers
source                    1..9
                          mol_type = protein
                          organism = Homo sapiens

SEQUENCE: 336
MQGLQTPHT                                                        9

SEQ ID NO: 337            moltype = AA   length = 8
FEATURE                   Location/Qualifiers
source                    1..8
                          mol_type = protein
                          organism = Homo sapiens

SEQUENCE: 337
QQTYSAPL                                                         8

SEQ ID NO: 338            moltype = AA   length = 9
FEATURE                   Location/Qualifiers
source                    1..9
                          mol_type = protein
                          organism = Homo sapiens

SEQUENCE: 338
MQTLQTPLT                                                        9

SEQ ID NO: 339            moltype = AA   length = 9
FEATURE                   Location/Qualifiers
source                    1..9
                          mol_type = protein
                          organism = Homo sapiens

SEQUENCE: 339
QQYGDSPGS                                                        9

SEQ ID NO: 340            moltype = AA   length = 9
FEATURE                   Location/Qualifiers
source                    1..9
                          mol_type = protein
                          organism = Homo sapiens

SEQUENCE: 340
QQANSFPPT                                                        9

SEQ ID NO: 341            moltype = AA   length = 8
FEATURE                   Location/Qualifiers
source                    1..8
                          mol_type = protein
                          organism = Homo sapiens

SEQUENCE: 341
QQYGNSRT                                                         8

SEQ ID NO: 342            moltype = AA   length = 9
FEATURE                   Location/Qualifiers
source                    1..9
                          mol_type = protein
                          organism = Homo sapiens

SEQUENCE: 342
```

-continued

```
QQSYSTPPT                                                        9

SEQ ID NO: 343            moltype = AA  length = 9
FEATURE                  Location/Qualifiers
source                   1..9
                         mol_type = protein
                         organism = Homo sapiens

SEQUENCE: 343
QQSYSSPYT                                                        9

SEQ ID NO: 344            moltype = AA  length = 9
FEATURE                  Location/Qualifiers
source                   1..9
                         mol_type = protein
                         organism = Homo sapiens

SEQUENCE: 344
QQSYSTPYT                                                        9

SEQ ID NO: 345            moltype = AA  length = 9
FEATURE                  Location/Qualifiers
source                   1..9
                         mol_type = protein
                         organism = Homo sapiens

SEQUENCE: 345
MQGAHWPPT                                                        9

SEQ ID NO: 346            moltype = AA  length = 9
FEATURE                  Location/Qualifiers
source                   1..9
                         mol_type = protein
                         organism = Homo sapiens

SEQUENCE: 346
QQSYRTPYT                                                        9

SEQ ID NO: 347            moltype = AA  length = 9
FEATURE                  Location/Qualifiers
source                   1..9
                         mol_type = protein
                         organism = Homo sapiens

SEQUENCE: 347
QESFTTQWT                                                        9

SEQ ID NO: 348            moltype = AA  length = 10
FEATURE                  Location/Qualifiers
source                   1..10
                         mol_type = protein
                         organism = Homo sapiens

SEQUENCE: 348
QQRSNWPLYT                                                      10

SEQ ID NO: 349            moltype = AA  length = 9
FEATURE                  Location/Qualifiers
source                   1..9
                         mol_type = protein
                         organism = Homo sapiens

SEQUENCE: 349
QQAISFPIT                                                        9

SEQ ID NO: 350            moltype = AA  length = 9
FEATURE                  Location/Qualifiers
source                   1..9
                         mol_type = protein
                         organism = Homo sapiens

SEQUENCE: 350
QQSYSSPFT                                                        9

SEQ ID NO: 351            moltype = AA  length = 9
FEATURE                  Location/Qualifiers
source                   1..9
                         mol_type = protein
                         organism = Homo sapiens

SEQUENCE: 351
QQAISFPLT                                                        9

SEQ ID NO: 352            moltype = AA  length = 9
FEATURE                  Location/Qualifiers
source                   1..9
                         mol_type = protein
                         organism = Homo sapiens
```

-continued

```
SEQUENCE: 352
QQSYTFPIT                                                                        9

SEQ ID NO: 353            moltype = AA   length = 9
FEATURE                   Location/Qualifiers
source                    1..9
                          mol_type = protein
                          organism = Homo sapiens
SEQUENCE: 353
QQYYSYPPT                                                                        9

SEQ ID NO: 354            moltype = AA   length = 9
FEATURE                   Location/Qualifiers
source                    1..9
                          mol_type = protein
                          organism = Homo sapiens
SEQUENCE: 354
QQSYSAPLT                                                                        9

SEQ ID NO: 355            moltype = AA   length = 9
FEATURE                   Location/Qualifiers
source                    1..9
                          mol_type = protein
                          organism = Homo sapiens
SEQUENCE: 355
QQSFSTFYT                                                                        9

SEQ ID NO: 356            moltype = AA   length = 9
FEATURE                   Location/Qualifiers
source                    1..9
                          mol_type = protein
                          organism = Homo sapiens
SEQUENCE: 356
QQSYSIPFT                                                                        9

SEQ ID NO: 357            moltype = AA   length = 9
FEATURE                   Location/Qualifiers
source                    1..9
                          mol_type = protein
                          organism = Homo sapiens
SEQUENCE: 357
QQSYSTPIT                                                                        9

SEQ ID NO: 358            moltype = AA   length = 9
FEATURE                   Location/Qualifiers
source                    1..9
                          mol_type = protein
                          organism = Homo sapiens
SEQUENCE: 358
QQSYTIPST                                                                        9

SEQ ID NO: 359            moltype = AA   length = 9
FEATURE                   Location/Qualifiers
source                    1..9
                          mol_type = protein
                          organism = Homo sapiens
SEQUENCE: 359
QQSYSAPPT                                                                        9

SEQ ID NO: 360            moltype = AA   length = 9
FEATURE                   Location/Qualifiers
source                    1..9
                          mol_type = protein
                          organism = Homo sapiens
SEQUENCE: 360
QQSYSTPWT                                                                        9

SEQ ID NO: 361            moltype = AA   length = 9
FEATURE                   Location/Qualifiers
source                    1..9
                          mol_type = protein
                          organism = Homo sapiens
SEQUENCE: 361
QQSYTTPLT                                                                        9

SEQ ID NO: 362            moltype = AA   length = 9
FEATURE                   Location/Qualifiers
source                    1..9
                          mol_type = protein
```

-continued

```
                         organism = Homo sapiens
SEQUENCE: 362
QQSYSAPIT                                                              9

SEQ ID NO: 363           moltype = AA  length = 10
FEATURE                  Location/Qualifiers
source                   1..10
                         mol_type = protein
                         organism = Homo sapiens
SEQUENCE: 363
QQRSNWPPVT                                                             10

SEQ ID NO: 364           moltype = AA  length = 9
FEATURE                  Location/Qualifiers
source                   1..9
                         mol_type = protein
                         organism = Homo sapiens
SEQUENCE: 364
QQSYSIPIT                                                              9

SEQ ID NO: 365           moltype = AA  length = 9
FEATURE                  Location/Qualifiers
source                   1..9
                         mol_type = protein
                         organism = Homo sapiens
SEQUENCE: 365
MQGLQPPGT                                                             9

SEQ ID NO: 366           moltype = AA  length = 9
FEATURE                  Location/Qualifiers
source                   1..9
                         mol_type = protein
                         organism = Homo sapiens
SEQUENCE: 366
QQSYNHFRT                                                             9

SEQ ID NO: 367           moltype = AA  length = 9
FEATURE                  Location/Qualifiers
source                   1..9
                         mol_type = protein
                         organism = Homo sapiens
SEQUENCE: 367
QRSDSTPLT                                                             9

SEQ ID NO: 368           moltype = AA  length = 9
FEATURE                  Location/Qualifiers
source                   1..9
                         mol_type = protein
                         organism = Homo sapiens
SEQUENCE: 368
QQLNSYPRT                                                             9

SEQ ID NO: 369           moltype = AA  length = 9
FEATURE                  Location/Qualifiers
source                   1..9
                         mol_type = protein
                         organism = Homo sapiens
SEQUENCE: 369
QQSYSIPYT                                                             9

SEQ ID NO: 370           moltype = AA  length = 9
FEATURE                  Location/Qualifiers
source                   1..9
                         mol_type = protein
                         organism = Homo sapiens
SEQUENCE: 370
QQTYSTPYT                                                             9

SEQ ID NO: 371           moltype = AA  length = 9
FEATURE                  Location/Qualifiers
source                   1..9
                         mol_type = protein
                         organism = Homo sapiens
SEQUENCE: 371
QQSYSTPQT                                                             9

SEQ ID NO: 372           moltype = AA  length = 8
FEATURE                  Location/Qualifiers
source                   1..8
```

-continued

```
                          mol_type = protein
                          organism = Homo sapiens
SEQUENCE: 372
MQGTHWPT                                                        8

SEQ ID NO: 373            moltype = AA   length = 9
FEATURE                   Location/Qualifiers
source                    1..9
                          mol_type = protein
                          organism = Homo sapiens
SEQUENCE: 373
QQTFSLPYT                                                       9

SEQ ID NO: 374            moltype = AA   length = 9
FEATURE                   Location/Qualifiers
source                    1..9
                          mol_type = protein
                          organism = Homo sapiens
SEQUENCE: 374
QQGYNMPLT                                                       9

SEQ ID NO: 375            moltype = AA   length = 9
FEATURE                   Location/Qualifiers
source                    1..9
                          mol_type = protein
                          organism = Homo sapiens
SEQUENCE: 375
QQTYSAPLT                                                       9

SEQ ID NO: 376            moltype = AA   length = 9
FEATURE                   Location/Qualifiers
source                    1..9
                          mol_type = protein
                          organism = Homo sapiens
SEQUENCE: 376
QQSYSFPWT                                                       9

SEQ ID NO: 377            moltype = AA   length = 9
FEATURE                   Location/Qualifiers
source                    1..9
                          mol_type = protein
                          organism = Homo sapiens
SEQUENCE: 377
QQTYSTPYI                                                       9

SEQ ID NO: 378            moltype = AA   length = 9
FEATURE                   Location/Qualifiers
source                    1..9
                          mol_type = protein
                          organism = Homo sapiens
SEQUENCE: 378
QQSYSSPWT                                                       9

SEQ ID NO: 379            moltype = AA   length = 9
FEATURE                   Location/Qualifiers
source                    1..9
                          mol_type = protein
                          organism = Homo sapiens
SEQUENCE: 379
QQYASAPRT                                                       9

SEQ ID NO: 380            moltype = AA   length = 9
FEATURE                   Location/Qualifiers
source                    1..9
                          mol_type = protein
                          organism = Homo sapiens
SEQUENCE: 380
QQSFTIPYT                                                       9

SEQ ID NO: 381            moltype = AA   length = 9
FEATURE                   Location/Qualifiers
source                    1..9
                          mol_type = protein
                          organism = Homo sapiens
SEQUENCE: 381
QQTYRTPPT                                                       9

SEQ ID NO: 382            moltype = AA   length = 9
FEATURE                   Location/Qualifiers
```

-continued

```
source                    1..9
                          mol_type = protein
                          organism = Homo sapiens SEQUENCE: 382
QQSLTTPFT                                                            9

SEQ ID NO: 383            moltype = AA   length = 9
FEATURE                   Location/Qualifiers
source                    1..9
                          mol_type = protein
                          organism = Homo sapiens SEQUENCE: 383
QQLNGYPGT                                                            9

SEQ ID NO: 384            moltype = AA   length = 9
FEATURE                   Location/Qualifiers
source                    1..9
                          mol_type = protein
                          organism = Homo sapiens SEQUENCE: 384
QQSYSLPLT                                                            9

SEQ ID NO: 385            moltype = AA   length = 9
FEATURE                   Location/Qualifiers
source                    1..9
                          mol_type = protein
                          organism = Homo sapiens SEQUENCE: 385
QQTYTTPRT                                                            9

SEQ ID NO: 386            moltype = AA   length = 9
FEATURE                   Location/Qualifiers
source                    1..9
                          mol_type = protein
                          organism = Homo sapiens SEQUENCE: 386
QQSYNTPYT                                                            9

SEQ ID NO: 387            moltype = AA   length = 9
FEATURE                   Location/Qualifiers
source                    1..9
                          mol_type = protein
                          organism = Homo sapiens SEQUENCE: 387
QQSYAPPPT                                                            9

SEQ ID NO: 388            moltype = AA   length = 9
FEATURE                   Location/Qualifiers
source                    1..9
                          mol_type = protein
                          organism = Homo sapiens SEQUENCE: 388
MQGLQTPLT                                                            9

SEQ ID NO: 389            moltype = AA   length = 9
FEATURE                   Location/Qualifiers
source                    1..9
                          mol_type = protein
                          organism = Homo sapiens SEQUENCE: 389
QQSDSIPVT                                                            9

SEQ ID NO: 390            moltype = AA   length = 9
FEATURE                   Location/Qualifiers
source                    1..9
                          mol_type = protein
                          organism = Homo sapiens SEQUENCE: 390
QQSYSTPYN                                                            9

SEQ ID NO: 391            moltype = AA   length = 8
FEATURE                   Location/Qualifiers
source                    1..8
                          mol_type = protein
                          organism = Homo sapiens SEQUENCE: 391
QHYGSSPA                                                             8

SEQ ID NO: 392            moltype = AA   length = 9
```

```
FEATURE                 Location/Qualifiers
source                  1..9
                        mol_type = protein
                        organism = Homo sapiens SEQUENCE: 392
QQAYTYPYT                                                                    9

SEQ ID NO: 393          moltype = AA  length = 9
FEATURE                 Location/Qualifiers
source                  1..9
                        mol_type = protein
                        organism = Homo sapiens SEQUENCE: 393
QQSYTTPNT                                                                    9

SEQ ID NO: 394          moltype = AA  length = 9
FEATURE                 Location/Qualifiers
source                  1..9
                        mol_type = protein
                        organism = Homo sapiens SEQUENCE: 394
QQSYSTPFT                                                                    9

SEQ ID NO: 395          moltype = AA  length = 9
FEATURE                 Location/Qualifiers
source                  1..9
                        mol_type = protein
                        organism = Homo sapiens SEQUENCE: 395
QQSYSMPLT                                                                    9

SEQ ID NO: 396          moltype = AA  length = 9
FEATURE                 Location/Qualifiers
source                  1..9
                        mol_type = protein
                        organism = Homo sapiens SEQUENCE: 396
QQSYTTPWT                                                                    9

SEQ ID NO: 397          moltype = AA  length = 9
FEATURE                 Location/Qualifiers
source                  1..9
                        mol_type = protein
                        organism = Homo sapiens SEQUENCE: 397
QQSYSSPLT                                                                    9

SEQ ID NO: 398          moltype = AA  length = 9
FEATURE                 Location/Qualifiers
source                  1..9
                        mol_type = protein
                        organism = Homo sapiens SEQUENCE: 398
QQSYSDPLT                                                                    9

SEQ ID NO: 399          moltype = AA  length = 10
FEATURE                 Location/Qualifiers
source                  1..10
                        mol_type = protein
                        organism = Homo sapiens SEQUENCE: 399
QQSYSTPPWT                                                                   10

SEQ ID NO: 400          moltype = AA  length = 9
FEATURE                 Location/Qualifiers
source                  1..9
                        mol_type = protein
                        organism = Homo sapiens SEQUENCE: 400
QQSYQTPLT                                                                    9

SEQ ID NO: 401          moltype = AA  length = 9
FEATURE                 Location/Qualifiers
source                  1..9
                        mol_type = protein
                        organism = Homo sapiens SEQUENCE: 401
QQSYTTPPT                                                                    9
```

-continued

```
SEQ ID NO: 402           moltype = AA   length = 9
FEATURE                  Location/Qualifiers
source                   1..9
                         mol_type = protein
                         organism = Homo sapiens
SEQUENCE: 402
QQANSFPIT                                                              9

SEQ ID NO: 403           moltype = AA   length = 9
FEATURE                  Location/Qualifiers
source                   1..9
                         mol_type = protein
                         organism = Homo sapiens
SEQUENCE: 403
QQSYTVPPT                                                              9

SEQ ID NO: 404           moltype = AA   length = 9
FEATURE                  Location/Qualifiers
source                   1..9
                         mol_type = protein
                         organism = Homo sapiens
SEQUENCE: 404
QQDDSFPLT                                                              9

SEQ ID NO: 405           moltype = AA   length = 122
FEATURE                  Location/Qualifiers
source                   1..122
                         mol_type = protein
                         organism = Homo sapiens
SEQUENCE: 405
QVQLVQSGAE VKKPGASVKV SCKASGGTFS SYAISWVRQA PGQGLEWMGI IDPSDGNTNY      60
AQNFQGRVTM TRDTSTSTVY MELSSLRSED TAVYYCAKER AAAGYYYYMD VWGQGTTVTV     120
SS                                                                   122

SEQ ID NO: 406           moltype = AA   length = 122
FEATURE                  Location/Qualifiers
source                   1..122
                         mol_type = protein
                         organism = Homo sapiens
SEQUENCE: 406
QVQLVQSGAE VKKPGASVKV SCKASGGTFN TYAINWVRQA PGQGLEWMGR IDPSSGGTKY      60
AQNFQGRVTM TRDTSTSTVY MELSSLRSED TAVYYCAKEH AAGTYYYYMD VWGKGTTVTV     120
SS                                                                   122

SEQ ID NO: 407           moltype = AA   length = 122
FEATURE                  Location/Qualifiers
source                   1..122
                         mol_type = protein
                         organism = Homo sapiens
SEQUENCE: 407
QVQLVQSGAE VKKPGASVKV SCKASGGTFS SYAINWVRQA PGQGLEWMGI IDPSGGNTNY      60
AQNFQGRVTM TRDTSTSTVY MELSSLRSED TAVYYCAKER AAAGYYYYMD VWGQGTTVTV     120
SS                                                                   122

SEQ ID NO: 408           moltype = AA   length = 119
FEATURE                  Location/Qualifiers
source                   1..119
                         mol_type = protein
                         organism = Homo sapiens
SEQUENCE: 408
QVQLVQSGAE VKKPGASVKV SCKASGYTFT DYYIQWVRQA PGQGLEWMGW INPNSGGTSY      60
AQKFQGRVTM TRDTSTSTVY MELSSLRSED TAVYYCAKEG DYYYGMDAWG QGTMVTVSS      119

SEQ ID NO: 409           moltype = AA   length = 117
FEATURE                  Location/Qualifiers
source                   1..117
                         mol_type = protein
                         organism = Homo sapiens
SEQUENCE: 409
QVQLVQSGAE VKKPGASVKV SCKASGYTFT RYDIHWVRQA PGQGLEWMGV INPNDGSTRY      60
AQNFQGRVTM TRDTSTSTVY MELSSLRSED TAVYYCARER GGMPDYWGQG TLVTVSS        117

SEQ ID NO: 410           moltype = AA   length = 116
FEATURE                  Location/Qualifiers
source                   1..116
                         mol_type = protein
                         organism = Homo sapiens
SEQUENCE: 410
QVQLVQSGAE VKKPGASVKV SCKASGYTFT SYAMNWVRQA PGQGLEWMGR INPNSGGTNY      60
```

```
AQKFQGRVTM TRDTSTSTVY MELSSLRSED TAVYYCARGH GIPKYWGQGT LVTVSS        116

SEQ ID NO: 411          moltype = AA  length = 117
FEATURE                 Location/Qualifiers
source                  1..117
                        mol_type = protein
                        organism = Homo sapiens
SEQUENCE: 411
QVQLVQSGAE VKKPGASVKV SCKASGYTFT SYYIHWVRQA PGQGLEWMGW MNPNSGNTGY        60
AQKFQGRVTM TRDTSTSTVY MELSSLRSED TAVYYCARVR SGSPQHWGQG TLVTVSS         117

SEQ ID NO: 412          moltype = AA  length = 120
FEATURE                 Location/Qualifiers
source                  1..120
                        mol_type = protein
                        organism = Homo sapiens
SEQUENCE: 412
QVQLVQSGAE VKKPGASVKV SCKASGHTFS RHYIHWVRQA PGQGLEWMGW MNPNSGNTGY        60
AQKFQGRVTM TRDTSTSTVY MELSSLRSED TAVYYCARGG PWIVDAFDIW GQGTMVTVSS      120

SEQ ID NO: 413          moltype = AA  length = 122
FEATURE                 Location/Qualifiers
source                  1..122
                        mol_type = protein
                        organism = Homo sapiens
SEQUENCE: 413
QVQLVQSGAE VKKPGASVKV SCKASGGTFS NTDINWVRQA PGQGLEWMGI INPSGGSTSY        60
AQKFQGRVTM TRDTSTSTVY MELSSLRSED TAVYYCAREA TWGPYYYYMD VWGKGTTVTV      120
SS                                                                    122

SEQ ID NO: 414          moltype = AA  length = 116
FEATURE                 Location/Qualifiers
source                  1..116
                        mol_type = protein
                        organism = Homo sapiens
SEQUENCE: 414
QVQLVQSGAE VKKPGASVKV SCKASGYTFT RSYVHWVRQA PGQGLEWMGW ISPYNGNTKY        60
AQKFQGRVTM TRDTSTSTVY MELSSLRSED TAVYYCVRNK DGLQHWGQGT LVTVSS         116

SEQ ID NO: 415          moltype = AA  length = 122
FEATURE                 Location/Qualifiers
source                  1..122
                        mol_type = protein
                        organism = Homo sapiens
SEQUENCE: 415
QVQLVQSGAE VKKPGASVKV SCKASGDTFT GYYMHWVRQA PGQGLEWMGI INPNSGDTKY        60
AHQFQGRVTM TRDTSTSTVY MELSSLRSED TAVYYCAKDA KRVGYYYYMD VWGKGTTVTV      120
SS                                                                    122

SEQ ID NO: 416          moltype = AA  length = 117
FEATURE                 Location/Qualifiers
source                  1..117
                        mol_type = protein
                        organism = Homo sapiens
SEQUENCE: 416
QVQLVQSGAE VKKPGASVKV SCKASGYTFT RYYMHWVRQA PGQGLEWMGR INPNSGGTNY        60
AQKFQGRVTM TRDTSTSTVY MELSSLRSED TAVYYCARLV GGSPDYWGQG TLVTVSS         117

SEQ ID NO: 417          moltype = AA  length = 115
FEATURE                 Location/Qualifiers
source                  1..115
                        mol_type = protein
                        organism = Homo sapiens
SEQUENCE: 417
QVQLVQSGAE VKKPGASVKV SCKASGYTFT NYDINWVRQA PGQGLEWMGR INPNSGGTNY        60
AENFQGRVTM TRDTSTSTVY MELSSLRSED TAVYYCARGA MVDYWGQGTL VTVSS          115

SEQ ID NO: 418          moltype = AA  length = 122
FEATURE                 Location/Qualifiers
source                  1..122
                        mol_type = protein
                        organism = Homo sapiens
SEQUENCE: 418
QVQLVQSGAE VKKPGASVKV SCKASGGTFS NTDINWVRQA PGQGLEWMGI INPSDGDTKY        60
AQEFQGRVTM TRDTSTSTVY MELSSLRSED TAVYYCARGN YVGSYYYGMD VWGQGTTVTV      120
SS                                                                    122

SEQ ID NO: 419          moltype = AA  length = 119
FEATURE                 Location/Qualifiers
```

-continued

```
source                    1..119
                          mol_type = protein
                          organism = Homo sapiens
SEQUENCE: 419
QVQLVQSGAE VKKPGASVKV SCKASGYTFT NYYLHWVRQA PGQGLEWMGW INPNSGDTKY  60
AQKFQGRVTM TRDTSTSTVY MELSSLRSED TAVYYCARDS RGDWYFDLWG RGTLVTVSS   119

SEQ ID NO: 420            moltype = AA  length = 118
FEATURE                   Location/Qualifiers
source                    1..118
                          mol_type = protein
                          organism = Homo sapiens
SEQUENCE: 420
QVQLVQSGAE VKKPGASVKV SCKASGYGFT RYSIHWVRQA PGQGLEWMGV IDPSGGSTSY  60
AQKFQGRVTM TRDTSTSTVY MELSSLRSED TAVYYCTRHG GRGLADYWGQ GTLVTVSS    118

SEQ ID NO: 421            moltype = AA  length = 122
FEATURE                   Location/Qualifiers
source                    1..122
                          mol_type = protein
                          organism = Homo sapiens
SEQUENCE: 421
QVQLVQSGAE VKKPGASVKV SCKASGYTFT SRDISWVRQA PGQGLEWMGW IDPKSGDTTY  60
AQKFQGRVTM TRDTSTSTVY MELSSLRSED TAVYYCARLK ELSSILDAFD IWGQGTMVTV  120
SS                                                                 122

SEQ ID NO: 422            moltype = AA  length = 122
FEATURE                   Location/Qualifiers
source                    1..122
                          mol_type = protein
                          organism = Homo sapiens
SEQUENCE: 422
QVQLVQSGAE VKKPGASVKV SCKASGYTFT SYDINWVRQA PGQGLEWMGM INPGAGSSTY  60
AQKFQGRVTM TRDTSTSTVY MELSSLRSED TAVYYCARER FGTGYYYYMD VWGQGTMVTV  120
SS                                                                 122

SEQ ID NO: 423            moltype = AA  length = 121
FEATURE                   Location/Qualifiers
source                    1..121
                          mol_type = protein
                          organism = Homo sapiens
SEQUENCE: 423
EVQLLESGGG LVQPGGSLRL SCAASGFTFS NSDMNWVRQA PGKGLEWVSL ISGDGGTTYY  60
ADSVKGRFTI SRDNSKNTLY LQMNSLRAED TAVYYCARVI GEMVDDAFDL WGQGTTVTVS  120
S                                                                  121

SEQ ID NO: 424            moltype = AA  length = 122
FEATURE                   Location/Qualifiers
source                    1..122
                          mol_type = protein
                          organism = Homo sapiens
SEQUENCE: 424
QVQLVQSGAE VKKPGASVKV SCKASGYTFT GYYMHWVRQA PGQGLEWMGS INPNSGDTGY  60
AQKFQGRVTM TRDTSTSTVY MELSSLRSED TAVYYCARER LFGTYYYYMD VWGKGTTVTV  120
SS                                                                 122

SEQ ID NO: 425            moltype = AA  length = 117
FEATURE                   Location/Qualifiers
source                    1..117
                          mol_type = protein
                          organism = Homo sapiens
SEQUENCE: 425
QVQLVQSGAE VKKPGSSVKV SCKASGYTFT TYDINWVRQA PGQGLEWMGR IIPIFGTANY  60
AQKFQGRVTI TADESTSTAY MELSSLRSED TAVYYCARAD GELTDYWGQG TLVTVSS     117

SEQ ID NO: 426            moltype = AA  length = 121
FEATURE                   Location/Qualifiers
source                    1..121
                          mol_type = protein
                          organism = Homo sapiens
SEQUENCE: 426
EVQLLESGGG LVQPGGSLRL SCAASGFTFS SYTMDWVRQA PGKGLEWVSA IGTGGGIYYA  60
DSVKGRFTIS RDNSKNTLYL QMNSLRAEDT AVYYCARHHL PAHYYYYMDV WGKGTTVTVS  120
S                                                                  121

SEQ ID NO: 427            moltype = AA  length = 122
FEATURE                   Location/Qualifiers
source                    1..122
                          mol_type = protein
```

```
                               organism = Homo sapiens
SEQUENCE: 427
QVQLVQSGAE VKKPGASVKV SCKASGGTFS RYDINWVRQA PGQGLEWMGR INPNSGDTNY    60
AQKFQGRVTM TRDTSTSTVY MELSSLRSED TAVYYCARDV PAGRYYYYMD VWGKGTLVTV   120
SS                                                                 122

SEQ ID NO: 428         moltype = AA  length = 122
FEATURE                Location/Qualifiers
source                 1..122
                       mol_type = protein
                       organism = Homo sapiens
SEQUENCE: 428
QVQLVQSGAE VKKPGASVKV SCKASGNTFT SYYMHWVRQA PGQGLEWMGM INPSDGSTRY    60
AQKFQGRVTM TRDTSTSTVY MELSSLRSED TAVYYCAKDR GVGRYYYYMD VWGKGTTVTV   120
SS                                                                 122

SEQ ID NO: 429         moltype = AA  length = 122
FEATURE                Location/Qualifiers
source                 1..122
                       mol_type = protein
                       organism = Homo sapiens
SEQUENCE: 429
QVQLVQSGAE VKKPGASVKV SCKASGGTFS RYAVSWVRQA PGQGLEWMGI INPSDGSTTY    60
AQKFQGRVTM TRDTSTSTVY MELSSLRSED TAVYYCAKDS RYGRYYYYMD VWGKGTTVTV   120
SS                                                                 122

SEQ ID NO: 430         moltype = AA  length = 122
FEATURE                Location/Qualifiers
source                 1..122
                       mol_type = protein
                       organism = Homo sapiens
SEQUENCE: 430
QVQLVQSGAE VKKPGSSVKV SCKASGGTFS NYAISWVRQA PGQGLEWMGI INPNGGSPSY    60
AQKFQGRVTI TADESTSTAY MELSSLRSED TAVYYCAKEI VVGPYYYYMD VWGKGTTVTV   120
SS                                                                 122

SEQ ID NO: 431         moltype = AA  length = 122
FEATURE                Location/Qualifiers
source                 1..122
                       mol_type = protein
                       organism = Homo sapiens
SEQUENCE: 431
QVQLVQSGAE VKKPGSSVKV SCKASGGTFT RYAISWVRQA PGQGLEWMGR INPNSGDTNY    60
AQKFQGRVTI TADESTSTAY MELSSLRSED TAVYYCARGM VRGPYYYYMD VWGKGTTVTV   120
SS                                                                 122

SEQ ID NO: 432         moltype = AA  length = 122
FEATURE                Location/Qualifiers
source                 1..122
                       mol_type = protein
                       organism = Homo sapiens
SEQUENCE: 432
QVQLVQSGAE VKKPGSSVKV SCKASGGTFS SYAISWVRQA PGQGLEWMGI INPSGGSTSY    60
AQTFQGRVTI TADESTSTAY MELSSLRSED TAVYYCAREG VTGPYYYYMD VWGQGTTVTV   120
SS                                                                 122

SEQ ID NO: 433         moltype = AA  length = 125
FEATURE                Location/Qualifiers
source                 1..125
                       mol_type = protein
                       organism = Homo sapiens
SEQUENCE: 433
QVQLVQSGAE VKKPGASVKV SCKASGGTFS RFDINWVRQA PGQGLEWMGI INPSDGSTDY    60
AQNFQGRVTM TRDTSTSTVY MELSSLRSED TAVYYCARDA AAGTRYYYYY GMDVWGQGTT   120
VTVSS                                                              125

SEQ ID NO: 434         moltype = AA  length = 122
FEATURE                Location/Qualifiers
source                 1..122
                       mol_type = protein
                       organism = Homo sapiens
SEQUENCE: 434
QVQLVQSGAE VKKPGASVKV SCKASGGTFS SHAISWVRQA PGQGLEWMGI INPSGGSTSY    60
AQKFQGRVTM TRDTSTSTVY MELSSLRSED TAVYYCAREL YSSTYYYYMD VWGKGTTVTV   120
SS                                                                 122

SEQ ID NO: 435         moltype = AA  length = 122
FEATURE                Location/Qualifiers
source                 1..122
```

```
                           mol_type = protein
                           organism = Homo sapiens
SEQUENCE: 435
QVQLVQSGAE VKKPGASVKV SCKASGGTFS SYAISWVRQA PGQGLEWMGR INPNTGGTNH  60
AQKFQGRVTM TRDTSTSTVY MELSSLRSED TAVYYCARAL YSGPYYYYMD VWGKGTTVTV  120
SS                                                                122

SEQ ID NO: 436            moltype = AA  length = 122
FEATURE                   Location/Qualifiers
source                    1..122
                          mol_type = protein
                          organism = Homo sapiens
SEQUENCE: 436
EVQLLESGGG LVQPGGSLRL SCAASGFTFS NSDMNWVRQA PGKGLEWVSA ISGSGGSTYY  60
ADSVKGRFTI SRDNSKNTLY LQMNSLRAED TAVYYCAKEH AAGTYYYYMD VWGKGTTVTV  120
SS                                                                122

SEQ ID NO: 437            moltype = AA  length = 122
FEATURE                   Location/Qualifiers
source                    1..122
                          mol_type = protein
                          organism = Homo sapiens
SEQUENCE: 437
QVQLVQSGAE VKKPGASVKV SCKASGGTFG SYGINWVRQA PGQGLEWMGW ISGYNGDTDY  60
ARKLQGRVTM TRDTSTSTVY MELSSLRSED TAVYYCARDS LVGRYYYYMD VWGKGTTVTV  120
SS                                                                122

SEQ ID NO: 438            moltype = AA  length = 115
FEATURE                   Location/Qualifiers
source                    1..115
                          mol_type = protein
                          organism = Homo sapiens
SEQUENCE: 438
QVQLVQSGAE VKKPGASVKV SCKASGYIFT DYDIYWVRQA PGQGLEWLGW ISADNGNTNY  60
EQKVQGRVTM TRDTSTSTVY MELSSLRSED TAVYYCARRS ELDYWGQGTL VTVSS       115

SEQ ID NO: 439            moltype = AA  length = 115
FEATURE                   Location/Qualifiers
source                    1..115
                          mol_type = protein
                          organism = Homo sapiens
SEQUENCE: 439
QVQLVQSGAE VKKPGASVKV SCKASGYTFT SYHMHWVRQA PGQGLEWMGW ISPNSGATHY  60
AQKFQGRVTM TRDTSTSTVY MELSSLRSED TAVYYCARGD DNDYWGQGTL VTVSS       115

SEQ ID NO: 440            moltype = AA  length = 115
FEATURE                   Location/Qualifiers
source                    1..115
                          mol_type = protein
                          organism = Homo sapiens
SEQUENCE: 440
QVQLVQSGAE VKKPGASVKV SCKASGYTFT SYDINWVRQA PGQGLEWMGW INPNSGNTGY  60
AKKFQGRVTM TRDTSTSTVY MELSSLRSED TAVYYCARGE EVDYWGQGTL VTVSS       115

SEQ ID NO: 441            moltype = AA  length = 116
FEATURE                   Location/Qualifiers
source                    1..116
                          mol_type = protein
                          organism = Homo sapiens
SEQUENCE: 441
QVQLVQSGAE VKKPGASVKV SCKASGYTFT SYPMNWVRQA PGQGLEWMGI INPSGGSTRY  60
AQKFQGRVTM TRDTSTSTVY MELSSLRSED TAVYYCARGR RVPDYWGQGT LVTVSS      116

SEQ ID NO: 442            moltype = AA  length = 116
FEATURE                   Location/Qualifiers
source                    1..116
                          mol_type = protein
                          organism = Homo sapiens
SEQUENCE: 442
QVQLVQSGAE VKKPGASVKV SCKASGYTFT DYYIHWVRQA PGQGLEWMGW INPKSGATNY  60
AQKFQGRVTM TRDTSTSTVY MELSSLRSED TAVYYCARGK VTTDYWGQGT LVTVSS      116

SEQ ID NO: 443            moltype = AA  length = 116
FEATURE                   Location/Qualifiers
source                    1..116
                          mol_type = protein
                          organism = Homo sapiens
SEQUENCE: 443
EVQLLESGGG LVQPGGSLRL SCAASGFTFS SFEMNWVRQA PGKGLEWVSR ISESGDSSFY  60
```

-continued

```
ADSVKGRFTI SRDNSKNTLY LQMNSLRAED TAVYYCASGR ELIEYWGQGT LVTVSS              116

SEQ ID NO: 444          moltype = AA  length = 115
FEATURE                 Location/Qualifiers
source                  1..115
                        mol_type = protein
                        organism = Homo sapiens
SEQUENCE: 444
EVQLLESGGG LVQPGGSLRL SCAASGFTFD DYAMHWVRQA PGKGLEWVSA IGTGGGTYYA          60
DSVKGRFTIS RDNSKNTLYL QMNSLRAEDT AVYYCARVYD FPDVWGQGTT VTVSS               115

SEQ ID NO: 445          moltype = AA  length = 117
FEATURE                 Location/Qualifiers
source                  1..117
                        mol_type = protein
                        organism = Homo sapiens
SEQUENCE: 445
QVQLVQSGAE VKKPGASVKV SCKASGYTFT DSYMHWVRQA PGQGLEWMGW MNPSNGDTGY          60
ARKFQGRVTM TRDTSTSTVY MELSSLRSED TAVYYCARST YSHIDYWGQG TLVTVSS             117

SEQ ID NO: 446          moltype = AA  length = 117
FEATURE                 Location/Qualifiers
source                  1..117
                        mol_type = protein
                        organism = Homo sapiens
SEQUENCE: 446
QVQLVQSGAE VKKPGASVKV SCKASGYTFT NYYMHWVRQA PGQGLEWMGT ISPSDGSTTY          60
AQRFQGRVTM TRDTSTSTVY MELSSLRSED TAVYYCARED SSGFDYWGQG TLVTVSS             117

SEQ ID NO: 447          moltype = AA  length = 117
FEATURE                 Location/Qualifiers
source                  1..117
                        mol_type = protein
                        organism = Homo sapiens
SEQUENCE: 447
QVQLVQSGAE VKKPGASVKV SCKASGYTFM NYYIHWVRQA PGQGLEWMGI INPSGGSTTY          60
AQKFQGRVTM TRDTSTSTVY MELSSLRSED TAVYYCARDQ GGGFDYWGQG TLVTVSS             117

SEQ ID NO: 448          moltype = AA  length = 117
FEATURE                 Location/Qualifiers
source                  1..117
                        mol_type = protein
                        organism = Homo sapiens
SEQUENCE: 448
QVQLVQSGAE VKKPGASVKV SCKASGYTFT SYYMHWVRQA PGQGLEWMGG FDPEDGETIY          60
AQKFQGRVTM TRDTSTSTVY MELSSLRSED TAVYYCARDQ GWGMDVWGQG TTVTVSS             117

SEQ ID NO: 449          moltype = AA  length = 117
FEATURE                 Location/Qualifiers
source                  1..117
                        mol_type = protein
                        organism = Homo sapiens
SEQUENCE: 449
QVQLVQSGAE VKKPGASVKV SCKASGYTFT SYYIHWVRQA PGQGLEWMGR INPKSGRTYY          60
AQNFQGRVTM TRDTSTSTVY MELSSLRSED TAVYYCARLT EGIPDYWGQG TLVTVSS             117

SEQ ID NO: 450          moltype = AA  length = 117
FEATURE                 Location/Qualifiers
source                  1..117
                        mol_type = protein
                        organism = Homo sapiens
SEQUENCE: 450
QVQLVQSGAE VKKPGASVKV SCKASGYTLN DYYIHWVRQA PGQGLEWMGV INPGGGSTTY          60
AQTFQGRVTM TRDTSTSTVY MELSSLRSED TAVYYCARDR YGPFDYWGQG TLVTVSS             117

SEQ ID NO: 451          moltype = AA  length = 118
FEATURE                 Location/Qualifiers
source                  1..118
                        mol_type = protein
                        organism = Homo sapiens
SEQUENCE: 451
QVQLVQSGAE VKKPGASVKV SCKASGYTFT SYDINWVRQA PGQGLEWMGL MNPKTGDTNY          60
AEKFQGRVTM TRDTSTSTVY MELSSLRSED TAVYYCTRLV AGGAPDYWGQ GTLVTVSS            118

SEQ ID NO: 452          moltype = AA  length = 118
FEATURE                 Location/Qualifiers
source                  1..118
                        mol_type = protein
                        organism = Homo sapiens
```

```
SEQUENCE: 452
QVQLVQSGAE VKKPGASVKV SCKASGYTFT GYYMHWVRQA PGQGLEWMGI IDPSDGYTSY    60
AQKFQGRVTM TRDTSTSTVY MELSSLRSED TAVYYCARDG FTGDIAYWGQ GTLVTVSS     118

SEQ ID NO: 453            moltype = AA  length = 118
FEATURE                   Location/Qualifiers
source                    1..118
                          mol_type = protein
                          organism = Homo sapiens
SEQUENCE: 453
QVQLVQSGAE VKKPGSSVKV SCKASGYTFT GYYMHWVRQA PGQGLEWMGW INPNSGGTNY    60
AQKFQGRVTI TADESTSTAY MELSSLRSED TAVYYCARVD DSSSPDYWGQ GTLVTVSS     118

SEQ ID NO: 454            moltype = AA  length = 118
FEATURE                   Location/Qualifiers
source                    1..118
                          mol_type = protein
                          organism = Homo sapiens
SEQUENCE: 454
QVQLVQSGAE VKKPGSSVKV SCKASGYTFT GYYLHWVRQA PGQGLEWMGG IMPISGTTIY    60
AQKFQGRVTI TADESTSTAY MELSSLRSED TAVYYCTTGP DGTEVDYWGQ GTLVTVSS     118

SEQ ID NO: 455            moltype = AA  length = 118
FEATURE                   Location/Qualifiers
source                    1..118
                          mol_type = protein
                          organism = Homo sapiens
SEQUENCE: 455
QVQLVQSGAE VKKPGASVKV SCKASGYTFT NHYMHWVRQA PGQGLEWMGW MNPNSGNTGY    60
AQKFQGRVTM TRDTSTSTVY MELSSLRSED TAVYYCASSE SGSDLDYWGQ GTLVTVSS     118

SEQ ID NO: 456            moltype = AA  length = 119
FEATURE                   Location/Qualifiers
source                    1..119
                          mol_type = protein
                          organism = Homo sapiens
SEQUENCE: 456
QVQLVQSGAE VKKPGASVKV SCKASGYTFT NYYIHWVRQA PGQGLEWMGW MSPTSGDTGY    60
AQKFQGRVTM TRDTSTSTVY MELSSLRSED TAVYYCAREV EIEGYMDVWG QGTTVTVSS    119

SEQ ID NO: 457            moltype = AA  length = 119
FEATURE                   Location/Qualifiers
source                    1..119
                          mol_type = protein
                          organism = Homo sapiens
SEQUENCE: 457
QVQLVQSGAE VKKPGASVKV SCKASGYTFT SYYMHWVRQA PGQGLEWMGW INPNSGDTSY    60
AQKFQGRVTM TRDTSTSTVY MELSSLRSED TAVYYCAKDL DDDWYMDVWG KGTTVTVSS    119

SEQ ID NO: 458            moltype = AA  length = 119
FEATURE                   Location/Qualifiers
source                    1..119
                          mol_type = protein
                          organism = Homo sapiens
SEQUENCE: 458
QVQLVQSGAE VKKPGASVKV SCKASGYTFT SYYMHWVRQA PGQGLEWMGI IDPSGDITSY    60
AQKFQGRVTM TRDTSTSTVY MELSSLRSED TAVYYCTTDS TTWDAFDIWG QGTMVTVSS    119

SEQ ID NO: 459            moltype = AA  length = 119
FEATURE                   Location/Qualifiers
source                    1..119
                          mol_type = protein
                          organism = Homo sapiens
SEQUENCE: 459
QVQLVQSGAE VKKPGASVKV SCKASGYTFT DYYMHWVRQA PGQGLEWMGW INPNSGGTNY    60
AQKFQGRVTM TRDTSTSTVY MELSSLRSED TAVYYCARVL VGSGSPDYWG QGTLVTVSS    119

SEQ ID NO: 460            moltype = AA  length = 119
FEATURE                   Location/Qualifiers
source                    1..119
                          mol_type = protein
                          organism = Homo sapiens
SEQUENCE: 460
QVQLVQSGAE VKKPGASVKV SCKASGYTFT ENEMHWVRQA PGQGLEWMGI IETSGGSTDY    60
AQKFQGRVTM TRDTSTSTVY MELSSLRSED TAVYYCAREA AAGLDFQHWG QGTLVTVSS    119

SEQ ID NO: 461            moltype = AA  length = 120
FEATURE                   Location/Qualifiers
source                    1..120
```

-continued

```
                            mol_type = protein
                            organism = Homo sapiens
SEQUENCE: 461
QVQLVQSGAE VKKPGASVKV SCKASGYTFA SYDMHWVRQA PGQGLEWMGI INPNSGGTNY   60
AQKLQGRVTM TRDTSTSTVY MELSSLRSED TAVYYCARAN SWDAMVIDYW GQGTLVTVSS   120

SEQ ID NO: 462          moltype = AA   length = 120
FEATURE                 Location/Qualifiers
source                  1..120
                        mol_type = protein
                        organism = Homo sapiens
SEQUENCE: 462
EVQLLESGGG LVQPGGSLRL SCAASGFTFS NSDMHWVRQA PGKGLEWVSV ISGSGVTTYY   60
ADSVKGRFTI SRDNSKNTLY LQMNSLRAED TAVYYCAREH SSSWYTFDYW GQGTLVTVSS   120

SEQ ID NO: 463          moltype = AA   length = 120
FEATURE                 Location/Qualifiers
source                  1..120
                        mol_type = protein
                        organism = Homo sapiens
SEQUENCE: 463
QVQLVQSGAE VKKPGASVKV SCKASGYTFT AYYMHWVRQA PGQGLEWLGW INPNSGGTDY   60
AQKFQGRVTM TRDTSTSTVY MELSSLRSED TAVYYCARDD DSSGYYLDYW GQGTLVTVSS   120

SEQ ID NO: 464          moltype = AA   length = 120
FEATURE                 Location/Qualifiers
source                  1..120
                        mol_type = protein
                        organism = Homo sapiens
SEQUENCE: 464
QVQLVQSGAE VKKPGASVKV SCKASGYTFT NYYIHWVRQA PGQGLEWMGM INPSGGSTTY   60
AQKFQGRVTM TRDTSTSTVY MELSSLRSED TAVYYCARAS GDYMDLIDYW GQGTLVTVSS   120

SEQ ID NO: 465          moltype = AA   length = 120
FEATURE                 Location/Qualifiers
source                  1..120
                        mol_type = protein
                        organism = Homo sapiens
SEQUENCE: 465
QVQLVQSGAE VKKPGASVKV SCKASGYTFT DYHMHWVRQA PGQGLEWLGW INPDSGGTNY   60
EQKFQGRVTM TRDTSTSTVY MELSSLRSED TAVYYCALVG SSGYLAPTHW GQGTLVTVSS   120

SEQ ID NO: 466          moltype = AA   length = 120
FEATURE                 Location/Qualifiers
source                  1..120
                        mol_type = protein
                        organism = Homo sapiens
SEQUENCE: 466
QVQLVQSGAE VKKPGSSVKV SCKASGYPFT DYYMHWVRQA PGQGLEWMGW MNPNSGNTGY   60
AQKFQGRVTI TADESTSTAY MELSSLRSED TAVYYCARVR GDGYNLGDYW GQGTLVTVSS   120

SEQ ID NO: 467          moltype = AA   length = 120
FEATURE                 Location/Qualifiers
source                  1..120
                        mol_type = protein
                        organism = Homo sapiens
SEQUENCE: 467
QVQLVQSGAE VKKPGASVKV SCKASGYTFS DYYMHWVRQA PGQGLEWMGW INPNSGGTNS   60
AQKFQGRVTM TRDTSTSTVY MELSSLRSED TAVYYCARDV DTAMGAGDYW GQGTLVTVSS   120

SEQ ID NO: 468          moltype = AA   length = 121
FEATURE                 Location/Qualifiers
source                  1..121
                        mol_type = protein
                        organism = Homo sapiens
SEQUENCE: 468
QVQLVQSGAE VKKPGASVKV SCKASGYTFT DYYIHWVRQA PGQGLEWIGI INPSGGSASY   60
AQKFQGRVTM TRDTSTSTVY MELSSLRSED TAVYYCARVA RWGYGDYPDY WGQGTLVTVS   120
S                                                                   121

SEQ ID NO: 469          moltype = AA   length = 121
FEATURE                 Location/Qualifiers
source                  1..121
                        mol_type = protein
                        organism = Homo sapiens
SEQUENCE: 469
QVQLVQSGAE VKKPGASVKV SCKASGDTFT THDINWVRQA PGQGLEWMGI ISPSDGSTSY   60
AQKLQGRVTM TRDTSTSTVY MELSSLRSED TAVYYCARDR NGDYYYGMDV WGQGTTVTVS   120
S                                                                   121
```

-continued

```
SEQ ID NO: 470            moltype = AA  length = 121
FEATURE                   Location/Qualifiers
source                    1..121
                          mol_type = protein
                          organism = Homo sapiens
SEQUENCE: 470
QVQLVQSGAE VKKPGASVKV SCKASGDTFT NYYIHWVRQA PGQGLEWMGW INPISGGTHY  60
AQKFQGRVTM TRDTSTSTVY MELSSLRSED TAVYYCAREG LGSSWYVLDY WGQGTLVTVS  120
S                                                                 121

SEQ ID NO: 471            moltype = AA  length = 121
FEATURE                   Location/Qualifiers
source                    1..121
                          mol_type = protein
                          organism = Homo sapiens
SEQUENCE: 471
QVQLVQSGAE VKKPGASVKV SCKASGYTFT SYDINWVRQA PGQGLEWMGW ISADNGDTSF  60
AQKFQGRVTM TRDTSTSTVY MELSSLRSED TAVYYCARDG SHYGYYGMDV WGQGTTVTVS  120
S                                                                 121

SEQ ID NO: 472            moltype = AA  length = 121
FEATURE                   Location/Qualifiers
source                    1..121
                          mol_type = protein
                          organism = Homo sapiens
SEQUENCE: 472
QVQLVQSGAE VKKPGSSVKV SCKASGYTFT SYDINWVRQA PGQGLEWMGG ISPIYGTPAY  60
AQKFQGRVTI TADESTSTAY MELSSLRSED TAVYYCASPG PEGYYYGMDV WGQGTTVTVS  120
S                                                                 121

SEQ ID NO: 473            moltype = AA  length = 121
FEATURE                   Location/Qualifiers
source                    1..121
                          mol_type = protein
                          organism = Homo sapiens
SEQUENCE: 473
QVQLVQSGAE VKKPGASVKV SCKASGYTFT DNYMHWVRQA PGQGLEWMGW MNPNSGNTGY  60
AQKFQGRVTM TRDTSTSTVY MELSSLRSED TAVYYCASYH WDYGDYRFDY WGQGTLVTVS  120
S                                                                 121

SEQ ID NO: 474            moltype = AA  length = 121
FEATURE                   Location/Qualifiers
source                    1..121
                          mol_type = protein
                          organism = Homo sapiens
SEQUENCE: 474
QVQLVQSGAE VKKPGASVKV SCKASGYTFT SYYIHWVRQA PGQGLEWMGW MNPNSGNTGY  60
AQKFQGRVTM TRDTSTSTVY MELSSLRSED TAVYYCARVE IDYGDSPPDY WGQGTLVTVS  120
S                                                                 121

SEQ ID NO: 475            moltype = AA  length = 121
FEATURE                   Location/Qualifiers
source                    1..121
                          mol_type = protein
                          organism = Homo sapiens
SEQUENCE: 475
QVQLVQSGAE VKKPGASVKV SCKASGGTSS SYAISWVRQA PGQGLEWMGI INPSDGDTSY  60
AQKFQGRVTM TRDTSTSTVY MELSSLRSED TAVYYCARGA EWELRYAFDI WGQGTMVTVS  120
S                                                                 121

SEQ ID NO: 476            moltype = AA  length = 122
FEATURE                   Location/Qualifiers
source                    1..122
                          mol_type = protein
                          organism = Homo sapiens
SEQUENCE: 476
QVQLVQSGAE VKKPGASVKV SCKASGYTFT TYDISWVRQA PGQGLEWMGT INPSGGTTTY  60
AQKFQGRVTM TRDTSTSTVY MELSSLRSED TAVYYCARET YYGLYYYGMD VWGKGTTVTV  120
SS                                                                122

SEQ ID NO: 477            moltype = AA  length = 122
FEATURE                   Location/Qualifiers
source                    1..122
                          mol_type = protein
                          organism = Homo sapiens
SEQUENCE: 477
QVQLVQSGAE VKKPGASVKV SCKASGYTFT SYDINWVRQA PGQGLEWMGW MNPKSGNTGY  60
AQKFQGRVTM TRDTSTSTVY MELSSLRSED TAVYYCARAP SLRGYSYGPD YWGQGTLVTV  120
```

```
SS                                                                       122

SEQ ID NO: 478          moltype = AA  length = 122
FEATURE                 Location/Qualifiers
source                  1..122
                        mol_type = protein
                        organism = Homo sapiens
SEQUENCE: 478
QVQLVQSGAE VKKPGASVKV SCKASGGTFT SYDINWVRQA PGQGLEWMGI INPSGGSTSY  60
AQKFQGRVTM TRDTSTSTVY MELSSLRSED TAVYYCAKDR QERYYYYYMD VWGKGTLVTV  120
SS                                                                       122

SEQ ID NO: 479          moltype = AA  length = 122
FEATURE                 Location/Qualifiers
source                  1..122
                        mol_type = protein
                        organism = Homo sapiens
SEQUENCE: 479
QVQLVQSGAE VKKPGASVKV SCKASGYTFT SYDINWVRQA PGQGLEWMGI INPSDGSTDY  60
AQKFQGRVTM TRDTSTSTVY MELSSLRSED TAVYYCAKDR SYGDYYYGMD VWGQGTTVTV  120
SS                                                                       122

SEQ ID NO: 480          moltype = AA  length = 122
FEATURE                 Location/Qualifiers
source                  1..122
                        mol_type = protein
                        organism = Homo sapiens
SEQUENCE: 480
QVQLVQSGAE VKKPGASVKV SCKASGGTFT SYDINWVRQA PGQGLEWMGI INPGGGNARH  60
TQKFQGRVTM TRDTSTSTVY MELSSLRSED TAVYYCAREV FSENYYYYMD VWGKGTTVTV  120
SS                                                                       122

SEQ ID NO: 481          moltype = AA  length = 122
FEATURE                 Location/Qualifiers
source                  1..122
                        mol_type = protein
                        organism = Homo sapiens
SEQUENCE: 481
QVQLVQSGAE VKKPGASVKV SCKASGYTFT SYYMHWVRQA PGQGLEWMGI INPSDGSTTY  60
AQKFQGRVTM TRDTSTSTVY MELSSLRSED TAVYYCAREW DYTHYYYGMD VWGQGTTVTV  120
SS                                                                       122

SEQ ID NO: 482          moltype = AA  length = 122
FEATURE                 Location/Qualifiers
source                  1..122
                        mol_type = protein
                        organism = Homo sapiens
SEQUENCE: 482
QVQLVQSGAE VKKPGASVKV SCKASGNTFT SHWIHWVRQA PGQGLEWMGG FDPEDGETVY  60
AQNFQGRVTM TRDTSTSTVY MELSSLRSED TAVYYCARGD SSGYYQYYFD YWGQGTLVTV  120
SS                                                                       122

SEQ ID NO: 483          moltype = AA  length = 122
FEATURE                 Location/Qualifiers
source                  1..122
                        mol_type = protein
                        organism = Homo sapiens
SEQUENCE: 483
QVQLVQSGAE VKKPGSSVKV SCKASGYTFT SYDINWVRQA PGQGLEWMGG ITPVFGIANY  60
AQKFQGRVTI TADESTSTAY MELSSLRSED TAVYYCARGS WDSSSWYIPE YWGQGTLVTV  120
SS                                                                       122

SEQ ID NO: 484          moltype = AA  length = 122
FEATURE                 Location/Qualifiers
source                  1..122
                        mol_type = protein
                        organism = Homo sapiens
SEQUENCE: 484
QVQLVQSGAE VKKPGASVKV SCKASGFTFS DYDIVWVRQA PGQGLEWMGI INPRGGSTNY  60
AQKFQGRVTM TRDTSTSTVY MELSSLRSED TAVYYCASLV WGGAYYYYMD VWGQGTTVTV  120
SS                                                                       122

SEQ ID NO: 485          moltype = AA  length = 122
FEATURE                 Location/Qualifiers
source                  1..122
                        mol_type = protein
                        organism = Homo sapiens
SEQUENCE: 485
QVQLVQSGAE VKKPGASVKV SCKASGYTFT SYGISWVRQA PGQGLEWMGW MNPNNGDTDY  60
```

```
AQKFQGRVTM TRDTSTSTVY MELSSLRSED TAVYYCTTPV FSGSYYWYFD PWGQGTLVTV    120
SS                                                                  122

SEQ ID NO: 486          moltype = AA  length = 123
FEATURE                 Location/Qualifiers
source                  1..123
                        mol_type = protein
                        organism = Homo sapiens
SEQUENCE: 486
QVQLVQSGAE VKKPGASVKV SCKASGYTFT SYDINWVRQA PGQGLEWMGI INPSGGGTSY    60
AQKFQGRVTM TRDTSTSTVY MELSSLRSED TAVYYCTTDQ AVAGPYYYGM DVWGQGTLVT    120
VSS                                                                 123

SEQ ID NO: 487          moltype = AA  length = 123
FEATURE                 Location/Qualifiers
source                  1..123
                        mol_type = protein
                        organism = Homo sapiens
SEQUENCE: 487
QVQLVQSGAE VKKPGASVKV SCKASGGTFS SYAISWVRQA PGQGLEWMGL INPGSGNTNY    60
AQKFQGRVTM TRDTSTSTVY MELSSLRSED TAVYYCARDR WLAGPYYYGM DVWGQGTTVT    120
VSS                                                                 123

SEQ ID NO: 488          moltype = AA  length = 123
FEATURE                 Location/Qualifiers
source                  1..123
                        mol_type = protein
                        organism = Homo sapiens
SEQUENCE: 488
QVQLVQSGAE VKKPGSSVKV SCKASGYMFT GHDMHWVRQA PGQGLEWMGG IIPIFGTPNY    60
AQKFQGRVTI TADESTSTAY MELSSLRSED TAVYYCARVM GPVDYYYYGM DVWGQGTTVT    120
VSS                                                                 123

SEQ ID NO: 489          moltype = AA  length = 123
FEATURE                 Location/Qualifiers
source                  1..123
                        mol_type = protein
                        organism = Homo sapiens
SEQUENCE: 489
QVQLVQSGAE VKKPGASVKV SCKASGYIFS NYDMHWVRQA PGQGLEWMGI INPSDGSTTY    60
AQKFQGRVTM TRDTSTSTVY MELSSLRSED TAVYYCARDL GPFGSYYYYM DVWGKGTTVT    120
VSS                                                                 123

SEQ ID NO: 490          moltype = AA  length = 123
FEATURE                 Location/Qualifiers
source                  1..123
                        mol_type = protein
                        organism = Homo sapiens
SEQUENCE: 490
EVQLVESGGG LVKPGGSLRL SCAASGFTFS SYAMTWVRQA PGKGLEWVST INGDGDDTDY    60
ADSVKGRFTI SRDDSKNTLY LQMNSLKTED TAVYYCAREG VVVPPYYYYM DVWGKGTTVT    120
VSS                                                                 123

SEQ ID NO: 491          moltype = AA  length = 123
FEATURE                 Location/Qualifiers
source                  1..123
                        mol_type = protein
                        organism = Homo sapiens
SEQUENCE: 491
QVQLVQSGAE VKKPGASVKV SCKASGYTFT TYYMHWVRQA PGQGLEWMGQ IDPNSGDTIY    60
PQKFQGRVTM TRDTSTSTVY MELSSLRSED TAVYYCARSS GWSRYYYYYM DVWGKGTTVT    120
VSS                                                                 123

SEQ ID NO: 492          moltype = AA  length = 123
FEATURE                 Location/Qualifiers
source                  1..123
                        mol_type = protein
                        organism = Homo sapiens
SEQUENCE: 492
QVQLVQSGAE VKKPGASVKV SCKASGSTFT NYQIHWVRQA PGQGLEWMGI INPSGGSTSY    60
AQKFQGRVTM TRDTSTSTVY MELSSLRSED TAVYYCARDN GMTTGYYYYM DVWGKGTTVT    120
VSS                                                                 123

SEQ ID NO: 493          moltype = AA  length = 123
FEATURE                 Location/Qualifiers
source                  1..123
                        mol_type = protein
                        organism = Homo sapiens
SEQUENCE: 493
```

-continued

```
QVQLVQSGAE VKKPGASVKV SCKASGYTFT SYDIVWVRQA PGQGLEWMGI INPSGGSTSY   60
AQKFQGRVTM TRDTSTSTVY MELSSLRSED TAVYYCARDR AMVTGYYYGM DVWGQGTTVT  120
VSS                                                                123

SEQ ID NO: 494          moltype = AA   length = 124
FEATURE                 Location/Qualifiers
source                  1..124
                        mol_type = protein
                        organism = Homo sapiens
SEQUENCE: 494
QVQLVQSGAE VKKPGASVKV SCKASGYTFT SYDINWVRQA PGQGLEWMGI VNPSDGNTNY   60
AQKFQGRVTM TRDTSTSTVY MELSSLRSED TAVYYCARDR GYGDRGYYYG MDVWGQGTTV  120
TVSS                                                               124

SEQ ID NO: 495          moltype = AA   length = 124
FEATURE                 Location/Qualifiers
source                  1..124
                        mol_type = protein
                        organism = Homo sapiens
SEQUENCE: 495
QVQLVQSGAE VKKPGASVKV SCKASGGTLS SYDINWVRQA PGQGLEWMGW INTYNGNTYY   60
AQKLQGRVTM TRDTSTSTVY MELSSLRSED TAVYYCATSP KATADYYYYY MDVWGKGTTV  120
TVSS                                                               124

SEQ ID NO: 496          moltype = AA   length = 124
FEATURE                 Location/Qualifiers
source                  1..124
                        mol_type = protein
                        organism = Homo sapiens
SEQUENCE: 496
QVQLVQSGAE VKKPGASVKV SCKASGYTFT SYDINWVRQA PGQGLEWMGI INPSDGITDY   60
AQRFQGRVTM TRDTSTSTVY MELSSLRSED TAVYYCTTST VTPSYYYYYG MDVWGQGTTV  120
TVSS                                                               124

SEQ ID NO: 497          moltype = AA   length = 125
FEATURE                 Location/Qualifiers
source                  1..125
                        mol_type = protein
                        organism = Homo sapiens
SEQUENCE: 497
QVQLVQSGAE VKKPGASVKV SCKASGYTFT SHAIHWVRQA PGQGLEWMGI INPRDGDTVY   60
AQKFQGRVTM TRDTSTSTVY MELSSLRSED TAVYYCAREP VAGTGYYYYY GMDVWGQGTL  120
VTVSS                                                              125

SEQ ID NO: 498          moltype = AA   length = 126
FEATURE                 Location/Qualifiers
source                  1..126
                        mol_type = protein
                        organism = Homo sapiens
SEQUENCE: 498
QVQLVQSGAE VKKPGASVKV SCKASGGTFN SYGINWVRQA PGQGLEWMGW MNPNSGNTGY   60
AQKFQGRVTM TRDTSTSTVY MELSSLRSED TAVYYCARDN LAGFWSDYYY YGMDVWGQGT  120
TVTVSS                                                             126

SEQ ID NO: 499          moltype = AA   length = 108
FEATURE                 Location/Qualifiers
source                  1..108
                        mol_type = protein
                        organism = Homo sapiens
SEQUENCE: 499
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ SYSTPLTFGG GTKVEIKR                108

SEQ ID NO: 500          moltype = AA   length = 108
FEATURE                 Location/Qualifiers
source                  1..108
                        mol_type = protein
                        organism = Homo sapiens
SEQUENCE: 500
DIQMTQSPSS LSASVGDRVT ITCQASQDIS NYLNWYQQKP GKAPKLLIYA ASSLQSGVPS   60
RFSGSGSGTD FTLTISSLQP EDFATYYCQQ SYSNLVSFGQ GTKVEIKR                108

SEQ ID NO: 501          moltype = AA   length = 108
FEATURE                 Location/Qualifiers
source                  1..108
                        mol_type = protein
                        organism = Homo sapiens
SEQUENCE: 501
DIQMTQSPSS LSASVGDRVT ITCRASQSIS SYLNWYQQKP GKAPKLLIYA ASSLQSGVPS   60
```

-continued

```
RFSGSGSGTD FTLTISSLQP EDFATYYCQQ SYSTPLTFGQ GTKVEIKR            108

SEQ ID NO: 502           moltype = AA  length = 113
FEATURE                  Location/Qualifiers
source                   1..113
                         mol_type = protein
                         organism = Homo sapiens
SEQUENCE: 502
DIVMTQSPLS LPVTPGEPAS ISCRSSQSLL HSNGYNYLDW YLQKPGQSPQ LLIYLGSNRA  60
SGVPDRFSGS GSGTDFTLKI SRVEAEDVGV YYCMQALQTP FTFGPGTKVD IKR         113

SEQ ID NO: 503           moltype = AA  length = 113
FEATURE                  Location/Qualifiers
source                   1..113
                         mol_type = protein
                         organism = Homo sapiens
SEQUENCE: 503
DIVMTQSPLS LPVTPGEPAS ISCRSSQSLL HSNGYNYLDW YLQKPGQSPQ LLIYLGSNRA  60
SGVPDRFSGS GSGTDFTLKI SRVEAEDVGV YYCMQGLQTP HTFGQGTKVE IKR         113

SEQ ID NO: 504           moltype = AA  length = 107
FEATURE                  Location/Qualifiers
source                   1..107
                         mol_type = protein
                         organism = Homo sapiens
SEQUENCE: 504
DIQMTQSPSS LSASVGDRVT ITCRASQSIS RNLNWYQQKP GKAPKLLIYK ASNLKGGVPS  60
RFSGSGSGTD FTLTISSLQP EDFATYYCQQ TYSAPLFGQG TKLEIKR                107

SEQ ID NO: 505           moltype = AA  length = 113
FEATURE                  Location/Qualifiers
source                   1..113
                         mol_type = protein
                         organism = Homo sapiens
SEQUENCE: 505
DIVMTQSPLS LPVTPGEPAS ISCRSSQSLL HSNGYNYLDW YLQKPGQSPQ LLIYLGSNRA  60
SGVPDRFSGS GSGTDFTLKI SRVEAEDVGV YYCMQTLQTP LTFGQGTKVE IKR         113

SEQ ID NO: 506           moltype = AA  length = 109
FEATURE                  Location/Qualifiers
source                   1..109
                         mol_type = protein
                         organism = Homo sapiens
SEQUENCE: 506
EIVMTQSPAT LSVSPGERAT LSCRASQSVS ASDLAWYQQK PGQAPRLLIY GASTRATGIP  60
ARFSGSGSGT EFTLTISSLQ SEDFAVYYCQ QYGDSPGSFG QGTKLEIKR             109

SEQ ID NO: 507           moltype = AA  length = 108
FEATURE                  Location/Qualifiers
source                   1..108
                         mol_type = protein
                         organism = Homo sapiens
SEQUENCE: 507
DIQMTQSPSS LSASVGDRVT ITCQASQDIG NYLNWYQQKP GKAPKLLIYA ASTLQRGVPS  60
RFSGSGSGTD FTLTISSLQP EDFATYYCQQ ANSFPPTFGG GTKVEIKR               108

SEQ ID NO: 508           moltype = AA  length = 107
FEATURE                  Location/Qualifiers
source                   1..107
                         mol_type = protein
                         organism = Homo sapiens
SEQUENCE: 508
EIVMTQSPAT LSVSPGERAT LSCRASQSIS THLAWYQQKP GQAPRLLIYG ASTRATGIPA  60
RFSGSGSGTE FTLTISSLQS EDFAVYYCQQ YGNSRTFGQG TKVEIKR                107

SEQ ID NO: 509           moltype = AA  length = 108
FEATURE                  Location/Qualifiers
source                   1..108
                         mol_type = protein
                         organism = Homo sapiens
SEQUENCE: 509
DIQMTQSPSS LSASVGDRVT ITCRASQTIS NYLNWYQQKP GKAPKLLIYA ASTLQSGVPS  60
RFSGSGSGTD FTLTISSLQP EDFATYYCQQ SYSTPPTFGQ GTKLEIKR               108

SEQ ID NO: 510           moltype = AA  length = 108
FEATURE                  Location/Qualifiers
source                   1..108
                         mol_type = protein
                         organism = Homo sapiens
```

-continued

```
SEQUENCE: 510
DIQMTQSPSS LSASVGDRVT ITCRASQGIR NDLGWYQQKP GKAPKLLIYD ASTLQSGVPS  60
RFSGSGSGTD FTLTISSLQP EDFATYYCQQ SYSSPYTFGQ GTKLEIKR                108

SEQ ID NO: 511          moltype = AA   length = 108
FEATURE                 Location/Qualifiers
source                  1..108
                        mol_type = protein
                        organism = Homo sapiens
SEQUENCE: 511
DIQMTQSPSS LSASVGDRVT ITCRASQSIS NYLNWYQQKP GKAPKLLIYA ASSLQSGVPS  60
RFSGSGSGTD FTLTISSLQP EDFATYYCQQ SYSTPYTFGQ GTKLEIKR                108

SEQ ID NO: 512          moltype = AA   length = 113
FEATURE                 Location/Qualifiers
source                  1..113
                        mol_type = protein
                        organism = Homo sapiens
SEQUENCE: 512
DIVMTQSPLS LPVTPGEPAS ISCRSSQSLL HSNGYNYLDW YLQKPGQSPQ LLIYLGSNRA  60
SGVPDRFSGS GSGTDFTLKI SRVEAEDVGV YYCMQGAHWP PTFGQGTKLE IKR          113

SEQ ID NO: 513          moltype = AA   length = 108
FEATURE                 Location/Qualifiers
source                  1..108
                        mol_type = protein
                        organism = Homo sapiens
SEQUENCE: 513
DIQMTQSPSS LSASVGDRVT ITCRASQGIS DSLAWYQQKP GKAPKLLIYG ASSLRSGVPS  60
RFSGSGSGTD FTLTISSLQP EDFATYYCQQ SYRTPYTFGQ GTKLEIKR                108

SEQ ID NO: 514          moltype = AA   length = 108
FEATURE                 Location/Qualifiers
source                  1..108
                        mol_type = protein
                        organism = Homo sapiens
SEQUENCE: 514
DIQMTQSPSS LSASVGDRVT ITCRASQSIS NYLNWYQQKP GKAPKLLIYA ASSLQSGVPS  60
RFSGSGSGTD FTLTISSLQP EDFATYYCQE SFTTQWTFGQ GTKVEIKR                108

SEQ ID NO: 515          moltype = AA   length = 108
FEATURE                 Location/Qualifiers
source                  1..108
                        mol_type = protein
                        organism = Homo sapiens
SEQUENCE: 515
DIQMTQSPSS LSASVGDRVT ITCQASQDIH NYLNWYQQKP GKAPKLLIYD ASNLETGVPS  60
RFSGSGSGTD FTLTISSLQP EDFATYYCQQ ANSFPPTFGP GTKVDIKR                108

SEQ ID NO: 516          moltype = AA   length = 109
FEATURE                 Location/Qualifiers
source                  1..109
                        mol_type = protein
                        organism = Homo sapiens
SEQUENCE: 516
DIQMTQSPSS LSASVGDRVT ITCQASQDIS NYLNWYQQKP GKAPKLLIYS ASSLQSGVPS  60
RFSGSGSGTD FTLTISSLQP EDFATYYCQQ RSNWPLYTFG QGTKVEIKR               109

SEQ ID NO: 517          moltype = AA   length = 108
FEATURE                 Location/Qualifiers
source                  1..108
                        mol_type = protein
                        organism = Homo sapiens
SEQUENCE: 517
DIQMTQSPSS LSASVGDRVT ITCRASQSIS DWLAWYQQKP GKAPKLLIYA ASSLQTGVPS  60
RFSGSGSGTD FTLTISSLQP EDFATYYCQQ AISFPITFGQ GTKVEIKR                108

SEQ ID NO: 518          moltype = AA   length = 108
FEATURE                 Location/Qualifiers
source                  1..108
                        mol_type = protein
                        organism = Homo sapiens
SEQUENCE: 518
DIQMTQSPSS LSASVGDRVT ITCQASQDIS NYLNWYQQKP GKAPKLLIYS ASTLQSGVPS  60
RFSGSGSGTD FTLTISSLQP EDFATYYCQQ SYSSPFTFGP GTKVDIKR                108

SEQ ID NO: 519          moltype = AA   length = 108
FEATURE                 Location/Qualifiers
source                  1..108
```

```
                        mol_type = protein
                        organism = Homo sapiens
SEQUENCE: 519
DIQMTQSPSS LSASVGDRVT ITCRASQSIS TWLAWYQQKP GKAPKLLIYA ASTLQSGVPS   60
RFSGSGSGTD FTLTISSLQP EDFATYYCQQ AISFPLTFGG GTKVEIKR                108

SEQ ID NO: 520          moltype = AA   length = 108
FEATURE                 Location/Qualifiers
source                  1..108
                        mol_type = protein
                        organism = Homo sapiens
SEQUENCE: 520
DIQMTQSPSS LSASVGDRVT ITCRASQSIS NYLNWYQQKP GKAPKLLIYA ASTLQSGVPS   60
RFSGSGSGTD FTLTISSLQP EDFATYYCQQ SYTFPITFGQ GTRLEIKR                108

SEQ ID NO: 521          moltype = AA   length = 113
FEATURE                 Location/Qualifiers
source                  1..113
                        mol_type = protein
                        organism = Homo sapiens
SEQUENCE: 521
DIVMTQSPLS LPVTPGEPAS ISCRSSQSLL HSNGYNYLDW YLQKPGQSPQ LLIYDASHLE   60
TGVPDRFSGS GSGTDFTLKI SRVEAEDVGV YYCQQYYSYP PTFGQGTKVE IKR          113

SEQ ID NO: 522          moltype = AA   length = 108
FEATURE                 Location/Qualifiers
source                  1..108
                        mol_type = protein
                        organism = Homo sapiens
SEQUENCE: 522
DIQMTQSPSS LSASVGDRVT ITCQASQDIS NYLNWYQQKP GKAPKLLIYA ASTLHSGVPS   60
RFSGSGSGTD FTLTISSLQP EDFATYYCQQ SYSAPLTFGP GTKVDIKR                108

SEQ ID NO: 523          moltype = AA   length = 108
FEATURE                 Location/Qualifiers
source                  1..108
                        mol_type = protein
                        organism = Homo sapiens
SEQUENCE: 523
DIQMTQSPSS LSASVGDRVT ITCQASQDIS NYLNWYQQKP GKAPKLLIYA ASTLQSGVPS   60
RFSGSGSGTD FTLTISSLQP EDFATYYCQQ SFSTFYTFGQ GTKVEIKR                108

SEQ ID NO: 524          moltype = AA   length = 108
FEATURE                 Location/Qualifiers
source                  1..108
                        mol_type = protein
                        organism = Homo sapiens
SEQUENCE: 524
DIQMTQSPSS LSASVGDRVT ITCQASQDIS NYLNWYQQKP GKAPKLLIYA ASTLQSGVPS   60
RFSGSGSGTD FTLTISSLQP EDFATYYCQQ SYSIPFTFGP GTKVDIKR                108

SEQ ID NO: 525          moltype = AA   length = 108
FEATURE                 Location/Qualifiers
source                  1..108
                        mol_type = protein
                        organism = Homo sapiens
SEQUENCE: 525
DIQMTQSPSS LSASVGDRVT ITCRASQSIN RFLNWYQQKP GKAPKLLIYA ASSLQNGVPS   60
RFSGSGSGTD FTLTISSLQP EDFATYYCQQ SYSTPYTFGQ GTKVEIKR                108

SEQ ID NO: 526          moltype = AA   length = 108
FEATURE                 Location/Qualifiers
source                  1..108
                        mol_type = protein
                        organism = Homo sapiens
SEQUENCE: 526
DIQMTQSPSS LSASVGDRVT ITCQASQDIS NYLNWYQQKP GKAPKLLIYA ASTLQSGVPS   60
RFSGSGSGTD FTLTISSLQP EDFATYYCQQ SYSTPITFGQ GTRLEIKR                108

SEQ ID NO: 527          moltype = AA   length = 108
FEATURE                 Location/Qualifiers
source                  1..108
                        mol_type = protein
                        organism = Homo sapiens
SEQUENCE: 527
DIQMTQSPSS LSASVGDRVT ITCRASQSVS TYLNWYQQKP GKAPKLLIYA ASSLQSGVPS   60
RFSGSGSGTD FTLTISSLQP EDFATYYCQQ SYTIPSTFGQ GTKVEIKR                108

SEQ ID NO: 528          moltype = AA   length = 108
```

-continued

```
FEATURE                   Location/Qualifiers
source                    1..108
                          mol_type = protein
                          organism = Homo sapiens
SEQUENCE: 528
DIQMTQSPSS LSASVGDRVT ITCQASQDIA KYLNWYQQKP GKAPKLLIYA ASSLQSGVPS   60
RFSGSGSGTD FTLTISSLQP EDFATYYCQQ SYSAPPTFGG GTKVEIKR                108

SEQ ID NO: 529           moltype = AA  length = 108
FEATURE                  Location/Qualifiers
source                   1..108
                         mol_type = protein
                         organism = Homo sapiens
SEQUENCE: 529
DIQMTQSPSS LSASVGDRVT ITCQASQGIT NYLNWYQQKP GKAPKLLIYG ASSLQSGVPS   60
RFSGSGSGTD FTLTISSLQP EDFATYYCQQ SYSTPWTFGP GTKVDIKR                108

SEQ ID NO: 530           moltype = AA  length = 108
FEATURE                  Location/Qualifiers
source                   1..108
                         mol_type = protein
                         organism = Homo sapiens
SEQUENCE: 530
DIQMTQSPSS LSASVGDRVT ITCQASQDIH NYLNWYQQKP GKAPKLLIYA ASTLQSGVPS   60
RFSGSGSGTD FTLTISSLQP EDFATYYCQQ SYTTPLTFGQ GTKVEIKR                108

SEQ ID NO: 531           moltype = AA  length = 108
FEATURE                  Location/Qualifiers
source                   1..108
                         mol_type = protein
                         organism = Homo sapiens
SEQUENCE: 531
DIQMTQSPSS LSASVGDRVT ITCQASQDIS NYLNWYQQKP GKAPKLLIYS AFSLQSGVPS   60
RFSGSGSGTD FTLTISSLQP EDFATYYCQQ SYSAPITFGQ GTRLEIKR                108

SEQ ID NO: 532           moltype = AA  length = 109
FEATURE                  Location/Qualifiers
source                   1..109
                         mol_type = protein
                         organism = Homo sapiens
SEQUENCE: 532
DIQMTQSPSS LSASVGDRVT ITCRASQSIS SYLNWYQQKP GKAPKLLIYS ASNLQSGVPS   60
RFSGSGSGTD FTLTISSLQP EDFATYYCQQ RSNWPPVTFG QGTKVEIKR               109

SEQ ID NO: 533           moltype = AA  length = 108
FEATURE                  Location/Qualifiers
source                   1..108
                         mol_type = protein
                         organism = Homo sapiens
SEQUENCE: 533
DIQMTQSPSS LSASVGDRVT ITCQANQDIS NFLEWYQQKP GKAPKLLIYD ASSLESGVPS   60
RFSGSGSGTD FTLTISSLQP EDFATYYCQQ SYSIPITFGQ GTRLEIKR                108

SEQ ID NO: 534           moltype = AA  length = 108
FEATURE                  Location/Qualifiers
source                   1..108
                         mol_type = protein
                         organism = Homo sapiens
SEQUENCE: 534
DIQMTQSPSS LSASVGDRVT ITCRASQGIS NNLNWYQQKP GKAPKLLIYE ASTLESGVPS   60
RFSGSGSGTD FTLTISSLQP EDFATYYCQQ SYSTPLTFGG GTKVEIKR                108

SEQ ID NO: 535           moltype = AA  length = 113
FEATURE                  Location/Qualifiers
source                   1..113
                         mol_type = protein
                         organism = Homo sapiens
SEQUENCE: 535
DIVMTQSPLS LPVTPGEPAS ISCRSSQSLL HSNGYNYLDW YLQKPGQSPQ LLIYGASTLE   60
TGVPDRFSGS GSGTDFTLKI SRVEAEDVGV YYCMQGLQPP GTFGQGTKVE IKR          113

SEQ ID NO: 536           moltype = AA  length = 108
FEATURE                  Location/Qualifiers
source                   1..108
                         mol_type = protein
                         organism = Homo sapiens
SEQUENCE: 536
DIQMTQSPSS LSASVGDRVT ITCRASQSIS RSLVWYQQKP GKAPKLLIYA ASTLQTGVPS   60
RFSGSGSGTD FTLTISSLQP EDFATYYCQQ SYNHFRTFGP GTKVDIKR                108
```

-continued

```
SEQ ID NO: 537          moltype = AA   length = 108
FEATURE                 Location/Qualifiers
source                  1..108
                        mol_type = protein
                        organism = Homo sapiens
SEQUENCE: 537
DIQMTQSPSS LSASVGDRVT ITCQASQDIS NYLNWYQQKP GKAPKLLIYD ASNLETGVPS    60
RFSGSGSGTD FTLTISSLQP EDFATYYCQR SDSTPLTFGG GTKVEIKR                 108

SEQ ID NO: 538          moltype = AA   length = 108
FEATURE                 Location/Qualifiers
source                  1..108
                        mol_type = protein
                        organism = Homo sapiens
SEQUENCE: 538
DIQMTQSPSS LSASVGDRVT ITCQASHDIS KSLNWYQQKP GKAPKLLIYG ASTLQSGVPS    60
RFSGSGSGTD FTLTISSLQP EDFATYYCQQ LNSYPRTFGG GTKVEIKR                 108

SEQ ID NO: 539          moltype = AA   length = 108
FEATURE                 Location/Qualifiers
source                  1..108
                        mol_type = protein
                        organism = Homo sapiens
SEQUENCE: 539
DIQMTQSPSS LSASVGDRVT ITCRASQDIG AYLAWYQQKP GKAPKLLIYA ASSLQSGVPS    60
RFSGSGSGTD FTLTISSLQP EDFATYYCQQ SYSIPYTFGQ GTKLEIKR                 108

SEQ ID NO: 540          moltype = AA   length = 108
FEATURE                 Location/Qualifiers
source                  1..108
                        mol_type = protein
                        organism = Homo sapiens
SEQUENCE: 540
DIQMTQSPSS LSASVGDRVT ITCRASQSIS SYLAWYQQKP GKAPKLLIYA ASSLQSGVPS    60
RFSGSGSGTD FTLTISSLQP EDFATYYCQQ SYSTPYTFGQ GTKLEIKR                 108

SEQ ID NO: 541          moltype = AA   length = 108
FEATURE                 Location/Qualifiers
source                  1..108
                        mol_type = protein
                        organism = Homo sapiens
SEQUENCE: 541
DIQMTQSPSS LSASVGDRVT ITCRASQGIR SYLAWYQQKP GKAPKLLIYG ASNLETGVPS    60
RFSGSGSGTD FTLTISSLQP EDFATYYCQQ SYSTPYTFGQ GTKLEIKR                 108

SEQ ID NO: 542          moltype = AA   length = 108
FEATURE                 Location/Qualifiers
source                  1..108
                        mol_type = protein
                        organism = Homo sapiens
SEQUENCE: 542
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ TYSTPYTFGQ GTKLEIKR                 108

SEQ ID NO: 543          moltype = AA   length = 108
FEATURE                 Location/Qualifiers
source                  1..108
                        mol_type = protein
                        organism = Homo sapiens
SEQUENCE: 543
DIQMTQSPSS LSASVGDRVT ITCRASQNIG TWLAWYQQKP GKAPKLLIYA ASTLQSGVPS    60
RFSGSGSGTD FTLTISSLQP EDFATYYCQQ SYSTPQTFGP GTKVDIKR                 108

SEQ ID NO: 544          moltype = AA   length = 108
FEATURE                 Location/Qualifiers
source                  1..108
                        mol_type = protein
                        organism = Homo sapiens
SEQUENCE: 544
DIQMTQSPSS LSASVGDRVT ITCRASQTIS YYLNWYQQKP GKAPKLLIYA ASTLQSGVPS    60
RFSGSGSGTD FTLTISSLQP EDFATYYCQQ SYRTPYTFGQ GTKLEIKR                 108

SEQ ID NO: 545          moltype = AA   length = 112
FEATURE                 Location/Qualifiers
source                  1..112
                        mol_type = protein
                        organism = Homo sapiens
SEQUENCE: 545
```

```
DIVMTQSPLS LPVTPGEPAS ISCRSSQSLL HSNGYNYLDW YLQKPGQSPQ LLIYMGSNRA  60
SGVPDRFSGS GSGTDFTLKI SRVEAEDVGV YYCMQGTHWP TFGQGTRLEI KR          112

SEQ ID NO: 546          moltype = AA  length = 108
FEATURE                 Location/Qualifiers
source                  1..108
                        mol_type = protein
                        organism = Homo sapiens
SEQUENCE: 546
DIQMTQSPSS LSASVGDRVT ITCRASQNIN NYLNWYQQKP GKAPKLLIYG ASSLQSGVPS  60
RFSGSGSGTD FTLTISSLQP EDFATYYCQQ TFSLPYTFGQ GTKVEIKR              108

SEQ ID NO: 547          moltype = AA  length = 108
FEATURE                 Location/Qualifiers
source                  1..108
                        mol_type = protein
                        organism = Homo sapiens
SEQUENCE: 547
DIQMTQSPSS LSASVGDRVT ITCRASQTIS TYLNWYQQKP GKAPKLLIYD ASNLETGVPS  60
RFSGSGSGTD FTLTISSLQP EDFATYYCQQ SYSTPYTFGQ GTKLEIKR              108

SEQ ID NO: 548          moltype = AA  length = 108
FEATURE                 Location/Qualifiers
source                  1..108
                        mol_type = protein
                        organism = Homo sapiens
SEQUENCE: 548
DIQMTQSPSS LSASVGDRVT ITCRASRGIG NDLAWYQQKP GKAPKLLIYD ASTLETGVPS  60
RFSGSGSGTD FTLTISSLQP EDFATYYCQQ GYNMPLTFGG GTKVEIKR              108

SEQ ID NO: 549          moltype = AA  length = 108
FEATURE                 Location/Qualifiers
source                  1..108
                        mol_type = protein
                        organism = Homo sapiens
SEQUENCE: 549
DIQMTQSPSS LSASVGDRVT ITCRASQTIG NYVNWYQQKP GKAPKLLIYG ASNLHTGVPS  60
RFSGSGSGTD FTLTISSLQP EDFATYYCQQ TYSAPLTFGG GTKVEIKR              108

SEQ ID NO: 550          moltype = AA  length = 108
FEATURE                 Location/Qualifiers
source                  1..108
                        mol_type = protein
                        organism = Homo sapiens
SEQUENCE: 550
DIQMTQSPSS LSASVGDRVT ITCRASQFIG SWLAWYQQKP GKAPKLLIYA ASTLQSGVPS  60
RFSGSGSGTD FTLTISSLQP EDFATYYCQQ SYSFPWTFGQ GTKVEIKR              108

SEQ ID NO: 551          moltype = AA  length = 108
FEATURE                 Location/Qualifiers
source                  1..108
                        mol_type = protein
                        organism = Homo sapiens
SEQUENCE: 551
DIQMTQSPSS LSASVGDRVT ITCRASQSIS SWMAWYQQKP GKAPKLLIYD ASNLETGVPS  60
RFSGSGSGTD FTLTISSLQP EDFATYYCQQ TYSTPYIFGQ GTKVEIKR              108

SEQ ID NO: 552          moltype = AA  length = 108
FEATURE                 Location/Qualifiers
source                  1..108
                        mol_type = protein
                        organism = Homo sapiens
SEQUENCE: 552
DIQMTQSPSS LSASVGDRVT ITCRASQGIS NNLNWYQQKP GKAPKLLIYD ASNLETGVPS  60
RFSGSGSGTD FTLTISSLQP EDFATYYCQQ SYSSPWTFGQ GTKVEIKR              108

SEQ ID NO: 553          moltype = AA  length = 114
FEATURE                 Location/Qualifiers
source                  1..114
                        mol_type = protein
                        organism = Homo sapiens
SEQUENCE: 553
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQYASA PRTFGQGTKL EIKR        114

SEQ ID NO: 554          moltype = AA  length = 108
FEATURE                 Location/Qualifiers
source                  1..108
                        mol_type = protein
```

```
                          organism = Homo sapiens
SEQUENCE: 554
DIQMTQSPSS LSASVGDRVT ITCRASQSIS SYLNWYQQKP GKAPKLLIYK TSSLESGVPS  60
RFSGSGSGTD FTLTISSLQP EDFATYYCQQ SFTIPYTFGQ GTKVEIKR               108

SEQ ID NO: 555            moltype = AA  length = 108
FEATURE                   Location/Qualifiers
source                    1..108
                          mol_type = protein
                          organism = Homo sapiens
SEQUENCE: 555
DIQMTQSPSS LSASVGDRVT ITCRVSQGIS SYLNWYQQKP GKAPKLLIYG ASSLQSGVPS  60
RFSGSGSGTD FTLTISSLQP EDFATYYCQQ SYSTPLTFGG GTKVEIKR               108

SEQ ID NO: 556            moltype = AA  length = 108
FEATURE                   Location/Qualifiers
source                    1..108
                          mol_type = protein
                          organism = Homo sapiens
SEQUENCE: 556
DIQMTQSPSS LSASVGDRVT ITCRASQSIS DWLAWYQQKP GKAPKLLIYD ASNLETGVPS  60
RFSGSGSGTD FTLTISSLQP EDFATYYCQQ SYSTPLTFGG GTKVEIKR               108

SEQ ID NO: 557            moltype = AA  length = 108
FEATURE                   Location/Qualifiers
source                    1..108
                          mol_type = protein
                          organism = Homo sapiens
SEQUENCE: 557
DIQMTQSPSS LSASVGDRVT ITCRASQGIS NYLAWYQQKP GKAPKLLIYS ASNLQSGVPS  60
RFSGSGSGTD FTLTISSLQP EDFATYYCQQ TYRTPPTFGP GTKVDIKR               108

SEQ ID NO: 558            moltype = AA  length = 108
FEATURE                   Location/Qualifiers
source                    1..108
                          mol_type = protein
                          organism = Homo sapiens
SEQUENCE: 558
DIQMTQSPSS LSASVGDRVT ITCRASQSIR NYLTWYQQKP GKAPKLLIYS ASNLQSGVPS  60
RFSGSGSGTD FTLTISSLQP EDFATYYCQQ SYSTPLTFGQ GTKVEIKR               108

SEQ ID NO: 559            moltype = AA  length = 108
FEATURE                   Location/Qualifiers
source                    1..108
                          mol_type = protein
                          organism = Homo sapiens
SEQUENCE: 559
DIQMTQSPSS LSASVGDRVT ITCRASQNIR LYLNWYQQKP GKAPKLLIYA ASTLQSGVPS  60
RFSGSGSGTD FTLTISSLQP EDFATYYCQQ SLTTPFTFGP GTKVDIKR               108

SEQ ID NO: 560            moltype = AA  length = 108
FEATURE                   Location/Qualifiers
source                    1..108
                          mol_type = protein
                          organism = Homo sapiens
SEQUENCE: 560
DIQMTQSPSS LSASVGDRVT ITCQASQDIR KFLNWYQQKP GKAPKLLIYA ASSLQSGVPS  60
RFSGSGSGTD FTLTISSLQP EDFATYYCQQ LNGYPGTFGQ GTRLEIKR               108

SEQ ID NO: 561            moltype = AA  length = 108
FEATURE                   Location/Qualifiers
source                    1..108
                          mol_type = protein
                          organism = Homo sapiens
SEQUENCE: 561
DIQMTQSPSS LSASVGDRVT ITCRASQSIS SYLNWYQQKP GKAPKLLIYT ASNLQSGVPS  60
RFSGSGSGTD FTLTISSLQP EDFATYYCQQ SYSLPLTFGG GTKVEIKR               108

SEQ ID NO: 562            moltype = AA  length = 108
FEATURE                   Location/Qualifiers
source                    1..108
                          mol_type = protein
                          organism = Homo sapiens
SEQUENCE: 562
DIQMTQSPSS LSASVGDRVT ITCQASQDIS NYLSWYQQKP GKAPKLLIYD ASNLQSGVPS  60
RFSGSGSGTD FTLTISSLQP EDFATYYCQQ TYTTPRTFGP GTKVDIKR               108

SEQ ID NO: 563            moltype = AA  length = 108
FEATURE                   Location/Qualifiers
```

-continued

```
source                  1..108
                        mol_type = protein
                        organism = Homo sapiens
SEQUENCE: 563
DIQMTQSPSS LSASVGDRVT ITCRASQNVR SWLAWYQQKP GKAPKLLIYA ASSLQSGVPS   60
RFSGSGSGTD FTLTISSLQP EDFATYYCQQ SYNTPYTFGQ GTKLEIKR              108

SEQ ID NO: 564          moltype = AA  length = 108
FEATURE                 Location/Qualifiers
source                  1..108
                        mol_type = protein
                        organism = Homo sapiens
SEQUENCE: 564
DIQMTQSPSS LSASVGDRVT ITCRASQGIG NDLGWYQQKP GKAPKLLIYA ASSLQSGVPS   60
RFSGSGSGTD FTLTISSLQP EDFATYYCQQ SYAPPPTFGQ GTKVEIKR              108

SEQ ID NO: 565          moltype = AA  length = 108
FEATURE                 Location/Qualifiers
source                  1..108
                        mol_type = protein
                        organism = Homo sapiens
SEQUENCE: 565
DIQMTQSPSS LSASVGDRVT ITCRASQSIS NWLAWYQQKP GKAPKLLIYG ASNLETGVPS   60
RFSGSGSGTD FTLTISSLQP EDFATYYCQQ SYSTPPTFGQ GTKLEIKR              108

SEQ ID NO: 566          moltype = AA  length = 113
FEATURE                 Location/Qualifiers
source                  1..113
                        mol_type = protein
                        organism = Homo sapiens
SEQUENCE: 566
DIVMTQSPLS LPVTPGEPAS ISCRSSQSLL HSNGYNYLDW YLQKPGQSPQ LLIYLGSNRA   60
SGVPDRFSGS GSGTDFTLKI SRVEAEDVGV YYCMQGLQTP LTFGQGTKVE IKR         113

SEQ ID NO: 567          moltype = AA  length = 108
FEATURE                 Location/Qualifiers
source                  1..108
                        mol_type = protein
                        organism = Homo sapiens
SEQUENCE: 567
DIQMTQSPSS LSASVGDRVT ITCRASQSIS SYLNWYQQKP GKAPKLLIYL ASSLQSGVPS   60
RFSGSGSGTD FTLTISSLQP EDFATYYCQQ SDSIPVTFGQ GTKVEIKR              108

SEQ ID NO: 568          moltype = AA  length = 108
FEATURE                 Location/Qualifiers
source                  1..108
                        mol_type = protein
                        organism = Homo sapiens
SEQUENCE: 568
DIQMTQSPSS LSASVGDRVT ITCQASQDIS NYLNWYQQKP GKAPKLLIYS TSSLQSGVPS   60
RFSGSGSGTD FTLTISSLQP EDFATYYCQQ SYSTPYNFGQ GTKLEIKR              108

SEQ ID NO: 569          moltype = AA  length = 108
FEATURE                 Location/Qualifiers
source                  1..108
                        mol_type = protein
                        organism = Homo sapiens
SEQUENCE: 569
DIQMTQSPSS LSASVGDRVT ITCRASESIG SWLAWYQQKP GKAPKLLIYA ASSLQSGVPS   60
RFSGSGSGTD FTLTISSLQP EDFATYYCQQ SYSTPYTFGQ GTKLEIKR              108

SEQ ID NO: 570          moltype = AA  length = 108
FEATURE                 Location/Qualifiers
source                  1..108
                        mol_type = protein
                        organism = Homo sapiens
SEQUENCE: 570
DIQMTQSPSS LSASVGDRVT ITCRASQSIS NYLNWYQQKP GKAPKLLIYA ASSLQRGVPS   60
RFSGSGSGTD FTLTISSLQP EDFATYYCQQ SYSTPLTFGQ GTKVEIKR              108

SEQ ID NO: 571          moltype = AA  length = 108
FEATURE                 Location/Qualifiers
source                  1..108
                        mol_type = protein
                        organism = Homo sapiens
SEQUENCE: 571
EIVMTQSPAT LSVSPGERAT LSCRASQSVT SNYLAWYQQK PGQAPRLLIY GASTRATGIP   60
ARFSGSGSGT EFTLTISSLQ SEDFAVYYCQ HYGSSPAFGQ GTRLEIKR              108
```

```
SEQ ID NO: 572            moltype = AA   length = 108
FEATURE                  Location/Qualifiers
source                   1..108
                         mol_type = protein
                         organism = Homo sapiens
SEQUENCE: 572
DIQMTQSPSS LSASVGDRVT ITCRASQGIS SYLAWYQQKP GKAPKLLIYA ASTLQSGVPS    60
RFSGSGSGTD FTLTISSLQP EDFATYYCQQ SYSTPPTFGP GTKVDIKR               108

SEQ ID NO: 573            moltype = AA   length = 108
FEATURE                  Location/Qualifiers
source                   1..108
                         mol_type = protein
                         organism = Homo sapiens
SEQUENCE: 573
DIQMTQSPSS LSASVGDRVT ITCRASQDIG NYLNWYQQKP GKAPKLLIYA ASSLQSGVPS    60
RFSGSGSGTD FTLTISSLQP EDFATYYCQQ AYTYPYTFGQ GTKLEIKR               108

SEQ ID NO: 574            moltype = AA   length = 108
FEATURE                  Location/Qualifiers
source                   1..108
                         mol_type = protein
                         organism = Homo sapiens
SEQUENCE: 574
DIQMTQSPSS LSASVGDRVT ITCQASQDIS NYLNWYQQKP GKAPKLLIYG ASSLQSGVPS    60
RFSGSGSGTD FTLTISSLQP EDFATYYCQQ SYTTPNTFGP GTKVDIKR               108

SEQ ID NO: 575            moltype = AA   length = 108
FEATURE                  Location/Qualifiers
source                   1..108
                         mol_type = protein
                         organism = Homo sapiens
SEQUENCE: 575
DIQMTQSPSS LSASVGDRVT ITCRASQGIS NYLAWYQQKP GKAPKLLIYA ASTLQSGVPS    60
RFSGSGSGTD FTLTISSLQP EDFATYYCQQ SYSTPYTFGQ GTKVEIKR               108

SEQ ID NO: 576            moltype = AA   length = 108
FEATURE                  Location/Qualifiers
source                   1..108
                         mol_type = protein
                         organism = Homo sapiens
SEQUENCE: 576
DIQMTQSPSS LSASVGDRVT ITCRASQGIS NGLSWYQQKP GKAPKLLIYD ASNLETGVPS    60
RFSGSGSGTD FTLTISSLQP EDFATYYCQQ SYSTPFTFGP GTKVDIKR               108

SEQ ID NO: 577            moltype = AA   length = 108
FEATURE                  Location/Qualifiers
source                   1..108
                         mol_type = protein
                         organism = Homo sapiens
SEQUENCE: 577
DIQMTQSPSS LSASVGDRVT ITCRASQNIR NYLNWYQQKP GKAPKLLIYG ASSLQSGVPS    60
RFSGSGSGTD FTLTISSLQP EDFATYYCQQ SYSTPLTFGG GTKVEIKR               108

SEQ ID NO: 578            moltype = AA   length = 108
FEATURE                  Location/Qualifiers
source                   1..108
                         mol_type = protein
                         organism = Homo sapiens
SEQUENCE: 578
DIQMTQSPSS LSASVGDRVT ITCQASLDIN NYLNWYQQKP GKAPKLLIYK ASSLESGVPS    60
RFSGSGSGTD FTLTISSLQP EDFATYYCQQ SYSMPLTFGP GTKVDIKR               108

SEQ ID NO: 579            moltype = AA   length = 108
FEATURE                  Location/Qualifiers
source                   1..108
                         mol_type = protein
                         organism = Homo sapiens
SEQUENCE: 579
DIQMTQSPSS LSASVGDRVT ITCQASQDIS NYLNWYQQKP GKAPKLLIYA ASSLQGGVPS    60
RFSGSGSGTD FTLTISSLQP EDFATYYCQQ SYTTPWTFGQ GTKLEIKR               108

SEQ ID NO: 580            moltype = AA   length = 108
FEATURE                  Location/Qualifiers
source                   1..108
                         mol_type = protein
                         organism = Homo sapiens
SEQUENCE: 580
DIQMTQSPSS LSASVGDRVT ITCQASQDIS NYLNWYQQKP GKAPKLLIYA ASSLQSGVPS    60
```

```
RFSGSGSGTD FTLTISSLQP EDFATYYCQQ SYSSPLTFGG GTKVEIKR                    108

SEQ ID NO: 581          moltype = AA   length = 108
FEATURE                 Location/Qualifiers
source                  1..108
                        mol_type = protein
                        organism = Homo sapiens
SEQUENCE: 581
DIQMTQSPSS LSASVGDRVT ITCQASQDIS NYLNWYQQKP GKAPKLLIYK ASSLESGVPS       60
RFSGSGSGTD FTLTISSLQP EDFATYYCQQ SYSDPLTFGQ GTKVEIKR                    108

SEQ ID NO: 582          moltype = AA   length = 108
FEATURE                 Location/Qualifiers
source                  1..108
                        mol_type = protein
                        organism = Homo sapiens
SEQUENCE: 582
DIQMTQSPSS LSASVGDRVT ITCQASQDIS NYLNWYQQKP GKAPKLLIYG ASTLQSGVPS       60
RFSGSGSGTD FTLTISSLQP EDFATYYCQQ SYSAPITFGQ GTRLEIKR                    108

SEQ ID NO: 583          moltype = AA   length = 108
FEATURE                 Location/Qualifiers
source                  1..108
                        mol_type = protein
                        organism = Homo sapiens
SEQUENCE: 583
DIQMTQSPSS LSASVGDRVT ITCRASQSIS NYLNWYQQKP GKAPKLLIYA ASNLQSGVPS       60
RFSGSGSGTD FTLTISSLQP EDFATYYCQQ SYTTPLTFGP GTKVDIKR                    108

SEQ ID NO: 584          moltype = AA   length = 109
FEATURE                 Location/Qualifiers
source                  1..109
                        mol_type = protein
                        organism = Homo sapiens
SEQUENCE: 584
DIQMTQSPSS LSASVGDRVT ITCRASQNIG NYLNWYQQKP GKAPKLLIYA ASTLQSGVPS       60
RFSGSGSGTD FTLTISSLQP EDFATYYCQQ SYSTPPWTFG QGTKVEIKR                   109

SEQ ID NO: 585          moltype = AA   length = 108
FEATURE                 Location/Qualifiers
source                  1..108
                        mol_type = protein
                        organism = Homo sapiens
SEQUENCE: 585
DIQMTQSPSS LSASVGDRVT ITCQASQDIS NYLNWYQQKP GKAPKLLIYA ASTLRSGVPS       60
RFSGSGSGTD FTLTISSLQP EDFATYYCQQ SYQTPLTFGG GTKVEIKR                    108

SEQ ID NO: 586          moltype = AA   length = 108
FEATURE                 Location/Qualifiers
source                  1..108
                        mol_type = protein
                        organism = Homo sapiens
SEQUENCE: 586
DIQMTQSPSS LSASVGDRVT ITCQASQDIS NYLNWYQQKP GKAPKLLIYA ASTLQSGVPS       60
RFSGSGSGTD FTLTISSLQP EDFATYYCQQ SYTTPPTFGQ GTKVEIKR                    108

SEQ ID NO: 587          moltype = AA   length = 108
FEATURE                 Location/Qualifiers
source                  1..108
                        mol_type = protein
                        organism = Homo sapiens
SEQUENCE: 587
DIQMTQSPSS LSASVGDRVT ITCQASQDIS NYLNWYQQKP GKAPKLLIYA ASSLHSGVPS       60
RFSGSGSGTD FTLTISSLQP EDFATYYCQQ SYSTPQTFGQ GTKVEIKR                    108

SEQ ID NO: 588          moltype = AA   length = 108
FEATURE                 Location/Qualifiers
source                  1..108
                        mol_type = protein
                        organism = Homo sapiens
SEQUENCE: 588
DIQMTQSPSS LSASVGDRVT ITCRASQGIR NDLNWYQQKP GKAPKLLIYA ASNLQSGVPS       60
RFSGSGSGTD FTLTISSLQP EDFATYYCQQ ANSFPITFGQ GTKLEIKR                    108

SEQ ID NO: 589          moltype = AA   length = 108
FEATURE                 Location/Qualifiers
source                  1..108
                        mol_type = protein
                        organism = Homo sapiens
```

```
SEQUENCE: 589
DIQMTQSPSS LSASVGDRVT ITCRASQGIN TWLAWYQQKP GKAPKLLIYA ASSLQSGVPS   60
RFSGSGSGTD FTLTISSLQP EDFATYYCQQ SYSTPYTFGQ GTRLEIKR               108

SEQ ID NO: 590          moltype = AA   length = 108
FEATURE                 Location/Qualifiers
source                  1..108
                        mol_type = protein
                        organism = Homo sapiens
SEQUENCE: 590
DIQMTQSPSS LSASVGDRVT ITCQASQDIS NYLNWYQQKP GKAPKLLIYA ASTLQSGVPS   60
RFSGSGSGTD FTLTISSLQP EDFATYYCQQ SYTVPPTFGQ GTKVEIKR               108

SEQ ID NO: 591          moltype = AA   length = 108
FEATURE                 Location/Qualifiers
source                  1..108
                        mol_type = protein
                        organism = Homo sapiens
SEQUENCE: 591
DIQMTQSPSS LSASVGDRVT ITCQASQDIR YFLNWYQQKP GKAPKLLIYA ASTLQSGVPS   60
RFSGSGSGTD FTLTISSLQP EDFATYYCQQ DDSFPLTFGG GTKVEIKR               108

SEQ ID NO: 592          moltype = AA   length = 546
FEATURE                 Location/Qualifiers
source                  1..546
                        mol_type = protein
                        organism = Nipah henipavirus
SEQUENCE: 592
MVVILDKRCY CNLLILILMI SECSVGILHY EKLSKIGLVK GVTRKYKIKS NPLTKDIVIK   60
MIPNVSNMSQ CTGSVMENYK TRLNGILTPI KGALEIYKNN THDLVGDVRL AGVIMAGVAI  120
GIATAAQITA GVALYEAMKN ADNINKLKSS IESTNEAVVK LQETAEKTVY VLTALQDYIN  180
TNLVPTIDKI SCKQTELSLD LALSKYLSDL LFVFGPNLQD PVSNSMTIQA ISQAFGGNYE  240
TLLRTLGYAT EDFDDLLESD SITGQIIYVD LSSYYIIVRV YFPILTEIQQ AYIQELLPVS  300
FNNDNSEWIS IVPNFILVRN TLISNIEIGF CLITKRSVIC NQDYATPMTN NMRECLTGST  360
EKCPRELVVS SHVPRFALSN GVLFANCISV TCQCQTTGRA ISQSGEQTLL MIDNTTCPTA  420
VLGNVIISLG KYLGSVNYNS EGIAIGPPVF TDKVDISSQI SSMNQSLQQS KDYIKEAQRL  480
LDTVNPSLIS MLSMIILYVL SIASLCIGLI TFISFIIVEK KRNTYSRLED RRVRPTSSGD  540
LYYIGT                                                            546

SEQ ID NO: 593          moltype = AA   length = 520
FEATURE                 Location/Qualifiers
source                  1..520
                        mol_type = protein
                        organism = Nipah henipavirus
SEQUENCE: 593
ILHYEKLSKI GLVKGVTRKY KIKSNPLTKD IVIKMIPNVS NMSQCTGSVM ENYKTRLNGI   60
LTPIKGALEI YKNNTHDLVG DVRLAGVIMA GVAIGIATAA QITAGVALYE AMKNADNINK  120
LKSSIESTNE AVVKLQETAE KTVYVLTALQ DYINTNLVPT IDKISCKQTE LSLDLALSKY  180
LSDLLFVFGP NLQDPVSNSM TIQAISQAFG GNYETLLRTL GYATEDFDDL LESDSITGQI  240
IYVDLSSYYI IVRVYFPILT EIQQAYIQEL LPVSFNNDNS EWISIVPNFI LVRNTLISNI  300
EIGFCLITKR SVICNQDYAT PMTNNMRECL TGSTEKCPRE LVVSSHVPRF ALSNGVLFAN  360
CISVTCQCQT TGRAISQSGE QTLLMIDNTT CPTAVLGNVI ISLGKYLGSV NYNSEGIAIG  420
PPVFTDKVDI SSQISSMNQS LQQSKDYIKE AQRLLDTVNP SLISMLSMII LYVLSIASLC  480
IGLITFISFI IVEKKRNTYS RLEDRRVRPT SSGDLYYIGT                        520

SEQ ID NO: 594          moltype = AA   length = 83
FEATURE                 Location/Qualifiers
source                  1..83
                        mol_type = protein
                        organism = Nipah henipavirus
SEQUENCE: 594
ILHYEKLSKI GLVKGVTRKY KIKSNPLTKD IVIKMIPNVS NMSQCTGSVM ENYKTRLNGI   60
LTPIKGALEI YKNNTHDLVG DVR                                          83

SEQ ID NO: 595          moltype = AA   length = 437
FEATURE                 Location/Qualifiers
source                  1..437
                        mol_type = protein
                        organism = Nipah henipavirus
SEQUENCE: 595
LAGVIMAGVA IGIATAAQIT AGVALYEAMK NADNINKLKS SIESTNEAVV KLQETAEKTV   60
YVLTALQDYI NTNLVPTIDK ISCKQTELSL DLALSKYLSD LLFVFGPNLQ DPVSNSMTIQ  120
AISQAFGGNY ETLLRTLGYA TEDFDDLLES DSITGQIIYV DLSSYYIIVR VYFPILTEIQ  180
QAYIQELLPV SFNNDNSEWI SIVPNFILVR NTLISNIEIG FCLITKRSVI CNQDYATPMT  240
NNMRECLTGS TEKCPRELVV SSHVPRFALS NGVLFANCIS VTCQCQTTGR AISQSGEQTL  300
LMIDNTTCPT AVLGNVIISL GKYLGSVNYN SEGIAIGPPV FTDKVDISSQ ISSMNQSLQQ  360
SKDYIKEAQR LLDTVNPSLI SMLSMIILYV LSIASLCIGL ITFISFIIVE KKRNTYSRLE  420
DRRVRPTSSG DLYYIGT                                                 437
```

-continued

---

```
SEQ ID NO: 596            moltype = AA   length = 500
FEATURE                   Location/Qualifiers
source                    1..500
                          mol_type = protein
                          organism = synthetic construct
                          note = Description of Artificial Sequence: Synthetic
                          polypeptide
SEQUENCE: 596
ILHYEKLSKI GLVKGVTRKY KIKSNPLTKD IVIKMIPNVS NMSQCTGSVM ENYKTRLNGI   60
LTPIKGALEI YKNNTHDLVG DVRLAGVIMA GVAIGIATAA QITAGVALYE AMKNADNINK  120
LKSSIESTNE AVVKLQETAE KTVYVLTALQ DYINTNLVPT IDKISCKQTE LSLDLALSKY  180
LSDLLFVFGP NLQDPVSNSM TIQAISQAFG GNYETLLRTL GYATEDFDDL LESDSITGQI  240
IYVDLSSYYI IVRVYFPILT EIQQAYIQEL LPVSFNNDNS EWISIVPNFI LVRNTLISNI  300
EIGFCLITKR SVICNQDYAT PMTNNMRECL TGSTEKCPRE LVVSSHVPRF ALSNGVLFAN  360
CISVTCQCQT TGRAISQSGE QTLLMIDNTT CPTAVLGNVI ISLGKYLGSV NYNSEGIAIG  420
PPVFTDKVDI SSQISSMNQS LQQSKDYIKE AQRLLDTVNP SLISMLSMII LYVLSIASLC  480
IGLITFISFI IVEKKRNTGT                                              500

SEQ ID NO: 597            moltype = AA   length = 417
FEATURE                   Location/Qualifiers
source                    1..417
                          mol_type = protein
                          organism = synthetic construct
                          note = Description of Artificial Sequence: Synthetic
                          polypeptide
SEQUENCE: 597
LAGVIMAGVA IGIATAAQIT AGVALYEAMK NADNINKLKS SIESTNEAVV KLQETAEKTV   60
YVLTALQDYI NTNLVPTIDK ISCKQTELSL DLALSKYLSD LLFVFGPNLQ DPVSNSMTIQ  120
AISQAFGGNY ETLLRTLGYA TEDFDDLLES DSITGQIIYV DLSSYYIIVR VYFPILTEIQ  180
QAYIQELLPV SFNNDNSEWI SIVPNFILVR NTLISNIEIGF FCLITKRSVI CNQDYATPMT  240
NNMRECLTGS TEKCPRELVV SSHVPRFALS NGVLFANCIS VTCQCQTTGR AISQSGEQTL  300
LMIDNTTCPT AVLGNVIISL GKYLGSVNYN SEGIAIGPPV FTDKVDISSQ ISSMNQSLQQ  360
SKDYIKEAQR LLDTVNPSLI SMLSMIILYV LSIASLCIGL ITFISFIIVE KKRNTGT     417

SEQ ID NO: 598            moltype = AA   length = 500
FEATURE                   Location/Qualifiers
source                    1..500
                          mol_type = protein
                          organism = synthetic construct
                          note = Description of Artificial Sequence: Synthetic
                          polypeptide
SEQUENCE: 598
ILHYEKLSKI GLVKGVTRKY KIKSNPLTKD IVIKMIPNVS NMSQCTGSVM ENYKTRLNGI   60
LTPIKGALEI YKNQTHDLVG DVRLAGVIMA GVAIGIATAA QITAGVALYE AMKNADNINK  120
LKSSIESTNE AVVKLQETAE KTVYVLTALQ DYINTNLVPT IDKISCKQTE LSLDLALSKY  180
LSDLLFVFGP NLQDPVSNSM TIQAISQAFG GNYETLLRTL GYATEDFDDL LESDSITGQI  240
IYVDLSSYYI IVRVYFPILT EIQQAYIQEL LPVSFNNDNS EWISIVPNFI LVRNTLISNI  300
EIGFCLITKR SVICNQDYAT PMTNNMRECL TGSTEKCPRE LVVSSHVPRF ALSNGVLFAN  360
CISVTCQCQT TGRAISQSGE QTLLMIDNTT CPTAVLGNVI ISLGKYLGSV NYNSEGIAIG  420
PPVFTDKVDI SSQISSMNQS LQQSKDYIKE AQRLLDTVNP SLISMLSMII LYVLSIASLC  480
IGLITFISFI IVEKKRNTGT                                              500

SEQ ID NO: 599            moltype = AA   length = 524
FEATURE                   Location/Qualifiers
source                    1..524
                          mol_type = protein
                          organism = synthetic construct
                          note = Description of Artificial Sequence: Synthetic
                          polypeptide
SEQUENCE: 599
MVVILDKRCY CNLLILILMI SECSVGILHY EKLSKIGLVK GVTRKYKIKS NPLTKDIVIK   60
MIPNVSNMSQ CTGSVMENYK TRLNGILTPI KGALEIYKNN THDLVGDVRL AGVIMAGVAI  120
GIATAAQITA GVALYEAMKN ADNINKLKSS IESTNEAVVK LQETAEKTVY VLTALQDYIN  180
TNLVPTIDKI SCKQTELSLD LALSKYLSDL LFVFGPNLQD PVSNSMTIQA ISQAFGGNYE  240
TLLRTLGYAT EDFDDLLESD SITGQIIYVD LSSYYIIVRV YFPILTEIQQ AYIQELLPVS  300
FNNDNSEWIS IVPNFILVRN TLISNIEIGF CLITKRSVIC NQDYATPMTN NMRECLTGST  360
EKCPRELVVS SHVPRFALSN GVLFANCISV TCQCQTTGRA ISQSGEQTLL MIDNTTCPTA  420
VLGNVIISLG KYLGSVNYNS EGIAIGPPVF TDKVDISSQI SSMNQSLQQS KDYIKEAQRL  480
LDTVNPSLIS MLSMIILYVL SIASLCIGLI TFISFIIVEK KRNT                   524

SEQ ID NO: 600            moltype = AA   length = 602
FEATURE                   Location/Qualifiers
source                    1..602
                          mol_type = protein
                          organism = Nipah henipavirus
SEQUENCE: 600
MGPAENKKVR FENTTSDKGK IPSKVIKSYY GTMDIKKINE GLLDSKILSA FNTVIALLGS   60
IVIIVMNIMI IQNYTRSTDN QAVIKDALQG IQQQIKGLAD KIGTEIGPKV SLIDTSSTIT  120
IPANIGLLGS KISQSTASIN ENVNEKCKFT LPPLKIHECN ISCPNPLPFR EYRPQTEGVS  180
```

```
NLVGLPNNIC LQKTSNQILK PKLISYTLPV VGQSGTCITD PLLAMDEGYF AYSHLERIGS   240
CSRGVSKQRI IGVGEVLDRG DEVPSLFMTN VWTPPNPNTV YHCSAVYNNE FYYVLCAVST   300
VGDPILNSTY WSGSLMMTRL AVKPKSNGGG YNQHQLALRS IEKGRYDKVM PYGPSGIKQG   360
DTLYFPAVGF LVRTEFKYND SNCPITKCQY SKPENCRLSM GIRPNSHYIL RSGLLKYNLS   420
DGENPKVVFI EISDQRLSIG SPSKIYDSLG QPVFYQASFS WDTMIKFGDV LTVNPLVVNW   480
RNNTVISRPG QSQCPRFNTC PEICWEGVYN DAFLIDRINW ISAGVFLDSN QTAENPVFTV   540
FKDNEILYRA QLASEDTNAQ KTITNCFLLK NKIWCISLVE IYDTGDNVIR PKLFAVKIPE   600
QC                                                                 602

SEQ ID NO: 601          moltype = AA  length = 597
FEATURE                 Location/Qualifiers
source                  1..597
                        mol_type = protein
                        organism = synthetic construct
                        note = Description of Artificial Sequence: Synthetic
                        polypeptide
SEQUENCE: 601
MGKVRFENTT SDKGKIPSKV IKSYYGTMDI KKINEGLLDS KILSAFNTVI ALLGSIVIIV   60
MNIMIIQNYT RSTDNQAVIK DALQGIQQQI KGLADKIGTE IGPKVSLIDT SSTITIPANI   120
GLLGSKISQS TASINENVNE KCKFTLPPLK IHECNISCPN PLPFREYRPQ TEGVSNLVGL   180
PNNICLQKTS NQILKPKLIS YTLPVVGQSG TCITDPLLAM DEGYFAYSHL ERIGSCSRGV   240
SKQRIIGVGE VLDRGDEVPS LFMTNVWTPP NPNTVYHCSA VYNNEFYYVL CAVSTVGDPI   300
LNSTYWSGSL MMTRLAVKPK SNGGGYNQHQ LALRSIEKGR YDKVMPYGPS GIKQGDTLYF   360
PAVGFLVRTE FKYNDSNCPI TKCQYSKPEN CRLSMGIRPN SHYILRSGLL KYNLSDGENP   420
KVVFIEISDQ RLSIGSPSKI YDSLGQPVFY QASFSWDTMI KFGDVLTVNP LVVNWRNNTV   480
ISRPGQSQCP RFNTCPEICW EGVYNDAFLI DRINWISAGV FLDSNQTAEN PVFTVFKDNE   540
ILYRAQLASE DTNAQKTITN CFLLKNKIWC ISLVEIYDTG DNVIRPKLFA VKIPEQC      597

SEQ ID NO: 602          moltype = AA  length = 592
FEATURE                 Location/Qualifiers
source                  1..592
                        mol_type = protein
                        organism = synthetic construct
                        note = Description of Artificial Sequence: Synthetic
                        polypeptide
SEQUENCE: 602
MGNTTSDKGK IPSKVIKSYY GTMDIKKINE GLLDSKILSA FNTVIALLGS IVIIVMNIMI   60
IQNYTRSTDN QAVIKDALQG IQQQIKGLAD KIGTEIGPKV SLIDTSSTIT IPANIGLLGS   120
KISQSTASIN ENVNEKCKFT LPPLKIHECN ISCPNPLPFR EYRPQTEGVS NLVGLPNNIC   180
LQKTSNQILK PKLISYTLPV VGQSGTCITD PLLAMDEGYF AYSHLERIGS CSRGVSKQRI   240
IGVGEVLDRG DEVPSLFMTN VWTPPNPNTV YHCSAVYNNE FYYVLCAVST VGDPILNSTY   300
WSGSLMMTRL AVKPKSNGGG YNQHQLALRS IEKGRYDKVM PYGPSGIKQG DTLYFPAVGF   360
LVRTEFKYND SNCPITKCQY SKPENCRLSM GIRPNSHYIL RSGLLKYNLS DGENPKVVFI   420
EISDQRLSIG SPSKIYDSLG QPVFYQASFS WDTMIKFGDV LTVNPLVVNW RNNTVISRPG   480
QSQCPRFNTC PEICWEGVYN DAFLIDRINW ISAGVFLDSN QTAENPVFTV FKDNEILYRA   540
QLASEDTNAQ KTITNCFLLK NKIWCISLVE IYDTGDNVIR PKLFAVKIPE QC           592

SEQ ID NO: 603          moltype = AA  length = 587
FEATURE                 Location/Qualifiers
source                  1..587
                        mol_type = protein
                        organism = synthetic construct
                        note = Description of Artificial Sequence: Synthetic
                        polypeptide
SEQUENCE: 603
MGKGKIPSKV IKSYYGTMDI KKINEGLLDS KILSAFNTVI ALLGSIVIIV MNIMIIQNYT   60
RSTDNQAVIK DALQGIQQQI KGLADKIGTE IGPKVSLIDT SSTITIPANI GLLGSKISQS   120
TASINENVNE KCKFTLPPLK IHECNISCPN PLPFREYRPQ TEGVSNLVGL PNNICLQKTS   180
NQILKPKLIS YTLPVVGQSG TCITDPLLAM DEGYFAYSHL ERIGSCSRGV SKQRIIGVGE   240
VLDRGDEVPS LFMTNVWTPP NPNTVYHCSA VYNNEFYYVL CAVSTVGDPI LNSTYWSGSL   300
MMTRLAVKPK SNGGGYNQHQ LALRSIEKGR YDKVMPYGPS GIKQGDTLYF PAVGFLVRTE   360
FKYNDSNCPI TKCQYSKPEN CRLSMGIRPN SHYILRSGLL KYNLSDGENP KVVFIEISDQ   420
RLSIGSPSKI YDSLGQPVFY QASFSWDTMI KFGDVLTVNP LVVNWRNNTV ISRPGQSQCP   480
RFNTCPEICW EGVYNDAFLI DRINWISAGV FLDSNQTAEN PVFTVFKDNE ILYRAQLASE   540
DTNAQKTITN CFLLKNKIWC ISLVEIYDTG DNVIRPKLFA VKIPEQC                 587

SEQ ID NO: 604          moltype = AA  length = 582
FEATURE                 Location/Qualifiers
source                  1..582
                        mol_type = protein
                        organism = synthetic construct
                        note = Description of Artificial Sequence: Synthetic
                        polypeptide
SEQUENCE: 604
MGSKVIKSYY GTMDIKKINE GLLDSKILSA FNTVIALLGS IVIIVMNIMI IQNYTRSTDN   60
QAVIKDALQG IQQQIKGLAD KIGTEIGPKV SLIDTSSTIT IPANIGLLGS KISQSTASIN   120
ENVNEKCKFT LPPLKIHECN ISCPNPLPFR EYRPQTEGVS NLVGLPNNIC LQKTSNQILK   180
PKLISYTLPV VGQSGTCITD PLLAMDEGYF AYSHLERIGS CSRGVSKQRI IGVGEVLDRG   240
DEVPSLFMTN VWTPPNPNTV YHCSAVYNNE FYYVLCAVST VGDPILNSTY WSGSLMMTRL   300
```

```
AVKPKSNGGG YNQHQLALRS IEKGRYDKVM PYGPSGIKQG DTLYFPAVGF LVRTEFKYND  360
SNCPITKCQY SKPENCRLSM GIRPNSHYIL RSGLLKYNLS DGENPKVVFI EISDQRLSIG  420
SPSKIYDSLG QPVFYQASFS WDTMIKFGDV LTVNPLVVNW RNNTVISRPG QSQCPRFNTC  480
PEICWEGVYN DAFLIDRINW ISAGVFLDSN QTAENPVFTV FKDNEILYRA QLASEDTNAQ  540
KTITNCFLLK NKIWCISLVE IYDTGDNVIR PKLFAVKIPE QC                     582

SEQ ID NO: 605          moltype = AA  length = 577
FEATURE                 Location/Qualifiers
source                  1..577
                        mol_type = protein
                        organism = synthetic construct
                        note = Description of Artificial Sequence: Synthetic
                         polypeptide
SEQUENCE: 605
MGSYYGTMDI KKINEGLLDS KILSAFNTVI ALLGSIVIIV MNIMIIQNYT RSTDNQAVIK  60
DALQGIQQQI KGLADKIGTE IGPKVSLIDT SSTITIPANI GLLGSKISQS TASINENVNE  120
KCKFTLPPLK IHECNISCPN PLPFREYRPQ TEGVSNLVGL PNNICLQKTS NQILKPKLIS  180
YTLPVVGQSG TCITDPLLAM DEGYFAYSHL ERIGSCSRGV SKQRIIGVGE VLDRGDEVPS  240
LFMTNVWTPP NPNTVYHCSA VYNNEFYYVL CAVSTVGDPI LNSTYWSGSL MMTRLAVKPK  300
SNGGGYNQHQ LALRSIEKGR YDKVMPYGPS GIKQGDTLYF PAVGFLVRTE FKYNDSNCPI  360
TKCQYSKPEN CRLSMGIRPN SHYILRSGLL KYNLSDGENP KVVFIEISDQ RLSIGSPSKI  420
YDSLGQPVFY QASFSWDTMI KFGDVLTVNP LVVNWRNNTV ISRPGQSQCP RFNTCPEICW  480
EGVYNDAFLI DRINWISAGV FLDSNQTAEN PVFTVFKDNE ILYRAQLASE DTNAQKTITN  540
CFLLKNKIWC ISLVEIYDTG DNVIRPKLFA VKIPEQC                          577

SEQ ID NO: 606          moltype = AA  length = 573
FEATURE                 Location/Qualifiers
source                  1..573
                        mol_type = protein
                        organism = synthetic construct
                        note = Description of Artificial Sequence: Synthetic
                         polypeptide
SEQUENCE: 606
MGTMDIKKIN EGLLDSKILS AFNTVIALLG SIVIIVMNIM IIQNYTRSTD NQAVIKDALQ  60
GIQQQIKGLA DKIGTEIGPK VSLIDTSSTI TIPANIGLLG SKISQSTASI NENVNEKCKF  120
TLPPLKIHEC NISCPNPLPF REYRPQTEGV SNLVGLPNNI CLQKTSNQIL KPKLISYTLP  180
VVGQSGTCIT DPLLAMDEGY FAYSHLERIG SCSRGVSKQR IIGVGEVLDR GDEVPSLFMT  240
NVWTPNPNT VYHCSAVYNN EFYYVLCAVS TVGDPILNST YWSGSLMMTR LAVKPKSNGG  300
GYNQHQLALR SIEKGRYDKV MPYGPSGIKQ GDTLYFPAVG FLVRTEFKYN DSNCPITKCQ  360
YSKPENCRLS MGIRPNSHYI LRSGLLKYNL SDGENPKVVF IEISDQRLSI GSPSKIYDSL  420
GQPVFYQASF SWDTMIKFGD VLTVNPLVVN WRNNTVISRP GQSQCPRFNT CPEICWEGVY  480
NDAFLIDRIN WISAGVFLDS NQTAENPVFT VFKDNEILYR AQLASEDTNA QKTITNCFLL  540
KNKIWCISLV EIYDTGDNVI RPKLFAVKIP EQC                              573

SEQ ID NO: 607          moltype = AA  length = 569
FEATURE                 Location/Qualifiers
source                  1..569
                        mol_type = protein
                        organism = synthetic construct
                        note = Description of Artificial Sequence: Synthetic
                         polypeptide
SEQUENCE: 607
MKKINEGLLD SKILSAFNTV IALLGSIVII VMNIMIIQNY TRSTDNQAVI KDALQGIQQQ  60
IKGLADKIGT EIGPKVSLID TSSTITIPAN IGLLGSKISQ STASINENVN EKCKFTLPPL  120
KIHECNISCP NPLPFREYRP QTEGVSNLVG LPNNICLPKLI SNQILKPKLI SYTLPVVGQS  180
GTCITDPLLA MDEGYFAYSH LERIGSCSRG VSKQRIIGVG EVLDRGDEVP SLFMTNVWTP  240
PNPNTVYHCS AVYNNEFYYV LCAVSTVGDP ILNSTYWSGS LMMTRLAVKP KSNGGGYNQH  300
QLALRSIEKG RYDKVMPYGP SGIKQGDTLY FPAVGFLVRT EFKYNDSNCP ITKCQYSKPE  360
NCRLSMGIRP NSHYILRSGL LKYNLSDGEN PKVVFIEISD QRLSIGSPSK IYDSLGQPVF  420
YQASFSWDTM IKFGDVLTVN PLVVNWRNNT VISRPGQSQC PRFNTCPAIC AEGVYNDAFL  480
IDRINWISAG VFLDSNATAA NPVFTVFKDN EILYRAQLAS EDTNAQKTIT NCFLLKNKIW  540
CISLVEIYDT GDNVIRPKLF AVKIPEQCT                                   569

SEQ ID NO: 608          moltype = AA  length = 546
FEATURE                 Location/Qualifiers
source                  1..546
                        mol_type = protein
                        organism = Hendra henipavirus
SEQUENCE: 608
MATQEVRLKC LLCGIIVLVL SLEGLGILHY EKLSKIGLVK GITRKYKIKS NPLTKDIVIK  60
MIPNVSNVSK CTGTVMENYK SRLTGILSPI KGAIELYNNN THDLVGDVKL AGVVMAGIAI  120
GIATAAQITA GVALYEAMKN ADNINKLKSS IESTNEAVVK LQETAEKTVY VLTALQDYIN  180
TNLVPTIDQI SCKQTELALD LALSKYLSDL LFVFGPNLQD PVSNSMTIQA ISQAFGGNYE  240
TLLRTLGYAT EDFDDLLESD SIAGQIVYVD LSSYYIIVRV YFPILTEIQQ AYVQELLPVS  300
FNNDNSEWIS IVPNFVLIRN TLISNIEVKY CLITKKSVIC NQDYATPMTA SVRECLTGST  360
DKCPRELVVS SHVPRRFALSG GVLFANCISV TCQCQTTGRA ISQSGEQTLL MIDNTTCTTV  420
VLGNIIISLG KYLGSINYNS ESIAVGPPVY TDKVDISSQI SSMNQSLQQS KDYIKEAQKI  480
LDTVNPSLIS MLSMIILYVL SIAALCIGLI TFISFVIVEK KRGNYSRLDD RQVRPVSNGD  540
LYYIGT                                                           546
```

-continued

```
SEQ ID NO: 609              moltype = AA  length = 604
FEATURE                     Location/Qualifiers
source                      1..604
                            mol_type = protein
                            organism = Hendra henipavirus
SEQUENCE: 609
MMADSKLVSL NNNLSGKIKD QGKVIKNYYG TMDIKKINDG LLDSKILGAF NTVIALLGSI  60
IIIVMNIMII QNYTRTTDNQ ALIKESLQSV QQQIKALTDK IGTEIGPKVS LIDTSSTITI  120
PANIGLLGSK ISQSTSSINE NVNDKCKFTL PPLKIHECNI SCPNPLPFRE YRPISQGVSD  180
LVGLPNQICL QKTTSTILKP RLISYTLPIN TREGVCITDP LLAVDNGFFA YSHLEKIGSC  240
TRGIAKQRII GVGEVLDRGD KVPSMFMTNV WTPPNPSTIH HCSSTYHEDF YYTLCAVSHV  300
GDPILNSTSW TESLSLIRLA VRPKSDSGDY NQKYIAITKV ERGKYDKVMP YGPSGIKQGD  360
TLYFPAVGFL PRTEFQYNDS NCPIIHCKYS KAENCRLSMG VNSKSHYILR SGLLKYNLSL  420
GGDIILQFIE IADNRLTIGS PSKIYNSLGQ PVFYQASYSW DTMIKLGDVD TVDPLRVQWR  480
NNSVISRPGQ SQCPRFNVCP EVCWEGTYND AFLIDRLNWV SAGVYLNSNQ TAENPVFAVF  540
KDNEILYQVP LAEDDTNAQK TITDCFLLEN VIWCISLVEI YDTGDSVIRP KLFAVKIPAQ  600
CSES                                                              604

SEQ ID NO: 610              moltype = AA  length = 526
FEATURE                     Location/Qualifiers
source                      1..526
                            mol_type = protein
                            organism = synthetic construct
                            note = Description of Artificial Sequence: Synthetic
                            polypeptide
SEQUENCE: 610
MVVILDKRCY CNLLILILMI SECSVGILHY EKLSKIGLVK GVTRKYKIKS NPLTKDIVIK  60
MIPNVSNMSQ CTGSVMENYK TRLNGILTPI KGALEIYKNN THDLVGDVRL AGVIMAGVAI  120
GIATAAQITA GVALYEAMKN ADNINKLKSS IESTNEAVVK LQETAEKTVY VLTALQDYIN  180
TNLVPTIDKI SCKQTELSLD LALSKYLSDL LFVFGPNLQD PVSNSMTIQA ISQAFGGNYE  240
TLLRTLGYAT EDFDDLLESD SITGQIIYVD LSSYYIIVRV YFPILTEIQQ AYIQELLPVS  300
FNNDNSEWIS IVPNFILVRN TLISNIEIGF CLITKRSVIC NQDYATPMTN NMRECLTGST  360
EKCPRELVVS SHVPRFALSN GVLFANCISV TCQCQTTGRA ISQSGEQTLL MIDNTTCPTA  420
VLGNVIISLG KYLGSVNYNS EGIAIGPPVF TDKVDISSQI SSMNQSLQQS KDYIKEAQRL  480
LDTVNPSLIS MLSMIILYVL SIASLCIGLI TFISFIIVEK KRNTGT               526

SEQ ID NO: 611              moltype = AA  length = 526
FEATURE                     Location/Qualifiers
source                      1..526
                            mol_type = protein
                            organism = synthetic construct
                            note = Description of Artificial Sequence: Synthetic
                            polypeptide
SEQUENCE: 611
MVVILDKRCY CNLLILILMI SECSVGILHY EKLSKIGLVK GVTRKYKIKS NPLTKDIVIK  60
MIPNVSNMSQ CTGSVMENYK TRLNGILTPI KGALEIYKNQ THDLVGDVRL AGVIMAGVAI  120
GIATAAQITA GVALYEAMKN ADNINKLKSS IESTNEAVVK LQETAEKTVY VLTALQDYIN  180
TNLVPTIDKI SCKQTELSLD LALSKYLSDL LFVFGPNLQD PVSNSMTIQA ISQAFGGNYE  240
TLLRTLGYAT EDFDDLLESD SITGQIIYVD LSSYYIIVRV YFPILTEIQQ AYIQELLPVS  300
FNNDNSEWIS IVPNFILVRN TLISNIEIGF CLITKRSVIC NQDYATPMTN NMRECLTGST  360
EKCPRELVVS SHVPRFALSN GVLFANCISV TCQCQTTGRA ISQSGEQTLL MIDNTTCPTA  420
VLGNVIISLG KYLGSVNYNS EGIAIGPPVF TDKVDISSQI SSMNQSLQQS KDYIKEAQRL  480
LDTVNPSLIS MLSMIILYVL SIASLCIGLI TFISFIIVEK KRNTGT               526

SEQ ID NO: 612              moltype = AA  length = 569
FEATURE                     Location/Qualifiers
source                      1..569
                            mol_type = protein
                            organism = synthetic construct
                            note = Description of Artificial Sequence: Synthetic
                            polypeptide
SEQUENCE: 612
MKKINEGLLD SKILSAFNTV IALLGSIVII VMNIMIIQNY TRSTDNQAVI KDALQGIQQQ  60
IKGLADKIGT EIGPKVSLID TSSTITIPAN IGLLGSKISQ STASINENVN EKCKFTLPPL  120
KIHECNISCP NPLPFREYRP QTEGVSNLVG LPNNICLQKT SNQILKPKLI SYTLPVVGQS  180
GTCITDPLLA MDEGFAYSH LERIGSCSRG VSKQRIIGVG EVLDRGDEVP SLFMTNVWTP  240
PNPNTVYHCS AVYNNEFYYV LCAVSTVGDP ILNSTYWSGS LMMTRLAVKP KSNGGGYNQH  300
QLALRSIEKG RYDKVMPYGP SGIKQGDTLY FPAVGFLVRT EFKYNDSNCP ITKCQYSKPE  360
NCRLSMGIRP NSHYILRSGL LKYNLSDGEN PKVVFIEISD QRLSIGSPSK IYDSLGQPVF  420
YQASFSWDTM IKFGDVLTVN PLVVNWRNNT VISRPGQSQC PRFNTCPEIC WEGVYNDAFL  480
IDRINWISAG VFLDSNQTAE NPVFTVFKDN EILYRAQLAS EDTNAQKTIT NCFLLKNKIW  540
CISLVEIYDT GDNVIRPKLF AVKIPEQCT                                  569

SEQ ID NO: 613              moltype = AA  length = 498
FEATURE                     Location/Qualifiers
source                      1..498
                            mol_type = protein
                            organism = synthetic construct
```

```
                         note = Description of Artificial Sequence: Synthetic
                         polypeptide
SEQUENCE: 613
ILHYEKLSKI GLVKGVTRKY KIKSNPLTKD IVIKMIPNVS NMSQCTGSVM ENYKTRLNGI  60
LTPIKGALEI YKNNTHDLVG DVRLAGVIMA GVAIGIATAA QITAGVALYE AMKNADNINK  120
LKSSIESTNE AVVKLQETAE KTVYVLTALQ DYINTNLVPT IDKISCKQTE LSLDLALSKY  180
LSDLLFVFGP NLQDPVSNSM TIQAISQAFG GNYETLLRTL GYATEDFDDL LESDSITGQI  240
IYVDLSSYYI IVRVYFPILT EIQQAYIQEL LPVSFNNDNS EWISIVPNFI LVRNTLISNI  300
EIGFCLITKR SVICNQDYAT PMTNNMRECL TGSTEKCPRE LVVSSHVPRF ALSNGVLFAN  360
CISVTCQCQT TGRAISQSGE QTLLMIDNTT CPTAVLGNVI ISLGKYLGSV NYNSEGIAIG  420
PPVFTDKVDI SSQISSMNQS LQQSKDYIKE AQRLLDTVNP SLISMLSMII LYVLSIASLC  480
IGLITFISFI IVEKKRNT                                                498

SEQ ID NO: 614          moltype = AA  length = 557
FEATURE                 Location/Qualifiers
source                  1..557
                        mol_type = protein
                        organism = Cedar henipavirus
SEQUENCE: 614
MSNKRTTVLI IISYTLFYLN NAAIVGFDFD KLNKIGVVQG RVLNYKIKGD PMTKDLVLKF  60
IPNIVNITEC VREPLSRYNE TVRRLLLPIH NMLGLYLNNT NAKMTGLMIA GVIMGGIAIG  120
IATAAQITAG FALYEAKKNT ENIQKLTDSI MKTQDSIDKL TDSVGTSILI LNKLQTYINN  180
QLVPNLELLS CRQNKIEFDL MLTKYLVDLM TVIGPNINNP VNKDMTIQSL SLLFDGNYDI  240
MMSELGYTPQ DFLDLIESKS ITGQIIYVDM ENLYVVIRTY LPTLIEVPDA QIYEFNKITM  300
SSNGGEYLST IPNFILIRGN YMSNIDVATC YMTKASVICN QDYSLPMSQN LRSCYQGETE  360
YCPVEAVIAS HSPRFALTNG VIFANCINTI CRCQDNGKTI TQNINQFVSM IDNSTCNDVM  420
VDKFTIKVGK YMGRKDINNI NIQIGPQIII DKVDLSNEIN KMNQSLKDSI FYLREAKRIL  480
DSVNISLISP SVQLFLIIIS VLSFIILLII IVYLYCKSKH SYKYNKFIDD PDYYNDYKRE  540
RINGKASKSN NIYYVGD                                                 557

SEQ ID NO: 615          moltype = AA  length = 545
FEATURE                 Location/Qualifiers
source                  1..545
                        mol_type = protein
                        organism = Mojiang henipavirus
SEQUENCE: 615
MALNKNMFSS LFLGYLLVYA TTVQSSIHYD SLSKVGVIKG LTYNYKIKGS PSTKLMVVKL  60
IPNIDSVKNC TQKQYDEYKN LVRKALEPVK MAIDTMLNNV KSGNNKYRFA GAIMAGVALG  120
VATAATVTAG IALHRSNENA QAIANMKSAI QNTNEAVKQL QLANKQTLAV IDTIRGEINN  180
NIIPVINQLS CDTIGLSVGI RLTQYYSEII TAFGPALQNP VNTRITIQAI SSVFNGNFDE  240
LLKIMGYTSG DLYEILHSEL IRGNIIDVDV DAGYIALEIE FPNLTLVPNA VVQELMPISY  300
NIDGDEWVTL VPRFVLTRTT LLSNIDTSRC TITDSSVICD NDYALPMSHE LIGCLQGDTS  360
KCAREKVVSS YVPKFALSDG LVYANCLNTI CRCMDTDTPI SQSLGATVSL LDNKRCSVYQ  420
VGDVLISVGS YLGDGEYNAD NVELGPPIVI DKIDIGNQLA GINQTLQEAE DYIEKSEEFL  480
KGVNPSIITL GSMVVLYIFM ILIAIVSVIA LVLSIKLTVK GNVVRQQFTY TQHVPSMENI  540
NYVSH                                                             545

SEQ ID NO: 616          moltype = AA  length = 662
FEATURE                 Location/Qualifiers
source                  1..662
                        mol_type = protein
                        organism = unidentified
                        note = Description of Unknown: Bat Paramyxovirus
                        Eid_hel/GH-M74a/GHA/2009 sequence
SEQUENCE: 616
MKKKTDNPTI SKRGHNHSRG IKSRALLRET DNYSNGLIVE NLVRNCHHPS KNNLNYTKTQ  60
KRDSTIPYRV EERKGHYPKI KHLIDKSYKH IKRGKRRNGH NGNIITIILL LILILKTQMS  120
EGAIHYETLS KIGLIKGITR EYKVKGTPSS KDIVIKLIPN VTGLNKCTNI SMENYKEQLD  180
KILIPINNII ELYANSTKSA PGNARFAGVI IAGVALGVAA AAQITAGIAL HEARQNAERI  240
NLLKDSISAT NNAVAELQEA TGGIVNVITG MQDYINTNLV PQIDKLQCSQ IKTALDISLS  300
QYYSEILTVF GPNLQNPVTT SMSIQAISQS FGGNIDLLLN LLGYTANDLL DLLESKSITG  360
QITYINLEHY FMVIRVYYPI MTTISNAYVQ ELIKISFNVD GSEWVSLVPS YILIRNSYLS  420
NIDISECLIT KNSVICRHDF AMPMSYTLKE CLTGDTEKCP REAVVTSYVP RFAISGGVIY  480
ANCLSTTCQC YQTGKVIAQD GSQTLMMIDN QTCSIVRIEE ILISTGKYLG SQEYNTMHVS  540
VGNPVFTDKL DITSQISNIN QSIEQSKFYL DKSKAILDKI NLNLIGSVPI SILFIIAILS  600
LILSIITFVI VMIIVRRYNK YTPLINSDPS SRRSTIQDVY IIPNPGEHSI RSAARSIDRD  660
RD                                                                662

SEQ ID NO: 617          moltype = AA  length = 5
FEATURE                 Location/Qualifiers
source                  1..5
                        mol_type = protein
                        organism = Homo sapiens
SEQUENCE: 617
RYAIS                                                             5

SEQ ID NO: 618          moltype = AA  length = 602
FEATURE                 Location/Qualifiers
source                  1..602
```

```
                            mol_type = protein
                            organism = Nipah henipavirus
SEQUENCE: 618
MPAENKKVRF ENTTSDKGKI PSKVIKSYYG TMDIKKINEG LLDSKILSAF NTVIALLGSI    60
VIIVMNIMII QNYTRSTDNQ AVIKDALQGI QQQIKGLADK IGTEIGPKVS LIDTSSTITI   120
PANIGLLGSK ISQSTASINE NVNEKCKFTL PPLKIHECNI SCPNPLPFRE YRPQTEGVSN   180
LVGLPNNICL QKTSNQILKP KLISYTLPVV GQSGTCITDP LLAMDEGYFA YSHLERIGSC   240
SRGVSKQRII GVGEVLDRGD EVPSLFMTNV WTPPNPNTVY HCSAVYNNEF YYVLCAVSTV   300
GDPILNSTYW SGSLMMTRLA VKPKSNGGGY NQHQLALRSI EKGRYDKVMP YGPSGIKQGD   360
TLYFPAVGFL VRTEFKYNDS NCPITKCQYS KPENCRLSMG IRPNSHYILR SGLLKYNLSD   420
GENPKVVFIE ISDQRLSIGS PSKIYDSLGQ PVFYQASFSW DTMIKFGDVL TVNPLVVNWR   480
NNTVISRPGQ SQCPRFNTCP EICWEGVYND AFLIDRINWI SAGVFLDSNQ TAENPVFTVF   540
KDNEILYRAQ LASEDTNAQK TITNCFLLKN KIWCISLVEI YDTGDNVIRP KLFAVKIPEQ   600
CT                                                                 602

SEQ ID NO: 619          moltype = AA  length = 622
FEATURE                 Location/Qualifiers
source                  1..622
                        mol_type = protein
                        organism = Cedar henipavirus
SEQUENCE: 619
MLSQLQKNYL DNSNQQGDKM NNPDKKLSVN FNPLELDKGQ KDLNKSYYVK NKNYNVSNLL    60
NESLHDIKFC IYCIFSLLII ITIINIITIS IVITRLKVHE ENNGMESPNL QSIQDSLSSL   120
TNMINTEITP RIGILVTATS VTLSSSINYV GTKTNQLVNE LKDYITKSCG FKVPELKLHE   180
CNISCADPKI SKSAMYSTNA YAELAGPPKI FCKSVSKDPD FRLKQIDYVI PVQQDRSICM   240
NNPLLDISDG FFTYIHYEGI NSCKKSDSFK VLLSHGEIVD RGDYRPSLYL LSSHYHPYSM   300
QVINCVPVTC NQSSFVFCHI SNNTKTLDNS DYSSDEYYIT YFNGIDRPKT KKIPINNMTA   360
DNRYIHFTFS GGGGVCLGEE FIIPVTTVIN TDVFTHDYCE SFNCSVQTGK SLKEICSESL   420
RSPTNSSRYN LNGIMIISQN NMTDFKIQLN GITYNKLSFG SPGRLSKTLG QVLYYQSSMS   480
WDTYLKAGFV EKWKPFTPNW MNNTVISRPN QGNCPRYHKC PEICYGGTYN DIAPLDLGKD   540
MYVSVILDSD QLAENPEITV FNSTTILYKE RVSKDELNTR STTTSCFLFL DEPWCISVLE   600
TNRFNGKSIR PEIYSYKIPK YC                                            622

SEQ ID NO: 620          moltype = AA  length = 632
FEATURE                 Location/Qualifiers
source                  1..632
                        mol_type = protein
                        organism = unidentified
                        note = Description of Unknown: Bat Paramyxovirus
                        Eid_hel/GH-M74a/GHA/2009 sequence
SEQUENCE: 620
MPQKTVEFIN MNSPLERGVS TLSDKKTLNQ SKITKQGYFG LGSHSERNWK KQKNQNDHYM    60
TVSTMILEIL VVLGIMFNLI VLTMVYYQND NINQRMAELT SNITVLNLNL NQLTNKIQRE   120
IIPRITLIDT ATTITIPSAI TYILATLTTR ISELLPSINQ KCEFKTPTLV LNDCRINCTP   180
PLNPSDGVKM SSLATNLVAH GPSPCRNFSS VPTIYYYRIP GLYNRTALDE RCILNPRLTI   240
SSTKFAYVHS EYDKNCTRGF KYYELMTFGE ILEGPEKEPR MFSRSFYSPT NAVNYHSCTP   300
IVTVNEGYFL CLECTSSDPL YKANLSNSTF HLVILRHNKD EKIVSMPSFN LSTDQEYVQI   360
IPAEGGGTAE SGNLYFPCIG RLLHKRVTHP LCKKSNCSRT DDESCLKSYY NQGSPQHQVV   420
NCLIRIRNAQ RDNPTWDVIT VDLTNTYPGS RSRIFGSFSK PMLYQSSVSW HTLLQVAEIT   480
DLDKYQLDWL DTPYISRPGG SECPFGNYCP TVCWEGTYND VYSLTPNNDL FVTVYLKSEQ   540
VAENPYFAIF SRDQILKEFP LDAWISSART TTISCFMFNN EIWCIAALEI TRLNDDIIRP   600
IYYSFWLPTD CRTPYPHTGK MTRVPLRSTY NY                                 632

SEQ ID NO: 621          moltype = AA  length = 625
FEATURE                 Location/Qualifiers
source                  1..625
                        mol_type = protein
                        organism = Mojiang henipavirus
SEQUENCE: 621
MATNRDNTIT SAEVSQEDKV KKYYGVETAE KVADSISGNK VFILMNTLLI LTGAIITITL    60
NITNLTAAKS QQNMLKIIQD DVNAKLEMFV NLDQLVKGEI KPKVSLINTA VSVSIPGQIS   120
NLQTKFLQKY VYLEESITKQ CTCNPLSGIF PTSGPTYPPT DKPDDDTTDD DKVDTTIKPI   180
EYPKPDGCNR TGDHFTMEPG ANFYTVPNLG PASSNSDECY TNPSFSIGSS IYMFSQEIRK   240
TDCTAGEILS IQIVLGRIVD KGQQGPQASP LLVWAVPNPK IINSCAVAAG DEMGWVLCSV   300
TLTAASGEPI PHMFDGFWLY KLEPDTEVVS YRITGYAYLL DKQYDSVFIG KGGGIQKGND   360
LYFQMYGLSR NRQSFKALCE HGSCLGTGGG GYQVLCDRAV MSFGSEESLI TNAYLKVNDL   420
ASGKPVIIGQ TFPPSDSYKG SNGRMYTIGD KYGLYLAPSS WNRYLRFGIT PDISVRSTTW   480
LKSQDPIMKI LSTCTNTDRD MCPEICNTRG YQDIFPLSED SEYYTYIGIT PNNGGTKNFV   540
AVRDSDGHIA SIDILQNYYS ITSATISCFM YKDEIWCIAI TEGKKQKDNP QRIYAHSYKI   600
RQMCYNMKSA TVTVGNAKNI TIRRY                                         625

SEQ ID NO: 622          moltype = AA  length = 552
FEATURE                 Location/Qualifiers
source                  1..552
                        mol_type = protein
                        organism = Hendra henipavirus
SEQUENCE: 622
FNTVIALLGS IVIIVMNIMI IQNYTRSTDN QAVIKDALQG IQQQIKGLAD KIGTEIGPKV    60
SLIDTSSTIT IPANIGLLGS KISQSTASIN ENVNEKCKFT LPPLKIHECN ISCPNPLPFR   120
```

```
EYRPQTEGVS NLVGLPNNIC LQKTSNQILK PKLISYTLPV VGQSGTCITD PLLAMDEGYF  180
AYSHLERIGS CSRGVSKQRI IGVGEVLDRG DEVPSLFMTN VWTPPNPNTV YHCSAVYNNE  240
FYYVLCAVST VGDPILNSTY WSGSLMMTRL AVKPKSNGGG YNQHQLALRS IEKGRYDKVM  300
PYGPSGIKQG DTLYFPAVGF LVRTEFKYND SNCPITKCQY SKPENCRLSM GIRPNSHYIL  360
RSGLLKYNLS DGENPKVVFI EISDQRLSIG SPSKIYDSLG QPVFYQASFS WDTMIKFGDV  420
LTVNPLVVNW RNNTVISRPG QSQCPRFNTC PEICWEGVYN DAFLIDRINW ISAGVFLDSN  480
QTAENPVFTV FKDNEILYRA QLASEDTNAQ KTITNCFLLK NKIWCISLVE IYDTGDNVIR  540
PKLFAVKIPE QC                                                       552

SEQ ID NO: 623           moltype = AA  length = 555
FEATURE                  Location/Qualifiers
source                   1..555
                         mol_type = protein
                         organism = Hendra henipavirus
SEQUENCE: 623
FNTVIALLGS IIIIVMNIMI IQNYTRTTDN QALIKESLQS VQQQIKALTD KIGTEIGPKV  60
SLIDTSSTIT IPANIGLLGS KISQSTSSIN ENVNDKCKFT LPPLKIHECN ISCPNPLPFR  120
EYRPISQGVS DLVGLPNQIC LQKTTSTILK PRLISYTLPI NTREGVCITD PLLAVDNGFF  180
AYSHLEKIGS CTRGIAKQRI IGVGEVLDRG DKVPSMFMTN VWTPPNPSTI HHCSSTYHED  240
FYYTLCAVSH VGDPILNSTS WTESLSLIRL AVRPKSDSGD YNQKYIAITK VERGKYDKVM  300
PYGPSGIKQG DTLYFPAVGF LPRTEFQYND SNCPIIHCKY SKAENCRLSM GVNSKSHYIL  360
RSGLLKYNLS LGGDIILQFI EIADNRLTIG SPSKIYNSLG QPVFYQASYS WDTMIKLGDV  420
DTVDPLRVQW RNNSVISRPG QSQCPRFNVC PEVCWEGTYN DAFLIDRLNW VSAGVYLNSN  480
QTAENPVFAV FKDNEILYQV PLAEDDTNAQ KTITDCFLLE NVIWCISLVE IYDTGDSVIR  540
PKLFAVKIPA QCSES                                                    555

SEQ ID NO: 624           moltype = AA  length = 26
FEATURE                  Location/Qualifiers
source                   1..26
                         mol_type = protein
                         organism = Nipah henipavirus
SEQUENCE: 624
MVVILDKRCY CNLLILILMI SECSVG                                        26

SEQ ID NO: 625           moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 625
GGGGGS                                                              6

SEQ ID NO: 626           moltype = AA  length = 50
FEATURE                  Location/Qualifiers
source                   1..50
                         mol_type = protein
                         organism = synthetic construct
                         note = Description of Artificial Sequence: Synthetic
                          polypeptide
VARIANT                  1..50
                         note = SITE - This sequence may encompass 1-10 GGGGS
                          repeating units
SEQUENCE: 626
GGGGSGGGGS GGGGSGGGGS GGGGSGGGGS GGGGSGGGGS GGGGSGGGGS             50

SEQ ID NO: 627           moltype = AA  length = 5
FEATURE                  Location/Qualifiers
source                   1..5
                         mol_type = protein
                         organism = synthetic construct
                         note = Description of Artificial Sequence: Synthetic peptide
SEQUENCE: 627
GGGGS                                                               5

SEQ ID NO: 628           moltype = AA  length = 600
FEATURE                  Location/Qualifiers
source                   1..600
                         mol_type = protein
                         organism = Nipah henipavirus
SEQUENCE: 628
PAENKKVRFE NTTSDKGKIP SKVIKSYYGT MDIKKINEGL LDSKILSAFN TVIALLGSIV  60
IIVMNIMIIQ NYTRSTDNQA VIKDALQGIQ QQIKGLADKI GTEIGPKVSL IDTSSTITIP  120
ANIGLLGSKI SQSTASINEN VNEKCKFTLP PLKIHECNIS CPNPLPFREY RPQTEGVSNL  180
VGLPNNICLQ KTSNQILKPK LISYTLPVVG QSGTCITDPL LAMDEGYFAY SHLERIGSCS  240
RGVSKQRIIG VGEVLDRGDE VPSLFMTNVW TPPNPNTVYH CSAVYNNEFY YVLCAVSTVG  300
DPILNSTYWS GSLMMTRLAV KPKSNGGGYN QHQLALRSIE KGRYDKVMPY GPSGIKQGDT  360
LYFPAVGFLV RTEFKYNDSN CPITKCQYSK PENCRLSMGI RPNSHYILRS GLLKYNLSDG  420
ENPKVVFIEI SDQRLSIGSP SKIYDSLGQP VFYQASFSWD TMIKFGDVLT VNPLVVNWRN  480
```

```
NTVISRPGQS QCPRFNTCPE ICWEGVYNDA FLIDRINWIS AGVFLDSNQT AENPVFTVFK   540
DNEILYRAQL ASEDTNAQKT ITNCFLLKNK IWCISLVEIY DTGDNVIRPK LFAVKIPEQC   600

SEQ ID NO: 629           moltype = AA  length = 595
FEATURE                  Location/Qualifiers
source                   1..595
                         mol_type = protein
                         organism = synthetic construct
                         note = Description of Artificial Sequence: Synthetic
                         polypeptide
SEQUENCE: 629
KVRFENTTSD KGKIPSKVIK SYYGTMDIKK INEGLLDSKI LSAFNTVIAL LGSIVIIVMN   60
IMIIQNYTRS TDNQAVIKDA LQGIQQQIKG LADKIGTEIG PKVSLIDTSS TITIPANIGL   120
LGSKISQSTA SINENVNEKC KFTLPPLKIH ECNISCPNPL PFREYRPQTE GVSNLVGLPN   180
NICLQKTSNQ ILKPKLISYT LPVVGQSGTC ITDPLLAMDE GYFAYSHLER IGSCSRGVSK   240
QRIIGVGEVL DRGDEVPSLF MTNVWTPPNP NTVYHCSAVY NNEFYYVLCA VSTVGDPILN   300
STYWSGSLMM TRLAVPKKSN GGGYNQHQLA LRSIEKGRYD KVMPYGPSGI KQGDTLYFPA   360
VGFLVRTEFK YNDSNCPITK CQYSKPENCR LSMGIRPNSH YILRSGLLKY NLSDGENPKV   420
VFIEISDQRL SIGSPSKIYD SLGQPVFYQA SFSWDTMIKF GDVLTVNPLV VNWRNNTVIS   480
RPGQSQCPRF NTCPEICWEG VYNDAFLIDR INWISAGVFL DSNQTAENPV FTVFKDNEIL   540
YRAQLASEDT NAQKTITNCF LLKNKIWCIS LVEIYDTGDN VIRPKLFAVK IPEQC        595

SEQ ID NO: 630           moltype = AA  length = 590
FEATURE                  Location/Qualifiers
source                   1..590
                         mol_type = protein
                         organism = synthetic construct
                         note = Description of Artificial Sequence: Synthetic
                         polypeptide
SEQUENCE: 630
NTTSDKGKIP SKVIKSYYGT MDIKKINEGL LDSKILSAFN TVIALLGSIV IIVMNIMIIQ   60
NYTRSTDNQA VIKDALQGIQ QQIKGLADKI GTEIGPKVSL IDTSSTITIP ANIGLLGSKI   120
SQSTASINEN VNEKCKFTLP PLKIHECNIS CPNPLPFREY RPQTEGVSNL VGLPNNICLQ   180
KTSNQILKPK LISYTLPVVG QSGTCITDPL LAMDEGYFAY SHLERIGSCS RGVSKQRIIG   240
VGEVLDRGDE VPSLFMTNVW TPPNPNTVYH CSAVYNNEFY YVLCAVSTVG DPILNSTYWS   300
GSLMMTRLAV KPKSNGGGYN QHQLALRSIE KGRYDKVMPY GPSGIKQGDT LYFPAVGFLV   360
RTEFKYNDSN CPITKCQYSK PENCRLSMGI RPNSHYILRS GLLKYNLSDG ENPKVVFIEI   420
SDQRLSIGSP SKIYDSLGQP VFYQASFSWD TMIKFGDVLT VNPLVVNWRN NTVISRPGQS   480
QCPRFNTCPE ICWEGVYNDA FLIDRINWIS AGVFLDSNQT AENPVFTVFK DNEILYRAQL   540
ASEDTNAQKT ITNCFLLKNK IWCISLVEIY DTGDNVIRPK LFAVKIPEQC             590

SEQ ID NO: 631           moltype = AA  length = 585
FEATURE                  Location/Qualifiers
source                   1..585
                         mol_type = protein
                         organism = synthetic construct
                         note = Description of Artificial Sequence: Synthetic
                         polypeptide
SEQUENCE: 631
KGKIPSKVIK SYYGTMDIKK INEGLLDSKI LSAFNTVIAL LGSIVIIVMN IMIIQNYTRS   60
TDNQAVIKDA LQGIQQQIKG LADKIGTEIG PKVSLIDTSS TITIPANIGL LGSKISQSTA   120
SINENVNEKC KFTLPPLKIH ECNISCPNPL PFREYRPQTE GVSNLVGLPN NICLQKTSNQ   180
ILKPKLISYT LPVVGQSGTC ITDPLLAMDE GYFAYSHLER IGSCSRGVSK QRIIGVGEVL   240
DRGDEVPSLF MTNVWTPPNP NTVYHCSAVY NNEFYYVLCA VSTVGDPILN STYWSGSLMM   300
TRLAVPKKSN GGGYNQHQLA LRSIEKGRYD KVMPYGPSGI KQGDTLYFPA VGFLVRTEFK   360
YNDSNCPITK CQYSKPENCR LSMGIRPNSH YILRSGLLKY NLSDGENPKV VFIEISDQRL   420
SIGSPSKIYD SLGQPVFYQA SFSWDTMIKF GDVLTVNPLV VNWRNNTVIS RPGQSQCPRF   480
NTCPEICWEG VYNDAFLIDR INWISAGVFL DSNQTAENPV FTVFKDNEIL YRAQLASEDT   540
NAQKTITNCF LLKNKIWCIS LVEIYDTGDN VIRPKLFAVK IPEQC                 585

SEQ ID NO: 632           moltype = AA  length = 580
FEATURE                  Location/Qualifiers
source                   1..580
                         mol_type = protein
                         organism = synthetic construct
                         note = Description of Artificial Sequence: Synthetic
                         polypeptide
SEQUENCE: 632
SKVIKSYYGT MDIKKINEGL LDSKILSAFN TVIALLGSIV IIVMNIMIIQ NYTRSTDNQA   60
VIKDALQGIQ QQIKGLADKI GTEIGPKVSL IDTSSTITIP ANIGLLGSKI SQSTASINEN   120
VNEKCKFTLP PLKIHECNIS CPNPLPFREY RPQTEGVSNL VGLPNNICLQ KTSNQILKPK   180
LISYTLPVVG QSGTCITDPL LAMDEGYFAY SHLERIGSCS RGVSKQRIIG VGEVLDRGDE   240
VPSLFMTNVW TPPNPNTVYH CSAVYNNEFY YVLCAVSTVG DPILNSTYWS GSLMMTRLAV   300
KPKSNGGGYN QHQLALRSIE KGRYDKVMPY GPSGIKQGDT LYFPAVGFLV RTEFKYNDSN   360
CPITKCQYSK PENCRLSMGI RPNSHYILRS GLLKYNLSDG ENPKVVFIEI SDQRLSIGSP   420
SKIYDSLGQP VFYQASFSWD TMIKFGDVLT VNPLVVNWRN NTVISRPGQS QCPRFNTCPE   480
ICWEGVYNDA FLIDRINWIS AGVFLDSNQT AENPVFTVFK DNEILYRAQL ASEDTNAQKT   540
ITNCFLLKNK IWCISLVEIY DTGDNVIRPK LFAVKIPEQC                       580
```

-continued

```
SEQ ID NO: 633          moltype = AA   length = 575
FEATURE                 Location/Qualifiers
source                  1..575
                        mol_type = protein
                        organism = synthetic construct
                        note = Description of Artificial Sequence: Synthetic
                        polypeptide
SEQUENCE: 633
SYYGTMDIKK INEGLLDSKI LSAFNTVIAL LGSIVIIVMN IMIIQNYTRS TDNQAVIKDA   60
LQGIQQQIKG LADKIGTEIG PKVSLIDTSS TITIPANIGL LGSKISQSTA SINENVNEKC  120
KFTLPPLKIH ECNISCPNPL PFREYRPQTE GVSNLVGLPN NICLQKTSNQ ILKPKLISYT  180
LPVVGQSGTC ITDPLLAMDE GYFAYSHLER IGSCSRGVSK QRIIGVGEVL DRGDEVPSLF  240
MTNVWTPPNP NTVYHCSAVY NNEFYYVLCA VSTVGDPILN STYWSGSLMM TRLAVKPKSN  300
GGGYNQHQLA LRSIEKGRYD KVMPYGPSGI KQGDTLYFPA VGFLVRTEFK YNDSNCPITK  360
CQYSKPENCR LSMGIRPNSH YILRSGLLKY NLSDGENPKV VFIEISDQRL SIGSPSKIYD  420
SLGQPVFYQA SFSWDTMIKF GDVLTVNPLV VNWRNNTVIS RPGQSQCPRF NTCPEICWEG  480
VYNDAFLIDR INWISAGVFL DSNQTAENPV FTVFKDNEIL YRAQLASEDT NAQKTITNCF  540
LLKNKIWCIS LVEIYDTGDN VIRPKLFAVK IPEQC                            575

SEQ ID NO: 634          moltype = AA   length = 571
FEATURE                 Location/Qualifiers
source                  1..571
                        mol_type = protein
                        organism = synthetic construct
                        note = Description of Artificial Sequence: Synthetic
                        polypeptide
SEQUENCE: 634
TMDIKKINEG LLDSKILSAF NTVIALLGSI VIIVMNIMII QNYTRSTDNQ AVIKDALQGI   60
QQQIKGLADK IGTEIGPKVS LIDTSSTITI PANIGLLGSK ISQSTASINE NVNEKCKFTL  120
PPLKIHECNI SCPNPLPFRE YRPQTEGVSN LVGLPNNICL QKTSNQILKP KLISYTLPVV  180
GQSGTCITDP LLAMDEGYFA YSHLERIGSC SRGVSKQRII GVGEVLDRGD EVPSLFMTNV  240
WTPPNPNTVY HCSAVYNNEF YYVLCAVSTV GDPILNSTYW SGSLMMTRLA VKPKSNGGGY  300
NQHQLALRSI EKGRYDKVMP YGPSGIKQGD TLYFPAVGFL VRTEFKYNDS NCPITKCQYS  360
KPENCRLSMG IRPNSHYILR SGLLKYNLSD GENPKVVFIE ISDQRLSIGS PSKIYDSLGQ  420
PVFYQASFSW DTMIKFGDVL TVNPLVVNWR NNTVISRPGQ SQCPRFNTCP EICWEGVYND  480
AFLIDRINWI SAGVFLDSNQ TAENPVFTVF KDNEILYRAQ LASEDTNAQK TITNCFLLKN  540
KIWCISLVEI YDTGDNVIRP KLFAVKIPEQ C                                571

SEQ ID NO: 635          moltype = AA   length = 568
FEATURE                 Location/Qualifiers
source                  1..568
                        mol_type = protein
                        organism = synthetic construct
                        note = Description of Artificial Sequence: Synthetic
                        polypeptide
SEQUENCE: 635
KKINEGLLDS KILSAFNTVI ALLGSIVIIV MNIMIIQNYT RSTDNQAVIK DALQGIQQQI   60
KGLADKIGTE IGPKVSLIDT SSTITIPANI GLLGSKISQS TASINENVNE KCKFTLPPLK  120
IHECNISCPN PLPFREYRPQ TEGVSNLVGL PNNICLQKTS NQILKPKLIS YTLPVVGQSG  180
TCITDPLLAM DEGYFAYSHL ERIGSCSRGV SKQRIIGVGE VLDRGDEVPS LFMTNVWTPP  240
NPNTVYHCSA VYNNEFYYVL CAVSTVGDPI LNSTYWSGSL MMTRLAVKPK SNGGGYNQHQ  300
LALRSIEKGR YDKVMPYGPS GIKQGDTLYF PAVGFLVRTE FKYNDSNCPI TKCQYSKPEN  360
CRLSMGIRPN SHYILRSGLL KYNLSDGENP KVVFIEISDQ RLSIGSPSKI YDSLGQPVFY  420
QASFSWDTMI KFGDVLTVNP LVVNWRNNTV ISRPGQSQCP RFNTCPAICA EGVYNDAFLI  480
DRINWISAGV FLDSNATAAN PVFTVFKDNE ILYRAQLASE DTNAQKTITN CFLLKNKIWC  540
ISLVEIYDTG DNVIRPKLFA VKIPEQCT                                    568

SEQ ID NO: 636          moltype = AA   length = 603
FEATURE                 Location/Qualifiers
source                  1..603
                        mol_type = protein
                        organism = Hendra henipavirus
SEQUENCE: 636
MADSKLVSLN NNLSGKIKDQ GKVIKNYYGT MDIKKINDGL LDSKILGAFN TVIALLGSII   60
IIVMNIMIIQ NYRTTDNQA LIKESLQSVQ QQIKALTDKI GTEIGPKVSL IDTSSTITIP  120
ANIGLLGSKI SQSTSSINEN VNDKCKFTLP LKIHECNIS CPNPLPFREY RPISQGVSDL  180
VGLPNQICLQ KTTSTILKPR LISYTLPINT REGVCITDPL LAVDNGFFAY SHLEKIGSCT  240
RGIAKQRIIG VGEVLDRGDK VPSMFMTNVW TPPNPSTIHK CSSTYHEDFY YTLCAVSHVG  300
DPILNSTSWT ESLSLIRLAV RPKSDSGDYN QKYIAITKVE RGKYDKVMPY GPSGIKQGDT  360
LYFPAVGFLP RTEFQYNDSN CPIIHCKYSK AENCRLSMGV NSKSHYILRS GLLKYNLSLG  420
GDIILQFIEI ADNRLTIGSP SKIYNSLGQP VFYQASYSWD TMIKLGDVDT VDPLRVQWRN  480
NSVISRPGQS QCPRFNVCPE VCWEGTYNDA FLIDRLNWVS AGVYLNSQT AENPVFAVFK  540
DNEILYQVPL AEDDTNAQKT ITDCFLLENV IWCISLVEIY DTGDSVIRPK LFAVKIPAQC  600
SES                                                               603

SEQ ID NO: 637          moltype = AA   length = 568
FEATURE                 Location/Qualifiers
source                  1..568
                        mol_type = protein
```

```
                        organism = synthetic construct
                        note = Description of Artificial Sequence: Synthetic
                        polypeptide
SEQUENCE: 637
KKINEGLLDS KILSAFNTVI ALLGSIVIIV MNIMIIQNYT RSTDNQAVIK DALQGIQQQI   60
KGLADKIGTE IGPKVSLIDT SSTITIPANI GLLGSKISQS TASINENVNE KCKFTLPPLK  120
IHECNISCPN PLPFREYRPQ TEGVSNLVGL PNNICLQKTS NQILKPKLIS YTLPVVGQSG  180
TCITDPLLAM DEGYFAYSHL ERIGSCSRGV SKQRIIGVGE VLDRGDEVPS LFMTNVWTPP  240
NPNTVYHCSA VYNNEFYYVL CAVSTVGDPI LNSTYWSGSL MMTRLAVKPK SNGGGYNQHQ  300
LALRSIEKGR YDKVMPYGPS GIKQGDTLYF PAVGFLVRTE FKYNDSNCPI TKCQYSKPEN  360
CRLSMGIRPN SHYILRSGLL KYNLSDGENP KVVFIEISDQ RLSIGSPSKI YDSLGQPVFY  420
QASFSWDTMI KFGDVLTVNP LVVNWRNNTV ISRPGQSQCP RFNTCPEICW EGVYNDAFLI  480
DRINWISAGV FLDSNQTAEN PVFTVFKDNE ILYRAQLASE DTNAQKTITN CFLLKNKIWC  540
ISLVEIYDTG DNVIRPKLFA VKIPEQCT                                     568

SEQ ID NO: 638       moltype = AA  length = 621
FEATURE              Location/Qualifiers
source               1..621
                     mol_type = protein
                     organism = Cedar henipavirus
SEQUENCE: 638
LSQLQKNYLD NSNQQGDKMN NPDKKLSVNF NPLELDKGQK DLNKSYYVKN KNYNVSNLLN   60
ESLHDIKFCI YCIFSLLIII TIINIITISI VITRLKVHEE NNGMESPNLQ SIQDSLSSLT  120
NMINTEITPR IGILVTATSV TLSSSINYVG TKTNQLVNEL KDYITKSCGF KVPELKLHEC  180
NISCADPKIS KSAMYSTNAY AELAGPPKIF CKSVSKDPDF RLKQIDYVIP VQQDRSICMN  240
NPLLDISDGF FTYIHYEGIN SCKKSDSFKV LLSHGEIVDR GDYRPSLYLL SSHYHPYSMQ  300
VINCVPVTCN QSSFVFCHIS NNTKTLDNSD YSSDEYYITY FNGIDRPKTK KIPINNMTAD  360
NRYIHFTFSG GGGVCLGEEF IIPVTTVINT DVFTHDYCES FNCSVQTGKS LKEICSESLR  420
SPTNSSRYNL NGIMIISQNN MTDFKIQLNG ITYNKLSFGS PGRLSKTLGQ VLYYQSSMSW  480
DTYLKAGFVE KWKPFTPNWM NNTVISRPNQ GNCPRYHKCP EICYGGTYND IAPLDLGKDM  540
YVSVILDSDQ LAENPEITVF NSTTILYKER VSKDELNTRS TTTSCFLFLD EPWCISVLET  600
NRFNGKSIRP EIYSYKIPKY C                                            621

SEQ ID NO: 639       moltype = AA  length = 631
FEATURE              Location/Qualifiers
source               1..631
                     mol_type = protein
                     organism = unidentified
                     note = Description of Unknown: Bat Paramyxovirus
                     Eid_hel/GH-M74a/GHA/2009 sequence
SEQUENCE: 639
PQKTVEFINM NSPLERGVST LSDKKTLNQS KITKQGYFGL GSHSERNWKK QKNQNDHYMT   60
VSTMILEILV VLGIMFNLIV LTMVYYQNDN INQRMAELTS NITVLNLNLN QLTNKIQREI  120
IPRITLIDTA TTITIPSAIT YILALTLTTRI SELLPSINQK CEFKTPTLVL NDCRINCTPP  180
LNPSDGVKMS SLATNLVAHG PSPCRNFSSV PTIYYYRIPG LYNRTALDER CILNPRLTIS  240
STKFAYVHSE YDKNCTRGFK YYELMTFGEI LEGPEKEPRM FSRSFYSPTN AVNYHSCTPI  300
VTVNEGYFLC LECTSSDPLY KANLSNSTFH LVILRHNKDE KIVSMPSFNL STDQEYVQII  360
PAEGGGTAES GNLYFPCIGR LLHKRVTHPL CKKSNCSRTD DESCLKSYYN QGSPQHQVVN  420
CLIRIRNAQR DNPTWDVITV DLTNTYPGSR SRIFGSFSKP MLYQSSVSWH TLLQVAEITD  480
LDKYQLDWLD TPYISRPGGS ECPFGNYCPT VCWEGTYNDV YSLTPNNDLF VTVYLKSEQV  540
AENPYFAIFS RDQILKEFPL DAWISSARTT TISCFMFNNE IWCIAALEIT RLNDDIIRPI  600
YYSFWLPTDC RTPYPHTGKM TRVPLRSTYN Y                                 631

SEQ ID NO: 640       moltype = AA  length = 624
FEATURE              Location/Qualifiers
source               1..624
                     mol_type = protein
                     organism = Mojiang henipavirus
SEQUENCE: 640
ATNRDNTITS AEVSQEDKVK KYYGVETAEK VADSISGNKV FILMNTLLIL TGAIITITLN   60
ITNLTAAKSQ QNMLKIIQDD VNAKLEMFVN LDQLVKGEIK PKVSLINTAV SVSIPGQISN  120
LQTKFLQKYV YLEESITKQC TCNPLSGIFP TSGPTYPPTD KPDDDTTDDD KVDTTIKPIE  180
YPKPDGCNRT GDHFTMEPGA NFYTVPNLGP ASSNSDECYT NPSFSIGSSI YMFSQEIRKT  240
DCTAGEILSI QIVLGRIVDK GQQGPQASPL LVWAVPNPKI INSCAVAAGD EMGWVLCSVT  300
LTAASGEPIP HMFDGFWLYK LEPDTEVVSY RITGYAYLLD KQYDSVFIGK GGGIQKGNDL  360
YFQMYGLSRN RQSFKALCEH GSCLGTGGGG YQVLCDRAVM SFGSEESLIT NAYLKVNDLA  420
SGKPVIIGQT FPPSDSYKGS NGRMYTIGDK YGLYLAPSSW NRYLRFGITP DISVRSTTWL  480
KSQDPIMKIL STCTNTDRDM CPEICNTRGY QDIFPPLSEDS EYYTYIGITP NNGGTKNFVA  540
VRDSDGHIAS IDILQNYYSI TSATISCFMY KDEIWCIAIT EGKKQKDNPQ RIYAHSYKIR  600
QMCYNMKSAT VTVGNAKNIT IRRY                                         624

SEQ ID NO: 641       moltype = AA  length = 530
FEATURE              Location/Qualifiers
source               1..530
                     mol_type = protein
                     organism = Cedar henipavirus
SEQUENCE: 641
DFDKLNKIGV VQGRVLNYKI KGDPMTKDLV LKFIPNIVNI TECVREPLSR YNETVRRLLL   60
PIHNMLGLYL NNTNAKMTGL MIAGVIMGGI AIGIATAAQI TAGFALYEAK KNTENIQKLT  120
```

```
DSIMKTQDSI DKLTDSVGTS ILILNKLQTY INNQLVPNLE LLSCRQNKIE FDLMLTKYLV   180
DLMTVIGPNI NNPVNKDMTI QSLSLLFDGN YDIMMSELGY TPQDFLDLIE SKSITGQIIY   240
VDMENLYVVI RTYLPTLIEV PDAQIYEFNK ITMSSNGGEY LSTIPNFILI RGNYMSNIDV   300
ATCYMTKASV ICNQDYSLPM SQNLRSCYQG ETEYCPVEAV IASHSPRFAL TNGVIFANCI   360
NTICRCQDNG KTITQNINQF VSMIDNSTCN DVMVDKFTIK VGKYMGRKDI NNINIQIGPG   420
IIIDKVDLSN EINKMNQSLK DSIFYLREAK RILDSVNISL ISPSVQLFLI IISVLSFIIL   480
LIIIVYLYCK SKHSYKYNKF IDDPDYYNDY KRERINGKAS KSNNIYYVGD              530

SEQ ID NO: 642                moltype = AA  length = 640
FEATURE                       Location/Qualifiers
source                        1..640
                              mol_type = protein
                              organism = unidentified
                              note = Description of Unknown: Bat Paramyxovirus
                              Eid_hel/GH-M74a/GHA/2009 sequence
SEQUENCE: 642
SRALLRETDN YSNGLIVENL VRNCHHPSKN NLNYTKTQKR DSTIPYRVEE RKGHYPKIKH   60
LIDKSYKHIK RGKRRNGHNG NIITIILLLI LILKTQMSEG AIHYETLSKI GLIKGITREY   120
KVKGTPSSKD IVIKLIPNVT GLNKCTNISM ENYKEQLDKI LIPINNIIEL YANSTKSAPG   180
NARFAGVIIA GVALGVAAAA QITAGIALHE ARQNAERINL LKDSISATNN AVAELQEATG   240
GIVNVITGMQ DYINTNLVPQ IDKLQCSQIK TALDISLSQY YSEILTVFGP NLQNPVTTSM   300
SIQAISQSFG GNIDLLLNLL GYTANDLLDL LESKSITGQI TYINLEHYFM VIRVYYPIMT   360
TISNAYVQEL IKISFNVDGS EWVSLVPSYI LIRNSYLSNI DISECLITKN SVICRHDFAM   420
PMSYTLKECL TGDTEKCPRE AVVTSYVPRF AISGGVIYAN CLSTTCQCYQ TGKVIAQDGS   480
QTLMMIDNQT CSIVRIEEIL ISTGKYLGSQ EYNTMHVSVG NPVFTDKLDI TSQISNINQS   540
IEQSKFYLDK SKAILDKINL NLIGSVPISI LFIIAILSLI LSIITFVIVM IIVRRYNKYT   600
PLINSDPSSR RSTIQDVYII PNPGEHSIRS AARSIDRDRD              640

SEQ ID NO: 643                moltype = AA  length = 520
FEATURE                       Location/Qualifiers
source                        1..520
                              mol_type = protein
                              organism = Hendra henipavirus
SEQUENCE: 643
ILHYEKLSKI GLVKGITRKY KIKSNPLTKD IVIKMIPNVS NVSKCTGTVM ENYKSRLTGI   60
LSPIKGAIEL YNNNTHDLVG DVKLAGVVMA GIAIGIATAA QITAGVALYE AMKNADNINK   120
LKSSIESTNE AVVKLQETAE KTVYVLTALQ DYINTNLVPT IDQISCKQTE LALDLALSKY   180
LSDLLFVFGP NLQDPVSNSM TIQAISQAFG GNYETLLRTL GYATEDFDDL LESDSIAGQI   240
VYVDLSSYYI IVRVYFPILT EIQQAYVQEL LPVSFNNDNS EWISIVPNFV LIRNTLISNI   300
EVKYCLITKK SVICNQDYAT PMTASVRECL TGSTDKCPRE LVVSSHVPRF ALSGGVLFAN   360
CISVTCQCQT TGRAISQSGE QTLLMIDNTT CTTVVLGNII ISLGKYLGSI NYNSESIAVG   420
PPVYTDKVDI SSQISSMNQS LQQSKDYIKE AQKILDTVNP SLISMLSMII LYVLSIAALC   480
IGLITFISFV IVEKKRGNYS RLDDRQVRPV SNGDLYYIGT              520

SEQ ID NO: 644                moltype = AA  length = 519
FEATURE                       Location/Qualifiers
source                        1..519
                              mol_type = protein
                              organism = Mojiang henipavirus
SEQUENCE: 644
IHYDSLSKVG VIKGLTYNYK IKGSPSTKLM VVKLIPNIDS VKNCTQKQYD EYKNLVRKAL   60
EPVKMAIDTM LNNVKSGNNK YRFAGAIMAG VALGVATAAT VTAGIALHRS NENAQAIANM   120
KSAIQNTNEA VKQLQLANKQ TLAVIDTIRG EINNNIIPVI NQLSCDTIGL SVGIRLTQYY   180
SEIITAFGPA LQNPVNTRIT IQAISSVFNG NFDELLKIMG YTSGDLYEIL HSELIRGNII   240
DVDVDAGYIA LEIEFPNLTL VPNAVVQELM PISYNIDGDE WVTLVPRFVL TRTTLLSNID   300
TSRCTITDSS VICDNDYALP MSHELIGCLQ GDTSKCAREK VVSSYVPKFA LSDGLVYANC   360
LNTICRCMDT DTPISQSLGA TVSLLDNKRC SVYQVGDVLI SVGSYLGDGE YNADNVELGP   420
PIVIDKIDIG NQLAGINQTL QEAEDYIEKS EEFLKGVNPS IITLGSMVVL YIFMILIAIV   480
SVIALVLSIK LTVKGNVVRQ QFTYTQHVPS MENINYVSH              519

SEQ ID NO: 645                moltype = AA  length = 40
FEATURE                       Location/Qualifiers
source                        1..40
                              mol_type = protein
                              organism = synthetic construct
                              note = Description of Artificial Sequence: Synthetic
                              polypeptide
VARIANT                       1..40
                              note = SITE - This sequence may encompass 1-10 GGGS
                              repeating units
SEQUENCE: 645
GGGSGGGSGG GSGGGSGGGS GGGSGGGSGG GSGGGSGGGS              40

SEQ ID NO: 646                moltype = AA  length = 15
FEATURE                       Location/Qualifiers
source                        1..15
                              mol_type = protein
                              organism = synthetic construct
                              note = Description of Artificial Sequence: Synthetic peptide
```

-continued

```
SEQUENCE: 646
GGGGSGGGGS GGGGS                                                      15

SEQ ID NO: 647      moltype = AA  length = 15
FEATURE             Location/Qualifiers
source              1..15
                    mol_type = protein
                    organism = synthetic construct
                    note = Description of Artificial Sequence: Synthetic peptide
SEQUENCE: 647
TTAASGSSGG SSSGA                                                      15

SEQ ID NO: 648      moltype = AA  length = 18
FEATURE             Location/Qualifiers
source              1..18
                    mol_type = protein
                    organism = synthetic construct
                    note = Description of Artificial Sequence: Synthetic peptide
SEQUENCE: 648
GSTSGSGKPG SGEGSTKG                                                   18

SEQ ID NO: 649      moltype = AA  length = 10
FEATURE             Location/Qualifiers
source              1..10
                    mol_type = protein
                    organism = Homo sapiens
SEQUENCE: 649
EGYYYYGMDV                                                            10

SEQ ID NO: 650      moltype = AA  length = 9
FEATURE             Location/Qualifiers
source              1..9
                    mol_type = protein
                    organism = Homo sapiens
SEQUENCE: 650
GIAVAGTDY                                                             9

SEQ ID NO: 651      moltype = AA  length = 119
FEATURE             Location/Qualifiers
source              1..119
                    mol_type = protein
                    organism = Homo sapiens
SEQUENCE: 651
QVQLVQSGAE VKKPGASVKV SCKASGYTFT GYYMHWVRQA PGQGLEWMGH INPNNGDTNY  60
AQNFQGRVTM TRDTSTSTVY MELSSLRSED TAVYYCAKEG YYYYGMDVWG QGTTVTVSS   119

SEQ ID NO: 652      moltype = AA  length = 118
FEATURE             Location/Qualifiers
source              1..118
                    mol_type = protein
                    organism = Homo sapiens
SEQUENCE: 652
QVQLVQSGAE VKKPGASVKV SCKASGYTFT SYGISWVRQA PGQGLEWMGW ISAHNGVTQY  60
AQKFQGRVTM TRDTSTSTVY MELSSLRSED TAVYYCARGI AVAGTDYWGQ GTLVTVSS    118

SEQ ID NO: 653      moltype = AA  length = 7
FEATURE             Location/Qualifiers
source              1..7
                    mol_type = protein
                    organism = Homo sapiens
SEQUENCE: 653
GGTFSSY                                                              7

SEQ ID NO: 654      moltype = AA  length = 7
FEATURE             Location/Qualifiers
source              1..7
                    mol_type = protein
                    organism = Homo sapiens
SEQUENCE: 654
GGTFNTY                                                              7

SEQ ID NO: 655      moltype = AA  length = 7
FEATURE             Location/Qualifiers
source              1..7
                    mol_type = protein
                    organism = Homo sapiens
SEQUENCE: 655
GYTFTGY                                                              7
```

-continued

```
SEQ ID NO: 656          moltype = AA   length = 7
FEATURE                 Location/Qualifiers
source                  1..7
                        mol_type = protein
                        organism = Homo sapiens
SEQUENCE: 656
GYTFTDY                                                              7

SEQ ID NO: 657          moltype = AA   length = 7
FEATURE                 Location/Qualifiers
source                  1..7
                        mol_type = protein
                        organism = Homo sapiens
SEQUENCE: 657
GYTFTRY                                                              7

SEQ ID NO: 658          moltype = AA   length = 7
FEATURE                 Location/Qualifiers
source                  1..7
                        mol_type = protein
                        organism = Homo sapiens
SEQUENCE: 658
GYTFTSY                                                              7

SEQ ID NO: 659          moltype = AA   length = 7
FEATURE                 Location/Qualifiers
source                  1..7
                        mol_type = protein
                        organism = Homo sapiens
SEQUENCE: 659
GHTFSRH                                                              7

SEQ ID NO: 660          moltype = AA   length = 7
FEATURE                 Location/Qualifiers
source                  1..7
                        mol_type = protein
                        organism = Homo sapiens
SEQUENCE: 660
GGTFSNT                                                              7

SEQ ID NO: 661          moltype = AA   length = 7
FEATURE                 Location/Qualifiers
source                  1..7
                        mol_type = protein
                        organism = Homo sapiens
SEQUENCE: 661
GYTFTRS                                                              7

SEQ ID NO: 662          moltype = AA   length = 7
FEATURE                 Location/Qualifiers
source                  1..7
                        mol_type = protein
                        organism = Homo sapiens
SEQUENCE: 662
GDTFTGY                                                              7

SEQ ID NO: 663          moltype = AA   length = 7
FEATURE                 Location/Qualifiers
source                  1..7
                        mol_type = protein
                        organism = Homo sapiens
SEQUENCE: 663
GYTFTNY                                                              7

SEQ ID NO: 664          moltype = AA   length = 7
FEATURE                 Location/Qualifiers
source                  1..7
                        mol_type = protein
                        organism = Homo sapiens
SEQUENCE: 664
GYGFTRY                                                              7

SEQ ID NO: 665          moltype = AA   length = 7
FEATURE                 Location/Qualifiers
source                  1..7
                        mol_type = protein
                        organism = Homo sapiens
SEQUENCE: 665
GYTFTSR                                                              7
```

-continued

```
SEQ ID NO: 666            moltype = AA   length = 7
FEATURE                   Location/Qualifiers
source                    1..7
                          mol_type = protein
                          organism = Homo sapiens SEQUENCE: 666
GFTFSNS                                                            7

SEQ ID NO: 667            moltype = AA   length = 7
FEATURE                   Location/Qualifiers
source                    1..7
                          mol_type = protein
                          organism = Homo sapiens SEQUENCE: 667
GYTFTTY                                                            7

SEQ ID NO: 668            moltype = AA   length = 7
FEATURE                   Location/Qualifiers
source                    1..7
                          mol_type = protein
                          organism = Homo sapiens SEQUENCE: 668
GFTFSSY                                                            7

SEQ ID NO: 669            moltype = AA   length = 7
FEATURE                   Location/Qualifiers
source                    1..7
                          mol_type = protein
                          organism = Homo sapiens SEQUENCE: 669
GGTFSRY                                                            7

SEQ ID NO: 670            moltype = AA   length = 7
FEATURE                   Location/Qualifiers
source                    1..7
                          mol_type = protein
                          organism = Homo sapiens SEQUENCE: 670
GNTFTSY                                                            7

SEQ ID NO: 671            moltype = AA   length = 7
FEATURE                   Location/Qualifiers
source                    1..7
                          mol_type = protein
                          organism = Homo sapiens SEQUENCE: 671
GGTFSNY                                                            7

SEQ ID NO: 672            moltype = AA   length = 7
FEATURE                   Location/Qualifiers
source                    1..7
                          mol_type = protein
                          organism = Homo sapiens SEQUENCE: 672
GGTFTRY                                                            7

SEQ ID NO: 673            moltype = AA   length = 7
FEATURE                   Location/Qualifiers
source                    1..7
                          mol_type = protein
                          organism = Homo sapiens SEQUENCE: 673
GGTFSRF                                                            7

SEQ ID NO: 674            moltype = AA   length = 7
FEATURE                   Location/Qualifiers
source                    1..7
                          mol_type = protein
                          organism = Homo sapiens SEQUENCE: 674
GGTFSSH                                                            7

SEQ ID NO: 675            moltype = AA   length = 7
FEATURE                   Location/Qualifiers
source                    1..7
                          mol_type = protein
                          organism = Homo sapiens

SEQUENCE: 675
```

-continued

```
GGTFGSY                                                           7

SEQ ID NO: 676              moltype = AA   length = 7
FEATURE                     Location/Qualifiers
source                      1..7
                            mol_type = protein
                            organism = Homo sapiens SEQUENCE: 676
GYIFTDY                                                           7

SEQ ID NO: 677              moltype = AA   length = 7
FEATURE                     Location/Qualifiers
source                      1..7
                            mol_type = protein
                            organism = Homo sapiens SEQUENCE: 677
GFTFSSF                                                           7

SEQ ID NO: 678              moltype = AA   length = 7
FEATURE                     Location/Qualifiers
source                      1..7
                            mol_type = protein
                            organism = Homo sapiens SEQUENCE: 678
GFTFDDY                                                           7

SEQ ID NO: 679              moltype = AA   length = 7
FEATURE                     Location/Qualifiers
source                      1..7
                            mol_type = protein
                            organism = Homo sapiens SEQUENCE: 679
GYTFTDS                                                           7

SEQ ID NO: 680              moltype = AA   length = 7
FEATURE                     Location/Qualifiers
source                      1..7
                            mol_type = protein
                            organism = Homo sapiens SEQUENCE: 680
GYTFMNY                                                           7

SEQ ID NO: 681              moltype = AA   length = 7
FEATURE                     Location/Qualifiers
source                      1..7
                            mol_type = protein
                            organism = Homo sapiens SEQUENCE: 681
GYTLNDY                                                           7

SEQ ID NO: 682              moltype = AA   length = 7
FEATURE                     Location/Qualifiers
source                      1..7
                            mol_type = protein
                            organism = Homo sapiens SEQUENCE: 682
GYTFTNH                                                           7

SEQ ID NO: 683              moltype = AA   length = 7
FEATURE                     Location/Qualifiers
source                      1..7
                            mol_type = protein
                            organism = Homo sapiens SEQUENCE: 683
GYTFTEN                                                           7

SEQ ID NO: 684              moltype = AA   length = 7
FEATURE                     Location/Qualifiers
source                      1..7
                            mol_type = protein
                            organism = Homo sapiens SEQUENCE: 684
GYTFASY                                                           7

SEQ ID NO: 685              moltype = AA   length = 7
FEATURE                     Location/Qualifiers
source                      1..7
                            mol_type = protein
                            organism = Homo sapiens
```

```
SEQUENCE: 685
GYTFTAY                                                                    7

SEQ ID NO: 686          moltype = AA  length = 7
FEATURE                 Location/Qualifiers
source                  1..7
                        mol_type = protein
                        organism = Homo sapiens
SEQUENCE: 686
GYPFTDY                                                                    7

SEQ ID NO: 687          moltype = AA  length = 7
FEATURE                 Location/Qualifiers
source                  1..7
                        mol_type = protein
                        organism = Homo sapiens
SEQUENCE: 687
GYTFSDY                                                                    7

SEQ ID NO: 688          moltype = AA  length = 7
FEATURE                 Location/Qualifiers
source                  1..7
                        mol_type = protein
                        organism = Homo sapiens
SEQUENCE: 688
GDTFTTH                                                                    7

SEQ ID NO: 689          moltype = AA  length = 7
FEATURE                 Location/Qualifiers
source                  1..7
                        mol_type = protein
                        organism = Homo sapiens
SEQUENCE: 689
GDTFTNY                                                                    7

SEQ ID NO: 690          moltype = AA  length = 7
FEATURE                 Location/Qualifiers
source                  1..7
                        mol_type = protein
                        organism = Homo sapiens
SEQUENCE: 690
GYTFTDN                                                                    7

SEQ ID NO: 691          moltype = AA  length = 7
FEATURE                 Location/Qualifiers
source                  1..7
                        mol_type = protein
                        organism = Homo sapiens
SEQUENCE: 691
GGTSSSY                                                                    7

SEQ ID NO: 692          moltype = AA  length = 7
FEATURE                 Location/Qualifiers
source                  1..7
                        mol_type = protein
                        organism = Homo sapiens
SEQUENCE: 692
GGTFTSY                                                                    7

SEQ ID NO: 693          moltype = AA  length = 7
FEATURE                 Location/Qualifiers
source                  1..7
                        mol_type = protein
                        organism = Homo sapiens
SEQUENCE: 693
GNTFTSH                                                                    7

SEQ ID NO: 694          moltype = AA  length = 7
FEATURE                 Location/Qualifiers
source                  1..7
                        mol_type = protein
                        organism = Homo sapiens
SEQUENCE: 694
GFTFSDY                                                                    7

SEQ ID NO: 695          moltype = AA  length = 7
FEATURE                 Location/Qualifiers
source                  1..7
                        mol_type = protein
```

-continued

```
                              organism = Homo sapiens
SEQUENCE: 695
GYMFTGH                                                          7

SEQ ID NO: 696         moltype = AA  length = 7
FEATURE                Location/Qualifiers
source                 1..7
                       mol_type = protein
                       organism = Homo sapiens
SEQUENCE: 696
GYIFSNY                                                          7

SEQ ID NO: 697         moltype = AA  length = 7
FEATURE                Location/Qualifiers
source                 1..7
                       mol_type = protein
                       organism = Homo sapiens
SEQUENCE: 697
GSTFTNY                                                          7

SEQ ID NO: 698         moltype = AA  length = 7
FEATURE                Location/Qualifiers
source                 1..7
                       mol_type = protein
                       organism = Homo sapiens
SEQUENCE: 698
GGTLSSY                                                          7

SEQ ID NO: 699         moltype = AA  length = 7
FEATURE                Location/Qualifiers
source                 1..7
                       mol_type = protein
                       organism = Homo sapiens
SEQUENCE: 699
GYTFTSH                                                          7

SEQ ID NO: 700         moltype = AA  length = 7
FEATURE                Location/Qualifiers
source                 1..7
                       mol_type = protein
                       organism = Homo sapiens
SEQUENCE: 700
GGTFNSY                                                          7

SEQ ID NO: 701         moltype = AA  length = 6
FEATURE                Location/Qualifiers
source                 1..6
                       mol_type = protein
                       organism = Homo sapiens
SEQUENCE: 701
DPSDGN                                                           6

SEQ ID NO: 702         moltype = AA  length = 6
FEATURE                Location/Qualifiers
source                 1..6
                       mol_type = protein
                       organism = Homo sapiens
SEQUENCE: 702
DPSSGG                                                           6

SEQ ID NO: 703         moltype = AA  length = 6
FEATURE                Location/Qualifiers
source                 1..6
                       mol_type = protein
                       organism = Homo sapiens
SEQUENCE: 703
DPSGGN                                                           6

SEQ ID NO: 704         moltype = AA  length = 6
FEATURE                Location/Qualifiers
source                 1..6
                       mol_type = protein
                       organism = Homo sapiens
SEQUENCE: 704
NPNNGD                                                           6

SEQ ID NO: 705         moltype = AA  length = 6
FEATURE                Location/Qualifiers
source                 1..6
```

-continued

```
                          mol_type = protein
                          organism = Homo sapiens
SEQUENCE: 705
NPNSGG                                                              6

SEQ ID NO: 706            moltype = AA  length = 6
FEATURE                   Location/Qualifiers
source                    1..6
                          mol_type = protein
                          organism = Homo sapiens
SEQUENCE: 706
NPNDGS                                                              6

SEQ ID NO: 707            moltype = AA  length = 6
FEATURE                   Location/Qualifiers
source                    1..6
                          mol_type = protein
                          organism = Homo sapiens
SEQUENCE: 707
NPNSGN                                                              6

SEQ ID NO: 708            moltype = AA  length = 6
FEATURE                   Location/Qualifiers
source                    1..6
                          mol_type = protein
                          organism = Homo sapiens
SEQUENCE: 708
SAHNGV                                                              6

SEQ ID NO: 709            moltype = AA  length = 6
FEATURE                   Location/Qualifiers
source                    1..6
                          mol_type = protein
                          organism = Homo sapiens
SEQUENCE: 709
NPSGGS                                                              6

SEQ ID NO: 710            moltype = AA  length = 6
FEATURE                   Location/Qualifiers
source                    1..6
                          mol_type = protein
                          organism = Homo sapiens
SEQUENCE: 710
SPYNGN                                                              6

SEQ ID NO: 711            moltype = AA  length = 6
FEATURE                   Location/Qualifiers
source                    1..6
                          mol_type = protein
                          organism = Homo sapiens
SEQUENCE: 711
NPNSGD                                                              6

SEQ ID NO: 712            moltype = AA  length = 6
FEATURE                   Location/Qualifiers
source                    1..6
                          mol_type = protein
                          organism = Homo sapiens
SEQUENCE: 712
NPSDGD                                                              6

SEQ ID NO: 713            moltype = AA  length = 6
FEATURE                   Location/Qualifiers
source                    1..6
                          mol_type = protein
                          organism = Homo sapiens
SEQUENCE: 713
DPSGGS                                                              6

SEQ ID NO: 714            moltype = AA  length = 6
FEATURE                   Location/Qualifiers
source                    1..6
                          mol_type = protein
                          organism = Homo sapiens
SEQUENCE: 714
DPKSGD                                                              6

SEQ ID NO: 715            moltype = AA  length = 6
FEATURE                   Location/Qualifiers
```

-continued

```
source                  1..6
                        mol_type = protein
                        organism = Homo sapiens
SEQUENCE: 715
NPGAGS                                                           6

SEQ ID NO: 716          moltype = AA  length = 6
FEATURE                 Location/Qualifiers
source                  1..6
                        mol_type = protein
                        organism = Homo sapiens
SEQUENCE: 716
SGDGGT                                                           6

SEQ ID NO: 717          moltype = AA  length = 6
FEATURE                 Location/Qualifiers
source                  1..6
                        mol_type = protein
                        organism = Homo sapiens
SEQUENCE: 717
IPIFGT                                                           6

SEQ ID NO: 718          moltype = AA  length = 5
FEATURE                 Location/Qualifiers
source                  1..5
                        mol_type = protein
                        organism = Homo sapiens
SEQUENCE: 718
GTGGG                                                            5

SEQ ID NO: 719          moltype = AA  length = 6
FEATURE                 Location/Qualifiers
source                  1..6
                        mol_type = protein
                        organism = Homo sapiens
SEQUENCE: 719
NPSDGS                                                           6

SEQ ID NO: 720          moltype = AA  length = 6
FEATURE                 Location/Qualifiers
source                  1..6
                        mol_type = protein
                        organism = Homo sapiens
SEQUENCE: 720
NPNGGS                                                           6

SEQ ID NO: 721          moltype = AA  length = 6
FEATURE                 Location/Qualifiers
source                  1..6
                        mol_type = protein
                        organism = Homo sapiens
SEQUENCE: 721
NPNTGG                                                           6

SEQ ID NO: 722          moltype = AA  length = 6
FEATURE                 Location/Qualifiers
source                  1..6
                        mol_type = protein
                        organism = Homo sapiens
SEQUENCE: 722
SGSGGS                                                           6

SEQ ID NO: 723          moltype = AA  length = 6
FEATURE                 Location/Qualifiers
source                  1..6
                        mol_type = protein
                        organism = Homo sapiens
SEQUENCE: 723
SGYNGD                                                           6

SEQ ID NO: 724          moltype = AA  length = 6
FEATURE                 Location/Qualifiers
source                  1..6
                        mol_type = protein
                        organism = Homo sapiens
SEQUENCE: 724
SADNGN                                                           6

SEQ ID NO: 725          moltype = AA  length = 6
```

-continued

```
FEATURE            Location/Qualifiers
source             1..6
                   mol_type = protein
                   organism = Homo sapiens
SEQUENCE: 725
SPNSGA                                                             6

SEQ ID NO: 726     moltype = AA  length = 6
FEATURE            Location/Qualifiers
source             1..6
                   mol_type = protein
                   organism = Homo sapiens
SEQUENCE: 726
NPKSGA                                                             6

SEQ ID NO: 727     moltype = AA  length = 6
FEATURE            Location/Qualifiers
source             1..6
                   mol_type = protein
                   organism = Homo sapiens
SEQUENCE: 727
SESGDS                                                             6

SEQ ID NO: 728     moltype = AA  length = 6
FEATURE            Location/Qualifiers
source             1..6
                   mol_type = protein
                   organism = Homo sapiens
SEQUENCE: 728
NPSNGD                                                             6

SEQ ID NO: 729     moltype = AA  length = 6
FEATURE            Location/Qualifiers
source             1..6
                   mol_type = protein
                   organism = Homo sapiens
SEQUENCE: 729
SPSDGS                                                             6

SEQ ID NO: 730     moltype = AA  length = 6
FEATURE            Location/Qualifiers
source             1..6
                   mol_type = protein
                   organism = Homo sapiens
SEQUENCE: 730
DPEDGE                                                             6

SEQ ID NO: 731     moltype = AA  length = 6
FEATURE            Location/Qualifiers
source             1..6
                   mol_type = protein
                   organism = Homo sapiens
SEQUENCE: 731
NPKSGR                                                             6

SEQ ID NO: 732     moltype = AA  length = 6
FEATURE            Location/Qualifiers
source             1..6
                   mol_type = protein
                   organism = Homo sapiens
SEQUENCE: 732
NPGGGS                                                             6

SEQ ID NO: 733     moltype = AA  length = 6
FEATURE            Location/Qualifiers
source             1..6
                   mol_type = protein
                   organism = Homo sapiens
SEQUENCE: 733
NPKTGD                                                             6

SEQ ID NO: 734     moltype = AA  length = 6
FEATURE            Location/Qualifiers
source             1..6
                   mol_type = protein
                   organism = Homo sapiens
SEQUENCE: 734
DPSDGY                                                             6
```

```
SEQ ID NO: 735          moltype = AA  length = 6
FEATURE                 Location/Qualifiers
source                  1..6
                        mol_type = protein
                        organism = Homo sapiens SEQUENCE: 735
MPISGT                                                                      6

SEQ ID NO: 736          moltype = AA  length = 6
FEATURE                 Location/Qualifiers
source                  1..6
                        mol_type = protein
                        organism = Homo sapiens SEQUENCE: 736
SPTSGD                                                                      6

SEQ ID NO: 737          moltype = AA  length = 6
FEATURE                 Location/Qualifiers
source                  1..6
                        mol_type = protein
                        organism = Homo sapiens SEQUENCE: 737
DPSGDI                                                                      6

SEQ ID NO: 738          moltype = AA  length = 6
FEATURE                 Location/Qualifiers
source                  1..6
                        mol_type = protein
                        organism = Homo sapiens SEQUENCE: 738
ETSGGS                                                                      6

SEQ ID NO: 739          moltype = AA  length = 6
FEATURE                 Location/Qualifiers
source                  1..6
                        mol_type = protein
                        organism = Homo sapiens SEQUENCE: 739
SGSGVT                                                                      6

SEQ ID NO: 740          moltype = AA  length = 6
FEATURE                 Location/Qualifiers
source                  1..6
                        mol_type = protein
                        organism = Homo sapiens SEQUENCE: 740
NPDSGG                                                                      6

SEQ ID NO: 741          moltype = AA  length = 6
FEATURE                 Location/Qualifiers
source                  1..6
                        mol_type = protein
                        organism = Homo sapiens SEQUENCE: 741
NPISGG                                                                      6

SEQ ID NO: 742          moltype = AA  length = 6
FEATURE                 Location/Qualifiers
source                  1..6
                        mol_type = protein
                        organism = Homo sapiens SEQUENCE: 742
SADNGD                                                                      6

SEQ ID NO: 743          moltype = AA  length = 6
FEATURE                 Location/Qualifiers
source                  1..6
                        mol_type = protein
                        organism = Homo sapiens SEQUENCE: 743
SPIYGT                                                                      6

SEQ ID NO: 744          moltype = AA  length = 6
FEATURE                 Location/Qualifiers
source                  1..6
                        mol_type = protein
                        organism = Homo sapiens SEQUENCE: 744
NPSGGT                                                                      6
```

-continued

```
SEQ ID NO: 745            moltype = AA   length = 6
FEATURE                   Location/Qualifiers
source                    1..6
                          mol_type = protein
                          organism = Homo sapiens
SEQUENCE: 745
NPKSGN                                                              6

SEQ ID NO: 746            moltype = AA   length = 6
FEATURE                   Location/Qualifiers
source                    1..6
                          mol_type = protein
                          organism = Homo sapiens
SEQUENCE: 746
NPGGGN                                                              6

SEQ ID NO: 747            moltype = AA   length = 6
FEATURE                   Location/Qualifiers
source                    1..6
                          mol_type = protein
                          organism = Homo sapiens
SEQUENCE: 747
TPVFGI                                                              6

SEQ ID NO: 748            moltype = AA   length = 6
FEATURE                   Location/Qualifiers
source                    1..6
                          mol_type = protein
                          organism = Homo sapiens
SEQUENCE: 748
NPRGGS                                                              6

SEQ ID NO: 749            moltype = AA   length = 6
FEATURE                   Location/Qualifiers
source                    1..6
                          mol_type = protein
                          organism = Homo sapiens
SEQUENCE: 749
NPSGGG                                                              6

SEQ ID NO: 750            moltype = AA   length = 6
FEATURE                   Location/Qualifiers
source                    1..6
                          mol_type = protein
                          organism = Homo sapiens
SEQUENCE: 750
NPGSGN                                                              6

SEQ ID NO: 751            moltype = AA   length = 6
FEATURE                   Location/Qualifiers
source                    1..6
                          mol_type = protein
                          organism = Homo sapiens
SEQUENCE: 751
NGDGDD                                                              6

SEQ ID NO: 752            moltype = AA   length = 6
FEATURE                   Location/Qualifiers
source                    1..6
                          mol_type = protein
                          organism = Homo sapiens
SEQUENCE: 752
DPNSGD                                                              6

SEQ ID NO: 753            moltype = AA   length = 6
FEATURE                   Location/Qualifiers
source                    1..6
                          mol_type = protein
                          organism = Homo sapiens
SEQUENCE: 753
NPSDGN                                                              6

SEQ ID NO: 754            moltype = AA   length = 6
FEATURE                   Location/Qualifiers
source                    1..6
                          mol_type = protein
                          organism = Homo sapiens
SEQUENCE: 754
```

-continued

NTYNGN                                                                                    6

SEQ ID NO: 755            moltype = AA   length = 6
FEATURE                   Location/Qualifiers
source                    1..6
                          mol_type = protein
                          organism = Homo sapiens SEQUENCE: 755
NPSDGI                                                                                    6

SEQ ID NO: 756            moltype = AA   length = 6
FEATURE                   Location/Qualifiers
source                    1..6
                          mol_type = protein
                          organism = Homo sapiens SEQUENCE: 756
NPRDGD                                                                                    6

SEQ ID NO: 757            moltype = AA   length = 11
FEATURE                   Location/Qualifiers
source                    1..11
                          mol_type = protein
                          organism = Homo sapiens SEQUENCE: 757
QASQDIRYFL N                                                                             11

SEQ ID NO: 758            moltype = AA   length = 8
FEATURE                   Location/Qualifiers
source                    1..8
                          mol_type = protein
                          organism = Homo sapiens SEQUENCE: 758
GGTFSSYA                                                                                  8

SEQ ID NO: 759            moltype = AA   length = 8
FEATURE                   Location/Qualifiers
source                    1..8
                          mol_type = protein
                          organism = Homo sapiens SEQUENCE: 759
GGTFNTYA                                                                                  8

SEQ ID NO: 760            moltype = AA   length = 8
FEATURE                   Location/Qualifiers
source                    1..8
                          mol_type = protein
                          organism = Homo sapiens SEQUENCE: 760
GYTFTGYY                                                                                  8

SEQ ID NO: 761            moltype = AA   length = 8
FEATURE                   Location/Qualifiers
source                    1..8
                          mol_type = protein
                          organism = Homo sapiens SEQUENCE: 761
GYTFTDYY                                                                                  8

SEQ ID NO: 762            moltype = AA   length = 8
FEATURE                   Location/Qualifiers
source                    1..8
                          mol_type = protein
                          organism = Homo sapiens SEQUENCE: 762
GYTFTRYD                                                                                  8

SEQ ID NO: 763            moltype = AA   length = 8
FEATURE                   Location/Qualifiers
source                    1..8
                          mol_type = protein
                          organism = Homo sapiens SEQUENCE: 763
GYTFTSYA                                                                                  8

SEQ ID NO: 764            moltype = AA   length = 8
FEATURE                   Location/Qualifiers
source                    1..8
                          mol_type = protein
                          organism = Homo sapiens -continued

```
SEQUENCE: 764
GYTFTSYY                                                            8

SEQ ID NO: 765        moltype = AA  length = 8
FEATURE               Location/Qualifiers
source                1..8
                      mol_type = protein
                      organism = Homo sapiens
SEQUENCE: 765
GHTFSRHY                                                            8

SEQ ID NO: 766        moltype = AA  length = 8
FEATURE               Location/Qualifiers
source                1..8
                      mol_type = protein
                      organism = Homo sapiens
SEQUENCE: 766
GYTFTSYG                                                            8

SEQ ID NO: 767        moltype = AA  length = 8
FEATURE               Location/Qualifiers
source                1..8
                      mol_type = protein
                      organism = Homo sapiens
SEQUENCE: 767
GGTFSNTD                                                            8

SEQ ID NO: 768        moltype = AA  length = 8
FEATURE               Location/Qualifiers
source                1..8
                      mol_type = protein
                      organism = Homo sapiens
SEQUENCE: 768
GYTFTRSY                                                            8

SEQ ID NO: 769        moltype = AA  length = 8
FEATURE               Location/Qualifiers
source                1..8
                      mol_type = protein
                      organism = Homo sapiens
SEQUENCE: 769
GDTFTGYY                                                            8

SEQ ID NO: 770        moltype = AA  length = 8
FEATURE               Location/Qualifiers
source                1..8
                      mol_type = protein
                      organism = Homo sapiens
SEQUENCE: 770
GYTFTRYY                                                            8

SEQ ID NO: 771        moltype = AA  length = 8
FEATURE               Location/Qualifiers
source                1..8
                      mol_type = protein
                      organism = Homo sapiens
SEQUENCE: 771
GYTFTNYD                                                            8

SEQ ID NO: 772        moltype = AA  length = 8
FEATURE               Location/Qualifiers
source                1..8
                      mol_type = protein
                      organism = Homo sapiens
SEQUENCE: 772
GYTFTNYY                                                            8

SEQ ID NO: 773        moltype = AA  length = 8
FEATURE               Location/Qualifiers
source                1..8
                      mol_type = protein
                      organism = Homo sapiens
SEQUENCE: 773
GYGFTRYS                                                            8

SEQ ID NO: 774        moltype = AA  length = 8
FEATURE               Location/Qualifiers
source                1..8
                      mol_type = protein
```

-continued

```
                             organism = Homo sapiens
SEQUENCE: 774
GYTFTSRD                                                          8

SEQ ID NO: 775              moltype = AA  length = 8
FEATURE                     Location/Qualifiers
source                      1..8
                            mol_type = protein
                            organism = Homo sapiens
SEQUENCE: 775
GYTFTSYD                                                          8

SEQ ID NO: 776              moltype = AA  length = 8
FEATURE                     Location/Qualifiers
source                      1..8
                            mol_type = protein
                            organism = Homo sapiens
SEQUENCE: 776
GFTFSNSD                                                          8

SEQ ID NO: 777              moltype = AA  length = 8
FEATURE                     Location/Qualifiers
source                      1..8
                            mol_type = protein
                            organism = Homo sapiens
SEQUENCE: 777
GYTFTTYD                                                          8

SEQ ID NO: 778              moltype = AA  length = 8
FEATURE                     Location/Qualifiers
source                      1..8
                            mol_type = protein
                            organism = Homo sapiens
SEQUENCE: 778
GFTFSSYT                                                          8

SEQ ID NO: 779              moltype = AA  length = 8
FEATURE                     Location/Qualifiers
source                      1..8
                            mol_type = protein
                            organism = Homo sapiens
SEQUENCE: 779
GGTFSRYD                                                          8

SEQ ID NO: 780              moltype = AA  length = 8
FEATURE                     Location/Qualifiers
source                      1..8
                            mol_type = protein
                            organism = Homo sapiens
SEQUENCE: 780
GNTFTSYY                                                          8

SEQ ID NO: 781              moltype = AA  length = 8
FEATURE                     Location/Qualifiers
source                      1..8
                            mol_type = protein
                            organism = Homo sapiens
SEQUENCE: 781
GGTFSRYA                                                          8

SEQ ID NO: 782              moltype = AA  length = 8
FEATURE                     Location/Qualifiers
source                      1..8
                            mol_type = protein
                            organism = Homo sapiens
SEQUENCE: 782
GGTFSNYA                                                          8

SEQ ID NO: 783              moltype = AA  length = 8
FEATURE                     Location/Qualifiers
source                      1..8
                            mol_type = protein
                            organism = Homo sapiens
SEQUENCE: 783
GGTFTRYA                                                          8

SEQ ID NO: 784              moltype = AA  length = 8
FEATURE                     Location/Qualifiers
source                      1..8
```

-continued

```
                             mol_type = protein
                             organism = Homo sapiens
SEQUENCE: 784
GGTFSRFD                                                        8

SEQ ID NO: 785               moltype = AA  length = 8
FEATURE                      Location/Qualifiers
source                       1..8
                             mol_type = protein
                             organism = Homo sapiens
SEQUENCE: 785
GGTFSSHA                                                        8

SEQ ID NO: 786               moltype = AA  length = 8
FEATURE                      Location/Qualifiers
source                       1..8
                             mol_type = protein
                             organism = Homo sapiens
SEQUENCE: 786
GGTFGSYG                                                        8

SEQ ID NO: 787               moltype = AA  length = 8
FEATURE                      Location/Qualifiers
source                       1..8
                             mol_type = protein
                             organism = Homo sapiens
SEQUENCE: 787
GYIFTDYD                                                        8

SEQ ID NO: 788               moltype = AA  length = 8
FEATURE                      Location/Qualifiers
source                       1..8
                             mol_type = protein
                             organism = Homo sapiens
SEQUENCE: 788
GYTFTSYH                                                        8

SEQ ID NO: 789               moltype = AA  length = 8
FEATURE                      Location/Qualifiers
source                       1..8
                             mol_type = protein
                             organism = Homo sapiens
SEQUENCE: 789
GYTFTSYP                                                        8

SEQ ID NO: 790               moltype = AA  length = 8
FEATURE                      Location/Qualifiers
source                       1..8
                             mol_type = protein
                             organism = Homo sapiens
SEQUENCE: 790
GFTFSSFE                                                        8

SEQ ID NO: 791               moltype = AA  length = 8
FEATURE                      Location/Qualifiers
source                       1..8
                             mol_type = protein
                             organism = Homo sapiens
SEQUENCE: 791
GFTFDDYA                                                        8

SEQ ID NO: 792               moltype = AA  length = 8
FEATURE                      Location/Qualifiers
source                       1..8
                             mol_type = protein
                             organism = Homo sapiens
SEQUENCE: 792
GYTFTDSY                                                        8

SEQ ID NO: 793               moltype = AA  length = 8
FEATURE                      Location/Qualifiers
source                       1..8
                             mol_type = protein
                             organism = Homo sapiens
SEQUENCE: 793
GYTFMNYY                                                        8

SEQ ID NO: 794               moltype = AA  length = 8
FEATURE                      Location/Qualifiers
```

-continued

```
source                  1..8
                        mol_type = protein
                        organism = Homo sapiens
SEQUENCE: 794
GYTLNDYY                                                           8

SEQ ID NO: 795         moltype = AA  length = 8
FEATURE                Location/Qualifiers
source                 1..8
                       mol_type = protein
                       organism = Homo sapiens
SEQUENCE: 795
GYTFTNHY                                                           8

SEQ ID NO: 796         moltype = AA  length = 8
FEATURE                Location/Qualifiers
source                 1..8
                       mol_type = protein
                       organism = Homo sapiens
SEQUENCE: 796
GYTFTENE                                                           8

SEQ ID NO: 797         moltype = AA  length = 8
FEATURE                Location/Qualifiers
source                 1..8
                       mol_type = protein
                       organism = Homo sapiens
SEQUENCE: 797
GYTFASYD                                                           8

SEQ ID NO: 798         moltype = AA  length = 8
FEATURE                Location/Qualifiers
source                 1..8
                       mol_type = protein
                       organism = Homo sapiens
SEQUENCE: 798
GYTFTAYY                                                           8

SEQ ID NO: 799         moltype = AA  length = 8
FEATURE                Location/Qualifiers
source                 1..8
                       mol_type = protein
                       organism = Homo sapiens
SEQUENCE: 799
GYTFTDYH                                                           8

SEQ ID NO: 800         moltype = AA  length = 8
FEATURE                Location/Qualifiers
source                 1..8
                       mol_type = protein
                       organism = Homo sapiens
SEQUENCE: 800
GYPFTDYY                                                           8

SEQ ID NO: 801         moltype = AA  length = 8
FEATURE                Location/Qualifiers
source                 1..8
                       mol_type = protein
                       organism = Homo sapiens
SEQUENCE: 801
GYTFSDYY                                                           8

SEQ ID NO: 802         moltype = AA  length = 8
FEATURE                Location/Qualifiers
source                 1..8
                       mol_type = protein
                       organism = Homo sapiens
SEQUENCE: 802
GDTFTTHD                                                           8

SEQ ID NO: 803         moltype = AA  length = 8
FEATURE                Location/Qualifiers
source                 1..8
                       mol_type = protein
                       organism = Homo sapiens
SEQUENCE: 803
GDTFTNYY                                                           8

SEQ ID NO: 804         moltype = AA  length = 8
```

-continued

```
FEATURE                Location/Qualifiers
source                 1..8
                       mol_type = protein
                       organism = Homo sapiens
SEQUENCE: 804
GYTFTDNY                                                              8

SEQ ID NO: 805         moltype = AA  length = 8
FEATURE                Location/Qualifiers
source                 1..8
                       mol_type = protein
                       organism = Homo sapiens
SEQUENCE: 805
GGTSSSYA                                                             8

SEQ ID NO: 806         moltype = AA  length = 8
FEATURE                Location/Qualifiers
source                 1..8
                       mol_type = protein
                       organism = Homo sapiens
SEQUENCE: 806
GGTFTSYD                                                             8

SEQ ID NO: 807         moltype = AA  length = 8
FEATURE                Location/Qualifiers
source                 1..8
                       mol_type = protein
                       organism = Homo sapiens
SEQUENCE: 807
GNTFTSHW                                                             8

SEQ ID NO: 808         moltype = AA  length = 8
FEATURE                Location/Qualifiers
source                 1..8
                       mol_type = protein
                       organism = Homo sapiens
SEQUENCE: 808
GFTFSDYD                                                             8

SEQ ID NO: 809         moltype = AA  length = 8
FEATURE                Location/Qualifiers
source                 1..8
                       mol_type = protein
                       organism = Homo sapiens
SEQUENCE: 809
GYMFTGHD                                                             8

SEQ ID NO: 810         moltype = AA  length = 8
FEATURE                Location/Qualifiers
source                 1..8
                       mol_type = protein
                       organism = Homo sapiens
SEQUENCE: 810
GYIFSNYD                                                             8

SEQ ID NO: 811         moltype = AA  length = 8
FEATURE                Location/Qualifiers
source                 1..8
                       mol_type = protein
                       organism = Homo sapiens
SEQUENCE: 811
GFTFSSYA                                                             8

SEQ ID NO: 812         moltype = AA  length = 8
FEATURE                Location/Qualifiers
source                 1..8
                       mol_type = protein
                       organism = Homo sapiens
SEQUENCE: 812
GYTFTTYY                                                             8

SEQ ID NO: 813         moltype = AA  length = 8
FEATURE                Location/Qualifiers
source                 1..8
                       mol_type = protein
                       organism = Homo sapiens
SEQUENCE: 813
GSTFTNYQ                                                             8
```

-continued

```
SEQ ID NO: 814         moltype = AA  length = 8
FEATURE                Location/Qualifiers
source                 1..8
                       mol_type = protein
                       organism = Homo sapiens
SEQUENCE: 814
GGTLSSYD                                                                   8

SEQ ID NO: 815         moltype = AA  length = 8
FEATURE                Location/Qualifiers
source                 1..8
                       mol_type = protein
                       organism = Homo sapiens
SEQUENCE: 815
GYTFTSHA                                                                   8

SEQ ID NO: 816         moltype = AA  length = 8
FEATURE                Location/Qualifiers
source                 1..8
                       mol_type = protein
                       organism = Homo sapiens
SEQUENCE: 816
GGTFNSYG                                                                   8

SEQ ID NO: 817         moltype = AA  length = 8
FEATURE                Location/Qualifiers
source                 1..8
                       mol_type = protein
                       organism = Homo sapiens
SEQUENCE: 817
IDPSDGNT                                                                   8

SEQ ID NO: 818         moltype = AA  length = 8
FEATURE                Location/Qualifiers
source                 1..8
                       mol_type = protein
                       organism = Homo sapiens
SEQUENCE: 818
IDPSSGGT                                                                   8

SEQ ID NO: 819         moltype = AA  length = 8
FEATURE                Location/Qualifiers
source                 1..8
                       mol_type = protein
                       organism = Homo sapiens
SEQUENCE: 819
IDPSGGNT                                                                   8

SEQ ID NO: 820         moltype = AA  length = 8
FEATURE                Location/Qualifiers
source                 1..8
                       mol_type = protein
                       organism = Homo sapiens
SEQUENCE: 820
INPNNGDT                                                                   8

SEQ ID NO: 821         moltype = AA  length = 8
FEATURE                Location/Qualifiers
source                 1..8
                       mol_type = protein
                       organism = Homo sapiens
SEQUENCE: 821
INPNSGGT                                                                   8

SEQ ID NO: 822         moltype = AA  length = 8
FEATURE                Location/Qualifiers
source                 1..8
                       mol_type = protein
                       organism = Homo sapiens
SEQUENCE: 822
INPNDGST                                                                   8

SEQ ID NO: 823         moltype = AA  length = 8
FEATURE                Location/Qualifiers
source                 1..8
                       mol_type = protein
                       organism = Homo sapiens
SEQUENCE: 823
MNPNSGNT                                                                   8
```

```
SEQ ID NO: 824            moltype = AA  length = 8
FEATURE                   Location/Qualifiers
source                    1..8
                          mol_type = protein
                          organism = Homo sapiens SEQUENCE: 824
ISAHNGVT                                                              8

SEQ ID NO: 825            moltype = AA  length = 8
FEATURE                   Location/Qualifiers
source                    1..8
                          mol_type = protein
                          organism = Homo sapiens SEQUENCE: 825
INPSGGST                                                              8

SEQ ID NO: 826            moltype = AA  length = 8
FEATURE                   Location/Qualifiers
source                    1..8
                          mol_type = protein
                          organism = Homo sapiens SEQUENCE: 826
ISPYNGNT                                                              8

SEQ ID NO: 827            moltype = AA  length = 8
FEATURE                   Location/Qualifiers
source                    1..8
                          mol_type = protein
                          organism = Homo sapiens SEQUENCE: 827
INPNSGDT                                                              8

SEQ ID NO: 828            moltype = AA  length = 8
FEATURE                   Location/Qualifiers
source                    1..8
                          mol_type = protein
                          organism = Homo sapiens SEQUENCE: 828
INPSDGDT                                                              8

SEQ ID NO: 829            moltype = AA  length = 8
FEATURE                   Location/Qualifiers
source                    1..8
                          mol_type = protein
                          organism = Homo sapiens SEQUENCE: 829
IDPSGGST                                                              8

SEQ ID NO: 830            moltype = AA  length = 8
FEATURE                   Location/Qualifiers
source                    1..8
                          mol_type = protein
                          organism = Homo sapiens SEQUENCE: 830
IDPKSGDT                                                              8

SEQ ID NO: 831            moltype = AA  length = 8
FEATURE                   Location/Qualifiers
source                    1..8
                          mol_type = protein
                          organism = Homo sapiens SEQUENCE: 831
INPGAGSS                                                              8

SEQ ID NO: 832            moltype = AA  length = 8
FEATURE                   Location/Qualifiers
source                    1..8
                          mol_type = protein
                          organism = Homo sapiens SEQUENCE: 832
ISGDGGTT                                                              8

SEQ ID NO: 833            moltype = AA  length = 8
FEATURE                   Location/Qualifiers
source                    1..8
                          mol_type = protein
                          organism = Homo sapiens

SEQUENCE: 833
```

```
IIPIFGTA                                                          8

SEQ ID NO: 834            moltype = AA   length = 7
FEATURE                   Location/Qualifiers
source                    1..7
                          mol_type = protein
                          organism = Homo sapiens SEQUENCE: 834
IGTGGGI                                                           7

SEQ ID NO: 835            moltype = AA   length = 8
FEATURE                   Location/Qualifiers
source                    1..8
                          mol_type = protein
                          organism = Homo sapiens SEQUENCE: 835
INPSDGST                                                          8

SEQ ID NO: 836            moltype = AA   length = 8
FEATURE                   Location/Qualifiers
source                    1..8
                          mol_type = protein
                          organism = Homo sapiens SEQUENCE: 836
INPNGGSP                                                          8

SEQ ID NO: 837            moltype = AA   length = 8
FEATURE                   Location/Qualifiers
source                    1..8
                          mol_type = protein
                          organism = Homo sapiens SEQUENCE: 837
INPNTGGT                                                          8

SEQ ID NO: 838            moltype = AA   length = 8
FEATURE                   Location/Qualifiers
source                    1..8
                          mol_type = protein
                          organism = Homo sapiens SEQUENCE: 838
ISGSGGST                                                          8

SEQ ID NO: 839            moltype = AA   length = 8
FEATURE                   Location/Qualifiers
source                    1..8
                          mol_type = protein
                          organism = Homo sapiens SEQUENCE: 839
ISGYNGDT                                                          8

SEQ ID NO: 840            moltype = AA   length = 8
FEATURE                   Location/Qualifiers
source                    1..8
                          mol_type = protein
                          organism = Homo sapiens SEQUENCE: 840
ISADNGNT                                                          8

SEQ ID NO: 841            moltype = AA   length = 8
FEATURE                   Location/Qualifiers
source                    1..8
                          mol_type = protein
                          organism = Homo sapiens SEQUENCE: 841
ISPNSGAT                                                          8

SEQ ID NO: 842            moltype = AA   length = 8
FEATURE                   Location/Qualifiers
source                    1..8
                          mol_type = protein
                          organism = Homo sapiens SEQUENCE: 842
INPNSGNT                                                          8

SEQ ID NO: 843            moltype = AA   length = 8
FEATURE                   Location/Qualifiers
source                    1..8
                          mol_type = protein
                          organism = Homo sapiens
```

```
SEQUENCE: 843
INPKSGAT                                                                8

SEQ ID NO: 844        moltype = AA  length = 8
FEATURE               Location/Qualifiers
source                1..8
                      mol_type = protein
                      organism = Homo sapiens
SEQUENCE: 844
ISESGDSS                                                                8

SEQ ID NO: 845        moltype = AA  length = 7
FEATURE               Location/Qualifiers
source                1..7
                      mol_type = protein
                      organism = Homo sapiens
SEQUENCE: 845
IGTGGGT                                                                 7

SEQ ID NO: 846        moltype = AA  length = 8
FEATURE               Location/Qualifiers
source                1..8
                      mol_type = protein
                      organism = Homo sapiens
SEQUENCE: 846
MNPSNGDT                                                                8

SEQ ID NO: 847        moltype = AA  length = 8
FEATURE               Location/Qualifiers
source                1..8
                      mol_type = protein
                      organism = Homo sapiens
SEQUENCE: 847
ISPSDGST                                                                8

SEQ ID NO: 848        moltype = AA  length = 8
FEATURE               Location/Qualifiers
source                1..8
                      mol_type = protein
                      organism = Homo sapiens
SEQUENCE: 848
FDPEDGET                                                                8

SEQ ID NO: 849        moltype = AA  length = 8
FEATURE               Location/Qualifiers
source                1..8
                      mol_type = protein
                      organism = Homo sapiens
SEQUENCE: 849
INPKSGRT                                                                8

SEQ ID NO: 850        moltype = AA  length = 8
FEATURE               Location/Qualifiers
source                1..8
                      mol_type = protein
                      organism = Homo sapiens
SEQUENCE: 850
INPGGGST                                                                8

SEQ ID NO: 851        moltype = AA  length = 8
FEATURE               Location/Qualifiers
source                1..8
                      mol_type = protein
                      organism = Homo sapiens
SEQUENCE: 851
MNPKTGDT                                                                8

SEQ ID NO: 852        moltype = AA  length = 8
FEATURE               Location/Qualifiers
source                1..8
                      mol_type = protein
                      organism = Homo sapiens
SEQUENCE: 852
IDPSDGYT                                                                8

SEQ ID NO: 853        moltype = AA  length = 8
FEATURE               Location/Qualifiers
source                1..8
                      mol_type = protein
```

```
                              organism = Homo sapiens
SEQUENCE: 853
IMPISGTT                                                               8

SEQ ID NO: 854           moltype = AA  length = 8
FEATURE                  Location/Qualifiers
source                   1..8
                         mol_type = protein
                         organism = Homo sapiens
SEQUENCE: 854
MSPTSGDT                                                               8

SEQ ID NO: 855           moltype = AA  length = 8
FEATURE                  Location/Qualifiers
source                   1..8
                         mol_type = protein
                         organism = Homo sapiens
SEQUENCE: 855
IDPSGDIT                                                               8

SEQ ID NO: 856           moltype = AA  length = 8
FEATURE                  Location/Qualifiers
source                   1..8
                         mol_type = protein
                         organism = Homo sapiens
SEQUENCE: 856
IETSGGST                                                               8

SEQ ID NO: 857           moltype = AA  length = 8
FEATURE                  Location/Qualifiers
source                   1..8
                         mol_type = protein
                         organism = Homo sapiens
SEQUENCE: 857
ISGSGVTT                                                               8

SEQ ID NO: 858           moltype = AA  length = 8
FEATURE                  Location/Qualifiers
source                   1..8
                         mol_type = protein
                         organism = Homo sapiens
SEQUENCE: 858
INPDSGGT                                                               8

SEQ ID NO: 859           moltype = AA  length = 8
FEATURE                  Location/Qualifiers
source                   1..8
                         mol_type = protein
                         organism = Homo sapiens
SEQUENCE: 859
INPSGGSA                                                               8

SEQ ID NO: 860           moltype = AA  length = 8
FEATURE                  Location/Qualifiers
source                   1..8
                         mol_type = protein
                         organism = Homo sapiens
SEQUENCE: 860
INPISGGT                                                               8

SEQ ID NO: 861           moltype = AA  length = 8
FEATURE                  Location/Qualifiers
source                   1..8
                         mol_type = protein
                         organism = Homo sapiens
SEQUENCE: 861
ISADNGDT                                                               8

SEQ ID NO: 862           moltype = AA  length = 8
FEATURE                  Location/Qualifiers
source                   1..8
                         mol_type = protein
                         organism = Homo sapiens
SEQUENCE: 862
ISPIYGTP                                                               8

SEQ ID NO: 863           moltype = AA  length = 8
FEATURE                  Location/Qualifiers
source                   1..8
```

-continued

```
                                 mol_type = protein
                                 organism = Homo sapiens
SEQUENCE: 863
INPSGGTT                                                             8

SEQ ID NO: 864         moltype = AA  length = 8
FEATURE                Location/Qualifiers
source                 1..8
                                 mol_type = protein
                                 organism = Homo sapiens
SEQUENCE: 864
MNPKSGNT                                                             8

SEQ ID NO: 865         moltype = AA  length = 8
FEATURE                Location/Qualifiers
source                 1..8
                                 mol_type = protein
                                 organism = Homo sapiens
SEQUENCE: 865
INPGGGNA                                                             8

SEQ ID NO: 866         moltype = AA  length = 8
FEATURE                Location/Qualifiers
source                 1..8
                                 mol_type = protein
                                 organism = Homo sapiens
SEQUENCE: 866
ITPVFGIA                                                             8

SEQ ID NO: 867         moltype = AA  length = 8
FEATURE                Location/Qualifiers
source                 1..8
                                 mol_type = protein
                                 organism = Homo sapiens
SEQUENCE: 867
INPRGGST                                                             8

SEQ ID NO: 868         moltype = AA  length = 8
FEATURE                Location/Qualifiers
source                 1..8
                                 mol_type = protein
                                 organism = Homo sapiens
SEQUENCE: 868
MNPNNGDT                                                             8

SEQ ID NO: 869         moltype = AA  length = 8
FEATURE                Location/Qualifiers
source                 1..8
                                 mol_type = protein
                                 organism = Homo sapiens
SEQUENCE: 869
INPSGGGT                                                             8

SEQ ID NO: 870         moltype = AA  length = 8
FEATURE                Location/Qualifiers
source                 1..8
                                 mol_type = protein
                                 organism = Homo sapiens
SEQUENCE: 870
INPGSGNT                                                             8

SEQ ID NO: 871         moltype = AA  length = 8
FEATURE                Location/Qualifiers
source                 1..8
                                 mol_type = protein
                                 organism = Homo sapiens
SEQUENCE: 871
IIPIFGTP                                                             8

SEQ ID NO: 872         moltype = AA  length = 8
FEATURE                Location/Qualifiers
source                 1..8
                                 mol_type = protein
                                 organism = Homo sapiens
SEQUENCE: 872
INGDGDDT                                                             8

SEQ ID NO: 873         moltype = AA  length = 8
FEATURE                Location/Qualifiers
```

-continued

```
source                  1..8
                        mol_type = protein
                        organism = Homo sapiens
SEQUENCE: 873
IDPNSGDT                                                                    8

SEQ ID NO: 874          moltype = AA  length = 8
FEATURE                 Location/Qualifiers
source                  1..8
                        mol_type = protein
                        organism = Homo sapiens
SEQUENCE: 874
VNPSDGNT                                                                    8

SEQ ID NO: 875          moltype = AA  length = 8
FEATURE                 Location/Qualifiers
source                  1..8
                        mol_type = protein
                        organism = Homo sapiens
SEQUENCE: 875
INTYNGNT                                                                    8

SEQ ID NO: 876          moltype = AA  length = 8
FEATURE                 Location/Qualifiers
source                  1..8
                        mol_type = protein
                        organism = Homo sapiens
SEQUENCE: 876
INPSDGIT                                                                    8

SEQ ID NO: 877          moltype = AA  length = 8
FEATURE                 Location/Qualifiers
source                  1..8
                        mol_type = protein
                        organism = Homo sapiens
SEQUENCE: 877
INPRDGDT                                                                    8

SEQ ID NO: 878          moltype = AA  length = 15
FEATURE                 Location/Qualifiers
source                  1..15
                        mol_type = protein
                        organism = Homo sapiens
SEQUENCE: 878
AKERAAGYY YYMDV                                                            15

SEQ ID NO: 879          moltype = AA  length = 15
FEATURE                 Location/Qualifiers
source                  1..15
                        mol_type = protein
                        organism = Homo sapiens
SEQUENCE: 879
AKEHAAGTYY YYMDV                                                           15

SEQ ID NO: 880          moltype = AA  length = 12
FEATURE                 Location/Qualifiers
source                  1..12
                        mol_type = protein
                        organism = Homo sapiens
SEQUENCE: 880
AKEGYYYYGM DV                                                              12

SEQ ID NO: 881          moltype = AA  length = 12
FEATURE                 Location/Qualifiers
source                  1..12
                        mol_type = protein
                        organism = Homo sapiens
SEQUENCE: 881
AKEGDYYYGM DA                                                              12

SEQ ID NO: 882          moltype = AA  length = 10
FEATURE                 Location/Qualifiers
source                  1..10
                        mol_type = protein
                        organism = Homo sapiens
SEQUENCE: 882
ARERGGMPDY                                                                 10

SEQ ID NO: 883          moltype = AA  length = 9
```

```
FEATURE              Location/Qualifiers
source               1..9
                     mol_type = protein
                     organism = Homo sapiens SEQUENCE: 883
ARGHGIPKY                                                              9

SEQ ID NO: 884       moltype = AA  length = 10
FEATURE              Location/Qualifiers
source               1..10
                     mol_type = protein
                     organism = Homo sapiens SEQUENCE: 884
ARVRSGSPQH                                                             10

SEQ ID NO: 885       moltype = AA  length = 13
FEATURE              Location/Qualifiers
source               1..13
                     mol_type = protein
                     organism = Homo sapiens SEQUENCE: 885
ARGGPWIVDA FDI                                                         13

SEQ ID NO: 886       moltype = AA  length = 11
FEATURE              Location/Qualifiers
source               1..11
                     mol_type = protein
                     organism = Homo sapiens SEQUENCE: 886
ARGIAVAGTD Y                                                           11

SEQ ID NO: 887       moltype = AA  length = 15
FEATURE              Location/Qualifiers
source               1..15
                     mol_type = protein
                     organism = Homo sapiens SEQUENCE: 887
AREATWGPYY YYMDV                                                       15

SEQ ID NO: 888       moltype = AA  length = 9
FEATURE              Location/Qualifiers
source               1..9
                     mol_type = protein
                     organism = Homo sapiens SEQUENCE: 888
VRNKDGLQH                                                              9

SEQ ID NO: 889       moltype = AA  length = 15
FEATURE              Location/Qualifiers
source               1..15
                     mol_type = protein
                     organism = Homo sapiens SEQUENCE: 889
AKDAKRVGYY YYMDV                                                       15

SEQ ID NO: 890       moltype = AA  length = 10
FEATURE              Location/Qualifiers
source               1..10
                     mol_type = protein
                     organism = Homo sapiens SEQUENCE: 890
ARLVGGSPDY                                                             10

SEQ ID NO: 891       moltype = AA  length = 8
FEATURE              Location/Qualifiers
source               1..8
                     mol_type = protein
                     organism = Homo sapiens SEQUENCE: 891
ARGAMVDY                                                               8

SEQ ID NO: 892       moltype = AA  length = 15
FEATURE              Location/Qualifiers
source               1..15
                     mol_type = protein
                     organism = Homo sapiens SEQUENCE: 892
ARGNYVGSYY YGMDV                                                       15
```

-continued

```
SEQ ID NO: 893            moltype = AA   length = 12
FEATURE                   Location/Qualifiers
source                    1..12
                          mol_type = protein
                          organism = Homo sapiens SEQUENCE: 893
ARDSRGDWYF DL                                                      12

SEQ ID NO: 894            moltype = AA   length = 11
FEATURE                   Location/Qualifiers
source                    1..11
                          mol_type = protein
                          organism = Homo sapiens SEQUENCE: 894
TRHGGRGLAD Y                                                       11

SEQ ID NO: 895            moltype = AA   length = 15
FEATURE                   Location/Qualifiers
source                    1..15
                          mol_type = protein
                          organism = Homo sapiens SEQUENCE: 895
ARLKELSSIL DAFDI                                                   15

SEQ ID NO: 896            moltype = AA   length = 15
FEATURE                   Location/Qualifiers
source                    1..15
                          mol_type = protein
                          organism = Homo sapiens SEQUENCE: 896
ARERFGTGYY YYMDV                                                   15

SEQ ID NO: 897            moltype = AA   length = 14
FEATURE                   Location/Qualifiers
source                    1..14
                          mol_type = protein
                          organism = Homo sapiens SEQUENCE: 897
ARVIGEMVDD AFDL                                                    14

SEQ ID NO: 898            moltype = AA   length = 15
FEATURE                   Location/Qualifiers
source                    1..15
                          mol_type = protein
                          organism = Homo sapiens SEQUENCE: 898
ARERLFGTYY YYMDV                                                   15

SEQ ID NO: 899            moltype = AA   length = 10
FEATURE                   Location/Qualifiers
source                    1..10
                          mol_type = protein
                          organism = Homo sapiens SEQUENCE: 899
ARADGELTDY                                                         10

SEQ ID NO: 900            moltype = AA   length = 15
FEATURE                   Location/Qualifiers
source                    1..15
                          mol_type = protein
                          organism = Homo sapiens SEQUENCE: 900
ARHHLPAHYY YYMDV                                                   15

SEQ ID NO: 901            moltype = AA   length = 15
FEATURE                   Location/Qualifiers
source                    1..15
                          mol_type = protein
                          organism = Homo sapiens SEQUENCE: 901
ARDVPAGRYY YYMDV                                                   15

SEQ ID NO: 902            moltype = AA   length = 15
FEATURE                   Location/Qualifiers
source                    1..15
                          mol_type = protein
                          organism = Homo sapiens SEQUENCE: 902
AKDRGVGRYY YYMDV                                                   15
```

```
SEQ ID NO: 903              moltype = AA  length = 15
FEATURE                    Location/Qualifiers
source                     1..15
                           mol_type = protein
                           organism = Homo sapiens SEQUENCE: 903
AKDSRYGRYY YYMDV                                                    15

SEQ ID NO: 904              moltype = AA  length = 15
FEATURE                    Location/Qualifiers
source                     1..15
                           mol_type = protein
                           organism = Homo sapiens SEQUENCE: 904
AKEIVVGPYY YYMDV                                                    15

SEQ ID NO: 905              moltype = AA  length = 15
FEATURE                    Location/Qualifiers
source                     1..15
                           mol_type = protein
                           organism = Homo sapiens SEQUENCE: 905
ARGMVRGPYY YYMDV                                                    15

SEQ ID NO: 906              moltype = AA  length = 15
FEATURE                    Location/Qualifiers
source                     1..15
                           mol_type = protein
                           organism = Homo sapiens SEQUENCE: 906
AREGVTGPYY YYMDV                                                    15

SEQ ID NO: 907              moltype = AA  length = 18
FEATURE                    Location/Qualifiers
source                     1..18
                           mol_type = protein
                           organism = Homo sapiens SEQUENCE: 907
ARDAAAGTRY YYYYGMDV                                                 18

SEQ ID NO: 908              moltype = AA  length = 15
FEATURE                    Location/Qualifiers
source                     1..15
                           mol_type = protein
                           organism = Homo sapiens SEQUENCE: 908
ARELYSSTYY YYMDV                                                    15

SEQ ID NO: 909              moltype = AA  length = 15
FEATURE                    Location/Qualifiers
source                     1..15
                           mol_type = protein
                           organism = Homo sapiens SEQUENCE: 909
ARALYSGPYY YYMDV                                                    15

SEQ ID NO: 910              moltype = AA  length = 15
FEATURE                    Location/Qualifiers
source                     1..15
                           mol_type = protein
                           organism = Homo sapiens SEQUENCE: 910
ARDSLVGRYY YYMDV                                                    15

SEQ ID NO: 911              moltype = AA  length = 8
FEATURE                    Location/Qualifiers
source                     1..8
                           mol_type = protein
                           organism = Homo sapiens SEQUENCE: 911
ARRSELDY                                                            8

SEQ ID NO: 912              moltype = AA  length = 8
FEATURE                    Location/Qualifiers
source                     1..8
                           mol_type = protein
                           organism = Homo sapiens

SEQUENCE: 912
```

-continued

```
ARGDDNDY                                                              8

SEQ ID NO: 913          moltype = AA   length = 8
FEATURE                 Location/Qualifiers
source                  1..8
                        mol_type = protein
                        organism = Homo sapiens SEQUENCE: 913
ARGEEVDY                                                              8

SEQ ID NO: 914          moltype = AA   length = 9
FEATURE                 Location/Qualifiers
source                  1..9
                        mol_type = protein
                        organism = Homo sapiens SEQUENCE: 914
ARGRRVPDY                                                             9

SEQ ID NO: 915          moltype = AA   length = 9
FEATURE                 Location/Qualifiers
source                  1..9
                        mol_type = protein
                        organism = Homo sapiens SEQUENCE: 915
ARGKVTTDY                                                             9

SEQ ID NO: 916          moltype = AA   length = 9
FEATURE                 Location/Qualifiers
source                  1..9
                        mol_type = protein
                        organism = Homo sapiens SEQUENCE: 916
ASGRELIEY                                                             9

SEQ ID NO: 917          moltype = AA   length = 9
FEATURE                 Location/Qualifiers
source                  1..9
                        mol_type = protein
                        organism = Homo sapiens SEQUENCE: 917
ARVYDFPDV                                                             9

SEQ ID NO: 918          moltype = AA   length = 10
FEATURE                 Location/Qualifiers
source                  1..10
                        mol_type = protein
                        organism = Homo sapiens SEQUENCE: 918
ARSTYSHIDY                                                            10

SEQ ID NO: 919          moltype = AA   length = 10
FEATURE                 Location/Qualifiers
source                  1..10
                        mol_type = protein
                        organism = Homo sapiens SEQUENCE: 919
AREDSSGFDY                                                            10

SEQ ID NO: 920          moltype = AA   length = 10
FEATURE                 Location/Qualifiers
source                  1..10
                        mol_type = protein
                        organism = Homo sapiens SEQUENCE: 920
ARDQGGGFDY                                                            10

SEQ ID NO: 921          moltype = AA   length = 10
FEATURE                 Location/Qualifiers
source                  1..10
                        mol_type = protein
                        organism = Homo sapiens SEQUENCE: 921
ARDQGWGMDV                                                            10

SEQ ID NO: 922          moltype = AA   length = 10
FEATURE                 Location/Qualifiers
source                  1..10
                        mol_type = protein
                        organism = Homo sapiens
```

-continued

```
SEQUENCE: 922
ARLTEGIPDY                                                                      10

SEQ ID NO: 923        moltype = AA  length = 10
FEATURE               Location/Qualifiers
source                1..10
                      mol_type = protein
                      organism = Homo sapiens SEQUENCE: 923
ARDRYGPFDY                                                                      10

SEQ ID NO: 924        moltype = AA  length = 11
FEATURE               Location/Qualifiers
source                1..11
                      mol_type = protein
                      organism = Homo sapiens SEQUENCE: 924
TRLVAGGAPD Y                                                                    11

SEQ ID NO: 925        moltype = AA  length = 11
FEATURE               Location/Qualifiers
source                1..11
                      mol_type = protein
                      organism = Homo sapiens SEQUENCE: 925
ARDGFTGDIA Y                                                                    11

SEQ ID NO: 926        moltype = AA  length = 11
FEATURE               Location/Qualifiers
source                1..11
                      mol_type = protein
                      organism = Homo sapiens SEQUENCE: 926
ARVDDSSSPD Y                                                                    11

SEQ ID NO: 927        moltype = AA  length = 11
FEATURE               Location/Qualifiers
source                1..11
                      mol_type = protein
                      organism = Homo sapiens SEQUENCE: 927
TTGPDGTEVD Y                                                                    11

SEQ ID NO: 928        moltype = AA  length = 11
FEATURE               Location/Qualifiers
source                1..11
                      mol_type = protein
                      organism = Homo sapiens SEQUENCE: 928
ASSESGSDLD Y                                                                    11

SEQ ID NO: 929        moltype = AA  length = 12
FEATURE               Location/Qualifiers
source                1..12
                      mol_type = protein
                      organism = Homo sapiens SEQUENCE: 929
AREVEIEGYM DV                                                                   12

SEQ ID NO: 930        moltype = AA  length = 12
FEATURE               Location/Qualifiers
source                1..12
                      mol_type = protein
                      organism = Homo sapiens SEQUENCE: 930
AKDLDDDWYM DV                                                                   12

SEQ ID NO: 931        moltype = AA  length = 12
FEATURE               Location/Qualifiers
source                1..12
                      mol_type = protein
                      organism = Homo sapiens SEQUENCE: 931
TTDSTTWDAF DI                                                                   12

SEQ ID NO: 932        moltype = AA  length = 12
FEATURE               Location/Qualifiers
source                1..12
                      mol_type = protein
```

-continued

```
                                          organism = Homo sapiens
SEQUENCE: 932
ARVLVGSGSP DY                                                        12

SEQ ID NO: 933        moltype = AA  length = 12
FEATURE               Location/Qualifiers
source                1..12
                      mol_type = protein
                      organism = Homo sapiens
SEQUENCE: 933
AREAAAGLDF QH                                                        12

SEQ ID NO: 934        moltype = AA  length = 13
FEATURE               Location/Qualifiers
source                1..13
                      mol_type = protein
                      organism = Homo sapiens
SEQUENCE: 934
ARANSWDAMV IDY                                                       13

SEQ ID NO: 935        moltype = AA  length = 13
FEATURE               Location/Qualifiers
source                1..13
                      mol_type = protein
                      organism = Homo sapiens
SEQUENCE: 935
AREHSSSWYT FDY                                                       13

SEQ ID NO: 936        moltype = AA  length = 13
FEATURE               Location/Qualifiers
source                1..13
                      mol_type = protein
                      organism = Homo sapiens
SEQUENCE: 936
ARDDDSSGYY LDY                                                       13

SEQ ID NO: 937        moltype = AA  length = 13
FEATURE               Location/Qualifiers
source                1..13
                      mol_type = protein
                      organism = Homo sapiens
SEQUENCE: 937
ARASGDYMDL IDY                                                       13

SEQ ID NO: 938        moltype = AA  length = 13
FEATURE               Location/Qualifiers
source                1..13
                      mol_type = protein
                      organism = Homo sapiens
SEQUENCE: 938
ALVGSSGYLA PTH                                                       13

SEQ ID NO: 939        moltype = AA  length = 13
FEATURE               Location/Qualifiers
source                1..13
                      mol_type = protein
                      organism = Homo sapiens
SEQUENCE: 939
ARVRGDGYNL GDY                                                       13

SEQ ID NO: 940        moltype = AA  length = 13
FEATURE               Location/Qualifiers
source                1..13
                      mol_type = protein
                      organism = Homo sapiens
SEQUENCE: 940
ARDVDTAMGA GDY                                                       13

SEQ ID NO: 941        moltype = AA  length = 14
FEATURE               Location/Qualifiers
source                1..14
                      mol_type = protein
                      organism = Homo sapiens
SEQUENCE: 941
ARVARWGYGD YPDY                                                      14

SEQ ID NO: 942        moltype = AA  length = 14
FEATURE               Location/Qualifiers
source                1..14
```

-continued

```
                                    mol_type = protein
                                    organism = Homo sapiens
SEQUENCE: 942
ARDRNGDYYY GMDV                                                    14

SEQ ID NO: 943          moltype = AA   length = 14
FEATURE                 Location/Qualifiers
source                  1..14
                        mol_type = protein
                        organism = Homo sapiens
SEQUENCE: 943
AREGLGSSWY VLDY                                                    14

SEQ ID NO: 944          moltype = AA   length = 14
FEATURE                 Location/Qualifiers
source                  1..14
                        mol_type = protein
                        organism = Homo sapiens
SEQUENCE: 944
ARDGSHYGYY GMDV                                                    14

SEQ ID NO: 945          moltype = AA   length = 14
FEATURE                 Location/Qualifiers
source                  1..14
                        mol_type = protein
                        organism = Homo sapiens
SEQUENCE: 945
ASPGPEGYYY GMDV                                                    14

SEQ ID NO: 946          moltype = AA   length = 14
FEATURE                 Location/Qualifiers
source                  1..14
                        mol_type = protein
                        organism = Homo sapiens
SEQUENCE: 946
ASYHWDYGDY RFDY                                                    14

SEQ ID NO: 947          moltype = AA   length = 14
FEATURE                 Location/Qualifiers
source                  1..14
                        mol_type = protein
                        organism = Homo sapiens
SEQUENCE: 947
ARVEIDYGDS PPDY                                                    14

SEQ ID NO: 948          moltype = AA   length = 14
FEATURE                 Location/Qualifiers
source                  1..14
                        mol_type = protein
                        organism = Homo sapiens
SEQUENCE: 948
ARGAEWELRY AFDI                                                    14

SEQ ID NO: 949          moltype = AA   length = 15
FEATURE                 Location/Qualifiers
source                  1..15
                        mol_type = protein
                        organism = Homo sapiens
SEQUENCE: 949
ARETYYGLYY YGMDV                                                   15

SEQ ID NO: 950          moltype = AA   length = 15
FEATURE                 Location/Qualifiers
source                  1..15
                        mol_type = protein
                        organism = Homo sapiens
SEQUENCE: 950
ARAPSLRGYS YGPDY                                                   15

SEQ ID NO: 951          moltype = AA   length = 15
FEATURE                 Location/Qualifiers
source                  1..15
                        mol_type = protein
                        organism = Homo sapiens
SEQUENCE: 951
AKDRQERYYY YYMDV                                                   15

SEQ ID NO: 952          moltype = AA   length = 15
FEATURE                 Location/Qualifiers
```

-continued

```
source                    1..15
                          mol_type = protein
                          organism = Homo sapiens
SEQUENCE: 952
AKDRSYGDYY YGMDV                                           15

SEQ ID NO: 953            moltype = AA   length = 15
FEATURE                   Location/Qualifiers
source                    1..15
                          mol_type = protein
                          organism = Homo sapiens
SEQUENCE: 953
AREVFSENYY YYMDV                                           15

SEQ ID NO: 954            moltype = AA   length = 15
FEATURE                   Location/Qualifiers
source                    1..15
                          mol_type = protein
                          organism = Homo sapiens
SEQUENCE: 954
AREWDYTHYY YGMDV                                           15

SEQ ID NO: 955            moltype = AA   length = 15
FEATURE                   Location/Qualifiers
source                    1..15
                          mol_type = protein
                          organism = Homo sapiens
SEQUENCE: 955
ARGDSSGYYQ YYFDY                                           15

SEQ ID NO: 956            moltype = AA   length = 15
FEATURE                   Location/Qualifiers
source                    1..15
                          mol_type = protein
                          organism = Homo sapiens
SEQUENCE: 956
ARGSWDSSSW YIPEY                                           15

SEQ ID NO: 957            moltype = AA   length = 15
FEATURE                   Location/Qualifiers
source                    1..15
                          mol_type = protein
                          organism = Homo sapiens
SEQUENCE: 957
ASLVWGGAYY YYMDV                                           15

SEQ ID NO: 958            moltype = AA   length = 15
FEATURE                   Location/Qualifiers
source                    1..15
                          mol_type = protein
                          organism = Homo sapiens
SEQUENCE: 958
TTPVFSGSYY WYFDP                                           15

SEQ ID NO: 959            moltype = AA   length = 16
FEATURE                   Location/Qualifiers
source                    1..16
                          mol_type = protein
                          organism = Homo sapiens
SEQUENCE: 959
TTDQAVAGPY YYGMDV                                          16

SEQ ID NO: 960            moltype = AA   length = 16
FEATURE                   Location/Qualifiers
source                    1..16
                          mol_type = protein
                          organism = Homo sapiens
SEQUENCE: 960
ARDRWLAGPY YYGMDV                                          16

SEQ ID NO: 961            moltype = AA   length = 16
FEATURE                   Location/Qualifiers
source                    1..16
                          mol_type = protein
                          organism = Homo sapiens
SEQUENCE: 961
ARVMGPVDYY YYGMDV                                          16

SEQ ID NO: 962            moltype = AA   length = 16
```

-continued

```
FEATURE              Location/Qualifiers
source               1..16
                     mol_type = protein
                     organism = Homo sapiens
SEQUENCE: 962
ARDLGPFGSY YYYMDV                                                                  16

SEQ ID NO: 963       moltype = AA  length = 16
FEATURE              Location/Qualifiers
source               1..16
                     mol_type = protein
                     organism = Homo sapiens
SEQUENCE: 963
AREGVVVPPY YYYMDV                                                                  16

SEQ ID NO: 964       moltype = AA  length = 16
FEATURE              Location/Qualifiers
source               1..16
                     mol_type = protein
                     organism = Homo sapiens
SEQUENCE: 964
ARSSGWSRYY YYYMDV                                                                  16

SEQ ID NO: 965       moltype = AA  length = 16
FEATURE              Location/Qualifiers
source               1..16
                     mol_type = protein
                     organism = Homo sapiens
SEQUENCE: 965
ARDNGMTTGY YYYMDV                                                                  16

SEQ ID NO: 966       moltype = AA  length = 16
FEATURE              Location/Qualifiers
source               1..16
                     mol_type = protein
                     organism = Homo sapiens
SEQUENCE: 966
ARDRAMVTGY YYGMDV                                                                  16

SEQ ID NO: 967       moltype = AA  length = 17
FEATURE              Location/Qualifiers
source               1..17
                     mol_type = protein
                     organism = Homo sapiens
SEQUENCE: 967
ARDRGYGDRG YYYGMDV                                                                 17

SEQ ID NO: 968       moltype = AA  length = 17
FEATURE              Location/Qualifiers
source               1..17
                     mol_type = protein
                     organism = Homo sapiens
SEQUENCE: 968
ATSPKATADY YYYYMDV                                                                 17

SEQ ID NO: 969       moltype = AA  length = 17
FEATURE              Location/Qualifiers
source               1..17
                     mol_type = protein
                     organism = Homo sapiens
SEQUENCE: 969
TTSTVTPSYY YYYGMDV                                                                 17

SEQ ID NO: 970       moltype = AA  length = 18
FEATURE              Location/Qualifiers
source               1..18
                     mol_type = protein
                     organism = Homo sapiens
SEQUENCE: 970
AREPVAGTGY YYYYGMDV                                                                18

SEQ ID NO: 971       moltype = AA  length = 19
FEATURE              Location/Qualifiers
source               1..19
                     mol_type = protein
                     organism = Homo sapiens
SEQUENCE: 971
ARDNLAGFWS DYYYYGMDV                                                               19
```

-continued

```
SEQ ID NO: 972           moltype = AA   length = 6
FEATURE                  Location/Qualifiers
source                   1..6
                         mol_type = protein
                         organism = Homo sapiens
SEQUENCE: 972
QSISSY                                                                  6

SEQ ID NO: 973           moltype = AA   length = 6
FEATURE                  Location/Qualifiers
source                   1..6
                         mol_type = protein
                         organism = Homo sapiens
SEQUENCE: 973
QDISNY                                                                  6

SEQ ID NO: 974           moltype = AA   length = 11
FEATURE                  Location/Qualifiers
source                   1..11
                         mol_type = protein
                         organism = Homo sapiens
SEQUENCE: 974
QSLLHSNGYN Y                                                           11

SEQ ID NO: 975           moltype = AA   length = 6
FEATURE                  Location/Qualifiers
source                   1..6
                         mol_type = protein
                         organism = Homo sapiens
SEQUENCE: 975
QSISRN                                                                  6

SEQ ID NO: 976           moltype = AA   length = 7
FEATURE                  Location/Qualifiers
source                   1..7
                         mol_type = protein
                         organism = Homo sapiens
SEQUENCE: 976
QSVSASD                                                                 7

SEQ ID NO: 977           moltype = AA   length = 6
FEATURE                  Location/Qualifiers
source                   1..6
                         mol_type = protein
                         organism = Homo sapiens
SEQUENCE: 977
QDIGNY                                                                  6

SEQ ID NO: 978           moltype = AA   length = 6
FEATURE                  Location/Qualifiers
source                   1..6
                         mol_type = protein
                         organism = Homo sapiens
SEQUENCE: 978
QSISTH                                                                  6

SEQ ID NO: 979           moltype = AA   length = 6
FEATURE                  Location/Qualifiers
source                   1..6
                         mol_type = protein
                         organism = Homo sapiens
SEQUENCE: 979
QTISNY                                                                  6

SEQ ID NO: 980           moltype = AA   length = 6
FEATURE                  Location/Qualifiers
source                   1..6
                         mol_type = protein
                         organism = Homo sapiens
SEQUENCE: 980
QGIRND                                                                  6

SEQ ID NO: 981           moltype = AA   length = 6
FEATURE                  Location/Qualifiers
source                   1..6
                         mol_type = protein
                         organism = Homo sapiens
SEQUENCE: 981
QSISNY                                                                  6
```

```
SEQ ID NO: 982          moltype = AA   length = 6
FEATURE                 Location/Qualifiers
source                  1..6
                        mol_type = protein
                        organism = Homo sapiens

SEQUENCE: 982
QGISDS                                                          6

SEQ ID NO: 983          moltype = AA   length = 6
FEATURE                 Location/Qualifiers
source                  1..6
                        mol_type = protein
                        organism = Homo sapiens

SEQUENCE: 983
QDIHNY                                                          6

SEQ ID NO: 984          moltype = AA   length = 6
FEATURE                 Location/Qualifiers
source                  1..6
                        mol_type = protein
                        organism = Homo sapiens

SEQUENCE: 984
QSISDW                                                          6

SEQ ID NO: 985          moltype = AA   length = 6
FEATURE                 Location/Qualifiers
source                  1..6
                        mol_type = protein
                        organism = Homo sapiens

SEQUENCE: 985
QSISTW                                                          6

SEQ ID NO: 986          moltype = AA   length = 6
FEATURE                 Location/Qualifiers
source                  1..6
                        mol_type = protein
                        organism = Homo sapiens

SEQUENCE: 986
QSINRF                                                          6

SEQ ID NO: 987          moltype = AA   length = 6
FEATURE                 Location/Qualifiers
source                  1..6
                        mol_type = protein
                        organism = Homo sapiens

SEQUENCE: 987
QSVSTY                                                          6

SEQ ID NO: 988          moltype = AA   length = 6
FEATURE                 Location/Qualifiers
source                  1..6
                        mol_type = protein
                        organism = Homo sapiens

SEQUENCE: 988
QDIAKY                                                          6

SEQ ID NO: 989          moltype = AA   length = 6
FEATURE                 Location/Qualifiers
source                  1..6
                        mol_type = protein
                        organism = Homo sapiens

SEQUENCE: 989
QGITNY                                                          6

SEQ ID NO: 990          moltype = AA   length = 6
FEATURE                 Location/Qualifiers
source                  1..6
                        mol_type = protein
                        organism = Homo sapiens

SEQUENCE: 990
QDISNF                                                          6

SEQ ID NO: 991          moltype = AA   length = 6
FEATURE                 Location/Qualifiers
source                  1..6
                        mol_type = protein
                        organism = Homo sapiens

SEQUENCE: 991
```

-continued

```
QGISNN                                                   6

SEQ ID NO: 992        moltype = AA   length = 6
FEATURE               Location/Qualifiers
source                1..6
                      mol_type = protein
                      organism = Homo sapiens

SEQUENCE: 992
QSISRS                                                   6

SEQ ID NO: 993        moltype = AA   length = 6
FEATURE               Location/Qualifiers
source                1..6
                      mol_type = protein
                      organism = Homo sapiens

SEQUENCE: 993
HDISKS                                                   6

SEQ ID NO: 994        moltype = AA   length = 6
FEATURE               Location/Qualifiers
source                1..6
                      mol_type = protein
                      organism = Homo sapiens

SEQUENCE: 994
QDIGAY                                                   6

SEQ ID NO: 995        moltype = AA   length = 6
FEATURE               Location/Qualifiers
source                1..6
                      mol_type = protein
                      organism = Homo sapiens

SEQUENCE: 995
QGIRSY                                                   6

SEQ ID NO: 996        moltype = AA   length = 6
FEATURE               Location/Qualifiers
source                1..6
                      mol_type = protein
                      organism = Homo sapiens

SEQUENCE: 996
QNIGTW                                                   6

SEQ ID NO: 997        moltype = AA   length = 6
FEATURE               Location/Qualifiers
source                1..6
                      mol_type = protein
                      organism = Homo sapiens

SEQUENCE: 997
QTISYY                                                   6

SEQ ID NO: 998        moltype = AA   length = 6
FEATURE               Location/Qualifiers
source                1..6
                      mol_type = protein
                      organism = Homo sapiens

SEQUENCE: 998
QNINNY                                                   6

SEQ ID NO: 999        moltype = AA   length = 6
FEATURE               Location/Qualifiers
source                1..6
                      mol_type = protein
                      organism = Homo sapiens

SEQUENCE: 999
QTISTY                                                   6

SEQ ID NO: 1000       moltype = AA   length = 6
FEATURE               Location/Qualifiers
source                1..6
                      mol_type = protein
                      organism = Homo sapiens

SEQUENCE: 1000
RGIGND                                                   6

SEQ ID NO: 1001       moltype = AA   length = 6
FEATURE               Location/Qualifiers
source                1..6
                      mol_type = protein
                      organism = Homo sapiens
```

-continued

```
SEQUENCE: 1001
QTIGNY                                                                          6

SEQ ID NO: 1002          moltype = AA   length = 6
FEATURE                  Location/Qualifiers
source                   1..6
                         mol_type = protein
                         organism = Homo sapiens
SEQUENCE: 1002
QFIGSW                                                                          6

SEQ ID NO: 1003          moltype = AA   length = 6
FEATURE                  Location/Qualifiers
source                   1..6
                         mol_type = protein
                         organism = Homo sapiens
SEQUENCE: 1003
QSISSW                                                                          6

SEQ ID NO: 1004          moltype = AA   length = 12
FEATURE                  Location/Qualifiers
source                   1..12
                         mol_type = protein
                         organism = Homo sapiens SEQUENCE: 1004
QSVLYSSNNK NY                                                                  12

SEQ ID NO: 1005          moltype = AA   length = 6
FEATURE                  Location/Qualifiers
source                   1..6
                         mol_type = protein
                         organism = Homo sapiens
SEQUENCE: 1005
QGISSY                                                                          6

SEQ ID NO: 1006          moltype = AA   length = 6
FEATURE                  Location/Qualifiers
source                   1..6
                         mol_type = protein
                         organism = Homo sapiens
SEQUENCE: 1006
QGISNY                                                                          6

SEQ ID NO: 1007          moltype = AA   length = 6
FEATURE                  Location/Qualifiers
source                   1..6
                         mol_type = protein
                         organism = Homo sapiens
SEQUENCE: 1007
QSIRNY                                                                          6

SEQ ID NO: 1008          moltype = AA   length = 6
FEATURE                  Location/Qualifiers
source                   1..6
                         mol_type = protein
                         organism = Homo sapiens
SEQUENCE: 1008
QNIRLY                                                                          6

SEQ ID NO: 1009          moltype = AA   length = 6
FEATURE                  Location/Qualifiers
source                   1..6
                         mol_type = protein
                         organism = Homo sapiens
SEQUENCE: 1009
QDIRKF                                                                          6

SEQ ID NO: 1010          moltype = AA   length = 6
FEATURE                  Location/Qualifiers
source                   1..6
                         mol_type = protein
                         organism = Homo sapiens
SEQUENCE: 1010
QNVRSW                                                                          6

SEQ ID NO: 1011          moltype = AA   length = 6
FEATURE                  Location/Qualifiers
source                   1..6
                         mol_type = protein
```

```
                        organism = Homo sapiens
SEQUENCE: 1011
QGIGND                                                            6

SEQ ID NO: 1012         moltype = AA  length = 6
FEATURE                 Location/Qualifiers
source                  1..6
                        mol_type = protein
                        organism = Homo sapiens
SEQUENCE: 1012
QSISNW                                                            6

SEQ ID NO: 1013         moltype = AA  length = 6
FEATURE                 Location/Qualifiers
source                  1..6
                        mol_type = protein
                        organism = Homo sapiens
SEQUENCE: 1013
ESIGSW                                                            6

SEQ ID NO: 1014         moltype = AA  length = 7
FEATURE                 Location/Qualifiers
source                  1..7
                        mol_type = protein
                        organism = Homo sapiens
SEQUENCE: 1014
QSVTSNY                                                           7

SEQ ID NO: 1015         moltype = AA  length = 6
FEATURE                 Location/Qualifiers
source                  1..6
                        mol_type = protein
                        organism = Homo sapiens
SEQUENCE: 1015
QGISNG                                                            6

SEQ ID NO: 1016         moltype = AA  length = 6
FEATURE                 Location/Qualifiers
source                  1..6
                        mol_type = protein
                        organism = Homo sapiens
SEQUENCE: 1016
QNIRNY                                                            6

SEQ ID NO: 1017         moltype = AA  length = 6
FEATURE                 Location/Qualifiers
source                  1..6
                        mol_type = protein
                        organism = Homo sapiens
SEQUENCE: 1017
LDINNY                                                            6

SEQ ID NO: 1018         moltype = AA  length = 6
FEATURE                 Location/Qualifiers
source                  1..6
                        mol_type = protein
                        organism = Homo sapiens
SEQUENCE: 1018
QNIGNY                                                            6

SEQ ID NO: 1019         moltype = AA  length = 6
FEATURE                 Location/Qualifiers
source                  1..6
                        mol_type = protein
                        organism = Homo sapiens
SEQUENCE: 1019
QGINTW                                                            6

SEQ ID NO: 1020         moltype = AA  length = 6
FEATURE                 Location/Qualifiers
source                  1..6
                        mol_type = protein
                        organism = Homo sapiens
SEQUENCE: 1020
QDIRYF                                                            6

SEQ ID NO: 1021         moltype =   length =
SEQUENCE: 1021
000
```

-continued

```
SEQ ID NO: 1022        moltype =   length =
SEQUENCE: 1022
000

SEQ ID NO: 1023        moltype =   length =
SEQUENCE: 1023
000

SEQ ID NO: 1024        moltype =   length =
SEQUENCE: 1024
000

SEQ ID NO: 1025        moltype =   length =
SEQUENCE: 1025
000

SEQ ID NO: 1026        moltype =   length =
SEQUENCE: 1026
000

SEQ ID NO: 1027        moltype =   length =
SEQUENCE: 1027
000

SEQ ID NO: 1028        moltype =   length =
SEQUENCE: 1028
000

SEQ ID NO: 1029        moltype =   length =
SEQUENCE: 1029
000

SEQ ID NO: 1030        moltype =   length =
SEQUENCE: 1030
000

SEQ ID NO: 1031        moltype =   length =
SEQUENCE: 1031
000

SEQ ID NO: 1032        moltype =   length =
SEQUENCE: 1032
000

SEQ ID NO: 1033        moltype =   length =
SEQUENCE: 1033
000

SEQ ID NO: 1034        moltype =   length =
SEQUENCE: 1034
000

SEQ ID NO: 1035        moltype = AA  length = 245
FEATURE                Location/Qualifiers
source                 1..245
                       mol_type = protein
                       organism = synthetic construct
                       note = Description of Artificial Sequence: Synthetic
                        polypeptide
SEQUENCE: 1035
QVQLVQSGAE VKKPGASVKV SCKASGGTFS SYAISWVRQA PGQGLEWMGI IDPSDGNTNY   60
AQNFQGRVTM TRDTSTSTVY MELSSLRSED TAVYYCAKER AAAGYYYYMD VWGQGTTVTV  120
SSGGGGSGGG GSGGGGSDIQ MTQSPSSLSA SVGDRVTITC RASQSISSYL NWYQQKPGKA  180
PKLLIYAASS LQSGVPSRFS GSGSGTDFTL TISSLQPEDF ATYYCQQSYS TPLTFGGGTK  240
VEIKR                                                              245

SEQ ID NO: 1036        moltype = AA  length = 245
FEATURE                Location/Qualifiers
source                 1..245
                       mol_type = protein
                       organism = synthetic construct
                       note = Description of Artificial Sequence: Synthetic
                        polypeptide
SEQUENCE: 1036
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ SYSTPLTFGG GTKVEIKRGG GGSGGGGSGG  120
GGSQVQLVQS GAEVKKPGAS VKVSCKASGG TFSSYAISWV RQAPGQGLEW MGIIDPSDGN  180
TNYAQNFQGR VTMTRDTSTS TVYMELSSLR SEDTAVYYCA KERAAAGYYY YMDVWGQGTT  240
```

-continued

```
VTVSS                                                                     245

SEQ ID NO: 1037          moltype = AA  length = 245
FEATURE                  Location/Qualifiers
source                   1..245
                         mol_type = protein
                         organism = synthetic construct
                         note = Description of Artificial Sequence: Synthetic
                         polypeptide
SEQUENCE: 1037
QVQLVQSGAE VKKPGASVKV SCKASGGTFS SYAISWVRQA PGQCLEWMGI IDPSDGNTNY  60
AQNFQGRVTM TRDTSTSTVY MELSSLRSED TAVYYCAKER AAAGYYYYMD VWGQGTTVTV  120
SSGGGGSGGG GSGGGGSDIQ MTQSPSSLSA SVGDRVTITC RASQSISSYL NWYQQKPGKA  180
PKLLIYAASS LQSGVPSRFS GSGSGTDFTL TISSLQPEDF ATYYCQQSYS TPLTFGCGTK  240
VEIKR                                                                     245

SEQ ID NO: 1038          moltype = AA  length = 245
FEATURE                  Location/Qualifiers
source                   1..245
                         mol_type = protein
                         organism = synthetic construct
                         note = Description of Artificial Sequence: Synthetic
                         polypeptide
SEQUENCE: 1038
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPLTFGC GTKVEIKRGG GGSGGGGSGG  120
GGSQVQLVQS GAEVKKPGAS VKVSCKASGG TFSSYAISWV RQAPGQCLEW MGIIDPSDGN  180
TNYAQNFQGR VTMTRDTSTS TVYMELSSLR SEDTAVYYCA KERAAAGYYY YMDVWGQGTT  240
VTVSS                                                                     245

SEQ ID NO: 1039          moltype = AA  length = 247
FEATURE                  Location/Qualifiers
source                   1..247
                         mol_type = protein
                         organism = synthetic construct
                         note = Description of Artificial Sequence: Synthetic
                         polypeptide
SEQUENCE: 1039
DIVMTQSPLS LPVTPGEPAS ISCRSSQSLL HSNGYNYLDW YLQKPGQSPQ LLIYLGSNRA  60
SGVPDRFSGS GSGTDFTLKI SRVEAEDVGV YYCMQGLQTP HTFGQGTKVE IKRGGGGSGG  120
GGSGGGGSQV QLVQSGAEVK KPGASVKVSC KASGYTFTDY YIQWVRQAPG QGLEWMGWIN  180
PNSGGTSYAQ KFQGRVTMTR DTSTSTVYME LSSLRSEDTA VYYCAKEGDY YYGMDAWGQG  240
TMVTVSS                                                                   247

SEQ ID NO: 1040          moltype = AA  length = 247
FEATURE                  Location/Qualifiers
source                   1..247
                         mol_type = protein
                         organism = synthetic construct
                         note = Description of Artificial Sequence: Synthetic
                         polypeptide
SEQUENCE: 1040
QVQLVQSGAE VKKPGASVKV SCKASGYTFT DYYIQWVRQA PGQGLEWMGW INPNSGGTSY  60
AQKFQGRVTM TRDTSTSTVY MELSSLRSED TAVYYCAKEG DYYYGMDAWG QGTMVTVSSG  120
GGGSGGGGSG GGGSDIVMTQ SPLSLPVTPG EPASISCRSS QSLLHSNGYN YLDWYLQKPG  180
QSPQLLIYLG SNRASGVPDR FSGSGSGTDF TLKISRVEAE DVGVYYCMQG LQTPHTFGQG  240
TKVEIKR                                                                   247

SEQ ID NO: 1041          moltype = AA  length = 247
FEATURE                  Location/Qualifiers
source                   1..247
                         mol_type = protein
                         organism = synthetic construct
                         note = Description of Artificial Sequence: Synthetic
                         polypeptide
SEQUENCE: 1041
QVQLVQSGAE VKKPGASVKV SCKASGYTFT DYYIQWVRQA PGQCLEWMGW INPNSGGTSY  60
AQKFQGRVTM TRDTSTSTVY MELSSLRSED TAVYYCAKEG DYYYGMDAWG QGTMVTVSSG  120
GGGSGGGGSG GGGSDIVMTQ SPLSLPVTPG EPASISCRSS QSLLHSNGYN YLDWYLQKPG  180
QSPQLLIYLG SNRASGVPDR FSGSGSGTDF TLKISRVEAE DVGVYYCMQG LQTPHTFGCG  240
TKVEIKR                                                                   247

SEQ ID NO: 1042          moltype = AA  length = 247
FEATURE                  Location/Qualifiers
source                   1..247
                         mol_type = protein
                         organism = synthetic construct
                         note = Description of Artificial Sequence: Synthetic
                         polypeptide
```

```
SEQUENCE: 1042
DIVMTQSPLS LPVTPGEPAS ISCRSSQSLL HSNGYNYLDW YLQKPGQSPQ LLIYLGSNRA   60
SGVPDRFSGS GSGTDFTLKI SRVEAEDVGV YYCMQGLQTP HTFGCGTKVE IKRGGGGSGG  120
GGSGGGGSQV QLVQSGAEVK KPGASVKVSC KASGYTFTDY YIQWVRQAPG QCLEWMGWIN  180
PNSGGTSYAQ KFQGRVTMTR DTSTSTVYME LSSLRSEDTA VYYCAKEGDY YYGMDAWGQG  240
TMVTVSS                                                            247

SEQ ID NO: 1043           moltype = AA  length = 240
FEATURE                   Location/Qualifiers
source                    1..240
                          mol_type = protein
                          organism = synthetic construct
                          note = Description of Artificial Sequence: Synthetic
                             polypeptide
SEQUENCE: 1043
QVQLVQSGAE VKKPGASVKV SCKASGYTFT SYYMHWVRQA PGQCLEWMGG FDPEDGETIY   60
AQKFQGRVTM TRDTSTSTVY MELSSLRSED TAVYYCARDQ GWGMDVWGQG TTVTVSSGGG  120
GSGGGGSGGG GSDIQMTQSP SSLSASVGDR VTITCRASQS ISSYLNWYQQ KPGKAPKLLI  180
YAASSLQSGV PSRFSGSGSG TDFTLTISSL QPEDFATYYC QQTYSTPYTF GCGTKLEIKR  240

SEQ ID NO: 1044           moltype = AA  length = 240
FEATURE                   Location/Qualifiers
source                    1..240
                          mol_type = protein
                          organism = synthetic construct
                          note = Description of Artificial Sequence: Synthetic
                             polypeptide
SEQUENCE: 1044
QVQLVQSGAE VKKPGASVKV SCKASGYTFT SYYMHWVRQA PGQGLEWMGG FDPEDGETIY   60
AQKFQGRVTM TRDTSTSTVY MELSSLRSED TAVYYCARDQ GWGMDVWGQG TTVTVSSGGG  120
GSGGGGSGGG GSDIQMTQSP SSLSASVGDR VTITCRASQS ISSYLNWYQQ KPGKAPKLLI  180
YAASSLQSGV PSRFSGSGSG TDFTLTISSL QPEDFATYYC QQTYSTPYTF GQGTKLEIKR  240

SEQ ID NO: 1045           moltype = AA  length = 240
FEATURE                   Location/Qualifiers
source                    1..240
                          mol_type = protein
                          organism = synthetic construct
                          note = Description of Artificial Sequence: Synthetic
                             polypeptide
SEQUENCE: 1045
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ TYSTPYTFGC GTKLEIKRGG GGSGGGGSGG  120
GGSQVQLVQS GAEVKKPGAS VKVSCKASGY TFTSYYMHWV RQAPGQCLEW MGGFDPEDGE  180
TIYAQKFQGR VTMTRDTSTS TVYMELSSLR SEDTAVYYCA RDQGWGMDVW GQGTTVTVSS  240

SEQ ID NO: 1046           moltype = AA  length = 240
FEATURE                   Location/Qualifiers
source                    1..240
                          mol_type = protein
                          organism = synthetic construct
                          note = Description of Artificial Sequence: Synthetic
                             polypeptide
SEQUENCE: 1046
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ TYSTPYTFGQ GTKLEIKRGG GGSGGGGSGG  120
GGSQVQLVQS GAEVKKPGAS VKVSCKASGY TFTSYYMHWV RQAPGQGLEW MGGFDPEDGE  180
TIYAQKFQGR VTMTRDTSTS TVYMELSSLR SEDTAVYYCA RDQGWGMDVW GQGTTVTVSS  240

SEQ ID NO: 1047           moltype = AA  length = 241
FEATURE                   Location/Qualifiers
source                    1..241
                          mol_type = protein
                          organism = synthetic construct
                          note = Description of Artificial Sequence: Synthetic
                             polypeptide
SEQUENCE: 1047
DIQMTQSPSS LSASVGDRVT ITCRASQTIG NYVNWYQQKP GKAPKLLIYG ASNLHTGVPS   60
RFSGSGSGTD FTLTISSLQP EDFATYYCQQ TYSAPLTFGG GTKVEIKRGG GGSGGGGSGG  120
GGSQVQLVQS GAEVKKPGAS VKVSCKASGY TFTNHYMHWV RQAPGQGLEW MGWMNPNSGN  180
TGYAQKFQGR VTMTRDTSTS TVYMELSSLR SEDTAVYYCA SSESGSDLDY WGQGTLVTVS  240
S                                                                  241

SEQ ID NO: 1048           moltype = AA  length = 241
FEATURE                   Location/Qualifiers
source                    1..241
                          mol_type = protein
                          organism = synthetic construct
                          note = Description of Artificial Sequence: Synthetic
```

```
                           polypeptide
SEQUENCE: 1048
QVQLVQSGAE VKKPGASVKV SCKASGYTFT NHYMHWVRQA PGQGLEWMGW MNPNSGNTGY  60
AQKFQGRVTM TRDTSTSTVY MELSSLRSED TAVYYCASSE SGSDLDYWGQ GTLVTVSSGG  120
GGSGGGGSGG GGSDIQMTQS PSSLSASVGD RVTITCRASQ TIGNYVNWYQ QKPGKAPKLL  180
IYGASNLHTG VPSRFSGSGS GTDFTLTISS LQPEDFATYY CQQTYSAPLT FGGGTKVEIK  240
R                                                                 241

SEQ ID NO: 1049         moltype = AA   length = 241
FEATURE                 Location/Qualifiers
source                  1..241
                        mol_type = protein
                        organism = synthetic construct
                        note = Description of Artificial Sequence: Synthetic
                          polypeptide
SEQUENCE: 1049
QVQLVQSGAE VKKPGASVKV SCKASGYTFT NHYMHWVRQA PGQCLEWMGW MNPNSGNTGY  60
AQKFQGRVTM TRDTSTSTVY MELSSLRSED TAVYYCASSE SGSDLDYWGQ GTLVTVSSGG  120
GGSGGGGSGG GGSDIQMTQS PSSLSASVGD RVTITCRASQ TIGNYVNWYQ QKPGKAPKLL  180
IYGASNLHTG VPSRFSGSGS GTDFTLTISS LQPEDFATYY CQQTYSAPLT FGCGTKVEIK  240
R                                                                 241

SEQ ID NO: 1050         moltype = AA   length = 241
FEATURE                 Location/Qualifiers
source                  1..241
                        mol_type = protein
                        organism = synthetic construct
                        note = Description of Artificial Sequence: Synthetic
                          polypeptide
SEQUENCE: 1050
DIQMTQSPSS LSASVGDRVT ITCRASQTIG NYVNWYQQKP GKAPKLLIYG ASNLHTGVPS  60
RFSGSGSGTD FTLTISSLQP EDFATYYCQQ TYSAPLTFGC GTKVEIKRGG GGSGGGGSGG  120
GGSQVQLVQS GAEVKKPGAS VKVSCKASGY TFTNHYMHWV RQAPGQCLEW MGWMNPNSGN  180
TGYAQKFQGR VTMTRDTSTS TVYMELSSLR SEDTAVYYCA SSESGSDLDY WGQGTLVTVS  240
S                                                                 241

SEQ ID NO: 1051         moltype = AA   length = 241
FEATURE                 Location/Qualifiers
source                  1..241
                        mol_type = protein
                        organism = synthetic construct
                        note = Description of Artificial Sequence: Synthetic
                          polypeptide
SEQUENCE: 1051
QVQLVQSGAE VKKPGASVKV SCKASGYTFT NHYMHWVRQA PGQGLEWMGI INPNSGNTGY  60
AQKFQGRVTM TRDTSTSTVY MELSSLRSED TAVYYCASSE SGSDLDYWGQ GTLVTVSSGG  120
GGSGGGGSGG GGSDIQMTQS PSSLSASVGD RVTITCRASQ TIGNYVNWYQ QKPGKAPKLL  180
IYGASNLHTG VPSRFSGSGS GTDFTLTISS LQPEDFATYY CQQTYSAPLT FGGGTKVEIK  240
R                                                                 241

SEQ ID NO: 1052         moltype = AA   length = 241
FEATURE                 Location/Qualifiers
source                  1..241
                        mol_type = protein
                        organism = synthetic construct
                        note = Description of Artificial Sequence: Synthetic
                          polypeptide
SEQUENCE: 1052
DIQMTQSPSS LSASVGDRVT ITCRASQTIG NYVNWYQQKP GKAPKLLIYG ASNLHTGVPS  60
RFSGSGSGTD FTLTISSLQP EDFATYYCQQ TYSAPLTFGG GTKVEIKRGG GGSGGGGSGG  120
GGSQVQLVQS GAEVKKPGAS VKVSCKASGY TFTNHYMHWV RQAPGQGLEW MGIINPNSGN  180
TGYAQKFQGR VTMTRDTSTS TVYMELSSLR SEDTAVYYCA SSESGSDLDY WGQGTLVTVS  240
S                                                                 241

SEQ ID NO: 1053         moltype = AA   length = 829
FEATURE                 Location/Qualifiers
source                  1..829
                        mol_type = protein
                        organism = synthetic construct
                        note = Description of Artificial Sequence: Synthetic
                          polypeptide
SEQUENCE: 1053
MKKINEGLLD SKILSAFNTV IALLGSIVII VMNIMIIQNY TRSTDNQAVI KDALQGIQQQ  60
IKGLADKIGT EIGPKVSLID TSSTITIPAN IGLLGSKISQ STASINENVN EKCKFTLPPL  120
KIHECNISCP NPLPFREYRP QTEGVSNLVG LPNNICLQKT SNQILKPKLI SYTLPVVGQS  180
GTCITDPLLA MDEGYFAYSH LERIGSCSRG VSKQRIIGVG EVLDRGDEVP SLFMTNVWTP  240
PNPNTVYHCS AVYNNEFYYV LCAVSTVGDP ILNSTYWSGS LMMTRLAVKP KSNGGGYNQH  300
QLALRSIEKG RYDKVMPYGP SGIKQGDTLY FPAVGFLVRT EFKYNDSNCP ITKCQYSKPE  360
NCRLSMGIRP NSHYILRSGL LKYNLSDGEN PKVVFIEISD QRLSIGSPSK IYDSLGQPVF  420
```

-continued

```
YQASFSWDTM IKFGDVLTVN PLVVNWRNNT VISRPGQSQC PRFNTCPAIC AEGVYNDAFL   480
IDRINWISAG VFLDSNATAA NPVFTVFKDN EILYRAQLAS EDTNAQKTIT NCFLLKNKIW   540
CISLVEIYDT GDNVIRPKLF AVKIPEQCTG GGGSGGGGSG GGGSQVQLVQ SGAEVKKPGA   600
SVKVSCKASG GTFSSYAISW VRQAPGQGLE WMGIIDPSDG NTNYAQNFQG RVTMTRDTST   660
STVYMELSSL RSEDTAVYYC AKERAAAGYY YYMDVWGQGT TVTVSSGGGG SGGGGSGGGG   720
SDIQMTQSPS SLSASVGDRV TITCRASQSI SSYLNWYQQK PGKAPKLLIY AASSLQSGVP   780
SRFSGSGSGT DFTLTISSLQ PEDFATYYCQ QSYSTPLTFG GGTKVEIKR            829

SEQ ID NO: 1054       moltype = AA  length = 831
FEATURE               Location/Qualifiers
source                1..831
                      mol_type = protein
                      organism = synthetic construct
                      note = Description of Artificial Sequence: Synthetic
                      polypeptide
SEQUENCE: 1054
MKKINEGLLD SKILSAFNTV IALLGSIVII VMNIMIIQNY TRSTDNQAVI KDALQGIQQQ   60
IKGLADKIGT EIGPKVSLID TSSTITIPAN IGLLGSKISQ STASINENVN EKCKFTLPPL   120
KIHECNISCP NPLPFREYRP QTEGVSNLVG LPNNICLQKT SNQILKPKLI SYTLPVVGQS   180
GTCITDPLLA MDEGYFAYSH LERIGSCSRG VSKQRIIGVG EVLDRGDEVP SLFMTNVWTP   240
PNPNTVYHCS AVYNNEFYYV LCAVSTVGDP ILNSTYWSGS LMMTRLAVKP KSNGGGYNQH   300
QLALRSIEKG RYDKVMPYGP SGIKQGDTLY FPAVGFLVRT EFKYNDSNCP ITKCQYSKPE   360
NCRLSMGIRP NSHYILRSGL LKYNLSDGEN PKVVFIEISD QRLSIGSPSK IYDSLGQPVF   420
YQASFSWDTM IKFGDVLTVN PLVVNWRNNT VISRPGQSQC PRFNTCPAIC AEGVYNDAFL   480
IDRINWISAG VFLDSNATAA NPVFTVFKDN EILYRAQLAS EDTNAQKTIT NCFLLKNKIW   540
CISLVEIYDT GDNVIRPKLF AVKIPEQCTG GGGSGGGGSG GGGSQVQLVQ SGAEVKKPGA   600
SVKVSCKASG YTFTDYYIQW VRQAPGQGLE WMGWINPNSG GTSYAQKFQG RVTMTRDTST   660
STVYMELSSL RSEDTAVYYC AKEGDYYYGM DAWGQGTMVT VSSGGGGSGG GGSGGGGSDI   720
VMTQSPLSLP VTPGEPASIS CRSSQSLLHS NGYNYLDWYL QKPGQSPQLL IYLGSNRASG   780
VPDRFSGSGS GTDFTLKISR VEAEDVGVYY CMQGLQTPHT FGQGTKVEIK R            831

SEQ ID NO: 1055       moltype = AA  length = 824
FEATURE               Location/Qualifiers
source                1..824
                      mol_type = protein
                      organism = synthetic construct
                      note = Description of Artificial Sequence: Synthetic
                      polypeptide
SEQUENCE: 1055
MKKINEGLLD SKILSAFNTV IALLGSIVII VMNIMIIQNY TRSTDNQAVI KDALQGIQQQ   60
IKGLADKIGT EIGPKVSLID TSSTITIPAN IGLLGSKISQ STASINENVN EKCKFTLPPL   120
KIHECNISCP NPLPFREYRP QTEGVSNLVG LPNNICLQKT SNQILKPKLI SYTLPVVGQS   180
GTCITDPLLA MDEGYFAYSH LERIGSCSRG VSKQRIIGVG EVLDRGDEVP SLFMTNVWTP   240
PNPNTVYHCS AVYNNEFYYV LCAVSTVGDP ILNSTYWSGS LMMTRLAVKP KSNGGGYNQH   300
QLALRSIEKG RYDKVMPYGP SGIKQGDTLY FPAVGFLVRT EFKYNDSNCP ITKCQYSKPE   360
NCRLSMGIRP NSHYILRSGL LKYNLSDGEN PKVVFIEISD QRLSIGSPSK IYDSLGQPVF   420
YQASFSWDTM IKFGDVLTVN PLVVNWRNNT VISRPGQSQC PRFNTCPAIC AEGVYNDAFL   480
IDRINWISAG VFLDSNATAA NPVFTVFKDN EILYRAQLAS EDTNAQKTIT NCFLLKNKIW   540
CISLVEIYDT GDNVIRPKLF AVKIPEQCTG GGGSGGGGSG GGGSQVQLVQ SGAEVKKPGA   600
SVKVSCKASG YTFTSYYMHW VRQAPGQGLE WMGGFDPEDG ETIYAQKFQG RVTMTRDTST   660
STVYMELSSL RSEDTAVYYC ARDQGWGMDV WGQGTTVTVS SGGGGSGGGG SGGGGSDIQM   720
TQSPSSLSAS VGDRVTITCR ASQSISSYLN WYQQKPGKAP KLLIYAASSL QSGVPSRFSG   780
SGSGTDFTLT ISSLQPEDFA TYYCQQYYST PYTFGQGTKL EIKR                   824

SEQ ID NO: 1056       moltype = AA  length = 825
FEATURE               Location/Qualifiers
source                1..825
                      mol_type = protein
                      organism = synthetic construct
                      note = Description of Artificial Sequence: Synthetic
                      polypeptide
SEQUENCE: 1056
MKKINEGLLD SKILSAFNTV IALLGSIVII VMNIMIIQNY TRSTDNQAVI KDALQGIQQQ   60
IKGLADKIGT EIGPKVSLID TSSTITIPAN IGLLGSKISQ STASINENVN EKCKFTLPPL   120
KIHECNISCP NPLPFREYRP QTEGVSNLVG LPNNICLQKT SNQILKPKLI SYTLPVVGQS   180
GTCITDPLLA MDEGYFAYSH LERIGSCSRG VSKQRIIGVG EVLDRGDEVP SLFMTNVWTP   240
PNPNTVYHCS AVYNNEFYYV LCAVSTVGDP ILNSTYWSGS LMMTRLAVKP KSNGGGYNQH   300
QLALRSIEKG RYDKVMPYGP SGIKQGDTLY FPAVGFLVRT EFKYNDSNCP ITKCQYSKPE   360
NCRLSMGIRP NSHYILRSGL LKYNLSDGEN PKVVFIEISD QRLSIGSPSK IYDSLGQPVF   420
YQASFSWDTM IKFGDVLTVN PLVVNWRNNT VISRPGQSQC PRFNTCPAIC AEGVYNDAFL   480
IDRINWISAG VFLDSNATAA NPVFTVFKDN EILYRAQLAS EDTNAQKTIT NCFLLKNKIW   540
CISLVEIYDT GDNVIRPKLF AVKIPEQCTG GGGSGGGGSG GGGSQVQLVQ SGAEVKKPGA   600
SVKVSCKASG YTFTNHYMHW VRQAPGQGLE WMGWMNPNSG NTGYAQKFQG RVTMTRDTST   660
STVYMELSSL RSEDTAVYYC ASSESGSDLD YWGQGTLVTV SGGGGSGGGG SGGGGSDIQ   720
MTQSPSSLSA SVGDRVTITC RASQTIGNYV NWYQQKPGKA PKLLIYGASN LHTGVPSRFS   780
GSGSGTDFTL TISSLQPEDF ATYYCQQTYS APLTFGGGTK VEIKR                  825

SEQ ID NO: 1057       moltype = AA  length = 17
FEATURE               Location/Qualifiers
```

-continued

```
source                  1..17
                        mol_type = protein
                        organism = synthetic construct
                        note = Description of Artificial Sequence: Synthetic peptide
SEQUENCE: 1057
RINPNSGGTN YAENFQG                                                17

SEQ ID NO: 1058         moltype = AA  length = 17
FEATURE                 Location/Qualifiers
source                  1..17
                        mol_type = protein
                        organism = synthetic construct
                        note = Description of Artificial Sequence: Synthetic peptide
SEQUENCE: 1058
IINPSGGSTS YAQTFQG                                                17

SEQ ID NO: 1059         moltype = AA  length = 17
FEATURE                 Location/Qualifiers
source                  1..17
                        mol_type = protein
                        organism = synthetic construct
                        note = Description of Artificial Sequence: Synthetic peptide
SEQUENCE: 1059
IINPSDGSTD YAQKFQG                                                17

SEQ ID NO: 1060         moltype = AA  length = 125
FEATURE                 Location/Qualifiers
source                  1..125
                        mol_type = protein
                        organism = Homo sapiens
SEQUENCE: 1060
QVQLVESGGG LVQAGGSLRL SCAASGRTFS GYVMGWFRQA PGKQRKFVAA ISRGGLSTSY   60
ADSVKGRFTI SRDNAKNTVF LQMNTLKPED TAVYYCAADR SDLYEITAAS NIDSWGQGTL  120
VTVSS                                                            125

SEQ ID NO: 1061         moltype = AA  length = 5
FEATURE                 Location/Qualifiers
source                  1..5
                        mol_type = protein
                        organism = Homo sapiens
SEQUENCE: 1061
GYVMG                                                              5

SEQ ID NO: 1062         moltype = AA  length = 17
FEATURE                 Location/Qualifiers
source                  1..17
                        mol_type = protein
                        organism = Homo sapiens
SEQUENCE: 1062
AISRGGLSTS YADSVKG                                                17

SEQ ID NO: 1063         moltype = AA  length = 16
FEATURE                 Location/Qualifiers
source                  1..16
                        mol_type = protein
                        organism = Homo sapiens
SEQUENCE: 1063
DRSDLYEITA ASNIDS                                                 16

SEQ ID NO: 1064         moltype = AA  length = 7
FEATURE                 Location/Qualifiers
source                  1..7
                        mol_type = protein
                        organism = Homo sapiens
SEQUENCE: 1064
GRTFSGY                                                            7

SEQ ID NO: 1065         moltype = AA  length = 6
FEATURE                 Location/Qualifiers
source                  1..6
                        mol_type = protein
                        organism = Homo sapiens
SEQUENCE: 1065
SRGGLS                                                             6

SEQ ID NO: 1066         moltype = AA  length = 8
FEATURE                 Location/Qualifiers
source                  1..8
                        mol_type = protein
```

```
                          organism = Homo sapiens
SEQUENCE: 1066
GRTFSGYV                                                              8

SEQ ID NO: 1067         moltype = AA  length = 8
FEATURE                 Location/Qualifiers
source                  1..8
                        mol_type = protein
                        organism = Homo sapiens
SEQUENCE: 1067
ISRGGLST                                                              8

SEQ ID NO: 1068         moltype = AA  length = 18
FEATURE                 Location/Qualifiers
source                  1..18
                        mol_type = protein
                        organism = Homo sapiens
SEQUENCE: 1068
AADRSDLYEI TAASNIDS                                                   18

SEQ ID NO: 1069         moltype = AA  length = 709
FEATURE                 Location/Qualifiers
source                  1..709
                        mol_type = protein
                        organism = Homo sapiens
SEQUENCE: 1069
MKKINEGLLD SKILSAFNTV IALLGSIVII VMNIMIIQNY TRSTDNQAVI KDALQGIQQQ    60
IKGLADKIGT EIGPKVSLID TSSTITIPAN IGLLGSKISQ STASINENVN EKCKFTLPPL    120
KIHECNISCP NPLPFREYRP QTEGVSNLVG LPNNICLQKT SNQILKPKLI SYTLPVVGQS    180
GTCITDPLLA MDEGYFAYSH LERIGSCSRG VSKQRIIGVG EVLDRGDEVP SLFMTNVWTP    240
PNPNTVYHCS AVYNNEFYYV LCAVSTVGDP ILNSTYWSGS LMMTRLAVKP KSNGGGYNQH    300
QLALRSIEKG RYDKVMPYGP SGIKQGDTLY FPAVGFLVRT EPKYNDSNCP ITKCQYSKPE    360
NCRLSMGIRP NSHYILRSGL LKYNLSDGEN PKVVFIEISD QRLSIGSPSK IYDSLGQPVF    420
YQASFSWDTM IKFGDVLTVN PLVVNWRNNT VISRPGQSQC PRFNTCPAIC AEGVYNDAFL    480
IDRINWISAG VFLDSNATAA NPVFTVFKDN EILYRAQLAS EDTNAQKTIT NCFLLKNKIW    540
CISLVEIYDT GDNVIRPKLF AVKIPEQCTG GGGSGGGGSG GGGSQVQLVE SGGGLVQAGG    600
SLRLSCAASG RTFSGYVMGW FRQAPGKQRK FVAAISRGGL STSYADSVKG RFTISRDNAK    660
NTVFLQMNTL KPEDTAVYYC AADRSDLYEI TAASNIDSWG QGTLVTVSS               709

SEQ ID NO: 1070         moltype = AA  length = 828
FEATURE                 Location/Qualifiers
source                  1..828
                        mol_type = protein
                        organism = Homo sapiens
SEQUENCE: 1070
KKINEGLLDS KILSAFNTVI ALLGSIVIIV MNIMIIQNYT RSTDNQAVIK DALQGIQQQI    60
KGLADKIGTE IGPKVSLIDT SSTITIPANI GLLGSKISQS TASINENVNE KCKFTLPPLK    120
IHECNISCPN PLPFREYRPQ TEGVSNLVGL PNNICLQKTS NQILKPKLIS YTLPVVGQSG    180
TCITDPLLAM DEGYFAYSHL ERIGSCSRGV SKQRIIGVGE VLDRGDEVPS LFMTNVWTPP    240
NPNTVYHCSA VYNNEFYYVL CAVSTVGDPI LNSTYWSGSL MMTRLAVKPK SNGGGYNQHQ    300
LALRSIEKGR YDKVMPYGPS GIKQGDTLYF PAVGFLVRTE FKYNDSNCPI TKCQYSKPEN    360
CRLSMGIRPN SHYILRSGLL KYNLSDGENP KVVFIEISDQ RLSIGSPSKI YDSLGQPVFY    420
QASFSWDTMI KFGDVLTVNP LVVNWRNNTV ISRPGQSQCP RFNTCPAICA EGVYNDAFLI    480
DRINWISAGV FLDSNATAAN PVFTVFKDNE ILYRAQLASE DTNAQKTITN CFLLKNKIWC    540
ISLVEIYDTG DNVIRPKLFA VKIPEQCTGG GGSGGGGSGG GGSQVQLVQS GAEVKKPGAS    600
VKVSCKASGG TFSSYAISWV RQAPGQGLEW MGIIDPSDGN TNYAQNFQGR VTMTRDTSTS    660
TVYMELSSLR SEDTAVYYCA KERAAAGYYY YMDVWGQGTT VTVSSGGGGS GGGGSGGGGS    720
DIQMTQSPSS LSASVGDRVT ITCRASQSIS SYLNWYQQKP GKAPKLLIYA ASSLQSGVPS    780
RFSGSGSGTD FTLTISSLQP EDFATYYCQQ SYSTPLTFGG GTKVEIKR                828

SEQ ID NO: 1071         moltype = AA  length = 830
FEATURE                 Location/Qualifiers
source                  1..830
                        mol_type = protein
                        organism = Homo sapiens
SEQUENCE: 1071
KKINEGLLDS KILSAFNTVI ALLGSIVIIV MNIMIIQNYT RSTDNQAVIK DALQGIQQQI    60
KGLADKIGTE IGPKVSLIDT SSTITIPANI GLLGSKISQS TASINENVNE KCKFTLPPLK    120
IHECNISCPN PLPFREYRPQ TEGVSNLVGL PNNICLQKTS NQILKPKLIS YTLPVVGQSG    180
TCITDPLLAM DEGYFAYSHL ERIGSCSRGV SKQRIIGVGE VLDRGDEVPS LFMTNVWTPP    240
NPNTVYHCSA VYNNEFYYVL CAVSTVGDPI LNSTYWSGSL MMTRLAVKPK SNGGGYNQHQ    300
LALRSIEKGR YDKVMPYGPS GIKQGDTLYF PAVGFLVRTE FKYNDSNCPI TKCQYSKPEN    360
CRLSMGIRPN SHYILRSGLL KYNLSDGENP KVVFIEISDQ RLSIGSPSKI YDSLGQPVFY    420
QASFSWDTMI KFGDVLTVNP LVVNWRNNTV ISRPGQSQCP RFNTCPAICA EGVYNDAFLI    480
DRINWISAGV FLDSNATAAN PVFTVFKDNE ILYRAQLASE DTNAQKTITN CFLLKNKIWC    540
ISLVEIYDTG DNVIRPKLFA VKIPEQCTGG GGSGGGGSGG GGSQVQLVQS GAEVKKPGAS    600
VKVSCKASGY TFTDYYIQWV RQAPGQGLEW MGWINPNSGG TSYAQKFQGR VTMTRDTSTS    660
TVYMELSSLR SEDTAVYYCA KEGDYYYGMD AWGQGTMVTV SSGGGGSGGG GSGGGGSDIV    720
MTQSPLSLPV TPGEPASISC RSSQSLLHSN GYNYLDWYLQ KPGQSPQLLI YLGSNRASGV    780
```

```
PDRFSGSGSG TDFTLKISRV EAEDVGVYYC MQGLQTPHTF GQGTKVEIKR          830

SEQ ID NO: 1072        moltype = AA   length = 823
FEATURE                Location/Qualifiers
source                 1..823
                       mol_type = protein
                       organism = Homo sapiens
SEQUENCE: 1072
KKINEGLLDS KILSAFNTVI ALLGSIVIIV MNIMIIQNYT RSTDNQAVIK DALQGIQQQI    60
KGLADKIGTE IGPKVSLIDT SSTITIPANI GLLGSKISQS TASINENVNE KCKFTLPPLK   120
IHECNISCPN PLPFREYRPQ TEGVSNLVGL PNNICLQKTS NQILKPKLIS YTLPVVGQSG   180
TCITDPLLAM DEGYFAYSHL ERIGSCSRGV SKQRIIGVGE VLDRGDEVPS LFMTNVWTPP   240
NPNTVYHCSA VYNNEFYYVL CAVSTVGDPI LNSTYWSGSL MMTRLAVKPK SNGGGYNQHQ   300
LALRSIEKGR YDKVMPYGPS GIKQGDTLYF PAVGFLVRTE FKYNDSNCPI TKCQYSKPEN   360
CRLSMGIRPN SHYILRSGLL KYNLSDGENP KVVFIEISDQ RLSIGSPSKI YDSLGQPVFY   420
QASFSWDTMI KFGDVLTVNP LVVNWRNNTV ISRPGQSQCP RFNTCPAICA EGVYNDAFLI   480
DRINWISAGV FLDSNATAAN PVFTVFKDNE ILYRAQLASE DTNAQKTITN CFLLKNKIWC   540
ISLVEIYDTG DNVIRPKLFA VKIPEQCTGG GGSGGGGSGG GGSQVQLVQS GAEVKKPGAS   600
VKVSCKASGY TFTSYMHWV RQAPGQGLEW MGGFDPEDGE TIYAQKFQGR VTMTRDTSTS   660
TVYMELSSLR SEDTAVYYCA RDQGWGMDVW GQGTTVTVSS GGGGSGGGGS GGGGSDIQMT   720
QSPSSLSASV GDRVTITCRA SQSISSYLNW YQQKPGKAPK LLIYAASSLQ SGVPSRFSGS   780
GSGTDFTLTI SSLQPEDFAT YYCQQTYSTP YTFGQGTKLE IKR                    823

SEQ ID NO: 1073        moltype = AA   length = 824
FEATURE                Location/Qualifiers
source                 1..824
                       mol_type = protein
                       organism = Homo sapiens
SEQUENCE: 1073
KKINEGLLDS KILSAFNTVI ALLGSIVIIV MNIMIIQNYT RSTDNQAVIK DALQGIQQQI    60
KGLADKIGTE IGPKVSLIDT SSTITIPANI GLLGSKISQS TASINENVNE KCKFTLPPLK   120
IHECNISCPN PLPFREYRPQ TEGVSNLVGL PNNICLQKTS NQILKPKLIS YTLPVVGQSG   180
TCITDPLLAM DEGYFAYSHL ERIGSCSRGV SKQRIIGVGE VLDRGDEVPS LFMTNVWTPP   240
NPNTVYHCSA VYNNEFYYVL CAVSTVGDPI LNSTYWSGSL MMTRLAVKPK SNGGGYNQHQ   300
LALRSIEKGR YDKVMPYGPS GIKQGDTLYF PAVGFLVRTE FKYNDSNCPI TKCQYSKPEN   360
CRLSMGIRPN SHYILRSGLL KYNLSDGENP KVVFIEISDQ RLSIGSPSKI YDSLGQPVFY   420
QASFSWDTMI KFGDVLTVNP LVVNWRNNTV ISRPGQSQCP RFNTCPAICA EGVYNDAFLI   480
DRINWISAGV FLDSNATAAN PVFTVFKDNE ILYRAQLASE DTNAQKTITN CFLLKNKIWC   540
ISLVEIYDTG DNVIRPKLFA VKIPEQCTGG GGSGGGGSGG GGSQVQLVQS GAEVKKPGAS   600
VKVSCKASGY TFTNHYMHWV RQAPGQGLEW MGWMNPNSGN TGYAQKFQGR VTMTRDTSTS   660
TVYMELSSLR SEDTAVYYCA SSESGSDLDY WGQGTLVTVS SGGGGSGGGG SGGGGSDIQM   720
TQSPSSLSAS VGDRVTITCR ASQTIGNYVN WYQQKPGKAP KLLIYGASNL HTGVPSRFSG   780
SGSGTDFTLT ISSLQPEDFA TYYCQQTYSA PLTFGGGTKV EIKR                   824

SEQ ID NO: 1074        moltype = AA   length = 708
FEATURE                Location/Qualifiers
source                 1..708
                       mol_type = protein
                       organism = Homo sapiens
SEQUENCE: 1074
KKINEGLLDS KILSAFNTVI ALLGSIVIIV MNIMIIQNYT RSTDNQAVIK DALQGIQQQI    60
KGLADKIGTE IGPKVSLIDT SSTITIPANI GLLGSKISQS TASINENVNE KCKFTLPPLK   120
IHECNISCPN PLPFREYRPQ TEGVSNLVGL PNNICLQKTS NQILKPKLIS YTLPVVGQSG   180
TCITDPLLAM DEGYFAYSHL ERIGSCSRGV SKQRIIGVGE VLDRGDEVPS LFMTNVWTPP   240
NPNTVYHCSA VYNNEFYYVL CAVSTVGDPI LNSTYWSGSL MMTRLAVKPK SNGGGYNQHQ   300
LALRSIEKGR YDKVMPYGPS GIKQGDTLYF PAVGFLVRTE FKYNDSNCPI TKCQYSKPEN   360
CRLSMGIRPN SHYILRSGLL KYNLSDGENP KVVFIEISDQ RLSIGSPSKI YDSLGQPVFY   420
QASFSWDTMI KFGDVLTVNP LVVNWRNNTV ISRPGQSQCP RFNTCPAICA EGVYNDAFLI   480
DRINWISAGV FLDSNATAAN PVFTVFKDNE ILYRAQLASE DTNAQKTITN CFLLKNKIWC   540
ISLVEIYDTG DNVIRPKLFA VKIPEQCTGG GGSGGGGSGG GGSQVQLVES GGGLVQAGGS   600
LRLSCAASGR TFSGYVMGWF RQAPGKQRKF VAAISRGGLS TSYADSVKGR FTISRDNAKN   660
TVFLQMNTLK PEDTAVYYCA ADRSDLYEIT AASNIDSWGQ GTLVTVSS               708

SEQ ID NO: 1075        moltype = AA   length = 245
FEATURE                Location/Qualifiers
source                 1..245
                       mol_type = protein
                       organism = Homo sapiens
SEQUENCE: 1075
DIQMTQTTSS LSASLGDRVT ISCRASQDIS KYLNWYQQKP DGTVKLLIYH TSRLHSGVPS    60
RFSGSGSGTD YSLTISNLEQ EDIATYFCQQ GNTLPYTFGG GTKLEITGST SGSGKPGSGE   120
GSTKGEVKLQ ESGPGLVAPS QSLSVTCTVS GVSLPDYGVS WIRQPPRKGL EWLGVIWGSE   180
TTYYNSALKS RLTIIKDNSK SQVFLKMNSL QTDDTAIYYC AKHYYYGGSY AMDYWGQGTS   240
VTVSS                                                              245

SEQ ID NO: 1076        moltype = AA   length = 242
FEATURE                Location/Qualifiers
source                 1..242
                       mol_type = protein
```

```
                              organism = Homo sapiens
SEQUENCE: 1076
DIQMTQTTSS LSASLGDRVT ISCRASQDIS KYLNWYQQKP DGTVKLLIYH TSRLHSGVPS    60
RFSGSGSGTD YSLTISNLEQ EDIATYFCQQ GNTLPYTFGG GTKLEITGGG GSGGGGSGGG   120
GSEVKLQESG PGLVAPSQSL SVTCTVSGVS LPDYGVSWIR QPPRKGLEWL GVIWGSETTY   180
YNSALKSRLT IIKDNSKSQV FLKMNSLQTD DTAIYYCAKH YYYGGSYAMD YWGQGTSVTV   240
SS                                                                 242

SEQ ID NO: 1077           moltype = AA  length = 118
FEATURE                   Location/Qualifiers
source                    1..118
                          mol_type = protein
                          organism = Homo sapiens
SEQUENCE: 1077
QVQLVESGGG LVQPGGSLRL SCAASGFTFT NHAMSWVRQA PGKGLELVSS ISGNGRTTYY    60
ADSVKGRFTI SRDISKNTLD LQMNSLRAED TAVYYCAKDG GETLVDSRGQ GTLVTVSS     118

SEQ ID NO: 1078           moltype = AA  length = 119
FEATURE                   Location/Qualifiers
source                    1..119
                          mol_type = protein
                          organism = Homo sapiens
SEQUENCE: 1078
QVQLVESGGG LVQPGGSLRL SCAASGFTFS SHAMTWVRQA PGKGLEWVAA ISGSGDFTHY    60
ADSVKGRFTI SRDNSKNTVS LQMNNLRAED TAVYYCAKDE DGGSLLGYRG QGTLVTVSS    119

SEQ ID NO: 1079           moltype = AA  length = 121
FEATURE                   Location/Qualifiers
source                    1..121
                          mol_type = protein
                          organism = Homo sapiens
SEQUENCE: 1079
EVQLLESGGG LVQPGGSLRL SCAASGFTFS SYAMSWVRQA PGKGLEWVSS ISGSGDYIYY    60
ADSVKGRFTI SRDISKNTLY LQMNSLRAED TAVYYCAKEG TGANSSLADY RGQGTLVTVS   120
S                                                                  121

SEQ ID NO: 1080           moltype = AA  length = 119
FEATURE                   Location/Qualifiers
source                    1..119
                          mol_type = protein
                          organism = Homo sapiens
SEQUENCE: 1080
EVQLLESGGG LIQPGGSLRL SCAASGFTFS SHAMTWVRQA PGKGLEWVSA ISGSGDYTHY    60
ADSVKGRFTI SRDNSKNTVY LQMNSLRAED SAVYYCAKDE DGGSLLGHRG QGTLVTVSS    119

SEQ ID NO: 1081           moltype = AA  length = 12
FEATURE                   Location/Qualifiers
source                    1..12
                          mol_type = protein
                          organism = Homo sapiens
SEQUENCE: 1081
ESKYGPPCPP CP                                                       12

SEQ ID NO: 1082           moltype = AA  length = 25
FEATURE                   Location/Qualifiers
source                    1..25
                          mol_type = protein
                          organism = Homo sapiens
SEQUENCE: 1082
TTTPAPRPPT PAPTIASQPL SLRPE                                         25

SEQ ID NO: 1083           moltype = AA  length = 39
FEATURE                   Location/Qualifiers
source                    1..39
                          mol_type = protein
                          organism = Homo sapiens
SEQUENCE: 1083
IEVMYPPPYL DNEKSNGTII HVKGKHLCPS PLFPGPSKP                          39

SEQ ID NO: 1084           moltype = AA  length = 44
FEATURE                   Location/Qualifiers
source                    1..44
                          mol_type = protein
                          organism = Homo sapiens
SEQUENCE: 1084
ACRPAAGGAV HTRGLDFACD IYIWAPLAGT CGVLLLSLVI TLYC                    44

SEQ ID NO: 1085           moltype = AA  length = 27
FEATURE                   Location/Qualifiers
```

-continued

```
source                  1..27
                        mol_type = protein
                        organism = Homo sapiens
SEQUENCE: 1085
FWVLVVVGGV LACYSLLVTV AFIIFWV                                    27

SEQ ID NO: 1086         moltype = AA   length = 41
FEATURE                 Location/Qualifiers
source                  1..41
                        mol_type = protein
                        organism = Homo sapiens
SEQUENCE: 1086
RSKRSRLLHS DYMNMTPRRP GPTRKHYQPY APPRDFAAYR S                    41

SEQ ID NO: 1087         moltype = AA   length = 42
FEATURE                 Location/Qualifiers
source                  1..42
                        mol_type = protein
                        organism = Homo sapiens
SEQUENCE: 1087
KRGRKKLLYI FKQPFMRPVQ TTQEEDGCSC RFPEEEEGGC EL                   42

SEQ ID NO: 1088         moltype = AA   length = 112
FEATURE                 Location/Qualifiers
source                  1..112
                        mol_type = protein
                        organism = Homo sapiens
SEQUENCE: 1088
RVKFSRSADA PAYQQGQNQL YNELNLGRRE EYDVLDKRRG RDPEMGGKPR RKNPQEGLYN 60
ELQKDKMAEA YSEIGMKGER RRGKGHDGLY QGLSTATKDT YDALHMQALP PR        112

SEQ ID NO: 1089         moltype = AA   length = 112
FEATURE                 Location/Qualifiers
source                  1..112
                        mol_type = protein
                        organism = Homo sapiens
SEQUENCE: 1089
RVKFSRSADA PAYKQGQNQL YNELNLGRRE EYDVLDKRRG RDPEMGGKPR RKNPQEGLYN 60
ELQKDKMAEA YSEIGMKGER RRGKGHDGLY QGLSTATKDT YDALHMQALP PR        112

SEQ ID NO: 1090         moltype = AA   length = 21
FEATURE                 Location/Qualifiers
source                  1..21
                        mol_type = protein
                        organism = Homo sapiens
SEQUENCE: 1090
MEFGLSWLFL VAILKGVQCS R                                          21

SEQ ID NO: 1091         moltype = AA   length = 41
FEATURE                 Location/Qualifiers
source                  1..41
                        mol_type = protein
                        organism = Homo sapiens
SEQUENCE: 1091
RSKRSRGGHS DYMNMTPRRP GPTRKHYQPY APPRDFAAYR S                    41

SEQ ID NO: 1092         moltype = AA   length = 498
FEATURE                 Location/Qualifiers
source                  1..498
                        mol_type = protein
                        organism = synthetic construct
                        note = Description of Artificial Sequence: Synthetic
                         polypeptide
SEQUENCE: 1092
ILHYEKLSKI GLVKGVTRKY KIKSNPLTKD IVIKMIPNVS NMSQCTGSVM ENYKTRLNGI 60
LTPIKGALEI YKNNTHDLVG DVRLAGVIMA GVAIGIATAA QITAGVALYE AMKNADNINK 120
LKSSIESTNE AVVKLQETAE KTVYVLTALQ DYINTNLVPT IDKISCKQTE LSLDLALSKY 180
LSDLLFVFGP NLQDPVSNSM TIQAISQAFG GNYETLLRTL GYATEDFDDL LESDSITGQI 240
IYVDLSSYYI IVRVYFPILT EIQQAYIQEL LPVSFNNDNS EWISIVPNFI LVRNTLISNI 300
EIGFCLITKR SVICNQDYAT PMTNNMRECL TGSTEKCPRE LVVSSHVPRF ALSNGVLFAN 360
CISVTCQCQT TGRAISQSGE QTLLMIDNTT CPTAVLGNVI ISLGKYLGSV NYNSEGIAIG 420
PPVFTDKVDI SSQISSMNQS LQQSKDYIKE AQRLLDTVNP SLISMLSMII LYVLSIASLC 480
IGLITFISFI IVEKKRNT                                              498

SEQ ID NO: 1093         moltype = AA   length = 415
FEATURE                 Location/Qualifiers
source                  1..415
                        mol_type = protein
                        organism = synthetic construct
```

-continued

```
                              note = Description of Artificial Sequence: Synthetic
                              polypeptide
SEQUENCE: 1093
LAGVIMAGVA IGIATAAQIT AGVALYEAMK NADNINKLKS SIESTNEAVV KLQETAEKTV  60
YVLTALQDYI NTNLVPTIDK ISCKQTELSL DLALSKYLSD LLFVFGPNLQ DPVSNSMTIQ  120
AISQAFGGNY ETLLRTLGYA TEDFDDLLES DSITGQIIYV DLSSYYIIVR VYFPILTEIQ  180
QAYIQELLPV SFNNDNSEWI SIVPNFILVR NTLISNIEIG FCLITKRSVI CNQDYATPMT  240
NNMRECLTGS TEKCPRELVV SSHVPRFALS NGVLFANCIS VTCQCQTTGR AISQSGEQTL  300
LMIDNTTCPT AVLGNVIISL GKYLGSVNYN SEGIAIGPPV FTDKVDISSQ ISSMNQSLQQ  360
SKDYIKEAQR LLDTVNPSLI SMLSMIILYV LSIASLCIGL ITFISFIIVE KKRNT       415

SEQ ID NO: 1094          moltype =   length =
SEQUENCE: 1094
000

SEQ ID NO: 1095          moltype =   length =
SEQUENCE: 1095
000

SEQ ID NO: 1096          moltype =   length =
SEQUENCE: 1096
000

SEQ ID NO: 1097          moltype =   length =
SEQUENCE: 1097
000

SEQ ID NO: 1098          moltype =   length =
SEQUENCE: 1098
000

SEQ ID NO: 1099          moltype =   length =
SEQUENCE: 1099
000

SEQ ID NO: 1100          moltype =   length =
SEQUENCE: 1100
000

SEQ ID NO: 1101          moltype =   length =
SEQUENCE: 1101
000

SEQ ID NO: 1102          moltype =   length =
SEQUENCE: 1102
000

SEQ ID NO: 1103          moltype =   length =
SEQUENCE: 1103
000

SEQ ID NO: 1104          moltype =   length =
SEQUENCE: 1104
000

SEQ ID NO: 1105          moltype =   length =
SEQUENCE: 1105
000

SEQ ID NO: 1106          moltype = AA  length = 21
FEATURE                  Location/Qualifiers
source                   1..21
                         mol_type = protein
                         organism = Homo sapiens
SEQUENCE: 1106
MALPVTALLL PLALLLHAAR P                                    21

SEQ ID NO: 1107          moltype = AA  length = 20
FEATURE                  Location/Qualifiers
source                   1..20
                         mol_type = protein
                         organism = unidentified
                         note = Description of Unknown: IgK signal peptide sequence
SEQUENCE: 1107
METDTLLLWV LLLWVPGSTG                                      20

SEQ ID NO: 1108          moltype = AA  length = 22
FEATURE                  Location/Qualifiers
source                   1..22
```

-continued

```
                             mol_type = protein
                             organism = Homo sapiens
SEQUENCE: 1108
MLLLVTSLLL CELPHPAFLL IP                                       22

SEQ ID NO: 1109          moltype = AA  length = 45
FEATURE                  Location/Qualifiers
source                   1..45
                         mol_type = protein
                         organism = Homo sapiens
SEQUENCE: 1109
TTTPAPRPPT PAPTIASQPL SLRPEACRPA AGGAVHTRGL DFACD              45

SEQ ID NO: 1110          moltype = AA  length = 39
FEATURE                  Location/Qualifiers
source                   1..39
                         mol_type = protein
                         organism = Homo sapiens
SEQUENCE: 1110
IEVMYPPPYL DNEKSNGTII HVKGKHLCPS PLFPGPSKP                     39

SEQ ID NO: 1111          moltype = AA  length = 12
FEATURE                  Location/Qualifiers
source                   1..12
                         mol_type = protein
                         organism = Homo sapiens
SEQUENCE: 1111
ESKYGPPCPP CP                                                  12

SEQ ID NO: 1112          moltype = AA  length = 12
FEATURE                  Location/Qualifiers
source                   1..12
                         mol_type = protein
                         organism = Homo sapiens
SEQUENCE: 1112
ESKYGPPCPS CP                                                  12

SEQ ID NO: 1113          moltype = AA  length = 229
FEATURE                  Location/Qualifiers
source                   1..229
                         mol_type = protein
                         organism = Homo sapiens
SEQUENCE: 1113
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGK            229

SEQ ID NO: 1114          moltype = AA  length = 24
FEATURE                  Location/Qualifiers
source                   1..24
                         mol_type = protein
                         organism = Homo sapiens
SEQUENCE: 1114
IYIWAPLAGT CGVLLLSLVI TLYC                                     24

SEQ ID NO: 1115          moltype = AA  length = 27
FEATURE                  Location/Qualifiers
source                   1..27
                         mol_type = protein
                         organism = Homo sapiens
SEQUENCE: 1115
FWVLVVVGGV LACYSLLVTV AFIIFWV                                  27

SEQ ID NO: 1116          moltype = AA  length = 42
FEATURE                  Location/Qualifiers
source                   1..42
                         mol_type = protein
                         organism = Homo sapiens
SEQUENCE: 1116
KRGRKKLLYI FKQPFMRPVQ TTQEEDGCSC RFPEEEEGGC EL                 42

SEQ ID NO: 1117          moltype = AA  length = 41
FEATURE                  Location/Qualifiers
source                   1..41
                         mol_type = protein
                         organism = Homo sapiens
SEQUENCE: 1117
RSKRSRLLHS DYMNMTPRRP GPTRKHYQPY APPRDFAAYR S                  41
```

-continued

```
SEQ ID NO: 1118          moltype = AA  length = 112
FEATURE                  Location/Qualifiers
source                   1..112
                         mol_type = protein
                         organism = Homo sapiens
SEQUENCE: 1118
RVKFSRSADA PAYQQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR          112

SEQ ID NO: 1119          moltype = AA  length = 245
FEATURE                  Location/Qualifiers
source                   1..245
                         mol_type = protein
                         organism = synthetic construct
                         note = Description of Artificial Sequence: Synthetic
                          polypeptide
SEQUENCE: 1119
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGST SGSGKPGSGE  120
GSTKGEVKLQ ESGPGLVAPS QSLSVTCTVS GVSLPDYGVS WIRQPPRKGL EWLGVIWGSE  180
TTYYNSALKS RLTIIKDNSK SQVFLKMNSL QTDDTAIYYC AKHYYYGGSY AMDYWGQGTS  240
VTVSS                                                              245

SEQ ID NO: 1120          moltype = AA  length = 107
FEATURE                  Location/Qualifiers
source                   1..107
                         mol_type = protein
                         organism = synthetic construct
                         note = Description of Artificial Sequence: Synthetic
                          polypeptide
SEQUENCE: 1120
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEIT                107

SEQ ID NO: 1121          moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 1121
QDISKY                                                             6

SEQ ID NO: 1122          moltype =   length =
SEQUENCE: 1122
000

SEQ ID NO: 1123          moltype = AA  length = 9
FEATURE                  Location/Qualifiers
source                   1..9
                         mol_type = protein
                         organism = synthetic construct
                         note = Description of Artificial Sequence: Synthetic peptide
SEQUENCE: 1123
QQGNTLPYT                                                          9

SEQ ID NO: 1124          moltype = AA  length = 18
FEATURE                  Location/Qualifiers
source                   1..18
                         mol_type = protein
                         organism = synthetic construct
                         note = Description of Artificial Sequence: Synthetic peptide
SEQUENCE: 1124
GSTSGSGKPG SGEGSTKG                                                18

SEQ ID NO: 1125          moltype = AA  length = 120
FEATURE                  Location/Qualifiers
source                   1..120
                         mol_type = protein
                         organism = synthetic construct
                         note = Description of Artificial Sequence: Synthetic
                          polypeptide
SEQUENCE: 1125
EVKLQESGPG LVAPSQSLSV TCTVSGVSLP DYGVSWIRQP PRKGLEWLGV IWGSETTYYN  60
SALKSRLTII KDNSKSQVFL KMNSLQTDDT AIYYCAKHYY YGGSYAMDYW GQGTSVTVSS  120

SEQ ID NO: 1126          moltype = AA  length = 8
FEATURE                  Location/Qualifiers
```

```
source                      1..8
                            mol_type = protein
                            organism = synthetic construct
                            note = Description of Artificial Sequence: Synthetic peptide
SEQUENCE: 1126
GVSLPDYG                                                                              8

SEQ ID NO: 1127             moltype = AA  length = 7
FEATURE                     Location/Qualifiers
source                      1..7
                            mol_type = protein
                            organism = synthetic construct
                            note = Description of Artificial Sequence: Synthetic peptide
SEQUENCE: 1127
IWGSETT                                                                               7

SEQ ID NO: 1128             moltype = AA  length = 14
FEATURE                     Location/Qualifiers
source                      1..14
                            mol_type = protein
                            organism = synthetic construct
                            note = Description of Artificial Sequence: Synthetic peptide
SEQUENCE: 1128
AKHYYYGGSY AMDY                                                                       14

SEQ ID NO: 1129             moltype = AA  length = 242
FEATURE                     Location/Qualifiers
source                      1..242
                            mol_type = protein
                            organism = synthetic construct
                            note = Description of Artificial Sequence: Synthetic
                             polypeptide
SEQUENCE: 1129
DIQMTQTTSS LSASLGDRVT ISCRASQDIS KYLNWYQQKP DGTVKLLIYH TSRLHSGVPS      60
RFSGSGSGTD YSLTISNLEQ EDIATYFCQQ GNTLPYTFGG GTKLEITGGG GSGGGGSGGG     120
GSEVKLQESG PGLVAPSQSL SVTCTVSGVS LPDYGVSWIR QPPRKGLEWL GVIWGSETTY     180
YNSALKSRLT IIKDNSKSQV FLKMNSLQTD DTAIYYCAKH YYYGGSYAMD YWGQGTSVTV     240
SS                                                                    242

SEQ ID NO: 1130             moltype = AA  length = 15
FEATURE                     Location/Qualifiers
source                      1..15
                            mol_type = protein
                            organism = synthetic construct
                            note = Description of Artificial Sequence: Synthetic peptide
SEQUENCE: 1130
GGGGSGGGGS GGGGS                                                                      15

SEQ ID NO: 1131             moltype = DNA  length = 1458
FEATURE                     Location/Qualifiers
source                      1..1458
                            mol_type = other DNA
                            organism = synthetic construct
                            note = Description of Artificial Sequence: Synthetic
                             polynucleotide
SEQUENCE: 1131
atggccttac cagtgaccgc cttgctcctg ccgctggcct tgctgctcca cgccgccagg      60
ccggacatcc agatgacaca gactacatcc tccctgtctg cctctctggg agacagagtc     120
accatcagtt gcagggcaag tcaggacatt agtaaatatt taaattggta tcagcagaaa     180
ccagatggaa ctgttaaact cctgatctac catacatcaa gattacactc aggagtccca     240
tcaaggttca gtggcagtgg gtctgggaca gattattctc tcaccattag caacctggag     300
caagaagata ttgccactta cttttgccaa caggtaata cgcttccgta cacgttcgga     360
gggggggacca agctggagat cacaggtggc ggtggctcgg cggtggtggt ggtcgggtggc     420
ggcggatctg aggtgaaact gcaggagtca ggacctggcc tggtggcgcc ctcacagagc     480
ctgtccgtca catgcactgt ctcaggggtc tcattacccg actatggtgt aagctggatt     540
cgccagcctc cacgaaaggg tctggagtgg ctgggagtaa tatggggtag tgaaaccaca     600
tactataatt cagctctcaa atccagactg accatcatca aggacaactc caagagccaa     660
gtttttcttaa aaatgaacag tctgcaaact gatgacacag ccatttacta ctgtgccaaa     720
cattattact acggtggtag ctatgctatg gactactggg gccaaggaac ctcagtcacc     780
gtctcctcaa ccacgacgcc agcgccgcga ccaccaacac cggcgcccac catcgcgtcg     840
cagcccctgt ccctgcgccc agaggcgtgc cggccagcgg cggggggcgc agtgcacacg     900
aggggggctgg acttcgcctg tgatatctac atctgggcgc ccttggccgg gacttgtggg     960
gtccttctcc tgtcactggt tatcaccctt tactgcaaac ggggcagaaa gaaactcctg    1020
tatatattca aacaaccatt tatgagacca gtacaaactc ctcaagagga gatggctgtg    1080
agctgccgat ttccagaaga agaagaagga ggatgtgaac tgagagtgaa gttcagcagg    1140
agcgcagacg ccccccgcgta caagcagggc cagaaccagc tctataacga gctcaatcta    1200
ggacgaagag aggagtacga tgttttggac aagagacgtg gccgggaccc tgagatgggg    1260
ggaaagccga gaaggaagaa ccctcaggaa ggcctgtaca tgaactgca gaaagataag    1320
atggcggagg cctacagtga gattgggatg aaaggcgagc gccggagggg caagggggcac    1380
```

```
gatggccttt accagggtct cagtacagcc accaaggaca cctacgacgc ccttcacatg    1440
caggccctgc ccctcgc                                                    1458

SEQ ID NO: 1132        moltype = AA   length = 486
FEATURE                Location/Qualifiers
source                 1..486
                       mol_type = protein
                       organism = synthetic construct
                       note = Description of Artificial Sequence: Synthetic
                       polypeptide
SEQUENCE: 1132
MALPVTALLL PLALLLHAAR PDIQMTQTTS SLSASLGDRV TISCRASQDI SKYLNWYQQK    60
PDGTVKLLIY HTSRLHSGVP SRFSGSGSGT DYSLTISNLE QEDIATYFCQ QGNTLPYTFG    120
GGTKLEITGG GGSGGGGSGG GGSEVKLQES GPGLVAPSQS LSVTCTVSGV SLPDYGVSWI    180
RQPPRKGLEW LGVIWGSETT YYNSALKSRL TIIKDNSKSQ VFLKMNSLQT DDTAIYYCAK    240
HYYYGGSYAM DYWGQGTSVT VSSTTTPAPR PPTPAPTIAS QPLSLRPEAC RPAAGGAVHT    300
RGLDFACDIY IWAPLAGTCG VLLLSLVITL YCKRGRKKLL YIFKQPFMRP VQTTQEEDGC    360
SCRFPEEEEG GCELRVKFSR SADAPAYKQG QNQLYNELNL GRREEYDVLD KRRGRDPEMG    420
GKPRRKNPQE GLYNELQKDK MAEAYSEIGM KGERRRGKGH DGLYQGLSTA TKDTYDALHM    480
QALPPR                                                                486

SEQ ID NO: 1133        moltype = DNA   length = 1383
FEATURE                Location/Qualifiers
source                 1..1383
                       mol_type = other DNA
                       organism = synthetic construct
                       note = Description of Artificial Sequence: Synthetic
                       polynucleotide
SEQUENCE: 1133
atgctgctgc tggtgaccag cctgctgctg tgcgagctgc cccaccccgc ctttctgctg    60
atccccgaca tccagatgac ccagaccacc tccagcctga gcgccagcct gggccgaccgg   120
gtgaccatca gctgccgggc cagccaggac atcagcaagt acctgaactg gtatcagcag    180
aagcccgacg gcaccgtcaa gctgctgatc taccacacca gccggctgca cagcggcgtg    240
cccagccggt ttagcggcag cggctccggc accgactaca ctccaacctg               300
gaacaggaag atatcgccac ctactttttgc cagcagggca acacactgcc ctacacctttt    360
ggcggcggaa caaagctgga aatcaccggc agcacctccg gcagcggcaa gcctggcagc    420
ggcgagggca gcaccaaggg cgaggtgaag ctgcaggaaa gcggccctgg cctggtggcc     480
cccagccaga gcctgagcgt gacctgcacc gtgagcggcg tgagcctgcc cgactacggc     540
gtgagctgga tccggcagcc ccccaggaag ggcctggaat ggctggggcgt gatctggggc    600
agcgagacca cctactacaa cagcgccctg aagagccggc tgaccatcat caaggacaac     660
agcaagagcc aggtgttcct gaagatgaac agcctgcaga ccgacgacac cgccatctac    720
tactgcgcca agcactacta ctacggcggc agctacgcca tggactactg gggccagggc    780
accagcgtga ccgtgagcag cgaatctaag tacggaccgc cctgcccccc ttgcccctatg    840
ttctggggtgc tggtggtggt cggaggcgtg ctggcctgct acagcctgct ggtcaccgtg     900
gccttcatca tctttttgggt gaaacggggc agaaagaaac tcctgtatat attcaaacaa     960
ccatttatga gaccagtaca aactactcaa gaggaagatg gctgtagctg ccgatttcca     1020
gaagaagaag aaggaggatg tgaactgcgg gtgaagttca gaagcagcgc cgacgccccct    1080
gcctaccagc agggccagaa tcagctgtac aacgagctga acctgggcag aagggaagag     1140
tacgacgtcc tggataagcg gagaggccgg gaccctgaga tgggcggcaa gcctcggcgg     1200
aagaaccccc aggaaggcct gtataacgaa ctgcagaaag acaagatggc cgaggcctac     1260
agcgagatcg gcatgaaggg cgagcggagg cggggcaagg gccacgacgg cctgtatcag     1320
ggcctgtcca ccgccaccaa ggatacctac gacgccctgc acatgcaggc cctgcccca      1380
agg                                                                  1383

SEQ ID NO: 1134        moltype = AA   length = 461
FEATURE                Location/Qualifiers
source                 1..461
                       mol_type = protein
                       organism = synthetic construct
                       note = Description of Artificial Sequence: Synthetic
                       polypeptide
SEQUENCE: 1134
MLLLVTSLLL CELPHPAFLL IPDIQMTQTT SSLSASLGDR VTISCRASQD ISKYLNWYQQ    60
KPDGTVKLLI YHTSRLHSGV PSRFSGSGSG TDYSLTISNL EQEDIATYFC QQGNTLPYTF    120
GGGTKLEITG STSGSGKPGS GEGSTKGEVK LQESGPGLVA PSQSLSVTCT VSGVSLPDYG    180
VSWIRQPPRK GLEWLGVIWG SETTYYNSAL KSRLTIIKDN SKSQVFLKMN SLQTDDTAIY    240
YCAKHYYYGG SYAMDYWGQG TSVTVSSESK YGPPCPPCPM FWVLVVVGGV LACYSLLVTV    300
APIIFWVKRG RKKLLYIFKQ PFMRPVQTTQ EEDGCSCRFP EEEEGGCELR VKFSRSADAP    360
AYQQGQNQLY NELNLGRREE YDVLDKRRGR DPEMGGKPRR KNPQEGLYNE LQKDKMAEAY    420
SEIGMKGERR RGKGHDGLYQ GLSTATKDTY DALHMQALPP R                        461

SEQ ID NO: 1135        moltype = DNA   length = 1467
FEATURE                Location/Qualifiers
source                 1..1467
                       mol_type = other DNA
                       organism = synthetic construct
                       note = Description of Artificial Sequence: Synthetic
                       polynucleotide
SEQUENCE: 1135
```

```
atgcttctcc tggtgacaag ccttctgctc tgtgagttac cacacccagc attcctcctg  60
atcccagaca tccagatgac acagactaca tcctccctgt ctgcctctct gggagacaga  120
gtcaccatca gttgcagggc aagtcaggac attagtaaat atttaaattg gtatcagcag  180
aaaccagatg gaactgttaa actcctgatc taccatacat caagattaca ctcaggagtc  240
ccatcaaggt tcagtggcag tgggtctgga acagattatt ctctcaccat tagcaacctg  300
gagcaagaag atattgccac ttactttgc caacagggta atacgcttcc gtacacgttc  360
ggagggggga ctaagttgga aataacaggc tccacctctg gatccggcaa gcccggatct  420
ggcgaggat ccaccaaggg cgaggtgaaa ctgcaggagt caggacctgg cctggtggcg  480
ccctcacaga gcctgtccgt cacatgcact gtctcagggg tctcattcac cgactatggt  540
gtaagctgga ttcgccagcc tccacgaaag ggtctggagt ggctgggagt aatatgggt  600
agtgaaacca catactataa ttcagctctc aaatccagac tgaccatcat caaggacaac  660
tccaagagcc aagttttctt aaaaatgaac agtctgcaaa ctgatgacac agccatttac  720
tactgtgcca acattatta ctacggtggt agctatgcta tggactactg gggtcaagga  780
acctcagtca ccgtctcctc agcggccgca attgaagtta tgtatcctcc tccttaccta  840
gacaatgaga agagcaatgg aaccattatc catgtgaaag ggaaacacct ttgtccaagt  900
ccctatttc ccggaccttc taagcccttt tgggtgctgg tggtggttgg gggagtcctg  960
gcttgctata gcttgctagt aacagtggc tttattattt tctgggtgag gagtaagagg  1020
agcaggctcc tgcacagtga ctacatgaac atgactcccc gccgccccgg gcccacccgc  1080
aagcattacc agccctatgc cccaccacgc gacttcgcag cctatcgctc cagagtgaag  1140
ttcagcagga gcgcagacgc ccccgcgtac agcaggggcc agaaccagct ctataacgag  1200
ctcaatctag gacgaagaga ggagtacgat gttttggaca gagacgtgg ccgggaccct  1260
gagatgggga gaaagccgag aaggaagaac cctcaggaag gcctgtacaa tgaactgcag  1320
aaagataaga tggcggaggc ctacagtgag attgggatga aaggcgagcg ccggaggggc  1380
aagggggcacg atggcctta ccagggtctc agtacagcca ccaaggacac ctacgacgcc  1440
cttcacatgc aggccctgcc ccctcgc                                      1467
```

SEQ ID NO: 1136          moltype = AA   length = 489
FEATURE                  Location/Qualifiers
source                   1..489
                         mol_type = protein
                         organism = synthetic construct
                         note = Description of Artificial Sequence: Synthetic
                          polypeptide
SEQUENCE: 1136
MLLLVTSLLL CELPHPAFLL IPDIQMTQTT SSLSASLGDR VTISCRASQD ISKYLNWYQQ  60
KPDGTVKLLI YHTSRLHSGV PSRFSGSGSG TDYSLTISNL EQEDIATYFC QQGNTLPYTF  120
GGGTKLEITG STSGSGKPGS GEGSTKGEVK LQESGPGLVA PSQSLSVTCT VSGVSLPDYG  180
VSWIRQPPRK GLEWLGVIWG SETTYYNSAL KSRLTIIKDN SLQTDDTAIY  240
YCAKHYYYGG SYAMDYWGQG TSVTVSSAAA IEVMYPPPYL DNEKSNGTII HVKGKHLCPS  300
PLFPGPSKPF WVLVVVGGVL ACYSLLVTVA FIIFWVRSKR SRLLHSDYMN MTPRRPGPTR  360
KHYQPYAPPR DFAAYRSRVK FSRSADAPAY QQGQNQLYNE LNLGRREEYD VLDKRRGRDP  420
EMGGKPRRKN PQEGLYNELQ KDKMAEAYSE IGMKGERRRG KGHDGLYQGL STATKDTYDA  480
LHMQALPPR                                                          489

SEQ ID NO: 1137          moltype = AA   length = 246
FEATURE                  Location/Qualifiers
source                   1..246
                         mol_type = protein
                         organism = synthetic construct
                         note = Description of Artificial Sequence: Synthetic
                          polypeptide
SEQUENCE: 1137
DIVLTQSPAI LSASPGEKVT MTCRASSSVN YMDWYQKKPG SSPKPWIYAT SNLASGVPAR  60
FSGSGSGTSY SLTISRVEAE DAATYYCQQW SFNPPTFGGG TKLEIKGSTS GSGKPGSGEG  120
STKGEVQLQQ SGAELVKPGA SVKMSCKASG YTFTSYNMHW VKQTPGQGLE WIGAIYPGNG  180
DTSYNQKFKG KATLTADKSS STAYMQLSSL TSEDSADYYC ARSNYYGSSY WFFDVWGAGT  240
TVTVSS                                                             246

SEQ ID NO: 1138          moltype = AA   length = 106
FEATURE                  Location/Qualifiers
source                   1..106
                         mol_type = protein
                         organism = synthetic construct
                         note = Description of Artificial Sequence: Synthetic
                          polypeptide
SEQUENCE: 1138
DIVLTQSPAI LSASPGEKVT MTCRASSSVN YMDWYQKKPG SSPKPWIYAT SNLASGVPAR  60
FSGSGSGTSY SLTISRVEAE DAATYYCQQW SFNPPTFGGG TKLEIK                 106

SEQ ID NO: 1139          moltype = AA   length = 10
FEATURE                  Location/Qualifiers
source                   1..10
                         mol_type = protein
                         organism = synthetic construct
                         note = Description of Artificial Sequence: Synthetic peptide
SEQUENCE: 1139
RASSSVNYMD                                                         10

SEQ ID NO: 1140          moltype = AA   length = 7

```
FEATURE                 Location/Qualifiers
source                  1..7
                        mol_type = protein
                        organism = synthetic construct
                        note = Description of Artificial Sequence: Synthetic peptide
SEQUENCE: 1140
ATSNLAS                                                            7

SEQ ID NO: 1141         moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 1141
QQWSFNPPT                                                          9

SEQ ID NO: 1142         moltype = AA  length = 122
FEATURE                 Location/Qualifiers
source                  1..122
                        mol_type = protein
                        organism = synthetic construct
                        note = Description of Artificial Sequence: Synthetic
                         polypeptide
SEQUENCE: 1142
EVQLQQSGAE LVKPGASVKM SCKASGYTFT SYNMHWVKQT PGQGLEWIGA IYPGNGDTSY  60
NQKFKGKATL TADKSSSTAY MQLSSLTSED SADYYCARSN YYGSSYWFFD VWGAGTTVTV  120
SS                                                                122

SEQ ID NO: 1143         moltype = AA  length = 5
FEATURE                 Location/Qualifiers
source                  1..5
                        mol_type = protein
                        organism = synthetic construct
                        note = Description of Artificial Sequence: Synthetic peptide
SEQUENCE: 1143
SYNMH                                                              5

SEQ ID NO: 1144         moltype = AA  length = 17
FEATURE                 Location/Qualifiers
source                  1..17
                        mol_type = protein
                        organism = synthetic construct
                        note = Description of Artificial Sequence: Synthetic peptide
SEQUENCE: 1144
AIYPGNGDTS YNQKFKG                                                 17

SEQ ID NO: 1145         moltype = AA  length = 246
FEATURE                 Location/Qualifiers
source                  1..246
                        mol_type = protein
                        organism = synthetic construct
                        note = Description of Artificial Sequence: Synthetic
                         polypeptide
SEQUENCE: 1145
QVQLQQSGPG LVKPSQTLSL TCAISGDSVS SNSAAWNWIR QSPSRGLEWL GRTYYRSKWY  60
NDYAVSVKSR ITINPDTSKN QFSLQLNSVT PEDTAVYYCA REVTGDLEDA FDIWGQGTMV  120
TVSSGGGGSG GGGSGGGGSD IQMTQSPSSL SASVGDRVTI TCRASQTIWS YLNWYQQRPG  180
KAPNLLIYAA SSLQSGVPSR FSGRGSGTDF TLTISSLQAE DFATYYCQQS YSIPQTFGQG  240
TKLEIK                                                            246

SEQ ID NO: 1146         moltype = AA  length = 124
FEATURE                 Location/Qualifiers
source                  1..124
                        mol_type = protein
                        organism = synthetic construct
                        note = Description of Artificial Sequence: Synthetic
                         polypeptide
SEQUENCE: 1146
QVQLQQSGPG LVKPSQTLSL TCAISGDSVS SNSAAWNWIR QSPSRGLEWL GRTYYRSKWY  60
NDYAVSVKSR ITINPDTSKN QFSLQLNSVT PEDTAVYYCA REVTGDLEDA FDIWGQGTMV  120
TVSS                                                              124

SEQ ID NO: 1147         moltype = AA  length = 10
FEATURE                 Location/Qualifiers
source                  1..10
                        mol_type = protein
                        organism = synthetic construct
                        note = Description of Artificial Sequence: Synthetic peptide
```

```
SEQUENCE: 1147
GDSVSSNSAA                                                                    10

SEQ ID NO: 1148          moltype = AA  length = 9
FEATURE                  Location/Qualifiers
source                   1..9
                         mol_type = protein
                         organism = synthetic construct
                         note = Description of Artificial Sequence: Synthetic peptide
SEQUENCE: 1148
TYYRSKWYN                                                                     9

SEQ ID NO: 1149          moltype = AA  length = 14
FEATURE                  Location/Qualifiers
source                   1..14
                         mol_type = protein
                         organism = synthetic construct
                         note = Description of Artificial Sequence: Synthetic peptide
SEQUENCE: 1149
AREVTGDLED AFDI                                                               14

SEQ ID NO: 1150          moltype = AA  length = 107
FEATURE                  Location/Qualifiers
source                   1..107
                         mol_type = protein
                         organism = synthetic construct
                         note = Description of Artificial Sequence: Synthetic
                          polypeptide
SEQUENCE: 1150
DIQMTQSPSS LSASVGDRVT ITCRASQTIW SYLNWYQQRP GKAPNLLIYA ASSLQSGVPS  60
RFSGRGSGTD FTLTISSLQA EDFATYYCQQ SYSIPQTFGQ GTKLEIK             107

SEQ ID NO: 1151          moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 1151
QTIWSY                                                                        6

SEQ ID NO: 1152          moltype =   length =
SEQUENCE: 1152
000

SEQ ID NO: 1153          moltype = AA  length = 9
FEATURE                  Location/Qualifiers
source                   1..9
                         mol_type = protein
                         organism = synthetic construct
                         note = Description of Artificial Sequence: Synthetic peptide
SEQUENCE: 1153
QQSYSIPQT                                                                     9

SEQ ID NO: 1154          moltype = AA  length = 246
FEATURE                  Location/Qualifiers
source                   1..246
                         mol_type = protein
                         organism = synthetic construct
                         note = Description of Artificial Sequence: Synthetic
                          polypeptide
SEQUENCE: 1154
QVQLQQSGPG MVKPSQTLSL TCAISGDSVS SNSVAWNWIR QSPSRGLEWL GRTYYRSTWY  60
NDYAVSMKSR ITINPDTNKN QFSLQLNSVT PEDTAVYYCA REVTGDLEDA FDIWGQGTMV  120
TVSSGGGGSG GGGSGGGGSD IQMIQSPSSL SASVGDRVTI TCRASQTIWS YLNWYRQRPG  180
EAPNLLIYAA SSLQSGVPSR FSGRGSGTDF TLTISSLQAE DFATYYCQQS YSIPQTFGQG  240
TKLEIK                                                            246

SEQ ID NO: 1155          moltype = AA  length = 124
FEATURE                  Location/Qualifiers
source                   1..124
                         mol_type = protein
                         organism = synthetic construct
                         note = Description of Artificial Sequence: Synthetic
                          polypeptide
SEQUENCE: 1155
QVQLQQSGPG MVKPSQTLSL TCAISGDSVS SNSVAWNWIR QSPSRGLEWL GRTYYRSTWY  60
NDYAVSMKSR ITINPDTNKN QFSLQLNSVT PEDTAVYYCA REVTGDLEDA FDIWGQGTMV  120
TVSS                                                              124
```

```
SEQ ID NO: 1156          moltype = AA  length = 10
FEATURE                  Location/Qualifiers
source                   1..10
                         mol_type = protein
                         organism = synthetic construct
                         note = Description of Artificial Sequence: Synthetic peptide
SEQUENCE: 1156
GDSVSSNSVA                                                                10

SEQ ID NO: 1157          moltype = AA  length = 9
FEATURE                  Location/Qualifiers
source                   1..9
                         mol_type = protein
                         organism = synthetic construct
                         note = Description of Artificial Sequence: Synthetic peptide
SEQUENCE: 1157
TYYRSTWYN                                                                 9

SEQ ID NO: 1158          moltype = AA  length = 14
FEATURE                  Location/Qualifiers
source                   1..14
                         mol_type = protein
                         organism = synthetic construct
                         note = Description of Artificial Sequence: Synthetic peptide
SEQUENCE: 1158
AREVTGDLED AFDI                                                           14

SEQ ID NO: 1159          moltype = AA  length = 107
FEATURE                  Location/Qualifiers
source                   1..107
                         mol_type = protein
                         organism = synthetic construct
                         note = Description of Artificial Sequence: Synthetic
                          polypeptide
SEQUENCE: 1159
DIQMIQSPSS LSASVGDRVT ITCRASQTIW SYLNWYRQRP GEAPNLLIYA ASSLQSGVPS  60
RFSGRGSGTD FTLTISSLQA EDFATYYCQQ SYSIPQTFGQ GTKLEIK               107

SEQ ID NO: 1160          moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 1160
QTIWSY                                                                    6

SEQ ID NO: 1161          moltype =    length =
SEQUENCE: 1161
000

SEQ ID NO: 1162          moltype = AA  length = 9
FEATURE                  Location/Qualifiers
source                   1..9
                         mol_type = protein
                         organism = synthetic construct
                         note = Description of Artificial Sequence: Synthetic peptide
SEQUENCE: 1162
QQSYSIPQT                                                                 9

SEQ ID NO: 1163          moltype = AA  length = 246
FEATURE                  Location/Qualifiers
source                   1..246
                         mol_type = protein
                         organism = synthetic construct
                         note = Description of Artificial Sequence: Synthetic
                          polypeptide
SEQUENCE: 1163
DIVLTQSPAS LAMSLGKRAT ISCRASESVS VIGAHLIHWY QQKPGQPPKL LIYLASNLET  60
GVPARFSGSG SGTDFTLTID PVEEDDVAIY SCLQSRIFPR TFGGGTKLEI KGSTSGSGKP 120
GSGEGSTKGQ IQLVQSGPEL KKPGETVKIS CKASGYTFTD YSINWVKRAP GKGLKWMGWI 180
NTETREPAYA YDFRGRFAFS LETSASTAYL QINNLKYEDT ATYFCALDYS YAMDYWGQGT 240
SVTVSS                                                           246

SEQ ID NO: 1164          moltype = AA  length = 111
FEATURE                  Location/Qualifiers
source                   1..111
                         mol_type = protein
```

```
                        organism = synthetic construct
                        note = Description of Artificial Sequence: Synthetic
                         polypeptide
SEQUENCE: 1164
DIVLTQSPAS LAMSLGKRAT ISCRASESVS VIGAHLIHWY QQKPGQPPKL LIYLASNLET  60
GVPARFSGSG SGTDFTLTID PVEEDDVAIY SCLQSRIFPR TFGGGTKLEI K           111

SEQ ID NO: 1165         moltype = AA  length = 15
FEATURE                 Location/Qualifiers
source                  1..15
                        mol_type = protein
                        organism = synthetic construct
                        note = Description of Artificial Sequence: Synthetic peptide
SEQUENCE: 1165
RASESVSVIG AHLIH                                                   15

SEQ ID NO: 1166         moltype = AA  length = 7
FEATURE                 Location/Qualifiers
source                  1..7
                        mol_type = protein
                        organism = synthetic construct
                        note = Description of Artificial Sequence: Synthetic peptide
SEQUENCE: 1166
LASNLET                                                            7

SEQ ID NO: 1167         moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 1167
LQSRIFPRT                                                          9

SEQ ID NO: 1168         moltype = AA  length = 117
FEATURE                 Location/Qualifiers
source                  1..117
                        mol_type = protein
                        organism = synthetic construct
                        note = Description of Artificial Sequence: Synthetic
                         polypeptide
SEQUENCE: 1168
QIQLVQSGPE LKKPGETVKI SCKASGYTFT DYSINWVKRA PGKGLKWMGW INTETREPAY  60
AYDFRGRFAF SLETSASTAY LQINNLKYED TATYFCALDY SYAMDYWGQG TSVTVSS     117

SEQ ID NO: 1169         moltype = AA  length = 5
FEATURE                 Location/Qualifiers
source                  1..5
                        mol_type = protein
                        organism = synthetic construct
                        note = Description of Artificial Sequence: Synthetic peptide
SEQUENCE: 1169
DYSIN                                                              5

SEQ ID NO: 1170         moltype = AA  length = 17
FEATURE                 Location/Qualifiers
source                  1..17
                        mol_type = protein
                        organism = synthetic construct
                        note = Description of Artificial Sequence: Synthetic peptide
SEQUENCE: 1170
WINTETREPA YAYDFRG                                                 17

SEQ ID NO: 1171         moltype = AA  length = 8
FEATURE                 Location/Qualifiers
source                  1..8
                        mol_type = protein
                        organism = synthetic construct
                        note = Description of Artificial Sequence: Synthetic peptide
SEQUENCE: 1171
DYSYAMDY                                                           8

SEQ ID NO: 1172         moltype = AA  length = 246
FEATURE                 Location/Qualifiers
source                  1..246
                        mol_type = protein
                        organism = synthetic construct
                        note = Description of Artificial Sequence: Synthetic
                         polypeptide
```

```
SEQUENCE: 1172
DIVLTQSPPS LAMSLGKRAT ISCRASESVT ILGSHLIYWY QQKPGQPPTL LIQLASNVQT  60
GVPARFSGSG SRTDFTLTID PVEEDDVAVY YCLQSRTIPR TFGGGTKLEI KGSTSGSGKP  120
GSGEGSTKGQ IQLVQSGPEL KKPGETVKIS CKASGYTFRH YSMNWVKQAP GKGLKWMGRI  180
NTESGVPIYA DDFKGRFAFS VETSASTAYL VINNLKDEDT ASYFCSNDYL YSLDFWGQGT  240
ALTVSS                                                            246

SEQ ID NO: 1173            moltype = AA  length = 111
FEATURE                    Location/Qualifiers
source                     1..111
                           mol_type = protein
                           organism = synthetic construct
                           note = Description of Artificial Sequence: Synthetic
                            polypeptide
SEQUENCE: 1173
DIVLTQSPPS LAMSLGKRAT ISCRASESVT ILGSHLIYWY QQKPGQPPTL LIQLASNVQT  60
GVPARFSGSG SRTDFTLTID PVEEDDVAVY YCLQSRTIPR TFGGGTKLEI K           111

SEQ ID NO: 1174            moltype = AA  length = 15
FEATURE                    Location/Qualifiers
source                     1..15
                           mol_type = protein
                           organism = synthetic construct
                           note = Description of Artificial Sequence: Synthetic peptide
SEQUENCE: 1174
RASESVTILG SHLIY                                                   15

SEQ ID NO: 1175            moltype = AA  length = 7
FEATURE                    Location/Qualifiers
source                     1..7
                           mol_type = protein
                           organism = synthetic construct
                           note = Description of Artificial Sequence: Synthetic peptide
SEQUENCE: 1175
LASNVQT                                                            7

SEQ ID NO: 1176            moltype = AA  length = 9
FEATURE                    Location/Qualifiers
source                     1..9
                           mol_type = protein
                           organism = synthetic construct
                           note = Description of Artificial Sequence: Synthetic peptide
SEQUENCE: 1176
LQSRTIPRT                                                          9

SEQ ID NO: 1177            moltype = AA  length = 117
FEATURE                    Location/Qualifiers
source                     1..117
                           mol_type = protein
                           organism = synthetic construct
                           note = Description of Artificial Sequence: Synthetic
                            polypeptide
SEQUENCE: 1177
QIQLVQSGPE LKKPGETVKI SCKASGYTFR HYSMNWVKQA PGKGLKWMGR INTESGVPIY  60
ADDFKGRFAF SVETSASTAY LVINNLKDED TASYFCSNDY LYSLDFWGQG TALTVSS     117

SEQ ID NO: 1178            moltype = AA  length = 5
FEATURE                    Location/Qualifiers
source                     1..5
                           mol_type = protein
                           organism = synthetic construct
                           note = Description of Artificial Sequence: Synthetic peptide
SEQUENCE: 1178
HYSMN                                                              5

SEQ ID NO: 1179            moltype = AA  length = 17
FEATURE                    Location/Qualifiers
source                     1..17
                           mol_type = protein
                           organism = synthetic construct
                           note = Description of Artificial Sequence: Synthetic peptide
SEQUENCE: 1179
RINTESGVPI YADDFKG                                                 17

SEQ ID NO: 1180            moltype = AA  length = 8
FEATURE                    Location/Qualifiers
source                     1..8
                           mol_type = protein
                           organism = synthetic construct
```

-continued

```
                             note = Description of Artificial Sequence: Synthetic peptide
SEQUENCE: 1180
DYLYSLDF                                                       8

SEQ ID NO: 1181          moltype = AA  length = 121
FEATURE                  Location/Qualifiers
source                   1..121
                         mol_type = protein
                         organism = synthetic construct
                         note = Description of Artificial Sequence: Synthetic
                          polypeptide
SEQUENCE: 1181
EVQLLESGGG LVQPGGSLRL SCAASGFTFS SYAMSWVRQA PGKGLEWVSS ISGSGDYIYY    60
ADSVKGRFTI SRDISKNTLY LQMNSLRAED TAVYYCAKEG TGANSSLADY RGQGTLVTVS   120
S                                                                   121

SEQ ID NO: 1182          moltype = AA  length = 8
FEATURE                  Location/Qualifiers
source                   1..8
                         mol_type = protein
                         organism = synthetic construct
                         note = Description of Artificial Sequence: Synthetic peptide
SEQUENCE: 1182
GFTFSSYA                                                       8

SEQ ID NO: 1183          moltype = AA  length = 8
FEATURE                  Location/Qualifiers
source                   1..8
                         mol_type = protein
                         organism = synthetic construct
                         note = Description of Artificial Sequence: Synthetic peptide
SEQUENCE: 1183
ISGSGDYI                                                       8

SEQ ID NO: 1184          moltype = AA  length = 14
FEATURE                  Location/Qualifiers
source                   1..14
                         mol_type = protein
                         organism = synthetic construct
                         note = Description of Artificial Sequence: Synthetic peptide
SEQUENCE: 1184
AKEGTGANSS LADY                                                14

SEQ ID NO: 1185          moltype =   length =
SEQUENCE: 1185
000

SEQ ID NO: 1186          moltype =   length =
SEQUENCE: 1186
000

SEQ ID NO: 1187          moltype =   length =
SEQUENCE: 1187
000

SEQ ID NO: 1188          moltype =   length =
SEQUENCE: 1188
000

SEQ ID NO: 1189          moltype =   length =
SEQUENCE: 1189
000

SEQ ID NO: 1190          moltype =   length =
SEQUENCE: 1190
000

SEQ ID NO: 1191          moltype =   length =
SEQUENCE: 1191
000

SEQ ID NO: 1192          moltype =   length =
SEQUENCE: 1192
000

SEQ ID NO: 1193          moltype =   length =
SEQUENCE: 1193
000
```

-continued

```
SEQ ID NO: 1194           moltype =   length =
SEQUENCE: 1194
000

SEQ ID NO: 1195           moltype =   length =
SEQUENCE: 1195
000

SEQ ID NO: 1196           moltype =   length =
SEQUENCE: 1196
000

SEQ ID NO: 1197           moltype =   length =
SEQUENCE: 1197
000

SEQ ID NO: 1198           moltype =   length =
SEQUENCE: 1198
000

SEQ ID NO: 1199           moltype =   length =
SEQUENCE: 1199
000

SEQ ID NO: 1200           moltype =   length =
SEQUENCE: 1200
000

SEQ ID NO: 1201           moltype =   length =
SEQUENCE: 1201
000

SEQ ID NO: 1202           moltype =   length =
SEQUENCE: 1202
000

SEQ ID NO: 1203           moltype =   length =
SEQUENCE: 1203
000

SEQ ID NO: 1204           moltype =   length =
SEQUENCE: 1204
000

SEQ ID NO: 1205           moltype =   length =
SEQUENCE: 1205
000

SEQ ID NO: 1206           moltype =   length =
SEQUENCE: 1206
000

SEQ ID NO: 1207           moltype =   length =
SEQUENCE: 1207
000

SEQ ID NO: 1208           moltype =   length =
SEQUENCE: 1208
000

SEQ ID NO: 1209           moltype =   length =
SEQUENCE: 1209
000

SEQ ID NO: 1210           moltype =   length =
SEQUENCE: 1210
000

SEQ ID NO: 1211           moltype =   length =
SEQUENCE: 1211
000

SEQ ID NO: 1212           moltype =   length =
SEQUENCE: 1212
000

SEQ ID NO: 1213           moltype = AA  length = 42
FEATURE                   Location/Qualifiers
source                    1..42
```

-continued

```
                          mol_type = protein
                          organism = Homo sapiens
SEQUENCE: 1213
AAAIEVMYPP PYLDNEKSNG TIIHVKGKHL CPSPLFPGPS KP                           42

SEQ ID NO: 1214           moltype = AA   length = 28
FEATURE                   Location/Qualifiers
source                    1..28
                          mol_type = protein
                          organism = Homo sapiens
SEQUENCE: 1214
MFWVLVVVGG VLACYSLLVT VAFIIFWV                                           28

SEQ ID NO: 1215           moltype = AA   length = 112
FEATURE                   Location/Qualifiers
source                    1..112
                          mol_type = protein
                          organism = synthetic construct
                          note = Description of Artificial Sequence: Synthetic
                          polypeptide
SEQUENCE: 1215
RVKFSRSADA PAYKQGQNQL YNELNLGRRE EYDVLDKRRG RDPEMGGKPR RKNPQEGLYN 60
ELQKDKMAEA YSEIGMKGER RRGKGHDGLY QGLSTATKDT YDALHMQALP PR       112

SEQ ID NO: 1216           moltype = DNA   length = 1467
FEATURE                   Location/Qualifiers
source                    1..1467
                          mol_type = other DNA
                          organism = synthetic construct
                          note = Description of Artificial Sequence: Synthetic
                          polynucleotide
SEQUENCE: 1216
atggccttac cagtgaccgc cttgctcctg ccgctggcct tgctgctcca cgccgccagg   60
ccggacatcc agatgacaca gactacatcc tccctgtctg cctctctggg agacagagtc   120
accatcagtt gcagggcaag tcaggacatt agtaaatatt taaattggta tcagcagaaa   180
ccagatggaa ctgttaaact cctgatctac catacatcaa gattacactc aggagtccca   240
tcaaggttca gtggcagtgg gtctggaaca gattattctc tcaccattag caacctggag   300
caagaagata ttgccactta cttttgccaa caggggtaata cgcttccgta cacgttcgga   360
gggggacca agctggagat cacaggctcc acctctggat ccggcaagcc ggatctggtc   420
gagggatcca ccaagggcga ggtgaaactg caggagtcag gacctggcct ggtggcgccc   480
tcacagagcc tgtccgtcac atgcactgtc tcaggggtct cattacccga ctatggtgta   540
agctggattc gccagcctcc acgaaagggg ctggagtggc tgggagtaat atggggtagt   600
gaaccacat actataattc agctctcaaa tccagactga ccatcatcaa ggacaactc   660
aagagccaag ttttcttaaa aatgaacagt ctgcaaactg atgacacagc catttactac   720
tgtgccaaac attattacta cggtggtagc tatgctatgg actactgggg ccaaggaacc   780
tcagtcaccg tctcctcaac cacgacgcca gcgccgcgac caccaacacc ggcgcccacc   840
atcgcgtcgc agcccctgtc cctgcgccca gaggcgtgcc ggggggccac gggggctgga   900
gtgcacacga gggggctgga cttcgcctgt gatatctaca tctgggcgcc cttggccggg   960
acttgtgggg tccttctcct gtcactggtt atcaccctt actgcaaacg gggcagaaag   1020
aaactcctgt atatattcaa acaaccattt atgagaccag tacaaactac tcaagaggaa   1080
gatggctgta gctgccgatt tccagaagaa gaagaaggag gatgtgaact gagagtgaag   1140
ttcagcagga gcgcagacgc ccccgcgtac cagcaggggc agaaccagct ctataacag   1200
ctcaatctag gacgaagaga ggagtacgat gttttggaca gagagacgtgg ccgggaccct   1260
gagatggggg gaaagccgag aaggaagaac cctcaggaag gcctgtacaa tgaactgcag   1320
aaagataaga tggcggaggc ctacagtgag attgggatga aagggagcg ccggaggggc   1380
aaggggcacg atggcctta ccagggtctc agtacagcca ccaaggacac ctacgacgcc   1440
cttcacatgc aggccctgcc ccctcgc                                      1467

SEQ ID NO: 1217           moltype = AA   length = 489
FEATURE                   Location/Qualifiers
source                    1..489
                          mol_type = protein
                          organism = synthetic construct
                          note = Description of Artificial Sequence: Synthetic
                          polypeptide
SEQUENCE: 1217
MALPVTALLL PLALLLHAAR PDIQMTQTTS SLSASLGDRV TISCRASQDI SKYLNWYQQK   60
PDGTVKLLIY HTSRLHSGVP SRFSGSGSGT DYSLTISNLE QEDIATYFCQ QGNTLPYTFG   120
GGTKLEITGS TSGSGKPGSG EGSTKGEVKL QESGPGLVAP SQSLSVTCTV SGVSLPDYGV   180
SWIRQPPRKG LEWLGVIWGS ETTYYNSALK SRLTIIKDNS KSQVFLKMNS LQTDDTAIYY   240
CAKHYYYGGS YAMDYWGQGT SVTVSSTTTP APRPPTPAPT IASQPLSLRP EACRPAAGGA   300
VHTRGLDFAC DIYIWAPLAG TCGVLLLSLV ITLYCKRGRK KLLYIFKQPF MRPVQTTQEE   360
DGCSCRFPEE EEGGCELRVK FSRSADAPAY QQGQNQLYNE LNLGRREEYD VLDKRRGRDP   420
EMGGKPRRKN PQEGLYNELQ KDKMAEAYSE IGMKGERRRG KGHDGLYQGL STAKTDTYDA   480
LHMQALPPR                                                          489

SEQ ID NO: 1218           moltype = AA   length = 243
FEATURE                   Location/Qualifiers
source                    1..243
```

```
                               mol_type = protein
                               organism = synthetic construct
                               note = Description of Artificial Sequence: Synthetic
                                 polypeptide
SEQUENCE: 1218
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ KYDLLTFGGG TKVEIKGSTS GSGKPGSGEG  120
STKGQLQLQE SGPGLVKPSE TLSLTCTVSG GSISSSSYYW GWIRQPPGKG LEWIGSISYS  180
GSTYYNPSLK SRVTISVDTS KNQFSLKLSS VTAADTAVYY CARDRGDTIL DVWGQGTMVT  240
VSS                                                                243

SEQ ID NO: 1219        moltype = AA  length = 106
FEATURE                Location/Qualifiers
source                 1..106
                       mol_type = protein
                       organism = synthetic construct
                       note = Description of Artificial Sequence: Synthetic
                         polypeptide
SEQUENCE: 1219
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ KYDLLTFGGG TKVEIK               106

SEQ ID NO: 1220        moltype = AA  length = 6
FEATURE                Location/Qualifiers
source                 1..6
                       mol_type = protein
                       organism = synthetic construct
                       note = Description of Artificial Sequence: Synthetic peptide
SEQUENCE: 1220
QSISSY                                                               6

SEQ ID NO: 1221        moltype =   length =
SEQUENCE: 1221
000

SEQ ID NO: 1222        moltype = AA  length = 8
FEATURE                Location/Qualifiers
source                 1..8
                       mol_type = protein
                       organism = synthetic construct
                       note = Description of Artificial Sequence: Synthetic peptide
SEQUENCE: 1222
QQKYDLLT                                                             8

SEQ ID NO: 1223        moltype = AA  length = 119
FEATURE                Location/Qualifiers
source                 1..119
                       mol_type = protein
                       organism = synthetic construct
                       note = Description of Artificial Sequence: Synthetic
                         polypeptide
SEQUENCE: 1223
QLQLQESGPG LVKPSETLSL TCTVSGGSIS SSSYYWGWIR QPPGKGLEWI GSISYSGSTY   60
YNPSLKSRVT ISVDTSKNQF SLKLSSVTAA DTAVYYCARD RGDTILDVWG QGTMVTVSS   119

SEQ ID NO: 1224        moltype = AA  length = 10
FEATURE                Location/Qualifiers
source                 1..10
                       mol_type = protein
                       organism = synthetic construct
                       note = Description of Artificial Sequence: Synthetic peptide
SEQUENCE: 1224
GGSISSSSYY                                                          10

SEQ ID NO: 1225        moltype = AA  length = 7
FEATURE                Location/Qualifiers
source                 1..7
                       mol_type = protein
                       organism = synthetic construct
                       note = Description of Artificial Sequence: Synthetic peptide
SEQUENCE: 1225
ISYSGST                                                              7

SEQ ID NO: 1226        moltype = AA  length = 11
FEATURE                Location/Qualifiers
source                 1..11
                       mol_type = protein
                       organism = synthetic construct
                       note = Description of Artificial Sequence: Synthetic peptide
```

```
SEQUENCE: 1226
ARDRGDTILD V                                                                          11

SEQ ID NO: 1227          moltype = DNA   length = 1503
FEATURE                  Location/Qualifiers
source                   1..1503
                         mol_type = other DNA
                         organism = synthetic construct
                         note = Description of Artificial Sequence: Synthetic
                         polynucleotide
SEQUENCE: 1227
atggccttac cagtgaccgc cttgctcctg ccgctggcct tgctgctcca cgccgccagg    60
ccggacatcc agatgaccca gtctccatcc tccctgtctg catctgtagg agacagagtc   120
accatcactt gccgggcaag tcagagcatt agcagctatt taaattggta tcagcagaaa   180
ccagggaaag cccctaagct cctgatctat gctgcatcca gtttgcaaag tggggtccca   240
tcaaggttca gtggcagtgg atctgggaca gatttcactc tcaccatcag cagtctgcaa   300
cctgaagatt ttgcaactta ctactgtcag caaaaatacg acctcctcac ttttggcgga   360
gggaccaagg ttgagatcaa aggcagcacc agcggctccg gcaagcctgg ctctggcgag   420
ggcagcacaa agggacagct gcagctgcag gagtcgggcc caggactggt gaagccttcg   480
gagaccctgt ccctcacctg cactgtctct ggtggctcca tcagcagtag tagttactac   540
tggggctgga tccgccagcc cccagggaag gggctggagt ggattgggag tatctcctat   600
agtgggagca cctactacaa cccgtccctc aagagtcgag tcaccatatc cgtagacacg   660
tccaagaacc agttctccct gaagctgagt tctgtgaccg ccgcagacac ggcggtgtac   720
tactgcgcca gagatcgtgg agacaccata ctagacgtat ggggtcaggg tacaatggtc   780
accgtcagct cattcgtgcc cgtgttcctg cccgccaaac ctaccaccac ccctgcccct   840
agacctccca ccccagcccc aacaatcgcc agccagcctc tgtctctgcg gcccgaagcc   900
tgtagacctg ctgccggcgg agccgtgcac accagaggcc tggacttcgc ctgcgacatc   960
tacatctggg cccctctggc cggcacctgt ggcgtgctgc tgctgagcct ggtgatcacc  1020
ctgtactgca accaccggaa caaacggggc agaaagaaac tcctgtatat attcaaacaa  1080
ccatttatga gaccagtaca aactactcaa gaggaagatg gctgtagctg ccgatttcca  1140
gaagaagaag aaggaggatg tgaactgaga gtgaagttca gcagatccgc cgacgcccct  1200
gcctaccagc agggacagaa ccagctgtac aacgagctga acctgggcag acgggaagag  1260
tacgacgtgc tggacaagcg gagaggccgg gaccccgaga tgggcggaaa gcccagacgg  1320
aagaaccccc aggaaggcct gtataacgaa ctgcagaaag acaagatggc cgaggcctac  1380
agcgagatcg gcatgaaggg cgagcggagg cgcggcaagg gccacgatgg cctgtaccag  1440
ggcctgagca ccgccaccaa ggacacctac gacgccctgc acatgcaggc cctgcccccc  1500
aga                                                                1503

SEQ ID NO: 1228          moltype = AA   length = 501
FEATURE                  Location/Qualifiers
source                   1..501
                         mol_type = protein
                         organism = synthetic construct
                         note = Description of Artificial Sequence: Synthetic
                         polypeptide
SEQUENCE: 1228
MALPVTALLL PLALLLHAAR PDIQMTQSPS SLSASVGDRV TITCRASQSI SSYLNWYQQK    60
PGKAPKLLIY AASSLQSGVP SRFSGSGSGT DFTLTISSLQ PEDFATYYCQ QKYDLLTFGG   120
GTKVEIKGST SGSGKPGSGE GSTKGQLQLQ ESGPGLVKPS ETLSLTCTVS GGSISSSSYY   180
WGWIRQPPGK GLEWIGSISY SGSTYYNPSL KSRVTISVDT SKNQFSLKLS SVTAADTAVY   240
YCARDRGDTI LDVWGQGTMV TVSSFVPVFL PAKPTTTPAP RPPTPAPTIA SQPLSLRPEA   300
CRPAAGGAVH TRGLDFACDI YIWAPLAGTC GVLLLSLVIT LYCNHRNKRG RKKLLYIFKQ   360
PPMRPVQTTQ EEDGCSCRFP EEEEGGCELR VKFSRSADAP AYQQGQNQLY NELNLGRREE   420
YDVLDKRRGR DPEMGGKPRR KNPQEGLYNE LQKDKMAEAY SEIGMKGERR RGKGHDGLYQ   480
GLSTATKDTY DALHMQALPP R                                            501

SEQ ID NO: 1229          moltype =   length =
SEQUENCE: 1229
000

SEQ ID NO: 1230          moltype =   length =
SEQUENCE: 1230
000

SEQ ID NO: 1231          moltype = AA   length = 468
FEATURE                  Location/Qualifiers
source                   1..468
                         mol_type = protein
                         organism = synthetic construct
                         note = Description of Artificial Sequence: Synthetic
                         polypeptide
```

-continued

```
SEQUENCE: 1231
DIQMTQTTSS LSASLGDRVT ISCRASQDIS KYLNWYQQKP DGTVKLLIYH TSRLHSGVPS    60
RFSGSGSGTD YSLTISNLEQ EDIATYFCQQ GNTLPYTFGG GTKLEITGST SGSGKPGSGE   120
GSTKGEVKLQ ESGPGLVAPS QSLSVTCTVS GVSLPDYGVS WIRQPPRKGL EWLGVIWGSE   180
TTYYNSALKS RLTIIKDNSK SQVFLKMNSL QTDDTAIYYC AKHYYYGGSY AMDYWGQGTS   240
VTVSSTTTPA PRPPTPAPTI ASQPLSLRPE ACRPAAGGAV HTRGLDFACD IYIWAPLAGT   300
CGVLLLSLVI TLYCKRGRKK LLYIFKQPFM RPVQTTQEED GCSCRFPEEE EGGCELRVKF   360
SRSADAPAYQ QGQNQLYNEL NLGRREEYDV LDKRRGRDPE MGGKPRRKNP QEGLYNELQK   420
DKMAEAYSEI GMKGERRRGK GHDGLYQGLS TATKDTYDAL HMQALPPR               468
```

CD8-SPECIFIC ANTIBODY CONSTRUCTS AND COMPOSITIONS THEREOF

CROSS-REFERENCE TO RELATED APPLICATIONS

This application is a continuation of U.S. application Ser. No. 17/715,253, filed Apr. 7, 2022, which claims priority to U.S. Provisional Application No. 63/299,254, filed Jan. 13, 2022, and U.S. Provisional Application No. 63/172,518, filed Apr. 8, 2021. The contents of these applications are each incorporated herein by reference in their entirety.

SEQUENCE LISTING

The instant application contains a Sequence Listing which has been submitted electronically in XML format and is hereby incorporated by reference in its entirety. Said XML copy, created on Jan. 31, 2023, is named 15147_0005-00000_SL.xml and is 1,128,670 bytes in size.

FIELD

The present disclosure relates to antibodies or antigen binding fragments thereof that specifically bind human CD8. Also disclosed are fusion proteins comprising a Henipavirus glycoprotein G and a CD8 antibody, or an antigen binding fragment thereof, for targeting and transducing cells expressing CD8. Viral vectors and other compositions containing the fusion proteins, antibodies, or antigen binding fragments thereof, as well as methods of using the fusion proteins, antibodies, or antigen binding fragments thereof are also disclosed.

BACKGROUND

CD8 (cluster of differentiation 8) is a transmembrane glycoprotein that serves as a co-receptor for the T cell receptor (TCR). CD8 serves multiple functions in immune responses against both both external and internal challenges. In T cells, the CD8 co-receptor functions primarily to bind to a major histocompatibility complex (MHC) molecule to facilitate T cell signaling and aid with cytotoxic T cell antigen interactions. While it is predominantly expressed on the surface of cytotoxic T cells, the CD8 co-receptor can also be found on natural killer cells, cortical thymocytes, and dendritic cells. The CD8 molecule is also used as a marker for cytotoxic T cell population.

There are two isoforms of the CD8 glycoprotein, alpha and beta, and each is encoded by a different gene. To function, CD8 forms a dimer, consisting of a pair of CD8 chains. The most common form of CD8 is composed of a CD8-$\alpha$ and CD8-$\beta$ chain. Homodimers of the CD8-$\alpha$ chain are also expressed on some cells. The molecular weight of each CD8 chain is about 34 kDa.

T lymphocytes are among the prime targets in gene therapy, even more so since chimeric antigen receptor (CAR) T cells have reached the clinic. Current approaches for T cell engineering mainly rely on ex vivo gene transfer methods. Following their isolation from either healthy donors or patients, lymphocytes are activated and subsequently transduced by lentiviral vectors. The modified lymphocytes are then expanded and either used in functional in vivo assays or used for in vivo applications. Ex vivo modification of T lymphocytes, however, has its disadvantages. The complexity of the overall procedure, cost of the manufacturing process, and prolonged ex vivo culture negatively impact the quality of the final product. Methods that improve T lymphocyte engineering that use in vivo delivery platforms are needed.

In vivo delivery platforms using fusogenic glycoproteins of viral vectors have been shown to be beneficial for targeting, binding, and transducing cells of interest. Certain fusogenic glycoproteins, however, may not be sufficiently stable or expressed on the surface of the viral vector. Thus, improved fusogenic glycoproteins and viral vectors containing those glycoproteins are needed. The provided disclosure addresses this need.

BRIEF SUMMARY

The present disclosure provides an antibody or antigen binding fragment thereof that specifically binds CD8$\alpha$ or CD8$\beta$, comprising certain heavy chain complementarity determining regions (HCDR1, HCDR2, and HCDR3) and/or light chain complementarity determining regions (LCDR1, LCDR2, and LCDR3). Another embodiment is an antibody or antigen binding fragment thereof specifically binding CD8$\alpha$ or CD8$\beta$, comprising certain heavy (VH) and/or light (VL) chain variable regions. The disclosure likewise provides for isolated polynucleotides, vectors, and host cells comprising the anti-CD8$\alpha$ or CD8$\beta$ antibody or antigen binding fragment thereof.

The present disclosure also provides a fusion protein comprising a Henipavirus glycoprotein G (G protein) or a biologically active portion thereof and at least one disclosed CD8 antibody or antigen binding fragment, wherein the antibody or antigen binding fragment is fused to the C-terminus of the G protein or the biologically active portion thereof.

The present disclosure also provides a viral vector comprising a henipavirus F protein molecule or biologically active portion thereof, a henipavirus envelope glycoprotein G (G protein) or a biologically active portion thereof, and at least one disclosed CD8 antibody or antigen binding fragment thereof, wherein the antibody or antigen binding fragment thereof is attached to the C-terminus of the G protein or the biologically active portion thereof.

The present disclosure likewise relates to methods of selectively modulating and transducing CD8+ T cells using the disclosed viral vectors. Also disclosed are methods of delivering an exogenous agent to a subject, comprising administering to the subject the disclosed viral vectors, in which the viral vector further comprises an exogenous agent. The present disclosure also relates to methods of treating cancer in a subject, comprising administering to the subject the disclosed viral vectors.

BRIEF DESCRIPTION OF DRAWINGS

FIGS. 8A-8B show the average titers (FIG. 8A) and titers by donor (905C, 703C, or 2101C) (FIG. 8B) of several CD8 scFvs of the disclosure on human PBMCs.

FIGS. 11A-11C depict tumor growth over time following injection of human peripheral blood mononuclear cells (hPBMC) (FIG. 11A), with prior T cell activation with CD3/CD28 complexes, and then injection a day after of CD8-CD19CAR LV, and following injection of non-activated hPBMC (without prior T cell activation), and then injection a day after of CD8-CD19CAR LV (FIG. 11B). FIG. 11C shows the percent of CD8$^+$CD19CAR$^+$ cells in total recovered live lymphocytes from spleen, bone marrow or peripheral blood following injection of CD8-CD19CAR LV, as indicated in top right quandrant of the FACs plots in both PBMC control (top plots) and CD8 fusosome-treated animals (bottom plots).

DETAILED DESCRIPTION

Figure 1A:
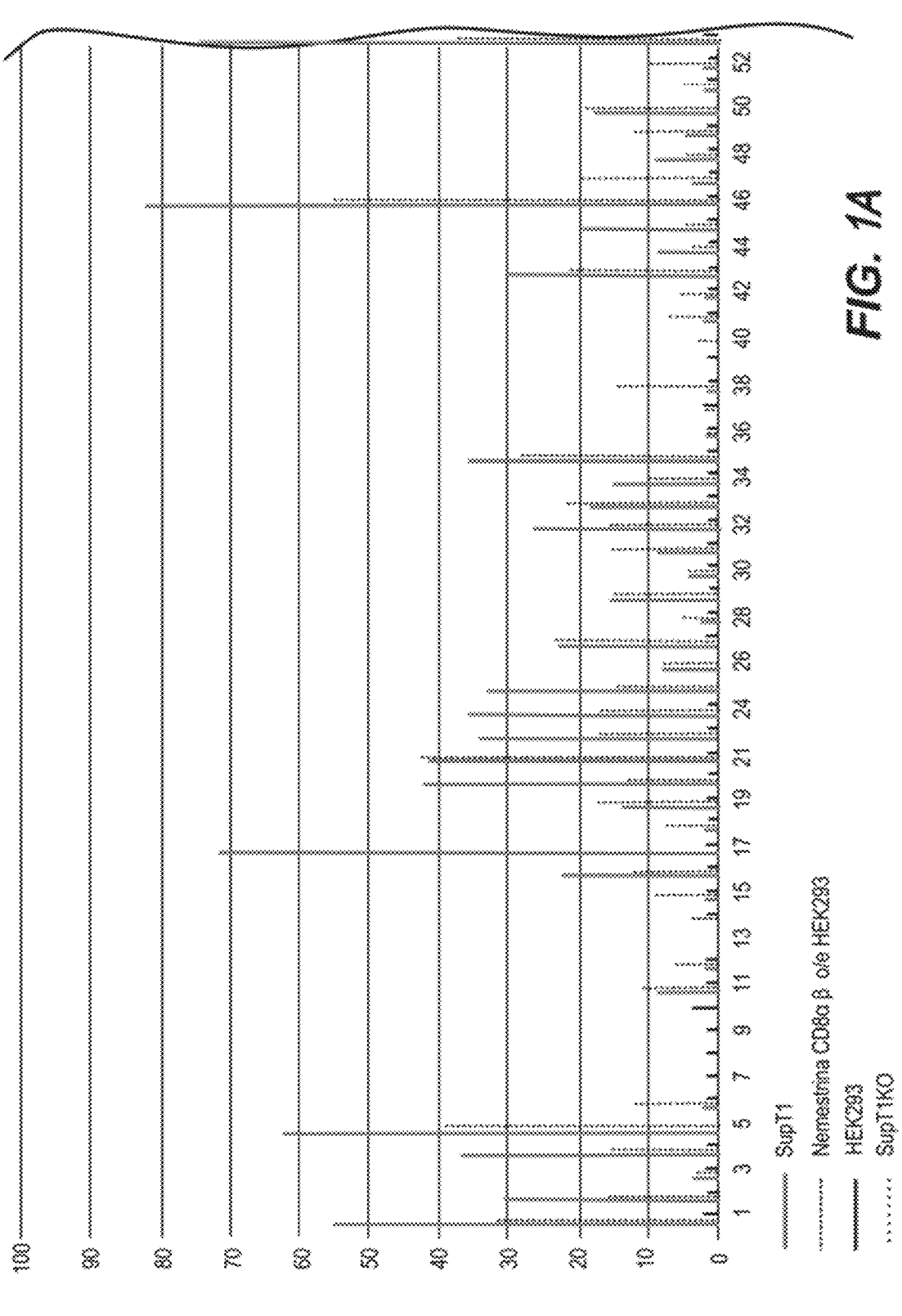
FIG. 1A-1B shows the transduction efficiencies of the disclosed anti-CD8 antibodies in several human cell lines and a cell line expressing *M. nemestrina* CD8$\alpha$ and CD8$\beta$.

Unless defined otherwise, all terms of art, notations, and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Unless defined otherwise, all technical and scientific terms, acronyms, and abbreviations used herein have the same meaning as commonly understood by one of ordinary skill in the art to which the disclosure pertains. Unless indicated otherwise, abbreviations and symbols for chemical and biochemical names is per IUPAC-IUB nomenclature. Unless indicated otherwise, all numerical ranges are inclusive of the values defining the range as well as all integer values in-between.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. In some embodiments, the term "about" when referring to a measurable value such as an amount, a temporal duration, and the like, is meant to encompass art-accepted variations based on standard errors in making such measurements. In some embodiments, the term "about" when referring to such values, is meant to encompass variations of ±20% or ±10%, more preferably ±5%, even more preferably ±1%, and still more preferably ±0.1% from the specified value, as such variations are appropriate to perform the disclosed methods.

As used herein, "CD8" or "cluster of differentiation 8" refers to a transmembrane glycoprotein which is a specific marker for a subclass of T cells (which includes cytotoxic T cells). CD8 assembles as either a heterodimer of the CD8 alpha ("CD8α" or "CD8A") and CD8 beta ("CD8β" or "CD8β") subunits ("CD8αβ" or "CD8AB"), or a CD8 alpha homodimer ("CD8αα" or "CD8AA"). The assembled dimeric CD8 complex acts as a co-receptor together with the T cell receptor (TCR) to recognize antigen presentation by MHC class I cells. CD8 plays a role in the development of T cells and activation of mature T cells.

As used herein, "affinity" refers to the strength of the sum total of noncovalent interactions between a single binding site of a molecule (e.g., an antibody) and its binding partner (e.g., an antigen). The affinity of a molecule for its partner can generally be represented by the equilibrium dissociation constant ($K_D$) (or its inverse equilibrium association constant, $K_A$). Affinity can be measured by common methods known in the art, including those described herein. See, for example, Pope M.E., Soste M. V., Eyford B. A., Anderson N. L., Pearson T. W., (2009) *J. Immunol. Methods.* 341 (1-2): 86-96 and methods described therein.

As used herein, "antibody" is meant in a broad sense and includes immunoglobulin molecules including monoclonal antibodies including murine, human, humanized and chimeric antibodies, antibody fragments, bispecific or multispecific antibodies formed from at least two intact antibodies or antibody fragments, dimeric, tetrameric or multimeric antibodies, single chain antibodies, and any other modified configuration of the immunoglobulin molecule that comprises an antigen recognition site of the required specificity.

Immunoglobulins can be assigned to five major classes, namely IgA, IgD, IgE, IgG, and IgM, depending on the heavy chain constant domain amino acid sequence. IgA and IgG are further sub-classified to IgA1, IgA2, IgG1, IgG2, IgG3, and IgG4. Antibody light chains of any vertebrate species can be assigned to one of two clearly distinct types, namely kappa (K) and lambda (A), based on the amino acid sequences of their constant domains.

As used herein, "antigen binding fragment" or "antibody fragment" refers to a portion of an immunoglobulin molecule that retains the heavy chain and/or the light chain antigen binding site, such as a heavy chain complementarity determining regions (HCDR) 1 (HCDR1), 2 (HCDR2), and 3 (HCDR3), a light chain complementarity determining regions (LCDR) 1 (LCDR1), 2 (LCDR2), and 3 (LCDR3), a heavy chain variable region (VH), or a light chain variable region (VL). Antibody fragments include a Fab fragment (a monovalent fragment consisting of the VL or the VH); a F(ab) 2 fragment (a bivalent fragment comprising two Fab fragments linked by a disulfide bridge at the hinge region); a Fd fragment consisting of the VH and CH1 domains; a Fv fragment consisting of the VL and VH domains of a single arm of an antibody; a dAb fragment, which consists of a VH domain; and a variable domain (VHH) from, e.g., human or camelid origin. VH and VL domains can be engineered and linked together via a synthetic linker to form various types of single chain antibody designs in which the VH/VL domains pair intramolecularly, or intermolecularly in those cases in which the VH and VL domains are expressed by separate single chain antibody constructs, to form a mon-ovalent antigen binding site, such as a single-chain Fv (scFv) or diabody. These antibody fragments are obtained using well known techniques and the fragments are characterized in the same manner as are intact antibodies.

An antibody variable region consists of a "framework" region interrupted by three "antigen binding sites." The antigen binding sites are defined using various terms, includ-ing, for example (i) "Complementarity Determining Regions" (CDRs), three in the VH (HCDR1, HCDR2, HCDR3) and three in the VL (LCDR1, LCDR2, LCDR3) (Wu and Kabat, *J Exp Med* 132:211-50, 1970; Kabat et al., Sequences of Proteins of Immunological Interest, 5th Ed. Public Health Service, National Institutes of Health, Bethesda, Md., 1991), and (ii) "Hypervariable regions," "HVR," or "HV," three in the VH (H1, H2, H3) and three in the VL (L1, L2, L3) (Chothia and Lesk *Mol Biol* 196:901-17, 1987). Other terms include "IMGT-CDRs" (Lefranc et al., *Dev Comparat Immunol* 27:55-77, 2003) and "Specific-ity Determining Residue Usage" (SDRU) (Almagro *Mol Recognit,* 17:132-43, 2004). The International ImMunoGe-neTics (IMGT) database (http://www_imgt org) provides a standardized numbering and definition of antigen-binding sites. The correspondence between CDRs, HVs, and IMGT delineations is described in Lefranc et al., *Dev Comparat Immunol* 27:55-77, 2003.

The term "framework," or "FR" or "framework sequence" refers to the remaining sequences of a variable region other than those sequences defined to be antigen binding sites. Because the antigen binding site can be defined by various terms as described above, the exact amino acid sequence of a framework depends on how the antigen-binding site was defined.

The term "CDR" denotes a complementarity determining region as defined by at least one manner of identification to one of skill in the art. The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Ka-bat" numbering scheme); Al-Lazikani et al., (1997) JMB 273,927-948 ("Chothia" numbering scheme); MacCallum et al., J. Mol. Biol. 262:732-745 (1996), "Antibody-antigen interactions: Contact analysis and binding site topography," J. Mol. Biol. 262, 732-745." ("Contact" numbering scheme); Lefranc M P et al., "IMGT unique numbering for immuno-globulin and T cell receptor variable domains and Ig super-family V-like domains," Dev Comp Immunol, 2003 January; 27 (1): 55-77 ("IMGT" numbering scheme); Honegger A and Pluckthun A, "Yet another numbering scheme for immu-noglobulin variable domains: an automatic modeling and analysis tool," J Mol Biol, 2001 Jun. 8;309 (3): 657-70, ("Aho" numbering scheme); and Martin et al., "Modeling antibody hypervariable loops: a combined algorithm," PNAS, 1989, 86 (23): 9268-9272, ("AbM" numbering scheme). The boundaries of a given CDR or FR may vary depending on the scheme used for identification. For example, the Kabat scheme is based on structural align-ments, while the Chothia scheme is based on structural information. Numbering for both the Kabat and Chothia schemes is based upon the most common antibody region sequence lengths, with insertions accommodated by inser-tion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. The AbM scheme is a compromise between Kabat and Chothia defi-nitions based on that used by Oxford Molecular's AbM antibody modeling software.

In some embodiments, CDRs can be defined in accor-dance with any of the Chothia numbering schemes, the Kabat numbering scheme, the IMGT numbering scheme, a combination of Kabat, IMGT, and Chothia, the AbM defi-nition, and/or the contact definition. A sdAb variable domain comprises three CDRs, designated CDR1, CDR2, and CDR3. Table 1, below, lists exemplary position boundaries of CDR-H1, CDR-H2, CDR-H3 as identified by Kabat, Chothia, AbM, and Contact schemes, respectively. For CDR-H1, residue numbering is listed using both the Kabat and Chothia numbering schemes. FRs are located between CDRs, for example, with FR-H1 located before CDR-H1, FR-H2 located between CDR-H1 and CDR-H2, FR-H3 located between CDR-H2 and CDR-H3 and so forth. It is noted that because the shown Kabat numbering scheme places insertions at H35A and H35B, the end of the Chothia CDR-H1 loop when numbered using the shown Kabat numbering convention varies between H32 and H34, depending on the length of the loop.

TABLE 1

Boundaries of CDRs according to various numbering schemes.

| CDR | Kabat | Chothia | AbM | Contact |
|---|---|---|---|---|
| CDR-H1 (Kabat Numbering[1]) | H31-H35B | H26-H32 . . . 34 | H26-H35B | H30-H35B |
| CDR-H1 (Chothia Numbering[2]) | H31-H35 | H26-H32 | H26-H35 | H30-H35 |
| CDR-H2 | H50-H65 | H52-H56 | H50-H58 | H47-H58 |
| CDR-H3 | H95-H102 | H95-H102 | H95-H102 | H93-H101 |

[1]Kabat et al. (1991), "Sequences of Proteins of Immunological Interest," 5th Ed. Public Health Service, National Institutes of Health, Bethesda, MD
[2]Al-Lazikani et al., (1997) JMB 273, 927-948.

Thus, unless otherwise specified, a "CDR" or "comple-mentary determining region," or individual specified CDRs (e.g., CDR-H1, CDR-H2, CDR-H3), of a given antibody or region thereof, such as a variable region thereof, should be understood to encompass a (or the specific) complementary determining region as defined by any of the aforementioned schemes. For example, where it is stated that a particular CDR (e.g., a CDR-H3) contains the amino acid sequence of a corresponding CDR in a given sdAb amino acid sequence, it is understood that such a CDR has a sequence of the corresponding CDR (e.g., CDR-H3) within the sdAb, as defined by any of the aforementioned schemes. It is under-stood that any antibody, such as a sdAb, includes CDRs and such can be identified according to any of the other afore-mentioned numbering schemes or other numbering schemes known to a skilled artisan.

As used herein, "Fv" refers to the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) may have the ability to recognize and bind an antigen, although at a lower affinity than the entire binding site.

As used herein, "single-chain Fv" or "scFv" antibody fragments comprise the VH and VL domains of an antibody, wherein these domains are present in a single polypeptide chain. Preferably, the Fv polypeptide further comprises a polypeptide linker between the VH and VL domains which enables the scFv to form the desired structure for antigen binding. For a review of scFv see Pluckthun in The Pharmacology of Monoclonal Antibodies, vol. 113, Rosenburg and Moore eds., Springer-Verlag, New York, pp. 269-315 (1994).

As used herein, "VHH" or "VHH antibodies" refer to single domain antibodies that consist of the variable region of a heavy chain of an IgG antibody. For example, the terms "VHH" and "VHH antibody" can refer to the antigen binding domain of a heavy chain IgG (hcIgG) mocleucle produced by a Camelidae family mammal (e.g., llamas, camels, and alpacas).

As used herein, the term "specifically binds" to a target molecule, such as an antigen, means that a binding molecule, such as a single domain antibody, reacts or associates more frequently, more rapidly, with greater duration, and/or with greater affinity with a particular target molecule than it does with alternative molecules. A binding molecule, such as a sdAb or scFv, "specifically binds" to a target molecule if it binds with greater affinity, avidity, more readily, and/or with greater duration than it binds to other molecules. It is understood that a binding molecule, such as a sdAb or scFv, that specifically binds to a first target may or may not specifically bind to a second target. As such, "specific binding" does not necessarily require (although it can include) exclusive binding.

As used herein, "percent (%) amino acid sequence identity" and "homology" with respect to a peptide, polypeptide or antibody sequence are used interchangeably and are defined as the percentage of amino acid residues in a candidate sequence that are identical with the amino acid residues in another peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, or MEGALIGN (DNASTAR) software. Those skilled in the art can determine appropriate parameters for measuring alignment, including any algorithms needed to achieve maximal alignment over the full length of the sequences being compared.

An amino acid substitution may include but is not limited to the replacement of one amino acid in a polypeptide with another amino acid. Exemplary substitutions are shown in Table 2. Amino acid substitutions may be introduced into an antibody of interest and the products screened for a desired activity, for example, retained/improved binding.

TABLE 2

| Original Residue | Exemplary Substitutions |
|---|---|
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. The term, "corresponding to" with reference to nucleotide or amino acid positions of a sequence, such as set forth in the Sequence Listing, refers to nucleotides or amino acid positions identified upon alignment with a target sequence based on structural sequence alignment or using a standard alignment algorithm, such as the GAP algorithm. For example, corresponding residues of a similar sequence (e.g. fragment or species variant) can be determined by alignment to a reference sequence by structural alignment methods. By aligning the sequences, one skilled in the art can identify corresponding residues, for example, using conserved and identical amino acid residues as guides.

The term "isolated" as used herein refers to a molecule that has been separated from at least some of the components with which it is typically found in nature or produced. For example, a polypeptide is referred to as "isolated" when it is separated from at least some of the components of the cell in which it was produced. When a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced. Thus, a DNA polynucleotide that is contained in a vector inside a host cell may be referred to as "isolated."

As used herein, "lipid particle" refers to any biological or synthetic particle that contains a bilayer of amphipathic lipids enclosing a lumen or cavity. Typically, a lipid particle does not contain a nucleus. Examples of lipid particles include nanoparticles, viral-derived particles, or cell-derived particles. Such lipid particles include, but are not limited to, viral particles (e.g. lentiviral particles), virus-like particles, viral vectors (e.g., lentiviral vectors), exosomes, enucleated cells, vesicles (e.g., microvesicles, membrane vesicles, extracellular membrane vesicles, plasma membrane vesicles, and giant plasma membrane vesicles), apoptotic bodies, mitoparticles, pyrenocytes, or lysosomes. In some embodiments, a lipid particle can be a fusosome. In some embodiments, the lipid particle is not a platelet.

As used herein a "biologically active portion," such as with reference to a protein such as a G protein or an F protein, refers to a portion of the protein that exhibits or retains an activity or property of the full-length of the protein. For example, a biologically active portion of an F protein retains fusogenic activity in conjunction with the G protein when each are embedded in a lipid bilayer. A biologically active portion of the G protein retains fusogenic activity in conjunction with an F protein when each is embedded in a lipid bilayer. The retained activity can include 10%-150% or more of the activity of a full-length or wild-type F protein or G protein. Examples of biologically active portions of F and G proteins include truncations of the cytoplasmic domain, e.g. truncations of up to 1, 2, 3, 4, 5, 6, 7, 8 9, 10, 11, 12, 13, 14, 15, 20, 22, 25, 30, 33, 34, 35, or more contiguous amino acids, see e.g. Khetawat and Broder 2010 Virology Journal 7:312; Witting et al. 2013 Gene Therapy 20:997-1005; published international; patent application No. WO/2013/148327.

As used herein, "G protein" refers to a henipavirus envelope attachment glycoprotein G or biologically active portion thereof. "F protein" refers to a henipavirus fusion protein F or biologically active portion thereof. The F and G proteins may be from a Hendra (HeV) or a Nipah (NiV) virus, and may be a wild-type protein or may be a variant thereof that exhibits reduced binding for the native binding partner. The F (fusion) and G (attachment) glycoproteins mediate cellular entry of Nipah virus. The G protein initiates infection by binding to the cellular surface receptor ephrin-B2 (EphB2) or EphB3. The subsequent release of the viral genome into the cytoplasm is mediated by the action of the F protein, which induces the fusion of the viral envelope with cellular membranes. The efficiency of transduction of targeted lipid particles can be improved by engineering hyperfusogenic mutations in one or both of the F protein (such as NiV-F) and G protein (such as NiV-G).

As used herein, "fusosome" refers to a particle containing a bilayer of amphipathic lipids enclosing a lumen or cavity and a fusogen that interacts with the amphipathic lipid bilayer. In some embodiments, the fusosome comprises a nucleic acid. In some embodiments, the fusosome is a membrane enclosed preparation. In some embodiments, the fusosome is derived from a source cell. As used herein, "fusosome composition" refers to a composition comprising one or more fusosomes.

As used herein, "fusogen" refers to an agent or molecule that creates an interaction between two membrane enclosed lumens. In embodiments, the fusogen facilitates fusion of the membranes. In other embodiments, the fusogen creates a connection, e.g., a pore, between two lumens (e.g., a lumen of a retroviral vector and a cytoplasm of a target cell). In some embodiments, the fusogen comprises a complex of two or more proteins, e.g., wherein neither protein has fusogenic activity alone. In some embodiments, the fusogen comprises a targeting domain.

As used herein, a "re-targeted fusogen" refers to a fusogen that comprises a targeting moiety having a sequence that is not part of the naturally-occurring form of the fusogen. In embodiments, the fusogen comprises a different targeting moiety relative to the targeting moiety in the naturally-occurring form of the fusogen. In embodiments, the naturally-occurring form of the fusogen lacks a targeting domain, and the re-targeted fusogen comprises a targeting moiety that is absent from the naturally-occurring form of the fusogen. In embodiments, the fusogen is modified to comprise a targeting moiety. In embodiments, the fusogen comprises one or more sequence alterations outside of the targeting moiety relative to the naturally-occurring form of the fusogen, e.g., in a transmembrane domain, fusogenically active domain, or cytoplasmic domain.

As used herein, a "targeted envelope protein" refers to a polypeptide that contains a henipavirus G protein (G protein) attached to a single domain antibody (sdAb) variable domain, such as a VL or VH sdAb, a scFv, a nanobody, a camelid VHH domain, a shark IgNAR, or fragments thereof, that target a molecule on a desired cell type. In some such embodiments, the attachment may be directly or indirectly via a linker, such as a peptide linker. The "targeted envelope protein" may also be referred to as a "fusion protein" comprising the G protein and antibodies or antigen binding fragments of the disclosure in which the antibody or antigen binding fragment is fused to the C-terminus of the G protein or a biologically active portion thereof.

As used herein, a "targeted lipid particle" refers to a lipid particle that contains a targeted envelope protein embedded in the lipid bilayer, e.g., targeting CD8. Such targeted lipid particles can be a viral particle, a virus-like particle, a nanoparticle, a vesicle, an exosome, a dendrimer, a lentivirus, a viral vector, an enucleated cell, a microvesicle, a membrane vesicle, an extracellular membrane vesicle, a plasma membrane vesicle, a giant plasma membrane vesicle, an apoptotic body, a mitoparticle, a pyrenocyte, a lysosome, another membrane enclosed vesicle, or a lentiviral vector, a viral based particle, a virus like particle (VLP), or a cell derived particle.

As used herein, a "retroviral nucleic acid" refers to a nucleic acid containing at least the minimal sequence requirements for packaging into a retrovirus or retroviral vector, alone or in combination with a helper cell, helper virus, or helper plasmid. In some embodiments, the retroviral nucleic acid further comprises or encodes an exogenous agent, a positive target cell-specific regulatory element, a non-target cell-specific regulatory element, or a negative TCSRE. In some embodiments, the retroviral nucleic acid comprises one or more of (e.g., all of) a 5' LTR (e.g., to promote integration), U3 (e.g., to activate viral genomic RNA transcription), R (e.g., a Tat-binding region), U5, a 3' LTR (e.g., to promote integration), a packaging site (e.g., psi (I')), and RRE (e.g., to bind to Rev and promote nuclear export). The retroviral nucleic acid can comprise RNA (e.g., when part of a virion) or DNA (e.g., when being introduced into a source cell or after reverse transcription in a recipient cell). In some embodiments, the retroviral nucleic acid is packaged using a helper cell, helper virus, or helper plasmid which comprises one or more of (e.g., all of) gag, pol, and env.

As used herein, a "target cell" refers to a cell of a type to which it is desired that a targeted lipid particle delivers an exogenous agent. In embodiments, a target cell is a cell of a specific tissue type or class, e.g., an immune effector cell, e.g., a T cell. In some embodiments, a target cell is a diseased cell, e.g., a cancer cell. In some embodiments, the fusogen, e.g., a re-targeted fusogen, leads to preferential delivery of the exogenous agent to a target cell compared to a non-target cell.

As used herein a "non-target cell" refers to a cell of a type to which it is not desired that a targeted lipid particle delivers an exogenous agent. In some embodiments, a non-target cell is a cell of a specific tissue type or class. In some embodiments, a non-target cell is a non-diseased cell, e.g., a non-cancerous cell. In some embodiments, the fusogen, e.g., a re-targeted fusogen, leads to lower delivery of the exogenous agent to a non-target cell compared to a target cell.

The term "effective amount" as used herein means an amount of a pharmaceutical composition which is sufficient to significantly and positively modify the symptoms and/or conditions to be treated (e.g., provide a positive clinical response). The effective amount of the targeted lipid particles of the disclosure for use in a pharmaceutical composition will vary with the particular condition being treated, the severity of the condition, the duration of treatment, the nature of concurrent therapy, the particular lipid particle) being employed, the particular pharmaceutically-acceptable excipient(s) and/or carrier(s) utilized, and like factors with the knowledge and expertise of the attending physician. An "exogenous agent" as used herein with reference to a targeted lipid particle, refers to an agent that is neither comprised by nor encoded in the corresponding wild-type virus or fusogen made from a corresponding wild-type source cell. In some embodiments, the exogenous agent does not naturally exist, such as a protein or nucleic acid that has a sequence that is altered (e.g., by insertion, deletion, or substitution) relative to a naturally occurring protein. In some embodiments, the exogenous agent does not naturally exist in the source cell. In some embodiments, the exogenous agent exists naturally in the source cell but is exogenous to the virus. In some embodiments, the exogenous agent does not naturally exist in the recipient cell. In some embodiments, the exogenous agent exists naturally in the recipient cell, but is not present at a desired level or at a desired time. In some embodiments, the exogenous agent comprises DNA, RNA, or protein.

As used herein, a "promoter" refers to a cis-regulatory DNA sequence that, when operably linked to a gene coding sequence, drives transcription of the gene. The promoter may comprise one or more transcription factor binding sites. In some embodiments, a promoter works in concert with one or more enhancers which are distal to the gene.

As used herein, a composition refers to any mixture of two or more products, substances, or compounds, including cells. It may be a solution, a suspension, liquid, powder, a paste, aqueous, non-aqueous, or any combination thereof.

As used herein, the term "pharmaceutically acceptable" refers to a material, such as a carrier or diluent, which does not abrogate the biological activity or properties of a therapeutic compound, and is relatively nontoxic, i.e., the material may be administered to an individual without causing undesirable biological effects or interacting in a deleterious manner with any of the components of the composition in which it is contained.

As used herein, the term "pharmaceutical composition" refers to a mixture of at least one targeted lipid particle of the disclosure with other chemical components, such as carriers, stabilizers, diluents, dispersing agents, suspending agents, thickening agents, and/or excipients. The pharmaceutical composition facilitates administration of the targeted lipid particle to an organism. Multiple techniques of administering targeted lipid particles of the disclosure exist in the art including, but not limited to, intravenous, oral, aerosol, parenteral, ophthalmic, pulmonary, and topical administration.

A "disease" or "disorder" as used herein refers to a condition in which treatment is needed and/or desired.

As used herein, the terms "treat," "treating," or "treatment" refer to ameliorating a disease or disorder, e.g., slowing or arresting or reducing the development of the disease or disorder or reducing at least one of the clinical symptoms thereof. For purposes of this disclosure, ameliorating a disease or disorder can include obtaining a beneficial or desired clinical result that includes, but is not limited to, any one or more of: alleviation of one or more symptoms, diminishment of extent of disease, preventing or delaying spread (for example, metastasis, for example metastasis to the lung or to the lymph node) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total).

The terms "individual" and "subject" are used interchangeably herein to refer to an animal; for example a mammal. The terms include human and veterinary animals. In some embodiments, methods of treating animals, including, but not limited to, humans, rodents, simians, felines, canines, equines, bovines, porcines, ovines, caprines, mammalian laboratory animals, mammalian farm animals, mammalian sport animals, and mammalian pets, are provided. The animal can be male or female and can be any suitable age, including infant, juvenile, adolescent, adult, and geriatric. In some examples, an "individual" or "subject" refers to an animal in need of treatment for a disease or disorder. In some embodiments, the animal to receive the treatment can be a "patient," designating the fact that the animal has been identified as having a disorder of relevance to the treatment, or being at adequate risk of contracting the disorder. In particular embodiments, the animal is a human, such as a human patient.

CD8-Specific Antibodies

Described herein are novel antibodies and antigen binding fragments thereof that specifically target and bind CD8α or CD8β. In some embodiments, the antibodies or antigen binding fragments thereof may cross-react with cynomolgus (or "cyno") or *M. nemestrina* CD8. In some embodiments, the antibodies or antigen binding fragments thereof are single-chain variable fragments (scFvs) composed of the antigen-binding domains derived from the heavy (VH) and the light (VL) chains of the IgG molecule and connected via a linker domain. In some embodiments, the antibodies or antigen binding fragments thereof are VHHs that correspond to the VH of the IgG molecule. The present disclosure also provides polynucleotides encoding the antibodies and fragments thereof, vectors, and host cells, and methods of using the antibodies or antigen binding fragments thereof. In some embodiments, e.g., the antibodies or antigen binding fragments thereof may be fused to henipavirus glycoprotein G for targeted binding and transduction to cells.

Sequences for exemplary antibodies and antigen binding fragments of the disclosure using the Kabat numbering scheme are shown in Tables 3-4 below. Sequences for exemplary HCDRs of the disclosure are shown in Table 3. Sequences for exemplary LCDRs of the disclosure are shown in Table 4.

The sequences for the disclosed VH and VL domains are provided in Tables 5-6. Tables 8-11 provided herein show the CDR sequences of the disclosed antibodies and antigen binding fragments thereof using both Chothia and IMGT numbering schemes. The full CD8 binder sequences of the variant CD8 scFvs and VHHs of the disclosure are shown in Table 12.

TABLE 3

| HCDRS in Kabat Numbering Scheme | | | | | |
| --- | --- | --- | --- | --- | --- |
| | H-CDR1 | | H-CDR2 | | H-CDR3 | |
| CD8 Binder | Sequence | SEQ ID NO: | Sequence | SEQ ID NO: | Sequence | SEQ ID NO: |
| 1 | SYAIS | 1 | IIDPSDGNTNYAQNFQG | 70 | ERAAAGYYYYMDV | 148 |
| 2 | TYAIN | 2 | RIDPSSGGTKYAQNFQG | 71 | EHAAGTYYYYMDV | 149 |
| 3 | SYAIN | 3 | IIDPSGGNTNYAQNFQG | 72 | ERAAAGYYYYMDV | 148 |
| 4 | GYYMH | 4 | HINPNNGDTNYAQNFQG | 73 | EGYYYYGMDV | 649 |
| 5 | DYYIQ | 5 | WINPNSGGTSYAQKFQG | 74 | EGDYYYGMDA | 150 |
| 6 | RYDIH | 6 | VINPNDGSTRYAQNFQG | 75 | ERGGMPDY | 151 |
| 7 | SYAMN | 7 | RINPNSGGTNYAQKFQG | 76 | GHGIPKY | 152 |
| 8 | SYYIH | 8 | WMNPNSGNTGYAQKFQG | 77 | VRSGSPQH | 153 |
| 9 | RHYIH | 9 | WMNPNSGNTGYAQKFQG | 77 | GGPWIVDAFDI | 154 |
| 10 | SYGIS | 10 | WISAHNGVTQYAQKFQG | 78 | GIAVAGTDY | 650 |
| 11 | NTDIN | 11 | IINPSGGSTSYAQKFQG | 79 | EATWGPYYYYMDV | 155 |
| 12 | RSYVH | 12 | WISPYNGNTKYAQKFQG | 80 | NKDGLQH | 156 |
| 13 | GYYMH | 13 | IINPNSGDTKYAHQFQG | 81 | DAKRVGYYYYMDV | 157 |
| 14 | RYYMH | 14 | RINPNSGGTNYAQKFQG | 76 | LVGGSPDY | 158 |
| 15 | NYDIN | 15 | RINPNSGGTNYAENFQG | 1057 | GAMVDY | 159 |
| 16 | NTDIN | 11 | IINPSDGDTKYAQEFQG | 82 | GNYVGSYYYGMDV | 160 |
| 17 | NYYLH | 16 | WINPNSGDTKYAQKFQG | 83 | DSRGDWYFDL | 161 |
| 18 | RYSIH | 17 | VIDPSGGSTSYAQKFQG | 84 | HGGRGLADY | 162 |
| 19 | SRDIS | 18 | WIDPKSGDTTYAQKFQG | 85 | LKELSSILDAFDI | 163 |
| 20 | SYDIN | 19 | MINPGAGSSTYAQKFQG | 86 | ERFGTGYYYYMDV | 164 |
| 21 | NSDMN | 20 | LISGDGGTTYYADSVKG | 87 | VIGEMVDDAFDL | 165 |
| 22 | GYYMH | 4 | SINPNSGDTGYAQKFQG | 88 | ERLFGTYYYYMDV | 166 |
| 23 | TYDIN | 21 | RIIPIFGTANYAQKFQG | 89 | ADGELTDY | 167 |
| 24 | SYTMD | 22 | AIGTGGGIYYADSVKG | 90 | HHLPAHYYYYMDV | 168 |
| 25 | RYDIN | 23 | RINPNSGDTNYAQKFQG | 91 | DVPAGRYYYYMDV | 169 |
| 26 | SYYMH | 24 | MINPSDGSTRYAQKFQG | 92 | DRGVGRYYYYMDV | 170 |
| 27 | RYAVS | 25 | IINPSDGSTTYAQKFQG | 93 | DSRYGRYYYYMDV | 171 |
| 28 | NYAIS | 26 | IINPNGGSPSYAQKFQG | 94 | EIVVGPYYYYMDV | 172 |
| 29 | RYAIS | 617 | RINPNSGDTNYAQKFQG | 91 | GMVRGPYYYYMDV | 173 |
| 30 | SYAIS | 1 | IINPSGGSTSYAQTFQG | 1058 | EGVTGPYYYYMDV | 174 |
| 31 | RFDIN | 28 | IINPSDGSTDYAQNFQG | 95 | DAAAGTRYYYYYGMDV | 175 |
| 32 | SHAIS | 29 | IINPSGGSTSYAQKFQG | 79 | ELYSSTYYYYMDV | 176 |
| 33 | SYAIS | 1 | RINPNTGGTNHAQKFQG | 96 | ALYSGPYYYYMDV | 177 |
| 34 | NSDMN | 20 | AISGSGGSTYYADSVKG | 97 | EHAAGTYYYYMDV | 149 |
| 35 | SYGIN | 30 | WISGYNGDTDYARKLQG | 98 | DSLVGRYYYYMDV | 178 |
| 36 | DYDIY | 31 | WISADNGNTNYEQKVQG | 99 | RSELDY | 179 |
| 37 | SYHMH | 32 | WISPNSGATHYAQKFQG | 100 | GDDNDY | 180 |

TABLE 3-continued

| | HCDRS in Kabat Numbering Scheme | | | | | |
|---|---|---|---|---|---|---|
| | H-CDR1 | | H-CDR2 | | H-CDR3 | |
| CD8 Binder | Sequence | SEQ ID NO: | Sequence | SEQ ID NO: | Sequence | SEQ ID NO: |
| 38 | SYDIN | 19 | WINPNSGNTGYAKKFQG | 101 | GEEVDY | 181 |
| 39 | SYPMN | 33 | IINPSGGSTRYAQKFQG | 102 | GRRVPDY | 182 |
| 40 | DYYIH | 34 | WINPKSGATNYAQKFQG | 103 | GKVTTDY | 183 |
| 41 | SFEMN | 35 | RISESGDSSFYADSVKG | 104 | GRELIEY | 184 |
| 42 | DYAMH | 36 | AIGTGGGTYYADSVKG | 105 | VYDFPDV | 185 |
| 43 | DSYMH | 37 | WMNPSNGDTGYARKFQG | 106 | STYSHIDY | 186 |
| 44 | NYYMH | 38 | TISPSDGSTTYAQRFQG | 107 | EDSSGFDY | 187 |
| 45 | NYYIH | 39 | IINPSGGSTTYAQKFQG | 108 | DQGGGFDY | 188 |
| 46 | SYYMH | 40 | GFDPEDGETIYAQKFQG | 109 | DQGWGMDV | 189 |
| 47 | SYYIH | 8 | RINPKSGRTYYAQNFQG | 110 | LTEGIPDY | 190 |
| 48 | DYYIH | 41 | VINPGGGSTTYAQTFQG | 111 | DRYGPFDY | 191 |
| 49 | SYDIN | 19 | LMNPKTGDTNYAEKFQG | 112 | LVAGGAPDY | 192 |
| 50 | GYYMH | 4 | IIDPSDGYTSYAQKFQG | 113 | DGFTGDIAY | 193 |
| 51 | GYYMH | 4 | WINPNSGGTNYAQKFQG | 114 | VDDSSSPDY | 194 |
| 52 | GYYLH | 42 | GIMPISGTTIYAQKFQG | 115 | GPDGTEVDY | 195 |
| 52 | NHYMH | 43 | WMNPSNGNTGYAQKFQG | 77 | SESGSDLDY | 196 |
| 54 | NYYIH | 44 | WMSPTSGDTGYAQKFQG | 116 | EVEIEGYMDV | 197 |
| 55 | SYYMH | 40 | WINPNSGDTSYAQKFQG | 117 | DLDDDWYMDV | 198 |
| 56 | SYYMH | 40 | IIDPSGDITSYAQKFQG | 118 | DSTTWDAFDI | 199 |
| 57 | DYYMH | 45 | WINPNSGGTNYAQKFQG | 114 | VLVGSGSPDY | 200 |
| 58 | ENEMH | 46 | IIETSGGSTDYAQKFQG | 119 | EAAAGLDFQH | 201 |
| 59 | SYDMH | 47 | IINPNSGGTNYAQKLQG | 120 | ANSWDADY | 202 |
| 60 | NSDMH | 48 | VISGSGVTTYYADSVKG | 121 | EHSSSWYTFDY | 203 |
| 61 | AYYMH | 49 | WINPNSGGTDYAQKFQG | 122 | DDDSSGYYLDY | 204 |
| 62 | NYYIH | 44 | MINPSGGSTTYAQKFQG | 123 | ASGDYMDLIDYMDY | 205 |
| 63 | DYHMH | 50 | WINPDSGGTNYEQKFQG | 124 | VGSSGYLAPTH | 206 |
| 64 | DYYMH | 51 | WMNPSNGNTGYAQKFQG | 77 | VRGDGYNLGDY | 207 |
| 65 | DYYMH | 52 | WINPNSGGTNSAQKFQG | 125 | DVDTAMGAGDY | 208 |
| 66 | DYYIH | 34 | IINPSGGSASYAQKFQG | 126 | VARWGYGDYPDY | 209 |
| 67 | THDIN | 53 | IISPSDGSTSYAQKLQG | 127 | DRNGDYYYGMDV | 210 |
| 68 | NYYIH | 54 | WINPISGGTHYAQKFQG | 128 | EGLGSSWYVLDY | 211 |
| 69 | SYDIN | 19 | WISADNGDTSFAQKFQG | 129 | DGSHYGYYGMDV | 212 |
| 70 | SYDIN | 19 | GISPIYGTPAYAQKFQG | 130 | PGPEGYYYGMDV | 213 |
| 71 | DNYMH | 55 | WMNPSNGNTGYAQKFQG | 77 | YHWDYGDYRFDY | 214 |
| 72 | SYYIH | 8 | WMNPSNGNTGYAQKFQG | 77 | VEIDYGDSPPDY | 215 |
| 73 | SYAIS | 56 | IINPSDGDTSYAQKFQG | 131 | GAEWELRYAFDI | 216 |

TABLE 3-continued

| | HCDRS in Kabat Numbering Scheme | | | | | |
|---|---|---|---|---|---|---|
| | H-CDR1 | | H-CDR2 | | H-CDR3 | |
| CD8 Binder | Sequence | SEQ ID NO: | Sequence | SEQ ID NO: | Sequence | SEQ ID NO: |
| 74 | TYDIS | 57 | TINPSGGTTTYAQKFQG | 132 | ETYYGLYYYGMDV | 217 |
| 75 | SYDIN | 19 | WMNPKSGNTGYAQKFQG | 133 | APSLRGYSYGPDY | 218 |
| 76 | SYDIN | 58 | IINPSGGSTSYAQKFQG | 79 | DRQERYYYYYMDV | 219 |
| 77 | SYDIN | 19 | IINPSDGSTDYAQKFQG | 1059 | DRSYGDYYYGMDV | 220 |
| 78 | SYDIN | 58 | IINPGGGNARHTQKFQG | 134 | EVFSENYYYYMDV | 221 |
| 79 | SYYMH | 40 | IINPSDGSTTYAQKFQG | 93 | EWDYTHYYYGMDV | 222 |
| 80 | SHWIH | 59 | GFDPEDGETVYAQNFQG | 135 | GDSSGYYQYYFDY | 223 |
| 81 | SYDIN | 19 | GITPVFGIANYAQKFQG | 136 | GSWDSSSWYIPEY | 224 |
| 82 | DYDIV | 60 | IINPRGGSTNYAQKFQG | 137 | LVWGGAYYYYMDV | 225 |
| 83 | SYGIS | 10 | WMNPNNGDTDYAQKFQG | 138 | PVFSGSYYWYFDP | 226 |
| 84 | SYDIN | 19 | IINPSGGGTSYAQKFQG | 139 | DQAVAGPYYYGMDV | 227 |
| 85 | SYAIS | 1 | LINPGSGNTNYAQKFQG | 140 | DRWLAGPYYYGMDV | 228 |
| 86 | GHDMH | 61 | GIIPIFGTPNYAQKFQG | 141 | VMGPVDYYYYGMDV | 229 |
| 87 | NYDMH | 62 | IINPSDGSTTYAQKFQG | 93 | DLGPFGSYYYYMDV | 230 |
| 88 | SYAMT | 63 | TINGDGDDTDYADSVKG | 142 | EGVVVPPYYYYMDV | 231 |
| 89 | TYYMH | 64 | QIDPNSGDTIYPQKFQG | 143 | SSGWSRYYYYYMDV | 232 |
| 90 | NYQIH | 65 | IINPSGGSTSYAQKFQG | 79 | DNGMTTGYYYYMDV | 233 |
| 91 | SYDIV | 66 | IINPSGGSTSYAQKFQG | 79 | DRAMVTGYYYGMDV | 234 |
| 92 | SYDIN | 19 | IVNPSDGNTNYAQKFQG | 144 | DRGYGDRGYYYGMDV | 235 |
| 93 | SYDIN | 67 | WINTYNGNTYYAQKLQG | 145 | SPKATADYYYYYMDV | 236 |
| 94 | SYDIN | 19 | IINPSDGITDYAQRFQG | 146 | STVTPSYYYYYGMDV | 237 |
| 95 | SHAIH | 68 | IINPRDGDTVYAQKFQG | 147 | EPVAGTGYYYYYGMDV | 238 |
| 96 | SYGIN | 69 | WMNPNSGNTGYAQKFQG | 77 | DNLAGFWSDYYYYGMDV | 239 |
| 97 | GYVMG | 1061 | AISRGGLSTSYADSVKG | 1062 | DRSDLYEITAASNIDS | 1063 |

TABLE 4

| | LCDRS in Kabat Numbering Scheme | | | | | |
|---|---|---|---|---|---|---|
| | L-CDR1 | | L-CDR2 | | L-CDR3 | |
| CD8 Binder | Sequence | SEQ ID NO: | Sequence | SEQ ID NO: | Sequence | SEQ ID NO: |
| 1 | RASQSISSYLN | 240 | AASSLQS | 294 | QQSYSTPLT | 333 |
| 2 | QASQDISNYLN | 241 | AASSLQS | 294 | QQSYSNLVS | 334 |
| 3 | RASQSISSYLN | 240 | AASSLQS | 294 | QQSYSTPLT | 333 |
| 4 | RSSQSLLHSNGYNYLD | 242 | LGSNRAS | 295 | MQALQTPFT | 335 |
| 5 | RSSQSLLHSNGYNYLD | 242 | LGSNRAS | 295 | MQGLQTPHT | 336 |
| 6 | RASQSISRNLN | 243 | KASNLKG | 296 | QQTYSAPL | 337 |
| 7 | RSSQSLLHSNGYNYLD | 242 | LGSNRAS | 295 | MQTLQTPLT | 338 |

TABLE 4-continued

| | LCDRS in Kabat Numbering Scheme | | | | | |
|---|---|---|---|---|---|---|
| | L-CDR1 | | L-CDR2 | | L-CDR3 | |
| CD8 Binder | Sequence | SEQ ID NO: | Sequence | SEQ ID NO: | Sequence | SEQ ID NO: |
| 8 | RASQSVSASDLA | 244 | GASTRAT | 297 | QQYGDSPGS | 339 |
| 9 | QASQDIGNYLN | 245 | AASTLQR | 298 | QQANSFPPT | 340 |
| 10 | RASQSISTHLA | 246 | GASTRAT | 297 | QQYGNSRT | 341 |
| 11 | RASQTISNYLN | 247 | AASTLQS | 299 | QQSYSTPPT | 342 |
| 12 | RASQGIRNDLG | 248 | DASTLQS | 300 | QQSYSSPYT | 343 |
| 13 | RASQSISNYLN | 249 | AASSLQS | 294 | QQSYSTPYT | 344 |
| 14 | RSSQSLLHSNGYNYLD | 242 | LGSNRAS | 295 | MQGAHWPPT | 345 |
| 15 | RASQGISDSLA | 250 | GASSLRS | 301 | QQSYRTPYT | 346 |
| 16 | RASQSISNYLN | 249 | AASSLQS | 294 | QESFTTQWT | 347 |
| 17 | QASQDIHNYLN | 251 | DASNLET | 302 | QQANSFPPT | 340 |
| 18 | QASQDISNYLN | 241 | SASSLQS | 303 | QQRSNWPLYT | 348 |
| 19 | RASQSISDWLA | 252 | AASSLQT | 304 | QQAISFPIT | 349 |
| 20 | QASQDISNYLN | 241 | SASTLQS | 305 | QQSYSSPFT | 350 |
| 21 | RASQSISTWLA | 253 | AASTLQS | 299 | QQAISFPLT | 351 |
| 22 | RASQSISNYLN | 249 | AASTLQS | 299 | QQSYTFPIT | 352 |
| 23 | RSSQSLLHSNGYNYLD | 242 | DASHLET | 306 | QQYYSYPPT | 353 |
| 24 | QASQDISNYLN | 241 | AASTLHS | 307 | QQSYSAPLT | 354 |
| 25 | QASQDISNYLN | 241 | AASTLQS | 299 | QQSFSTFYT | 355 |
| 26 | QASQDISNYLN | 241 | AASTLQS | 299 | QQSYSIPFT | 356 |
| 27 | RASQSINRFLN | 254 | AASSLQN | 308 | QQSYSTPYT | 344 |
| 28 | RASQSISSYLN | 240 | AASSLQS | 294 | QQSYSTPLT | 333 |
| 29 | QASQDISNYLN | 241 | AASTLQS | 299 | QQSYSTPIT | 357 |
| 30 | RASQSVSTYLN | 255 | AASSLQS | 294 | QQSYTIPST | 358 |
| 31 | QASQDIAKYLN | 256 | AASSLQS | 294 | QQSYSAPPT | 359 |
| 32 | QASQGITNYLN | 257 | GASSLQS | 309 | QQSYSTPWT | 360 |
| 33 | RASQSISSYLN | 240 | AASSLQS | 294 | QQSYSTPLT | 333 |
| 34 | QASQDIHNYLN | 251 | AASTLQS | 299 | QQSYTTPLT | 361 |
| 35 | QASQDISNYLN | 241 | SAFSLQS | 310 | QQSYSAPIT | 362 |
| 36 | RASQSISSYLN | 240 | SASNLQS | 311 | QQRSNWPPVT | 363 |
| 37 | QANQDISNFLE | 258 | DASSLES | 312 | QQSYSIPIT | 364 |
| 38 | RASQGISNNLN | 259 | EASTLES | 313 | QQSYSTPLT | 333 |
| 39 | RSSQSLLHSNGYNYLD | 242 | GASTLET | 314 | MQGLQPPGT | 365 |
| 40 | RASQSISRSLV | 260 | AASTLQT | 315 | QQSYNHFRT | 366 |
| 41 | QASQDISNYLN | 241 | DASNLET | 302 | QRSDSTPLT | 367 |
| 42 | QASHDISKSLN | 261 | GASTLQS | 316 | QQLNSYPRT | 368 |
| 43 | RASQDIGAYLA | 262 | AASSLQS | 294 | QQSYSIPYT | 369 |

TABLE 4-continued

| | LCDRS in Kabat Numbering Scheme | | | | | |
|---|---|---|---|---|---|---|
| | L-CDR1 | | L-CDR2 | | L-CDR3 | |
| CD8 Binder | Sequence | SEQ ID NO: | Sequence | SEQ ID NO: | Sequence | SEQ ID NO: |
| 44 | RASQSISSYLA | 263 | AASSLQS | 294 | QQSYSTPYT | 344 |
| 45 | RASQGIRSYLA | 264 | GASNLET | 317 | QQSYSTPYT | 344 |
| 46 | RASQSISSYLN | 240 | AASSLQS | 294 | QQTYSTPYT | 370 |
| 47 | RASQNIGTWLA | 265 | AASTLQS | 299 | QQSYSTPQT | 371 |
| 48 | RASQTISYYLN | 266 | AASTLQS | 299 | QQSYRTPYT | 346 |
| 49 | RSSQSLLHSNGYNYLD | 242 | MGSNRAS | 318 | MQGTHWPT | 372 |
| 50 | RASQNINNYLN | 267 | GASSLQS | 309 | QQTFSLPYT | 373 |
| 51 | RASQTISTYLN | 268 | DASNLET | 302 | QQSYSTPYT | 344 |
| 52 | RASRGIGNDLA | 269 | DASTLET | 319 | QQGYNMPLT | 374 |
| 52 | RASQTIGNYVN | 270 | GASNLHT | 320 | QQTYSAPLT | 375 |
| 54 | RASQFIGSWLA | 271 | AASTLQS | 299 | QQSYSFPWT | 376 |
| 55 | RASQSISSWMA | 272 | DASNLET | 302 | QQTYSTPYI | 377 |
| 56 | RASQGISNNLN | 259 | DASNLET | 302 | QQSYSSPWT | 378 |
| 57 | KSSQSVLYSSNNKNYLA | 273 | WASTRES | 321 | QQYASAPRT | 379 |
| 58 | RASQSISSYLN | 240 | KTSSLES | 322 | QQSFTIPYT | 380 |
| 59 | RVSQGISSYLN | 274 | GASSLQS | 309 | QQSYSTPLT | 333 |
| 60 | RASQSISDWLA | 252 | DASNLET | 302 | QQSYSTPLT | 333 |
| 61 | RASQGISNYLA | 275 | SASNLQS | 311 | QQTYRTPPT | 381 |
| 62 | RASQSIRNYLT | 276 | SASNLQS | 311 | QQSYSTPLT | 333 |
| 63 | RASQNIRLYLN | 277 | AASTLQS | 299 | QQSLTTPFT | 382 |
| 64 | QASQDIRKFLN | 278 | AASSLQS | 294 | QQLNGYPGT | 383 |
| 65 | RASQSISSYLN | 240 | TASNLQS | 323 | QQSYSLPLT | 384 |
| 66 | QASQDISNYLS | 279 | DASNLQS | 324 | QQTYTTPRT | 385 |
| 67 | RASQNVRSWLA | 280 | AASSLQS | 294 | QQSYNTPYT | 386 |
| 68 | RASQGIGNDLG | 281 | AASSLQS | 294 | QQSYAPPPT | 387 |
| 69 | RASQSISNWLA | 282 | GASNLET | 317 | QQSYSTPPT | 342 |
| 70 | RSSQSLLHSNGYNYLD | 242 | LGSNRAS | 295 | MQGLQTPLT | 388 |
| 71 | RASQSISSYLN | 240 | LASSLQS | 325 | QQSDSIPVT | 389 |
| 72 | QASQDISNYLN | 241 | STSSLQS | 326 | QQSYSTPYN | 390 |
| 73 | RASESIGSWLA | 283 | AASSLQS | 294 | QQSYSTPYT | 344 |
| 74 | RASQSISNYLN | 249 | AASSLQR | 327 | QQSYSTPLT | 333 |
| 75 | RASQSVTSNYLA | 284 | GASTRAT | 297 | QHYGSSPA | 391 |
| 76 | RASQSISSYLN | 240 | AASSLQS | 294 | QQSYSTPLT | 333 |
| 77 | RASQGISSYLA | 285 | AASTLQS | 299 | QQSYSTPPT | 342 |
| 78 | RASQDIGNYLN | 286 | AASSLQS | 294 | QQAYTYPYT | 392 |
| 79 | QASQDISNYLN | 241 | GASSLQS | 309 | QQSYTTPNT | 393 |
| 80 | RASQGISNYLA | 275 | AASTLQS | 299 | QQSYSTPYT | 344 |

TABLE 4-continued

| | LCDRS in Kabat Numbering Scheme | | | | | |
|---|---|---|---|---|---|---|
| | L-CDR1 | | L-CDR2 | | L-CDR3 | |
| CD8 Binder | Sequence | SEQ ID NO: | Sequence | SEQ ID NO: | Sequence | SEQ ID NO: |
| 81 | RASQGISNGLS | 287 | DASNLET | 302 | QQSYSTPFT | 394 |
| 82 | RASQNIRNYLN | 288 | GASSLQS | 309 | QQSYSTPLT | 333 |
| 83 | QASLDINNYLN | 289 | KASSLES | 328 | QQSYSMPLT | 395 |
| 84 | QASQDISNYLN | 241 | AASSLQG | 329 | QQSYTTPWT | 396 |
| 85 | QASQDISNYLN | 241 | AASSLQS | 294 | QQSYSSPLT | 397 |
| 86 | QASQDISNYLN | 241 | KASSLES | 328 | QQSYSDPLT | 398 |
| 87 | QASQDISNYLN | 241 | GASTLQS | 316 | QQSYSAPIT | 362 |
| 88 | RASQSISNYLN | 249 | AASNLQS | 330 | QQSYTTPLT | 361 |
| 89 | RASQNIGNYLN | 290 | AASTLQS | 299 | QQSYSTPPWT | 399 |
| 90 | QASQDISNYLN | 241 | AASTLRS | 331 | QQSYQTPLT | 400 |
| 91 | QASQDISNYLN | 241 | AASTLQS | 299 | QQSYTTPPT | 401 |
| 92 | QASQDISNYLN | 241 | AASSLHS | 332 | QQSYSTPQT | 371 |
| 93 | RASQGIRNDLN | 291 | AASNLQS | 330 | QQANSFPIT | 402 |
| 94 | RASQGINTWLA | 292 | AASSLQS | 294 | QQSYSTPYT | 344 |
| 95 | QASQDISNYLN | 241 | AASTLQS | 299 | QQSYTVPPT | 403 |
| 96 | RASQFIGSWLA | 293 | AASTLQS | 299 | QQDDSFPLT | 404 |

In some embodiments, an antibody or antigen binding fragment thereof capable of binding CD8α or CD8β is disclosed, comprising a heavy chain variable region and a light chain variable region, wherein the heavy chain variable region comprises three heavy chain complementarity determining regions (HCDR1, HCDR2, and HCDR3), and the light chain variable region comprises three light chain complementarity determining regions (LCDR1, LCDR2, and LCDR3). In some embodiments, the HCDR1, HCDR2, and HCDR3 comprise amino acid sequences of any one of the SEQ ID NOs recited in Tables 3, 8, and 10, and the LCDR1, LCDR2, and LCDR3 comprise amino acid sequences of any one of the SEQ ID NOs recited in Tables 3, 9, and 11. In some embodiments, the heavy chain variable region (VH) comprises an amino acid sequence of any one of SEQ ID NOs: 405-498 (Table 5) and the light chain variable region (VL) comprises an amino acid sequence of any one of SEQ ID NOs: 499-591 (Table 6).

In another embodiment, the antibody or antigen binding fragment thereof comprises a VH having an amino acid sequence with at least 90%, 95%, 96%, 97%, 98%, 99%, or 100% identity to a sequence selected from SEQ ID NOs: 405-498.

In another embodiment, the antibody or antigen binding fragment thereof comprises a VL having an amino acid sequence with at least 90%, 95%, 96%, 97%, 98%, 99%, or 100% identity to a sequence selected from SEQ ID NOs: 499-591.

In another embodiment, the antibody or antigen binding fragment comprises a VH having an amino acid sequence with at least 90%, 95%, 96%, 97%, 98%, 99%, or 100% identity to a sequence selected from SEQ ID NOs: 405-498 and a VL having an amino acid sequence with at least 90%, 95%, 96%, 97%, 98%, 99%, or 100% identity to a sequence selected from SEQ ID NOs: 499-591.

In another embodiment, the antibody or antigen binding fragment thereof comprises a VH having an amino acid sequence with at least 90%, 95%, 96%, 97%, 98%, 99%, or 100% identity to SEQ ID NO: 1060.

In another embodiment, the antibody or antigen binding fragment thereof comprises the VH of SEQ ID NO: 405 and the VL of SEQ ID NO: 499.

In another embodiment, the antibody or antigen binding fragment thereof comprises the VH of SEQ ID NO: 408 and the VL of SEQ ID NO: 503.

In another embodiment, the antibody or antigen binding fragment thereof comprises the VH of SEQ ID NO: 448 and the VL of SEQ ID NO: 542.

In another embodiment, the antibody or antigen binding fragment thereof comprises the VH of SEQ ID NO: 455 and the VL of SEQ ID NO: 549.

In another embodiment, the antibody or antigen binding fragment thereof comprises the VH of SEQ ID NO: 1060.

In another embodiment, the antibody or antigen binding fragment thereof comprises the HCDR1, HCDR2, HCDR3, LCDR1, LCDR2, and LCDR3 of SEQ ID NOs: 1, 70, 148, 240, 294, and 333, respectively.

In another embodiment, the antibody or antigen binding fragment thereof comprises the HCDR1, HCDR2, HCDR3, LCDR1, LCDR2, and LCDR3 of SEQ ID NOs: 5, 74, 150, 242, 295, and 336, respectively.

In another embodiment, the antibody or antigen binding fragment thereof comprises the HCDR1, HCDR2, HCDR3, LCDR1, LCDR2, and LCDR3 of SEQ ID NOs: 40, 109, 189, 240, 294, and 370, respectively.

In another embodiment, the antibody or antigen binding fragment thereof comprises the HCDR1, HCDR2, HCDR3, LCDR1, LCDR2, and LCDR3 of SEQ ID NOs: 43, 77, 196, 270, 320, and 375, respectively.

In another embodiment, the antibody or antigen binding fragment thereof comprises the HCDR1, HCDR2, and HCDR3 of SEQ ID NOs: 1061, 1062, and 1063, respectively.

In some embodiments, the single domain antibody can be human or humanized. In some embodiments, the single domain antibody or portion thereof is naturally occurring. In some embodiments, the single domain antibody or portion thereof is synthetic.

In some embodiments, the single domain antibodies are antibodies whose complementary determining regions are part of a single domain polypeptide. In some embodiments, the single domain antibody is a heavy chain only antibody variable domain. In some embodiments, the single domain antibody does not include light chains.

In various embodiments, any of the antibodies or antigen binding fragments described herein can comprise a heavy chain constant region and a light chain constant region. The heavy chain constant region may be an IgG, IgM, IgA, IgD, or IgE isotype, or a derivative or fragment thereof that retains at least one effector function of the intact heavy chain. The heavy chain constant region may be a human IgG isotype. The heavy chain constant region may be a human IgG1 or human IgG4 isotypes. The heavy chain constant region may be a human IgG1 isotype. The light chain constant region may be a human kappa light chain or lambda light chain or a derivative or fragment thereof that retains at least one effector function of the intact light chain. The light chain constant region may be a human kappa light chain.

In various embodiments, any of the disclosed antibodies or antigen binding fragments may be a rodent antibody or antigen binding fragment thereof, a chimeric antibody or an antigen binding fragment thereof, a CDR-grafted antibody or an antigen binding fragment thereof, or a humanized antibody or an antigen binding fragment thereof. In another embodiment, any of the disclosed antibodies or antigen binding fragments comprises human or human-derived heavy and light chain variable regions, including human frameworks or human frameworks with one or more back-mutations. In various embodiments, any of the disclosed antibodies or antigen binding fragments may be a Fab, Fab', F(ab')2, Fd, scFv, (scFv) 2, scFv-Fc, VHH, or Fv fragment.

Antibodies whose heavy chain CDR, light chain CDR, VH, or VL amino acid sequences differ insubstantially from those shown in Tables 3-6 are encompassed within the scope of the disclosure. Typically, this involves one or more conservative amino acid substitutions with an amino acid having similar charge, hydrophobic, or stereo chemical characteristics in the antigen-binding site or in the framework without adversely altering the properties of the antibody. Conservative substitutions may also be made to improve antibody properties, for example stability or affinity. 1, 2, 3, 4, 5, 6, 7, 8, 9, 10, 11, 12, 13, 14, or 15 amino acid substitutions can be made to the VH or VL sequence. For example, a "conservative amino acid substitution" may involve a substitution of a native amino acid residue with a nonnative residue such that there is little or no effect on the polarity or charge of the amino acid residue at that position. Desired amino acid substitutions can be determined by those skilled in the art at the time such substitutions are desired. For example, amino acid substitutions can be used to identify important residues of the molecule sequence, or to increase or decrease the affinity of the molecules described herein. The following eight groups contain amino acids that are conservative amino acid substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine(S), Threonine (T); and 8) Cysteine (C), Methionine (M).

In some embodiments, the antibody or antigen binding fragment thereof binds to human CD8α or CD8β. In some embodiments, the antibody or antigen binding fragment thereof binds to a human CD8α homodimer composed of two α chains. In some embodiments, the antibody or antigen binding fragment thereof binds to a human CD8 heterodimer composed of one α chain and one β chain.

In some embodiments, the antibody or antigen binding fragment binding CD8 is a single-chain variable fragment. In embodiments involving a single polypeptide containing both a heavy chain variable region and a light chain variable region, both orientations of these variable regions are contemplated. In some cases, the heavy chain variable region is on the N-terminal side of the light chain variable region, which means the heavy chain variable region is closer to the N-terminus of the polypeptide. In other cases, the light chain variable region is on the N-terminal side of the heavy chain variable region, which means the light chain variable region is closer to the N-terminus of the polypeptide than the heavy chain variable region.

In some embodiments, the scFv binding proteins comprise a linker. In some embodiments, the linker is between the heavy chain variable region (VH) and the light chain variable region (VL) (or vice versa). In some embodiments, the linker comprises the amino acid sequence of GS, GGS, GGGS (SEQ ID NO: 645), GGGGS (SEQ ID NO: 627), GGGGGS (SEQ ID NO: 625), any one of SEQ ID NOs: 645-648, or combinations thereof. Substitutions to introduce new disulfide bonds are also within the scope of the disclosure, e.g., by making substitutions G44C in the VH FR 2 and G100C in the VL FR4.

In some embodiments, the anti-CD8 antibody or antigen binding fragment binds to human CD8 with an affinity constant ($K_D$) of between about 1 nM and about 900 nM. In some embodiments, the $K_D$ to human CD8 is between about 5 nM about 500 nM, about 6 nM to about 10 nM, about 11 nM to about 20 nM, about 25 nM to about 40 nM, about 40 nM to about 60 nM, about 70 nM to about 90 nM, about 100 nM to about 120 nM, about 125 nM to about 140 nM, about 145 nM to about 160 nM, about 170 nM and to about 200 nM, about 210 nM to about 250 nM, about 260 nM to about 300 nM, about 310 nM to about 350 nM, about 360 nM to about 400 nM, about 410 nM to about 450 nM, and about 460 nM to about 500 nM. In some embodiments, the anti-CD8 antibody or antigen binding fragment binds to human CD8 with an affinity constant ($K_D$) of 500 nM, 400 nM, 300 nM, 200 nM, 100 nM, 50 nM, 20 nM, or 10 nM or lower. In some embodiments, the anti-CD8 antibody or antigen binding fragment binds to human CD8 and cynomolgus, M. mulatta (rhesus monkey), or M. nemestrina CD8 with comparable binding affinity ($K_D$).

In some embodiments, the anti-CD8 antibody or antigen binding fragment binds to cynomolgus, M. mulatta (rhesus monkey), or N. nemestrina CD8. In some embodiments, the anti-CD8 antibody or antigen binding binds to mouse, dog, pig, etc., CD8. In some embodiments, the $K_D$ to cynomolgus or M. nemestrina CD8 is between about 5 nM about 500 nM, about 6 nM to about 10 nM, about 11 nM to about 20 nM, about 25 nM to about 40 nM, about 40 nM to about 60 nM, about 70 nM to about 90 nM, about 100 nM to about 120 nM, about 125 nM to about 140 nM, about 145 nM to about 160 nM, about 170 nM and to about 200 nM, about 210 nM to about 250 nM, about 260 nM to about 300 nM, about 310 nM to about 350 nM, about 360 nM to about 400 nM, about 410 nM to about 450 nM, and about 460 nM to about 500 nM. In some embodiments, the anti-CD8 antibody or antigen binding fragment binds to cynomolgus or *M. nemestrina* CD8 with an affinity constant ($K_D$) of 500 nM, 400 nM, 300 nM, 200 nM, 100 nM, 50 nM, 20 nM, or 10 nM or lower.

An antibody or antigen binding fragment thereof that specifically binds CD8α or CD8β refers to an antibody or binding fragment that preferentially binds to CD8α or CD8β, respectively, over other antigen targets. As used herein, the term is interchangeable with an "anti-CD8" antibody or an "antibody that binds CD8." In some embodiments, the antibody or binding fragment capable of binding to CD8α or CD8β can do so with higher affinity for that antigen than others. In some embodiments, the antibody or binding fragment capable of binding CD8α or CD8β can bind to that antigen with a $K_D$ of at least about $10^{-1}$, $10^{-2}$, $10^{-3}$, $10^{-4}$, $10^{-5}$, $10^{-6}$, $10^{-7}$, $10^{-8}$, $10^{-9}$, $10^{-10}$, $10^{-11}$, $10^{-12}$ or greater (or any value in between), e.g., as measured by surface plasmon resonance or other methods known to those skilled in the art.

Another embodiment of the disclosure is an isolated polynucleotide encoding any of the antibody heavy chain variable regions or the antibody light chain variable regions of the disclosure. Certain exemplary polynucleotides are disclosed herein, however, other polynucleotides which, given the degeneracy of the genetic code or codon preferences in a given expression system, encode the antibodies or antigen binding fragments thereof of the disclosure are also within the scope of the disclosure. The polynucleotide sequences encoding a VH or a VL or a fragment thereof of the antibody or antigen binding fragments thereof of the disclosure can be operably linked to one or more regulatory elements, such as a promoter and enhancer, that allow expression of the nucleotide sequence in the intended host cell. The polynucleotide may be a cDNA.

Another embodiment of the disclosure is a vector comprising the polynucleotide of the disclosure. Such vectors may be plasmid vectors, viral vectors, vectors for baculovirus expression, transposon-based vectors, or any other vector suitable for introduction of the polynucleotide of the disclosure into a given organism or genetic background by any means. For example, polynucleotides encoding light and heavy chain variable regions of the antibodies of the disclosure, optionally linked to constant regions, may be inserted into expression vectors. The light and heavy chains can be cloned in the same or different expression vectors. The DNA segments encoding immunoglobulin chains may be operably linked to control sequences in the expression vector(s) that ensure the expression of immunoglobulin polypeptides. Such control sequences include signal sequences, promoters (e.g., naturally associated or heterologous promoters), enhancer elements, and transcription termination sequences, and are chosen to be compatible with the host cell chosen to express the antibody. Once the vector has been incorporated into the appropriate host, the host is maintained under conditions suitable for high level expression of the proteins encoded by the incorporated polynucleotides.

Suitable expression vectors are typically replicable in the host organisms either as episomes or as an integral part of the host chromosomal DNA. Commonly, expression vectors contain selection markers such as ampicillin-resistance, hygromycin-resistance, tetracycline resistance, kanamycin resistance, or neomycin resistance to permit detection of those cells transformed with the desired DNA sequences. Suitable vectors, promoter, and enhancer elements are known in the art; many are commercially available for generating subject recombinant constructs.

Another embodiment of the disclosure is a host cell comprising the vector of the disclosure. The term "host cell" refers to a cell into which a vector has been introduced. It is understood that the term host cell is intended to refer not only to the particular subject cell but to the progeny of such a cell. Because certain modifications may occur in succeeding generations due to either mutation or environmental influences, such progeny may not be identical to the parent cell, but are still included within the scope of the term "host cell" as used herein. Such host cells may be eukaryotic cells, prokaryotic cells, plant cells, or archeal cells. *Escherichia coli*, bacilli, such as *Bacillus subtilis*, and other enterobacteriaceae, such as *Salmonella, Serratia*, and various *Pseudomonas* species are examples of prokaryotic host cells. Other microbes, such as yeast, are also useful for expression. *Saccharomyces* (e.g., *S. cerevisiae*) and *Pichia* are examples of suitable yeast host cells. Exemplary eukaryotic cells may be of mammalian, insect, avian, or other animal origins.

Fusion Proteins Targeting CD8

Also provided herein are fusion proteins targeting CD8 that may be exposed on the surface on a lipid particle or viral vector. In some embodiments, the CD8 binders disclosed herein may be fused to an envelope glycoprotein G, H, and/or an F protein of the Paramyxoviridae family. In some embodiments the fusogen contains a Nipah virus protein F, a measles virus F protein, a tupaia paramyxovirus F protein, a paramyxovirus F protein, a Hendra virus F protein, a Henipavirus F protein, a Morbilivirus F protein, a respirovirus F protein, a Sendai virus F protein, a rubulavirus F protein, or an avulavirus F protein. In some embodiments, the lipid particle contains a henipavirus envelope attachment glycoprotein G (G protein) or a biologically active portion thereof and/or a henipavirus envelope fusion glycoprotein F (F protein) or a biologically active portion thereof.

In particular embodiments, the fusogen is glycoprotein GP64 of baculovirus, or glycoprotein GP64 variant E45K/T259A.

In some embodiments, the fusogen is a hemagglutinin-neuraminidase (HN) and/or fusion (F) protein (F/HN) from a respiratory paramyxovirus. In some embodiments, the respiratory paramyxovirus is a Sendai virus. The HN and F glycoproteins of Sendai viruses function to attach to sialic acids via the HN protein, and to mediate cell fusion for entry into cells via the F protein. In some embodiments, the fusogen is a F and/or HN protein from the murine parainfluenza virus type 1 (See e.g., U.S. Pat. No. 10,704,061).

In some embodiments, the lipid particle (e.g. viral vector) is psedutoptyed with viral glycoproteins as described herein such as a NiV-F and/or NiV-G protein.

In some embodiments, the viral vector further comprises a vector-surface targeting moiety which specifically binds to a target ligand. In some embodiments, the vector-surface targeting moiety is a polypeptide. In some embodiments, a nucleic acid encoding the Paramyxovirus envelope protein (e.g. G protein) is modified with a targeting moiety to specifically bind to a target molecule on a target cells. In some embodiments, the targeting moiety can be any targeting protein, including but not necessarily limited to antibodies and antigen binding fragments thereof.

It has been reported that the henipavirus F proteins from various species exhibit compatibility with G proteins from other species to trigger fusion (Brandel-Tretheway et al. Journal of Virology. 2019. 93 (13): e00577-19). In some aspects of the provided lipid particles (e.g. lentiviral vectors), the F protein is heterologous to the G protein, i.e. the F and G proteins or biologically active portions thereof are from different henipavirus species. For example, in some embodiments the G protein is from Hendra virus and the F protein is a NiV-F as described. In other aspects, the F and/or G protein are chimeric F and/or G protein containing regions of F and/or G proteins from different species of Henipavirus. In some embodiments, replacing a portion of the F protein with amino acids from a heterologous sequence of Henipavirus results in fusion to the G protein with the heteroglous sequence. (Brandel-Tretheway et al. 2019). In some cases, the chimeric F and/or G protein contains an extracellular domain from one henipavirus species and a transmembrane and/or cytoplasmic domain from a different henipavirus species. For example, in some embodiments the F protein contains an extracellular domain of Hendra virus and a transmembrane/cytoplasmic domain of Nipah virus.

In some embodiments, the fusion protein contains a henipavirus envelope attachment glycoprotein G (G protein) or a biologically active portion thereof and a single domain antibody (sdAb) variable domain or a single chain variable fragment (scFv). The sdAb variable domain or scFv can be linked directly or indirectly to the G protein. In particular embodiments, the sdAb variable domain or scFv is linked to the C-terminus (C-terminal amino acid) of the G protein or the biologically active portion thereof. The linkage can be via a peptide linker, such as a flexible peptide linker. Table 7 provides a list of non-limiting examples of G proteins. Exemplary full length fusion protein sequences of the disclosure are disclosed in Table 13.

In some embodiments the G protein is a Henipavirus G protein or a biologically active portion thereof. In some embodiments, the Henipavirus G protein is a Hendra (HeV) virus G protein, a Nipah (NIV) virus G-protein (NIV-G), a Cedar (CedPV) virus G-protein, a Mojiang virus G-protein, a bat Paramyxovirus G-protein, or a biologically active portion thereof. Non-limiting examples of G proteins include those corresponding to SEQ ID NOs: 609, 618, 619, 620, and 621.

In some embodiments, the attachment G proteins are type II transmembrane glycoproteins containing an N-terminal cytoplasmic tail (e.g., corresponding to amino acids 1-49 of SEQ ID NO: 600), a transmembrane domain (e.g., corresponding to amino acids 50-70 of SEQ ID NO: 600), and an extracellular domain containing an extracellular stalk (e.g., corresponding to amino acids 71-187 of SEQ ID NO: 600), and a globular head (corresponding to amino acids 188-602 of SEQ ID NO: 600). In such embodiments, the N-terminal cytoplasmic domain is within the inner lumen of the lipid bilayer and the C-terminal portion is the extracellular domain that is exposed on the outside of the lipid bilayer. Regions of the stalk in the C-terminal region (e.g. corresponding to amino acids 159-167 of NiV-G) have been shown to be involved in interactions with F protein and triggering of F protein fusion (Liu et al. 2015 J of Virology 89:1838). In wild-type G protein, the globular head mediates receptor binding to henipavirus entry receptors eprhin B2 and ephrin B3, but is dispensable for membrane fusion (Brandel-Tretheway et al. Journal of Virology. 2019. 93 (13) e00577-19). In particular embodiments herein, tropism of the G protein is altered by linkage of the G protein or biologically active fragment thereof (e.g. cytoplasmic truncation) to a sdAb variable domain. Binding of the G protein to a binding partner can trigger fusion mediated by a compatible F protein or a biologically active portion thereof. G protein sequences disclosed herein are predominantly disclosed as expressed sequences including an N-terminal methionine required for start of translation. As such N-terminal methionines are commonly cleaved co-or post-translationally, the mature protein sequences for all G protein sequences disclosed herein are also contemplated as lacking the N-terminal methionine.

G glycoproteins are highly conserved among henipavirus species. For example, the G proteins of NiV and HeV viruses share 79% amino acid identity. Studies have shown a high degree of compatibility among G proteins with F proteins of different species as demonstrated by heterotypic fusion activation (Brandel-Tretheway et al. *Journal of* Virology. 2019). As described further below, a targeted lipid particle can contain heterologous G and F proteins from different species.

In some embodiments, the G protein has a sequence set forth in any of SEQ ID NOs: 600, 609, 618, 619, 620, 621, 628, 636, or 638-640, or is a functionally active variant or biologically active portion thereof that has a sequence that is at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% identical to any one of SEQ ID NOs: 600, 609, 618, 619, 620, 621, 628, 636, or 638-640. In particular embodiments, the G protein or functionally active variant or biologically active portion is a protein that retains fusogenic activity in conjunction with a Henipavirus F protein, such as an F protein (e.g. NiV-F or HeV-F). Fusogenic activity includes the activity of the G protein in conjunction with a Henipavirus F protein to promote or facilitate fusion of two membrane lumens, such as the lumen of the targeted lipid particle having embedded in its lipid bilayer a henipavirus F and G protein, and a cytoplasm of a target cell, e.g. a cell that contains a surface receptor or molecule that is recognized or bound by the targeted envelope protein. In some embodiments, the F protein and G protein are from the same Henipavirus species (e.g. NiV-G and NiV-F). In some embodiments, the F protein and G protein are from different Henipavirus species (e.g. NiV-G and HeV-F).

In particular embodiments, the G protein has the sequence of amino acids set forth in SEQ ID NOs: 600, 609, 618, 619, 620, 621, 628, 636, or 638-640, or is a functionally active variant thereof or a biologically active portion thereof that retains fusogenic activity. In some embodiments, the functionally active variant comprises an amino acid sequence having at least at or about 80%, at least at or about 85%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to any one of SEQ ID NOs: 600, 609, 618, 619, 620, 621, 628, 636, or 638-640 and retains fusogenic activity in conjunction with a Henipavirus F protein (e.g., NiV-F or HeV-F). In some embodiments, the biologically active portion has an amino acid sequence having at least at or about 80%, at least at or about 85%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to any one of SEQ ID NOs: 600, 609, 618, 619, 620, 621, 628, 636, or 638-640 and retains fusogenic activity in conjunction with a Henipavirus F protein (e.g., NiV-F or HeV-F).

Reference to retaining fusogenic activity includes activity (in conjunction with a Henipavirus F protein) that is at or about 10% to at or about 150% or more of the level or degree of binding of the corresponding wild-type G protein, such as set forth in any one of SEQ ID NOs: 600, 609, 618, 619, 620, 621, 628, 636, or 638-640, such as at least or at least about 10% of the level or degree of fusogenic activity of the corresponding wild-type G protein, such as at least or at least about 15% of the level or degree of fusogenic activity of the corresponding wild-type G protein, such as at least or at least about 20% of the level or degree of fusogenic activity of the corresponding wild-type G protein, such as at least or at least about 25% of the level or degree of fusogenic activity of the corresponding wild-type G protein, such as at least or at least about 30% of the level or degree of fusogenic activity of the corresponding wild-type G protein, such as at least or at least about 35% of the level or degree of fusogenic activity of the corresponding wild-type G protein, such as at least or at least about 40% of the level or degree of fusogenic activity of the corresponding wild-type G protein, such as at least or at least about 45% of the level or degree of fusogenic activity of the corresponding wild-type G protein, such as at least or at least about 50% of the level or degree of fusogenic activity of the corresponding wild-type G protein, such as at least or at least about 55% of the level or degree of fusogenic activity of the corresponding wild-type G protein, such as at least or at least about 60% of the level or degree of fusogenic activity of the corresponding wild-type G protein, such as at least or at least about 65% of the level or degree of fusogenic activity of the corresponding wild-type G protein, such as at least or at least about 70% of the level or degree of fusogenic activity of the corresponding wild-type G protein, such as at least or at least about 75% of the level or degree of fusogenic activity of the corresponding wild-type G protein, such as at least or at least about 80% of the level or degree of fusogenic activity of the corresponding wild-type G protein, such as at least or at least about 85% of the level or degree of fusogenic activity of the corresponding wild-type G protein, such as at least or at least about 90% of the level or degree of fusogenic activity of the corresponding wild-type G protein, such as at least or at least about 95% of the level or degree of fusogenic activity of the corresponding wild-type G protein, such as at least or at least about 100% of the level or degree of fusogenic activity of the corresponding wild-type G protein, or such as at least or at least about 120% of the level or degree of fusogenic activity of the corresponding wild-type G protein.

In some embodiments, the G protein is a mutant G protein that is a functionally active variant or biologically active portion containing one or more amino acid mutations, such as one or more amino acid insertions, deletions, substitutions, or truncations. In some embodiments, the mutations described herein relate to amino acid insertions, deletions, substitutions, or truncations of amino acids compared to a reference G protein sequence. In some embodiments, the reference G protein sequence is the wild-type sequence of a G protein or a biologically active portion thereof. In some embodiments, the functionally active variant or the biologically active portion thereof is a mutant of a wild-type Hendra (HeV) virus G protein, a wild-type Nipah (NiV) virus G-protein (NIV-G), a wild-type Cedar (CedPV) virus G-protein, a wild-type Mojiang virus G-protein, a wild-type bat Paramyxovirus G-protein, or biologically active portions thereof. In some embodiments, the wild-type G protein has the sequence set forth in any one of SEQ ID NOs: 600, 609, 618, 619, 620, 621, 628, 636, or 638-640.

In some embodiments, the G protein is a mutant G protein that is a biologically active portion that is an N-terminally and/or C-terminally truncated fragment of a wild-type Hendra (HeV) virus G protein, a wild-type Nipah (NiV) virus G-protein (NIV-G), a wild-type Cedar (CedPV) virus G-protein, a wild-type Mojiang virus G-protein, or a wild-type bat Paramyxovirus G-protein. In particular embodiments, the truncation is an N-terminal truncation of all or a portion of the cytoplasmic domain. In some embodiments, the mutant G protein is a biologically active portion that is truncated and lacks up to 49 contiguous amino acid residues at or near the N-terminus of the wild-type G protein, such as a wild-type G protein set forth in any one of SEQ ID NOs: 600, 609, 618, 619, 620, 621, 628, 636, or 638-640. In some embodiments, the mutant G protein is truncated and lacks up to 49 contiguous amino acids, such as up to 49, 48, 47, 46, 45, 44, 43, 42, 41, 40, 30, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2 or 1 contiguous amino acid(s) at the N-terminus of the wild-type G protein.

In some embodiments, the G protein is a wild-type Nipah virus G (NiV-G) protein or a Hendra virus G protein, or is a functionally active variant or biologically active portion thereof. In some embodiments, the G protein is a NiV-G protein that has the sequence set forth in SEQ ID NO:600, SEQ ID NO:618, or SEQ ID NO:628, or is a functional variant or a biologically active portion thereof that has an amino acid sequence having at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:600, SEQ ID NO:618, or SEQ ID NO:628.

In some embodiments, the G protein is a mutant NiV-G protein that is a biologically active portion of a wild-type NiV-G. In some embodiments, the biologically active portion is an N-terminally truncated fragment. In some embodiments, the mutant NiV-G protein is truncated and lacks up to 5 contiguous amino acid residues at or near the N-terminus of the wild-type NiV-G protein (SEQ ID NO:600, SEQ ID NO:618, or SEQ ID NO:628), up to 6 contiguous amino acid residues at or near the N-terminus of the wild-type NiV-G protein (SEQ ID NO:600, SEQ ID NO:618, or SEQ ID NO:628), up to 7 contiguous amino acid residues at or near the N-terminus of the wild-type NiV-G protein (SEQ ID NO: 600, SEQ ID NO: 618, or SEQ ID NO:628), up to 8 contiguous amino acid residues at or near the N-terminus of the wild-type NiV-G protein (SEQ ID NO:600, SEQ ID NO: 618, or SEQ ID NO: 628), up to 9 contiguous amino acid residues at or near the N-terminus of the wild-type NiV-G protein (SEQ ID NO:600, SEQ ID NO:618, or SEQ ID NO: 628), up to 10 contiguous amino acid residues at or near the N-terminus of the wild-type NiV-G protein (SEQ ID NO:600, SEQ ID NO:618, or SEQ ID NO:628), up to 11 contiguous amino acid residues at or near the N-terminus of the wild-type NiV-G protein (SEQ ID NO:600, SEQ ID NO:618, or SEQ ID NO:628), up to 12 contiguous amino acid residues at or near the N-terminus of the wild-type NiV-G protein (SEQ ID NO:600, SEQ ID NO: 618, or SEQ ID NO:628), up to 13 contiguous amino acid residues at or near the N-terminus of the wild-type NiV-G protein (SEQ ID NO:600, SEQ ID NO:618, or SEQ ID NO: 628), up to 14 contiguous amino acid residues at or near the N-terminus of the wild-type NiV-G protein (SEQ ID NO:600, SEQ ID NO:618, or SEQ ID NO:628), up to 15 contiguous amino acid residues at or near the N-terminus of the wild-type NiV-G protein (SEQ ID NO:600, SEQ ID NO:618, or SEQ ID NO:628), up to 16 contiguous amino acid residues at or near the N-terminus of the wild-type NiV-G protein (SEQ ID NO:600, SEQ ID NO: 618, or SEQ ID NO:628), up to 17 contiguous amino acid residues at or near the N-terminus of the wild-type NiV-G protein (SEQ ID NO:600, SEQ ID NO:618, or SEQ ID NO: 628), up to 18 contiguous amino acid residues at or near the N-terminus of the wild-type NiV-G protein (SEQ ID NO:600, SEQ ID NO:618, or SEQ ID NO:628), up to 19 contiguous amino acid residues at or near the N-terminus of the wild-type NiV-G protein (SEQ ID NO:600, SEQ ID NO:618, or SEQ ID NO:628), up to 20 contiguous amino acid residues at or near the N-terminus of the wild-type NiV-G protein (SEQ ID NO:600, SEQ ID NO: 618, or SEQ ID NO:628), up to 21 contiguous amino acid residues at or near the N-terminus of the wild-type NiV-G protein (SEQ ID NO:600, SEQ ID NO:618, or SEQ ID NO: 628), up to 22 contiguous amino acid residues at or near the N-terminus of the wild-type NiV-G protein (SEQ ID NO:600, SEQ ID NO:618, or SEQ ID NO:628), up to 23 contiguous amino acid residues at or near the N-terminus of the wild-type NiV-G protein (SEQ ID NO:600, SEQ ID NO:618, or SEQ ID NO:628), up to 24 contiguous amino acid residues at or near the N-terminus of the wild-type NiV-G protein (SEQ ID NO:600, SEQ ID NO: 618, or SEQ ID NO:628), up to 25 contiguous amino acid residues at or near the N-terminus of the wild-type NiV-G protein (SEQ ID NO:600, SEQ ID NO:618, or SEQ ID NO: 628), up to 26 contiguous amino acid residues at or near the N-terminus of the wild-type NiV-G protein (SEQ ID NO:600, SEQ ID NO:618, or SEQ ID NO:628), up to 27 contiguous amino acid residues at or near the N-terminus of the wild-type NiV-G protein (SEQ ID NO:600, SEQ ID NO:618, or SEQ ID NO:628), up to 28 contiguous amino acid residues at or near the N-terminus of the wild-type NiV-G protein (SEQ ID NO:600, SEQ ID NO: 618, or SEQ ID NO:628), up to 29 contiguous amino acid residues at or near the N-terminus of the wild-type NiV-G protein (SEQ ID NO:600, SEQ ID NO:618, or SEQ ID NO: 628), up to 30 contiguous amino acid residues at or near the N-terminus of the wild-type NiV-G protein (SEQ ID NO:600, SEQ ID NO:618, or SEQ ID NO:628), up to 31 contiguous amino acid residues at or near the N-terminus of the wild-type NiV-G protein (SEQ ID NO:600, SEQ ID NO:618, or SEQ ID NO:628), up to 32 contiguous amino acid residues at or near the N-terminus of the wild-type NiV-G protein (SEQ ID NO:600, SEQ ID NO: 618, or SEQ ID NO:628), up to 33 contiguous amino acid residues at or near the N-terminus of the wild-type NiV-G protein (SEQ ID NO:600, SEQ ID NO:618, or SEQ ID NO: 628), up to 34 contiguous amino acid residues at or near the N-terminus of the wild-type NiV-G protein (SEQ ID NO:600, SEQ ID NO:618, or SEQ ID NO:628), up to 35 contiguous amino acid residues at or near the N-terminus of the wild-type NiV-G protein (SEQ ID NO:600, SEQ ID NO:618, or SEQ ID NO:628), up to 36 contiguous amino acid residues at or near the N-terminus of the wild-type NiV-G protein (SEQ ID NO:600, SEQ ID NO: 618, or SEQ ID NO:628), up to 37 contiguous amino acid residues at or near the N-terminus of the wild-type NiV-G protein (SEQ ID NO:600, SEQ ID NO:618, or SEQ ID NO: 628), up to 38 contiguous amino acid residues at or near the N-terminus of the wild-type NiV-G protein (SEQ ID NO:600, SEQ ID NO:618, or SEQ ID NO:628), up to 39 contiguous amino acid residues at or near the N-terminus of the wild-type NiV-G protein (SEQ ID NO:600, SEQ ID NO:618, or SEQ ID NO:628), up to 40 contiguous amino acid residues at or near the N-terminus of the wild-type NiV-G protein (SEQ ID NO:600, SEQ ID NO: 618, or SEQ ID NO:628), up to 41 contiguous amino acid residues at or near the N-terminus of the wild-type NiV-G protein (SEQ ID NO:600, SEQ ID NO:618, or SEQ ID NO: 628), up to 42 contiguous amino acid residues at or near the N-terminus of the wild-type NiV-G protein (SEQ ID NO:600, SEQ ID NO:618, or SEQ ID NO:628), up to 43 contiguous amino acid residues at or near the N-terminus of the wild-type NiV-G protein (SEQ ID NO:600, SEQ ID NO:618, or SEQ ID NO:628), up to 44 contiguous amino acid residues at or near the N-terminus of the wild-type NiV-G protein (SEQ ID NO:600, SEQ ID NO: 618, or SEQ ID NO: 628), or up to 45 contiguous amino acid residues at or near the N-terminus of the wild-type NiV-G protein (SEQ ID NO:600, SEQ ID NO:618, or SEQ ID NO: 628).

In some embodiments, the NiV-G protein is a biologically active portion that does not contain a cytoplasmic domain. In some embodiments, the NiV-G protein without the cytoplasmic domain is encoded by SEQ ID NO:622.

In some embodiments, the mutant NiV-G protein comprises a sequence set forth in any of SEQ ID NOs: 601-606, 629-634, 612, 622, or 637, or is a functional variant thereof that has an amino acid sequence having at least at or about 80%, at least at or about 81%, at least at or about 82%, at least at or about 83%, at least at or about 84%, at least at or about 85%, at least at or about 86%, or at least at or about 87%, at least at or about 88%, or at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NOs: 601-606, 629-634, 612, 622, or 637.

In some embodiments, the mutant NiV-G protein has a 5 amino acid truncation at or near the N-terminus of the wild-type NiV-G protein (SEQ ID NO:600, SEQ ID NO:618, or SEQ ID NO:628), such as set forth in SEQ ID NO:601 or a functional variant thereof having at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:601, or as set forth in SEQ ID NO:629 or a functional variant thereof having at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:629 or a functional variant thereof having at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO: 629.

In some embodiments, the mutant NiV-G protein has a 10 amino acid truncation at or near the N-terminus of the wild-type NiV-G protein (SEQ ID NO:600, SEQ ID NO:618, or SEQ ID NO:628), such as set forth in SEQ ID NO:602 or a functional variant thereof having at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:602, or such as set forth in SEQ ID NO:630 or a functional variant thereof having at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at or about 96%, at least at or about 97%, at least at or about 98%, or at least at or about 99% sequence identity to SEQ ID NO:630.

In some embodiments, the mutant NiV-G protein has a 15 amino acid truncation at or near the N-terminus of the wild-type NiV-G protein (SEQ ID NO:600, SEQ ID NO:618, or SEQ ID NO:628), such as set forth in SEQ ID NO:603 or a functional variant thereof that has an amino acid sequence having at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:603, or such as set forth in SEQ ID NO: 631 or a functional variant thereof having at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:631.

In some embodiments, the mutant NiV-G protein has a 20 amino acid truncation at or near the N-terminus of the wild-type NiV-G protein (SEQ ID NO:600, SEQ ID NO:618, or SEQ ID NO:628) such as set forth in SEQ ID NO:604, or a functional variant thereof having at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least or about 96%, at least at or about 97%, at least at or about 98%, or at least at or about 99% sequence identity to SEQ ID NO:604, or such as set forth in SEQ ID NO:632 or a functional variant thereof having at least at or about 80%, at least at or about 81%, at least at or about 82%, at least at or about 83%, at least or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:632.

In some embodiments, the mutant NiV-G protein has a 25 amino acid truncation at or near the N-terminus of the wild-type NiV-G protein (SEQ ID NO:600, SEQ ID NO:618, or SEQ ID NO:628), such as set forth in SEQ ID NO:605 or a functional variant thereof having at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least or about 96%, at least at or about 97%, at least at or about 98%, or at least at or about 99% sequence identity to SEQ ID NO:605, or such as set forth in SEQ ID NO:633 or a functional variant thereof having at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:633.

In some embodiments, the mutant NiV-G protein has a 30 amino acid truncation at or near the N-terminus of the wild-type NiV-G protein (SEQ ID NO:600, SEQ ID NO:618, or SEQ ID NO:628), such as set forth in SEQ ID NO:606 or a functional variant thereof having at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:606, or such as set forth in SEQ ID NO:634 or a functional variant thereof having at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:634.

In some embodiments, the mutant NiV-G protein has a 33 amino acid truncation at or near the N-terminus of the wild-type NiV-G protein (SEQ ID NO:600, SEQ ID NO:618, or SEQ ID NO:628) or a functional variant thereof having at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:612, or such as set forth in SEQ ID NO:635 or a functional variant thereof having at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:635.

In some embodiments, the mutant NiV-G protein has a 34 amino acid truncation at or near the N-terminus of the wild-type NiV-G protein (SEQ ID NO:600, SEQ ID NO:618, or SEQ ID NO:628), such as set forth in SEQ ID NO:612 or a functional variant thereof having at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:612, or such as set forth in SEQ ID NO:635 or a functional variant thereof having at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:635.

In a preferred embodiment, the NiV-G protein has a 34 amino acid truncation at or near the N-terminus of the wild-type NiV-G protein (SEQ ID NO: 600, SEQ ID NO: 618, or SEQ ID NO: 628) and one or more amino acid substitutions corresponding to amino acid substitutions selected from E501A, W504A, Q530A, and E533A with reference to the numbering set forth in SEQ ID NO: 618.

In some embodiments, the mutant NiV-G protein lacks the N-terminal cytoplasmic domain of the wild-type NiV-G protein (SEQ ID NO:600, SEQ ID NO:618, or SEQ ID NO: 628), such as set forth in SEQ ID NO: 622 or a functional variant thereof having at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:622.

In some embodiments, the mutant G protein is a mutant HeV-G protein that has the sequence set forth in SEQ ID NO:609 or 636, or is a functional variant or biologically active portion thereof that has an amino acid sequence having at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least or about 96%, at least at or about 97%, at least at or about 98%, or at least at or about 99% sequence identity to SEQ ID NO:609 or 636.

In some embodiments, the G protein is a mutant HeV-G protein that is a biologically active portion of a wild-type HeV-G. In some embodiments, the biologically active portion is an N-terminally truncated fragment. In some embodiments, the mutant HeV-G protein is truncated and lacks up to 5 contiguous amino acid residues at or near the N-terminus of the wild-type HeV-G protein (SEQ ID NO:609 or 636), up to 6 contiguous amino acid residues at or near the N-terminus of the wild-type HeV-G protein (SEQ ID NO: 609 or 636), up to 7 contiguous amino acid residues at or near the N-terminus of the wild-type HeV-G protein (SEQ ID NO:609 or 636), up to 8 contiguous amino acid residues at or near the N-terminus of the wild-type HeV-G protein (SEQ ID NO:609 or 636), up to 9 contiguous amino acid residues at or near the N-terminus of the wild-type HeV-G protein (SEQ ID NO:609 or 636), up to 10 contiguous amino acid residues at or near the N-terminus of the wild-type HeV-G protein (SEQ ID NO:609 or 636), up to 11 contiguous amino acid residues at or near the N-terminus of the wild-type HeV-G protein (SEQ ID NO:609 or 636), up to 12 contiguous amino acid residues at or near the N-terminus of the wild-type HeV-G protein (SEQ ID NO:609 or 636), up to 13 contiguous amino acid residues at or near the N-terminus of the wild-type HeV-G protein (SEQ ID NO: 609 or 636), up to 14 contiguous amino acid residues at or near the N-terminus of the wild-type HeV-G protein (SEQ ID NO:609 or 636), up to 15 contiguous amino acid residues at or near the N-terminus of the wild-type HeV-G protein (SEQ ID NO:609 or 636), up to 16 contiguous amino acid residues at or near the N-terminus of the wild-type HeV-G protein (SEQ ID NO:609 or 636), up to 17 contiguous amino acid residues at or near the N-terminus of the wild-type HeV-G protein (SEQ ID NO:609 or 636), up to 18 contiguous amino acid residues at or near the N-terminus of the wild-type HeV-G protein (SEQ ID NO:609 or 636), up to 19 contiguous amino acid residues at or near the N-terminus of the wild-type HeV-G protein (SEQ ID NO:609 or 636), up to 20 contiguous amino acid residues at or near the N-terminus of the wild-type HeV-G protein (SEQ ID NO: 609 or 636), up to 21 contiguous amino acid residues at or near the N-terminus of the wild-type HeV-G protein (SEQ ID NO:609 or 636), up to 22 contiguous amino acid residues at or near the N-terminus of the wild-type HeV-G protein (SEQ ID NO:609 or 636), up to 23 contiguous amino acid residues at or near the N-terminus of the wild-type HeV-G protein (SEQ ID NO:609 or 636), up to 24 contiguous amino acid residues at or near the N-terminus of the wild-type HeV-G protein (SEQ ID NO:609 or 636), up to 25 contiguous amino acid residues at or near the N-terminus of the wild-type HeV-G protein (SEQ ID NO:609 or 636), up to 26 contiguous amino acid residues at or near the N-terminus of the wild-type HeV-G protein (SEQ ID NO:609 or 636), up to 27 contiguous amino acid residues at or near the N-terminus of the wild-type HeV-G protein (SEQ ID NO: 609 or 636), up to 28 contiguous amino acid residues at or near the N-terminus of the wild-type HeV-G protein (SEQ ID NO:609 or 636), up to 29 contiguous amino acid residues at or near the N-terminus of the wild-type HeV-G protein (SEQ ID NO:609 or 636), up to 30 contiguous amino acid residues at or near the N-terminus of the wild-type HeV-G protein (SEQ ID NO:609 or 636), up to 31 contiguous amino acid residues at or near the N-terminus of the wild-type HeV-G protein (SEQ ID NO:609 or 636), up to 32 contiguous amino acid residues at or near the N-terminus of the wild-type HeV-G protein (SEQ ID NO:609 or 636), up to 33 contiguous amino acid residues at or near the N-terminus of the wild-type HeV-G protein (SEQ ID NO:609 or 636), up to 34 contiguous amino acid residues at or near the N-terminus of the wild-type HeV-G protein (SEQ ID NO: 609 or 636), up to 35 contiguous amino acid residues at or near the N-terminus of the wild-type HeV-G protein (SEQ ID NO:609 or 636), up to 36 contiguous amino acid residues at or near the N-terminus of the wild-type HeV-G protein (SEQ ID NO:609 or 636), up to 37 contiguous amino acid residues at or near the N-terminus of the wild-type HeV-G protein (SEQ ID NO:609 or 636), up to 38 contiguous amino acid residues at or near the N-terminus of the wild-type HeV-G protein (SEQ ID NO:609 or 636), up to 39 contiguous amino acid residues at or near the N-terminus of the wild-type HeV-G protein (SEQ ID NO:609 or 636), up to 40 contiguous amino acid residues at or near the N-terminus of the wild-type HeV-G protein (SEQ ID NO:609 or 636), up to 41 contiguous amino acid residues at or near the N-terminus of the wild-type HeV-G protein (SEQ ID NO: 609 or 636), up to 42 contiguous amino acid residues at or near the N-terminus of the wild-type HeV-G protein (SEQ ID NO:609 or 636), up to 43 contiguous amino acid residues at or near the N-terminus of the wild-type HeV-G protein (SEQ ID NO:609 or 636), up to 44 contiguous amino acid residues at or near the N-terminus of the wild-type HeV-G protein (SEQ ID NO:609 or 636), or up to 45 contiguous amino acid residues at or near the N-terminus of the wild-type HeV-G protein (SEQ ID NO:609 or 636).

In some embodiments, the HeV-G protein is a biologically active portion that does not contain a cytoplasmic domain. In some embodiments, the mutant HeV-G protein lacks the N-terminal cytoplasmic domain of the wild-type HeV-G protein (SEQ ID NO:609 or 636), such as set forth in SEQ ID NO:623 or a functional variant thereof having at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO: 623.

In some embodiments, the G protein or the functionally active variant or biologically active portion thereof binds to Ephrin B2 or Ephrin B3. In some aspects, the G protein has the sequence of amino acids set forth in any one of SEQ ID NO:600, SEQ ID NO: 609, SEQ ID NO: 618, SEQ ID NO: 619, SEQ ID NO:628, SEQ ID NO:620, or SEQ ID NO: 621, or is a functionally active variant thereof or a biologically active portion thereof that is able to bind to Ephrin B2 or Ephrin B3. In some embodiments, the functionally active variant or biologically active portion has an amino acid sequence having at least at or about 80%, at least at or about 85%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO: 600, SEQ ID NO: 609, SEQ ID NO: 618, SEQ ID NO:619, SEQ ID NO:628, SEQ ID NO: 620, or SEQ ID NO: 621, or a functionally active variant or biologically active portion thereof, and retains binding to Ephrin B2 or B3.

Reference to retaining binding to Ephrin B2 or B3 includes binding that is at least or at least about 5% of the level or degree of binding of the corresponding wild-type G protein, such as set forth in SEQ ID NO:600, SEQ ID NO:609, SEQ ID NO:618, SEQ ID NO: 619, SEQ ID NO: 628, SEQ ID NO: 620, or SEQ ID NO:621, or a functionally active variant or biologically active portion thereof, 10% of the level or degree of binding of the corresponding wild-type G protein, such as set forth in SEQ ID NO:600, SEQ ID NO: 609, SEQ ID NO:618, SEQ ID NO:619, SEQ ID NO:628, SEQ ID NO:620, or SEQ ID NO: 621, or a functionally active variant or biologically active portion thereof, 15% of the level or degree of binding of the corresponding wild-type G protein, such as set forth in SEQ ID NO: 600, SEQ ID NO:609, SEQ ID NO:618, SEQ ID NO:619, SEQ ID NO:628, SEQ ID NO:620, or SEQ ID NO:621, or a functionally active variant or biologically active portion thereof, 20% of the level or degree of binding of the corresponding wild-type G protein, such as set forth in SEQ ID NO:600, SEQ ID NO:609, SEQ ID NO:618, SEQ ID NO: 619, SEQ ID NO: 628, SEQ ID NO: 620, or SEQ ID NO: 621, or a functionally active variant or biologically active portion thereof, 25% of the level or degree of binding of the corresponding wild-type G protein, such as set forth in SEQ ID NO:600, SEQ ID NO: 609, SEQ ID NO:618, SEQ ID NO: 619, SEQ ID NO:628, SEQ ID NO:620, or SEQ ID NO: 621, or a functionally active variant or biologically active portion, 30% of the level or degree of binding of the corresponding wild-type G protein, such as set forth in SEQ ID NO: 600, SEQ ID NO: 609, SEQ ID NO: 618, SEQ ID NO:619, SEQ ID NO:628, SEQ ID NO: 620, or SEQ ID NO:621, or a functionally active variant or biologically active portion thereof, 35% of the level or degree of binding of the corresponding wild-type G protein, such as set forth in SEQ ID NO:600, SEQ ID NO:609, SEQ ID NO:618, SEQ ID NO: 619, SEQ ID NO: 628, SEQ ID NO: 620, or SEQ ID NO: 621, or a functionally active variant or biologically active portion thereof, 40% of the level or degree of binding of the corresponding wild-type G protein, such as set forth in SEQ ID NO:600, SEQ ID NO: 609, SEQ ID NO: 618, SEQ ID NO:619, SEQ ID NO:628, SEQ ID NO:620, or SEQ ID NO: 621, or a functionally active variant or biologically active portion thereof, 45% of the level or degree of binding of the corresponding wild-type G protein, such as set forth in SEQ ID NO:600, SEQ ID NO:609, SEQ ID NO:618, SEQ ID NO:619, SEQ ID NO:628, SEQ ID NO:620, or SEQ ID NO:621, or a functionally active variant or biologically active portion thereof, 50% of the level or degree of binding of the corresponding wild-type G protein, such as set forth in SEQ ID NO:600, SEQ ID NO:609, SEQ ID NO:618, SEQ ID NO: 619, SEQ ID NO: 628, SEQ ID NO: 620, or SEQ ID NO: 621, or a functionally active variant or biologically active portion thereof, 55% of the level or degree of binding of the corresponding wild-type G protein, such as set forth in SEQ ID NO:600, SEQ ID NO: 609, SEQ ID NO: 618, SEQ ID NO:619, SEQ ID NO:628, SEQ ID NO:620, or SEQ ID NO: 621, or a functionally active variant or biologically active portion thereof, 60% of the level or degree of binding of the corresponding wild-type G protein, such as set forth in SEQ ID NO:600, SEQ ID NO:609, SEQ ID NO:618, SEQ ID NO:619, SEQ ID NO:628, SEQ ID NO:620, or SEQ ID NO:621, or a functionally active variant or biologically active portion thereof, 65% of the level or degree of binding of the corresponding wild-type G protein, such as set forth in SEQ ID NO:600, SEQ ID NO:609, SEQ ID NO:618, SEQ ID NO: 619, SEQ ID NO: 628, SEQ ID NO: 620, or SEQ ID NO: 621, or a functionally active variant or biologically active portion thereof, 70% of the level or degree of binding of the corresponding wild-type G protein, such as set forth in SEQ ID NO:600, SEQ ID NO: 609, SEQ ID NO: 618, SEQ ID NO: 619, SEQ ID NO:628, SEQ ID NO:620, or SEQ ID NO: 621, or a functionally active variant or bio-logically active portion thereof, such as at least or at least about 75% of the level or degree of binding of the corre-sponding wild-type G protein, such as set forth in SEQ ID NO:600, SEQ ID NO:609, SEQ ID NO:618, SEQ ID NO:619, SEQ ID NO: 628, SEQ ID NO: 620, or SEQ ID NO:621, or a functionally active variant or biologically active portion thereof, such as at least or at least about 80% of the level or degree of binding of the corresponding wild-type G protein, such as set forth in SEQ ID NO: 600, SEQ ID NO:609, SEQ ID NO:618, SEQ ID NO:619, SEQ ID NO: 628, SEQ ID NO: 620, or SEQ ID NO: 621, or a functionally active variant or biologically active portion thereof, such as at least or at least about 85% of the level or degree of binding of the corresponding wild-type G protein, such as set forth in SEQ ID NO: 600, SEQ ID NO: 609, SEQ ID NO: 618, SEQ ID NO:619, SEQ ID NO:628, SEQ ID NO: 620, or SEQ ID NO: 621, or a functionally active variant or biologically active portion thereof, such as at least or at least about 90% of the level or degree of binding of the corresponding wild-type G protein, such as set forth in SEQ ID NO:600, SEQ ID NO: 609, SEQ ID NO: 618, SEQ ID NO: 619, SEQ ID NO:628, SEQ ID NO:620, or SEQ ID NO: 621, or a functionally active variant or biologically active portion thereof, or such as at least or at least about 95% of the level or degree of binding of the corresponding wild-type protein, such as set forth in SEQ ID NO:600, SEQ ID NO:609, SEQ ID NO: 618, SEQ ID NO: 619, SEQ ID NO: 628, SEQ ID NO:620, or SEQ ID NO:621, or a functionally active variant or biologically active portion thereof. In some embodiments, the G protein is NiV-G or a functionally active variant or biologically active portion thereof and binds to Ephrin B2 or Ephrin B3.

In some aspects, the NiV-G has the sequence of amino acids set forth in SEQ ID NO: 600, SEQ ID NO: 618, or SEQ ID NO: 628, or is a functionally active variant thereof or a biologically active portion thereof that is able to bind to Ephrin B2 or Ephrin B3. In some embodiments, the func-tionally active variant or biologically active portion has an amino acid sequence having at least at or about 80%, at least at or about 85%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:600, SEQ ID NO:618, or SEQ ID NO:628 and retains binding to Eprhin B2 or B3. Exemplary biologically active portions include N-terminally truncated variants lacking all or a portion of the cytoplasmic domain, e.g. 1 or more, such as 1 to 49 contiguous N-terminal amino acid residues, e.g. set forth in any one of SEQ ID NOS: 601-606, 622, and 629-634.

Reference to retaining binding to Ephrin B2 or B3 includes binding that is at least or at least about 5% of the level or degree of binding of the corresponding wild-type NiV-G, such as set forth in SEQ ID NO:600, SEQ ID NO:618, or SEQ ID NO:628, 10% of the level or degree of binding of the corresponding wild-type NiV-G, such as set forth in SEQ ID NO:600, SEQ ID NO:618, or SEQ ID NO:628, 15% of the level or degree of binding of the corresponding wild-type NiV-G, such as set forth in SEQ ID NO:600, SEQ ID NO: 618, or SEQ ID NO: 628, 20% of the level or degree of binding of the corresponding wild-type NiV-G, such as set forth in SEQ ID NO:600, SEQ ID NO:618, or SEQ ID NO:6284, 25% of the level or degree of binding of the corresponding wild-type NiV-G, such as set forth in SEQ ID NO:600, SEQ ID NO:618, or SEQ ID NO:628, 30% of the level or degree of binding of the corresponding wild-type NiV-G, such as set forth in S SEQ ID NO:600, SEQ ID NO:618, or SEQ ID NO:628, 35% of the level or degree of binding of the corresponding wild-type NiV-G, such as set forth in SEQ ID NO:600, SEQ ID NO: 618, or SEQ ID NO: 628, 40% of the level or degree of binding of the corresponding wild-type NiV-G, such as set forth in SEQ ID NO:600, SEQ ID NO:618, or SEQ ID NO:628, 45% of the level or degree of binding of the corresponding wild-type NiV-G, such as set forth in SEQ ID NO:600, SEQ ID NO:618, or SEQ ID NO:628, 50% of the level or degree of binding of the corresponding wild-type NiV-G, such as set forth in SEQ ID NO:600, SEQ ID NO:618, or SEQ ID NO:628, 55% of the level or degree of binding of the corresponding wild-type NiV-G, such as set forth in SEQ ID NO:600, SEQ ID NO: 618, or SEQ ID NO: 628, 60% of the level or degree of binding of the corre-sponding wild-type NiV-G, such as set forth in SEQ ID NO:600, SEQ ID NO:618, or SEQ ID NO:628, 65% of the level or degree of binding of the corresponding wild-type NiV-G, such as set forth in SEQ ID NO:600, SEQ ID NO:618, or SEQ ID NO:628, 70% of the level or degree of binding of the corresponding wild-type NiV-G, such as set forth in SEQ ID NO:600, SEQ ID NO:618, or SEQ ID NO:628, such as at least or at least about 75% of the level or degree of binding of the corresponding wild-type NiV-G, such as set forth in SEQ ID NO:600, SEQ ID NO:618, or SEQ ID NO:628, such as at least or at least about 80% of the level or degree of binding of the corresponding wild-type NIV-G, such as set forth in SEQ ID NO:600, SEQ ID NO:618, or SEQ ID NO:628, such as at least or at least about 85% of the level or degree of binding of the corresponding wild-type NiV-G, such as set forth in SEQ ID NO:600, SEQ ID NO:618, or SEQ ID NO:628, such as at least or at least about 90% of the level or degree of binding of the corre-sponding wild-type NiV-G, such as set forth in SEQ ID NO:600, SEQ ID NO:618, or SEQ ID NO:628, or such as at least or at least about 95% of the level or degree of binding of the corresponding wild-type NiV-G, such as set forth in SEQ ID NO:600, SEQ ID NO: 618, or SEQ ID NO:628.

In some embodiments, the G protein is HeV-G or a functionally active variant or biologically active portion thereof and binds to Ephrin B2 or Ephrin B3. In some aspects, the HeV-G has the sequence of amino acids set forth in SEQ ID NO:609 or 636, or is a functionally active variant thereof or a biologically active portion thereof that is able to bind to Ephrin B2 or Ephrin B3. In some embodiments, the functionally active variant or biologically active portion has an amino acid sequence having at least at or about 80%, at least at or about 85%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:609 or 636 and retains binding to Eprhin B2 or B3. Exemplary biologically active portions include N-terminally truncated variants lacking all or a portion of the cytoplasmic domain, e.g. 1 or more, such as 1 to 49 contiguous N-terminal amino acid residues, e.g. set forth in any one of SEQ ID NO:623.

Reference to retaining binding to Ephrin B2 or B3 includes binding that is at least or at least about 5% of the level or degree of binding of the corresponding wild-type HeV-G, such as set forth in SEQ ID NO:609 or 636, 10% of the level or degree of binding of the corresponding wild-type HeV-G, such as set forth in SEQ ID NO:609 or 636, 15% of the level or degree of binding of the corresponding wild-type HeV-G, such as set forth in SEQ ID NO:609 or 636, 20% of the level or degree of binding of the corresponding wild-type HeV-G, such as set forth in SEQ ID NO:609 or 636, 25% of the level or degree of binding of the corresponding wild-type HeV-G, such as set forth in SEQ ID NO:609 or 636, 30% of the level or degree of binding of the corresponding wild-type HeV-G, such as set forth in SEQ ID NO:609 or 636, 35% of the level or degree of binding of the corresponding wild-type HeV-G, such as set forth in SEQ ID NO:609 or 636, 40% of the level or degree of binding of the corresponding wild-type HeV-G, such as set forth in SEQ ID NO:609 or 636, 45% of the level or degree of binding of the corresponding wild-type HeV-G, such as set forth in SEQ ID NO:609 or 636, 50% of the level or degree of binding of the corresponding wild-type HeV-G, such as set forth in SEQ ID NO:609 or 636, 55% of the level or degree of binding of the corresponding wild-type HeV-G, such as set forth in SEQ ID NO:609 or 636, 60% of the level or degree of binding of the corresponding wild-type HeV-G, such as set forth in SEQ ID NO:609 or 636, 65% of the level or degree of binding of the corresponding wild-type HeV-G, such as set forth in SEQ ID NO:609 or 636, 70% of the level or degree of binding of the corresponding wild-type HeV-G, such as set forth in SEQ ID NO:609 or 636, such as at least or at least about 75% of the level or degree of binding of the corresponding wild-type HeV-G, such as set forth in SEQ ID NO:609 or 636, such as at least or at least about 80% of the level or degree of binding of the corresponding wild-type NIV-G, such as set forth in SEQ ID NO: 609 or 636, such as at least or at least about 85% of the level or degree of binding of the corresponding wild-type HeV-G, such as set forth in SEQ ID NO:609 or 636, such as at least or at least about 90% of the level or degree of binding of the corresponding wild-type HeV-G, such as set forth in SEQ ID NO:609 or 636, or such as at least or at least about 95% of the level or degree of binding of the corresponding wild-type HeV-G, such as set forth in SEQ ID NO:609 or 636.

In some embodiments, the G protein or the biologically thereof is a mutant G protein that exhibits reduced binding for the native binding partner of a wild-type G protein. In some embodiments, the mutant G protein or the biologically active portion thereof is a mutant of wild-type Niv-G and exhibits reduced binding to one or both of the native binding partners Ephrin B2 or Ephrin B3. In some embodiments, the mutant G-protein or the biologically active portion, such as a mutant NiV-G protein, exhibits reduced binding to the native binding partner. In some embodiments, the reduced binding to Ephrin B2 or Ephrin B3 is reduced by greater than at or about 5%, at or about 10%, at or about 15%, at or about 20%, at or about 25%, at or about 30%, at or about 40%, at or about 50%, at or about 60%, at or about 70%, at or about 80%, at or about 90%, or at or about 100%.

In some embodiments, the mutations described herein can improve transduction efficiency. In some embodiments, the mutations described herein allow for specific targeting of other desired cell types that are not Ephrin B2 or Ephrin B3. In some embodiments, the mutations described herein result in at least the partial inability to bind at least one natural receptor, such as to reduce the binding to at least one of Ephrin B2 or Ephrin B3. In some embodiments, the mutations described herein interfere with natural receptor recognition.

In some embodiments, the mutant NiV-G protein or the biologically active portion thereof is truncated and lacks up to 5 contiguous amino acid residues at or near the N-terminus of the wild-type NiV-G protein (SEQ ID NO:618), 6 contiguous amino acid residues at or near the N-terminus of the wild-type NiV-G protein (SEQ ID NO:618), 7 contiguous amino acid residues at or near the N-terminus of the wild-type NiV-G protein (SEQ ID NO: 618), 8 contiguous amino acid residues at or near the N-terminus of the wild-type NiV-G protein (SEQ ID NO:618), 9 contiguous amino acid residues at or near the N-terminus of the wild-type NiV-G protein (SEQ ID NO:618), 10 contiguous amino acid residues at or near the N-terminus of the wild-type NiV-G protein (SEQ ID NO:618), 11 contiguous amino acid residues at or near the N-terminus of the wild-type NiV-G protein (SEQ ID NO:618), 12 contiguous amino acid residues at or near the N-terminus of the wild-type NiV-G protein (SEQ ID NO:618), 13 contiguous amino acid residues at or near the N-terminus of the wild-type NiV-G protein (SEQ ID NO:618), 14 contiguous amino acid residues at or near the N-terminus of the wild-type NiV-G protein (SEQ ID NO:618), 15 contiguous amino acid residues at or near the N-terminus of the wild-type NiV-G protein (SEQ ID NO:618), 16 contiguous amino acid residues at or near the N-terminus of the wild-type NiV-G protein (SEQ ID NO:618), 17 contiguous amino acid residues at or near the N-terminus of the wild-type NiV-G protein (SEQ ID NO:618), 18 contiguous amino acid residues at or near the N-terminus of the wild-type NiV-G protein (SEQ ID NO: 618), 19 contiguous amino acid residues at or near the N-terminus of the wild-type NiV-G protein (SEQ ID NO:618), 20 contiguous amino acid residues at or near the N-terminus of the wild-type NiV-G protein (SEQ ID NO:618), 21 contiguous amino acid residues at or near the N-terminus of the wild-type NiV-G protein (SEQ ID NO:618), 22 contiguous amino acid residues at or near the N-terminus of the wild-type NiV-G protein (SEQ ID NO:618), 23 contiguous amino acid residues at or near the N-terminus of the wild-type NiV-G protein (SEQ ID NO:618), 24 contiguous amino acid residues at or near the N-terminus of the wild-type NiV-G protein (SEQ ID NO:618), 25 contiguous amino acid residues at or near the N-terminus of the wild-type NiV-G protein (SEQ ID NO:618), 26 contiguous amino acid residues at or near the N-terminus of the wild-type NiV-G protein (SEQ ID NO:618), 27 contiguous amino acid residues at or near the N-terminus of the wild-type NiV-G protein (SEQ ID NO:618), 28 contiguous amino acid residues at or near the N-terminus of the wild-type NiV-G protein (SEQ ID NO:618), 29 contiguous amino acid residues at or near the N-terminus of the wild-type NiV-G protein (SEQ ID NO: 618), 30 contiguous amino acid residues at or near the N-terminus of the wild-type NiV-G protein (SEQ ID NO:618), 31 contiguous amino acid residues at or near the N-terminus of the wild-type NiV-G protein (SEQ ID NO:618), 32 contiguous amino acid residues at or near the N-terminus of the wild-type NiV-G protein (SEQ ID NO:618), 33 contiguous amino acid residues at or near the N-terminus of the wild-type NiV-G protein (SEQ ID NO:618), 34 contiguous amino acid residues at or near the N-terminus of the wild-type NiV-G protein (SEQ ID NO:618), 35 contiguous amino acid residues at or near the N-terminus of the wild-type NiV-G protein (SEQ ID NO:618), 36 contiguous amino acid residues at or near the N-terminus of the wild-type NiV-G protein (SEQ ID NO:618), 37 contiguous amino acid residues at or near the N-terminus of the wild-type NiV-G protein (SEQ ID NO:618), 38 contiguous amino acid residues at or near the N-terminus of the wild-type NiV-G protein (SEQ ID NO:618), 39 contiguous amino acid residues at or near the N-terminus of the wild-type NiV-G protein (SEQ ID NO:618), or 40 contiguous amino acid residues at or near the N-terminus of the wild-type NiV-G protein (SEQ ID NO:618).

In some embodiments, the G protein contains one or more amino acid substitutions in a residue that is involved in the interaction with one or both of Ephrin B2 and Ephrin B3. In some embodiments, the amino acid substitutions correspond to mutations E501A, W504A, Q530A, and E533A with reference to numbering set forth in SEQ ID NO:618.

In some embodiments, the G protein is a mutant G protein containing one or more amino acid substitutions selected from the group consisting of E501A, W504A, Q530A, and E533A with reference to numbering set forth in SEQ ID NO:618. In some embodiments, the G protein is a mutant G protein that contains one or more amino acid substitutions selected from the group consisting of E501A, W504A, Q530A, and E533A with reference to SEQ ID NO:618 or a biologically active portion thereof containing an N-terminal truncation. In some embodiments, the G protein is a mutant G protein that contains one or more amino acid substitutions selected from the group consisting of E501A, W504A, Q530A, and E533A in combination with any one of the N-terminal truncations disclosed above with reference to SEQ ID NO:618 or a biologically active portion thereof. In some embodiments, any of the mutant G proteins described above contains one, two, three, or all four amino acid selected from the group consisting of E501A, W504A, Q530A, and E533A with reference to numbering set forth in SEQ ID NO: 618, in all pairwise and triple combinations thereof.

In some embodiments, the mutant NiV-G protein has the amino acid sequence set forth in SEQ ID NO: 607 or 635 or an amino acid sequence having at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO: 607 or 635. In particular embodiments, the G protein has the sequence of amino acids set forth in SEQ ID NO: 607 or 635.

In some embodiments, the targeted envelope protein contains a G protein or a functionally active variant or biologically active portion thereof and an sdAb variable domain, in which the targeted envelope protein exhibits increased binding for another molecule that is different from the native binding partner of a wild-type G protein. In some embodiments, the other molecule can be a protein expressed on the surface of desired target cell. In some embodiments, the increased binding to the other molecule is increased by greater than at or about 25%, at or about 30%, at or about 40%, at or about 50%, at or about 60%, at or about 70%, at or about 80%, at or about 90%, or at or about 100%. In particular embodiments, the binding confers re-targeted binding compared to the binding of a wild-type G protein in which a new or different binding activity is conferred.

In some embodiments, the C-terminus of the single domain antibody is attached to the C-terminus of the G protein or biologically active portion thereof. In some embodiments, the N-terminus of the single domain antibody is exposed on the exterior surface of the lipid bilayer. In some embodiments, the N-terminus of the single domain antibody binds to a cell surface molecule of a target cell. In some embodiments, the single domain antibody specifically binds to a cell surface molecule present on a target cell. In some embodiments, the cell surface molecule is a protein, glycan, lipid, or low molecular weight molecule.

In some embodiments, the cell surface molecule of a target cell is an antigen or portion thereof. In some embodiments, the single domain antibody or portion thereof is an antibody having a single monomeric domain antigen binding/recognition domain that is able to bind selectively to a specific antigen. In some embodiments, the single domain antibody binds an antigen present on a target cell.

Exemplary cells include immune effector cells, peripheral blood mononuclear cells (PBMC) such as lymphocytes (T cells, B cells, natural killer cells) and monocytes, granulocytes (neutrophils, basophils, eosinophils), macrophages, dendritic cells, cytotoxic T lymphocytes, polymorphonuclear cells (also known as PMN, PML, or PMNL), stem cells, embryonic stem cells, neural stem cells, mesenchymal stem cells (MSCs), hematopoietic stem cells (HSCs), human myogenic stem cells, muscle-derived stem cells (MuStem), embryonic stem cells (ES or ESCs), limbal epithelial stem cells, cardio-myogenic stem cells, cardiomyocytes, progenitor cells, allogenic cells, resident cardiac cells, induced pluripotent stem cells (iPS), adipose-derived or phenotypic modified stem or progenitor cells, CD133+ cells, aldehyde dehydrogenase-positive cells (ALDH+), umbilical cord blood (UCB) cells, peripheral blood stem cells (PBSCs), neurons, neural progenitor cells, pancreatic beta cells, glial cells, or hepatocytes.

In some embodiments, the target cell is a cell of a target tissue. The target tissue can include liver, lungs, heart, spleen, pancreas, gastrointestinal tract, kidney, testes, ovaries, brain, reproductive organs, central nervous system, peripheral nervous system, skeletal muscle, endothelium, inner ear, or eye.

In some embodiments, the target cell is a muscle cell (e.g., skeletal muscle cell), kidney cell, liver cell (e.g. hepatocyte), or a cadiac cell (e.g. cardiomyocyte). In some embodiments, the target cell is a cardiac cell, e.g., a cardiomyocyte (e.g., a quiescent cardiomyocyte), a hepatoblast (e.g., a bile duct hepatoblast), an epithelial cell, a T cell (e.g. a naive T cell), a macrophage (e.g., a tumor infiltrating macrophage), or a fibroblast (e.g., a cardiac fibroblast).

In some embodiments, the target cell is a tumor-infiltrating lymphocyte, a T cell, a neoplastic or tumor cell, a virus-infected cell, a stem cell, a central nervous system (CNS) cell, a hematopoeietic stem cell (HSC), a liver cell or a fully differentiated cell. In some embodiments, the target cell is a CD3+ T cell, a CD4+ Tcell, a CD8+ T cell, a hepatocyte, a haematepoietic stem cell, a CD34+ haematepoietic stem cell, a CD105+ haematepoietic stem cell, a CD117+ haematopoietic stem cell, a CD105+ endothelial cell, a B cell, a CD20+B cell, a CD19+B cell, a cancer cell, a CD133+ cancer cell, an EpCAM+ cancer cell, a CD19+ cancer cell, a Her2/Neu+ cancer cell, a GluA2+ neuron, a GluA4+ neuron, a NKG2D+ natural killer cell, a SLC1A3+ astrocyte, a SLC7A10+ adipocyte, or a CD30+ lung epithelial cell.

In some embodiments, the target cell is an antigen presenting cell, an MHC class II+ cell, a professional antigen presenting cell, an atypical antigen presenting cell, a macrophage, a dendritic cell, a myeloid dendritic cell, a plasmacyteoid dendritic cell, a CD11c+ cell, a CD11b+ cell, a splenocyte, a B cell, a hepatocyte, a endothelial cell, or a non-cancerous cell. In some embodiments, the cell surface molecule is any one of CD8.

In some embodiments, the G protein or functionally active variant or biologically active portion thereof is linked directly to the sdAb variable domain (e.g., a VHH) or scFv. In some embodiments, the targeted envelope protein is a fusion protein that has the following structure: (N'-single domain antibody-C')-(C'-G protein-N'). In some embodiments, the targeted envelope protein is a fusion protein that has the following structure: (N'-scFv-C')-(C'-G protein-N').

In some embodiments, the G protein or functionally active variant or biologically active portion thereof is linked indirectly via a linker to the the sdAb variable domain or scFv. In some embodiments, the linker is a peptide linker. In some embodiments, the linker is a chemical linker.

In some embodiments, the linker is a peptide linker and the targeted envelope protein is a fusion protein containing the G protein or functionally active variant or biologically active portion thereof linked via a peptide linker to the sdAb variable domain or svFv. In some embodiments, the targeted envelope protein is a fusion protein that has the following structure: (N'-single domain antibody-C')-Linker-(C'-G protein-N'). In some embodiments, the targeted envelope protein is a fusion protein that has the following structure: (N'-scFv-C')-Linker-(C'-G protein-N'). In some embodiments, the peptide linker is up to 65 amino acids in length. In some embodiments, the peptide linker comprises from or from about 2 to 65 amino acids, 2 to 60 amino acids, 2 to 56 amino acids, 2 to 52 amino acids, 2 to 48 amino acids, 2 to 44 amino acids, 2 to 40 amino acids, 2 to 36 amino acids, 2 to 32 amino acids, 2 to 28 amino acids, 2 to 24 amino acids, 2 to 20 amino acids, 2 to 18 amino acids, 2 to 14 amino acids, 2 to 12 amino acids, 2 to 10 amino acids, 2 to 8 amino acids, 2 to 6 amino acids, 6 to 65 amino acids, 6 to 60 amino acids, 6 to 56 amino acids, 6 to 52 amino acids, 6 to 48 amino acids, 6 to 44 amino acids, 6 to 40 amino acids, 6 to 36 amino acids, 6 to 32 amino acids, 6 to 28 amino acids, 6 to 24 amino acids, 6 to 20 amino acids, 6 to 18 amino acids, 6 to 14 amino acids, 6 to 12 amino acids, 6 to 10 amino acids, 6 to 8 amino acids, 8 to 65 amino acids, 8 to 60 amino acids, 8 to 56 amino acids, 8 to 52 amino acids, 8 to 48 amino acids, 8 to 44 amino acids, 8 to 40 amino acids, 8 to 36 amino acids, 8 to 32 amino acids, 8 to 28 amino acids, 8 to 24 amino acids, 8 to 20 amino acids, 8 to 18 amino acids, 8 to 14 amino acids, 8 to 12 amino acids, 8 to 10 amino acids, 10 to 65 amino acids, 10 to 60 amino acids, 10 to 56 amino acids, 10 to 52 amino acids, 10 to 48 amino acids, 10 to 44 amino acids, 10 to 40 amino acids, 10 to 36 amino acids, 10 to 32 amino acids, 10 to 28 amino acids, 10 to 24 amino acids, 10 to 20 amino acids, 10 to 18 amino acids, 10 to 14 amino acids, 10 to 12 amino acids, 12 to 65 amino acids, 12 to 60 amino acids, 12 to 56 amino acids, 12 to 52 amino acids, 12 to 48 amino acids, 12 to 44 amino acids, 12 to 40 amino acids, 12 to 36 amino acids, 12 to 32 amino acids, 12 to 28 amino acids, 12 to 24 amino acids, 12 to 20 amino acids, 12 to 18 amino acids, 12 to 14 amino acids, 14 to 65 amino acids, 14 to 60 amino acids, 14 to 56 amino acids, 14 to 52 amino acids, 14 to 48 amino acids, 14 to 44 amino acids, 14 to 40 amino acids, 14 to 36 amino acids, 14 to 32 amino acids, 14 to 28 amino acids, 14 to 24 amino acids, 14 to 20 amino acids, 14 to 18 amino acids, 18 to 65 amino acids, 18 to 60 amino acids, 18 to 56 amino acids, 18 to 52 amino acids, 18 to 48 amino acids, 18 to 44 amino acids, 18 to 40 amino acids, 18 to 36 amino acids, 18 to 32 amino acids, 18 to 28 amino acids, 18 to 24 amino acids, 18 to 20 amino acids, 20 to 65 amino acids, 20 to 60 amino acids, 20 to 56 amino acids, 20 to 52 amino acids, 20 to 48 amino acids, 20 to 44 amino acids, 20 to 40 amino acids, 20 to 36 amino acids, 20 to 32 amino acids, 20 to 28 amino acids, 20 to 26 amino acids, 20 to 24 amino acids, 24 to 65 amino acids, 24 to 60 amino acids, 24 to 56 amino acids, 24 to 52 amino acids, 24 to 48 amino acids, 24 to 44 amino acids, 24 to 40 amino acids, 24 to 36 amino acids, 24 to 32 amino acids, 24 to 30 amino acids, 24 to 28 amino acids, 28 to 65 amino acids, 28 to 60 amino acids, 28 to 56 amino acids, 28 to 52 amino acids, 28 to 48 amino acids, 28 to 44 amino acids, 28 to 40 amino acids, 28 to 36 amino acids, 28 to 34 amino acids, 28 to 32 amino acids, 32 to 65 amino acids, 32 to 60 amino acids, 32 to 56 amino acids, 32 to 52 amino acids, 32 to 48 amino acids, 32 to 44 amino acids, 32 to 40 amino acids, 32 to 38 amino acids, 32 to 36 amino acids, 36 to 65 amino acids, 36 to 60 amino acids, 36 to 56 amino acids, 36 to 52 amino acids, 36 to 48 amino acids, 36 to 44 amino acids, 36 to 40 amino acids, 40 to 65 amino acids, 40 to 60 amino acids, 40 to 56 amino acids, 40 to 52 amino acids, 40 to 48 amino acids, 40 to 44 amino acids, 44 to 65 amino acids, 44 to 60 amino acids, 44 to 56 amino acids, 44 to 52 amino acids, 44 to 48 amino acids, 48 to 65 amino acids, 48 to 60 amino acids, 48 to 56 amino acids, 48 to 52 amino acids, 50 to 65 amino acids, 50 to 60 amino acids, 50 to 56 amino acids, 50 to 52 amino acids, 54 to 65 amino acids, 54 to 60 amino acids, 54 to 56 amino acids, 58 to 65 amino acids, 58 to 60 amino acids, or 60 to 65 amino acids. In some embodiments, the peptide linker is a polypeptide that is 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65 amino acids in length.

In particular embodiments, the linker is a flexible peptide linker. In some such embodiments, the linker is 1-20 amino acids, such as 1-20 amino acids predominantly composed of glycine. In some embodiments, the linker is 1-20 amino acids, such as 1-20 amino acids predominantly composed of glycine and serine. In some embodiments, the linker is a flexible peptide linker containing amino acids Glycine and Serine, referred to as GS-linkers. In some embodiments, the peptide linker includes the sequences GS, GGS, GGGGS (SEQ ID NO:627), GGGGGS (SEQ ID NO:625) or combinations thereof. In some embodiments, the polypeptide linker has the sequence (GGS) n, wherein n is 1 to 10. In some embodiments, the polypeptide linker has the sequence (GGGGS) n, (SEQ ID NO: 626) wherein n is 1 to 10. In some embodiments, the polypeptide linker has the sequence (GGGGGS) n (SEQ ID NO:27), wherein n is 1 to 6.

Also provided herein are polynucleotides comprising a nucleic acid sequence encoding a targeted envelope protein. In some embodiments, the polynucleotides comprise a nucleic acid sequence encoding a G protein or biologically active portion thereof. In some embodiments, the polynucleotides further comprise a nucleic acid sequence encoding a single domain antibody (sdAb) variable domain or scFv or biologically active portion thereof. The polynucleotides may include a sequence of nucleotides encoding any of the targeted envelope proteins described above. The polynucleotide can be a synthetic nucleic acid. Also provided are expression vectors containing any of the provided polynucleotides.

In some of any embodiments, expression of natural or synthetic nucleic acids is typically achieved by operably linking a nucleic acid encoding the gene of interest to a promoter and incorporating the construct into an expression vector. In some embodiments, vectors can be suitable for replication and integration in eukaryotes. In some embodiments, cloning vectors contain transcription and translation terminators, initiation sequences, and promoters useful for expression of the desired nucleic acid sequence. In some of any embodiments, a plasmid comprises a promoter suitable for expression in a cell.

In some embodiments, the polynucleotides contain at least one promoter that is operatively linked to control expression of the targeted envelope protein containing the G protein and the single domain antibody (sdAb) variable domain or scFv. For expression of the targeted envelope protein, at least one module in each promoter functions to position the start site for RNA synthesis. The best-known example of this is the TATA box, but in some promoters lacking a TATA box, such as the promoter for the mammalian terminal deoxynucleotidyl transferase gene and the promoter for the SV40 genes, a discrete element overlying the start site itself helps to fix the place of initiation.

In some embodiments, additional promoter elements, e.g., enhancers, regulate the frequency of transcriptional initiation. In some embodiments, additional promoter elements are located in the region 30-110 bp upstream of the start site, although a number of promoters have been shown to contain functional elements downstream of the start site as well. In some embodiments, spacing between promoter elements frequently is flexible, so that promoter function is preserved when elements are inverted or moved relative to one another. In some embodiments, such as with the thymidine kinase (tk) promoter, the spacing between promoter elements can be increased to 50 bp apart before activity begins to decline. In some embodiments, depending on the promoter, individual elements can function either cooperatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR, in connection with the compositions disclosed herein.

In some embodiments, a suitable promoter is the immediate early cytomegalovirus (CMV) promoter sequence. In some embodiments, the promoter sequence is a strong constitutive promoter sequence capable of driving high levels of expression of any polynucleotide sequence operatively linked thereto. In some embodiments, a suitable promoter is Elongation Growth Factor-Ia (EF-I a). In some embodiments, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter.

In some embodiments, the promoter is an inducible promoter. In some embodiments, the inducible promoter provides a molecular switch capable of turning on expression of the polynucleotide sequence to which it is operatively linked when such expression is desired, or turning off the expression when expression is not desired. In some embodiments, inducible promoters comprise a metallothionine promoter, a glucocorticoid promoter, a progesterone promoter, and a tetracycline promoter.

In some embodiments, exogenously controlled inducible promoters can be used to regulate expression of the G protein and single domain antibody (sdAb) variable domain or scFv. For example, radiation-inducible promoters, heat-inducible promoters, and/or drug-inducible promoters can be used to selectively drive transgene expression in, for example, targeted regions. In such embodiments, the location, duration, and level of transgene expression can be regulated by the administration of the exogenous source of induction.

In some embodiments, expression of the targeted envelope protein containing a G protein and single domain antibody (sdAb) variable domain or scFv is regulated using a drug-inducible promoter. For example, in some cases, the promoter, enhancer, or transactivator comprises a Lac operator sequence, a tetracycline operator sequence, a galactose operator sequence, a doxycycline operator sequence, a rapamycin operator sequence, a tamoxifen operator sequence, or a hormone-responsive operator sequence, or an analog thereof. In some instances, the inducible promoter comprises a tetracycline response element (TRE). In some embodiments, the inducible promoter comprises an estrogen response element (ERE), which can activate gene expression in the presence of tamoxifen. In some instances, a drug-inducible element, such as a TRE, can be combined with a selected promoter to enhance transcription in the presence of drug, such as doxycycline. In some embodiments, the drug-inducible promoter is a small molecule-inducible promoter.

Any of the provided polynucleotides can be modified to remove CpG motifs and/or to optimize codons for translation in a particular species, such as human, canine, feline, equine, ovine, bovine, etc. species. In some embodiments, the polynucleotides are optimized for human codon usage (i.e., human codon-optimized). In some embodiments, the polynucleotides are modified to remove CpG motifs. In other embodiments, the provided polynucleotides are modified to remove CpG motifs and are codon-optimized, such as human codon-optimized. Methods of codon optimization and CpG motif detection and modification are well-known. Typically, polynucleotide optimization enhances transgene expression, increases transgene stability and preserves the amino acid sequence of the encoded polypeptide.

In order to assess the expression of the targeted envelope protein, the expression vector to be introduced into a cell can also contain either a selectable marker gene or a reporter gene or both to facilitate identification and selection of expressing particles, e.g. viral particles. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000, FEBS Lett. 479:79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of the desired polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Lipid Particles Targeting CD8

Also provided herein are targeted lipid particles (e.g. targeting CD8), such as targeted viral vectors, that comprise a henipavirus F protein molecule or biologically active portion thereof, and a fusion protein comprising (i) a henipavirus envelope attachment glycoprotein G (G protein) or a biologically active portion thereof, and (ii) a single domain antibody (sdAb) variable domain or scFv, wherein the single domain antibody variable domain or scFv is attached to the C-terminus of the G protein or the biologically active portion, wherein each is exposed on the outer surface of the targeted viral vector. In particular embodiments, the provided targeted lipid particles exhibit fusogenic activity, which is mediated by the targeted envelope protein that facilitates binding to a target cell and contains the G protein or biologically active portion thereof, and the F protein or biologically active portion thereof that is involved in facilitating the merger or fusion of the two lumens of the lipid particle and the target cell membranes. Table 7 provides non-limiting examples of G and F proteins for use in the targeted lipid particles of the disclosure.

In some embodiments, the targeted lipid particle provided herein (e.g. targeted lentiviral vector) has increased or greater expression of the targeted envelope protein compared to a reference lipid particle (e.g. reference lentiviral vector) that incorporates a similar envelope protein but that is fused to an alternative targeting moiety other than a sdAb variable domain, such as a single chain variable fragment (scFv). In some embodiments, the targeted viral vectors are produced by pseudotyping of viral vectors (e.g lentiviral particles) following co-transfection of the packaging cells with the transfer, envelope, and gag-pol plasmids.

In some embodiments, the expression is increased by at or greater than 5%, 10%, 20%, 30%, 40%, 50%, 60%, 70%, 80%, 90%, 100%, 125%, 150%, 200%, 300%, 400%, 500% or more, compared to a reference lipid particle (e.g. reference lentiviral vector), e.g. a reference lipid particle containing a similar envelope protein but that is fused to an scFv. In some examples, the expression is increased by at or greater than 1.5-fold, 2-fold, 3-fold, 4-fold, 5-fold, 6-fold, 7-fold, 8-fold, 9-fold, 10-fold, 15-fold, 20-fold, 30-fold or more, compared to a reference lipid particle (e.g. reference lentiviral vector), e.g. a reference lipid particle containing a similar envelope protein but that is fused to an scFv. In some embodiments, expression can be assayed in vitro using flow cytometry, e.g. FACs. In some embodiments, expression can be depicted as the number or density of targeted envelope protein on the surface of a targeted viral vector (e.g. targeted lentiviral vector). In some embodiments, expression can be depicted as the mean fluorescent intensity (MFI) of surface expression of the targeted envelope protein on the surface of a targeted viral vector (e.g. targeted lentiviral vector). In some embodiments, expression can be depicted as the percent of lipid particle (e.g. lentiviral vectors) in a population that are surface positive for the targeted envelope protein.

In some embodiments, in a population of targeted lipid particles (e.g. targeted lentiviral vectors) greater than at or about 50% of the lipid particles are surface positive for the targeted envelope protein. For example, in a population of provided targeted viral vectors (e.g. targeted lentiviral vectors) greater than at or about 55%, greater than at or about 60%, greater than at or about 65%, greater than at or about 70%, or greater than at or about 75% of the viral vectors in the population are surface positive for the targeted envelope protein.

In some embodiments, titer of the targeted lipid particles following introduction into target cells, such as by transduction (e.g. transduced cells), is increased compared to titer into the same target cells of reference lipid particles (e.g. reference lentiviral vector) that incorporate a similar envelope protein but fused to an alternative targeting moiety other than a sdAb variable domain, such as a single chain variable fragment (scFv). Typically, the alternative targeting moiety recognizes or binds the same target molecule as the sdAb variable domain of the targeted envelope protein of the targeted lipid particles. In some embodiments, the titer is increased by at or greater than 5%, 10%, 20%, 30%, 40%, 50%, 60%, 70%, 80%, 90%, 100%, 125%, 150%, 200%, 300%, 400%, 500% or more, compared to titer of a reference lipid particle (e.g. reference lentiviral vector), e.g. a reference lipid particle containing a similar envelope protein but that is fused to an scFv. In some examples, the titer is increased by at or greater than 1.5-fold, 2-fold, 3-fold, 4-fold, 5-fold, 6-fold, 7-fold, 8-fold, 9-fold, 10-fold, 15-fold, 20-fold, 30-fold or more, compared to the titer of a reference lipid particle (e.g. reference lentiviral vector), e.g. a reference viral vector containing a similar envelope protein but that is fused to an scFv. In some embodiments, the titer of the targeted viral vectors in target cells (e.g. transduced cells) is greater than at or about $1 \times 10^6$ transduction units (TU)/mL. For example, the titer of the targeted viral vectors in target cells (e.g. transduced cells) is greater than at or about $2 \times 10^6$ TU/mL, greater than at or about $3 \times 10^6$ TU/mL, greater than at or about $4 \times 10^6$ TU/mL, greater than at or about $5\times10^6$ TU/mL, greater than at or about $6\times10^6$ TU/mL, greater than at or about $7\times10^6$ TU/mL, greater than at or about $8\times10^6$ TU/mL, greater than at or about $9\times10^6$ TU/mL, or greater than at or about $1\times10^7$ TU/mL.

A. F Proteins

In some embodiments, the targeted lipid particle comprises one or more fusogens, e.g. henipavirus F proteins. In some embodiments, the targeted lipid particle contains an exogenous or overexpressed fusogen. In some embodiments, the fusogen is disposed in the lipid bilayer. In some embodiments, the fusogen facilitates the fusion of the targeted particle's lipid bilayer to a membrane. In some embodiments, the membrane is a plasma cell membrane.

In some embodiments, fusogens comprise protein based, lipid based, and chemical based fusogens. In some embodiments, the targeted lipid particle comprises a first fusogen comprising a protein fusogen and a second fusogen comprising a lipid fusogen or chemical fusogen. In some embodiments, the fusogen binds a fusogen binding partner on a target cell surface.

In some embodiments, the fusogen comprises a protein with a hydrophobic fusion peptide domain. In some embodiments, the fusogen comprises a henipavirus F protein molecule or biologically active portion thereof. In some embodiments, the Henipavirus F protein is a Hendra (Hev) virus F protein, a Nipah (NiV) virus F-protein, a Cedar (CedPV) virus F protein, a Mojiang virus F protein, a bat Paramyxovirus F protein, or a biologically active portion thereof.

In some embodiments, the N-terminal hydrophobic fusion peptide domain of the F protein molecule or biologically active portion thereof is exposed on the outside of a lipid bilayer.

F proteins of henipaviruses are encoded as $F_0$ precursors containing a signal peptide (e.g. corresponding to amino acid residues 1-26 of SEQ ID NO: 592). Following cleavage of the signal peptide, the mature $F_0$ (e.g. SEQ ID NO: 593) is transported to the cell surface, then endocytosed and cleaved by cathepsin L (e.g. between amino acids 109-110 of SEQ ID NO: 592) into the mature fusogenic subunits F1 (e.g. corresponding to amino acids 110-546 of SEQ ID NO:592; set forth in SEQ ID NO:595) and F2 (e.g. corresponding to amino acid residues 27-109 of SEQ ID NO:1; set forth in SEQ ID NO:594). The F1 and F2 subunits are associated by a disulfide bond and recycled back to the cell surface. The F1 subunit contains the fusion peptide domain located at the N terminus of the F1 subunit (e.g., corresponding to amino acids 110-129 of SEQ ID NO:592) where it is able to insert into a cell membrane to drive fusion. In some cases, fusion activity is blocked by association of the F protein with G protein, until G engages with a target molecule resulting in its disassociation from F and exposure of the fusion peptide to mediate membrane fusion.

Among different henipavirus species, the sequence and activity of the F protein is highly conserved. For examples, the F protein of NiV and HeV viruses share 89% amino acid sequence identity. Further, in some cases, the henipavirus F proteins exhibit compatibility with G proteins from other species to trigger fusion (Brandel-Tretheway et al. Journal of Virology. 2019. 93 (13): e00577-19). In some aspects of the provided targeted lipid particle, the F protein is heterologous to the G protein, i.e., the F and G protein or biologically active portions thereof are from different henipavirus species. For example, the F protein is from Hendra virus and the G protein is from Nipah virus. In other aspects, the F protein can be a chimeric F protein containing regions of F proteins from different species of Henipavirus. In some embodiments, switching a region of amino acid residues of the F protein from one species of Henipavirus to another can result in fusion to the G protein of the species comprising the amino acid insertion. (Brandel-Tretheway et al. 2019). In some cases, the chimeric F protein contains an extracellular domain from one henipavirus species and a transmembrane and/or cytoplasmic domain from a different henipavirus species. For example, the F protein may contain an extracellular domain of Hendra virus and a transmembrane/cytoplasmic domain of Nipah virus. F protein sequences disclosed herein are predominantly disclosed as expressed sequences including an N-terminal signal sequence. Such N-terminal signal sequences are commonly cleaved co-or post-translationally, thus the mature protein sequences for all F protein sequences disclosed herein are also contemplated as lacking the N-terminal signal sequence.

In some embodiments, the F protein is encoded by a nucleotide sequence that encodes the sequence set forth by any one of SEQ ID NOs: 592, 593, 608, 614-616, or 641-644, or is a functionally active variant or a biologically active portion thereof that has a sequence that is at least at or about 80%, at least at or about 85%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% identical to any one of SEQ ID NOS: 592, 593, 608, 614-616, or 641-644. In particular embodiments, the F protein or the functionally active variant or biologically active portion thereof retains fusogenic activity in conjunction with a Henipavirus G protein, such as a G protein set forth herein. Fusogenic activity includes the activity of the F protein in conjunction with a Henipavirus G protein to promote or facilitate fusion of two membrane lumens, such as the lumen of the targeted lipid particle having embedded in its lipid bilayer a henipavirus F and G protein, and a cytoplasm of a target cell, e.g., a cell that contains a surface receptor or molecule that is recognized or bound by the targeted envelope protein. In some embodiments, the F protein and G protein are from the same Henipavirus species (e.g. NiV-G and NiV-F). In some embodiments, the F protein and G protein are from different Henipavirus species (e.g., NiV-G and HeV-F). In particular embodiments, the F protein of the functionally active variant or biologically active portion retains the cleavage site cleaved by cathepsin L (e.g., corresponding to the cleavage site between amino acids 109-110 of SEQ ID NO:592).

In particular embodiments, the F protein has the sequence of amino acids set forth in SEQ ID NO:592, SEQ ID NO:593, SEQ ID NO:608, SEQ ID NO:614, SEQ ID NO:615, SEQ ID NO:616, SEQ ID NO:641, SEQ ID NO:642, SEQ ID NO:643, or SEQ ID NO:644 or is a functionally active variant thereof or a biologically active portion thereof that retains fusogenic activity. In some embodiments, the functionally active variant comprises an amino acid sequence having at least at or about 80%, at least at or about 85%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:592, SEQ ID NO:593, SEQ ID NO:608, SEQ ID NO: 614, SEQ ID NO: 615, SEQ ID NO:616, SEQ ID NO:641, SEQ ID NO:642, SEQ ID NO: 643, or SEQ ID NO: 644 and retains fusogenic activity in conjunction with a Henipavirus G protein (e.g., NiV-G or HeV-G). In some embodiments, the biologically active portion has an amino acid sequence having at least at or about 80%, at least at or about 85%, at least at or about 90%, at least at or about 91%, at least at or about 92%, at least at or about 93%, at least at or about 94%, at least at or about 95%, at or about 96%, at least at or about 97%, at least at or about 98%, or at least at or about 99% sequence identity to SEQ ID NO:592, SEQ ID NO:593, SEQ ID NO:608, SEQ ID NO: 614, SEQ ID NO: 615, SEQ ID NO: 616, SEQ ID NO:641, SEQ ID NO:642, SEQ ID NO: 643, or SEQ ID NO: 644 and retains fusogenic activity in conjunction with a Henipavirus G protein (e.g., NiV-G or HeV-G).

Reference to retaining fusogenic activity includes activity (in conjunction with a Henipavirus G protein) that is at or about 10% to at or about 150% or more of the level or degree of binding of the corresponding wild-type F protein, such as set forth in SEQ ID NO: 592, SEQ ID NO:593, SEQ ID NO:608, SEQ ID NO:614, SEQ ID NO:615, SEQ ID NO: 616, SEQ ID NO: 641, SEQ ID NO: 642, SEQ ID NO: 643, or SEQ ID NO:644, such as at least or at least about 10% of the level or degree of fusogenic activity of the corresponding wild-type F protein, such as at least or at least about 15% of the level or degree of fusogenic activity of the corresponding wild-type F protein, such as at least or at least about 20% of the level or degree of fusogenic activity of the corresponding wild-type F protein, such as at least or at least about 25% of the level or degree of fusogenic activity of the corresponding wild-type F protein, such as at least or at least about 30% of the level or degree of fusogenic activity of the corresponding wild-type F protein, such as at least or at least about 35% of the level or degree of fusogenic activity of the corresponding wild-type F protein, such as at least or at least about 40% of the level or degree of fusogenic activity of the corresponding wild-type F protein, such as at least or at least about 45% of the level or degree of fusogenic activity of the corresponding wild-type F protein, such as at least or at least about 50% of the level or degree of fusogenic activity of the corresponding wild-type F protein, such as at least or at least about 55% of the level or degree of fusogenic activity of the corresponding wild-type f protein, such as at least or at least about 60% of the level or degree of fusogenic activity of the corresponding wild-type F protein, such as at least or at least about 65% of the level or degree of fusogenic activity of the corresponding wild-type F protein, such as at least or at least about 70% of the level or degree of fusogenic activity of the corresponding wild-type F protein, such as at least or at least about 75% of the level or degree of fusogenic activity of the corresponding wild-type F protein, such as at least or at least about 80% of the level or degree of fusogenic activity of the corresponding wild-type F protein, such as at least or at least about 85% of the level or degree of fusogenic activity of the corresponding wild-type F protein, such as at least or at least about 90% of the level or degree of fusogenic activity of the corresponding wild-type F protein, such as at least or at least about 95% of the level or degree of fusogenic activity of the corresponding wild-type F protein, such as at least or at least about 100% of the level or degree of fusogenic activity of the corresponding wild-type F protein, or such as at least or at least about 120% of the level or degree of fusogenic activity of the corresponding wild-type F protein.

In some embodiments, the F protein is a mutant F protein that is a functionally active fragment or a biologically active portion containing one or more amino acid mutations, such as one or more amino acid insertions, deletions, substitutions, or truncations. In some embodiments, the mutations described herein relate to amino acid insertions, deletions, substitutions, or truncations of amino acids compared to a reference F protein sequence. In some embodiments, the reference F protein sequence is the wild-type sequence of an F protein or a biologically active portion thereof. In some embodiments, the mutant F protein or the biologically active portion thereof is a mutant of a wild-type Hendra (Hev) virus F protein, a Nipah (NiV) virus F-protein, a Cedar (CedPV) virus F protein, a Mojiang virus F protein, or a bat Paramyxovirus F protein. In some embodiments, the wild-type F protein is encoded by a sequence of nucleotides that encodes any one of SEQ ID NO: 592, 593, 608, 614-616, or 641-644.

In some embodiments, the mutant F protein is a biologically active portion of a wild-type F protein that is an N-terminally and/or C-terminally truncated fragment. In some embodiments, the mutant F protein or the biologically active portion of a wild-type F protein thereof comprises one or more amino acid substitutions. In some embodiments, the mutations described herein can improve transduction efficiency. In some embodiments, the mutations described herein can increase fusogenic capacity. Exemplary mutations include any as described, see e.g. Khetawat and Broder 2010 Virology Journal 7:312; Witting et al. 2013 Gene Therapy 20:997-1005; published international; patent application No. WO/2013/148327.

In some embodiments, the mutant F protein is a biologically active portion that is truncated and lacks up to 20 contiguous amino acid residues at or near the C-terminus of the wild-type F protein, such as a wild-type F protein encoded by a sequence of nucleotides encoding the F protein set forth in any one of SEQ ID NOS: 592, 593, 608, or 614-616. In some embodiments, the mutant F protein is truncated and lacks up to 19 contiguous amino acids, such as up to 18, 17, 16, 15, 14, 13, 12, 11, 10, 9, 8, 7, 6, 5, 4, 3, 2, or 1 contiguous amino acid(s) at the C-terminus of the wild-type F protein.

In some embodiments, the F protein or the functionally active variant or biologically active portion thereof comprises an F1 subunit or a fusogenic portion thereof. In some embodiments, the F1 subunit is a proteolytically cleaved portion of the F0 precursor. In some embodiments, the F0 precursor is inactive. In some embodiments, the cleavage of the F0 precursor forms a disulfide-linked F1+F2 heterodimer. In some embodiments, the cleavage exposes the fusion peptide and produces a mature F protein. In some embodiments, the cleavage occurs at or around a single basic residue. In some embodiments, the cleavage occurs at Arginine 109 of NiV-F protein. In some embodiments, cleavage occurs at Lysine 109 of the Hendra virus F protein.

In some embodiments, the F protein is a wild-type Nipah virus F (NIV-F) protein or is a functionally active variant or biologically active porteion thereof. In some embodiments, the $F_0$ precursor is encoded by a sequence of nucleotides encoding the sequence set forth in SEQ ID NO:592. The encoding nucleic acid can encode a signal peptide sequence that has the sequence MVVILDKRCY CNLLILILMI SECSVG (SEQ ID NO: 624) or another signal peptide sequence. In some embodiments, the F protein has the sequence set forth in SEQ ID NO:593. In some examples, the F protein is cleaved into an F1 subunit comprising the sequence set forth in SEQ ID NO:595 and an F2 subunit comprising the sequence set forth in SEQ ID NO:594.

In some embodiments, the F protein is a NiV-F protein that is encoded by a sequence of nucleotides encoding the sequence set forth in SEQ ID NO:592, or is a functionally active variant or biologically active portion thereof that has an amino acid sequence having at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:592. In some embodiments, the NiV-F-protein has the sequence of set forth in SEQ ID NO:593, or is a functionally active variant or a biologically active portion thereof that has an amino acid sequence having at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:593. In particular embodiments, the F protein or the functionally active variant or biologically active portion thereof retains the cleavage site cleaved by cathepsin L (e.g., corresponding to the cleavage site between amino acids 109-110 of SEQ ID NO:592).

In some embodiments, the F protein or the functionally active variant or the biologically active portion thereof includes an F1 subunit that has the sequence set forth in SEQ ID NO: 595, or an amino acid sequence having, at least at or about 80%, at least at or about 81%, at least at or about 82%, at least at or about 83%, at least at or about 84%, at least at or about 85%, at least at or about 86%, at least at or about 87%, at least at or about 88%, at least at or about 89% at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:595.

In some embodiments, the F protein or the functionally active variant or biologically active portion thereof includes an F2 subunit that has the sequence set forth in SEQ ID NO: 594, or an amino acid sequence having, at least at or about 80%, at least at or about 81%, at least at or about 82%, at least at or about 83%, at least at or about 84%, at least at or about 85%, at least at or about 86%, at least at or about 87%, at least at or about 88%, at least at or about 89% at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:594.

In some embodiments, the F protein is a mutant NiV-F protein that is a biologically active portion thereof that is truncated and lacks up to 20 contiguous amino acid residues at or near the C-terminus of the wild-type NiV-F protein (e.g., set forth SEQ ID NO: 593). In some embodiments, the mutant NiV-F protein comprises an amino acid sequence set forth in SEQ ID NO:596. In some embodiments, the mutant NiV-F protein has a sequence that has at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:596. In some embodiments, the mutant F protein contains an F1 protein that has the sequence set forth in SEQ ID NO:597. In some embodiments, the mutant F protein has a sequence that has at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO: 597.

In some embodiments, the F protein is a mutant NiV-F protein that is a biologically active portion thereof that comprises a 20 amino acid truncation at or near the C-terminus of the wild-type NiV-F protein (SEQ ID NO:593); and a point mutation on an N-linked glycosylation site. In some embodiments, the mutant NiV-F protein comprises an amino acid sequence set forth in SEQ ID NO:598. In some embodiments, the mutant NiV-F protein has a sequence that has at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:598.

In some embodiments, the F protein is a mutant NiV-F protein that is a biologically active portion thereof that comprises a 22 amino acid truncation at or near the C-terminus of the wild-type NiV-F protein (SEQ ID NO:593). In some embodiments, the NiV-F protein comprises an amino acid sequence set forth in SEQ ID NO:599. In some embodiments, the NiV-F protein has a sequence with at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:599. In some embodiments, the NiV-F protein comprises an amino acid sequence set forth in SEQ ID NO:1092. In some embodiments, the NiV-F protein has a sequence with at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO: 1092. In some embodiments, the NiV-F protein comprises an amino acid sequence set forth in SEQ ID NO:1093. In some embodiments, the NiV-F protein has a sequence with at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO: 1093. In particular embodiments, the variant F protein is a mutant Niv-F protein that has the sequence of amino acids set forth in SEQ ID NO:613. In some embodiments, the NiV-F protein has a sequence with at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% sequence identity to SEQ ID NO:613.

B. Lipid Bilayer

In some embodiments, the targeted lipid particle includes a naturally derived bilayer of amphipathic lipids that encloses a lumen or cavity. In some embodiments, the targeted lipid particle comprises a lipid bilayer as the outermost surface. In some embodiments, the lipid bilayer encloses a lumen. In some embodiments, the lumen is aqueous. In some embodiments, the lumen is in contact with the hydrophilic head groups on the interior of the lipid bilayer. In some embodiments, the lumen is a cytosol. In some embodiments, the cytosol contains cellular components present in a source cell. In some embodiments, the cytosol does not contain cellular components present in a source cell. In some embodiments, the lumen is a cavity. In some embodiments, the cavity contains an aqueous environment. In some embodiments, the cavity does not contain an aqueous environment.

In some aspects, the lipid bilayer is derived from a source cell during a process to produce a lipid-containing particle. In some embodiments, the lipid bilayer includes membrane components of the cell from which the lipid bilayer is produced, e.g., phospholipids, membrane proteins, etc. In some embodiments, the lipid bilayer includes a cytosol that includes components found in the cell from which the lipid bilayer is produced, e.g., solutes, proteins, nucleic acids, etc., but not all of the components of a cell, e.g., it lacks a nucleus. In some embodiments, the lipid bilayer is considered to be exosome-like. The lipid particle may vary in size, and in some instances have a diameter ranging from 30 and 300 nm, such as from 30 and 150 nm, and including from 40 to 100 nm.

In some embodiments, the lipid bilayer is a viral envelope. In some embodiments, the viral envelope is obtained from a source cell. In some embodiments, the viral envelope is obtained by the viral capsid from the source cell plasma membrane. In some embodiments, the lipid bilayer is obtained from a membrane other than the plasma membrane of a host cell. In some embodiments, the viral envelope lipid bilayer is embedded with viral proteins, including viral glycoproteins.

In other aspects, the lipid bilayer includes synthetic lipid complex. In some embodiments, the synthetic lipid complex is a liposome. In some embodiments, the lipid particle is a vesicular structure characterized by a phospholipid bilayer membrane and an inner aqueous medium. In some embodiments, the lipid bilayer has multiple lipid layers separated by aqueous medium. In some embodiments, the lipid bilayer forms spontaneously when phospholipids are suspended in an excess of aqueous solution. In some examples, the lipid components undergo self-rearrangement before the formation of closed structures and entrap water and dissolved solutes between the lipid bilayers.

In some embodiments, a targeted envelope protein and fusogen, such as any described above including any that are exogenous or overexpressed relative to the source cell, is disposed in the lipid bilayer.

In some embodiments, the targeted lipid particle comprises several different types of lipids. In some embodiments, the lipids are amphipathic lipids. In some embodiments, the amphipathic lipids are phospholipids. In some embodiments, the phospholipids comprise phosphatidylcholine, phosphatidylethanolamine, phosphatidylinositol, and phosphatidylserine. In some embodiments, the lipids comprise phospholipids such as phosphocholines and phosphoinositols. In some embodiments, the lipids comprise DMPC, DOPC, and DSPC.

In some embodiments, the bilayer may be comprised of one or more lipids of the same or different type. In some embodiments, the source cell comprises a cell selected from CHO cells, BHK cells, MDCK cells, C3H 10T1/2 cells, FLY cells, Psi-2 cells, BOSC 23 cells, PA317 cells, WEHI cells, COS cells, BSC 1 cells, BSC 40 cells, BMT 10 cells, VERO cells, W138 cells, MRC5 cells, A549 cells, HT1080 cells, 293 cells, 293T cells, B-50 cells, 3T3 cells, NIH3T3 cells, HepG2 cells, Saos-2 cells, Huh7 cells, Hela cells, W163 cells, 211 cells, and 211A cells.

C. Exogenous Agent

In some embodiments, the targeted lipid particle further comprises an agent that is exogenous relative to the source cell (also referred to herein as a "cargo" or "payload"). In some embodiments, the exogenous agent is a small molecule, a protein, or a nucleic acid (e.g., a DNA, a chromosome (e.g. a human artificial chromosome), an RNA, e.g., an mRNA or miRNA). In some embodiments, the exoneous agent or cargo encodes a cytosolic protein. In some embodiments the exogenous agent or cargo comprises or encodes a membrane protein. In some embodiments, the exogenous agent or cargo comprises a therapeutic agent. In some embodiments, the therapeutic agent is chosen from one or more of a protein, e.g., an enzyme, a transmembrane protein, a receptor, an antibody; a nucleic acid, e.g., DNA, a chromosome (e.g. a human artificial chromosome), RNA, mRNA, siRNA, miRNA; or a small molecule.

In some embodiments, the exogenous agent is present in at least, or no more than, 10, 20, 50, 100, 200, 500, 1,000, 2,000, 5,000, 10,000, 20,000, 50,000, 100,000, 200,000, 500,000, 1,000,000, 5,000,000, 10,000,000, 50,000,000, 100,000,000, 500,000,000, or 1,000,000,000 copies. In some embodiments, the targeted lipid particle has an altered, e.g., increased or decreased level of one or more endogenous molecules, e.g., protein or nucleic acid (e.g., in some embodiments, endogenous relative to the source cell, and in some embodiments, endogenous relative to the target cell), e.g., due to treatment of the source cell, e.g., mammalian source cell with a siRNA or gene editing enzyme. In some embodiments, the endogenous molecule is present in at least, or no more than, 10, 20, 50, 100, 200, 500, 1,000, 2,000, 5,000, 10,000, 20,000, 50,000, 100,000, 200,000, 500,000, 1,000,000, 5,000,000, 10,000,000, 50,000,000, 100,000,000, 500,000,000, or 1,000,000,000 copies. In some embodiments, the endogenous molecule (e.g., an RNA or protein) is present at a concentration of at least 1, 2, 3, 4, 5, 10, 20, 50, 100, 500, $10^3$, $5.0\times10^3$, $10^4$, $5.0\times10^4$, $10^5$, $5.0\times10^5$, $10^6$, $5.0\times10^6$, $1.0\times10^7$, $5.0\times10^7$, or $1.0\times10^8$, greater than its concentration in the source cell. In some embodiments, the endogenous molecule (e.g., an RNA or protein) is present at a concentration of at least 1, 2, 3, 4, 5, 10, 20, 50, 100, 500, $10^3$, $5.0\times10^3$, $10^4$, $5.0\times10^4$, $10^5$, $5.0\times10^5$, $10^6$, $5.0\times10^6$, $1.0\times10^7$, $5.0\times10^7$, or $1.0\times10^8$ less than its concentration in the source cell.

In some embodiments, the targeted lipid particle (e.g., targeted viral vector) delivers to a target cell at least 10%, 20%, 30%, 40%, 50%, 60%, 70%, 80%, 90%, 95%, 96%, 97%, 98%, or 99% of the cargo (e.g., a therapeutic agent, e.g., an exogenous therapeutic agent) comprised by the targeted lipid particle. In some embodiments, the targeted lipid particle that fuses with the target cell(s) delivers to the target cell an average of at least 10%, 20%, 30%, 40%, 50%, 60%, 70%, 80%, 90%, 95%, 96%, 97%, 98%, or 99% of the cargo (e.g., a therapeutic agent, e.g., an an exogenous therapeutic agent) comprised by the targeted lipid particle that fuses with the target cell(s). In some embodiments, the targeted lipid particle composition delivers to a target tissue at least 10%, 20%, 30%, 40%, 50%, 60%, 70%, 80%, 90%, 95%, 96%, 97%, 98%, or 99% of the cargo (e.g., a therapeutic agent, e.g., an exogenous therapeutic agent) comprised by the targeted lipid particle composition.

In some embodiments, the exogenous agent or cargo is not expressed naturally in the cell from which the targeted lipid particle is derived. In some embodiments, the exogenous agent or cargo is expressed naturally in the cell from which the viral vector is derived. In some embodiments, the exogenous agent or cargo is loaded into the targeted lipid particle via expression in the cell from which the viral vector is derived (e.g. expression from DNA or mRNA introduced via transfection, transduction, or electroporation). In some embodiments, the exogenous agent or cargo is expressed from DNA integrated into the genome or maintained episosomally. In some embodiments, expression of the exogenous agent or cargo is constitutive. In some embodiments, expression of the exogenous agent or cargo is induced. In some embodiments, expression of the exogenous agent or cargo is induced immediately prior to generating the targeted lipid particle. In some embodiments, expression of the exogenous agent or cargo is induced at the same time as expression of the fusogen.

In some embodiments, the exogenous agent or cargo is loaded into the viral vector via electroporation into the viral vector itself or into the cell from which the viral vector is derived. In some embodiments, the exogenous agent or cargo is loaded into the viral vector via transfection (e.g., of a DNA or mRNA encoding the cargo) into the viral vector itself or into the cell from which the viral vector is derived.

In some embodiments, the exogenous agent or cargo may include one or more nucleic acid sequences, one or more polypeptides, a combination of nucleic acid sequences and/or polypeptides, one or more organelles, and any combination thereof. In some embodiments, the exogenous agent or cargo may include one or more cellular components. In some embodiments, the exogenous agent or cargo includes one or more cytosolic and/or nuclear components.

In some embodiments, the exogenous agent or cargo includes a nucleic acid, e.g., DNA, nDNA (nuclear DNA), mtDNA (mitochondrial DNA), protein coding DNA, gene, operon, chromosome, genome, transposon, retrotransposon, viral genome, intron, exon, modified DNA, mRNA (messenger RNA), tRNA (transfer RNA), modified RNA, microRNA, siRNA (small interfering RNA), tmRNA (transfer messenger RNA), rRNA (ribosomal RNA), mtRNA (mitochondrial RNA), snRNA (small nuclear RNA), small nucleolar RNA (snoRNA), SmY RNA (mRNA trans-splicing RNA), gRNA (guide RNA), TERC (telomerase RNA component), aRNA (antisense RNA), cis-NAT (Cis-natural antisense transcript), CRISPR RNA (crRNA), lncRNA (long noncoding RNA), piRNA (piwi-interacting RNA), shRNA (short hairpin RNA), tasiRNA (trans-acting siRNA), eRNA (enhancer RNA), satellite RNA, pcRNA (protein coding RNA), dsRNA (double stranded RNA), RNAi (interfering RNA), circRNA (circular RNA), reprogramming RNAs, aptamers, and any combination thereof. In some embodiments, the nucleic acid is a wild-type nucleic acid. In some embodiments, the nucleic acid is a mutant nucleic acid. In some embodiments the nucleic acid is a fusion or chimera of multiple nucleic acid sequences.

In some embodiments, the exogenous agent or cargo may include a nucleic acid. For example, the exogenous agent or cargo may comprise RNA to enhance expression of an endogenous protein, or a siRNA or miRNA that inhibits protein expression of an endogenous protein. For example, the endogenous protein may modulate structure or function in the target cells. In some embodiments, the cargo may include a nucleic acid encoding an engineered protein that modulates structure or function in the target cells. In some embodiments, the exogenous agent or cargo is a nucleic acid that targets a transcriptional activator that modulate structure or function in the target cells.

In some embodiments, the exogenous agent or cargo includes a polypeptide, e.g., enzymes, structural polypeptides, signaling polypeptides, regulatory polypeptides, transport polypeptides, sensory polypeptides, motor polypeptides, defense polypeptides, storage polypeptides, transcription factors, antibodies, cytokines, hormones, catabolic polypeptides, anabolic polypeptides, proteolytic polypeptides, metabolic polypeptides, kinases, transferases, hydrolases, lyases, isomer ases, ligases, enzyme modulator polypeptides, protein binding polypeptides, lipid binding polypeptides, membrane fusion polypeptides, cell differentiation polypeptides, epigenetic polypeptides, cell death polypeptides, nuclear transport polypeptides, nucleic acid binding polypeptides, reprogramming polypeptides, DNA editing polypeptides, DNA repair polypeptides, DNA recombination polypeptides, transposase polypeptides, DNA integration polypeptides, targeted endonucleases (e.g. Zinc-finger nucleases, transcription-activator-like nucleases (TALENs), cas9 and homologs thereof), recombinases, and any combination thereof. In some embodiments the protein targets a protein in the cell for degradation. In some embodiments the protein targets a protein in the cell for degradation by localizing the protein to the proteasome. In some embodiments, the protein is a wild-type protein. In some embodiments, the protein is a mutant protein. In some embodiments the protein is a fusion or chimeric protein.

In some embodiments, the exogenous agent or cargo includes a small molecule, e.g., ions (e.g. $Ca^{2+}$, $C1-$, $Fe^{2+}$), carbohydrates, lipids, reactive oxygen species, reactive nitrogen species, isoprenoids, signaling molecules, heme, polypeptide cofactors, electron accepting compounds, electron donating compounds, metabolites, ligands, and any combination thereof. In some embodiments the small molecule is a pharmaceutical that interacts with a target in the cell. In some embodiments the small molecule targets a protein in the cell for degradation. In some embodiments the small molecule targets a protein in the cell for degradation by localizing the protein to the proteasome. In some embodiments that small molecule is a proteolysis targeting chimera molecule (PROTAC).

In some embodiments, the exogenous agent or cargo includes a mixture of proteins, nucleic acids, or metabolites, e.g., multiple polypeptides, multiple nucleic acids, multiple small molecules; combinations of nucleic acids, polypeptides, and small molecules; ribonucleoprotein complexes (e.g. Cas9-gRNA complex); multiple transcription factors, multiple epigenetic factors, reprogramming factors (e.g. Oct4, Sox2, cMyc, and Klf4); multiple regulatory RNAs; and any combination thereof.

In some embodiments, the exogenous agent or cargo includes one or more organelles, e.g., chondrisomes, mitochondria, lysosomes, nucleus, cell membrane, cytoplasm, endoplasmic reticulum, ribosomes, vacuoles, endosomes, spliceosomes, polymerases, capsids, acrosome, autophagosome, centriole, glycosome, glyoxysome, hydrogenosome, melanosome, mitosome, myofibril, cnidocyst, peroxisome, proteasome, vesicle, stress granule, networks of organelles, and any combination thereof.

In some embodiments, the exogenous agent encodes a therapeutic agent or a diagnostic agent. In some embodiments, the therapeutic agent is a chimeric antigen receptor (CAR) or T-cell receptor (TCR). In some embodiments, the CAR targets a tumor antigen selected from CD19, CD20, CD22, or BCMA. In another embodiment, the CAR is engineered to comprise an intracellular signaling domain of the T cell antigen receptor complex zeta chain (e.g., CD3 zeta). In a preferred embodiment, the intracellular domain is selected from a CD137 (4-1BB) signaling domain, a CD28 signaling domain, and a CD3zeta signaling domain.

D. Methods of Generating Targeted Lipid Particles Derived from Virus

Provided herein are targeted lipid particles that are derived from virus, such as viral particles or virus-like particles, including those derived from retroviruses or lentiviruses. In some embodiments, the targeted lipid particle's bilayer of amphipathic lipids is or comprises the viral envelope. In some embodiments, the targeted lipid particle's bilayer of amphipathic lipids is or comprises lipids derived from a producer cell. In some embodiments, the viral envelope may comprise a fusogen, e.g., a fusogen that is endogenous to the virus or a pseudotyped fusogen. In some embodiments, the targeted lipid particles's lumen or cavity comprises a viral nucleic acid, e.g., a retroviral nucleic acid, e.g., a lentiviral nucleic acid. In some embodiments, the viral nucleic acid may be a viral genome. In some embodiments, the targeted lipid particle further comprises one or more viral non-structural proteins, e.g., in its cavity or lumen. In some embodiments, the targeted lipid particles is or comprises a virus-like particle (VLP). In some embodiments, the VLP does not comprise an envelope. In some embodiments, the VLP comprises an envelope.

In some embodiments, the viral particle or virus-like particle, such as a retrovirus or retrovirus-like particle, comprises one or more of a Gag polyprotein, polymerase (e.g., Pol), integrase (IN, e.g., a functional or non-functional variant), protease (PR), Rev, Tat, and a fusogen. In some embodiments, the targeted lipid particle comprises Rev. In some embodiments, the targeted lipid particle comprises Tat. In some embodiments, one or more of the aforesaid proteins are encoded in the retroviral genome, and in some embodiments, one or more of the aforesaid proteins are provided in trans, e.g., by a helper cell, helper virus, or helper plasmid. In some embodiments, the targeted lipid particle nucleic acid (e.g., retroviral nucleic acid) comprises one or more of the following nucleic acid sequences: 5' LTR (e.g., comprising U5 and lacking a functional U3 domain), Psi packaging element (Psi), Central polypurine tract (cPPT) Promoter operatively linked to the payload gene, payload gene (optionally comprising an intron before the open reading frame), Poly A tail sequence, WPRE, and 3' LTR (e.g., comprising U5 and lacking a functional U3). In some embodiments the targeted lipid particle nucleic acid further comprises one or more insulator elements. In some embodiments, the recognition sites are situated between the poly A tail sequence and the WPRE.

In some embodiments, the targeted lipid particle comprises supramolecular complexes formed by viral proteins that self-assemble into capsids. In some embodiments, the targeted lipid particle is a viral particle or virus-like particle derived from viral capsids. In some embodiments, the targeted lipid particle is a viral particle or virus-like particle derived from viral nucleocapsids. In some embodiments, the targeted lipid particle comprises nucleocapsid-derived proteins that retain the property of packaging nucleic acids. In some embodiments, the viral particles or virus-like particles comprises only viral structural glycoproteins. In some embodiments, the targeted lipid particle does not contain a viral genome.

In some embodiments, the targeted lipid particle packages nucleic acids from host cells during the expression process. In some embodiments, the nucleic acids do not encode any genes involved in virus replication. In particular embodiments, the targeted lipid particle is a virus-like particle, e.g. retrovirus-like particle such as a lentivirus-like particle, that is replication defective.

In some cases, the targeted lipid particle is a viral particle that is morphologically indistinguishable from the wild type infectious virus. In some embodiments, the viral particle presents the entire viral proteome as an antigen. In some embodiments, the viral particle presents only a portion of the proteome as an antigen.

In some embodiments, the viral particle or virus-like particle is produced utilizing proteins (e.g., envelope proteins) from a virus within the Paramyxoviridae family. In some embodiments, the Paramyxoviridae family comprises members within the Henipavirus genus. In some embodiments, the Henipavirus is or comprises a Hendra (HeV) or a Nipah (NiV) virus. In particular embodiments, the viral particles or virus-like particles incorporate a targeted envelope protein and fusogen.

In some embodiments, viral particles or virus-like particles may be produced in multiple cell culture systems including bacteria, mammalian cell lines, insect cell lines, yeast, and plant cells.

Suitable cell lines which can be used include, for example, CHO cells, BHK cells, MDCK cells, C3H 10T1/2 cells, FLY cells, Psi-2 cells, BOSC 23 cells, PA317 cells, WEHI cells, COS cells, BSC 1 cells, BSC 40 cells, BMT 10 cells, VERO cells, W138 cells, MRC5 cells, A549 cells, HT1080 cells, 293 cells, 293T cells, B-50 cells, 3T3 cells, NIH3T3 cells, HepG2 cells, Saos-2 cells, Huh7 cells, Hela cells, W163 cells, 211 cells, 211A cells, and cyno and *Macaca* nemestrina cell lines. In embodiments, the packaging cells are 293 cells, 293T cells, or A549 cells.

In some embodiments, a source cell line includes a cell line which is capable of producing recombinant retroviral particles, comprising a producer cell line and a transfer vector construct comprising a packaging signal. Methods of preparing viral stock solutions are illustrated by, e.g., Y. Soneoka et al. (1995) *Nucl. Acids Res.* 23:628-633, and N. R. Landau et al. (1992) *J. Virol.* 66:5110-5113, which are incorporated herein by reference.

In some embodiments, the assembly of a viral particle or virus-like particle is initiated by binding of the core protein to a unique encapsidation sequence within the viral genome (e.g. UTR with stem-loop structure). In some embodiments, the interaction of the core with the encapsidation sequence facilitates oligomerization.

In some embodiments, the targeted lipid particle is a virus-like particle which comprises a sequence that is devoid of or lacking viral RNA. In some embodiments, such particles may be the result of removing or eliminating the viral RNA from the sequence. In some embodiments, this may be achieved by using an endogenous packaging signal binding site on Gag. In some embodiments, the endogenous packaging signal binding site is on Pol. In some embodiments, the RNA which is to be delivered will contain a cognate packaging signal. In some embodiments, a heterologous binding domain (which is heterologous to Gag) located on the RNA to be delivered, and a cognate binding site located on Gag or Pol, can be used to ensure packaging of the RNA to be delivered. In some embodiments, the heterologous sequence could be non-viral or it could be viral, in which case it may be derived from the same virus or a different virus. In some embodiments, the vector particles could be used to deliver therapeutic RNA, in which case functional integrase and/or reverse transcriptase is not required. In some embodiments, the vector particles could also be used to deliver a therapeutic gene of interest, in which case Pol is typically included. In some embodiments, the retroviral nucleic acid comprises one or more of (e.g., all of): a 5' promoter (e.g., to control expression of the entire packaged RNA), a 5' LTR (e.g., that includes R (polyadenylation tail signal) and/or U5 which includes a primer activation signal), a primer binding site, a Psi packaging signal, a RRE element for nuclear export, a promoter directly upstream of the transgene to control transgene expression, a transgene (or other exogenous agent element), a polypurine tract, and a 3' LTR (e.g., that includes a mutated U3, a R, and U5). In some embodiments, the retroviral nucleic acid further comprises one or more of a cPPT, a WPRE, and/or an insulator element.

A retrovirus typically replicates by reverse transcription of its genomic RNA into a linear double-stranded DNA copy and subsequently covalently integrates its genomic DNA into a host genome. Illustrative retroviruses suitable for use in particular embodiments, include, but are not limited to: Moloney murine leukemia virus (M-MuLV), Moloney murine sarcoma virus (MOMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV), Rous Sarcoma Virus (RSV), and other lentiviruses.

In some embodiments the retrovirus is a Gammaretrovirus. In some embodiments the retrovirus is an Epsilonretrovirus. In some embodiments the retrovirus is an Alpharetrovirus. In some embodiments the retrovirus is a Betaretrovirus. In some embodiments the retrovirus is a Deltaretrovirus. In some embodiments the retrovirus is a Lentivirus. In some embodiments the retrovirus is a Spumaretrovirus. In some embodiments the retrovirus is an endogenous retrovirus.

Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In some embodiments, HIV based vector backbones (i.e., HIV cis-acting sequence elements) are used.

In some embodiments, a vector herein is a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses.

In some embodiments, a viral vector comprises a nucleic acid molecule (e.g., a transfer plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s). In some embodiments, a viral vector comprises e.g., a virus or viral particle capable of transferring a nucleic acid into a cell, or the transferred nucleic acid (e.g., as naked DNA). In some embodiments, a viral vectors and transfer plasmids comprise structural and/or functional genetic elements that are primarily derived from a virus. A retroviral vector can comprise a viral vector or plasmid containing structural and functional genetic elements, or portions thereof, that are primarily derived from a retrovirus. A lentiviral vector can comprise a viral vector or plasmid containing structural and functional genetic elements, or portions thereof, including LTRs that are primarily derived from a lentivirus.

In embodiments, a lentiviral vector (e.g., lentiviral expression vector) may comprise a lentiviral transfer plasmid (e.g., as naked DNA) or an infectious lentiviral particle. With respect to elements such as cloning sites, promoters, regulatory elements, heterologous nucleic acids, etc., it is to be understood that the sequences of these elements can be present in RNA form in lentiviral particles and can be present in DNA form in DNA plasmids.

In some embodiments, in the vectors described herein at least part of one or more protein coding regions that contribute to or are essential for replication may be absent compared to the corresponding wild-type virus. In some embodiments, the viral vector is replication-defective. In some embodiments, the vector is capable of transducing a target non-dividing host cell and/or integrating its genome into a host genome.

In some embodiments, different cells differ in their usage of particular codons. In some embodiments, this codon bias corresponds to a bias in the relative abundance of particular tRNAs in the cell type. In some embodiments, by altering the codons in the sequence so that they are tailored to match with the relative abundance of corresponding tRNAs, it is possible to increase expression. In some embodiments, it is possible to decrease expression by deliberately choosing codons for which the corresponding tRNAs are known to be rare in the particular cell type. In some embodiments, an additional degree of translational control is available. An additional description of codon optimization is found, e.g., in WO 99/41397, which is herein incorporated by reference in its entirety.

Conventional techniques for generating retrovirus vectors (and, in particular, lentivirus vectors) with or without the use of packaging/helper vectors are known to those skilled in the art and may be used to generate targeted lipid particles according to the present disclosure. (See, e.g., Derse and Newbold 1993 Virology 194:530-6; Maury et al. 1994 Virology 200:632-42; Wanisch et al. 2009. Mol Ther. 1798: 1316-1332; Martarano et al. 1994 J. Virol. 68:3102-11; Naldini et al., (1996a, 1996b, and 1998); Zufferey et al., 1999, J. Virol., 73:2886; Huang et al., Mol. Cell. Biol., 5:3864; Liu et al., 1995, Genes Dev., 9:1766; Cullen et al., 1991. J. Virol. 65:1053; and Cullen et al., 1991. Cell 58:423; Dull et al., 1998, U.S. Pat. Nos. 6,013,516; and 5,994,136; PCT patent applications WO 99/15683, WO 98/17815, WO 99/32646, and WO 01/79518). Conventional techniques relating to packaging vectors and producer cells known in the art may also be used according to the present disclosure. (See, e.g., Yao et al, 1998; Jones et al, 2005.)

Provided herein are targeted lipid particles that comprise a naturally derived membrane. In some embodiments, the naturally derived membrane comprises membrane vesicles prepared from cells or tissues. In some embodiments, the targeted lipid particle comprises a vesicle that is obtainable from a cell. In some embodiments, the targeted lipid particle comprises a microvesicle, an exosome, a membrane enclosed body, an apoptotic body (from apoptotic cells), a particle (which may be derived from e.g. platelets), an ectosome (derivable from, e.g., neutrophiles and monocytes in serum), a prostatosome (obtainable from prostate cancer cells), or a cardiosome (derivable from cardiac cells).

In some embodiments, the source cell is an endothelial cell, a fibroblast, a blood cell (e.g., a macrophage, a neutrophil, a granulocyte, a leukocyte), a stem cell (e.g., a mesenchymal stem cell, an umbilical cord stem cell, bone marrow stem cell, a hematopoietic stem cell, an induced pluripotent stem cell e.g., an induced pluripotent stem cell derived from a subject's cells), an embryonic stem cell (e.g., a stem cell from embryonic yolk sac, placenta, umbilical cord, fetal skin, adolescent skin, blood, bone marrow, adipose tissue, erythropoietic tissue, hematopoietic tissue), a myoblast, a parenchymal cell (e.g., hepatocyte), an alveolar cell, a neuron (e.g., a retinal neuronal cell), a precursor cell (e.g., a retinal precursor cell, a myeloblast, myeloid precursor cells, a thymocyte, a meiocyte, a megakaryoblast, a promegakaryoblast, a melanoblast, a lymphoblast, a bone marrow precursor cell, a normoblast, or an angioblast), a progenitor cell (e.g., a cardiac progenitor cell, a satellite cell, a radial gial cell, a bone marrow stromal cell, a pancreatic progenitor cell, an endothelial progenitor cell, a blast cell), or an immortalized cell (e.g., HeEa, HEK293, HFF-I, MRC-5, WI-38, IMR 90, IMR 91, PER.C6, HT-1080, or BJ cell). In some embodiments, the source cell is other than a 293 cell, HEK cell, human endothelial cell, or a human epithelial cell, monocyte, macrophage, dendritic cell, or stem cell.

In some embodiments, the targeted lipid particle has a density of <1, 1-1.1, 1.05-1.15, 1.1-1.2, 1.15-1.25, 1.2-1.3, 1.25-1.35, or >1.35 g/ml. In some embodiments, the targeted lipid particle composition comprises less than 0.01%, 0.05%, 0.1%, 0.5%, 1%, 1.5%, 2%, 2.5%, 3%, 4%, 5%, or 10% source cells by protein mass, or less than 0.01%, 0.05%, 0.1%, 0.5%, 1%, 1.5%, 2%, 2.5%, 3%, 4%, 5%, or 10% of cells having a functional nucleus.

In embodiments, the targeted lipid particle has a size, or the population of targeted lipid particles have an average size, that is less than about 0.01%, 0.05%, 0.1%, 0.5%, 1%, 2%, 3%, 4%, 5%, 10%, 20%, 30%, 40%, 50%, 60%, 70%, 80%, 90%, of that of the source cell.

In some embodiments the targeted lipid particle comprises an extracellular vesicle, e.g., a cell-derived vesicle comprising a membrane that encloses an internal space and has a smaller diameter than the cell from which it is derived. In embodiments the extracellular vesicle has a diameter from 20 nm to 1000 nm. In embodiments the targeted lipid particle comprises an apoptotic body, a fragment of a cell, a vesicle derived from a cell by direct or indirect manipulation, a vesiculated organelle, and a vesicle produced by a living cell (e.g., by direct plasma membrane budding or fusion of the late endosome with the plasma membrane). In embodiments the extracellular vesicle is derived from a living or dead organism, explanted tissues or organs, or cultured cells.

In embodiments, the targeted lipid particle comprises a nanovesicle, e.g., a cell-derived small (e.g., between 20-250 nm in diameter, or 30-150 nm in diameter) vesicle comprising a membrane that encloses an internal space, and which is generated from said cell by direct or indirect manipulation. The production of nanovesicles can, in some instances, result in the destruction of the source cell. The nanovesicle may comprise a lipid or fatty acid and polypeptide.

In embodiments, the targeted lipid particle comprises an exosome. In some embodiments, the exosome is a cell-derived small (e.g., between 20-300 nm in diameter, or 40-200 nm in diameter) vesicle comprising a membrane that encloses an internal space, and which is generated from said cell by direct plasma membrane budding or by fusion of the late endosome with the plasma membrane. In embodiments, production of exosomes does not result in the destruction of the source cell. In embodiments, the exosome comprises lipid or fatty acid and polypeptide.

In some embodiments, the targeted lipid particle is derived from a source cell with a genetic modification which results in increased expression of an immunomodulatory agent. In some embodiments, the immunosuppressive agent is on an exterior surface of the cell. In some embodiments, the immunosuppressive agent is incorporated into the exterior surface of the targeted lipid particle. In some embodiments, the targeted lipid particle comprises an immunomodulatory agent attached to the surface of the solid particle by a covalent or non-covalent bond.

a. Generation of Cell-Derived Particles

In some embodiments, targeted lipid particles are generated by inducing budding of an exosome, microvesicle, membrane vesicle, extracellular membrane vesicle, plasma membrane vesicle, giant plasma membrane vesicle, apoptotic body, mitoparticle, pyrenocyte, lysosome, or other membrane enclosed vesicle.

In some embodiments, targeted lipid particles are generated by inducing cell enucleation. Enucleation may be performed using assays such as genetic, chemical (e.g., using Actinomycin D, see Bayona-Bafaluyet al., "A chemical enucleation method for the transfer of mitochondrial DNA to p° cells" Nucleic Acids Res. 2003 Aug. 15; 31 (16): e98), or mechanical methods (e.g., squeezing or aspiration, see Lee et al., "A comparative study on the efficiency of two enucleation methods in pig somatic cell nuclear transfer: effects of the squeezing and the aspiration methods." Anim Biotechnol. 2008; 19 (2): 71-9), or combinations thereof.

In some embodiments, the targeted lipid particles are generated by inducing cell fragmentation. In some embodiments, cell fragmentation can be performed using the following methods, including, but not limited to: chemical methods, mechanical methods (e.g., centrifugation (e.g., ultracentrifugation, or density centrifugation), freeze-thaw, or sonication), or combinations thereof.

In some embodiments, the targeted lipid particle is a microvesicle. In some embodiments the microvesicle has a diameter of about 100 nm to about 2000 nm. In some embodiments, a targeted lipid particle comprises a cell ghost. In some embodiments, a vesicle is a plasma membrane vesicle, e.g., a giant plasma membrane vesicle.

In some embodiments, a characteristic of a targeted lipid particle is described by comparison to a reference cell. In embodiments, the reference cell is the source cell. In embodiments, the reference cell is a Hela, HEK293, HFF-1, MRC-5, WI-38, IMR 90, IMR 91, PER.C6, HT-1080, or BJ cell. In some embodiments, for example when the source cell used to make the targeted lipid particle is not available for testing after the targeted lipid particle is made, a characteristic of a population of targeted lipid particle is described by comparison to a population of reference cells, e.g., a population of source cells, or a population of HeLa, HEK293, HFF-1, MRC-5, WI-38, IMR 90, IMR 91, PER.C6, HT-1080, or BJ cells.

Pharmaceutical Compositions

The present disclosure also provides, in some aspects, a pharmaceutical composition comprising the targeted lipid particle (e.g., targeted viral vectors) composition described herein and a pharmaceutically acceptable carrier. The pharmaceutical compositions can include any of the described targeted viral vectors.

In some embodiments, the targeted viral vector meets a pharmaceutical or good manufacturing practices (GMP) standard. In some embodiments, the targeted viral vector is made according to good manufacturing practices (GMP). In some embodiments, the targeted viral vector has a pathogen level below a predetermined reference value, e.g., is substantially free of pathogens. In some embodiments, the targeted viral vector has a contaminant level below a predetermined reference value, e.g., is substantially free of contaminants. In some embodiments, the targeted viral vector has low immunogenicity.

In some embodiments, provided herein are the use of pharmaceutical compositions to practice the methods of the disclosure. Such a pharmaceutical composition may consist of at least one targeted lipid particle of the disclosure in a form suitable for administration to a subject, or the pharmaceutical composition may comprise at least one targeted lipid particle of the disclosure and one or more pharmaceutically acceptable carriers, one or more additional ingredients, or some combination of these.

In some embodiments, the relative amounts of the targeted lipid particle, the pharmaceutically acceptable carrier, and any additional ingredients in a pharmaceutical composition of the disclosure will vary, depending upon the identity, size, and condition of the subject treated and further depending upon the route by which the composition is to be administered. In some embodiments, the composition may comprise between 0.1% and 100% (w/w) of the targeted lipid particles of the disclosure.

In some embodiments, pharmaceutical compositions that are useful in the methods of the disclosure may be suitably developed for intravenous, intratumoral, oral, rectal, vaginal, parenteral, topical, pulmonary, intranasal, buccal, ophthalmic, or another route of administration. In some embodiments, a composition useful within the methods of the disclosure may be directly administered to the skin, vagina or any other tissue of a mammal. In some embodiments, formulations include liposomal preparations, resealed erythrocytes containing the targeted lipid particles of the disclosure, and immunologically based formulations. In some embodiments, the route(s) of administration will be readily apparent to the skilled artisan and will depend upon any number of factors including the type and severity of the disease being treated, the type and age of the veterinary or human subject being treated, and the like.

In some embodiments, formulations of the pharmaceutical compositions described herein may be prepared by any method known or hereafter developed in the art of pharmacology. In some embodiments, preparatory methods include the step of bringing the targeted lipid particles of the disclosure into association with a carrier or one or more other accessory ingredients, and then, if necessary or desirable, shaping or packaging the product into a desired single- or multi-dose unit.

In some embodiments, a "unit dose" is a discrete amount of the pharmaceutical composition comprising a predetermined amount of the targeted lipid particles of the disclosure. In some embodiments, the amount is generally equal to the dosage that would be administered to a subject or a convenient fraction of such a dosage such as, for example, one-half or one-third of such a dosage. In some embodiments, the unit dosage form may be for a single daily dose or one of multiple daily doses (e.g., about 1 to 4 or more times per day). In some embodiments, when multiple daily doses are used, the unit dosage form may be the same or different for each dose.

In some embodiments, although the descriptions of pharmaceutical compositions provided herein are principally directed to pharmaceutical compositions that are suitable for ethical administration to humans, it will be understood by the skilled artisan that such compositions are generally suitable for administration to animals of all sorts. In some embodiments, modification of pharmaceutical compositions suitable for administration to humans in order to render the compositions suitable for administration to various animals is well understood, and the ordinarily skilled veterinary pharmacologist may design and perform such modification with merely ordinary, if any, experimentation. In some embodiments, subjects to which administration of the pharmaceutical compositions of the disclosure is contemplated include humans and other primates, mammals including commercially relevant mammals such as cattle, pigs, horses, sheep, cats, and dogs.

In some of any embodiments, the compositions of the disclosure are formulated using one or more pharmaceutically acceptable excipients or carriers. In one embodiment, the pharmaceutical compositions of the disclosure comprise a therapeutically effective amount of a targeted lipid particle of the disclosure and a pharmaceutically acceptable carrier. In some embodiments, pharmaceutically acceptable carriers that are useful, include, but are not limited to, glycerol, water, saline, ethanol, and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

In some embodiments, the carrier may be a solvent or dispersion medium containing, for example, water, ethanol, polyol (for example, glycerol, propylene glycol, and liquid polyethylene glycol, and the like), suitable mixtures thereof, and vegetable oils. In some embodiments, the proper fluidity may be maintained, for example, by the use of a coating such as lecithin, by the maintenance of the required particle size in the case of dispersion and by the use of surfactants. In some embodiments, prevention of the action of microorganisms may be achieved by various antibacterial and antifungal agents, for example, parabens, chlorobutanol, phenol, ascorbic acid, thimerosal, and the like. In some embodiments, it is preferable to include isotonic agents, for example, sugars, sodium chloride, or polyalcohols such as mannitol and sorbitol, in the composition. In some embodiments, prolonged absorption of the injectable compositions may be brought about by including in the composition an agent that delays absorption, for example, aluminum monostearate or gelatin. In one embodiment, the pharmaceutically acceptable carrier is not DMSO alone.

In some embodiments, formulations may be employed in admixtures with conventional excipients, i.e., pharmaceutically acceptable organic or inorganic carrier substances suitable for oral, vaginal, parenteral, nasal, intravenous, subcutaneous, enteral, or any other suitable mode of administration, known to the art. In some embodiments, the pharmaceutical preparations may be sterilized and, if desired, mixed with auxiliary agents, e.g., lubricants, preservatives, stabilizers, wetting agents, emulsifiers, salts for influencing osmotic pressure buffers, coloring, flavoring, and/or aromatic substances and the like. In some embodiments, pharmaceutical preparations may also be combined with other active agents, e.g., other analgesic agents.

In some embodiments, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. In some embodiments, "additional ingredients" that may be included in the pharmaceutical compositions of the disclosure are known in the art and described, for example in Genaro, ed. (1985, Remington's Pharmaceutical Sciences, Mack Publishing Co., Easton, Pa.), which is incorporated herein by reference.

In some embodiments, the composition of the disclosure may comprise a preservative from about 0.005% to 2.0% by total weight of the composition. In some embodiments, the preservative is used to prevent spoilage in the case of exposure to contaminants in the environment. In some embodiments, examples of preservatives useful in accordance with the disclosure included but are not limited to those selected from the group consisting of benzyl alcohol, sorbic acid, parabens, imidurea and combinations thereof. In some embodiments, a particularly preferred preservative is a combination of about 0.5% to 2.0% benzyl alcohol and 0.05% to 0.5% sorbic acid.

In some embodiments, liquid suspensions may be prepared using conventional methods to achieve suspension of the targeted lipid particles of the disclosure in an aqueous or oily vehicle. In some embodiments, aqueous vehicles include, for example, water, and isotonic saline. In some embodiments, oily vehicles include, for example, almond oil, oily esters, ethyl alcohol, vegetable oils such as *arachis*, olive, sesame, or coconut oil, fractionated vegetable oils, and mineral oils such as liquid paraffin. In some embodiments, liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. In some embodiments, oily suspensions may further comprise a thickening agent. In some embodiments, suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. In some embodiments, dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

In some embodiments, liquid solutions of the targeted lipid particles of the disclosure in aqueous or oily solvents may be prepared in substantially the same manner as liquid suspensions, the primary difference being that the targeted lipid particles of the disclosure is dissolved, rather than suspended in the solvent. As used herein, an "oily" liquid is one which comprises a carbon-containing liquid molecule and which exhibits a less polar character than water. In some embodiments, liquid solutions of the pharmaceutical composition of the disclosure may comprise each of the components described with regard to liquid suspensions, it being understood that suspending agents will not necessarily aid dissolution of the targeted lipid particles of the disclosure in the solvent. In some embodiments, aqueous solvents include, for example, water, and isotonic saline. In some embodiments, oily solvents include, for example, almond oil, oily esters, ethyl alcohol, vegetable oils such as *arachis*, olive, sesame, or coconut oil, fractionated vegetable oils, and mineral oils such as liquid paraffin.

In some embodiments, powdered and granular formulations of a pharmaceutical preparation of the disclosure may be prepared using known methods. In some embodiments, formulations may be administered directly to a subject, used, for example, to form tablets, to fill capsules, or to prepare an aqueous or oily suspension or solution by addition of an aqueous or oily vehicle thereto. In some of any embodiments, formulations may further comprise one or more of dispersing or wetting agent, a suspending agent, and a preservative. Additional excipients, such as fillers and sweetening, flavoring, or coloring agents, may also be included in these formulations.

In some embodiments, a pharmaceutical composition of the disclosure may also be prepared, packaged, or sold in the form of oil-in-water emulsion or a water-in-oil emulsion. In some embodiments, the oily phase may be a vegetable oil such as olive or *arachis* oil, a mineral oil such as liquid paraffin, or a combination of these. In some embodiments, compositions further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. In some embodiments, emulsions may also contain additional ingredients including, for example, sweetening or flavoring agents.

Methods of Treatment

Provided herein are methods of administering a lentiviral vector comprising a CD8 binding agent to a subject. In some embodiments the method comprises a) obtaining whole blood from the subject; b) collecting the fraction of blood containing leukocyte components including CD8+ T cells; c) contacting the leukocyte components including CD8+ T cells with a composition comprising the lentiviral vector to create a transfection mixture; and d) reinfusing the contacted leukocyte components including CD8+ T cells and/or the transfection mixture to the subject, thereby administering the lipid particle and/or payload gene to the subject. In some embodiments, the T cells (e.g. CD8+ T cells) are not activated during the method. In some embodiments, step (c) of the method is carried out for no more than 24 hours, e.g., no more than 20, 16, 12, 8, 6, 5, 4, 3, 2, or 1 hour.

In some embodiments, the method according to the present disclosure is capable of delivering a lentiviral particle to an ex vivo system. The method includes the use of a combination of various apheresis machine hardware components, a software control module, and a sensor module to measure citrate or other solute levels in-line to ensure the maximum accuracy and safety of treatment prescriptions, and the use of replacement fluids designed to fully exploit the design of the system according to the present methods. It is understood that components described for one system according to the present invention can be implemented within other systems according to the present invention as well.

In some embodiments, the method for administration of the lentiviral vector to the subject comprises the use of a blood processing set for obtaining whole blood from the subject, a separation chamber for collecting the fraction of blood containing leukocyte components including CD8+ T cells, a contacting container for contacting the CD8+ T cells with the composition comprising the lentiviral vector, and a further fluid circuit for reinfusion of CD8+ T cells to the patient. In some embodiments, the method further comprises any of i) a washing component for concentrating T cells, and ii) a sensor and/or module for monitoring cell density and/or concentration. In some embodiments, the methods allow processing of blood directly from the patient, transduction with the lentiviral vector, and reinfusion directly to the patient without any steps of selection for T cells or for CD8+ T cells. Further, in some embodiments the methods are carried out without cryopreserving or freezing any cells before or between any one or more of the steps, such that there is no step of formulating cells with a cryoprotectant, e.g. DMSO. In some embodiments, the provided methods do not include a lymphodepletion regimen. In some embodiments, the method including steps (a)-(d) are carried out for a time of no more than 24 hours, such as between 2 hours and 12 hours, for example 3 hours to 6 hours.

In some embodiments, the method is performed in-line (or in situ). In some embodiments, the method is performed in a closed fluid circuit, or a functionally closed fluid circuit. In some embodiments, each of steps (a)-(d) are performed in-line in a closed fluid circuit in which all parts of the system are operably connected, such as via at least one tubing line. In some embodiments, the system is sterile. In some embodiments, the closed fluid circuit is sterile.

Figure 14:
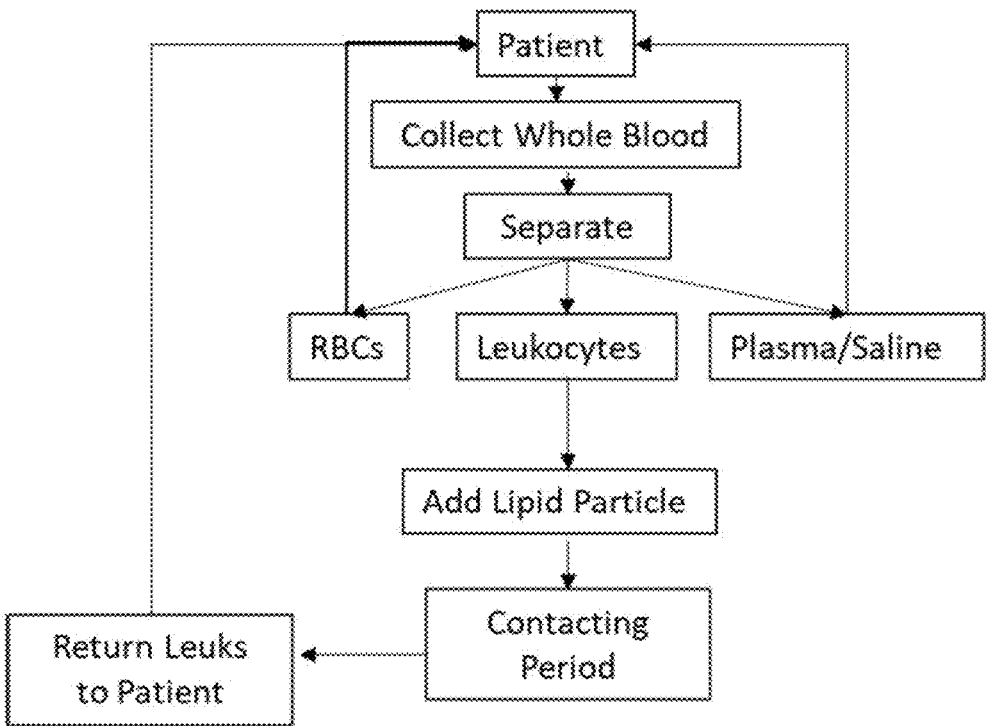
FIG. 14 depicts an exemplary system for administration of a lentiviral vector comprising a CD8 binding agent to a subject.

Also provided herein are systems for administration of a lentiviral vector comprising a CD8 binding agent to a subject. An exemplary system for administration is shown in FIG. 14.

In some embodiments, the targeted lipid particles (e.g. targeted viral vectors) provided herein, or pharmaceutical compositions thereof as described herein can be administered to a subject, e.g. a mammal, e.g. a human. In such embodiments, the subject may be at risk of, may have a symptom of, or may be diagnosed with or identified as having, a particular disease or condition. In one embodiment, the subject has cancer. In one embodiment, the subject has an infectious disease. In some embodiments, the targeted viral vector contains nucleic acid sequences encoding an exogenous agent for treating the disease or condition in the subject. For example, the exogenous agent is one that targets or is specific for a protein of a neoplastic cells and the targeted lipid particle is administered to a subject for treating a tumor or cancer in the subject. In another example, the exogenous agent is an inflammatory mediator or immune molecule, such as a cytokine, and targeted lipid particle is administered to a subject for treating any condition in which it is desired to modulate (e.g., increase) the immune response, such as a cancer or infectious disease. In some embodiments, the targeted viral vector is administered in an effective amount or dose to effect treatment of the disease, condition or disorder. Provided herein are uses of any of the provided targeted viral vector in such methods and treatments, and in the preparation of a medicament in order to carry out such therapeutic methods. In some embodiments, the methods are carried out by administering the targeted viral vector or compositions comprising the same, to the subject having, having had, or suspected of having the disease or condition or disorder. In some embodiments, the methods thereby treat the disease or condition or disorder in the subject. Also provided herein are uses of any of the compositions, such as pharmaceutical compositions provided herein, for the treatment of a disease, condition or disorder associated with a particular gene or protein targeted by or provided by the exogenous agent.

In some embodiments, the provided methods or uses involve administration of a pharmaceutical composition comprising oral, inhaled, transdermal or parenteral (including intravenous, intratumoral, intraperitoneal, intramuscular, intracavity, and subcutaneous) administration. In some embodiments, the targeted viral vector may be administered alone or formulated as a pharmaceutical composition. In some embodiments, the targeted viral vector or compositions described herein can be administered to a subject, e.g., a mammal, e.g., a human. In some of any embodiments, the subject may be at risk of, may have a symptom of, or may be diagnosed with or identified as having, a particular disease or condition (e.g., a disease or condition described herein). In some embodiments, the disease is a disease or disorder. In some embodiments, the disease is a B cell malignancy.

In some embodiments, the targeted viral vectors may be administered in the form of a unit-dose composition, such as a unit dose oral, parenteral, transdermal, or inhaled composition. In some embodiments, the compositions are prepared by admixture and are adapted for oral, inhaled, transdermal, or parenteral administration, and as such may be in the form of tablets, capsules, oral liquid preparations, powders, granules, lozenges, reconstitutable powders, injectable, and infusable solutions or suspensions, or suppositories or aerosols.

In some embodiments, the regimen of administration may affect what constitutes an effective amount. In some embodiments, the therapeutic formulations may be administered to the subject either prior to or after a diagnosis of disease. In some embodiments, several divided dosages, as well as staggered dosages may be administered daily or sequentially, or the dose may be continuously infused, or may be a bolus injection. In some embodiments, the dosages of the therapeutic formulations may be proportionally increased or decreased as indicated by the exigencies of the therapeutic or prophylactic situation.

In some embodiments, the administration of the compositions of the present disclosure to a subject, preferably a mammal, more preferably a human, may be carried out using known procedures, at dosages and for periods of time effective to prevent or treat disease. In some embodiments, an effective amount of the targeted lipid particle of the disclosure necessary to achieve a therapeutic effect may vary according to factors such as the activity of the particular lipid particle employed; the time of administration; the rate of excretion; the duration of the treatment; other drugs, compounds or materials used in combination with the targeted lipid particle of the disclosure; the state of the disease or disorder, age, sex, weight, condition, general health and prior medical history of the subject being treated, and like factors well-known in the medical arts. In some embodiments, the dosage regimens may be adjusted to provide the optimum therapeutic response. In some embodiments, several divided doses may be administered daily or the dose may be proportionally reduced as indicated by the exigencies of the therapeutic situation. One of ordinary skill in the art would be able to study the relevant factors and make the determination regarding the effective amount of the therapeutic targeted lipid particle of the disclosure without undue experimentation.

In some embodiments, dosage levels of the targeted lipid particles in the pharmaceutical compositions of this disclosure may be varied so as to obtain an amount that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. In some embodiments, the physician or veterinarian could start doses of the targeted lipid particles of the disclosure employed in the pharmaceutical composition at levels lower than that required in order to achieve the desired therapeutic effect and gradually increase the dosage until the desired effect is achieved.

In some embodiments, the term "container" includes any receptacle for holding the pharmaceutical composition. In some embodiments, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. It should be understood that the instructions for use of the pharmaceutical composition may be contained on the packaging containing the pharmaceutical composition, and as such the instructions form an increased functional relationship to the packaged product. In some embodiments, instructions may contain information pertaining to the pharacetuical composition's ability to perform its intended function, e.g., treating or preventing a disease in a subject, or delivering an imaging or diagnostic agent to a subject.

In some embodiments, routes of administration of any of the compositions disclosed herein include oral, nasal, rectal, parenteral, sublingual, transdermal, transmucosal (e.g., sublingual, lingual, (trans) buccal, (trans) urethral, vaginal (e.g., trans- and perivaginally), (intra) nasal, and (trans) rectal), intravesical, intrapulmonary, intraduodenal, intragastrical, intrathecal, subcutaneous, intramuscular, intradermal, intraarterial, intravenous, intrabronchial, inhalation, and topical administration.

In some of any embodiments, suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration, and the like.

In some embodiments, the targeted lipid particle composition comprising an exogenous agent or cargo, may be used to deliver such exogenous agent or cargo to a cell tissue or subject. In some embodiments, delivery of a cargo by administration of a targeted lipid particle composition described herein may modify cellular protein expression levels. In certain embodiments, the administered composition directs upregulation (via expression in the cell, delivery in the cell, or induction within the cell) of one or more cargo (e.g., a polypeptide or mRNA) that provide a functional activity which is substantially absent or reduced in the cell in which the polypeptide is delivered. In some embodiments, the missing functional activity may be enzymatic, structural, or regulatory in nature. In some embodiments, the administered composition directs up-regulation of one or more polypeptides that increases (e.g., synergistically) a functional activity which is present but substantially deficient in the cell in which the polypeptide is upregulated. In some of any embodiments, the administered composition directs downregulation of (via expression in the cell, delivery in the cell, or induction within the cell) of one or more cargo (e.g., a polypeptide, siRNA, or miRNA) that repress a functional activity which is present or upregulated in the cell in which the polypeptide, siRNA, or miRNA is delivered. In some embodiments, the upregulated functional activity may be enzymatic, structural, or regulatory in nature. In some embodiments, the administered composition directs downregulation of one or more polypeptides that decreases (e.g., synergistically) a functional activity which is present or upregulated in the cell in which the polypeptide is downregulated. In some embodiments, the administered composition directs upregulation of certain functional activities and downregulation of other functional activities.

In some of any embodiments, the targeted lipid particle composition (e.g., one comprising mitochondria or DNA) mediates an effect on a target cell, and the effect lasts for at least 1, 2, 3, 4, 5, 6, or 7 days, 2, 3, or 4 weeks, or 1, 2, 3, 6, or 12 months. In some embodiments (e.g., wherein the targeted viral vector composition comprises an exogenous protein), the effect lasts for less than 1, 2, 3, 4, 5, 6, or 7 days, 2, 3, or 4 weeks, or 1, 2, 3, 6, or 12 months.

In some of any embodiments, the targeted lipid particle composition described herein is delivered ex-vivo to a cell or tissue, e.g., a human cell or tissue. In embodiments, the composition improves function of a cell or tissue ex-vivo, e.g., improves cell viability, respiration, or other function (e.g., another function described herein).

In some embodiments, the composition is delivered to an ex vivo tissue that is in an injured state (e.g., from trauma, disease, hypoxia, ischemia or other damage).

In some embodiments, the composition is delivered to an ex-vivo transplant (e.g., a tissue explant or tissue for transplantation, e.g., a human vein, a musculoskeletal graft such as bone or tendon, cornea, skin, heart valves, nerves; or an isolated or cultured organ, e.g., an organ to be transplanted into a human, e.g., a human heart, liver, lung, kidney, pancreas, intestine, thymus, eye). In some embodiments, the composition is delivered to the tissue or organ before, during and/or after transplantation.

In some embodiments, the composition is delivered, administered, or contacted with a cell, e.g., a cell preparation. In some embodiments, the cell preparation may be a cell therapy preparation (a cell preparation intended for administration to a human subject). In embodiments, the cell preparation comprises cells expressing a T-cell receptor (TCR) or chimeric antigen receptor (CAR), e.g., expressing a recombinant CAR. The cells expressing the CAR may be, e.g., T cells, Natural Killer (NK) cells, cytotoxic T lymphocytes (CTL), regulatory T cells. In embodiments, the cell preparation is a neural stem cell preparation. In embodiments, the cell preparation is a mesenchymal stem cell (MSC) preparation. In embodiments, the cell preparation is a hematopoietic stem cell (HSC) preparation. In embodiments, the cell preparation is an islet cell preparation.

In some embodiments, the viral vector comprising an anti-CD8 sdAb or scFv composition described herein is used to deliver a CAR or TCR. In some embodiments, the viral vector transduces a cell expressing CD8 (e.g., a CD8+ T cell) and expresses and amplifies the CAR or TCR. The amplified CAR or TCR T cells then mediate targeted cell killing. Thus, the disclosure includes the use of viral vector comprising an anti-CD8 scFv fusogen construct to elicit an immune response specific to the antigen binding moiety of the CAR or TCR. In some embodiments, the CAR is used to target a tumor antigen selected from CD19, CD20, CD22, or BCMA. In another embodiment, the CAR is engineered to comprise an intracellular signaling domain of the T cell antigen receptor complex zeta chain (e.g., CD3 zeta). In a preferred embodiment, the intracellular domain is selected from a CD137 (4-1BB) signaling domain, a CD28 signaling domain, and a CD3zeta signaling domain.

Engineered Receptor Payloads

In some embodiments, the targeted lipid particles (e.g. targeted viral vectors) disclosed herein encode an engineered receptor. In some embodiments, the cells for use in or administered in connection with the provided methods contain or are engineered to contain an engineered receptor, e.g., an engineered antigen receptor, such as a chimeric antigen receptor (CAR). Also provided are populations of such cells, compositions containing such cells and/or enriched for such cells, such as in which cells of a certain type such as T cells or CD8+ cells are enriched or selected. Among the compositions are pharmaceutical compositions and formulations for administration, such as for adoptive cell therapy. Also provided are therapeutic methods for administering the cells and compositions to subjects, e.g., patients, in accord with the provided methods, and/or with the provided articles of manufacture or compositions.

In some embodiments, gene transfer is accomplished without first stimulating the cells, such as by combining it with a stimulus that induces a response such as proliferation, survival, and/or activation, e.g., as measured by expression of a cytokine or activation marker, followed by introduction of the nucleic acids, e.g., by transduction, into the stimulated cells, and optionally incubation or expansion in culture to numbers sufficient for clinical applications.

The viral vectors may express recombinant receptors, such as antigen receptors including chimeric antigen receptors (CARs), and other antigen-binding receptors such as transgenic T cell receptors (TCRs). Also among the receptors are other chimeric receptors.

a. Chimeric Antigen Receptors (CARs)

In some embodiments of the provided methods and uses, chimeric receptors, such as a CARs, contain one or more domains that combine an antigen- or ligand-binding domain (e.g. antibody or antibody fragment) that provides specificity for a desired antigen (e.g., tumor antigen) with intracellular signaling domains. In some embodiments, the intracellular signaling domain is a stimulating or an activating intracellular domain portion, such as a T cell stimulating or activating domain, providing a primary activation signal or a primary signal. In some embodiments, the intracellular signaling domain contains or additionally contains a costimulatory signaling domain to facilitate effector functions. In some embodiments, chimeric receptors when genetically engineered into immune cells can modulate T cell activity, and, in some cases, can modulate T cell differentiation or homeostasis, thereby resulting in genetically engineered cells with improved longevity, survival and/or persistence in vivo, such as for use in adoptive cell therapy methods.

Exemplary antigen receptors, including CARs, and methods for engineering and introducing such receptors into cells, include those described, for example, in WO200014257, WO2013126726, WO2012/129514, WO2014031687, WO2013/166321, WO2013/071154, WO2013/123061, U.S. patent app. Pub. Nos. US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent app. No. EP2537416, and/or those described by Sadelain et al., Cancer Discov. 2013 April; 3 (4): 388-398; Davila et al. (2013) PLOS ONE 8 (4): e61338; Turtle et al., Curr. Opin. Immunol., 2012 October; 24 (5): 633-39; Wu et al., Cancer, 2012 Mar. 18 (2): 160-75. In some aspects, the antigen receptors include a CAR as described in U.S. Pat. No. 7,446,190, and those described in WO/2014055668.

Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., (2013) Nature Reviews Clinical Oncology, 10, 267-276; Wang et al. (2012) J. Immunother. 35 (9): 689-701; and Brentjens et al., Sci Transl Med. 2013 5 (177). See also WO2014031687, U.S. Pat. Nos. 8,339,645, 7,446,179, US 2013/0149337, U.S. Pat. No. 7,446,190, and 8,389,282. The recombinant receptors, such as CARs, generally include an extracellular antigen binding domain, such as a portion of an antibody molecule, generally a variable heavy (VH) chain region and/or variable light (VL) chain region of the antibody, e.g., an scFv antibody fragment. In some embodiments, the antigen binding domain of the CAR molecule comprises an antibody, an antibody fragment, an scFv, a Fv, a Fab, a (Fab') 2, a single domain antibody (SdAb), a VH or VL domain, or a camelid VHH domain.

In some embodiments, the antigen targeted by the receptor is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In some embodiments, the antigen targeted by the receptor includes antigens associated with a B cell malignancy, such as any of a number of known B cell marker. In some embodiments, the antigen targeted by the receptor is CD20, CD19, CD22, ROR1, CD45, CD47, CD21, CD5, CD33, Igkappa, Iglambda, CD79a, CD79b or CD30.

In some embodiments, the chimeric antigen receptor includes an extracellular portion containing an antibody or antibody fragment. In some aspects, the chimeric antigen receptor includes an extracellular portion containing the antibody or fragment and an intracellular signaling domain. In some embodiments, the antibody or fragment includes an scFv.

In some embodiments, the antigen targeted by the antigen-binding domain is CD19. In some aspects, the antigen-binding domain of the recombinant receptor, e.g., CAR, and the antigen-binding domain binds, such as specifically binds or specifically recognizes, a CD19, such as a human CD19. In some embodiments, the scFv contains a VH and a VL derived from an antibody or an antibody fragment specific to CD19. In some embodiments, the antibody or antibody fragment that binds CD19 is a mouse derived antibody such as FMC63 and SJ25C1. In some embodiments, the antibody or antibody fragment is a human antibody, e.g., as described in U.S. Patent Publication No. US 2016/0152723.

In some embodiments, the antigen is CD19. In some embodiments, the scFv contains a VH and a VL derived from an antibody or an antibody fragment specific to CD 19. In some embodiments, the antibody or antibody fragment that binds CD 19 is a mouse derived antibody such as FMC63 and SJ25C1. In some embodiments, the antibody or antibody fragment is a human antibody, e.g., as described in U.S. Patent Publication No. US 2016/0152723.

In some embodiments, the scFv is derived from FMC63. FMC63 generally refers to a mouse monoclonal IgGI antibody raised against Nalm-1 and -16 cells expressing CD19 of human origin (Fing, N. R., et al. (1987). Leucocyte typing III. 302).

In some embodiments, the antigen targeted by the antigen-binding domain is BCMA. In some aspects, the antigen-binding domain of the recombinant receptor, e.g., CAR, and the antigen-binding domain binds, such as specifically binds or specifically recognizes, a BCMA, such as a human BCMA. In some embodiments, the antigen-binding domain is a fully human VH sdAb disclosed in US2020/0138865 (disclosed herein by reference in its entirety), e.g., FHVH74, FHVH32, FHVH33, or FHVH93.

In some embodiments, the CD19 specific CAR includes an anti-CD19 single-chain antibody fragment (scFv), a transmembrane domain such as one derived from human CD8α, a 4-1BB (CD137) co-stimulatory signaling domain, and a CD3ζ signaling domain. In some embodiments, the CD22 specific CAR includes an anti-CD22 scFv, a transmembrane domain such as one derived from human CD8α, a 4-1BB (CD137) co-stimulatory signaling domain, and a CD34 signaling domain. In some embodiments, the CD19/CD22-bispecific CAR includes an anti-CD19 scFv, an anti-CD22 scFv, a transmembrane domain such as one derived from human CD8α, a 4-1BB (CD137) co-stimulatory signaling domain, and a CD3ζ signaling domain.

In some embodiments, the CAR comprises a commercial CAR construct carried by a T cell. Non-limiting examples of commercial CAR-T cell based therapies include brexucabtagene autoleucel (TECARTUS®), axicabtagene ciloleucel (YESCARTA®), idecabtagene vicleucel (ABECMA®), lisocabtagene maraleucel (BREYANZI®), tisagenlecleucel (KYMRIAH®), Descartes-08 and Descartes-11 from Cartesian Therapeutics, CTL110 from Novartis, P-BMCA-101 from Poseida Therapeutics, AUTO4 from Autolus Limited, UCARTCS from Cellectis, PBCAR19B and PBCAR269A from Precision Biosci-ences, FT819 from Fate Therapeutics, and CYAD-211 from Clyad Oncology.

In some embodiments, a chimeric antigen receptor (CAR) comprises an antigen binding domain. In some embodiments, the CAR is or comprises a first generation CAR comprising an antigen binding domain, a transmembrane domain, and at least one signaling domain (e.g., one, two or three signaling domains). In some embodiments, the CAR comprises a second generation CAR comprising an antigen binding domain, a transmembrane domain, and at least two signaling domains. In some embodiments, the CAR comprises a third generation CAR comprising an antigen binding domain, a transmembrane domain, and at least three signaling domains. In some embodiments, a fourth generation CAR comprising an antigen binding domain, a transmembrane domain, three or four signaling domains, and a domain which upon successful signaling of the CAR induces expression of a cytokine gene. In some embodiments, the antigen binding domain is or comprises an antibody, an antibody fragment, an scFv or a Fab.

1. Antigen Binding Domain (ABD) Targets an Antigen Characteristic of a Neo-Plastic or Cancer Cell In some embodiments, the antigen binding domain (ABD) targets an antigen characteristic of a neoplastic cell. In other words, the antigen binding domain targets an antigen expressed by a neoplastic or cancer cell. In some embodiments, the ABD binds a tumor associated antigen. In some embodiments, the antigen characteristic of a neoplastic cell (e.g., antigen associated with a neoplastic or cancer cell) or a tumor associated antigen is selected from a cell surface receptor, an ion channel-linked receptor, an enzyme-linked receptor, a G protein-coupled receptor, receptor tyrosine kinase, tyrosine kinase associated receptor, receptor-like tyrosine phosphatase, receptor serine/threonine kinase, receptor guanylyl cyclase, histidine kinase associated receptor, epidermal growth factor receptors (EGFR) (including ErbB1/EGFR, ErbB2/HER2, ErbB3/HER3, and ErbB4/HER4), fibroblast growth factor receptors (FGFR) (including FGF1, FGF2, FGF3, FGF4, FGF5, FGF6, FGF7, FGF18, and FGF21), vascular endothelial growth factor receptors (VEGFR) (including VEGF-A, VEGF-B, VEGF-C, VEGF-D, and PlGF), RET Receptor and the Eph Receptor Family (including EphA1, EphA2, EphA3, EphA4, EphA5, EphA6, EphA7, EphA8, EphA9, EphA10, EphB1, EphB2. EphB3, EphB4, and EphB6), CXCR1, CXCR2, CXCR3, CXCR4, CXCR6, CCR1, CCR2, CCR3, CCR4, CCR5, CCR6, CCR8, CFTR, CIC-1, CIC-2, CIC-4, CIC-5, CIC-7, CIC-Ka, CIC-Kb, Bestrophins, TMEM16A, GABA receptor, glycin receptor, ABC transporters, NAV1.1, NAV1.2, NAV1.3, NAV1.4, NAV1.5, NAV1.6, NAV1.7, NAV1.8, NAV1.9, sphingosin-1-phosphate receptor (S1P1R), NMDA channel, transmembrane protein, multi-span transmembrane protein, T-cell receptor motifs, T-cell alpha chains, T-cell β chains, T-cell γ chains, T-cell δ chains, CCR7, CD3, CD4, CD5, CD7, CD8, CD11b, CD11c, CD16, CD19, CD20, CD21, CD22, CD25, CD28, CD34, CD35, CD40, CD45RA, CD45RO, CD52, CD56, CD62L, CD68, CD80, CD95, CD117, CD127, CD133, CD137 (4-1BB), CD163, F4/80, IL-4Ra, Sca-1, CTLA-4, GITR, GARP, LAP, granzyme B, LFA-1, transferrin receptor, NKp46, perforin, CD4+, Th1, Th2, Th17, Th40, Th22, Th9, Tfh, canonical Treg. FoxP3+, Tr1, Th3, Treg17, TREG; CDCP, NT5E, EpCAM, CEA, gpA33, mucins, TAG-72, carbonic anhydrase IX, PSMA, folate binding protein, gangliosides (e.g., CD2, CD3, GM2), Lewis-γ$^2$, VEGF, VEGFR 1/2/3, αVβ3, α5β1, ErbB1/EGFR, ErbB1/HER2, ErB3, c-MET, IGF1R, EphA3, TRAIL-R1, TRAIL-R2, RANKL, FAP, Tenascin, PDL-1, BAFF, HDAC, ABL, FLT3, KIT, MET, RET, IL-1β, ALK, RANKL, mTOR, CTLA-4, IL-6, IL-6R, JAK3, BRAF, PTCH, Smoothened, PlGF, ANPEP, TIMP1, PLAUR, PTPRJ, LTBR, ANTXR1, folate receptor alpha (FRa), ERBB2 (Her2/neu), EphA2, IL-13Ra2, epidermal growth factor receptor (EGFR), mesothelin, TSHR, CD19, CD123, CD22, CD30, CD171, CS-1, CLL-1, CD33, EGFRvIII, GD2, GD3, BCMA, MUC16 (CA125), L1CAM, LeY, MSLN, IL13Rx1, L1-CAM, Tn Ag, prostate specific membrane antigen (PSMA), ROR1, FLT3, FAP, TAG72, CD38, CD44v6, CEA, EPCAM, B7H3, KIT, interleukin-11 receptor a (IL-11Ra), PSCA, PRSS21, VEGFR2, LewisY, CD24, platelet-derived growth factor receptor-beta (PDGFR-beta), SSEA-4, CD20, MUC1, NCAM, Prostase, PAP, ELF2M, Ephrin B2, IGF-1 receptor, CAIX, LMP2, gp100, bcr-abl, tyrosinase, Fucosyl GM1, sLe, GM3, TGS5, HMWMAA, o-acetyl-GD2, folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, ETV6-AML, sperm protein 17, XAGE1, Tie 2, MAD-CT-1, MAD-CT-2, major histocompatibility complex class I-related gene protein (MR1), uro-kinase-type plasminogen activator receptor (uPAR), Fos-related antigen 1, p53, p53 mutant, prostein, survivin, telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, androgen receptor, cyclin B1, MYCN, RhoC, TRP-2, CYPIB I, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, a neoantigen, CD133, CD15, CD184, CD24, CD56, CD26, CD29, CD44, HLA-A, HLA-B, HLA-C, (HLA-A,B,C)

CD49f, CD151 CD340, CD200, tkrA, trkB, or trkC, or an antigenic fragment or antigenic portion thereof.

2. ABD Targets an Antigen Characteristic of a T Cell

In some embodiments, the antigen binding domain targets an antigen characteristic of a T cell. In some embodiments, the ABD binds an antigen associated with a T cell. In some instances, such an antigen is expressed by a T cell or is located on the surface of a T cell. In some embodiments, the antigen characteristic of a T cell or the T cell associated antigen is selected from a cell surface receptor, a membrane transport protein (e.g., an active or passive transport protein such as, for example, an ion channel protein, a pore-forming protein, etc.), a transmembrane receptor, a membrane enzyme, and/or a cell adhesion protein characteristic of a T cell. In some embodiments, an antigen characteristic of a T cell may be a G protein-coupled receptor, receptor tyrosine kinase, tyrosine kinase associated receptor, receptor-like tyrosine phosphatase, receptor serine/threonine kinase, receptor guanylyl cyclase, histidine kinase associated receptor, AKT1; AKT2; AKT3; ATF2; BCL10; CALM1; CD3D (CD3δ); CD3E (CD3ε); CD3G (CD3γ); CD4; CD8; CD28; CD45; CD80 (B7-1); CD86 (B7-2); CD247 (CD3ζ); CTLA-4 (CD152); ELK1; ERK1 (MAPK3); ERK2; FOS; FYN; GRAP2 (GADS); GRB2; HLA-DRA; HLA-DRB1; HLA-DRB3; HLA-DRB4; HLA-DRB5; HRAS; IKBKA (CHUK); IKBKB; IKBKE; IKBKG (NEMO); IL2; ITPR1; ITK; JUN; KRAS2; LAT; LCK; MAP2K1 (MEK1); MAP2K2 (MEK2); MAP2K3 (MKK3); MAP2K4 (MKK4); MAP2K6 (MKK6); MAP2K7 (MKK7); MAP3K1 (MEKK1); MAP3K3; MAP3K4; MAP3K5; MAP3K8; MAP3K14 (NIK); MAPK8 (JNK1); MAPK9 (JNK2); MAPK10 (JNK3); MAPK11 (p38β); MAPK12 (p38γ); MAPK13 (p38δ); MAPK14 (p38α); NCK; NFAT1; NFAT2; NFKB1; NFKB2; NFKBIA; NRAS; PAK1; PAK2; PAK3; PAK4; PIK3C2B; PIK3C3 (VPS34); PIK3CA; PIK3CB; PIK3CD; PIK3R1; PKCA; PKCB; PKCM; PKCQ; PLCY1; PRF1 (Perforin); PTEN; RAC1; RAF1; RELA; SDF1; SHP2; SLP76; SOS; SRC; TBK1; TCRA; TEC; TRAF6; VAV1; VAV2; or ZAP70.

3. ABD Targets an Antigen Characteristic of an Autoimmune or Inflammatory DisOrder In some embodiments, the antigen binding domain targets an antigen characteristic of an autoimmune or inflammatory disorder. In some embodiments, the ABD binds an antigen associated with an autoimmune or inflammatory disorder. In some instances, the antigen is expressed by a cell associated with an autoimmune or inflammatory disorder. In some embodiments, the autoimmune or inflammatory disorder is selected from chronic graft-vs-host disease (GVHD), lupus, arthritis, immune complex glomerulone-phritis, goodpasture syndrome, uveitis, hepatitis, systemic sclerosis or sclero-derma, type I diabetes, multiple sclerosis, cold agglutinin disease, Pemphigus vulgaris, Grave's disease, autoimmune hemolytic anemia, Hemophilia A, Primary Sjogren's Syn-drome, thrombotic thrombocytopenia purrpura, neuromy-elits optica, Evan's syndrome, IgM mediated neuropathy, cryoglobulinemia, dermatomyositis, idiopathic thrombocy-topenia, ankylosing spondylitis, bullous pemphigoid, acquired angioedema, chronic urticarial, antiphospholipid demyelinating polyneuropathy, and autoimmune thrombo-cytopenia or neutropenia or pure red cell aplasias, while exemplary non-limiting examples of alloim-mune diseases include allosensitization (see, for example, Blazar et al., 2015, Am. J. Transplant, 15 (4): 931-41) or xenosensitiza-tion from hematopoietic or solid organ transplantation, blood transfusions, pregnancy with fetal allosensitization, neonatal alloim-mune thrombocytopenia, hemolytic disease of the newborn, sensitization to foreign antigens such as can occur with replacement of inherited or acquired deficiency disorders treated with enzyme or protein replacement therapy, blood products, and gene therapy. In some embodi-ments, the antigen characteristic of an autoimmune or inflammatory disorder is selected from a cell surface recep-tor, an ion channel-linked receptor, an en-zyme-linked receptor, a G protein-coupled receptor, receptor tyrosine kinase, tyrosine kinase associated receptor, receptor-like tyrosine phosphatase, receptor serine/threonine kinase, receptor guanylyl cyclase, or histidine kinase associated receptor. In some embodiments, an antigen binding domain of a CAR binds to a ligand expressed on B cells, plasma cells, or plasmablasts. In some embodiments, an antigen binding domain of a CAR binds to CD10, CD19, CD20, CD22, CD24, CD27, CD38, CD45R, CD138, CD319, BAFFR, BCMA, CD28, TNF, interferon receptors, GM-CSF, ZAP-70, LFA-1, CD3 gamma, CD5 or CD2. See, e.g., US 2003/0077249; WO 2017/058753; WO 2017/058850, the contents of which are herein incorporated by reference.

4. ABD Targets an Antigen Characteristic of Senescent Cells

In some embodiments, the antigen binding domain targets an antigen characteristic of senescent cells, e.g., urokinase-type plasminogen activator receptor (uPAR). In some embodiments, the ABD binds an antigen associated with a senescent cell. In some instances, the antigen is expressed by a senescent cell. In some embodiments, the CAR may be used for treatment or prophylaxis of disorders characterized by the aberrant accumulation of senescent cells, e.g., liver and lung fibrosis, atherosclerosis, diabetes and osteoarthritis.

5. ABD Targets an Antigen Characteristic of an Infectious Disease

In some embodiments, the antigen binding domain targets an antigen characteristic of an infectious disease. In some embodiments, the ABD binds an antigen associated with an infectious disease. In some instances, the antigen is expressed by a cell affected by an infectious disease. In some embodiments, wherein the infectious disease is selected from HIV, hepatitis B virus, hepatitis C virus, Human herpes virus, Human herpes virus 8 (HHV-8, Kaposi sarcoma-associated herpes virus (KSHV)), Human T-lymphotrophic vi-rus-1 (HTLV-1), Merkel cell polyomavirus (MCV), Sim-ian virus 40 (SV40), Epstein-Barr virus, CMV, human papillomavirus. In some embodiments, the antigen charac-teristic of an infectious disease is selected from a cell surface receptor, an ion channel-linked receptor, an enzyme-linked receptor, a G protein-coupled receptor, receptor tyrosine kinase, tyrosine kinase associated receptor, receptor-like tyrosine phosphatase, receptor serine/threonine kinase, receptor guanylyl cyclase, histidine kinase associated recep-tor, HIV Env, gpl20, or CD4-induced epitope on HIV-1 Env.

6. ABD Binds to a Cell Surface Antigen of a Cell

In some embodiments, an antigen binding domain binds to a cell surface antigen of a cell. In some embodiments, a cell surface antigen is characteristic of (e.g., expressed by) a particular or specific cell type. In some embodiments, a cell surface antigen is characteristic of more than one type of cell.

In some embodiments, a CAR antigen binding domain binds a cell surface antigen characteristic of a T cell, such as a cell surface antigen on a T cell. In some embodiments, an antigen characteristic of a T cell may be a cell surface receptor, a membrane transport protein (e.g., an active or passive transport protein such as, for example, an ion channel protein, a pore-forming protein, etc.), a transmem-brane receptor, a membrane enzyme, and/or a cell adhesion protein characteristic of a T cell. In some embodiments, an antigen characteristic of a T cell may be a G protein-coupled receptor, receptor tyrosine kinase, tyrosine kinase associated receptor, receptor-like tyrosine phosphatase, receptor serine/ threonine kinase, receptor guanylyl cyclase, or histidine kinase associated receptor.

In some embodiments, an antigen binding domain of a CAR binds a T cell receptor. In some embodiments, a T cell receptor may be AKT1; AKT2; AKT3; ATF2; BCL10; CALM1; CD3D (CD30); CD3E (CD3E); CD3G (CD3γ); CD4; CD8; CD28; CD45; CD80 (B7-1); CD86 (B7-2); CD247 (CD3ζ); CTLA-4 (CD152); ELK1; ERK1 (MAPK3); ERK2; FOS; FYN; GRAP2 (GADS); GRB2; HLA-DRA; HLA-DRB1; HLA-DRB3; HLA-DRB4; HLA-DRB5; HRAS; IKBKA (CHUK); IKBKB; IKBKE; IKBKG (NEMO); IL2; ITPR1; ITK; JUN; KRAS2; LAT; LCK; MAP2K1 (MEK1); MAP2K2 (MEK2); MAP2K3 (MKK3); MAP2K4 (MKK4); MAP2K6 (MKK6); MAP2K7 (MKK7); MAP3K1 (MEKK1); MAP3K3; MAP3K4; MAP3K5; MAP3K8; MAP3K14 (NIK); MAPK8 (JNK1); MAPK9 (JNK2); MAPK10 (JNK3); MAPK11 (p38β); MAPK12 (p38γ); MAPK13 (p38δ); MAPK14 (p38α); NCK; NFAT1; NFAT2; NFKB1; NFKB2; NFKBIA; NRAS; PAK1; PAK2; PAK3; PAK4; PIK3C2B; PIK3C3 (VPS34); PIK3CA; PIK3CB; PIK3CD; PIK3R1; PKCA; PKCB; PKCM; PKCQ; PLCY1; PRF1 (Perforin); PTEN; RAC1; RAF1; RELA; SDF1; SHP2; SLP76; SOS; SRC; TBK1; TCRA; TEC; TRAF6; VAV1; VAV2; or ZAP70.

7. Transmembrane Domain

In some embodiments, the CAR transmembrane domain comprises at least a transmembrane region of the alpha, beta or zeta chain of a T cell receptor, CD28, CD3 epsilon, CD45, CD4, CD5, CD8, CD9, CD16, CD22, CD33, CD37, CD64, CD80, CD86, CD134, CD137, CD154, or functional variant thereof. In some embodiments, the transmembrane domain comprises at least a transmembrane region(s) of CD8α, CD8β, 4-1BB/CD137, CD28, CD34, CD4, FcεRIγ, CD16, OX40/CD134, CD3ζ, CD3δ, CD3γ, CD3δ, TCRα, TCRβ, TCRζ, CD32, CD64, CD64, CD45, CD5, CD9, CD22, CD37, CD80, CD86, CD40, CD40L/CD154, VEGFR2, FAS, and FGFR2B, or functional variant thereof. antigen binding domain binds

8. Signaling Domain or Plurality of Signaling Domains

In some embodiments, a CAR described herein comprises one or at least one signaling domain selected from one or more of B7-1/CD80; B7-2/CD86; B7-H1/PD-L1; B7-H2; B7-H3; B7-H4; B7-H6; B7-H7; BTLA/CD272; CD28; CTLA-4; Gi24/VISTA/B7-H5; ICOS/CD278; PD-1; PD-L2/B7-DC; PDCD6); 4-1BB/TNFSF9/CD137; 4-1BB Lig-and/TNFSF9; BAFF/BLyS/TNFSF13B; BAFF R/TNFRSF13C; CD27/TNFRSF7; CD27 Ligand/TNFSF7; CD30/TNFRSF8; CD30 Ligand/TNFSF8; CD40/TN-FRSF5; CD40/TNFSF5; CD40 Ligand/TNFSF5; DR3/TN-FRSF25; GITR/TNFRSF18; GITR Lig-and/TNFSF18; HVEM/TNFRSF14; LIGHT/TNFSF14; Lymphotoxin-al-pha/TNF-beta; OX40/TNFRSF4; OX40 Ligand/TNFSF4; RELT/TNFRSF19L; TACI/TNFRSF13B; TL1A/TNFSF15; TNF-alpha; TNF RII/TNFRSF1B); 2B4/CD244/SLAMF4; BLAME/SLAMF8; CD2; CD2F-10/SLAMF9; CD48/SLAMF2; CD58/LFA-3; CD84/SLAMF5; CD229/SLAMF3; CRACC/SLAMF7; NTB-A/SLAMF6; SLAM/CD150); CD2; CD7; CD53; CD82/Kai-1; CD90/Thyl; CD96; CD160; CD200; CD300a/LMIR1; HLA Class I; HLA-DR; Ikaros; Integrin alpha 4/CD49d; Integrin alpha 4 beta 1; Integrin alpha 4 beta 7/LPAM-1; LAG-3; TCL1A; TCL1B; CRTAM; DAP12; Dectin-1/CLEC7A; DPPIV/CD26; EphB6; TIM-1/KIM-1/HAVCR; TIM-4; TSLP; TSLP R; lymphocyte function associated antigen-1 (LFA-1); NKG2C, a CD3 zeta domain, an immunoreceptor tyro-sine-based activation motif (ITAM), CD27, CD28, 4-1BB, CD134/OX40, CD30, CD40, PD-1, ICOS, lymphocyte function-associated antigen-1 (LFA-1), CD2, CD7, LIGHT, NKG2C, B7-H3, a ligand that specifically binds with CD83, or functional fragment thereof.

In some embodiments, the at least one signaling domain comprises a CD3 zeta domain or an immunoreceptor tyro-sine-based activation motif (ITAM), or functional variant thereof. In other embodiments, the at least one signaling domain comprises (i) a CD3 zeta domain, or an immuno-receptor tyrosine-based activation motif (ITAM), or func-tional variant thereof; and (ii) a CD28 domain, or a 4-1BB domain, or functional variant thereof. In yet other embodi-ments, the at least one signaling domain comprises a (i) a CD3 zeta domain, or an immunoreceptor tyrosine-based activation motif (ITAM), or functional variant thereof; (ii) a CD28 domain or functional variant thereof; and (iii) a 4-1BB domain, or a CD134 domain, or functional variant thereof. In some embodiments, the at least one signaling domain comprises a (i) a CD3 zeta domain, or an immuno-receptor tyrosine-based activation motif (ITAM), or func-tional variant thereof; (ii) a CD28 domain or func-tional variant thereof; (iii) a 4-1BB domain, or a CD134 domain, or functional variant thereof; and (iv) a cytokine or costimu-latory ligand transgene.

In some embodiments, the at least two signaling domains comprise a CD3 zeta domain or an immunoreceptor tyro-sine-based activation motif (ITAM), or functional variant thereof. In other embodiments, the at least two signaling domains comprise (i) a CD3 zeta domain, or an immuno-receptor tyrosine-based activation motif (ITAM), or func-tional variant thereof; and (ii) a CD28 domain, or a 4-1BB domain, or functional variant thereof.

In yet other embodiments, the at least one signaling domain comprises a (i) a CD3 zeta domain, or an immuno-receptor tyrosine-based activation motif (ITAM), or func-tional variant thereof; (ii) a CD28 domain or functional variant thereof; and (iii) a 4-1BB domain, or a CD134 domain, or functional variant thereof. In some embodiments, the at least two signaling domains comprise a (i) a CD3 zeta domain, or an immunoreceptor tyrosine-based activation motif (ITAM), or functional variant thereof; (ii) a CD28 domain or func-tional variant thereof; (iii) a 4-1BB domain, or a CD134 domain, or functional variant thereof; and (iv) a cytokine or costimulatory ligand transgene.

In some embodiments, the at least three signaling domains comprise a CD3 zeta domain or an immunoreceptor tyrosine-based activation motif (ITAM), or functional vari-ant thereof. In other embodiments, the at least three signal-ing domains comprise (i) a CD3 zeta domain, or an immu-noreceptor tyrosine-based activation motif (ITAM), or functional variant thereof; and (ii) a CD28 domain, or a 4-1BB domain, or functional variant thereof. In yet other embodiments, the least three signaling domains comprises a (i) a CD3 zeta domain, or an immunoreceptor tyrosine-based activation motif (ITAM), or functional variant thereof; (ii) a CD28 domain or functional variant thereof; and (iii) a 4-1BB domain, or a CD134 domain, or functional variant thereof. In some embodiments, the at least three signaling domains comprise a (i) a CD3 zeta domain, or an immuno-receptor tyrosine-based activation motif (ITAM), or func-tional variant thereof; (ii) a CD28 domain or func-tional variant thereof; (iii) a 4-1BB domain, or a CD134 domain, or functional variant thereof; and (iv) a cytokine or costimu-latory ligand transgene.

In some embodiments, the CAR comprises a CD3 zeta domain or an immunoreceptor tyrosine-based activation motif (ITAM), or functional variant thereof. In some embodiments, the CAR comprises (i) a CD3 zeta domain, or an immunoreceptor tyrosine-based activation motif (ITAM), or functional variant thereof; and (ii) a CD28 domain, or a 4-1BB domain, or functional variant thereof.

In some embodiments, the CAR comprises a (i) a CD3 zeta domain, or an immunoreceptor tyrosine-based activation motif (ITAM), or functional variant thereof; (ii) a CD28 domain or functional variant thereof; and (iii) a 4-1BB domain, or a CD134 domain, or functional variant thereof.

In some embodiments, the CAR comprises (i) a CD3 zeta domain, or an immunoreceptor tyrosine-based activation motif (ITAM), or functional variant thereof; (ii) a CD28 domain, or a 4-1BB domain, or functional variant thereof, and/or (iii) a 4-1BB domain, or a CD134 domain, or functional variant thereof.

In some embodiments, the CAR comprises a (i) a CD3 zeta domain, or an immunoreceptor tyrosine-based activation motif (ITAM), or functional variant thereof; (ii) a CD28 domain or functional variant thereof; (iii) a 4-1BB domain, or a CD134 domain, or func-tional variant thereof; and (iv) a cytokine or costimulatory ligand transgene.

9. Domain which Upon Successful Signaling of the CAR Induces Expression of a Cytokine Gene In some embodiments, a first, second, third, or fourth generation CAR further comprises a domain which upon successful signaling of the CAR induces expression of a cytokine gene. In some embodiments, a cytokine gene is endogenous or exogenous to a target cell comprising a CAR which comprises a domain which upon successful signaling of the CAR induces expression of a cytokine gene. In some embodiments, a cytokine gene encodes a pro-inflammatory cytokine. In some embodiments, a cytokine gene encodes IL-1, IL-2, IL-9, IL-12, IL-18, TNF, or IFN-gamma, or functional fragment thereof. In some embodiments, a domain which upon successful signaling of the CAR induces expression of a cytokine gene is or comprises a transcription factor or functional domain or fragment thereof. In some embodiments, a domain which upon successful signaling of the CAR induces expression of a cytokine gene is or comprises a transcription factor or functional domain or fragment thereof. In some embodiments, a transcription factor or functional domain or fragment thereof is or com-prises a nuclear factor of activated T cells (NFAT), an NF-kB, or functional domain or fragment thereof. See, e.g., Zhang. C. et al., Engineering CAR-T cells. Biomarker Research. 5:22 (2017); WO 2016126608; Sha, H. et al. Chimaeric antigen receptor T-cell therapy for tumour immu-notherapy. Bio-science Reports Jan. 27, 2017, 37 (1).

In some embodiments, the CAR further comprises one or more spacers, e.g., wherein the spacer is a first spacer between the antigen binding domain and the transmembrane domain. In some embodiments, the first spacer includes at least a portion of an immunoglobulin constant region or variant or modified version thereof. In some embodiments, the spacer is a second spacer between the transmembrane domain and a signaling domain. In some embodiments, the second spacer is an oligopeptide, e.g., wherein the oligo-peptide comprises glycine and serine residues such as but not limited to glycine-serine doublets. In some embodi-ments, the CAR comprises two or more spacers, e.g., a spacer between the antigen binding domain and the trans-membrane domain and a spacer between the transmembrane domain and a signaling domain.

In some embodiments, any one of the cells described herein comprises a nucleic acid encoding a CAR or a first generation CAR. In some embodiments, a first generation CAR comprises an antigen binding domain, a transmem-brane domain, and signaling domain. In some embodiments, a signaling domain mediates downstream signaling during T cell activation.

In some embodiments, the methods and compositions disclosed herein comprise a nucleic acid encoding a CAR or a second generation CAR. In some embodiments, a second generation CAR comprises an antigen binding domain, a transmembrane domain, and two signaling domains. In some embodiments, a signaling domain mediates downstream signaling during T cell activation. In some embodiments, a signaling domain is a costimulatory domain. In some embodiments, a costimulatory domain enhances cytokine production, CAR-T cell proliferation, and/or CAR-T cell persistence during T cell activation.

In some embodiments, any one of the compositions and methods described herein comprises a nucleic acid encoding a CAR or a third generation CAR. In some embodiments, a third generation CAR comprises an antigen binding domain, a transmembrane domain, and at least three signaling domains. In some embodiments, a signaling domain medi-ates downstream signaling during T cell activation. In some embodiments, a signaling domain is a costimulatory domain. In some embodiments, a costimulatory domain enhances cytokine production, CAR-T cell proliferation, and or CAR-T cell persistence during T cell activation. In some embodiments, a third generation CAR comprises at least two costimulatory domains. In some embodiments, the at least two costimulatory domains are not the same.

In some embodiments, any one of the compositions and methods described herein comprises a nucleic acid encoding a CAR or a fourth generation CAR. In some embodiments, a fourth generation CAR comprises an antigen binding domain, a transmembrane domain, and at least two, three, or four signaling domains. In some embodiments, a signaling domain mediates downstream signaling during T cell acti-vation. In some embodiments, a signaling domain is a costimulatory domain. In some embodiments, a costimula-tory domain enhances cytokine production, CAR-T cell proliferation, and or CAR-T cell persistence during T cell activation.

10. ABD comprising an antibody or antigen-binding portion thereof.

In some embodiments, a CAR antigen binding domain is or comprises an antibody or antigen-binding portion thereof. In some embodiments, a CAR antigen binding domain is or comprises an scFv or Fab. In some embodiments, a CAR antigen binding domain comprises an scFv or Fab fragment of a CD19 antibody; CD22 antibody; T-cell alpha chain antibody; T-cell β chain antibody; T-cell γ chain antibody; T-cell δ chain antibody; CCR7 antibody; CD3 antibody; CD4 antibody; CD5 antibody; CD7 antibody; CD8 anti-body; CD11b antibody; CD11c antibody; CD16 antibody; CD20 antibody; CD21 antibody; CD25 antibody; CD28 antibody; CD34 antibody; CD35 antibody; CD40 antibody; CD45RA antibody; CD45RO antibody; CD52 antibody; CD56 antibody; CD62L antibody; CD68 antibody; CD80 antibody; CD95 antibody; CD117 antibody; CD127 anti-body; CD133 antibody; CD137 (4-1 BB) antibody; CD163 antibody; F4/80 antibody; IL-4Ra antibody; Sca-1 antibody; CTLA-4 antibody; GITR antibody GARP antibody; LAP antibody; granzyme B antibody; LFA-1 antibody; MR1 antibody; uPAR antibody; or transferrin receptor antibody.

In some embodiments, a CAR comprises a signaling domain which is a costimulatory domain. In some embodiments, a CAR comprises a second costimulatory domain. In some embodiments, a CAR comprises at least two costimulatory domains. In some embodiments, a CAR comprises at least three costimulatory domains. In some embodiments, a CAR comprises a costimulatory domain selected from one or more of CD27, CD28, 4-1BB, CD134/OX40, CD30, CD40, PD-1, ICOS, lymphocyte function-associated antigen-1 (LFA-1), CD2, CD7, LIGHT, NKG2C, B7-H3, a ligand that specifically binds with CD83. In some embodiments, if a CAR comprises two or more costimulatory domains, two costimulatory domains are different. In some embodiments, if a CAR comprises two or more costimulatory domains, two costimulatory domains are the same.

In addition to the CARs described herein, various chimeric antigen receptors and nucleotide sequences encoding the same are known in the art and would be suitable for fu-sosomal delivery and reprogramming of target cells in vivo and in vitro as described herein. See, e.g., WO2013040557; WO2012079000; WO2016030414; Smith T, et al., Nature Nanotechnology. 2017. DOI: 10.1038/NNANO.2017.57, the disclosures of which are herein incorporated by reference.

11. Additional Descriptions of CARs

In certain embodiments, the compositions and methods may comprise a polynucleotide encoding a CAR. CARs (also known as chimeric immunoreceptors, chimeric T cell receptors, or artificial T cell receptors) are receptor proteins that have been engineered to give host cells (e.g., T cells) the new ability to target a specific protein. The receptors are chimeric because they combine both antigen-binding and T cell activating functions into a single receptor. The polycistronic vector of the present disclosure may be used to express one or more CARs in a host cell (e.g., a T cell) for use in therapies against various target antigens. The CARs expressed by the one or more expression cassettes may be the same or different. In these embodiments, the CAR may comprise an extracellular binding domain (also referred to as a "binder") that specifically binds a target antigen, a transmembrane domain, and an intracellular signaling domain. In certain embodiments, the CAR may further comprise one or more additional elements, including one or more signal peptides, one or more extracellular hinge domains, and/or one or more intracellular costimulatory domains. Domains may be directly adjacent to one another, or there may be one or more amino acids linking the domains. The nucleotide sequence encoding a CAR may be derived from a mammalian sequence, for example, a mouse sequence, a primate sequence, a human sequence, or combinations thereof. In the cases where the nucleotide sequence encoding a CAR is non-human, the sequence of the CAR may be humanized. The nucleotide sequence encoding a CAR may also be codon-optimized for expression in a mammalian cell, for example, a human cell. In any of these embodiments, the nucleotide sequence encoding a CAR may be at least 80% identical (e.g., at least 80%, at least 85%, at least 90%, at least 95%, at least 96%, at least 97%, at least 98%, at least 99%, or 100% identical) to any of the nucleotide sequences disclosed herein. The sequence variations may be due to codon-optimalization, humanization, restriction enzyme-based cloning scars, and/or additional amino acid residues linking the functional domains, etc.

In certain embodiments, the CAR may comprise a signal peptide at the N-terminus. Non-limiting examples of signal peptides include CD8α signal peptide, IgK signal peptide, and granulocyte-macrophage colony-stimulating factor receptor subunit alpha (GMCSFR-α, also known as colony stimulating factor 2 receptor subunit alpha (CSF2RA)) signal peptide, and variants thereof, the amino acid sequences of which are provided in Table A below.

TABLE A

| Exemplary sequences of signal peptides | | |
| --- | --- | --- |
| SEQ ID NO: | Sequence | Description |
| 1106 | MALPVTALLLPLALLLHAARP | CD8α signal peptide |
| 1107 | METDTLLLWVLLLWVPGSTG | IgK signal peptide |
| 1108 | MLLLVTSLLLCELPHPAFLLIP | GMCSFR-α (CSF2RA) signal peptide |
| 1090 | MEFGLSWLFLVAILKGVQCSR | Immunoglobulin heavy chain signal peptide |

In certain embodiments, the extracellular binding domain of the CAR may comprise one or more antibodies specific to one target antigen or multiple target antigens. The antibody may be an antibody fragment, for example, an scFv, or a single-domain antibody fragment, for example, a VHH. In certain embodiments, the scFv may comprise a heavy chain variable region ($V_H$) and a light chain variable region ($V_L$) of an antibody connected by a linker. The VH and the VL may be connected in either order, i.e., $V_H$-linker-$V_L$ or $V_L$-linker-$V_H$. Non-limiting examples of linkers include Whitlow linker, (G4S) n (n can be a positive integer, e.g., 1, 2, 3, 4, 5, 6, etc.) linker, and variants thereof. In certain embodiments, the antigen may be an antigen that is exclusively or preferentially expressed on tumor cells, or an antigen that is characteristic of an autoimmune or inflammatory disease. Exemplary target antigens include, but are not limited to, CD5, CD19, CD20, CD22, CD23, CD30, CD70, Kappa, Lambda, and B cell maturation agent (BCMA), G-protein coupled receptor family C group 5 member D (GPRC5D) (associated with leukemias); CS1/SLAMF7, CD38, CD138, GPRC5D, TACI, and BCMA (associated with myelomas); GD2, HER2, EGFR, EGFRvIII, B7H3, PSMA, PSCA, CAIX, CD171, CEA, CSPG4, EPHA2, FAP, FRa, IL-13Ra, Mesothelin, MUC1, MUC16, and ROR1 (associated with solid tumors). In any of these embodiments, the extracellular binding domain of the CAR can be codon-optimized for expression in a host cell or have variant sequences to increase functions of the extracellular binding domain.

In certain embodiments, the CAR may comprise a hinge domain, also referred to as a spacer. The terms "hinge" and "spacer" may be used interchangeably in the present disclosure. Non-limiting examples of hinge domains include CD8α hinge domain, CD28 hinge domain, IgG4 hinge domain, IgG4 hinge-CH2-CH3 domain, and variants thereof, the amino acid sequences of which are provided in Table B below.

TABLE B

Exemplary sequences of hinge domains

| SEQ ID NO: | Sequence | Description |
|---|---|---|
| 1109 | TTTPAPRPPTPAPTI-ASQPLSLRPEACRPAAGGAVHTRGLDFACD | CD8α hinge domain |
| 1110 | IEVMYPPPYLDNEKSNGTIIHVKGKHLCP-SPLFPGPSKP | CD28 hinge domain |
| 1091 | AAAIEVMYPPPYLDNEKSNGTIIHVKGKHLCP-SPLFPGPSKP | CD28 hinge domain |
| 1111 | ESKYGPPCPPCP | IgG4 hinge domain |
| 1112 | ESKYGPPCPSCP | IgG4 hinge domain |
| 1113 | ESKYGPPCPPCPAPEFLGGPSVFLFPPKPKD-TLMISRTPEVTCVVVDVSQEDPEVQFNWY-VDGVEVHNAKTKPREEQFNSTYRVVSVLTVL-HQDWLNGKEYKCKVSNKGLPSSIEK-TISKAKGQPREPQVYTLPP-SQEEMTKNQVSLTCLVKGFYPSDIAVEWESN-GQPENNYKTTPPVLDSDGSFFLYSRL-TVDKSRWQEGNVFSCSVM-HEALHNHYTQKSLSLSLGK | IgG4 hinge-CH2-CH3 domain |

In certain embodiments, the transmembrane domain of the CAR may comprise a transmembrane region of the alpha, beta, or zeta chain of a T cell receptor, CD28, CD38, CD45, CD4, CD5, CD8, CD9, CD16, CD22, CD33, CD37, CD64, CD80, CD86, CD134, CD137, CD154, or a functional variant thereof, including the human versions of each of these sequences. In other embodiments, the transmembrane domain may comprise a transmembrane region of CD8α, CD8β, 4-1BB/CD137, CD28, CD34, CD4, FcεRIγ, CD16, OX40/CD134, CD3ζ, CD3ε, CD3γ, CD3δ, TCRα, TCRβ, TCRζ, CD32, CD64, CD64, CD45, CD5, CD9, CD22, CD37, CD80, CD86, CD40, CD40L/CD154, VEGFR2, FAS, and FGFR2B, or a functional variant thereof, including the human versions of each of these sequences. Table C provides the amino acid sequences of a few exemplary transmembrane domains.

TABLE C

Exemplary sequences of transmembrane domains

| SEQ ID NO: | Sequence | Description |
|---|---|---|
| 1114 | IYIWAPLAGTCGVLLLSLVITLYC | CD8α transmembrane domain |
| 1115 | FWVLVVVGGVLACYSLLVTVAFII FWV | CD28 transmembrane domain |
| 1214 | MFWVLVVVGGVLACYSLLVTVAFII-FWV | CD28 transmembrane domain |

In certain embodiments, the intracellular signaling domain and/or intracellular costimulatory domain of the CAR may comprise one or more signaling domains selected from B7-1/CD80, B7-2/CD86, B7-H1/PD-L1, B7-H2, B7-H3, B7-H4, B7-H6, B7-H7, BTLA/CD272, CD28, CTLA-4, Gi24/VISTA/B7-H5, ICOS/CD278, PD-1, PD-L2/B7-DC, PDCD6, 4-1BB/TNFSF9/CD137, 4-1BB Ligand/TNFSF9, BAFF/BLyS/TNFSF13B, BAFF R/TNFRSF13C, CD27/TNFRSF7, CD27 Ligand/TNFSF7, CD30/TNFRSF8, CD30 Lig-and/TNFSF8, CD40/TNFRSF5, CD40/TNFSF5, CD40 Ligand/TNFSF5, DR3/TNFRSF25, GITR/TNFRSF18, GITR Ligand/TNFSF18, HVEM/TNFRSF14, LIGHT/TNFSF14, Lymphotoxin-alpha/TNFβ, OX40/TNFRSF4, OX40 Ligand/TNFSF4, RELT/TNFRSF19L, TACI/TNFRSF13B, TL1A/TNFSF15, TNFα, TNF RII/TNFRSF1B, 2B4/CD244/SLAMF4, BLAME/SLAMF8, CD2, CD2F-10/SLAMF9, CD48/SLAMF2, CD58/LFA-3, CD84/SLAMF5, CD229/SLAMF3, CRACC/SLAMF7, NTB-A/SLAMF6, SLAM/CD150, CD2, CD7, CD53, CD82/Kai-1, CD90/Thy1, CD96, CD160, CD200, CD300a/LMIR1, HLA Class I, HLA-DR, Ikaros, Integrin alpha 4/CD49d, Integrin alpha 4 beta 1, Integrin alpha 4 beta 7/LPAM-1, LAG-3, TCL1A, TCL1B, CRTAM, DAP12, Dec-tin-1/CLEC7A, DPPIV/CD26, EphB6, TIM-1/KIM-1/HAVCR, TIM-4, TSLP, TSLP R, lymphocyte function associated antigen-1 (LFA-1), NKG2C, CD3ζ, an immunoreceptor tyrosine-based activation motif (ITAM), CD27, CD28, 4-1BB, CD134/OX40, CD30, CD40, PD-1, ICOS, lymphocyte function-associated antigen-1 (LFA-1), CD2, CD7, LIGHT, NKG2C, B7-H3, a ligand that specifically binds with CD83, and a functional variant thereof including the human versions of each of these sequences. In some embodiments, the intracellular signaling domain and/or intracellular costimulatory domain comprises one or more signaling domains selected from a CD3ζ domain, an ITAM, a CD28 domain, 4-1BB domain, or a functional variant thereof. Table D provides the amino acid sequences of a few exemplary intracellular costimulatory and/or signaling domains. In certain embodiments, as in the case of tisagenlecleucel as described below, the CD3ζ signaling domain of SEQ ID NO: 1118 may have a mutation, e.g., a glutamine (Q) to lysine (K) mutation, at amino acid position 14 (see SEQ ID NO:1215).

TABLE D

Exemplary sequences of intracellular costimulatory
and/or signaling domains

| SEQ ID NO: | Sequence | Description |
|---|---|---|
| 1116 | KRGRKKLLY- IFKQPFMRPVQTTQEEDGCSCRF- PEEEEGGCEL | 4-1BB costimulatory domain |
| 1117 | RSKRS- RLLHSDYMNMTPRRPGPTRKHYQPYAPPR DFAAYRS | CD28 costimulatory domain |
| 1091 | RSKRS- RGGHSDYMNMTPRRPGPTRKHYQPYA PPRDFAAYRS | CD28 costimulatory domain (LL > GG mutant) |
| 1118 | RVKFSRSADAPA- YQQGQNQLYNELNLGR- REEYDVLDKRRGRDPEMGGKPRR- KNPQEGLYNEL- QKDKMAEAYSEIGMKGERRRGKGHDGL YQGLSTATKDTYDALHMQALPPR | CD3ζ signaling domain |
| 1215 | RVKFSRSADAPA- YKQGQNQLYNELNLGR- REEYDVLDKRRGRDPEMGGKPRR- KNPQEGLYNEL- QKDKMAEAYSEIGMKGERRRGKGHDGLYQ GLSTATKDTYDALHMQALPPR | CD3ζ signaling domain (with Q to K mutation at position 14) |

In certain embodiments where the polycistronic vector encodes two or more CARs, the two or more CARs may comprise the same functional domains, or one or more different functional domains, as described. For example, the two or more CARs may comprise different signal peptides, extracellular binding domains, hinge domains, transmembrane domains, costimulatory domains, and/or intracellular signaling domains, in order to minimize the risk of recombination due to sequence similarities. Or, alternatively, the two or more CARs may comprise the same domains. In the cases where the same domain(s) and/or backbone are used, it is optional to introduce codon divergence at the nucleotide sequence level to minimize the risk of recombination.

CD19 CAR

In some embodiments, the CAR is a CD19 CAR ("CD19-CAR"), and in these embodiments, the polycistronic vector comprises an expression cassette that contains a nucleotide sequence encoding a CD19 CAR. In some embodiments, the CD19 CAR may com-prise a signal peptide, an extracellular binding domain that specifically binds CD19, a hinge domain, a transmembrane domain, an intracellular costimu-latory domain, and/or an intracellular signaling domain in tandem.

In some embodiments, the signal peptide of the CD19 CAR comprises a CD8α signal peptide. In some embodi-ments, the CD8α signal peptide comprises or consists of an amino acid sequence set forth in SEQ ID NO: 1106 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1106. In some embodiments, the signal peptide com-prises an IgK signal peptide. In some embodiments, the IgK signal peptide comprises or consists of an amino acid sequence set forth in SEQ ID NO: 1107 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1107. In some embodiments, the signal peptide comprises a GMCSFR-α or CSF2RA signal peptide. In some embodi-ments, the GMCSFR-α or CSF2RA signal peptide com-prises or consists of an amino acid sequence set forth in SEQ ID NO: 1108 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:1108.

In some embodiments, the extracellular binding domain of the CD19 CAR is specific to CD19, for example, human CD19. The extracellular binding domain of the CD19 CAR can be codon-optimized for expression in a host cell or to have variant sequences to in-crease functions of the extra-cellular binding domain. In some embodiments, the extra-cellular binding domain comprises an immunogenically active portion of an immunoglobulin molecule, for example, an scFv.

In some embodiments, the extracellular binding domain of the CD19 CAR comprises an scFv derived from the FMC63 monoclonal antibody (FMC63), which comprises the heavy chain variable region ($V_H$) and the light chain variable region ($V_L$) of FMC63 con-nected by a linker. FMC63 and the derived scFv have been described in Nich-olson et al., Mol. Immun. 34 (16-17): 1157-1165 (1997) and PCT Application Publication No. WO2018/213337, the entire contents of each of which are incorporated by refer-ence herein. In some embodiments, the amino acid sequences of the entire FMC63-derived scFv (also referred to as FMC63 scFv) and its different portions are provided in Table E below. In some embodiments, the CD19-specific scFv comprises or consists of an amino acid sequence set forth in SEQ ID NO: 1075, 1119, 1120, or 1125, or an amino acid sequence that is at least 80% identical (e.g., at least 80%, at least 85%, at least 90%, at least 95%, at least 96%, at least 97%, at least 98%, at least 99%, or 100% iden-tical) to the amino acid sequence set forth in SEQ ID NO: 1075, 1119, 1120, or 1125. In some embodiments, the CD19-specific scFv may comprise one or more CDRs having amino acid sequences set forth in SEQ ID NOs: 1121-1123 and 1126-1128. In some embodiments, the CD19-specific scFv may comprise a light chain with one or more CDRs having amino acid sequences set forth in SEQ ID NOs: 1121-1123. In some embodiments, the CD19-specific scFv may comprise a heavy chain with one or more CDRs having amino acid sequences set forth in SEQ ID NOs: 1126-1128. In any of these embodiments, the CD19-specific scFv may comprise one or more CDRs comprising one or more amino acid substitutions, or comprising a sequence that is at least 80% identical (e.g., at least 80%, at least 85%, at least 90%, at least 95%, at least 96%, at least 97%, at least 98%, at least 99%, or 100% identical), to any of the sequences identified. In some embodiments, the extracellular binding domain of the CD19 CAR comprises or consists of the one or more CDRs as described herein.

In some embodiments, the linker linking the $V_H$ and the $V_L$ portions of the scFv is a Whit-low linker having an amino acid sequence set forth in SEQ ID NO: 1124. In some embodiments, the Whitlow linker may be replaced by a different linker, for example, a 3xG₄S linker having an amino acid sequence set forth in SEQ ID NO: 1130, which gives rise to a different FMC63-derived scFv having an amino acid sequence set forth in SEQ ID NO: 1129. In certain of these embodiments, the CD19-specific scFv com-prises or consists of an amino acid sequence set forth in SEQ ID NO: 1129 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1129.

TABLE E

Exemplary sequences of anti-CD19 scFv and components

| SEQ ID NO: | Amino Acid Sequence | Description |
|---|---|---|
| 1119 | DIQMTQTTSSLSASLGDRVTIS-CRASQDISKY-LNWYQQKPDGTVKLLI-YHTSRLHSGVPSRFSGSGSGTDYS LTISNLEQEDIATYFCQQGN-TLPYTFGGGTKLEIT-GSTSGSGKPGSGEGSTKGEV-KLQESGPGLVAPSQSLSVTCTVSG VSLPDYGVSWIRQP-PRKGLEWLGVIWGSET-TYYNSALKSRLTIIKDNSKSQVFLK-MNSLQTDDTAIYYCAKHYYYGGSY AMDYWGQGTSVTVSS | Anti-CD19 FMC63 scFv entire sequence, with Whitlow linker |
| 1120 | DIQMTQTTSSLSASLGDRVTIS-CRASQDISKY-LNWYQQKPDGTVKLLI-YHTSRLHSGVPSRFSGSGSGTDYS LTISNLEQEDIATYFCQQGN-TLPYTFGGGTKLEIT | Anti-CD19 FMC63 scFv light chain variable region |
| 1121 | QDISKY | Anti-CD19 FMC63 scFv light chain CDR1 |
| 1122 | HTS | Anti-CD19 FMC63 scFv light chain CDR2 |
| 1123 | QQGNTLPYT | Anti-CD19 FMC63 scFv light chain CDR3 |
| 1124 | GSTSGSGKPGSGEGSTKG | Whitlow linker |
| 1125 | EVKLQESGPGLVAP-SQSLSVTCTVSGVSLPDY-GVSWIRQP-PRKGLEWLGVIWGSET-TYYNSALKSRLTIIKDNSKSQVFLKM NSLQTDD-TAIYYCAKHYYYGGSYAMDYWGQ GTSVTVSS | Anti-CD19 FMC63 scFv heavy chain variable region |
| 1126 | GVSLPDYG | Anti-CD19 FMC63 scFv heavy bchain CDR1 |
| 1127 | IWGSETT | Anti-CD19 FMC63 scFv heavy chain CDR2 |
| 1128 | AKHYYYGGSYAMDY | Anti-CD19 FMC63 scFv heavy chain CDR3 |
| 1129 | DIQMTQTTSSLSASLGDRVTIS-CRASQDISKY-LNWYQQKPDGTVKLLI-YHTSRLHSGVPSRFSGSGSGTDYS LTISNLEQEDIATYFCQQGN-TLPYTFGGGTKLEIT-GGGGSGGGGSGGGGSEV-KLQESGPGLVAPSQSLSVTCTVSG VSLPDYGVSWIRQP-PRKGLEWLGVIWGSET-TYYNSALKSRLTIIKDNSKSQVFLK-MNSLQTDDTAIYYCAKHYYYGGSY AMDYWGQGTSVTVSS | Anti-CD19 FMC63 scFv entire sequence, with 3xG₄S linker |
| 1130 | GGGGSGGGGSGGGGS | 3xG₄S linker |

In some embodiments, the extracellular binding domain of the CD19 CAR is derived from an antibody specific to CD19, including, for example, SJ25C1 (Bejcek et al., Cancer Res. 55:2346-2351 (1995)), HD37 (Pezutto et al., J. Immunol. 138 (9): 2793-2799 (1987)), 4G7 (Meeker et al., Hybridoma 3:305-320 (1984)), B43 (Bejcek (1995)), BLY3 (Bejcek (1995)), B4 (Freedman et al., 70:418-427 (1987)), B4 HB12b (Kansas & Tedder, J. Immunol. 147:4094-4102 (1991); Yazawa et al., Proc. Natl. Acad. Sci. USA 102: 15178-15183 (2005); Herbst et al., J. Pharmacol. Exp. Ther. 335:213-222 (2010)), BU12 (Callard et al., J. Immunology, 148 (10): 2983-2987 (1992)), and CLB-CD19 (De Rie Cell. Immunol. 118:368-381 (1989)). In any of these embodiments, the extracellular binding domain of the CD19 CAR can comprise or consist of the $V_H$, the $V_L$, and/or one or more CDRs of any of the antibodies.

In some embodiments, the hinge domain of the CD19 CAR comprises a CD8α hinge domain, for example, a human CD8α hinge domain. In some embodiments, the CD8α hinge domain comprises or consists of an amino acid sequence set forth in SEQ ID NO: 1109 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1109. In some embodiments, the hinge domain comprises a CD28 hinge domain, for example, a human CD28 hinge domain. In some embodiments, the CD28 hinge domain comprises or consists of an amino acid sequence set forth in SEQ ID NO: 1110 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1110. In some embodiments, the hinge domain comprises an IgG4 hinge domain, for example, a human IgG4 hinge domain. In some embodiments, the IgG4 hinge domain comprises or consists of an amino acid sequence set forth in SEQ ID NO: 1111 or SEQ ID NO: 1112, or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1111 or SEQ ID NO: 1112. In some embodiments, the hinge domain comprises a IgG4 hinge-Ch2-Ch3 domain, for example, a human IgG4 hinge-Ch2-Ch3 domain. In some embodiments, the IgG4 hinge-Ch2-Ch3 domain comprises or consists of an amino acid sequence set forth in SEQ ID NO: 1113 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1113. In some embodiments, the transmembrane domain of the CD19 CAR comprises a CD8α transmembrane domain, for example, a human CD8α transmembrane domain. In some embodiments, the CD8α transmembrane domain comprises or consists of an amino acid sequence set forth in SEQ ID NO: 1114 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO: 1114. In some embodiments, the transmembrane domain comprises a CD28 transmembrane domain, for example, a human CD28 transmembrane domain. In some embodiments, the CD28 transmembrane domain comprises or con-sists of an amino acid sequence set forth in SEQ ID NO: 1115 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO: 1115.

In some embodiments, the intracellular costimulatory domain of the CD19 CAR comprises a 4-1BB costimulatory domain. 4-1BB, also known as CD137, transmits a potent costimulatory signal to T cells, promoting differentiation and enhancing long-term sur-vival of T lymphocytes. In some embodiments, the 4-1BB costimulatory domain is hu-man. In some embodiments, the 4-1BB costimulatory domain comprises or consists of an amino acid sequence set forth in SEQ ID NO: 1116 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO: 1116. In some embodiments, the intracel-lular costim-ulatory domain comprises a CD28 costimula-tory domain. CD28 is another co-stimula-tory molecule on T cells. In some embodiments, the CD28 costimulatory domain is hu-man. In some embodiments, the CD28 costimulatory domain comprises or consists of an amino acid sequence set forth in SEQ ID NO: 1117 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO: 1117. In some embodiments, the intracellular costim-ulatory domain of the CD19 CAR comprises a 4-1BB costimulatory domain and a CD28 costimulatory domain as described.

In some embodiments, the intracellular signaling domain of the CD19 CAR comprises a CD3 zeta (ζ) signaling domain. CD3ζ associates with T cell receptors (TCRs) to pro-duce a signal and contains immunoreceptor tyrosine-based activation motifs (ITAMs). The CD3ζ signaling domain refers to amino acid residues from the cytoplasmic domain of the zeta chain that are sufficient to functionally transmit an initial signal necessary for T cell activation. In some embodiments, the CD3ζ signaling domain is human. In some embodiments, the CD3ζ signaling domain com-prises or consists of an amino acid sequence set forth in SEQ ID NO: 1118 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO: 1118.

In some embodiments, the polycistronic vector comprises an expression cassette that contains a nucleotide sequence encoding a CD19 CAR, including, for example, a CD19 CAR comprising the CD19-specific scFv having sequences set forth in SEQ ID NO: 1119 or SEQ ID NO: 1129, the CD8α hinge domain of SEQ ID NO: 1109, the CD8α transmembrane domain of SEQ ID NO: 1114, the 4-1BB costimulatory domain of SEQ ID NO: 1116, the CD3ζ signaling domain of SEQ ID NO: 1118, and/or variants (i.e., hav-ing a sequence that is at least 80% identical, for example, at least 80%, at least 85%, at least 90%, at least 95%, at least 96%, at least 97%, at least 98%, or at least 99 identical to the disclosed sequence) thereof. In any of these embodiments, the CD19 CAR may additionally comprise a signal peptide (e.g., a CD8α signal peptide) as described. In some embodiments, the polycistronic vector comprises an expression cassette that contains a nucleotide sequence encoding a CD19 CAR, including, for example, a CD19 CAR comprising the CD19-specific scFv having sequences set forth in SEQ ID NO: 1119 or SEQ ID NO: 1129, the IgG4 hinge domain of SEQ ID NO: 1111 or SEQ ID NO: 1112, the CD28 transmembrane domain of SEQ ID NO:

1115, the 4-1BB costimulatory domain of SEQ ID NO: 1116, the CD3ζ signaling domain of SEQ ID NO: 1118, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof. In any of these embodiments, the CD19 CAR may additionally comprise a signal peptide (e.g., a CD8α signal peptide) as described.

In some embodiments, the polycistronic vector comprises an expression cassette that contains a nucleotide sequence encoding a CD19 CAR, including, for example, a CD19 CAR comprising the CD19-specific scFv having sequences set forth in SEQ ID NO: 1075, SEQ ID NO: 1119, or SEQ ID NO: 1129, the CD28 hinge domain of SEQ ID NO: 1110, the CD28 transmembrane domain of SEQ ID NO: 1115, the CD28 costimulatory domain of SEQ ID NO: 1117, the CD3ζ signaling domain of SEQ ID NO: 1118, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof. In any of these embodiments, the CD19 CAR may additionally comprise a signal peptide (e.g., a CD8α signal peptide) as described.

In some embodiments, the polycistronic vector comprises an expression cassette that contains a nucleotide sequence encoding a CD19 CAR comprising the CD19-specific scFv having the sequence set forth in SEQ ID NO: 1075 (see Table 14), the CD8 hinge domain of SEQ ID NO: 1109, the CD8 transmembrane domain of SEQ ID NO: 1114, the 4-1BB costimulatory domain of SEQ ID NO: 1116, the CD3ζ signaling domain of SEQ ID NO: 1118, and/or variants (i.e., having a sequence that is at least 80% iden-tical, for ex-ample, at least 80%, at least 85%, at least 90%, at least 95%, at least 96%, at least 97%, at least 98%, or at least 99 identical to the disclosed sequence) thereof. In any of these embodiments, the CD19 CAR may additionally comprise a signal peptide (e.g., a CD8α signal peptide) as described.

In some embodiments, the polycistronic vector comprises an expression cassette that contains a nucleotide sequence encoding a CD19 CAR as set forth in SEQ ID NO: 1216 or is at least 80% identical (e.g., at least 80%, at least 85%, at least 90%, at least 95%, at least 96%, at least 97%, at least 98%, at least 99%, or 100% identical) to the nucleotide sequence set forth in SEQ ID NO: 1216 (see Table F). The encoded CD19 CAR has a corresponding amino acid sequence set forth in SEQ ID NO: 1217 or is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1217, with the following components: CD8α signal peptide, FMC63 scFv ($V_L$-Whitlow linker-$V_H$), CD8α hinge domain, CD8α transmembrane domain, 4-1BB costimulatory domain, and CD3ζ signaling domain.

In some embodiments, the polycistronic vector comprises an expression cassette that contains a nucleotide sequence encoding a commercially available embodiment of CD19 CAR. Non-limiting examples of commercially available embodiments of CD19 CARs expressed and/or encoded by T cells include tisagenlecleucel, lisocabtagene mar-aleucel, axicabtagene ciloleucel, and brexucabtagene autoleucel.

In some embodiments, the polycistronic vector comprises an expression cassette that contains a nucleotide sequence encoding tisagenlecleucel or portions thereof. Tisagenle-cleucel comprises a CD19 CAR with the following compo-nents: CD8α signal peptide, FMC63 scFv ($V_L$-3x$G_4$S linker-V$_H$), CD8α hinge domain, CD8α transmembrane domain, 4-1BB costimulatory domain, and CD3ζ signaling domain. The nucleotide and amino acid sequence of the CD19 CAR in tisagenlecleucel are provided in Table F, with anno-tations of the sequences provided in Table G.

In some embodiments, the polycistronic vector comprises an expression cassette that contains a nucleotide sequence encoding lisocabtagene maraleucel or portions thereof. Liso-cabtagene maraleucel comprises a CD19 CAR with the following components: GMCSFR-α or CSF2RA signal pep-tide, FMC63 scFv (V$_L$-Whitlow linker-V$_H$), IgG4 hinge domain, CD28 transmembrane domain, 4-1BB costimula-tory domain, and CD3ζ signal-ing domain. The nucleotide and amino acid sequence of the CD19 CAR in lisocab-tagene maraleucel are provided in Table F, with annotations of the sequences provided in Table H.

In some embodiments, the polycistronic vector comprises an expression cassette that contains a nucleotide sequence encoding axicabtagene ciloleucel or portions thereof. Axi-cabtagene ciloleucel comprises a CD19 CAR with the following components: GMCSFR-α or CSF2RA signal pep-tide, FMC63 scFv (V$_L$-Whitlow linker-V$_H$), CD28 hinge domain, CD28 transmembrane domain, CD28 costimulatory domain, and CD3ζ signal-ing domain. The nucleotide and amino acid sequence of the CD19 CAR in axi-cabtagene ciloleucel are provided in Table F, with annotations of the sequences pro-vided in Table I.

In some embodiments, the polycistronic vector comprises an expression cassette that contains a nucleotide sequence encoding brexucabtagene autoleucel or portions thereof. Brexucabtagene autoleucel comprises a CD19 CAR with the following components: GMCSFR-α signal peptide, FMC63 scFv, CD28 hinge domain, CD28 transmembrane domain, CD28 costimulatory domain, and CD3ζ signaling domain. In some embodiments, the polycistronic vector comprises an expression cassette that contains a nucleotide sequence encoding a CD19 CAR as set forth in SEQ ID NO: 1131, 1133, or 1135, or is at least 80% identical (e.g., at least 80%, at least 85%, at least 90%, at least 95%, at least 96%, at least 97%, at least 98%, at least 99%, or 100% identical) to the nucleotide sequence set forth in SEQ ID NO: 1131, 1133, or 1135. The encoded CD19 CAR has a corresponding amino acid sequence set forth in SEQ ID NO: 1132, 1134, or 1136, respectively, or is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1132, 1134, or 1136, respectively.

TABLE F

| | Exemplary sequences of CD19 CARs | |
| --- | --- | --- |
| SEQ ID NO: | Sequence | Description |
| 1216 | atggccttaccagtgaccgccttgctcctgccgctggcctt-gctgctccac-gccgccaggccggacatccagatgacacagactacatc ctccctgtctgcctctctgggagacagagtcaccatcagtt-gcagggcaagtcaggacatt-agtaaatatttaaattggtatcagcagaaaccagatggaa ctgttaaactcctgatctaccatacatcaagattacactcag-gagtcccatcaaggttcag-tggcagtgggtctggaacagattattctctcaccattagcaa cctggagcaagaagatattgccacttactttt-gccaacagggtaatacgcttccgtacac-gttcggagggggggaccaagctggagatcacaggctcca cctctggatccggcaagcccg-gatctggcgagggatccaccaagggcgaggtgaaactg-cag-gagtcaggacctggcctggtggcgccctcacagagcctgt ccgtcacatgcactgtctcaggggtctcattacccgac-tatggtgtaagctggat-tcgccagcctccacgaaagggtctggagtggctgggagt aatatggggtagtgaaaccacatacta-taattcagctctcaaatccagactgac-catcatcaaggacaactccaagagccaagtttttcttaaaa atgaacagtctg-caaactgatgacacagccatttactactgtgccaaacattat tactacggtggtagctatgctatggac-tactggggccaaggaacctcagtcac-cgtctcctcaaccacgacgccagcgccgcgaccaccaa caccggcgccaccatcgcgtcg-cagccctgtccctgcgcccagaggcgtgccggccagcg gcggggggcgcagtgcacacgagggggctg-gacttcgcctgtga-tatctacatctgggcgcccttggccgggacttgtggggtcctt ctcctgtcactggttatcacccttttactgcaaacgggg-cagaaagaaactcctgtata-tattcaaacaaccatttatgagaccagtacaaactactcaa gaggaagatggctgtagctgccgatttccagaagaa-gaagaaggaggatgtgaactgagag-tgaagttcagcaggagcgcagacgcccccgcgtaccag cagggccagaaccagctctataacgagctcaatctag-gacgaagagaggagtacgatgtttt-ggacaagagacgtggccgggaccctgagatggggggga aagccgagaaggaagaaccctcaggaaggcctg-tacaatgaactgcagaaagataa-gatggcggaggcctacagtgagattgggatgaaaggcg agcgccggaggggcaaggggcacgatggcctttac- | Exemplary CD19 CAR nucleotide sequence |

TABLE F-continued

| Exemplary sequences of CD19 CARs | | |
|---|---|---|
| SEQ ID NO: | Sequence | Description |
| | caggtctcagtacagccac-caaggacacctacgacgccttcacatgcaggccctgcccctcgc | |
| 1217 | MAL-PVTALLLPLALLLHAARPDIQMTQTTSSLSASLGDRVTISCRASQDISKY-LNWYQQKPDGTVKLLI-YHTSRLHSGVPSRFSGSGSGTDYS-LTISNLEQEDIATYFCQQGNTLPYTFGGGTKLEITGSTSGSGKPGSGEGSTKGEV-KLQESGPGLVAP-SQSLSVTCTVSGVSLPDY-GVSWIRQPPRKGLEWLGVIWGSETTYYNSALKSRLTIIKDNSKSQVFLKMNSLQTDD-TAIYYCAKHYYYGGSYAMDYWGQGTSVTVSSTTTPAPRPPTPAPTI-ASQPLSLRPEACRPAAGGAVHTRGLD-FACDIYIWAPLAG-TCGVLLLSLVITLYCKRGRKKLLYIFKQPFMRPVQTTQEEDGCSCRFPEEEE-GGCELRVKFSRSADAPA-YQQGQNQLYNELNLGR-REEYDVLDKRRGRDPEMGGKPRRKNPQEGLYNEL-QKDKMAEAYSEIGMKGERRRGKGH-DGLYQGLSTATKDTYDALHMQALPPR | Exemplary CD19 CAR amino acid sequence |
| 1231 | DIQMTQTTSSLSASLGDRVTIS-CRASQDISKYLNWYQQKPDGTVKLLI-YHTSRLHSGVPSRFSGSGSGTDYSLTISNLEQEDIATYFCQQGN-TLPYTFGGGTKLEIT-GSTSGSGKPGSGEGSTKGEV-KLQESGPGLVAP-SQSLSVTCTVSGVSLPDYGVSWIRQPPRKGLEWLGVIWGSETTYYNSALKSRLTIIK-DNSKSQVFLKMNSLQTDD-TAIYYCAKHYYYGGSYAMDYWGQGTSVTVSSTTTPAPRPPTPAPTI-ASQPLSLRPEACRPAAGGAVHTRGLD-FACDIYIWAPLAG-TCGVLLLSLVITLYCKRGRKKLLYIFKQPFMRPVQTTQEEDGCSCRFPEEEE-GGCELRVKFSRSADAPA-YQQGQNQLYNELNLGR-REEYDVLDKRRGRDPEMGGKPRRKNPQEGLYNEL-QKDKMAEAYSEIGMKGERRRGKGH-DGLYQGLSTATKDTYDALHMQALPPR | Exemplary CD19 CAR amino acid sequence (no signal sequence) |
| 1131 | atggccttaccagtgaccgccttgctcctgccgctggcctt-gctgctccac-gccgccaggccggacatccagatgacacagactacatcctccctgtctgcctctctgggagacagagtcaccatcagtt-gcagggcaagtcaggacatt-agtaaatatttaaattggtatcagcagaaaccagatggaactgttaaactcctgatctaccatacatcaagattacactcag-gagtcccatcaaggttcag-tggcagtgggtctggaacagattattctctcaccattagcaacctggagcaagaagatattgccacttactttt-gccaacagggtaatacgcttccgtacac-gttcggaggggggaccaagctggagatcacaggtggcggtggctcgggcggtggtgggtcgggtggcggcg-gatctgaggtgaaactgcaggagtcag-gacctggcctggtggcgccctcacagagcctgtccgtcacatgcactgtctcaggggtctcattacccgactatggtgtaa-gctggattcgccagcctccac-gaaagggtctggagtggctgggagtaatatggggtagtgaaaccacatactataattcagctctcaaatccagactgac-catcatcaaggacaactccaa-gagccaagttttcttaaaaatgaacagtctgcaaactgatgacacagccatttactactgtgccaaacattattactac-ggtggtagctatgctatggac-tactggggccaaggaacctcagtcaccgtctcctcaaccacgacgccagcgccgcgaccaccaacac- | Tisagenlecleucel CD19 CAR nucleotide sequence |

TABLE F-continued

Exemplary sequences of CD19 CARs

| SEQ ID NO: | Sequence | Description |
|---|---|---|
| | cggcgcccaccatcgcgtcg-<br>cagcccctgtccctgcgcccagaggcgtgccggccagcg<br>gcggggggcgcagtgcacacgaggggggctg-<br>gacttcgcctgtga-<br>tatctacatctgggcgcccttggccgggacttgtggggtcctt<br>ctcctgtcactggttatcacctttactgcaaacgggg-<br>cagaaagaaactcctgtata-<br>tattcaaacaaccatttatgagaccagtacaaactactcaa<br>gaggaagatggctgtagctgccgatttccagaagaa-<br>gaagaaggaggatgtgaactgagag-<br>tgaagttcagcaggagcgcagacgcccccgcgtacaag<br>cagggccagaaccagctctataacgagctcaatctag-<br>gacgaagagaggagtacgatgtttt-<br>ggacaagagacgtggccgggaccctgagatggggggga<br>aagccgagaaggaagaaccctcaggaaggcctg-<br>tacaatgaactgcagaaagataa-<br>gatggcggaggcctacagtgagattgggatgaaaggcg<br>agcgccggaggggcaaggggcacgatggcctttac-<br>cagggtctcagtacagccac-<br>caaggacacctacgacgcccttcacatgcaggccctgcc<br>ccctcgc | |
| 1132 | MAL-<br>PVTALLLPLALLLHAARPDIQMTQTTSSLS<br>ASLGDRVTISCRASQDISKY-<br>LNWYQQKPDGTVKLLI-<br>YHTSRLHSGVPSRFSGSGSGTDYS-<br>LTISNLEQEDIATYFCQQGNTLPYTFGGGT<br>KLEITGGGGSGGGGSGGGGSEV-<br>KLQESGPGLVAP-<br>SQSLSVTCTVSGVSLPDYGVSWIRQP-<br>PRKGLEWLGVIWGSETTYYNSALKSRLTII<br>KDNSKSQVFLKMNSLQTDD-<br>TAIYYCAKHYYYGGSYAMDYWGQGTSVT<br>VSSTTTPAPRPPTPAPTI-<br>ASQPLSLRPEACRPAAGGAVHTRGLD-<br>FACDIYIWAPLAG-<br>TCGVLLLSLVITLYCKRGRKKLLYIFKQPFM<br>RPVQTTQEEDGCSCRFPEEEE-<br>GGCELRVKFSRSADAPA-<br>YKQGQNQLYNELNLGR-<br>REEYDVLDKRRGRDPEMGGKPRRKNPQ<br>EGLYNEL-<br>QKDKMAEAYSEIGMKGERRRGKGH-<br>DGLYQGLSTATKDTYDALHMQALPPR | Tisagenlecleucel<br>CD19 CAR<br>amino acid<br>sequence |
| 1133 | atgctgctgctggtgac-<br>cagcctgctgctgtgcgagctgccccaccccgcctttctgct<br>gatccccgacatccagatgacccagaccac-<br>ctccagcctgagcgccagcctgggcgac-<br>cgggtgaccatcagctgccgggccagccaggacatcag<br>caagtacctgaactggtatcagcagaagcccgacgg-<br>caccgtcaagctgctgatctac-<br>cacaccagccggctgcacagcggcgtgcccagccggttt<br>agcggcagcggctccggcaccgactacagcctgac-<br>catctccaacctggaacaggaaga-<br>tatcgccacctacttttgccagcagggcaacacactgccct<br>acacctttggcggcggaacaaagctggaaatcaccgg-<br>cagcacctccggcagcggcaa-<br>gcctggcagcggcgagggcagcaccaagggcgaggtg<br>aagctgcaggaaa-<br>gcggccctggcctggtggcccccagccagagcctgagcg<br>tgacctgcaccgtgagcggcgtgagcctgcccgactac-<br>ggcgtgagctggatccgg-<br>cagcccccaggaagggcctggaatggctgggcgtgatc<br>tggggcagcgagaccacctactacaacagcgccctgaa-<br>gagccggctgac-<br>catcatcaaggacaacagcaagagccaggtgttcctgaa<br>gatgaacagcctgcagaccgacgacac-<br>cgccatctactactgcgccaagcactactactac-<br>ggcggcagctacgccatggactactggggccagggcac<br>cagcgtgaccgtgagcagcgaatctaagtacggac-<br>cgccctgcccccctt-<br>gccctatgttctgggtgctggtggtggtcggaggcgtgctgg<br>cctgctacagcctgctggtcaccgtggccttcatcatctttt-<br>gggtgaaacggggcagaaa- | Lisocabtagene<br>maraleucel<br>CD19 CAR<br>nucleotide<br>sequence |

TABLE F-continued

| | Exemplary sequences of CD19 CARs | |
|---|---|---|
| SEQ ID NO: | Sequence | Description |
| | gaaactcctgtatatattcaaacaaccatttatgagaccagt<br>acaaactactcaagaggaagatggctgtagctgccgat-<br>ttccagaagaagaagaaggag-<br>gatgtgaactgcgggtgaagttcagcagaagcgccgacg<br>cccctgcctaccagcagggccagaatcagctgtacaac-<br>gagctgaacctgggcagaagggaa-<br>gagtacgacgtcctggataagcggagaggccgggaccc<br>tgagatgggcggcaagcctcggcggaagaacccccag-<br>gaaggcctgtataacgaactg-<br>cagaaagacaagatggccgaggcctacagcgagatcg<br>gcatgaagggcgagcggaggcggggcaagggccac-<br>gacggcctgtatcagggcctgtccac-<br>cgccaccaaggatacctacgacgccctgcacatgcaggc<br>cctgccccccaagg | |
| 1134 | MLLLVTSLLLCELPHPAFL-<br>LIPDIQMTQTTSSLSASLGDRVTIS-<br>CRASQDISKY-<br>LNWYQQKPDGTVKLLIYHTSRLHSGVPSR<br>FSGSGSGTDYSLTISNLEQEDIATY-<br>FCQQGNTLPYTFGGGTKLEIT-<br>GSTSGSGKPGSGEGSTKGEVKLQESGPG<br>LVAPSQSLSVTCTVSGVSLPDY-<br>GVSWIRQPPRKGLEWLGVIWGSET-<br>TYYNSALKSRLTIIK-<br>DNSKSQVFLKMNSLQTDDTAIYYCAKHYY<br>YGGSYAMDYWGQGTSVTVSSESKYGPP<br>CPPCPMFWVLVVVGGVLACYSLLVTVAFI-<br>IFWVKRGRKKLLY-<br>IFKQPFMRPVQTTQEEDGCSCRFPEEEEG<br>GCELRVKFSRSADAPA-<br>YQQGQNQLYNELNLGR-<br>REEYDVLDKRRGRDPEMGGKPRR-<br>KNPQEGLYNELQKDKMAEAYSEIGMKGE<br>RRRGKGHDGLYQGLSTAT-<br>KDTYDALHMQALPPR | Lisocabtagene<br>maraleucel<br>CD19 CAR<br>amino acid<br>sequence |
| 1135 | atgcttctcctggtgacaagccttctgctctgtgagttac-<br>cacacccag-<br>cattcctcctgatcccagacatccagatgacacagactac<br>atcctccctgtctgcctctctgggagacagagtcac-<br>catcagttgcagggcaagtcag-<br>gacattagtaaatatttaaattggtatcagcagaaaccaga<br>tggaactgttaaactcctgatctaccatacatcaagat-<br>tacactcaggag-<br>tcccatcaaggttcagtggcagtgggtctggaacagattatt<br>ctctcaccattagcaacctggagcaagaagatattgccac-<br>ttacttttgccaacagggtaa-<br>tacgcttccgtacacgttcggaggggggactaagttggaa<br>ataacaggctccacctctggatccggcaagcccg-<br>gatctggcgagggatccac-<br>caagggcgaggtgaaactgcaggagtcaggacctggcc<br>tggtggcgccctcacagagcctgtccgtcacatgcac-<br>tgtctcaggggtctcattacccgac-<br>tatggtgtaagctggattcgccagcctccacgaaagggtct<br>ggagtggctgggagtaatatggggtagtgaaac-<br>cacatacta-<br>taattcagctctcaaatccagactgaccatcatcaaggaca<br>actccaagagccaagtttttcttaaaaatgaacagtctg-<br>caaactgatgacacagccatttactactgtgccaaacattat<br>tactacggtggtagctatgctatggac-<br>tactggggtcaaggaacctcagtcac-<br>cgtctcctcagcggccgcaattgaagttatgtatcctcctcct<br>tacctagacaatgagaagagcaatggaac-<br>cattatccatgtgaaaggggaaacaccttt-<br>gtccaagtcccctatttcccggaccttctaagccctttgggt<br>gctggtggtggttgggggagtcctggcttgctatagctt-<br>gctagtaacag-<br>tggcctttattattttctgggtgaggagtaagaggagcaggc<br>tcctgcacagtgac-<br>tacatgaacatgactccccgccgccccgggcccacccg-<br>caagcattac-<br>cagccctatgccccaccacgcgacttcgcagcctatcgct<br>ccagagtgaagttcagcaggagcgcagac-<br>gcccccgcgtaccagcagggccagaaccagctc-<br>tataacgagctcaatctaggacgaagagaggagtacgat | Axicabtagene<br>ciloleucel CD19<br>CAR nucleotide<br>sequence |

TABLE F-continued

| Exemplary sequences of CD19 CARs | | |
|---|---|---|
| SEQ ID NO: | Sequence | Description |
| | gttttggacaagagacgtggccgggaccctga-<br>gatgggggaaagccgagaaggaa-<br>gaaccctcaggaaggcctgtacaatgaactgcagaaag<br>ataagatggcggaggcctacagtgagattgg-<br>gatgaaaggcgagcgccggaggggcaagggg-<br>cacgatggcctttaccagggtctcagtacagccaccaagg<br>acacctacgac-<br>gcccttcacatgcaggccctgcccctcgc | |
| 1136 | MLLLVTSLLLCELPHPAFL-<br>LIPDIQMTQTTSSLSASLGDRVTIS-<br>CRASQDISKY-<br>LNWYQQKPDGTVKLLIYHTSRLHSGVPSR<br>FSGSGSGTDYSLTISNLEQEDIATY-<br>FCQQGNTLPYTFGGGTKLEIT-<br>GSTSGSGKPGSGEGSTKGEVKLQESGPG<br>LVAPSQSLSVTCTVSGVSLPDY-<br>GVSWIRQPPRKGLEWLGVIWGSET-<br>TYYNSALKSRLTIIK-<br>DNSKSQVFLKMNSLQTDDTAIYYCAKHYY<br>YGGSYAMDYWGQGTSVTVSSAAAIEVMY<br>PPPYLDNEKSNGTIIHVKGKHLCPSPLF-<br>PGPSKPFWVLVVVGGVLACYSLLVTVAFII-<br>FWVRSKRSRLLHSDYMNMTPRRPGPTRK<br>HYQPYAPPRDFAAYRSRVKFSRSADAPA-<br>YQQGQNQLYNELNLGR-<br>REEYDVLDKRRGRD-<br>PEMGGKPRRKNPQEGLYNELQKDKMAEA<br>YSEIGMKGERRRGKGHDGLYQGLSTAT-<br>KDTYDALHMQALPPR | Axicabtagene<br>ciloleucel CD19<br>CAR amino acid<br>sequence |

TABLE G

| Annotation of tisagenlecleucel CD19 CAR sequences | | |
|---|---|---|
| Feature | Nucleotide<br>Sequence Position | Amino Acid<br>Sequence Position |
| CD8α signal peptide | 1-63 | 1-21 |
| FMC63 scFv<br>(V$_L$-3xG$_4$S linker-V$_H$) | 64-789 | 22-263 |
| CD8α hinge domain | 790-924 | 264-308 |
| CD8α transmembrane domain | 925-996 | 309-332 |
| 4-1BB costimulatory domain | 997-1122 | 333-374 |
| CD3ζ signaling domain | 1123-1458 | 375-486 |

TABLE H

| Annotation of lisocabtagene maraleucel CD19 CAR sequences | | |
|---|---|---|
| Feature | Nucleotide<br>Sequence Position | Amino Acid<br>Sequence Position |
| GMCSFR-α signal peptide | 1-66 | 1-22 |
| FMC63 scFv<br>(V$_L$-Whitlow linker-V$_H$) | 67-801 | 23-267 |
| IgG4 hinge domain | 802-837 | 268-279 |
| CD28 transmembrane domain | 838-921 | 280-307 |
| 4-1BB costimulatory domain | 922-1047 | 308-349 |
| CD3ζ signaling domain | 1048-1383 | 350-461 |

TABLE I

| Annotation of axicabtagene ciloleucel CD19 CAR sequences | | |
|---|---|---|
| Feature | Nucleotide<br>Sequence Position | Amino Acid<br>Sequence Position |
| CSF2RA signal peptide | 1-66 | 1-22 |
| FMC63 scFv<br>(V$_L$-Whitlow linker-V$_H$) | 67-801 | 23-267 |
| CD28 hinge domain | 802-927 | 268-309 |
| CD28 transmembrane domain | 928-1008 | 310-336 |
| CD28 costimulatory domain | 1009-1131 | 337-377 |
| CD3ζ signaling domain | 1132-1467 | 378-489 |

In some embodiments, the polycistronic vector comprises an expression cassette that contains a nucleotide sequence encoding CD19 CAR as set forth in SEQ ID NO: 1131, 1133, or 1135, or at least 80% identical (e.g., at least 80%, at least 85%, at least 90%, at least 95%, at least 96%, at least 97%, at least 98%, at least 99%, or 100% identical) to the nucleotide sequence set forth in SEQ ID NO: 1131, 1133, or 1135. The encoded CD19 CAR has a corresponding amino acid sequence set forth in SEQ ID NO: 1132, 1134, or 1136, respectively, is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1132, 1134, or 1136, respectively.

CD20 CAR

In some embodiments, the CAR is a CD20 CAR ("CD20-CAR"), and in these embodiments, the polycistronic vector comprises an expression cassette that contains a nucleotide sequence encoding a CD20 CAR. CD20 is an antigen found on the surface of B cells as early at the pro-B phase and progressively at increasing levels until B cell ma-turity, as well as on the cells of most B-cell neoplasms. CD20 positive cells are also sometimes found in cases of Hodgkins disease, myeloma, and thymoma. In some embodiments, the CD20 CAR may comprise a signal peptide, an extracellular binding domain that specifically binds CD20, a hinge domain, a transmembrane domain, an intracellular costimulatory domain, and/or an intracellular signaling domain in tandem. In some embodiments, the signal peptide of the CD20 CAR comprises a CD8α signal peptide. In some embodiments, the CD8α signal peptide comprises or consists of an amino acid sequence set forth in SEQ ID NO: 1106 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1106. In some embodiments, the signal peptide comprises an IgK signal peptide. In some embodiments, the IgK signal peptide comprises or consists of an amino acid sequence set forth in SEQ ID NO: 1107 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1107. In some embodiments, the signal peptide comprises a GMCSFR-α or CSF2RA signal peptide. In some embodiments, the GMCSFR-α or CSF2RA signal peptide comprises or consists of an amino acid sequence set forth in SEQ ID NO: 1108 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1108.

In some embodiments, the extracellular binding domain of the CD20 CAR is specific to CD20, for example, human CD20. The extracellular binding domain of the CD20 CAR can be codon-optimized for expression in a host cell or to have variant sequences to in-crease functions of the extracellular binding domain. In some embodiments, the extracellular binding domain comprises an immunogenically active portion of an immunoglobulin molecule, for example, an scFv.

In some embodiments, the extracellular binding domain of the CD20 CAR is derived from an antibody specific to CD20, including, for example, Leu16, IF5, 1.5.3, rituximab, obinutuzumab, ibritumomab, ofatumumab, tositumumab, odronextamab, veltuzumab, ublituximab, and ocrelizumab. In any of these embodiments, the extracellular binding domain of the CD20 CAR can comprise or consist of the $V_H$, the $V_L$, and/or one or more CDRs of any of the antibodies.

In some embodiments, the extracellular binding domain of the CD20 CAR comprises an scFv derived from the Leu16 monoclonal antibody, which comprises the heavy chain variable region ($V_H$) and the light chain variable region ($V_L$) of Leu16 connected by a linker. See Wu et al., Protein Engineering. 14 (12): 1025-1033 (2001). In some embodiments, the linker is a 3xG$_4$S linker. In other embodiments, the linker is a Whitlow linker as described herein. In some embodiments, the amino acid sequences of different portions of the entire Leu16-derived scFv (also referred to as Leu16 scFv) and its different portions are provided in Table J below. In some embodiments, the CD20-specific scFv comprises or consists of an amino acid sequence set forth in SEQ ID NO: 1137, 1138, or 1142, or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1137, 1138, or 1142. In some embodiments, the CD20-specific scFv may comprise one or more CDRs having amino acid sequences set forth in SEQ ID NOs: 1139-1141, 1143 and 1144. In some embodiments, the CD20-specific scFv may comprise a light chain with one or more CDRs having amino acid sequences set forth in SEQ ID NOs: 1139-1141. In some embodiments, the CD20-specific scFv may comprise a heavy chain with one or more CDRs having amino acid sequences set forth in SEQ ID NOs: 1143-1144. In any of these embodiments, the CD20-specific scFv may comprise one or more CDRs comprising one or more amino acid substitutions, or comprising a sequence that is at least 80% identical (e.g., at least 80%, at least 85%, at least 90%, at least 95%, at least 96%, at least 97%, at least 98%, at least 99%, or 100% identical), to any of the sequences identified. In some embodiments, the extracellular binding domain of the CD20 CAR comprises or consists of the one or more CDRs as described herein.

TABLE J

Exemplary sequences of anti-CD20 scFv and components

| SEQ ID NO: | Amino Acid Sequence | Description |
|---|---|---|
| 1137 | DIVLTQSPAILSASPGEKVT MT-CRASSSVNYMDWYQKKP GSSPKP-WIYATSNLAS-GV PARFSGSGSGTSYSLTISRV EAEDAATYYCQQWS-FNPPT FGGGTKLEIKGSTSGSGKPG SGEGSTKGEVQLQQSGAELV KP-GASVKMSCKASGYTFTS YN-MHWVKQTPGQGLEWIGA I-YPGNGDTSYNQKFKGKAT LTADKSSSTAYMQLSSLTSE D-SADYYCARSNYYGSSYWF FDVW-GAGTTVTVSS | Anti-CD20 Leu16 scFv entire sequence, with Whitlow linker |
| 1138 | DIVLTQSPAILSASPGEKVT MT-CRASSSVNYMDWYQKKP GSSPKP-WIYATSNLAS-GV PARFSGSGSGTSYSLTISRV EAEDAATYYCQQWS-FNPPT FGGGTKLEIK | Anti-CD20 Leu16 scFv light chain variable region |
| 1139 | RASSSVNYMD | Anti-CD20 Leu16 scFv light chain CDR1 |
| 1140 | ATSNLAS | Anti-CD20 Leu16 scFv light chain CDR2 |
| 1141 | QQWSFNPPT | Anti-CD20 Leu16 scFv light chain CDR3 |
| 1142 | EVQLQQSGAELVKPGASVKM SCK-ASGYTFTSYN-MHWVK QTPGQGLEWIGAIYPGNG-D TSYNQKFKGKATLTADKSSS TAYMQLSSLTSED-SADYYC ARSNYYGSSYWFFDVW-GAG TTVTVSS | Anti-CD20 Leu16 scFv heavy chain |
| 1143 | SYNMH | Anti-CD20 Leu16 scFv heavy chain CDR1 |
| 1144 | AIYPGNGDTSYNQKFKG | Anti-CD20 Leu16 scFv heavy chain CDR2 |

In some embodiments, the hinge domain of the CD20 CAR comprises a CD8α hinge domain, for example, a human CD8α hinge domain. In some embodiments, the CD8α hinge domain comprises or consists of an amino acid sequence set forth in SEQ ID NO: 1109 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1109. In some embodiments, the hinge domain comprises a CD28 hinge domain, for example, a human CD28 hinge domain. In some embodiments, the CD28 hinge domain comprises or consists of an amino acid sequence set forth in SEQ ID NO: 1110 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1110. In some embodiments, the hinge domain comprises an IgG4 hinge domain, for example, a human IgG4 hinge domain. In some embodiments, the IgG4 hinge domain comprises or consists of an amino acid sequence set forth in SEQ ID NO: 1111 or SEQ ID NO: 1112, or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1111 or SEQ ID NO: 1112. In some embodiments, the hinge domain comprises a IgG4 hinge-Ch2-Ch3 domain, for example, a human IgG4 hinge-Ch2-Ch3 domain. In some embodiments, the IgG4 hinge-Ch2-Ch3 domain comprises or consists of an amino acid sequence set forth in SEQ ID NO: 1113 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1113. In some embodiments, the transmembrane domain of the CD20 CAR comprises a CD8α transmembrane domain, for example, a human CD8α transmembrane domain. In some embodiments, the CD8α transmembrane domain comprises or consists of an amino acid sequence set forth in SEQ ID NO: 1114 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO: 1114. In some embodiments, the transmembrane domain comprises a CD28 transmembrane domain, for example, a human CD28 transmembrane domain. In some embodiments, the CD28 transmembrane domain comprises or con-sists of an amino acid sequence set forth in SEQ ID NO: 1115 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO: 1115.

In some embodiments, the intracellular costimulatory domain of the CD20 CAR comprises a 4-1BB costimulatory domain, for example, a human 4-1BB costimulatory domain. In some embodiments, the 4-1BB costimulatory domain comprises or consists of an amino acid sequence set forth in SEQ ID NO: 1116 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO: 1116. In some embodi-ments, the intracellular costim-ulatory domain comprises a CD28 costimulatory domain, for example, a human CD28 costimulatory domain. In some embodiments, the CD28 costimulatory domain comprises or consists of an amino acid sequence set forth in SEQ ID NO: 1117 or an amino acid sequence that is at least 80% identical (e.g., at least 80%, at least 85%, at least 90%, at least 95%, at least 96%, at least 97%, at least 98%, at least 99%, or 100% iden-tical) to the amino acid sequence set forth in SEQ ID NO: 1117.

In some embodiments, the intracellular signaling domain of the CD20 CAR comprises a CD3 zeta (ζ) signaling domain, for example, a human CD3ζ signaling domain. In some embodiments, the CD3ζ signaling domain comprises or consists of an amino acid sequence set forth in SEQ ID NO: 1118 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO: 1118.

In some embodiments, the polycistronic vector comprises an expression cassette that contains a nucleotide sequence encoding a CD20 CAR, including, for example, a CD20 CAR comprising the CD20-specific scFv having sequences set forth in SEQ ID NO: 1137, the CD8α hinge domain of SEQ ID NO: 1109, the CD8α transmembrane domain of SEQ ID NO: 1114, the 4-1BB costimulatory domain of SEQ ID NO: 1116, the CD3ζ signaling domain of SEQ ID NO: 1118, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof.

In some embodiments, the polycistronic vector comprises an expression cassette that contains a nucleotide sequence encoding a CD20 CAR, including, for example, a CD20 CAR comprising the CD20-specific scFv having sequences set forth in SEQ ID NO: 1137, the CD28 hinge domain of SEQ ID NO: 1110, the CD8α transmembrane domain of SEQ ID NO: 1114, the 4-1BB costimulatory domain of SEQ ID NO: 1116, the CD3ζ signaling domain of SEQ ID NO: 1118, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof.

In some embodiments, the polycistronic vector comprises an expression cassette that contains a nucleotide sequence encoding a CD20 CAR, including, for example, a CD20 CAR comprising the CD20-specific scFv having sequences set forth in SEQ ID NO: 1137, the IgG4 hinge domain of SEQ ID NO: 1111 or SEQ ID NO: 1112, the CD8α trans-membrane domain of SEQ ID NO: 1114, the 4-1BB costimulatory domain of SEQ ID NO: 1116, the CD3ζ signaling domain of SEQ ID NO: 1118, and/or variants (i.e., hav-ing a sequence that is at least 80% identical, for example, at least 80%, at least 85%, at least 90%, at least 95%, at least 96%, at least 97%, at least 98%, or at least 99 identical to the disclosed sequence) thereof.

In some embodiments, the polycistronic vector comprises an expression cassette that contains a nucleotide sequence encoding a CD20 CAR, including, for example, a CD20 CAR comprising the CD20-specific scFv having sequences set forth in SEQ ID NO: 1137, the CD8α hinge domain of SEQ ID NO: 1109, the CD28 transmembrane domain of SEQ ID NO: 1115, the 4-1BB costimulatory domain of SEQ ID NO: 1116, the CD3ζ signaling domain of SEQ ID NO: 1118, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof.

In some embodiments, the polycistronic vector comprises an expression cassette that contains a nucleotide sequence encoding a CD20 CAR, including, for example, a CD20

CAR comprising the CD20-specific scFv having sequences set forth in SEQ ID NO: 1137, the CD28 hinge domain of SEQ ID NO: 1110, the CD28 transmembrane domain of SEQ ID NO: 1115, the 4-1BB costimulatory domain of SEQ ID NO: 1116, the CD3ζ signaling domain of SEQ ID NO: 1118, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof.

In some embodiments, the polycistronic vector comprises an expression cassette that contains a nucleotide sequence encoding a CD20 CAR, including, for example, a CD20 CAR comprising the CD20-specific scFv having sequences set forth in SEQ ID NO: 1137, the IgG4 hinge domain of SEQ ID NO: 1111 or SEQ ID NO: 1112, the CD28 transmembrane domain of SEQ ID NO: 1115, the 4-1BB costimulatory domain of SEQ ID NO: 1116, the CD3ζ signaling domain of SEQ ID NO: 1118, and/or variants (i.e., hav-ing a sequence that is at least 80% identical, for example, at least 80%, at least 85%, at least 90%, at least 95%, at least 96%, at least 97%, at least 98%, or at least 99 identical to the disclosed sequence) thereof.

CD22 CAR

In some embodiments, the CAR is a CD22 CAR ("CD22-CAR"), and in these embodiments, the polycistronic vector comprises an expression cassette that contains a nucleotide sequence encoding a CD22 CAR. CD22, which is a trans-membrane protein found mostly on the surface of mature B cells that functions as an inhibitory receptor for B cell receptor (BCR) signaling. CD22 is expressed in 60-70% of B cell lymphomas and leukemias (e.g., B-chronic lympho-cytic leukemia, hairy cell leukemia, acute lymphocytic leu-kemia (ALL), and Burkitt's lymphoma) and is not present on the cell surface in early stages of B cell development or on stem cells. In some embodiments, the CD22 CAR may comprise a signal peptide, an extracellular binding domain that specifically binds CD22, a hinge domain, a transmem-brane domain, an intracellular costimulatory domain, and/or an intracellular signaling domain in tandem.

In some embodiments, the signal peptide of the CD22 CAR comprises a CD8α signal peptide. In some embodi-ments, the CD8α signal peptide comprises or consists of an amino acid sequence set forth in SEQ ID NO: 1106 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1106. In some embodiments, the signal peptide com-prises an IgK signal peptide. In some embodiments, the IgK signal peptide comprises or consists of an amino acid sequence set forth in SEQ ID NO: 1107 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1107. In some embodiments, the signal peptide comprises a GMCSFR-α or CSF2RA signal peptide. In some embodi-ments, the GMCSFR-α or CSF2RA signal peptide com-prises or consists of an amino acid sequence set forth in SEQ ID NO: 1108 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1108.

In some embodiments, the extracellular binding domain of the CD22 CAR is specific to CD22, for example, human CD22. The extracellular binding domain of the CD22 CAR can be codon-optimized for expression in a host cell or to have variant sequences to in-crease functions of the extra-cellular binding domain. In some embodiments, the extra-cellular binding domain comprises an immunogenically active portion of an immunoglobulin molecule, for example, an scFv.

In some embodiments, the extracellular binding domain of the CD22 CAR is derived from an antibody specific to CD22, including, for example, SM03, inotuzumab, epratuzumab, moxetumomab, and pinatuzumab. In any of these embodiments, the extracellular binding domain of the CD22 CAR can comprise or consist of the $V_H$, the $V_L$, and/or one or more CDRs of any of the antibodies.

In some embodiments, the extracellular binding domain of the CD22 CAR comprises an scFv derived from the m971 monoclonal antibody (m971), which comprises the heavy chain variable region ($V_H$) and the light chain variable region ($V_L$) of m971 connected by a linker. In some embodi-ments, the linker is a 3xG$_4$S linker. In other embodiments, the Whitlow linker may be used instead. In some embodi-ments, the amino acid sequences of the entire m971-derived scFv (also referred to as m971 scFv) and its different portions are provided in Table K below. In some embodi-ments, the CD22-specific scFv comprises or consists of an amino acid sequence set forth in SEQ ID NO: 1145, 1146, or 1150, or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1145, 1146, or 1150. In some embodi-ments, the CD22-specific scFv may comprise one or more CDRs having amino acid sequences set forth in SEQ ID NOs: 1147-1149 and 1151-1153. In some embodiments, the CD22-specific scFv may comprise a heavy chain with one or more CDRs having amino acid sequences set forth in SEQ ID NOs: 1147-1149. In some embodiments, the CD22-specific scFv may comprise a light chain with one or more CDRs having amino acid sequences set forth in SEQ ID NOs: 1151-1153. In any of these embodiments, the CD22-specific scFv may comprise one or more CDRs comprising one or more amino acid substitutions, or comprising a sequence that is at least 80% identical (e.g., at least 80%, at least 85%, at least 90%, at least 95%, at least 96%, at least 97%, at least 98%, at least 99%, or 100% identical), to any of the sequences identified. In some embodiments, the extracellular binding domain of the CD22 CAR comprises or consists of the one or more CDRs as described herein.

In some embodiments, the extracellular binding domain of the CD22 CAR comprises an scFv derived from m971-L7, which is an affinity matured variant of m971 with significantly improved CD22 binding affinity compared to the parental antibody m971 (improved from about 2 nM to less than 50 pM). In some embodiments, the scFv derived from m971-L7 comprises the $V_H$ and the $V_L$ of m971-L7 connected by a 3xG$_4$S linker. In other embodiments, the Whitlow linker may be used instead. In some embodiments, the amino acid sequences of the entire m971-L7-derived scFv (also referred to as m971-L7 scFv) and its different portions are provided in Table K below. In some embodi-ments, the CD22-specific scFv comprises or consists of an amino acid sequence set forth in SEQ ID NO: 1154, 1155, or 1159, or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1154, 1155, or 1159. In some embodiments, the CD22-specific scFv may comprise one or more CDRs having amino acid sequences set forth in SEQ ID NOs: 1156-1158 and 1160-1162. In some embodiments, the CD22-specific scFv may comprise a heavy chain with one or more CDRs having amino acid sequences set forth in SEQ ID NOs: 1156-1158. In some embodiments, the CD22-specific scFv may com-prise a light chain with one or more CDRs having amino acid sequences set forth in SEQ ID NOs: 1160-1162. In any of these embodiments, the CD22-specific scFv may comprise one or more CDRs comprising one or more amino acid substitutions, or comprising a sequence that is at least 80% identical (e.g., at least 80%, at least 85%, at least 90%, at least 95%, at least 96%, at least 97%, at least 98%, at least 99%, or 100% identical), to any of the sequences identified. In some embodiments, the extracellular binding domain of the CD22 CAR comprises or consists of the one or more CDRs as described herein.

TABLE K

Exemplary sequences of anti-CD22
scFv and components

| SEQ ID NO: | Amino Acid Sequence | Description |
|---|---|---|
| 1145 | QVQLQQSGPGLVKP-SQTLS LTCAISGDSVSS-NSAAWNW IRQSPSR-GLEWLGRTYYRS KWYNDYAVSVKSRITINPDT SKNQFSLQLNSVTPED-TAV YYCAREVTGDLEDAFD-IWG QGTMVTVSSGGGGSGGGGSG GGGSDIQMTQSPSSLSASVG -DRVTITCRASQTI-WSYLN WYQQRPGKAPNLLIYAAS-S LQSGVPSRFSGRGSGTDFTL TISSLQAEDFA-TYYCQQSY SIPQTFGQGTKLEIK | Anti-CD22 m971 scFv entire sequence, with 3xG₄S linker |
| 1146 | QVQLQQSGPGLVKP-SQTLS LTCAISGDSVSS-NSAAWNW IRQSPSR-GLEWLGRTYYRS KWYNDYAVSVKSRITINPDT SKNQFSLQLNSVTPED-TAV YYCAREVTGDLEDAFD-IWG QGTMVTVSS | Anti-CD22 m971 scFv heavy chain variable region |
| 1147 | GDSVSSNSAA | Anti-CD22 m971 scFv heavy chain CDR1 |
| 1148 | TYYRSKWYN | Anti-CD22 m971 scFv heavy chain CDR2 |
| 1149 | AREVTGDLEDAFDI | Anti-CD22 m971 scFv heavy chain CDR3 |
| 1150 | DIQMTQSPSSLSASVG-DRV TITCRASQTI-WSYLNWYQQ RPGKAPNLLIYAAS-SLQSG VPSRFSGRGSGTDFTLTISS LQAEDFA-TYYCQQSYSIPQ TFGQGTKLEIK | Anti-CD22 m971 scFv light chain |
| 1151 | QTIWSY | Anti-CD22 m971 scFv light chain CDR1 |
| 1152 | AAS | Anti-CD22 m971 scFv light chain CDR2 |
| 1153 | QQSYSIPQT | Anti-CD22 m971 scFv light chain CDR3 |
| 1154 | QVQLQQSGPGMVKP-SQTLS LTCAISGDSVSS-NSVAWNW IRQSPSR-GLEWLGRTYYRS | Anti-CD22 m971-L7 scFv entire sequence, with 3xG₄S linker |

TABLE K-continued

Exemplary sequences of anti-CD22
scFv and components

| SEQ ID NO: | Amino Acid Sequence | Description |
|---|---|---|
| | T-WYNDYAVSMKSRITINPD TNKNQFSLQLNSVTPEDTAV YYCAREV-TGDLEDAFD-IW GQGTMVTVSSGGGGSGGGGS GGGGSDIQMIQSPSSLSASV G-DRVTITCRASQTI-WSYL NWYRQRPGEAPNLLIYAAS- SLQSGVPSRFSGRGSGTDFT LTISSLQAEDFA-TYYCQQS YSIPQTFGQGTKLEIK | |
| 1155 | QVQLQQSGPGMVKP-SQTLS LTCAISGDSVSS-NSVAWNW IRQSPSR-GLEWLGRTYYRS T-WYNDYAVSMKSRITINPD TNKNQFSLQLNSVTPEDTAV YYCAREV-TGDLEDAFDIWG QGTMVTVSS | Anti-CD22 m971-L7 scFv heavy chain vari-able region |
| 1156 | GDSVSSNSVA | Anti-CD22 m971-L7 scFv heavy chain CDR1 |
| 1157 | TYYRSTWYN | Anti-CD22 m971-L7 scFv heavy chain CDR2 |
| 1158 | AREVTGDLEDAFDI | Anti-CD22 m971-L7 scFv heavy chain CDR3 |
| 1159 | DIQMIQSPSSLSASVG-DRV TITCRASQTI-WSYLNWYRQ RPGEAPNLLIYAAS-SLQSG VPSRFSGRGSGTDFTLTISS LQAEDFA-TYYCQQSYSIPQ TFGQGTKLEIK | Anti-CD22 m971-L7 scFv light chain variable region |
| 1160 | QTIWSY | Anti-CD22 m971-L7 scFv light chain CDR1 |
| 1161 | AAS | Anti-CD22 m971-L7 scFv light chain CDR2 |
| 1162 | QQSYSIPQT | Anti-CD22 m971-L7 scFv light chain CDR3 |

In some embodiments, the extracellular binding domain of the CD22 CAR comprises immunotoxins HA22 or BL22. Immunotoxins BL22 and HA22 are therapeutic agents that comprise an scFv specific for CD22 fused to a bacterial toxin, and thus can bind to the surface of the cancer cells that express CD22 and kill the cancer cells. BL22 comprises a dsFv of an anti-CD22 antibody, RFB4, fused to a 38-kDa truncated form of Pseudomonas exotoxin A (Bang et al., Clin. Cancer Res., 11:1545-50 (2005)). HA22 (CAT8015, moxetumomab pasudotox) is a mutated, higher affinity ver-sion of BL22 (Ho et al., J. Biol. Chem., 280 (1): 607-17 (2005)). Suitable sequences of antigen binding domains of HA22 and BL22 specific to CD22 are disclosed in, for example, U.S. Pat. Nos. 7,541,034; 7,355,012; and 7,982, 011, which are hereby incorporated by reference in their entirety.

In some embodiments, the hinge domain of the CD22 CAR comprises a CD8α hinge domain, for example, a human CD8α hinge domain. In some embodiments, the CD8α hinge domain comprises or consists of an amino acid sequence set forth in SEQ ID NO: 1109 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1109. In some embodiments, the hinge domain comprises a CD28 hinge domain, for example, a human CD28 hinge domain. In some embodiments, the CD28 hinge domain comprises or consists of an amino acid sequence set forth in SEQ ID NO: 1110 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1110. In some embodiments, the hinge domain comprises an IgG4 hinge domain, for example, a human IgG4 hinge domain. In some embodiments, the IgG4 hinge domain comprises or consists of an amino acid sequence set forth in SEQ ID NO: 1111 or SEQ ID NO: 1112, or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1111 or SEQ ID NO: 1112. In some embodiments, the hinge domain comprises a IgG4 hinge-Ch2-Ch3 domain, for example, a human IgG4 hinge-Ch2-Ch3 domain. In some embodiments, the IgG4 hinge-Ch2-Ch3 domain comprises or consists of an amino acid sequence set forth in SEQ ID NO: 1113 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1113. In some embodiments, the transmembrane domain of the CD22 CAR comprises a CD8α transmembrane domain, for example, a human CD8α transmembrane domain. In some embodiments, the CD8α transmembrane domain comprises or consists of an amino acid sequence set forth in SEQ ID NO: 1114 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO: 1114. In some embodiments, the transmembrane domain comprises a CD28 transmembrane domain, for example, a human CD28 transmembrane domain. In some embodiments, the CD28 transmembrane domain comprises or con-sists of an amino acid sequence set forth in SEQ ID NO:1115 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO: 1115.

In some embodiments, the intracellular costimulatory domain of the CD22 CAR comprises a 4-1BB costimulatory domain, for example, a human 4-1BB costimulatory domain. In some embodiments, the 4-1BB costimulatory domain comprises or consists of an amino acid sequence set forth in SEQ ID NO: 1116 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO: 1116. In some embodi-ments, the intracellular costim-ulatory domain comprises a CD28 costimulatory domain, for example, a human CD28 costimulatory domain. In some embodiments, the CD28 costimulatory domain comprises or consists of an amino acid sequence set forth in SEQ ID NO: 1117 or an amino acid sequence that is at least 80% identical (e.g., at least 80%, at least 85%, at least 90%, at least 95%, at least 96%, at least 97%, at least 98%, at least 99%, or 100% iden-tical) to the amino acid sequence set forth in SEQ ID NO: 1117.

In some embodiments, the intracellular signaling domain of the CD22 CAR comprises a CD3 zeta (ζ) signaling domain, for example, a human CD3ζ signaling domain. In some embodiments, the CD3ζ signaling domain comprises or consists of an amino acid sequence set forth in SEQ ID NO: 1118 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO: 1118.

In some embodiments, the polycistronic vector comprises an expression cassette that contains a nucleotide sequence encoding a CD22 CAR, including, for example, a CD22 CAR comprising the CD22-specific scFv having sequences set forth in SEQ ID NO: 1145 or SEQ ID NO: 1154, the CD8α hinge domain of SEQ ID NO:9, the CD8α trans-membrane domain of SEQ ID NO: 1114, the 4-1BB costimulatory domain of SEQ ID NO: 1116, the CD3ζ signaling domain of SEQ ID NO: 1118, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof.

In some embodiments, the polycistronic vector comprises an expression cassette that contains a nucleotide sequence encoding a CD22 CAR, including, for example, a CD22 CAR comprising the CD22-specific scFv having sequences set forth in SEQ ID NO: 1145 or SEQ ID NO: 1154, the CD28 hinge domain of SEQ ID NO: 1110, the CD8α transmembrane domain of SEQ ID NO: 1114, the 4-1BB costimulatory domain of SEQ ID NO: 1116, the CD3ζ signaling domain of SEQ ID NO: 1118, and/or variants (i.e., hav-ing a sequence that is at least 80% identical, for example, at least 80%, at least 85%, at least 90%, at least 95%, at least 96%, at least 97%, at least 98%, or at least 99 identical to the disclosed sequence) thereof.

In some embodiments, the polycistronic vector comprises an expression cassette that contains a nucleotide sequence encoding a CD22 CAR, including, for example, a CD22 CAR comprising the CD22-specific scFv having sequences set forth in SEQ ID NO: 1145 or SEQ ID NO: 1154, the IgG4 hinge domain of SEQ ID NO: 1111 or SEQ ID NO: 1112, the CD8α transmembrane domain of SEQ ID NO: 1114, the 4-1BB costimulatory domain of SEQ ID NO: 1116, the CD3ζ signaling domain of SEQ ID NO: 1118, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof.

In some embodiments, the polycistronic vector comprises an expression cassette that contains a nucleotide sequence encoding a CD22 CAR, including, for example, a CD22 CAR comprising the CD22-specific scFv having sequences set forth in SEQ ID NO: 1145 or SEQ ID NO: 1154, the CD8α hinge domain of SEQ ID NO:9, the CD28 transmem-brane domain of SEQ ID NO: 1115, the 4-1BB costimula-tory domain of SEQ ID NO: 1116, the CD3ζ signaling domain of SEQ ID NO: 1118, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof.

In some embodiments, the polycistronic vector comprises an expression cassette that contains a nucleotide sequence encoding a CD22 CAR, including, for example, a CD22

CAR comprising the CD22-specific scFv having sequences set forth in SEQ ID NO: 1145 or SEQ ID NO: 1154, the CD28 hinge domain of SEQ ID NO: 1110, the CD28 transmembrane domain of SEQ ID NO: 1115, the 4-1BB costimulatory domain of SEQ ID NO: 1116, the CD3ζ signaling domain of SEQ ID NO: 1118, and/or variants (i.e., hav-ing a sequence that is at least 80% identical, for example, at least 80%, at least 85%, at least 90%, at least 95%, at least 96%, at least 97%, at least 98%, or at least 99 identical to the disclosed sequence) thereof.

In some embodiments, the polycistronic vector comprises an expression cassette that contains a nucleotide sequence encoding a CD22 CAR, including, for example, a CD22 CAR comprising the CD22-specific scFv having sequences set forth in SEQ ID NO: 1145 or SEQ ID NO: 1154, the IgG4 hinge domain of SEQ ID NO: 1111 or SEQ ID NO: 1112, the CD28 transmembrane domain of SEQ ID NO: 1115, the 4-1BB costimulatory domain of SEQ ID NO: 1116, the CD3ζ signaling domain of SEQ ID NO: 1118, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof.

BCMA CAR

In some embodiments, the CAR is a BCMA CAR ("BCMA-CAR"), and in these embodiments, the polycis-tronic vector comprises an expression cassette that contains a nucleotide sequence encoding a BCMA CAR. BCMA is a tumor necrosis family receptor (TNFR) member expressed on cells of the B cell lineage, with the highest expression on terminally differentiated B cells or mature B lymphocytes. BCMA is involved in mediat-ing the survival of plasma cells for maintaining long-term humoral immunity. The expres-sion of BCMA has been recently linked to a number of cancers, such as multiple myeloma, Hodgkin's and non-Hodgkin's lymphoma, various leukemias, and glioblas-toma. In some embodiments, the BCMA CAR may comprise a signal peptide, an extracellular binding domain that spe-cifically binds BCMA, a hinge domain, a transmembrane domain, an intracellular costimulatory domain, and/or an intracellular signaling domain in tandem.

In some embodiments, the signal peptide of the BCMA CAR comprises a CD8α signal peptide. In some embodi-ments, the CD8α signal peptide comprises or consists of an amino acid sequence set forth in SEQ ID NO: 1106 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1106. In some embodiments, the signal peptide com-prises an IgK signal peptide. In some embodiments, the IgK signal peptide comprises or consists of an amino acid sequence set forth in SEQ ID NO: 1107 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1107. In some embodiments, the signal peptide comprises a GMCSFR-α or CSF2RA signal peptide. In some embodi-ments, the GMCSFR-α or CSF2RA signal peptide com-prises or consists of an amino acid sequence set forth in SEQ ID NO: 1108 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1108.

In some embodiments, the extracellular binding domain of the BCMA CAR is specific to BCMA, for example, human BCMA. The extracellular binding domain of the BCMA CAR can be codon-optimized for expression in a host cell or to have variant sequences to in-crease functions of the extracellular binding domain.

In some embodiments, the extracellular binding domain comprises an immunogenically active portion of an immu-noglobulin molecule, for example, an scFv. In some embodi-ments, the extracellular binding domain of the BCMA CAR is derived from an antibody specific to BCMA, including, for example, belantamab, erlanatamab, teclistamab, LCAR-B38M, and ciltacabtagene. In any of these embodiments, the extracellular binding domain of the BCMA CAR can com-prise or consist of the $V_H$, the $V_L$, and/or one or more CDRs of any of the antibodies.

In some embodiments, the extracellular binding domain of the BCMA CAR comprises an scFv derived from C11D5.3, a murine monoclonal antibody as described in Carpenter et al., Clin. Cancer Res. 19 (8): 2048-2060 (2013). See also PCT Application Publication No. WO2010/104949. The C11D5.3-derived scFv may comprise the heavy chain variable region ($V_H$) and the light chain variable region ($V_L$) of C11D5.3 connected by the Whitlow linker, the amino acid sequences of which is provided in Table L below. In some embodiments, the BCMA-specific extracellular binding domain comprises or con-sists of an amino acid sequence set forth in SEQ ID NO: 1163, 1164, or 1168, or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1163, 1164, or 1168.

In some embodiments, the BCMA-specific extracellular binding domain may comprise one or more CDRs having amino acid sequences set forth in SEQ ID NOs: 1165-1167 and 1169-1171. In some embodiments, the BCMA-specific extracellular binding domain may comprise a light chain with one or more CDRs having amino acid sequences set forth in SEQ ID NOs: 1165-1167. In some embodiments, the BCMA-specific extracellular binding domain may comprise a heavy chain with one or more CDRs having amino acid sequences set forth in SEQ ID NOs: 1169-1171. In any of these embodiments, the BCMA-specific scFv may comprise one or more CDRs comprising one or more amino acid substitutions, or comprising a sequence that is at least 80% identical (e.g., at least 80%, at least 85%, at least 90%, at least 95%, at least 96%, at least 97%, at least 98%, at least 99%, or 100% identical), to any of the sequences identified. In some embodiments, the extracellular binding domain of the BCMA CAR comprises or consists of the one or more CDRs as described herein.

In some embodiments, the extracellular binding domain of the BCMA CAR comprises an scFv derived from another murine monoclonal antibody, C12A3.2, as described in Carpenter et al., Clin. Cancer Res. 19 (8): 2048-2060 (2013) and PCT Application Publication No. WO2010/104949, the amino acid sequence of which is also provided in Table L below. In some embodiments, the BCMA-specific extracel-lular binding domain comprises or consists of an amino acid sequence set forth in SEQ ID NO: 1172, 1173, or 1177, or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1172, 1173, or 1177. In some embodiments, the BCMA-specific extracellular binding domain may comprise one or more CDRs having amino acid sequences set forth in SEQ ID NOs: 1174-1176 and 1178-1180. In some embodiments, the BCMA-specific extracellular binding domain may comprise a light chain with one or more CDRs having amino acid sequences set forth in SEQ ID NOs: 1174-1176. In some embodiments, the BCMA-specific extracellular binding domain may comprise a heavy chain with one or more CDRs having amino acid sequences set forth in SEQ ID NOs: 1178-1180. In any of these embodiments, the BCMA-specific scFv may comprise one or more CDRs comprising one or more amino acid substitutions, or comprising a sequence that is at least 80% identical (e.g., at least 80%, at least 85%, at least 90%, at least 95%, at least 96%, at least 97%, at least 98%, at least 99%, or 100% identical), to any of the sequences identified. In some embodiments, the extracellular binding domain of the BCMA CAR comprises or consists of the one or more CDRs as described herein.

In some embodiments, the extracellular binding domain of the BCMA CAR comprises a murine monoclonal antibody with high specificity to human BCMA, referred to as BB2121 in Friedman et al., Hum. Gene Ther. 29 (5): 585-601 (2018)). See also, PCT Application Publication No. WO2012163805.

In some embodiments, the extracellular binding domain of the BCMA CAR comprises single variable fragments of two heavy chains (VHH) that can bind to two epitopes of BCMA as described in Zhao et al., J. Hematol. Oncol. 11 (1): 141 (2018), also referred to as LCAR-B38M. See also, PCT Application Publication No. WO2018/028647.

In some embodiments, the extracellular binding domain of the BCMA CAR comprises a fully human heavy-chain variable domain (FHVH) as described in Lam et al., Nat. Com-mun. 11 (1): 283 (2020), also referred to as FHVH33. See also, PCT Application Publication No. WO2019/006072. The amino acid sequences of FHVH33 and its CDRs are provided in Table L below. In some embodiments, the BCMA-specific extracellular binding domain comprises or consists of an amino acid sequence set forth in SEQ ID NO: 1181 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1181. In some embodiments, the BCMA-specific extracellular binding domain may comprise one or more CDRs having amino acid sequences set forth in SEQ ID NOs: 1182-1184. In any of these embodiments, the BCMA-specific extracellular binding domain may comprise one or more CDRs comprising one or more amino acid substitutions, or comprising a sequence that is at least 80% identical (e.g., at least 80%, at least 85%, at least 90%, at least 95%, at least 96%, at least 97%, at least 98%, at least 99%, or 100% identical), to any of the sequences identified. In some embodiments, the extracellular binding domain of the BCMA CAR comprises or consists of the one or more CDRs as described herein.

In some embodiments, the extracellular binding domain of the BCMA CAR comprises an scFv derived from CT103A (or CAR0085) as described in U.S. Pat. No. 11,026,975 B2, the amino acid sequence of which is provided in Table L below. In some embodiments, the BCMA-specific extracellular binding domain comprises or consists of an amino acid sequence set forth in SEQ ID NO: 1218, 1219, or 1223, or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1218, 1219, or 1223. In some embodiments, the BCMA-specific extracellular binding domain may comprise one or more CDRs having amino acid sequences set forth in SEQ ID NOs: 1220-1222 and 1224-1226. In some embodiments, the BCMA-specific extracellular binding domain may com-prise a light chain with one or more CDRs having amino acid sequences set forth in SEQ ID NOs: 1220-1222. In some embodiments, the BCMA-specific extracellular binding domain may comprise a heavy chain with one or more CDRs having amino acid sequences set forth in SEQ ID NOs: 1224-1226. In any of these embodiments, the BCMA-specific scFv may comprise one or more CDRs comprising one or more amino acid substitutions, or comprising a sequence that is at least 80% identical (e.g., at least 80%, at least 85%, at least 90%, at least 95%, at least 96%, at least 97%, at least 98%, at least 99%, or 100% identical), to any of the sequences identified. In some embodiments, the extracellular binding domain of the BCMA CAR comprises or consists of the one or more CDRs as described herein.

Additionally, CARs and binders directed to BCMA have been described in U.S. Application Publication Nos. 2020/0246381 A1 and 2020/0339699 A1, the entire contents of each of which are incorporated by reference herein.

TABLE L

Exemplary sequences of anti-BCMA binder and components

| SEQ ID NO: | Amino Acid Sequence | Description |
|---|---|---|
| 1163 | DIVLTQSPASLAMSLGKRAT IS-CRASESVSVIGAHLIHW YQQKPGQPPKLLIYLASN-L ETGVPARFSGSGSGTDFT-L TIDPVEEDDVAIYSCLQSRI FPRT-FGGGTKLEIKGSTSG SGKPGSGEGSTKGQIQLVQS GPELKKPGETVKISCKASGY TFTDYSINWVKRAPGKGLKW MGWIN-TETREPAYAYDFRG RFAFSLETSASTAYLQINNL KYEDTATYFCAL-DYSYAMD YWGQGTSVTVSS | Anti-BCMA C11D5.3 scFv entire sequence, with Whitlow linker |
| 1164 | DIVLTQSPASLAMSLGKRAT IS-CRASESVSVIGAHLIHW YQQKPGQPPKLLIYLASN-L ETGVPARFSGSGSGTDFT-L TIDPVEEDDVAIYSCLQSRI FPRT-FGGGTKLEIK | Anti-BCMA C11D5.3 scFv light chain variable region |
| 1165 | RASESVSVIGAHLIH | Anti-BCMA C11D5.3 scFv light chain CDR1 |
| 1166 | LASNLET | Anti-BCMA C11D5.3 scFv light chain CDR2 |
| 1167 | LQSRIFPRT | Anti-BCMA C11D5.3 scFv light chain CDR3 |
| 1168 | QIQLVQSGPELKKPGETVKI SCK-ASGYTFTDYSINWVKR APGKGLK-WMGWIN-TETRE PAYAYDFRGRFAFSLETSAS TAYLQINNLKYEDTATYFCA L-DYSYAMDYWGQGTSVTVS S | Anti-BCMA C11D5.3 scFv heavy chain variable region |
| 1169 | DYSIN | Anti-BCMA C11D5.3 scFv heavy chain CDR1 |

TABLE L-continued

Exemplary sequences of anti-BCMA
binder and components

| SEQ ID NO: | Amino Acid Sequence | Description |
|---|---|---|
| 1170 | WINTETREPAYAYDFRG | Anti-BCMA C11D5.3 scFv heavy chain CDR2 |
| 1171 | DYSYAMDY | Anti-BCMA C11D5.3 scFv heavy chain CDR3 |
| 1172 | DIVLTQSPPSLAMSLGKRAT IS-CRASESVTILGSHLI-Y WYQQKPGQPPTLLIQ-LASN VQTGVPARFSGSGSRTDFTL TIDPVEEDDVAVYYCLQSRT IPRT-FGGGTKLEIKGSTSG SGKPGSGEGSTKGQIQLVQS GPELKKPGETVKISCKASGY TFRHYSMNWVKQAPGKGLKW MGRINTESGVPIYADD-FKG RFAFSVETSASTAYL-VINN LKDEDTASYFCSNDYLYSLD -FWGQGTALTVSS | Anti-BCMA C12A3.2 scFv entire sequence, with Whitlow linker |
| 1173 | DIVLTQSPPSLAMSLGKRAT IS-CRASESVTILGSHLI-YWYQ QKPGQPPTLLIQ-LASNVQT GVPARFSGSGSRTDFTLTID PVEEDDVAVYYCLQSRTIPR T-FGGGTKLEIK | Anti-BCMA C12A3.2 scFv light chain variable region |
| 1174 | RASESVTILGSHLIY | Anti-BCMA C12A3.2 scFv light chain CDR1 |
| 1175 | LASNVQT | Anti-BCMA C12A3.2 scFv light chain CDR2 |
| 1176 | LQSRTIPRT | Anti-BCMA C12A3.2 scFv light chain CDR3 |
| 1177 | QIQLVQSGPELKKPGETVKI SCK-ASGYTFRHYSMNWVKQ APGKGLK-WMGRINTESGVP IYADDFKGRFAFSVETSAST AYL-VINNLKDEDTASYFCS NDYLYSLD-FWGQGTALTVS S | Anti-BCMA C12A3.2 scFv heavy chain variable region |
| 1178 | HYSMN | Anti-BCMA C12A3.2 scFv heavy chain CDR1 |
| 1179 | RINTESGVPIYADDFKG | Anti-BCMA C12A3.2 scFv heavy chain CDR2 |
| 1180 | DYLYSLDF | Anti-BCMA C12A3.2 scFv heavy chain CDR3 |
| 1181 | EVQLLESGGGLVQPGGSLRL S-CAASGFTFSSYAMSWVR- QAPGKGLEWVSSISGSGDYI Y-YADSVKGRFTISRDISKN TLYLQMNSLRAEDTAVYYCA KEGTGANSSLADYRGQGTLV TVSS | Anti-BCMA FHVH33 entire sequence |
| 1182 | GFTFSSYA | Anti-BCMA FHVH33 CDR1 |
| 1183 | ISGSGDYI | Anti-BCMA FHVH33 CDR2 |

TABLE L-continued

Exemplary sequences of anti-BCMA
binder and components

| SEQ ID NO: | Amino Acid Sequence | Description |
|---|---|---|
| 1184 | AKEGTGANSSLADY | Anti-BCMA FHVH33 CDR3 |
| 1218 | DIQMTQSPSSLSASVG-DRV TITCRASQSIS-SYLNWYQQ KPGKAPKLLIYAAS-SLQSG VPSRFSGSGSGTDFTLTISS LQPEDFA-TYYCQQKYDLLT FGGGTKVEIKGSTSGSGKPG SGEGSTKGQLQLQESGPGLV KPSETLSLTCTVSGGSIS-S SSYYWGWIRQPPGKGLEWIG -SISYSGSTYYNPSLKSRVT ISVDTSKNQFSLKLSSVTAA DTAVYYCARDRGDTILDVWG QGTMVTVSS | Anti-BCMA CT103A scFv entire sequence, with Whitlow linker |
| 1219 | DIQMTQSPSSLSASVG-DRV TITCRASQSIS-SYLNWYQQ KPGKAPKLLIYAAS-SLQSG VPSRFSGSGSGTDFTLTISS LQPEDFA-TYYCQQKYDLLT FGGGTKVEIK | Anti-BCMA CT103A scFv light chain variable region |
| 1220 | QSISSY | Anti-BCMA CT103A scFv light chain CDR1 |
| 1221 | AAS | Anti-BCMA CT103A scFv light chain CDR2 |
| 1222 | QQKYDLLT | Anti-BCMA CT103A scFv light chain CDR3 |
| 1223 | QLQLQESGPGLVKP-SETLS LTCTVSGGSIS-SSSYYWGW IRQPPGKGLEWIG-SISYSG STYYNPSLKSRVTISVDTSK NQFSLKLSSVTAADTAVYYC ARDRGDTILDVWGQGTMVTV SS | Anti-BCMA CT103A scFv heavy chain variable region |
| 1224 | GGSISSSSYY | Anti-BCMA CT103A scFv heavy chain CDR1 |
| 1225 | ISYSGST | Anti-BCMA CT103A scFv heavy chain CDR2 |
| 1226 | ARDRGDTILDV | Anti-BCMA CT103A scFv heavy chain CDR3 |

In some embodiments, the hinge domain of the BCMA CAR comprises a CD8α hinge domain, for example, a human CD8α hinge domain. In some embodiments, the CD8α hinge domain comprises or consists of an amino acid sequence set forth in SEQ ID NO: 1109 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1109. In some embodiments, the hinge domain comprises a CD28 hinge domain, for example, a human CD28 hinge domain. In some embodiments, the CD28 hinge domain comprises or consists of an amino acid sequence set forth in SEQ ID NO: 1110 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1110. In some embodiments, the hinge domain comprises an IgG4 hinge domain, for example, a human IgG4 hinge domain. In some embodiments, the IgG4 hinge domain comprises or consists of an amino acid sequence set forth in SEQ ID NO: 1111 or SEQ ID NO: 1112, or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1111 or SEQ ID NO: 1112. In some embodiments, the hinge domain comprises a IgG4 hinge-Ch2-Ch3 domain, for example, a human IgG4 hinge-Ch2-Ch3 domain. In some embodiments, the IgG4 hinge-Ch2-Ch3 domain comprises or consists of an amino acid sequence set forth in SEQ ID NO: 1113 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1113. In some embodiments, the transmembrane domain of the BCMA CAR comprises a CD8α transmembrane domain, for example, a human CD8α transmembrane domain. In some embodiments, the CD8α transmembrane domain comprises or consists of an amino acid sequence set forth in SEQ ID NO: 1114 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO: 1114. In some embodiments, the transmembrane domain comprises a CD28 transmembrane domain, for example, a human CD28 transmembrane domain. In some embodiments, the CD28 transmembrane domain comprises or consists of an amino acid sequence set forth in SEQ ID NO: 1115 or an amino acid sequence that is at least 80% identical (e.g., at least 80%, at least 85%, at least 90%, at least 95%, at least 96%, at least 97%, at least 98%, at least 99%, or 100% iden-tical) to the amino acid sequence set forth in SEQ ID NO: 1115.

In some embodiments, the intracellular costimulatory domain of the BCMA CAR comprises a 4-1BB costimula-tory domain, for example, a human 4-1BB costimulatory domain. In some embodiments, the 4-1BB costimulatory domain comprises or consists of an amino acid sequence set forth in SEQ ID NO: 1116 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO: 1116. In some embodi-ments, the intracellular costim-ulatory domain comprises a CD28 costimulatory domain, for example, a human CD28 costimulatory domain. In some embodiments, the CD28 costimulatory domain comprises or consists of an amino acid sequence set forth in SEQ ID NO: 1117 or an amino acid sequence that is at least 80% identical (e.g., at least 80%, at least 85%, at least 90%, at least 95%, at least 96%, at least 97%, at least 98%, at least 99%, or 100% iden-tical) to the amino acid sequence set forth in SEQ ID NO: 1117.

In some embodiments, the intracellular signaling domain of the BCMA CAR comprises a CD3 zeta (ζ) signaling domain, for example, a human CD3ζ signaling domain. In some embodiments, the CD3ζ signaling domain comprises or consists of an amino acid sequence set forth in SEQ ID NO: 1118 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO: 1118.

In some embodiments, the polycistronic vector comprises an expression cassette that contains a nucleotide sequence encoding a BCMA CAR, including, for example, a BCMA CAR comprising any of the BCMA-specific extracellular binding domains as described, the CD8α hinge domain of SEQ ID NO: 1109, the CD8α transmembrane domain of SEQ ID NO: 1114, the 4-1BB costimulatory domain of SEQ ID NO: 1116, the CD3ζ signaling domain of SEQ ID NO: 1118, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof. In any of these embodiments, the BCMA CAR may additionally comprise a signal peptide (e.g., a CD8α signal peptide) as described. In some embodiments, the polycis-tronic vector comprises an expression cassette that contains a nucleotide sequence encoding a BCMA CAR, including, for example, a BCMA CAR comprising any of the BCMA-specific extracellular binding domains as described, the CD8α hinge domain of SEQ ID NO: 1109, the CD8α transmembrane domain of SEQ ID NO: 1114, the CD28 costimulatory domain of SEQ ID NO: 1117, the CD3ζ signaling domain of SEQ ID NO: 1118, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof. In any of these embodiments, the BCMA CAR may additionally comprise a signal peptide as described.

In some embodiments, the polycistronic vector comprises an expression cassette that contains a nucleotide sequence encoding a BCMA CAR as set forth in SEQ ID NO: 1227 or is at least 80% identical (e.g., at least 80%, at least 85%, at least 90%, at least 95%, at least 96%, at least 97%, at least 98%, at least 99%, or 100% identical) to the nucleotide sequence set forth in SEQ ID NO: 1227 (see Table M). The encoded BCMA CAR has a corresponding amino acid sequence set forth in SEQ ID NO: 1228 or is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 1228, with the following components: CD8α signal peptide, CT103A scFv ($V_L$-Whitlow linker-$V_H$), CD8α hinge domain, CD8α transmembrane domain, 4-1BB costimulatory domain, and CD3ζ signaling domain.

In some embodiments, the polycistronic vector comprises an expression cassette that contains a nucleotide sequence encoding a commercially available embodiment of BCMA CAR, including, for example, idecabtagene vicleucel (ide-cel, also called bb2121). In some embodiments, the poly-cistronic vector comprises an expression cassette that con-tains a nucleotide sequence encoding idecabtagene vicleucel or portions thereof. Idecabtagene vicleucel comprises a BCMA CAR with the following components: the BB2121 binder, CD8α hinge domain, CD8α transmembrane domain, 4-1BB costimulatory domain, and CD3ζ signaling domain.

TABLE M

| Exemplary sequences of BCMA CARs | | |
|---|---|---|
| SEQ ID NO: | Sequence | Description |
| 1227 | atggccttaccagtgaccgc cttgctcctgccgctggcct t-gctgctccac-gccgcca | Exemplary BCMA CAR nucleotide sequence |

TABLE M-continued

Exemplary sequences of BCMA CARs

| SEQ ID NO: | Sequence | Description |
|---|---|---|
| | ggccggacatccagatgacc cagtctccatcctccctgtc tgcatctgtaggagacagag tcaccatcac-ttgccgggc aagtcagagcatt-agcagc tatttaaattggtatcagca gaaaccagggaaagcccta agctcctgatctatgctgca tccagttt-gcaaagtgggg tcccatcaaggttcag-tgg cagtggatctgggacagatt tcactctcaccatcagcagt ctgcaacctgaagattttgc aacttactactgtcag-caa aaatacgacctcctcac-tt ttggcggagggaccaaggtt gagatcaaaggcagcaccag cggctccggcaagcctggct ctggcgagggcag-cacaaa gggacagctgcagctgcag- gagtcgggcccaggactggt gaagccttcggagaccctgt ccctcacctgcactgtctct ggtggctccatcagcag-ta gtagttactactggggctg- gatccgccagccccaggga aggggctggagtggattggg agtatctcctatagtgggag cacctacta-caacccgtcc ctcaagagtcgagtcac-ca tatccgtagacacgtccaag aaccagttctccctgaagct gagttctgtgaccgccgcag acacggcggtg-tactactg cgccagagatcgtggagaca c-catactagacgtatgggg tcagggtacaatggtcaccg tcagctcattcgtgcccgtg ttcctgcccgccaaacctac -caccacccctgcccctaga c-ctcccacccagccccaa caatcgccagccagcctctg tctctgcggcccgaagcctg tagacctgctgccggcg-ga gccgtgcacaccagaggcct g-gacttcgcctgcgacatc tacatctgggcccctctggc cggcac-ctgtggcgtgctg ctgctgagcctggtgatcac cctg-tactgcaaccaccg- gaacaaacggggcagaaga aactcctgtatatattcaaa caaccatttatgagaccagt acaaactactcaagag-gaa gatggctgtagctgccgat- ttccagaagaagaagaagga ggatgtgaactgagagtgaa gttcagcagatccgccgacg cccctgcctaccag-caggg acagaaccagctgtacaac- gagctgaacctgggcagacg ggaagagtacgacgtgctgg acaagcggagaggccgggac cccgagatgggcg-gaaagc ccagacggaagaacccccag -gaaggcctgtataacgaac tgcagaaagacaagatggcc gaggcctacagcgagatcgg -catgaaggcgagcggagg cgcggcaagggccac-gatg gcctgtaccagggcctgagc accgccaccaaggacaccta cgacgccctg-cacatgcag gccctgcccccaga | |

TABLE M-continued

Exemplary sequences of BCMA CARs

| SEQ ID NO: | Sequence | Description |
|---|---|---|
| 1228 | MAL-PVTALLLPLALLLHAA RPDIQMTQSPSSLSASVGDR VTITCRASQSIS-SYLNWYQ QKPGKAPKLLIYAAS-SLQS GVPSRFSGSGSGTDFT-LTI SSLQPEDFATYYCQQKYDLL TFGGGTKVEIKGSTSGSGKP GSGEGSTKGQLQLQESGPGL VKPSETLSLTCTVSGGSIS- SSSYYWGWIRQPPGKGLEWI G-SISYSGSTYYNPSLKSRV TISVDTSKNQFSLKLSSVTA ADTAVYYCARDRGDTIL-DV WGQGTMVTVSS-FVPVFLPA KPTTTPAPRPPTPAP-TIAS QPLSLRPEACRPAAGGAVHT RGLDFACDIYIWAPLAGTCG VLLLSLVITLYC-NHRNKRG RKKLLY-IFKQPFMRPVQTT QEEDGCSCRFPEEEEGGCEL RVKFSRSADAPA-YQQGQNQ LYNELNLGR-REEYDVLDKR RGRDPEMGGKPRR-KNPQEG LYNELQKDKMAEAYSEIGMK GERRRGKGHDGLYQGLSTAT -KDTYDALHMQALPPR | Exemplary BCMA CAR amino acid sequence |

In some embodiments, the antibody portion of the recombinant receptor, e.g., CAR, further includes spacer between the transmembrane domain and extracellular antigen binding domain. In some embodiments, the spacer includes at least a portion of an immunoglobulin constant region, such as a hinge region, e.g., an IgG4 hinge region, and/or a CH1/CL and/or Fc region. In some embodiments, the constant region or portion is of a human IgG, such as IgG4 or IgGI. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. Exemplary spacers include, but are not limited to, those described in Hudecek et al. (2013) Clin. Cancer Res., 19:3153, WO2014031687, U.S. Pat. No. 8,822,647 or published app. No. US 2014/0271635. In some embodiments, the constant region or portion is of a human IgG, such as IgG4 or IgGI.

In some embodiments, the antigen receptor comprises an intracellular domain linked directly or indirectly to the extracellular domain. In some embodiments, the chimeric antigen receptor includes a transmembrane domain linking the extracellular domain and the intracellular signaling domain. In some embodiments, the intracellular signaling domain comprises an ITAM. For example, in some aspects, the antigen recognition domain (e.g. extracellular domain) generally is linked to one or more intracellular signaling components, such as signaling components that mimic activation through an antigen receptor complex, such as a TCR complex, in the case of a CAR, and/or signal via another cell surface receptor. In some embodiments, the chimeric receptor comprises a transmembrane domain linked or fused between the extracellular domain (e.g. scFv) and intracellular signaling domain. Thus, in some embodiments, the antigen-binding component (e.g., antibody) is linked to one or more transmembrane and intracellular signaling domains.

In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD 134, CD 137, CD 154. Alternatively, the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s). In some aspects, the transmembrane domain contains a transmembrane portion of CD28.

In some embodiments, the extracellular domain and transmembrane domain can be linked directly or indirectly. In some embodiments, the extracellular domain and transmembrane are linked by a spacer, such as any described herein. In some embodiments, the receptor contains extracellular portion of the molecule from which the transmembrane domain is derived, such as a CD28 extracellular portion.

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

The receptor, e.g., the CAR, generally includes at least one intracellular signaling component or components. In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or IT AMs. Examples of IT AM containing primary cytoplasmic signaling sequences include those derived from CD3 zeta chain, FcR gamma, CD3 gamma, CD3 delta and CD3 epsilon. In some embodiments, cytoplasmic signaling molecule(s) in the CAR contain(s) a cytoplasmic signaling domain, portion thereof, or sequence derived from CD3 zeta.

In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD transmembrane domains. In some embodiments, the intracellular component is or includes a CD3-zeta intracellular signaling domain. In some embodiments, the intracellular component is or includes a signaling domain from Fc receptor gamma chain. In some embodiments, the receptor, e.g., CAR, includes the intracellular signaling domain and further includes a portion, such as a transmembrane domain and/or hinge portion, of one or more additional molecules such as CD8, CD4, CD25, or CD 16. For example, in some aspects, the CAR or other chimeric receptor is a chimeric molecule of CD3-zeta (CD3-z) or Fc receptor g and a portion of one of CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

In some embodiments, the chimeric antigen receptor contains an intracellular domain of a T cell costimulatory molecule. In some embodiments, the CAR includes a signaling domain and/or transmembrane portion of a costimulatory receptor, such as CD28, 4-1BB, 0X40, DAP10, and ICOS. In some aspects, the same CAR includes both the activating and costimulatory components. In some embodiments, the chimeric antigen receptor contains an intracellular domain derived from a T cell costimulatory molecule or a functional variant thereof, such as between the transmembrane domain and intracellular signaling domain. In some aspects, the T cell costimulatory molecule is CD28 or 41BB.

In some embodiments, the activating domain is included within one CAR, whereas the costimulatory component is provided by another CAR recognizing another antigen. In some embodiments, the CARs include activating or stimulatory CARs, costimulatory CARs, both expressed on the same cell (see WO2014/055668). In some aspects, the cells include one or more stimulatory or activating CAR and/or a costimulatory CAR. In some embodiments, the cells further include inhibitory CARs (iCARs, see Fedorov et al., Sci. Transl. Medicine, 5 (215) (December 2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments the intracellular signaling domain includes intracellular components of a 4-1BB signaling domain and a CD3-zeta signaling domain. In some embodiments, the intracellular signaling domain includes intracellular components of a CD28 signaling domain and a CD3zeta signaling domain.

In some embodiments, the CAR comprises an extracellular antigen binding domain (e.g., antibody or antibody fragment, such as an scFv) that binds to an antigen (e.g. tumor antigen), a spacer (e.g. containing a hinge domain, such as any as described herein), a transmembrane domain (e.g. any as described herein), and an intracellular signaling domain (e.g. any intracellular signaling domain, such as a primary signaling domain or costimulatory signaling domain as described herein). In some embodiments, the intracellular signaling domain is or includes a primary cytoplasmic signaling domain. In some embodiments, the intracellular signaling domain additionally includes an intracellular signaling domain of a costimulatory molecule (e.g., a costimulatory domain). Examples of exemplary components of a CAR are described in Table 14. In provided aspects, the sequences of each component in a CAR can include any combination listed in Table 14.

TABLE 14

| Component | Sequence | SEQ ID NO: |
|---|---|---|
| Extracellular binding domain | | |
| Anti-CD19 scFv (FMC63) | DIQMTQTTSSLSASLGDRVT ISCRASQDISKYLNWYQQKP DGTVKLLIYHTSRLHSGVPS RFSGSGSGTDYSLTISNLEQ EDIATYFCQQGNTLPYTFGG GTKLEITGSTSGSGKPGSGE GSTKGEVKLQESGPGLVAPS QSLSVTCTVSGVSLPDYGVS WIRQPPRKGLEWLGVIWGSE TTYYNSALKSRLTIIKDNSK SQVFLKMNSLQTDDTAIYYC AKHYYYGGSYAMDYWGQGTS VTVSS | 1075 |
| Anti-CD19 scFv (FMC63) | DIQMTQTTSSLSASLGDRVT ISCRASQDISKYLNWYQQKP DGTVKLLIYHTSRLHSGVPS RFSGSGSGTDYSLTISNLEQ | 1076 |

TABLE 14-continued

| Component | Sequence | SEQ ID NO: |
|---|---|---|
| | EDIATYFCQQGNTLPYTFGG GTKLEITGGGGSGGGGSGGG GSEVKLQESGPGLVAPSQSL SVTCTVSGVSLPDYGVSWIR QPPRKGLEWLGVIWGSETTY YNSALKSRLTIIKDNSKSQV FLKMNSLQTDDTAIYYCAKH YYYGGSYAMDYWGQGTSVTV SS | |
| Anti-BCMA sdAb (FHVH74) | QVQLVESGGGLVQPGGSLRL SCAASGFTFTNHAMSWVRQA PGKGLELVSSISGNGRTTYY ADSVKGRFTISRDISKNTLD LQMNSLRAEDTAVYYCAKDG GETLVDSRGQGTLVTVSS | 1077 |
| Anti-BCMA sdAb (FHVH32) | QVQLVESGGGLVQPGGSLRL SCAASGFTFSSHAMTWVRQA PGKGLEWVAAISGSGDFTHY ADSVKGRFTISRDNSKNTVS LQMNNLRAEDTAVYYCAKDE DGGSLLGYRGQGTLVTVSS | 1078 |
| Anti-BCMA sdAb (FHVH33) | EVQLLESGGGLVQPGGSLRL SCAASGFTFSSYAMSWVRQA PGKGLEWVSSISGSGDYIYY ADSVKGRFTISRDISKNTLY LQMNSLRAEDTAVYYCAKEG TGANSSLADYRGQGTLVTVS S | 1079 |
| Anti-BCMA sdAb (FHVH93) | EVQLLESGGGLIQPGGSLRL SCAASGFTFSSHAMTWVRQA PGKGLEWVSAISGSGDYTHY ADSVKGRFTISRDNSKNTVY LQMNSLRAEDSAVYYCAKDE DGGSLLGHRGQGTLVTVSS | 1080 |
| Spacer (e.g. hinge) | | |
| IgG4 Hinge | ESKYGPPCPPCP | 1081 |
| CD8 Hinge | TTTPAPRPPTPAPTIASQPL SLRPE | 1082 |
| CD28 | IEVMYPPPYLDNEKSNGTII HVKGKHLCPSPLFPGPSKP | 1083 |
| Transmembrane | | |
| CD8 | ACRPAAGGAVHTRGLDFACD IYIWAPLAGTCGVLLLSL-V ITLYC | 1084 |
| CD28 | FWVLVVVGGVLACYSLLVTV AFIIFWV | 1085 |
| CD28 | MFWVLVVVGGVLACYSLLVT VAFIIFWV | 1214 |
| Costimulatory domain | | |
| CD28 | RSKRSRLLHSDYMNMTPRRP GPTRKHYQPYAPPRDFAAYR S | 1086 |
| 4-1BB | KRGRKKLLYIFKQPFMRPVQ TTQEEDGCSCRFPEEEEGGC EL | 1087 |

131

TABLE 14-continued

| Component | Sequence | SEQ ID NO: |
|---|---|---|
| Primary Signaling Domain | | |
| CD3zeta | RVKFSRSADAPAYQQGQNQL YNELNLGR-REEYDVLDKRR GRDPEMGGKPRRKNPQEGLY NEL-QKDKMAEAYSEIGMKG ERRRGKGHDGLYQGLSTATK DTYDALHMQALPPR | 1088 |
| CD3zeta (Q > K) | RVKFSRSADAPAYKQGQNQL YNELNLGR-REEYDVLDKRR GRDPEMGGKPRRKNPQEGLY NEL-QKDKMAEAYSEIGMKG ERRRGKGHDGLYQGLSTATK DTYDALHMQALPPR | 1089 |

In some embodiments, the antigen receptor further includes a marker and/or cells expressing the CAR or other antigen receptor further includes a surrogate marker, such as a cell surface marker, which may be used to confirm transduction or engineering of the cell to express the receptor. In some aspects, the marker includes all or part (e.g., truncated form) of CD34, a NGFR, or epidermal growth factor receptor, such as truncated version of such a cell surface receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in published patent application No. WO2014031687. For example, the marker can be a truncated EGFR (tEGFR) that is, optionally, linked to a linker sequence, such as a T2A cleavable linker sequence.

In some embodiments, the marker is a molecule, e.g., cell surface protein, not naturally found on T cells or not naturally found on the surface of T cells, or a portion thereof. In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD 137; in some aspects, a third generation CAR is one that includes multiple costimulatory domains of different costimulatory receptors.

For example, in some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-IBB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some aspects, the spacer contains only a hinge region of an IgG, such as only a hinge of IgG4 or IgG. In other embodiments, the spacer is or contains an Ig hinge, e.g., an IgG4-derived hinge, optionally linked to a CH2 and/or CH3 domains. In some embodiments, the spacer is an Ig hinge, e.g., an IgG4 hinge, linked to CH2 and CH3 domains. In some embodiments, the spacer is an Ig hinge, e.g., an IgG4 hinge, linked to a CH3 domain only. In some embodiments, the spacer is or comprises a glycine-serine rich sequence or other flexible linker such as known flexible linkers.

For example, in some embodiments, the CAR includes an antibody such as an antibody fragment, including scFvs, a spacer, such as a spacer containing a portion of an immunoglobulin molecule, such as a hinge region and/or one or more constant regions of a heavy chain molecule, such as an Ig-hinge containing spacer, a transmembrane domain containing all or a portion of a CD28-derived transmembrane domain, a CD28-derived intracellular signaling domain, and a CD3 zeta signaling domain. In some embodiments, the CAR includes an antibody or fragment, such as scFv, a spacer such as any of the Ig-hinge containing spacers, a CD28-derived transmembrane domain, a 4-IBB-derived intracellular signaling domain, and a CD3 zeta-derived signaling domain.

The recombinant receptors, such as CARs, expressed by the cells administered to the subject generally recognize or specifically bind to a molecule that is expressed in, associated with, and/or specific for the disease or condition or cells thereof being treated. Upon specific binding to the molecule, e.g., antigen, the receptor generally delivers an immunostimulatory signal, such as an ITAM-transduced signal, into the cell, thereby promoting an immune response targeted to the disease or condition. For example, in some embodiments, the cells express a CAR that specifically binds to an antigen expressed by a cell or tissue of the disease or condition or associated with the disease or condition.

b. T Cell Receptors Antigen Receptors (TCRs)

In some embodiments, engineered cells, such as T cells, used in connection with the provided methods, uses, articles of manufacture or compositions are cells that express a T cell receptor (TCR) or antigen-binding portion thereof that recognizes an peptide epitope or T cell epitope of a target polypeptide, such as an antigen of a tumor, viral or autoimmune protein.

In some embodiments, a "T cell receptor" or "TCR" is a molecule that contains a variable a and b chains (also known as TCRalpha and TCRbeta, respectively) or a variable g and d chains (also known as TCRalpha and TCRbeta, respectively), or antigen-binding portions thereof, and which is capable of specifically binding to a peptide bound to an MHC molecule. In some embodiments, the TCR is in the ab form. Typically, TCRs that exist in ab and gd forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules.

Unless otherwise stated, the term "TCR" should be understood to encompass full TCRs as well as antigen-binding portions or antigen-binding fragments thereof. In some embodiments, the TCR is an intact or full-length TCR, including TCRs in the ab form or gd form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable a chain and variable b chain of a TCR, sufficient to form a binding site for binding to a specific MHC-peptide complex. Generally, the variable chains of a TCR contain complementarity determining regions involved in recognition of the peptide, MHC and/or MHC-peptide complex.

c. Multi-Targeting

In some embodiments, the cells used in connection with the provided methods, uses, articles of manufacture and compositions include cells employing multi-targeting strategies, such as expression of two or more genetically engineered receptors on the cell, each recognizing the same of a different antigen and typically each including a different intracellular signaling component. Such multi-targeting strategies are described, for example, in WO 2014055668 (describing combinations of activating and costimulatory CARs, e.g., targeting two different antigens present individually on off-target, e.g., normal cells, but present together only on cells of the disease or condition to be treated) and Fedorov et al., Sci. Transl. Medicine, 5 (215) (2013) (describing cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat).

For example, in some embodiments, the cells include a receptor expressing a first genetically engineered antigen receptor (e.g., CAR) which is capable of inducing an activating or stimulatory signal to the cell, generally upon specific binding to the antigen recognized by the first receptor, e.g., the first antigen. In some embodiments, the cell further includes a second genetically engineered antigen receptor (e.g., CAR), e.g., a chimeric costimulatory receptor, which is capable of inducing a costimulatory signal to the immune cell, generally upon specific binding to a second antigen recognized by the second receptor. In some embodiments, the first antigen and second antigen are the same. In some embodiments, the first antigen and second antigen are different.

In some embodiments, the first and/or second genetically engineered antigen receptor (e.g. CAR) is capable of inducing an activating signal to the cell. In some embodiments, the receptor includes an intracellular signaling component containing ITAM or ITAM-like motifs. In some embodiments, the activation induced by the first receptor involves a signal transduction or change in protein expression in the cell resulting in initiation of an immune response, such as ITAM phosphorylation and/or initiation of IT AM-mediated signal transduction cascade, formation of an immunological synapse and/or clustering of molecules near the bound receptor (e.g. CD4 or CD8, etc.), activation of one or more transcription factors, such as NF-KB and/or AP-1, and/or induction of gene expression of factors such as cytokines, proliferation, and/or survival.

In some embodiments, the first and/or second receptor includes intracellular signaling domains or regions of costimulatory receptors such as CD28, CD137 (4-1BB), OX40, and/or ICOS. In some embodiments, the first and second receptor include an intracellular signaling domain of a costimulatory receptor that are different. In one embodiment, the first receptor contains a CD28 costimulatory signaling region and the second receptor contain a 4-IBB co-stimulatory signaling region or vice versa.

In some embodiments, the first and/or second receptor includes both an intracellular signaling domain containing ITAM or ITAM-like motifs and an intracellular signaling domain of a costimulatory receptor.

In some embodiments, the first receptor contains an intracellular signaling domain containing ITAM or IT AM-like motifs and the second receptor contains an intracellular signaling domain of a costimulatory receptor. The costimulatory signal in combination with the activating signal induced in the same cell is one that results in an immune response, such as a robust and sustained immune response, such as increased gene expression, secretion of cytokines and other factors, and T cell mediated effector functions such as cell killing.

In some embodiments, neither ligation of the first receptor alone nor ligation of the second receptor alone induces a robust immune response. In some aspects, if only one receptor is ligated, the cell becomes tolerized or unresponsive to antigen, or inhibited, and/or is not induced to proliferate or secrete factors or carry out effector functions. In some such embodiments, however, when the plurality of receptors are ligated, such as upon encounter of a cell expressing the first and second antigens, a desired response is achieved, such as full immune activation or stimulation, e.g., as indicated by secretion of one or more cytokine, proliferation, persistence, and/or carrying out an immune effector function such as cytotoxic killing of a target cell.

In some embodiments, the two receptors induce, respectively, an activating and an inhibitory signal to the cell, such that binding by one of the receptor to its antigen activates the cell or induces a response, but binding by the second inhibitory receptor to its antigen induces a signal that suppresses or dampens that response. Examples are combinations of activating CARs and inhibitory CARs or iCARs. Such a strategy may be used, for example, in which the activating CAR binds an antigen expressed in a disease or condition but which is also expressed on normal cells, and the inhibitory receptor binds to a separate antigen which is expressed on the normal cells but not cells of the disease or condition.

In some embodiments, the multi-targeting strategy is employed in a case where an antigen associated with a particular disease or condition is expressed on a non-diseased cell and/or is expressed on the engineered cell itself, either transiently (e.g., upon stimulation in association with genetic engineering) or permanently. In such cases, by requiring ligation of two separate and individually specific antigen receptors, specificity, selectivity, and/or efficacy may be improved.

In some embodiments, the plurality of antigens, e.g., the first and second antigens, are expressed on the cell, tissue, or disease or condition being targeted, such as on the cancer cell. In some aspects, the cell, tissue, disease or condition is multiple myeloma or a multiple myeloma cell. In some embodiments, one or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is achieved.

d. Chimeric Auto-Antibody Receptor (CAAR)

In some embodiments, the recombinant receptor is a chimeric autoantibody receptor (CAAR). In some embodiments, the CAAR binds, e.g., specifically binds, or recognizes, an autoantibody. In some embodiments, a cell expressing the CAAR, such as a T cell engineered to express a CAAR, can be used to bind to and kill autoantibody-expressing cells, but not normal antibody expressing cells. In some embodiments, CAAR-expressing cells can be used to treat an autoimmune disease associated with expression of self-antigens, such as autoimmune diseases. In some embodiments, CAAR-expressing cells can target B cells that ultimately produce the autoantibodies and display the autoantibodies on their cell surfaces, mark these B cells as disease-specific targets for therapeutic intervention. In some embodiments, CAAR-expressing cells can be used to efficiently targeting and killing the pathogenic B cells in auto-immune diseases by targeting the disease-causing B cells using an antigen-specific chimeric autoantibody receptor. In some embodiments, the recombinant receptor is a CAAR, such as any described in U.S. Patent Application Pub. No. US 2017/0051035.

In some embodiments, the CAAR comprises an autoantibody binding domain, a transmembrane domain, and one or more intracellular signaling region or domain (also interchangeably called a cytoplasmic signaling domain or region). In some embodiments, the intracellular signaling region comprises an intracellular signaling domain. In some embodiments, the intracellular signaling domain is or comprises a primary signaling domain, a signaling domain that is capable of stimulating and/or inducing a primary activation signal in a T cell, a signaling domain of a T cell receptor (TCR) component (e.g. an intracellular signaling domain or region of a CD3-zeta) chain or a functional variant or signaling portion thereof), and/or a signaling domain comprising an immunoreceptor tyrosine-based activation motif (ITAM).

In some embodiments, the autoantibody binding domain comprises an autoantigen or a fragment thereof. The choice of autoantigen can depend upon the type of autoantibody being targeted. For example, the autoantigen may be chosen because it recognizes an autoantibody on a target cell, such as a B cell, associated with a particular disease state, e.g. an autoimmune disease, such as an autoantibody-mediated autoimmune disease. In some embodiments, the autoimmune disease includes pemphigus vulgaris (PV). Exemplary autoantigens include desmoglein 1 (Dsg1) and Dsg3.

In some embodiments, the encoded nucleic acid is operatively linked to a "positive target cell-specific regulatory element" (or positive TCSRE). In some embodiments, the positive TCSRE is a functional nucleic acid sequence. In some embodiments, the positive TCSRE comprises a promoter or enhancer. In some embodiments, the TCSRE is a nucleic acid sequence that increases the level of an exogenous agent in a target cell. In some embodiments, the positive target cell-specific regulatory element comprises a T cell-specific promoter, a T cell-specific enhancer, a T cell-specific splice site, a T cell-specific site extending half-life of an RNA or protein, a T cell-specific mRNA nuclear export promoting site, a T cell-specific translational enhancing site, or a T cell-specific post-translational modification site. In some embodiments, the T cell-specific promoter is a promoter described in Immgen consortium, herein incorporated by reference in its entirety, e.g., the T cell-specific promoter is an IL2RA (CD25), LRRC32, FOXP3, or IKZF2 promoter. In some embodiments, the T cell-specific promoter or enhancer is a promoter or enhancer described in Schmidl et a, Blood. 2014 Apr. 24;123 (17): e68-78, herein incorporated by reference in its entirety. In some embodiments, the T cell-specific promoter is a transcriptionally active fragment of any of the foregoing. In some embodiments, the T-cell specific promoter is a variant having at least 70%, 75%, 80%, 85%, 90%, 95%, 96%, 97%, 98%, or 99% identity to any of the foregoing.

In some embodiments, the encoded nucleic acid is operatively linked to a "negative target cell-specific regulatory element" (or negative TCSRE). In some embodiments, the negative TCSRE is a functional nucleic acid sequence. In some embodiments, the negative TCSRE is a miRNA recognition site that causes degradation of inhibition of the viral vector in a non-target cell. In some embodiments, the exogenous agent is operatively linked to a "non-target cell-specific regulatory element" (or NTCSRE). In some embodiments, the NTCSRE comprises a nucleic acid sequence that decreases the level of an exogenous agent in a non-target cell compared to in a target cell. In some embodiments, the NTCSRE comprises a non-target cell-specific miRNA recognition sequence, non-target cell-specific protease recognition site, non-target cell-specific ubiquitin ligase site, non-target cell-specific transcriptional repression site, or non-target cell-specific epigenetic repression site. In some embodiments, the NTCSRE comprises a tissue-specific miRNA recognition sequence, tissue-specific protease recognition site, tissue-specific ubiquitin ligase site, tissue-specific transcriptional repression site, or tissue-specific epigenetic repression site. In some embodiments, the NTCSRE comprises a non-target cell-specific miRNA recognition sequence, non-target cell-specific protease recognition site, non-target cell-specific ubiquitin ligase site, non-target cell-specific transcriptional repression site, or non-target cell-specific epigenetic repression site. In some embodiments, the NTCSRE comprises a non-target cell-specific miRNA recognition sequence and the miRNA recognition sequence is able to be bound by one or more of miR3 1, miR363, or miR29c. In some embodiments, the NTCSRE is situated or encoded within a transcribed region encoding the exogenous agent, optionally wherein an RNA produced by the transcribed region comprises the miRNA recognition sequence within a UTR or coding region.

In some embodiments, the viral vector comprising an anti-CD8 scFv or sdAb composition described herein can be administered to a subject, e.g., a mammal, e.g., a human. In such embodiments, the subject may be at risk of, may have a symptom of, or may be diagnosed with or identified as having, a particular disease or condition (e.g., a disease or condition described herein).

In some aspects, resting or non-activated T cells are contacted with a viral vector of the disclosure (e.g., a retroviral vector or lentiviral vector) that includes a CD8 binding agent. The contacting may be performed in vitro (e.g., with T cells derived from a healthy donor or a donor in need of cellular therapy) or in vivo by administration of the viral vector to a subject.

In some embodiments, the resting or non-activated T cells are not treated with one or more T cell stimulatory molecules (e.g., an anti CD-3 antibody), one or more T cell costimulatory molecules, and/or one or more T cell activating cytokines. In some embodiments, the resting or non-activated T cells are not treated with any of one or more T cell stimulatory molecules (e.g., an anti CD-3 antibody), one or more T cell costimulatory molecules, and/or one or more T cell activating cytokines.

In additional aspects, the application includes methods of administration to a subject of a viral vector that includes an anti-CD8 binding agent, wherein the subject is not administered or has not been administered a T cell activating treatment. In some embodiments, the T cell activating treatment includes one or more T cell stimulatory molecules (e.g., an anti CD-3 antibody), one or more T cell costimulatory molecules, and/or one or more T cell activating cytokines. In some embodiments, the subject is not administered or has not been administered any of one or more T cell stimulatory molecules (e.g., an anti CD-3 antibody), one or more T cell costimulatory molecules, and/or one or more T cell activating cytokines. In some embodiments, the T cell activating treatment is lymphodepletion. In certain embodiments, the subject is not administered or has not been administered the T cell activating treatment within 1 month before or after administration of the viral vector. In some embodiments, the subject is not administered or has not been administered the T cell activating treatment within 1 month before administration of the viral vector, such as within or at or about 4 weeks, 3 weeks, 2 weeks or 1 weeks, such as at or about 1 day, 2 days, 3 days, 4 days, 5 days, 6 days or 7 days before administration of the viral vector. In some embodiments, the subject is not administered the T cell activating treatment within 1 month after administration of the viral vector, such as within or at or about 4 weeks, 3 weeks, 2 weeks or 1 weeks, such as at or about 1 day, 2 days, 3 days, 4 days, 5 days, 6 days or 7 days after administration of the viral vector.

In some aspects, the viral vectors of the disclosure do not include one or more T cell stimulatory molecules (e.g., an anti CD-3 antibody), one or more T cell costimulatory molecules, and/or one or more T cell activating cytokines.

The use of anti-CD3 antibodies is well-known for activation of T cells. The anti-CD3 antibodies can be of any species, e.g., mouse, rabbit, human, humanized, or camelid. Exemplary antibodies include OKT3, CRIS-7, 12C the anti-CD3 antibody included in DYNABEADS Human T-Activator CD3/CD28 (Thermo Fisher), and the anti-CD3 domains of approved and clinically studied molecules such as blinatumomab, catumaxomab, fotetuzumab, teclistamab, ertumaxomab, epcoritamab, talquetamab, odronextamab, cibistamab, obrindatamab, tidutamab, duvortuxizumab, solitomab, eluvixtamab, pavurutamab, tepoditamab, vibecotamab, plamotamab, glofitamab, etevritamab, and tarlatamab.

In some embodiments, the one or more T cell costimulatory molecuels include CD28 ligands (e.g., CD80 and CD86); antibodies that bind to CD28 such as CD28.2, the anti-CD28 antibody included in DYNABEADS Human T-Activator CD3/CD28 (Thermo Fisher) and anti-CD28 domains disclosed in US2020/0199234, US2020/0223925, US2020/0181260, US2020/0239576, US2020/0199233, US2019/0389951, US2020/0299388, US2020/0399369, and US2020/0140552; CD137 ligand (CD137L); anti-CD137 antibodies such as urelumab and utomilumab; ICOS ligand (ICOS-L); and anti-ICOS antibodies such as feladilimab, vopratelimab, and the anti-ICOS domain of izuralimab.

In some embodiments, the one or more T cell activating cytokines include IL-2, IL-7, IL-15, IL-21, interferons (e.g., interferon-gamma), and functional variants and modified versions thereof.

Lymhpodepletion may be induced by various treatments that destroy lymphocytes and T cells in the subject. For example, the lymphodepletion may include myeloablative chemotherapies, such as fludarabine, cyclophosphamide, bendamustine, and combinations thereof. Lymphodepletion may also be induced by irradiation (e.g., full-body irradiation) of the subject.

In some embodiments, the source of targeted lipid particles are from the same subject that is administered a targeted viral vector composition. In other embodiments, they are different. In some embodiments, the source of targeted viral vectors and recipient tissue may be autologous (from the same subject) or heterologous (from different subjects). In some embodiments, the donor tissue for targeted viral vector compositions described herein may be a different tissue type than the recipient tissue. In some embodiments, the donor tissue may be muscular tissue and the recipient tissue may be connective tissue (e.g., adipose tissue). In other embodiments, the donor tissue and recipient tissue may be of the same or different type, but from different organ systems.

In some embodiments, the targeted lipid particles (e.g, viral vector) composition described herein may be administered to a subject having a cancer, an autoimmune disease, an infectious disease, a metabolic disease, a neurodegenerative disease, or a genetic disease (e.g., enzyme deficiency). In some embodiments, the subject is in need of regeneration.

In some embodiments, the cancer is a T cell-mediated cancer. In another embodiment, the antigen binding moiety portion of a CAR is designed to treat a particular cancer. In some embodiments, the targeted viral vector can be used to treat cancers and disorders including but are not limited to Non-Hodgkin lymphoma (NHL), acute lymphocytic leukemia (ALL), chronic lymphocytic leukemia (CLL), multiple myeloma, and the like. I some embodiments, the targeted viral vector can be used to treat B cell malignancies, e.g., refractory B cell malignincies.

In some embodiments, the targeted viral vector is co-administered with an inhibitor of a protein that inhibits membrane fusion. For example, Suppressyn is a human protein that inhibits cell-cell fusion (Sugimoto et al., "A novel human endogenous retroviral protein inhibits cell-cell fusion" Scientific Reports 3:1462 DOI: 10.1038/srep01462). In some embodiments, the targeted lipid particle is co-administered with an inhibitor of sypressyn, e.g., a siRNA or inhibitory antibody.

EXAMPLES

The present disclosure may be further described by the following non-limiting examples, in which standard techniques known to the skilled artisan and techniques analogous to those described in these examples may be used where appropriate. It is understood that the skilled artisan will envision additional embodiments consistent with the disclosure provided herein.

Example 1: Characterization of CD8 scFvs and VHH

This example describes methods to generate and characterize functional titers of Nipah G/F pseudo-typed lentivirus functionalized with a CD8-specific scFv or VHH. Eliminating binding of Nipah G to EphrinB2/B3 and functionalizing Nipah G with a CD8-specific binder allows for targeting of CD8-expressing cells with the lentiviral vector.

Lentiviral production was performed as follows: HEK-293LX cells were plated 24 hours in advance of transfection. On the day of transfection, HEK-293LX cells were transfected with a lentiviral packaging plasmid, a lentiviral transfer plasmid encoding GFP (pSFFV-GFP), and plasmids encoding for Nipah G protein retargeted for CD8 receptor targeting (NIV-G (CD8)) and Nipah F fusion protein (NiV-Fd22). After 24 hours, a media change was performed, and after another 24 hours, the lentivirus was harvested. To harvest the lentivirus, supernatant was removed from the HEK293LX cells and spun at 1000×g for 5 minutes. The supernatant was removed and immediately added to CD8-positive target cells or T cells, or frozen at −80° C. for later use.

Several cell lines were used to characterize specificity and transduction efficiency of the lentiviral vectors described above. A SupT1 CD8αβ knockout line was generated from SupT1 human T lymphoblast cells. On the day of transduction, SupT1 and SupT1 CD8αβ knock out cells, HEK293LX cells expressing *M. nemestrina* CD8αβ and HEK293LX background lines were plated in a 96 well cell plate. Two hours later, the lentivirus was serial diluted and added to the recipient cells. The lentivirus and cells were incubated at 37° C. at 5% CO2 for three days and analyzed by flow cytometry for GFP expression. Briefly, HEK293LX and HEK293LX cells overexpressing *M. nemestrina* CD8αβ cells were harvested from the 96-well cell plate by trypsinization, transferred to a 96-well U-bottom sample plate, and pelleted by centrifugation at 1000×g for 5 min. The cells were then resuspended in 200 μL of PBS before flow cytometry analysis. SupT1 and SupT1 CD8αβ knock-out cells were pelleted by centrifugation and resuspended in 200 uL PBS+2% FBS for flow cytometry analysis.

Figure 1B:
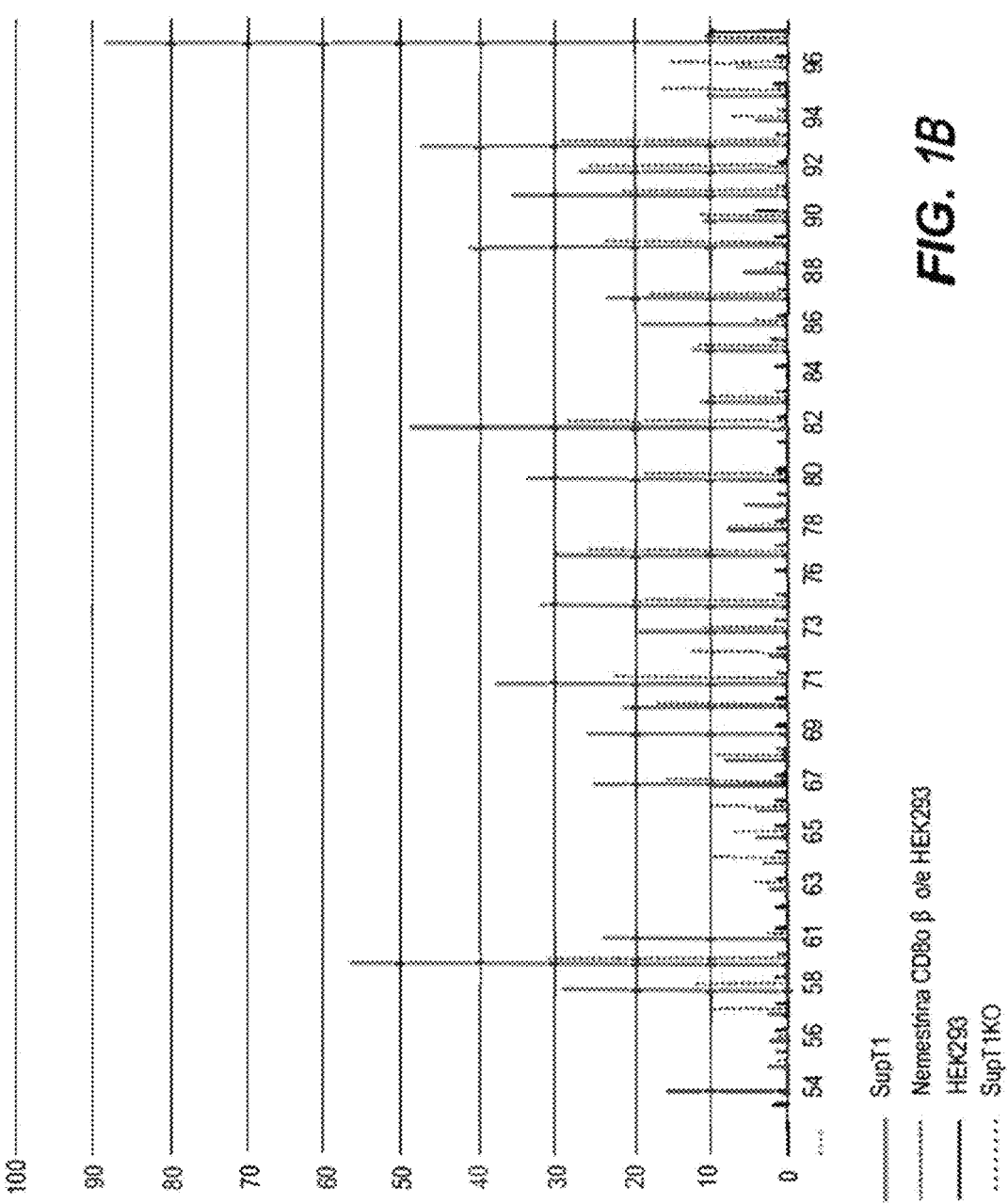

The cells were measured for GFP fluorescence using a BD Celesta cytometer. GFP was excited with a 488 nm laser and emission captured at 513±26 nm. Forward and side scatter gating was initially used to capture cell-sized events and discard small debris. Events positive for GFP were determined by gating at the minimum level for which the negative control cell samples (cells not treated with lentivirus) showed <0.5% of events positive for GFP expression. The gated cells positive for GFP fluorescence were then assessed for the % of GFP-positive cells of the total cells. To calculate lentiviral functional titer, a transduced cell well showing a GFP % positive that was between 5% and 20% of cells was used to determine titer. The formula for virus titer calculation: titer={(F×Cn)/V}×DF. F is the frequency of GFP-positive cells determined by flow cytometry; Cn=The total number of target cells infected. V=The volume of the inoculum, and DF=dilution factor (see FIG. 1).

Figure 2:
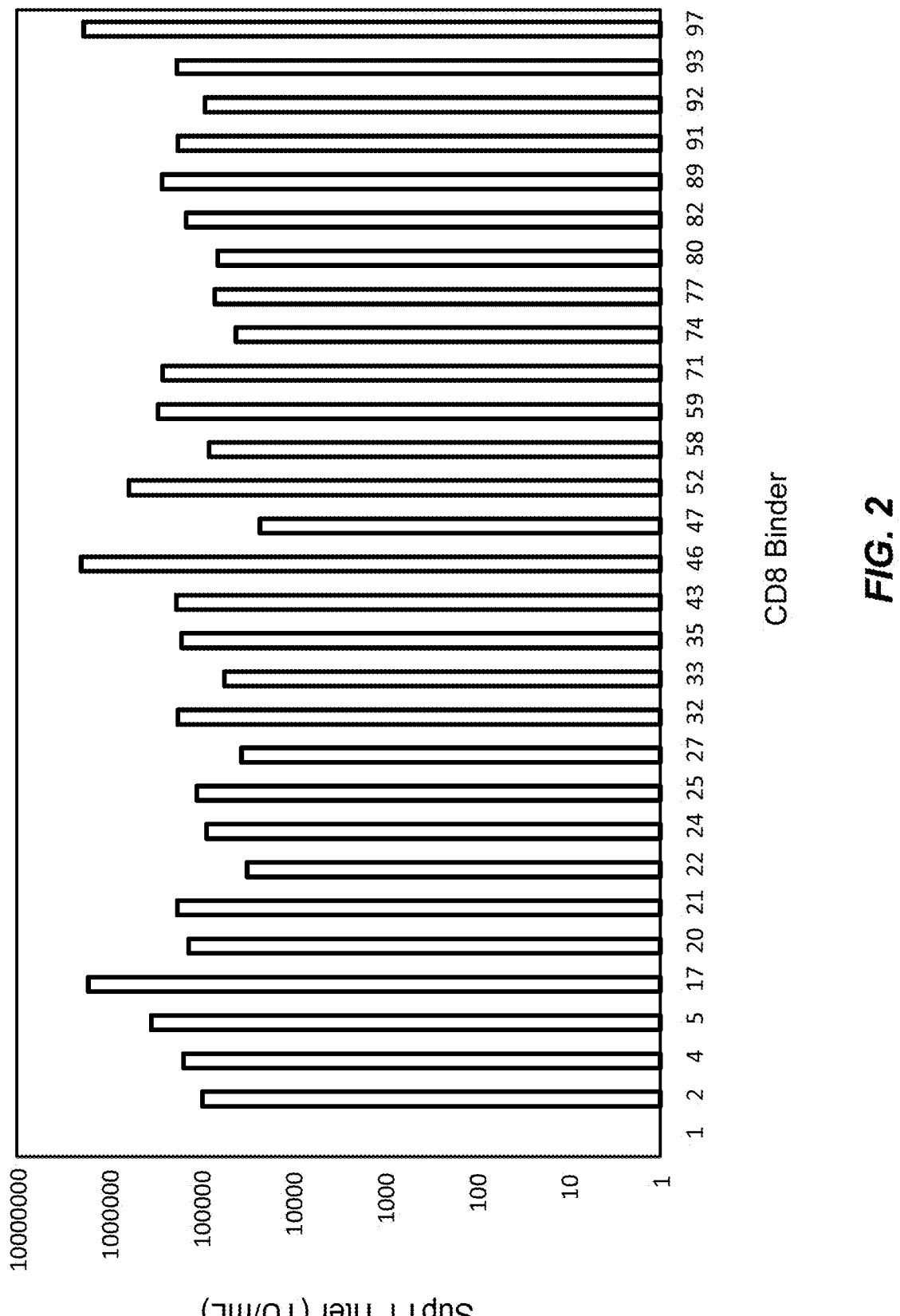
FIG. 2 shows the titers of the disclosed anti-CD8 antibodies on SupT1 cells.

Lentivirus with CD8 binders 97 (VHH) and 46 (scFv) were further tested on additional non-CD8-expressing cell lines and the CD8 positive cell line SupT1 as above (see FIG. 2). Maximal transduction of the cells over various dilution factors is indicated below (Table Y). VSV-G was used as a non-cell specific control. These results indicate that the binders are specific for CD8.

TABLE 15

| | CD8 Binder 97 | CD8 Binder 46 | VSV-G |
|---|---|---|---|
| SupT1 | 87.0 | 99.0 | 98.0 |
| 293 Lenti-X | 6.0 | 3.0 | 81.0 |

TABLE 15-continued

| | CD8 Binder 97 | CD8 Binder 46 | VSV-G |
|---|---|---|---|
| Ramos | 9.0 | 4.0 | 68.0 |
| HUVEC | 10.0 | 5.0 | 94.0 |
| C2C12 | 0 | 0 | 63.0 |
| HEL 92.1.7 | 0 | 2.0 | 100.0 |
| HeLa | 1.0 | 0 | 97.0 |
| HepG2 | 0 | 0 | 99.0 |
| hFOB | 0.1 | 0.6 | 68.3 |
| HULEC-5a | 2.0 | 4.0 | 83.0 |
| Kasumi 1 | 0 | 3.0 | 74.0 |
| SK-N-AS | 1.0 | 2.0 | 99.0 |
| U-937 | 0 | 0 | 100.0 |

Binding to human and *M. nemestrina* CD8 was also evaluated. On the day of transduction, SupT1 and SupT1 CD8αβ knockout cell lines, HEK293LX cells expressing *M. nemestrina* CD8αβ and HEK293LX background lines were plated in a 96 well cell plate. Two hours later, the lentivirus was serial diluted and added to the recipient cells. The lentivirus and cells were incubated at 37° C. at 5% CO2 for three days and analyzed by flow cytometry for GFP expression. Briefly, HEK293LX and HEK293LX cells overexpressing *M. nemestrina* CD8αβ cells were harvested from the 96-well cell plate by trypsinization, transferred to a 96-well U-bottom sample plate, and pelleted by centrifugation at 1000×g for 5 min. The cells were then resuspended in 200 μL of PBS before flow cytometry analysis. SupT1 and SupT1 CD8αβ knock-out cells were pelleted by centrifugation and resuspended in 200 uL PBS+2% FBS for flow cytometry analysis.

Figure 3:
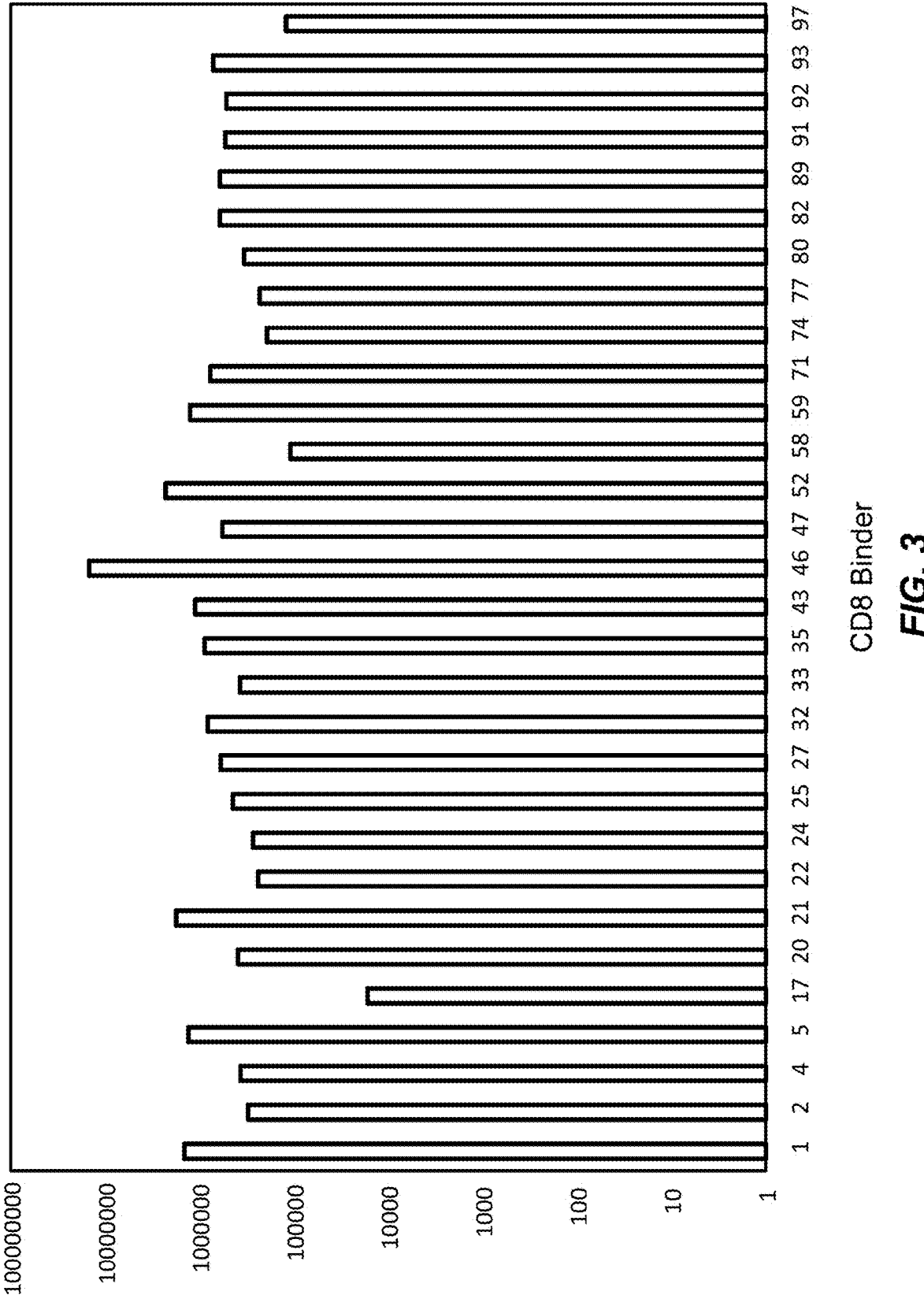
FIG. 3 shows the titers of the disclosed anti-CD8 antibodies on cells expressing *M. nemestrina* CD8$\alpha$ and CD8$\beta$.

The cells were measured for GFP fluorescence using a BD Celesta cytometer. GFP was excited with a 488 nm laser and emission captured at 513±26 nm. Forward and side scatter gating was initially used to capture cell-sized events and discard small debris. Events positive for GFP were determined by gating at the minimum level for which the negative control cell samples (cells not treated with lentivirus) showed <0.5% of events positive for GFP expression. The gated cells positive for GFP fluorescence were then assessed for the % of GFP-positive cells of the total cells. To calculate lentiviral functional titer, a transduced cell well showing a GFP % positive that was between 5% and 20% of cells was used to determine titer. The formula for virus titer calculation: titer={(F×Cn)/V}×DF. F is the frequency of GFP-positive cells determined by flow cytometry; Cn=The total number of target cells infected. V=The volume of the inoculum, and DF=dilution factor. Titer for human CD8 (SupT1) is presented in FIG. 2. Titer for *M. nemestrina* CD8 (HEK293LX cells expressing *M. nemestrina* CD8αβ) is presented in FIG. 3.

Lentiviral production was performed as follows: LV-Max HEK293 cells were seeded 24 hours in advance of transfection. On the day of transfection, LV-Max HEK293 cells were transfected with lentiviral packaging plasmid, the lentiviral transfer plasmid encoding GFP (pSFFV-GFP), and plasmids encoding Nipah G protein retargeted for CD8 receptor targeting (NIV-G (CD8)) and Nipah F fusion protein (NiV-Fd22). Two days later supernatant from the transfected cells was harvested, passed through a 0.45 μm filter, and concentrated by ultracentrifugation at 120,000×g for 90 minutes. After ultracentrifugation the lentiviral pellet was resuspended in PBS, and either used immediately for transduction or aliquoted and frozen at −80° C. for use later.

Human CD8α and human CD8αβ overexpressing cell lines were generated from HEK293LX cells. On the day of transduction, human CD8α, human CD8αβ overexpressing and HEK293LX background cell lines were plated in a 96 well cell plate. Two hours later, the lentivirus was serial diluted and added to the recipient cells. The lentivirus and cells were incubated at 37° C. at 5% CO2 for three days and analyzed by flow cytometry for GFP expression. Briefly, human CD8α, human CD8αβ overexpressing, and HEK293LX background cell lines were harvested from the 96-well cell plate by trypsinization, transferred to a 96-well U-bottom sample plate, and pelleted by centrifugation at 1000×g for 5 min. The cells were then resuspended in 200 μL of PBS before flow cytometry analysis.

Figure 4:
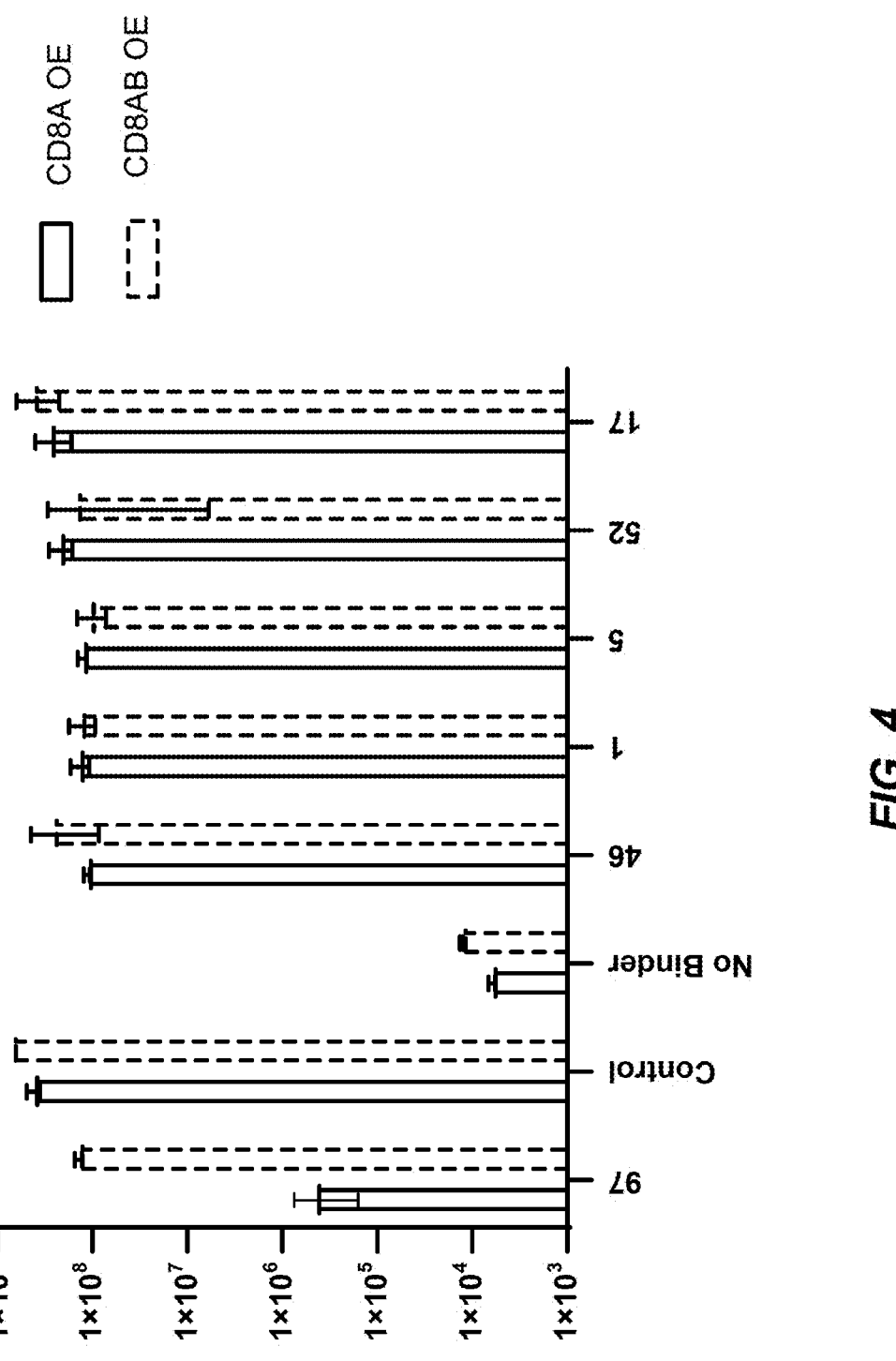
FIG. 4 shows the titers of select CD8 binders on CD8$\alpha$ only or CD8$\alpha\beta$ overexpressing cells.
Figure 5:
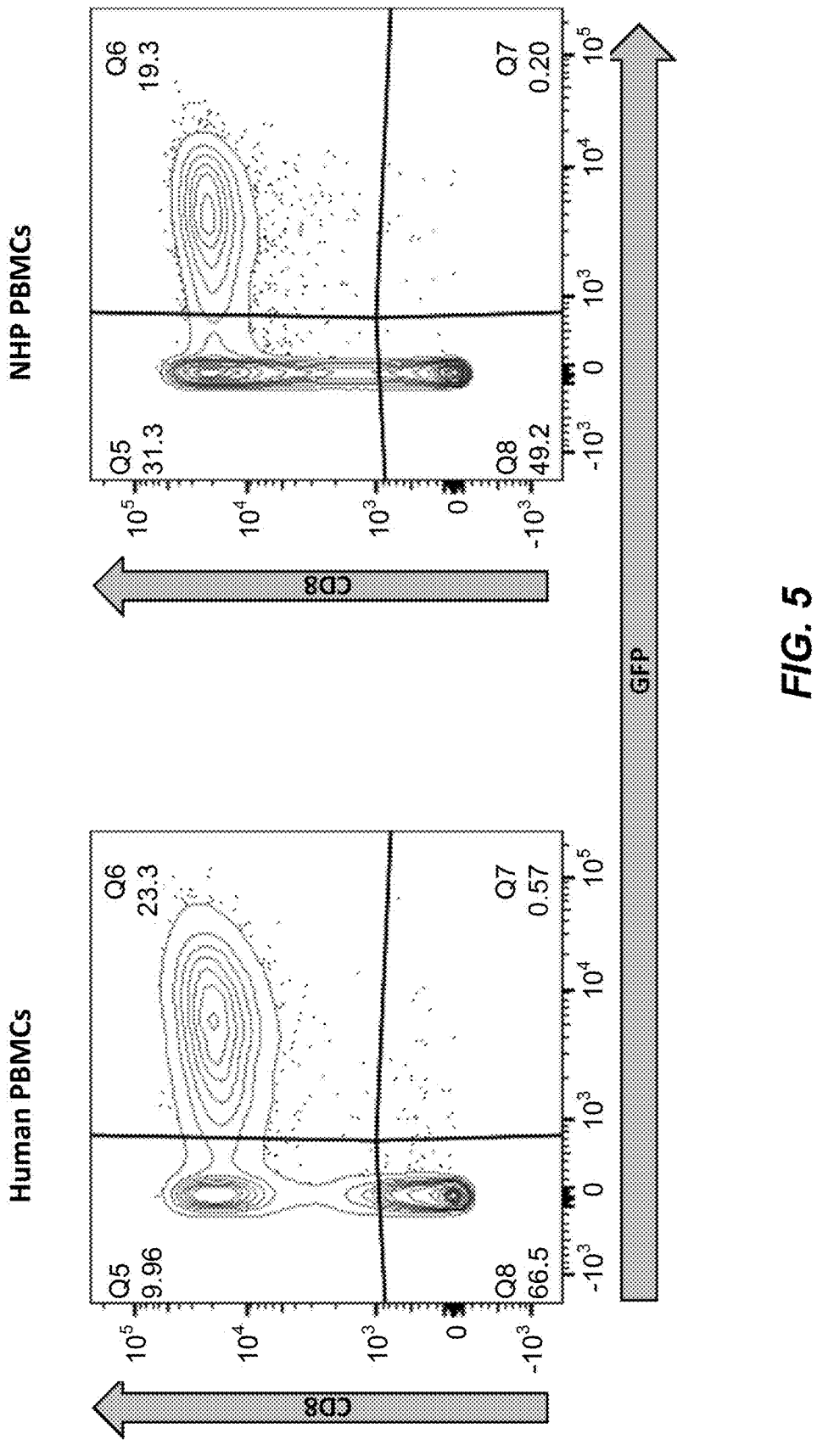
FIG. 5 shows the transduction efficiencies of a CD8 scFv (CD8 binder 52) of the disclosure on human or *M. nemestrina* (NHP) peripheral blood mononuclear cells (PBMCs).
Figure 6:
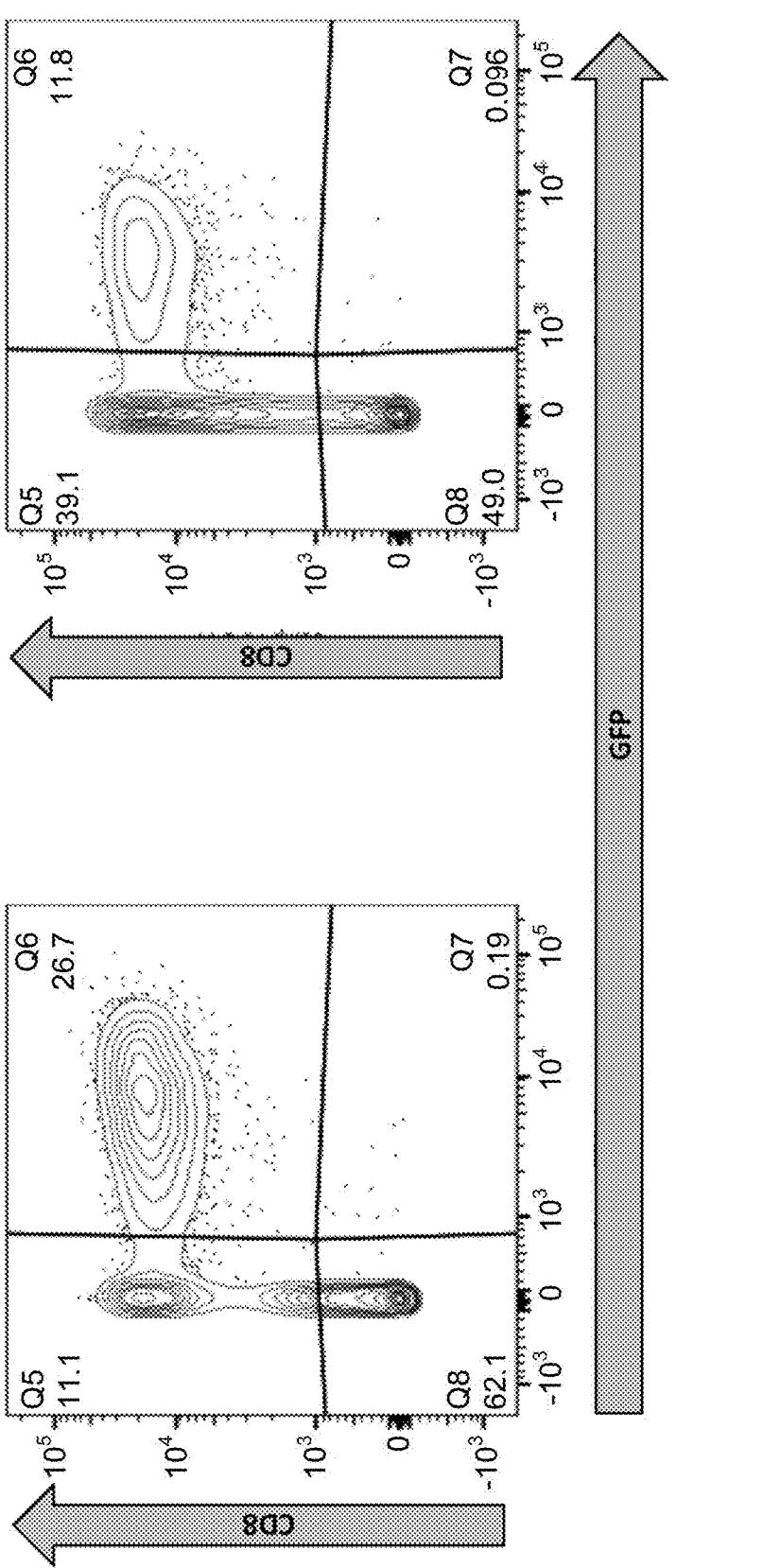
FIG. 6 shows the transduction efficiencies of a CD8 scFv (CD8 binder 46) of the disclosure on human or *M. nemestrina* (NHP) PBMCs.
Figures 7A, 7B, 7C, 7D:
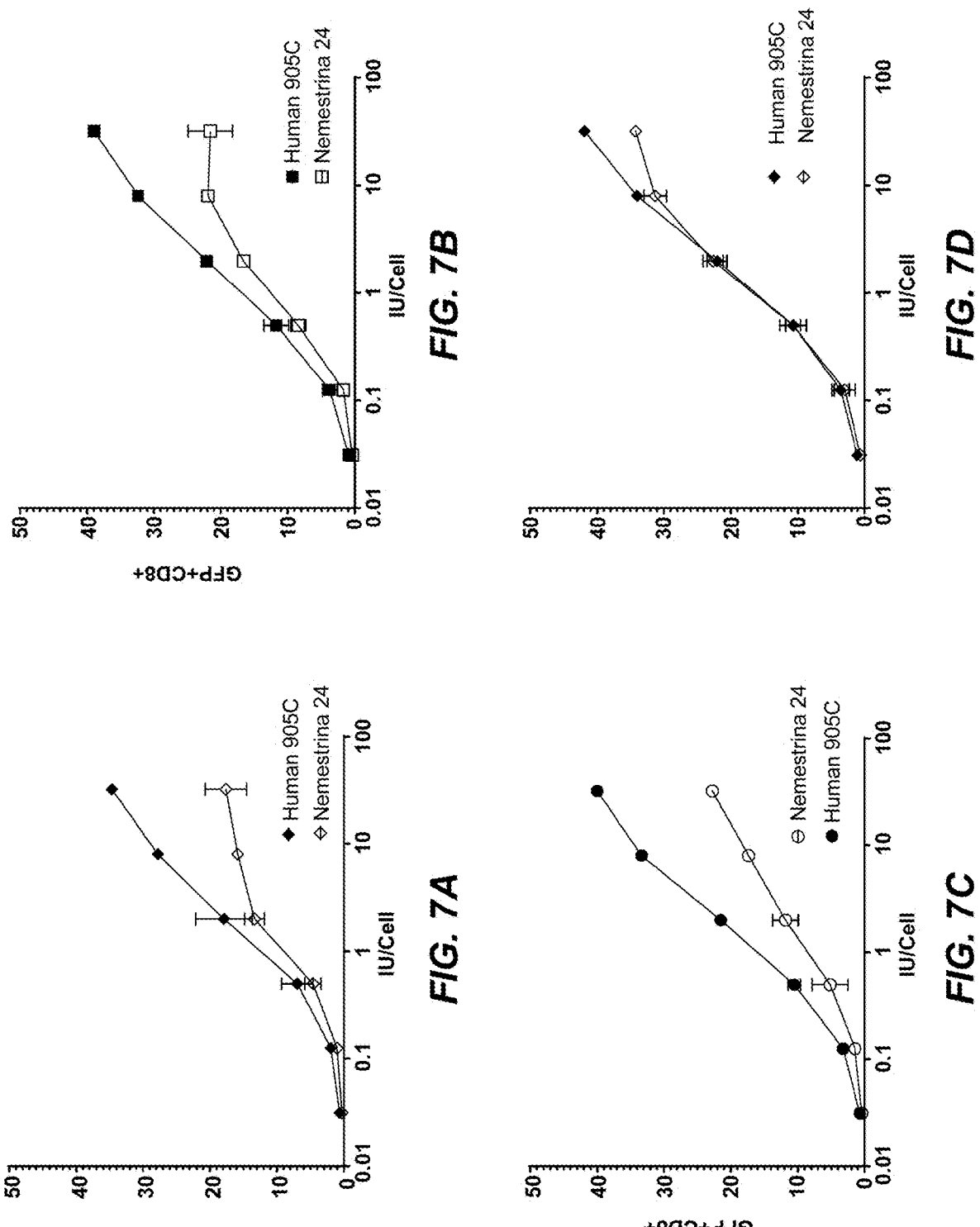
FIGS. 7A-7D shows the transduction effects of a Nipah G pseudotyped viral vector attached to CD8 binder 1 (FIG. 7A), CD8 binder 5 (FIG. 7B), CD8 binder 46 (FIG. 7C), and CD8 binder 52 (FIG. 7D) of the disclosure on human and nemestrina PBMCs (human donor 905C and nemestrina donor 24).

The cells were measured for GFP fluorescence using a BD Celesta cytometer. GFP was excited with a 488 nm laser and emission captured at 513±26 nm. Forward and side scatter gating was initially used to capture cell-sized events and discard small debris. Events positive for GFP were determined by gating at the minimum level for which the negative control cell samples (cells not treated with lentivirus) showed <0.5% of events positive for GFP expression. The gated cells positive for GFP fluorescence were then assessed for the % of GFP-positive cells of the total cells. To calculate lentiviral functional titer, a transduced cell well showing a GFP % positive that was between 5% and 20% of cells was used to determine titer. The formula for virus titer calculation: titer={(F×Cn)/V}×DF. F is the frequency of GFP-positive cells determined by flow cytometry; Cn=The total number of target cells infected. V=The volume of the inoculum, and DF=dilution factor. As shown in FIG. 4, CD8 binders 46, 1, 52, and 17 showed similar titer in human CD8α and human CD8αβ overexpressing cell lines, indicating that those binders are specific for CD8α. However, CD8 binder 97 had a significantly higher titer on human CD8αβ overexpressing cell Ine as compared to the cell line expressing only CD8α, indicating that CD8 binder 97 is specific for CD8β.

Binding Assessment and Affinity Vs Human CD8αβ Heterodimer

Binders were generated as crude preparations of scFvs with a v5 tag and captured onto a Streptavidin BLI sensor that was functionalized with an anti-V5 tag antibody for analysis via a ForteBio Octet HTX instrument. Sensors were exposed to 300 nM of human CD8αβ followed by dissociation into assay buffer. A positive binding response was referenced by buffer subtraction with a negative control scFv and fit using a 1:1 Langmuir model to determine off-rates.

A subset of scFvs were produced as recombinant, purified scFv with a mIgG2a Fc tag. scFv-mIgG2a proteins were loaded onto anti-mouse Fc capture sensors for analysis via ForteBio Octet RED96 instrument. Sensors were exposed to a serial dilution of human CD8 alpha beta starting at 500 nM, followed by dissociation into assay buffer. A positive binding response was referenced by buffer subtraction and fit using a 1:1 Langmuir model to determine on and off-rates and calculate a $K_D$.

Binding Assessment Vs Human CD8α

Binders were generated as crude preparations of scFvs with a v5 tag and captured onto a HC200M SPRi sensor that was functionalized with an anti-V5 tag antibody for analysis via a Carterra LSA instrument. A serial dilution of human CD8α starting at 5 uM was injected over the sensor, followed by an injection of assay buffer for dissociation. A positive binding response was referenced by buffer subtraction with a negative control scFv and fit using a 1:1 Langmuir model to determine binding response.

Binding Assessment Vs Human CD8β

A subset of scFvs were produced as recombinant, purified scFv or VHH with a mIgG2a Fc tag. Human CD8β protein was biotinylated and loaded onto a Streptavidin sensor for analysis via ForteBio Octet RED96 instrument. Sensors were exposed to a serial dilution of concentrations of scFv-mIgG2a or VHH-mIgG2a starting at 500 nM, followed by dissociation into assay buffer. A positive binding response was referenced by buffer subtraction and fit using a 1:1 Langmuir model to determine on and off-rates and calculate a $K_D$.

Binding Assessment Vs Cyno CD8α Homodimer

Binders were generated as crude preparations of scFvs with a v5 tag and captured onto a HC200M SPRi sensor that was functionalized with an anti-V5 tag antibody for analysis via a Carterra LSA instrument. A serial dilution of cyno CD8α-hFc starting at 1 uM was injected over the sensor, followed by an injection of assay buffer for dissociation. A positive binding response was referenced by buffer subtraction with a negative control scFv and fit using a 1:1 Langmuir model to determine off-rates.

A subset of scFvs and VHH were produced as recombinant, purified scFv or VHH with a mIgG2a Fc tag. scFv-mIgG2a or VHH-mIgG2a proteins were loaded onto anti-mouse Fc capture sensors for analysis via ForteBio Octet RED96 instrument. Sensors were exposed to a serial dilution of concentrations of cyno CD8α-hFc starting at 500 nM, followed by dissociation into assay buffer. A positive binding response was referenced by buffer subtraction and fit using a 1:1 Langmuir model to determine on and off-rates and calculate a $K_D$.

The binding affinities of select CD8 binders are shown in Table 16.

TABLE 16

| | Binding summary of select CD8 scFvs. | | | | |
|---|---|---|---|---|---|
| CD8 Binder | Crude Titers Sup1T1 (TU/mL) | Highest Response (nm) | $K_D$ (M) | $k_{on}$ (1/Ms) | $k_{off}$ (1/s) |
| 46 | 4.90E+06 | 0.4906 | 9.52E−08 | 8.63E+04 | 8.21E−03 |
| 1 | 1.05E+06 | 0.1334 | 2.03E−08 | 3.08E+04 | 6.23E−04 |
| 5 | 1.83E+06 | 0.2201 | 4.01E−07 | 3.84E+04 | 1.54E−02 |
| 97 | 3.47E+06 | 0.4651 | 5.30E−09 | 5.14E+04 | 2.72E−04 |

Example 2: Generation and Characterization of Viral Vectors Pseudotyped with CD8 Binders Methods for Generating Nipah G Pseudotyped Viruses This example describes methods to generate and characterize functional titers of Nipah G/F pseudo-typed lentivirus functionalized with a CD8-specific scFv or VHH. Eliminating binding of Nipah G to EphrinB2/B3 and functionalizing Nipah G with a CD8-specific binder allows for targeting of CD8-expressing cells with the lentiviral vector. Nipah G (d34, E501A; W504A; Q530A; E533A) was modified by the addition of a glycine/serine linker (G4Sx3) followed by a CD8-specific binder (scFv or VHH) at the C-terminus. The Nipah G-linker-binder construct was codon optimized for expression in human cells and sub-cloned into an expression vector for lentivirus generation.

Crude lentiviral production was performed as follows: HEK-293LX cells were plated 24 hours in advance of transfection. On the day of transfection, HEK-293LX cells were transfected with the lentiviral packaging plasmid (ps-PAX2), the lentiviral transfer plasmid encoding GFP (pSFFV-GFP), and the plasmids encoding for Nipah G protein retargeted for CD8 receptor targeting (NIV-G (CD8)) and Nipah F fusion protein (NIV-Fd22). After 24 hours, a media change was performed, and after another 24 hours, the lentivirus was harvested. To harvest the lentivirus, supernatant was removed from the HEK293LX cells and spun at 1000×g for 5 minutes. The supernatant was removed and immediately added to CD8-positive target cells or T cells, or frozen at −80° C. for later use.

Concentrated lentiviral production was performed as follows: LV-Max HEK293 cells were seeded 24 hours in advance of transfection. On the day of transfection, LV-Max HEK293 cells were transfected with the lentiviral packaging plasmid (psPAX2), the lentiviral transfer plasmid encoding GFP (pSFFV-GFP), and the plasmids encoding for Nipah G protein retargeted for CD8 receptor targeting (NIV-G (CD8)) and Nipah F fusion protein (NiV-Fd22). Two days later supernatant from the transfected cells was harvested, passed through a 0.45 μm filter, and concentrated by ultra-centrifugation at 120,000×g for 90 minutes. After ultracentrifugation the lentiviral pellet was resuspended in PBS, and either used immediately for transduction or aliquoted and frozen at −80° C. for use later.

Transduction Efficiency on Human and Nemestrina Primary Cells

Lentiviral production was performed as follows: LV-Max HEK293 cells were seeded 24 hours in advance of trans-fection. On the day of transfection, LV-Max HEK293 cells were transfected with the lentiviral packaging plasmid (ps-PAX2), the lentiviral transfer plasmid encoding GFP (pSFFV-GFP), and the plasmids encoding for Nipah G protein retargeted for CD8 receptor targeting (NIV-G (CD8)) and Nipah F fusion protein (NIV-Fd22). Two days later supernatant from the transfected cells was harvested, passed through a 0.45 μm filter, and concentrated by ultra-centrifugation at 120,000×g for 90 minutes. After ultracentrifugation the lentiviral pellet was resuspended in PBS, and either used immediately for transduction or aliquoted and frozen at −80° C. for use later.

Primary isolated Human PanT cells or PBMCs were obtained from StemCell Technologies and activated with anti-human CD3/CD28 with IL-2 supplemented in the media. *M. nemestrina* PBMCs were obtained from BioIVT and activated using anti-CD3/CD28 beads from Miltenyi Biotec with IL-2 supplemented in the media. 72 hours after activation, cells were harvested and plated in a 96-well plate. A serial dilution of lentivirus was performed and added to the primary PanT or PBMC cells. A spinfection was per-formed at 1000×g for 90 minutes at 25° C. The cells were then incubated at 37° C. with 5% CO2 for 72 hours. After 72 hours, cells were harvested via centrifugation at 1000×g for 5 minutes and stained with a live/dead exclusionary stain and an antibody panel to identify CD3 positive, CD8 posi-tive and CD4 positive populations.

The cells were measured for GFP fluorescence using a BD Celesta cytometer. Forward and side scatter gating was initially used to capture cell-sized events and discard small debris. Forward scatter height and forward scatter width was used to capture single cells. Events negative for live/dead stain were selected. For PanT cells, cells were gated on either CD8 positive and GFP positive or CD4 negative and GFP positive to assess transduction in CD8-expressing cells. GFP expression in CD8 positive cells was calculated based upon the percent of cells expressing GFP from a CD8 positive population or CD4 negative population. Events positive for GFP were determined by gating at the minimum level for which the negative control cell samples (cells not treated with lentivirus) showed <0.5% of events positive for GFP expression. To calculate lentiviral functional titer, a transduced cell well showing a GFP % positive of CD8 positive cells that was between 5% and 20% of cells was used to determine titer. The formula for virus titer calcula-tion: titer={(F×Cn)/V}×DF. F is the frequency of GFP-positive cells determined by flow cytometry; Cn=The total number of target cells infected. V=The volume of the inoculum, and DF=dilution factor.

For PBMC cells, cells were measured for GFP fluores-cence using a BD Fortessa cytometer. Cells were gated to be CD3 positive, and then gated for either CD8 positive and GFP positive or CD4 negative and GFP positive to assess transduction in CD8-expressing cells. GFP expression in CD8 positive cells was calculated based upon the percent of cells expressing GFP from a CD8 positive population or CD4 negative population. Events positive for GFP were determined by gating at the minimum level for which the negative control cell samples (cells not treated with lentivi-rus) showed <0.5% of events positive for GFP expression. To calculate lentiviral functional titer, a transduced cell well showing a GFP positive % of CD8 positive cells that was between 5% and 20% of cells was used to determine titer. The formula for virus titer calculation: titer={(F×Cn)/V}× DF. F is the frequency of GFP-positive cells determined by flow cytometry; Cn=The total number of target cells infected. V=The volume of the inoculum, and DF=dilution factor (see FIGS. 5-8).

In Vivo Specificity

Figures 9A, 9B:
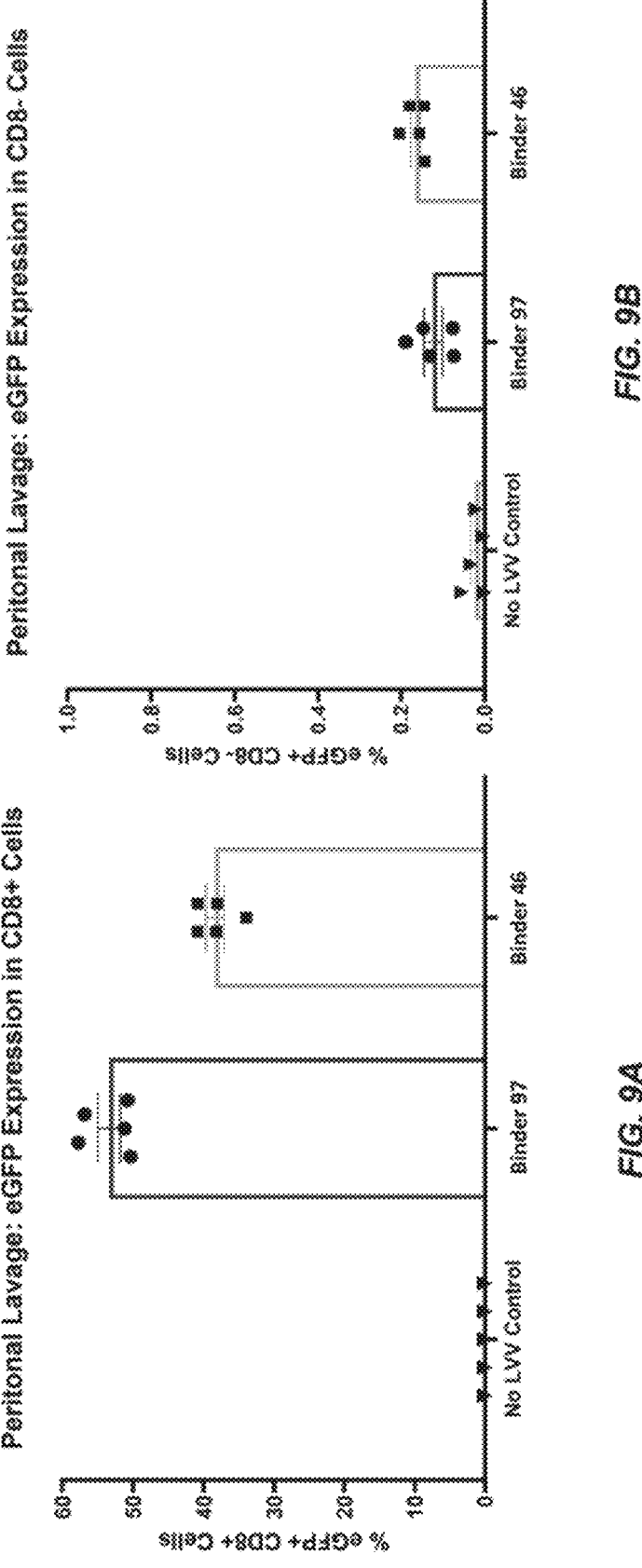
FIGS. 9A-9B depict the transduction efficiencies of the CD8 binders of the disclosure on human PBMC in transgenic mice in vivo using CD8+ (FIG. 9A) and CD8– (FIG. 9B) cells.

To demonstrate specific in vivo transduction, GFP-ex-pressing lentivirus with CD8 binders 97 and 46 were pro-duced as above and administered to mice. T cells in human PBMCs were activated for 3 days via CD3/CD28 treatment and 1E7 cells were intraperitoneally injected into NOD-scid-IL2rγ*null* mice. One day later 1E7 TU of CD8 fusosome (binder 97 or 46) or vehicle control were intraperitoneally injected. 7 days later peritoneal cells were harvested by peritoneal lavage and analyzed by flow cytometry for on-target GFP expression and off-target expression. Approxi-mately 35-55% of the CD8+ cells in the mice were GFP positive following treatment with the CD8-targeted lentivi-ral vectors (FIG. 9A), whereas less than 0.2% of (FIG. 9B) were GFP positive, indicating CD8-specific transduction in the mice.

Tumor Killing

Figure 10B:
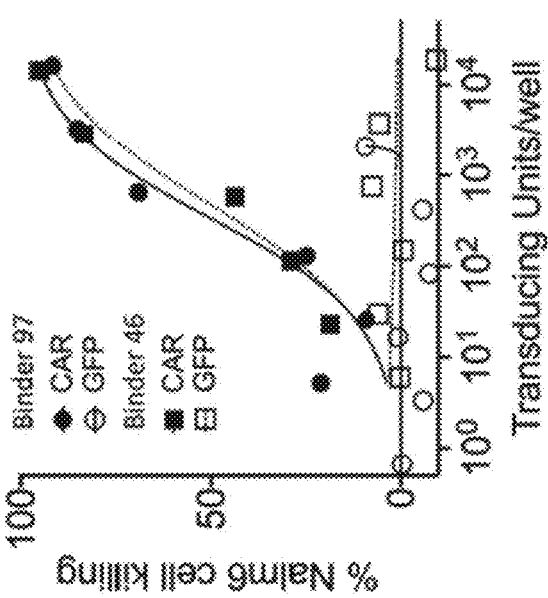
FIGS. 10A-10B depict tumor killing in vitro using CD8 fusogen-generated CD19CAR T cells.
Figure 10A:
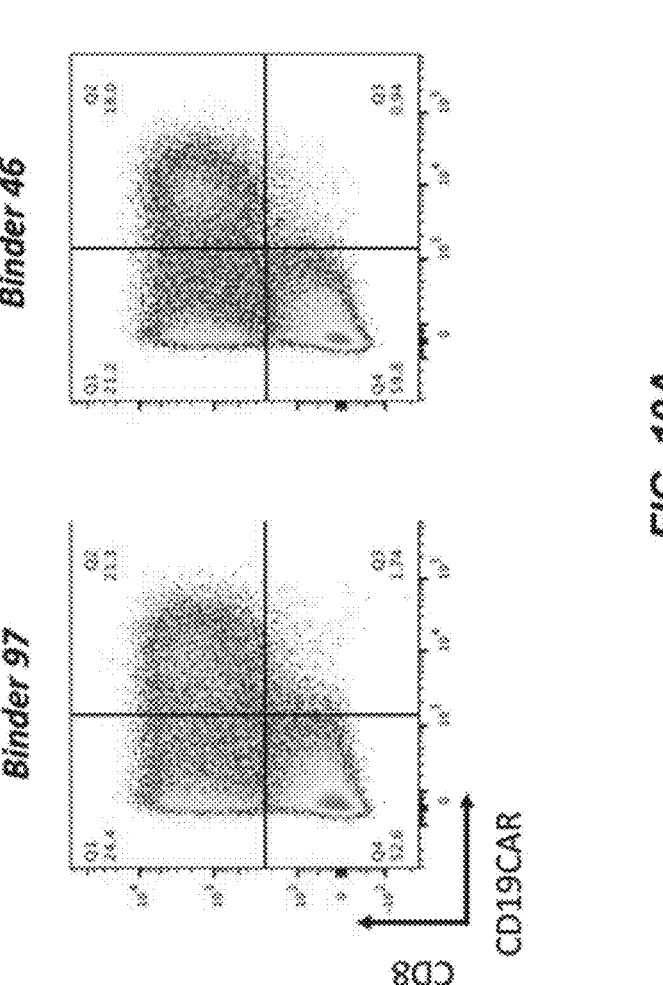

To evaluate tumor killing in vitro, human PBMC were activated with anti-CD3/CD28 reagent and cells were trans-duced with CD8-targeted fusosomes (VHH binder 97 or scFv binder 46) expressing CD19CAR or GFP. RFP+ Nalm6 cells were added to the cultures on day 3, and elimination of Nalm6 cells was evaluated by flow cytometry 18 hours after CD19CAR expression was detected specifically in CD8+ cells with both CD8 fusogens 4 days after transduction (FIG. 10A). Fusogen-generated CD19CAR T cells (solid symbols) mediated potent and fusosome dose-dependent killing of CD19-expressing Nalm6 cells. In contrast, fusogen gener-ated GFP+ T cells (open symbols) did not exhibit target cell killing (FIG. 10B).

Example 3: In Vivo Delivery of a CD8 Targeted Fusogens in Nalm6 Tumor Models as a Function of T Cell Activation State This Example describes the assessment of the transduc-tion efficiency of CD8 retargeted Nipah fusogens and VSV-G.

Briefly, sixty-two (62) female NSG mice were injected with 1E6 Nalm6-Luc leukemia B cells via intravenous (IV) injection, followed three days later by an IV injection of 2E6 human peripheral blood mononuclear cells (hPBMC), with or without prior T cell activation with CD3/CD28 complexes. A day after hPBMC injection, CD8 binder 97 Nipah fusogen pseudotyped lentiviral vector (LV) expressing a CD19 CAR were injected at a range of integrating units (IU), 2E6-5E7, into separate groups of animals. Nalm6 tumor progression was tracked via bioluminescent imaging (BLI) using the Lago X imaging system weekly throughout the duration of the study. The CD19CAR contained an anti-scFv directed against CD19 and an intracellular signaling domain containing intracellular components of 4-1BB and CD3-zeta. Peripheral blood analysis was performed on half of the mice from each group to assess circulating T and B cell frequencies, circulating CAR-T cell frequencies, and cytokine levels throughout the duration of the study. The study was concluded 28 days post-hPBMC injection, or earlier based on individual animal health. Animals were sacrificed and cells from peripheral blood, spleen, and bone marrow tissues were harvested and analyzed by flow cytometry for CD19CAR expressing cells and cytokine analysis.

Figure 11C:
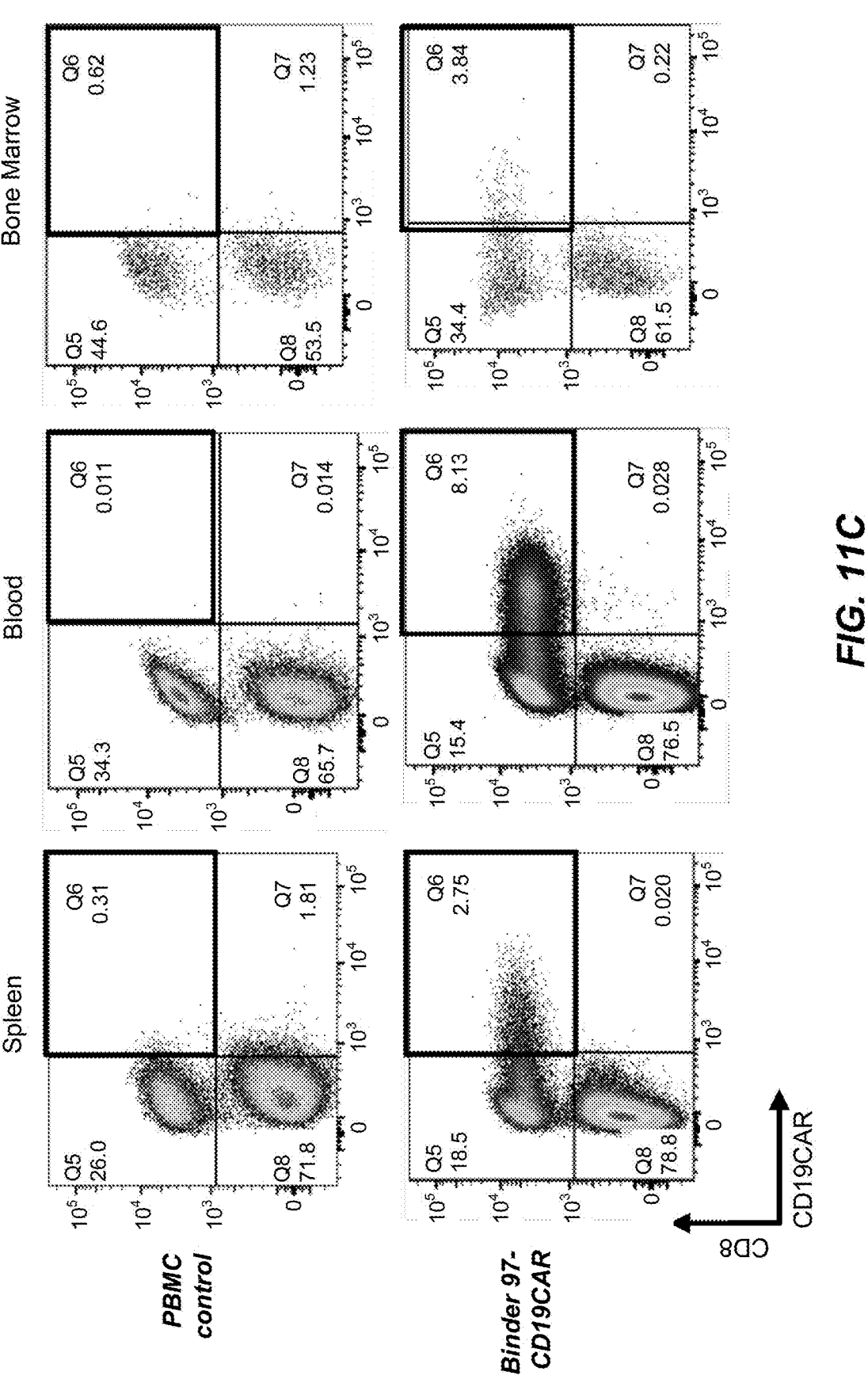

As shown in FIG. 11A, CD8-CD19CAR LV and activated hPBMC treatment resulted in robust control of Nalm6 tumor growth over time. As shown in FIG. 11B, high dose CD8-CD19CAR LV and non-activated hPBMC treatment resulted in slightly delayed yet robust control of Nalm6 tumor growth. FIG. 11C shows the percent of on-target CD19CAR expressing cells (CD8$^+$CD19CAR$^+$) in total recovered live lymphocytes as indicated in top right quandrant of the FACs plots in both PBMC control (top plots) and CD8 fusosome-treated animals (bottom plots). There was no statistical difference in the frequency of CAR-T cells in the bone marrow of animals that received 5 E7 IU of CD8-CD19CAR LV, either with or without hPBMC activation. The results indicate that CD19-specific CAR T cells could be detected in CD8+ T cells up to 28 days post-treatment in the peripheral blood, spleen and bone marrow.

Example 4: A 5 and 7-Week Single Dose Pharmacokinetic and Pharmacodynamic Study of CD8-SFFV-CD20CAR by Intravenous Infusion in Juvenile Female Nemestrina Macaques This Example describes a lentiviral vector pseudotyped with an anti-CD8 binding protein (binder 46) targeting CD8+ T cells to deliver a CD20 CAR transgene (CD8-SFFV-CD20CAR). The CD20CAR contained an anti-scFv directed against CD20 and an intracellular signaling domain containing intracellular components of 4-1BB and CD3-zeta. The objective of this study was to characterize the ability of CD8-SFFV-CD20CAR to transduce T cells and deplete normal, healthy CD20+B cells, the biodistribution of viral integration, and tolerability of intravenous administration. Eight juvenile female nemestrina macaques were administered CD8-SFFV-CD20CAR at a single maximum feasible dose of 7.69E8 IU/kg (n=6) or saline control at 10 ml/kg (n=2) intravenously over 1 hour. Animals were evaluated at baseline (Day −35, −28 and −21) for frequency of B and T-cells together with an assessment of hematological and clinical chemistry parameters. On-study animals were monitored daily for clinical observations, weekly for changes in body weight, temperature, neurological battery, and hematology and clinical chemistry. CSF samples were collected pre-study, on Day 7 and at termination (from days 35-52). All animals underwent routine blood sampling and flow cytometry immune-phenotyping for changes in B and T-cell frequencies on Day 3, 5, 7, 10, 14, 17, 21, 28, and 35. At termination, animals underwent a full necropsy, blood, CSF, and tissues were harvested for: flow cytometry of lymphoid tissues, cytokine analyses by Luminex, transgene expression by PCR, vector copy number (VCN) by ddPCR, insertion site distribution (ISD) by deep sequencing, clinical pathology (hematology and clinical chemistry), tissue immunohistochemistry, and anatomic histopathology.

Figure 12:
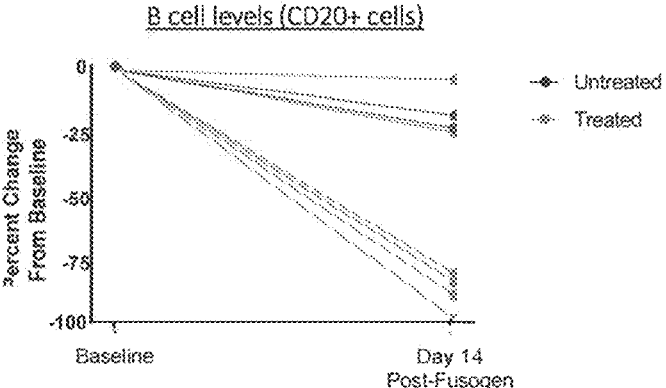
FIG. 12 depicts B cell levels in a non-human primate (NHP) model following administration of a lentiviral vector pseudotyped with an anti-CD8 binding protein targeting CD8+ T cells to deliver a CD20 CAR transgene.
Figure 13:
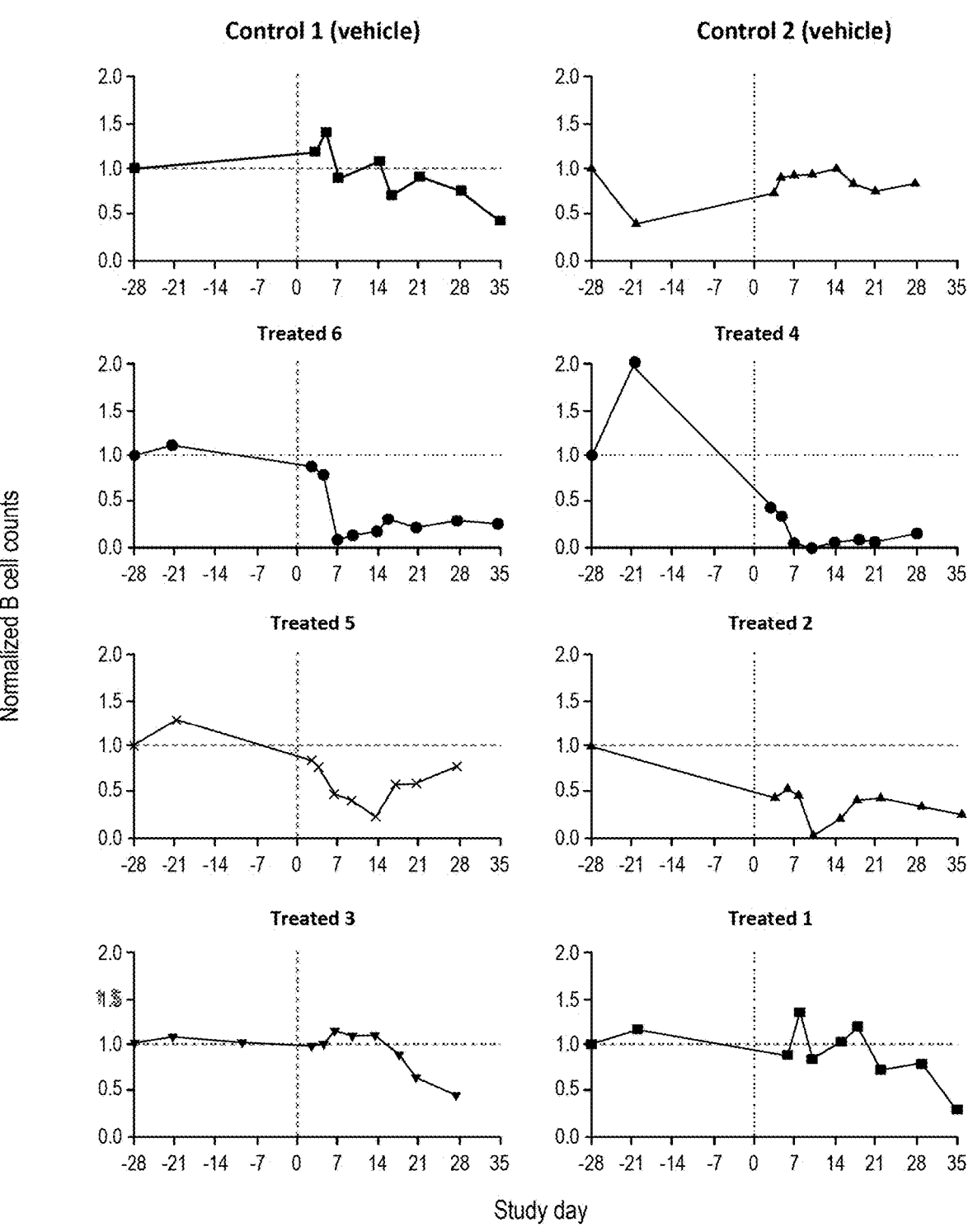
FIG. 13 depicts normalized B cell counts in non-human primates following administration of vehicle (Control 1-2) or a lentiviral vector pseudotyped with an anti-CD8 binding protein targeting CD8+ T cells to deliver a CD20 CAR transgene (Treated 1-6).

Interim data to Day 35 demonstrated that administration CD8-SFFV-CD20CAR at a single maximum feasible dose of 7.69E8 IU/kg was well-tolerated in all animals. There were no compound-related changes in clinical observations including neurological signs, body temperature nor clinical chemistry values across all sampling times. There were transient minimal reductions of platelets and neutrophils on Day 7-10 that returned to baseline by Day 14. There were transient, minimal decreases in hematocrit and associated increase in reticulocyte counts in two animals, which may be attributed to repeated blood sampling. As shown in FIG. 12, flow cytometric analyses demonstrated a significant decrease in CD20+ B cells in 4 of 6 treated animals beginning on Day 7 in peripheral blood compared to intra-animal pre-dosing, that was sustained through Day 35. Normalized B cell counts through day 28/35 are presented in FIG. 13. These data are consistent with the anticipated pharmacological activity of the anti-CD20CAR.

Preliminary VCN measurements using ddPCR were performed on samples from 2 control and 4 treated animals from Day-35 and Day 14 and 35 in peripheral blood mononuclear cells (PBMC's), and at termination in spleen and bone marrow. At Day-35, and 35 post-injection, VCN in PBMC's was observed though the values were below limit of quantitation (BLQ) in all animals. By comparison in the spleen VCN was detected in treated animals whereas control animals were BLQ. At Day 35, 0.04 to 1.3% of splenocytes (ie. 67 to 1,970 cells) contained at least one inserted copy in CD8-SFFV-CD20CAR treated animals examined. CD20 CAR mRNA was also detected in the spleen of the treated monkeys but not in the control animals.

Additional VCN measurements of transgene integration in the genome was measured via droplet digital polymerase chain reaction (ddPCR) using the WPRE (Woodchuck hepatitis virus Post-transcriptional Response Element) amplicon. Transgene was quantifiable or detectable in PBMCs of all (6 of 6) fusosome-dosed animals collected on study days 3 through 9/10 (Table 17), and detectable on days 14 through days 27/28 in PBMC samples in Animals 1, 4, and 6.

TABLE 17

| | | | | | | | | | | |
|---|---|---|---|---|---|---|---|---|---|---|
| Transgene integration measured by vector copy number (VCN) for PBMC samples collected in-life. | | | | | | | | | | |
| Animal | Day −28 | Day 3 | Day 5 | Day 7 | Days 9/10 | Day 14 | Days 16-18 | Day 21 | Days 27/28 | Day 35 |
| Control 1 | U | U | U | U | U | U | U | U | U | U |
| Control 2 | U | U | U | U | U | No sample | U | U | U | U |

TABLE 17-continued

Transgene integration measured by vector copy number (VCN) for
PBMC samples collected in-life.

| Animal | Day −28 | Day 3 | Day 5 | Day 7 | Days 9/10 | Day 14 | Days 16-18 | Day 21 | Days 27/28 | Day 35 |
|---|---|---|---|---|---|---|---|---|---|---|
| 1 | U | 0.00342 | 0.00273 | D | 0.00220 | U | D | D | D | U |
| 2 | U | D | D | 0.00207 | 0.00263 | U | U | U | U | U |
| 3 | U | D | D | D | 0.00283 | U | U | U | U | U |
| 4 | U | 0.00331 | D | 0.00326 | 0.00230 | D | D | U | U | U |
| 5 | U | 0.00254 | 0.00179 | 0.00289 | 0.00131 | U | U | U | U | U |
| 6 | U | 0.00820 | 0.00718 | No Sample | No Sample | D | D | D | U | U |

Vector copy number (VCN) was only reported when WPRE copies were in range of quantitation (50 to 120,000 copies per reaction). VCN was calculated as WPRE copies ×2/TERT and reported as VCN (integrations per diploid genome). If WPRE VCN copies were below LLOQ (Lower limit of quantification of < 50 copies per reaction) but above LLOD (Lower limit of detection of < 10 copies per reaction) WPRE VCN was reported as detectable. If WPRE copies were below WPRE VCN was reported undetectable.
D, detectable;
U, undetectable.

These data demonstrate on-target activity of CD8-SFFV-CD20CAR in immune competent animals that was well tolerated and was correlated with presence of vector in cells in the spleen, even in the absence of administration of T-cell activating treatment.

TABLE 5

VH Sequences

| CD8 Binder | VH Sequence | SEQ ID NO: |
|---|---|---|
| 1 | QVQLVQSGAEVKKPGASVKVSCKASGGTFS SYAISWVRQAPGQGLEWMGIIDPSDGNTNY A-QNFQGRVTMTRDTSTSTVYMELSSLRSE DTAVYYCAKERAAAGYYYYMDVWGQGTTVT VSS | 405 |
| 2 | QVQLVQSGAEVKKPGASVKVSCKASGGTFN TYAINWVRQAPGQGLEWMGRIDPSSGGTKY A-QNFQGRVTMTRDTSTSTVYMELSSLRSE DTAVYYCAKEHAAGTYYYYMDVWGKGTTVT VSS | 406 |
| 3 | QVQLVQSGAEVKKPGASVKVSCKASGGTFS SYAINWVRQAPGQGLEWMGIIDPSGGNTNY A-QNFQGRVTMTRDTSTSTVYMELSSLRSE DTAVYYCAKERAAAGYYYYMDVWGQGTTVT VSS | 407 |
| 4 | QVQLVQSGAEVKKPGASVKVSCKASGYTFT GYYMHWVRQAPGQGLEWMGHINPNNGDTNY A-QNFQGRVTMTRDTSTSTVYMELSSLRSE DTAVYYCAKEGYYYYGMDVWGQGTTVTVSS | 651 |
| 5 | QVQLVQSGAEVKKPGASVKVSCKASGYTFT DYYIQWVRQAPGQGLEWMGWINPNSGGTSY A-QKFQGRVTMTRDTSTSTVYMELSSLRSE DTAVYYCAKEGDYYYGMDAWGQGTMVTVSS | 408 |
| 6 | QVQLVQSGAEVKKPGASVKVSCKASGYTFT RYDIHWVRQAPGQGLEWMGVINPNDGSTRY A-QNFQGRVTMTRDTSTSTVYMELSSLRSE DTAVYYCARERGGMPDYWGQGTLVTVSS | 409 |
| 7 | QVQLVQSGAEVKKPGASVKVSCKASGYTFT SYAMNWVRQAPGQGLEWMGRINPNSGGTNY A-QKFQGRVTMTRDTSTSTVYMELSSLRSE DTAVYYCARGHGIPKYWGQGTLVTVSS | 410 |
| 8 | QVQLVQSGAEVKKPGASVKVSCKASGYTFT SYYIHWVRQAPGQGLEWMGWMNPNSGNTGY A-QKFQGRVTMTRDTSTSTVYMELSSLRSE DTAVYYCARVRSGSPQHWGQGTLVTVSS | 411 |

TABLE 5-continued

VH Sequences

| CD8 Binder | VH Sequence | SEQ ID NO: |
|---|---|---|
| 9 | QVQLVQSGAEVKKPGASVKVSCKASGHTFS RHYIHWVRQAPGQGLEWMGWMNPNSGNTGY A-QKFQGRVTMTRDTSTSTVYMELSSLRSE DTAVYYCARGGPWIVDAFDIWGQGTMVTVS S | 412 |
| 10 | QVQLVQSGAEVKKPGASVKVSCKASGYTFT SYGISWVRQAPGQGLEWMGWISAHNGVTQY A-QKFQGRVTMTRDTSTSTVYMELSSLRSE DTAVYYCARGIAVAGTDYWGQGTLVTVSS | 652 |
| 11 | QVQLVQSGAEVKKPGASVKVSCKASGGTFS NTDINWVRQAPGQGLEWMGIINPSGGSTSY A-QKFQGRVTMTRDTSTSTVYMELSSLRSE DTAVYYCAREATWGPYYYYMDVWGKGTTVT VSS | 413 |
| 12 | QVQLVQSGAEVKKPGASVKVSCKASGYTFT RSYVHWVRQAPGQGLEWMGWISPYNGNTKY A-QKFQGRVTMTRDTSTSTVYMELSSLRSE DTAVYYCVRNKDGLQHWGQGTLVTVSS | 414 |
| 13 | QVQLVQSGAEVKKPGASVKVSCKASGDTFT GYYMHWVRQAPGQGLEWMGI-INPNSGDTK YAHQFQGRVTMTRDTSTSTVYMELSSLRSE DTAVYYCAKDAKRVGYYYYMDVWGKGTTVT VSS | 415 |
| 14 | QVQLVQSGAEVKKPGASVKVSCKASGYTFT RYYMHWVRQAPGQGLEWMGRINPNSGGTNY A-QKFQGRVTMTRDTSTSTVYMELSSLRSE DTAVYYCARLVGGSPDYWGQGTLVTVSS | 416 |
| 15 | QVQLVQSGAEVKKPGASVKVSCKASGYTFT NYDINWVRQAPGQGLEW-MGRINPNSGGTN YAENFQGRVTMTRDTSTSTVYMELSSLRSE DTAVYYCARGAMVDYWGQGTLVTVSS | 417 |
| 16 | QVQLVQSGAEVKKPGASVKVSCKASGGTFS NTDINWVRQAPGQGLEWMGIINPSDGDTKY A-QEFQGRVTMTRDTSTSTVYMELSSLRSE DTAVYYCARGNYVGSYYYGMDVWGQGTTVT VSS | 418 |
| 17 | QVQLVQSGAEVKKPGASVKVSCKASGYTFT NYYLHWVRQAPGQGLEWMGWINPNSGDTKY A-QKFQGRVTMTRDTSTSTVYMELSSLRSE DTAVYYCARDSRGDWYFDLWGRGTLVTVSS | 419 |

TABLE 5-continued

VH Sequences

| CD8 Binder | VH Sequence | SEQ ID NO: |
|---|---|---|
| 18 | QVQLVQSGAEVKKPGASVKVSCKASGYGFT RYSIHWVRQAPGQGLEWMGVIDPSGGSTSY A-QKFQGRVTMTRDTSTSTVYMELSSLRSE DTAVYYCTRHGGRGLADYWGQGTLVTVSS | 420 |
| 19 | QVQLVQSGAEVKKPGASVKVSCKASGYTFT SRDISWVRQAPGQGLEWMGWIDPKSGDTTY A-QKFQGRVTMTRDTSTSTVYMELSSLRSE DTAVYYCARLKELSSILDAFDIWGQGTMVT VSS | 421 |
| 20 | QVQLVQSGAEVKKPGASVKVSCKASGYTFT SYDINWVRQAPGQGLEWMGMINPGAGSSTY A-QKFQGRVTMTRDTSTSTVYMELSSLRSE DTAVYYCARERFGTGYYYYMDVWGQGTMVT VSS | 422 |
| 21 | EVQLLESGGGLVQPGGSLRLSCAASGFTFS NSDMNWVRQAPGKGLEWVSLISGDGGTTY- YADSVKGRFTISRDNSKNTLYLQMNSLRAE DTAVYYCARVIGEMVDDAFDLWGQGTTVTV SS | 423 |
| 22 | QVQLVQSGAEVKKPGASVKVSCKASGYTFT GYYMHWVRQAPGQGLEWMGSINPNSGDTGY A-QKFQGRVTMTRDTSTSTVYMELSSLRSE DTAVYYCARERLFGTYYYYMDVWGQGTTVT VSS | 424 |
| 23 | QVQLVQSGAEVKKPGSSVKVSCKASGYTFT TYDINWVRQAPGQGLEWMGRIIPIFGTANY A-QKFQGRVTITADESTSTAYMELSSLRSE DTAVYYCARADGELTDYWGQGTLVTVSS | 425 |
| 24 | EVQLLESGGGLVQPGGSLRLSCAASGFTFS SYTMDWVRQAPGKGLEWVSAIGTGGGIY-Y ADSVKGRFTISRDNSKNTLYLQMNSLRAED TAVYYCARHHLPAHYYYYMDVWGKGTTVTV SS | 426 |
| 25 | QVQLVQSGAEVKKPGASVKVSCKASGGTFS RYDINWVRQAPGQGLEWMGRINPNSGDTNY A-QKFQGRVTMTRDTSTSTVYMELSSLRSE DTAVYYCARDVPAGRYYYYMDVWGKGTLVT VSS | 427 |
| 26 | QVQLVQSGAEVKKPGASVKVSCKASGNTFT SYYMHWVRQAPGQGLEWMGMINPSDGSTRY A-QKFQGRVTMTRDTSTSTVYMELSSLRSE DTAVYYCAKDRGVGRYYYYMDVWGKGTTVT VSS | 428 |
| 27 | QVQLVQSGAEVKKPGASVKVSCKASGGTFS RYAVSWVRQAPGQGLEWMGIINPSDGSTTY A-QKFQGRVTMTRDTSTSTVYMELSSLRSE DTAVYYCAKDSRYGRYYYYMDVWGKGTTVT VSS | 429 |
| 28 | QVQLVQSGAEVKKPGSSVKVSCKASGGTFS NYAISWVRQAPGQGLEWMGIINPNGGSPSY A-QKFQGRVTITADESTSTAYMELSSLRSE DTAVYYCAKEIVVGPYYYYMDVWGKGTTVT VSS | 430 |
| 29 | QVQLVQSGAEVKKPGSSVKVSCKASGGTFT RYAISWVRQAPGQGLEWMGRINPNSGDTNY A-QKFQGRVTITADESTSTAYMELSSLRSE DTAVYYCARGMVRGPYYYYMDVWGKGTTVT VSS | 431 |

TABLE 5-continued

VH Sequences

| CD8 Binder | VH Sequence | SEQ ID NO: |
|---|---|---|
| 30 | QVQLVQSGAEVKKPGSSVKVSCKASGGTFS SYAISWVRQAPGQGLEWMGI-INPSGGSTS YAQTFQGRVTITADESTSTAYMELSSLRSE DTAVYYCAREGVTGPYYYYMDVWGQGTTVT VSS | 432 |
| 31 | QVQLVQSGAEVKKPGASVKVSCKASGGTFS RFDINWVRQAPGQGLEWMGIINPSDGSTDY A-QNFQGRVTMTRDTSTSTVYMELSSLRSE DTAVYYCARDAAAGTRYYYYYGMDVWGQGT TVTVSS | 433 |
| 32 | QVQLVQSGAEVKKPGASVKVSCKASGGTFS SHAISWVRQAPGQGLEWMGIINPSGGSTSY A-QKFQGRVTMTRDTSTSTVYMELSSLRSE DTAVYYCARELYSSTYYYYMDVWGKGTTVT VSS | 434 |
| 33 | QVQLVQSGAEVKKPGASVKVSCKASGGTFS SYAISWVRQAPGQGLEW-MGRINPNTGGTN HAQKFQGRVTMTRDTSTSTVYMELSSLRSE DTAVYYCARALYSGPYYYYMDVWGKGTTVT VSS | 435 |
| 34 | EVQLLESGGGLVQPGGSLRLSCAASGFTFS NSDMNWVRQAPGKGLEWVSAISGSGGSTY- YADSVKGRFTISRDNSKNTLYLQMNSLRAE DTAVYYCAKEHAAGTYYYYMDVWGKGTTVT VSS | 436 |
| 35 | QVQLVQSGAEVKKPGASVKVSCKASGGTFG SYGINWVRQAPGQGLEWMGWIS-GYNGDTD YARKLQGRVTMTRDTSTSTVYMELSSLRSE DTAVYYCARDSLVGRYYYYMDVWGKGTTVT VSS | 437 |
| 36 | QVQLVQSGAEVKKPGASVKVSCKASGYIFT DYDIYWVRQAPGQGLEWL-GWISADNGNTN YEQKVQGRVTMTRDTSTSTVYMELSSLRSE DTAVYYCARRSELDYWGQGTLVTVSS | 438 |
| 37 | QVQLVQSGAEVKKPGASVKVSCKASGYTFT SYHMHWVRQAPGQGLEWMGWISPNSGATH- YAQKFQGRVTMTRDTSTSTVYMELSSLRSE DTAVYYCARGDDNDYWGQGTLVTVSS | 439 |
| 38 | QVQLVQSGAEVKKPGASVKVSCKASGYTFT SYDINWVRQAPGQGLEW-MGWINPNSGNTG YAKKFQGRVTMTRDTSTSTVYMELSSLRSE DTAVYYCARGEEVDYWGQGTLVTVSS | 440 |
| 39 | QVQLVQSGAEVKKPGASVKVSCKASGYTFT SYPMNWVRQAPGQGLEWMGIINPSGGSTRY A-QKFQGRVTMTRDTSTSTVYMELSSLRSE DTAVYYCARGRRVPDYWGQGTLVTVSS | 441 |
| 40 | QVQLVQSGAEVKKPGASVKVSCKASGYTFT DYYIHWVRQAPGQGLEWMGWINPKSGATNY A-QKFQGRVTMTRDTSTSTVYMELSSLRSE DTAVYYCARGKVTTDYWGQGTLVTVSS | 442 |
| 41 | EVQLLESGGGLVQPGGSLRLSCAASGFTFS SFEMNWVRQAPGKGLEWVSRISESGDSS-F YADSVKGRFTISRDNSKNTLYLQMNSLRAE DTAVYYCASGRELIEYWGQGTLVTVSS | 443 |
| 42 | EVQLLESGGGLVQPGGSLRLSCAASGFTFD DYAMHWVRQAPGKGLEWVSAIGTGGGTY-Y ADSVKGRFTISRDNSKNTLYLQMNSLRAED TAVYYCARVYDFPDVWGQGTTVTVSS | 444 |

TABLE 5-continued

VH Sequences

| CD8 Binder | VH Sequence | SEQ ID NO: |
|---|---|---|
| 43 | QVQLVQSGAEVKKPGASVKVSCKASGYTFT DSYMHWVRQAPGQGLEWMGWMNP-SNGDTG YARKFQGRVTMTRDTSTSTVYMELSSLRSE DTAVYYCARSTYSHIDYWGQGTLVTVSS | 445 |
| 44 | QVQLVQSGAEVKKPGASVKVSCKASGYTFT NYYMHWVRQAPGQGLEWMGTISPSDGSTTY A-QRFQGRVTMTRDTSTSTVYMELSSLRSE DTAVYYCAREDSSGFDYWGQGTLVTVSS | 446 |
| 45 | QVQLVQSGAEVKKPGASVKVSCKASGYTFM NYYIHWVRQAPGQGLEWMGIINPSGGTTY A-QKFQGRVTMTRDTSTSTVYMELSSLRSE DTAVYYCARDQGGGFDYWGQGTLVTVSS | 447 |
| 46 | QVQLVQSGAEVKKPGASVKVSCKASGYTFT SYYMHWVRQAPGQGLEWGGFDPEDGETIY A-QKFQGRVTMTRDTSTSTVYMELSSLRSE DTAVYYCARDQGWGMDVWGQGTTVTVSS | 448 |
| 47 | QVQLVQSGAEVKKPGASVKVSCKASGYTFT SYYIHWVRQAPGQGLEWMGRINPKSGRTYY A-QNFQGRVTMTRDTSTSTVYMELSSLRSE DTAVYYCARLTEGIPDYWGQGTLVTVSS | 449 |
| 48 | QVQLVQSGAEVKKPGASVKVSCKASGYTLN DYYIHWVRQAPGQGLEW-MGVINPGGGSTT YAQTFQGRVTMTRDTSTSTVYMELSSLRSE DTAVYYCARDRYGPFDYWGQGTLVTVSS | 450 |
| 49 | QVQLVQSGAEVKKPGASVKVSCKASGYTFT SYDINWVRQAPGQGLEWMGLM-NPKTGDTN YAEKFQGRVTMTRDTSTSTVYMELSSLRSE DTAVYYCTRLVAGGAPDYWGQGTLVTVSS | 451 |
| 50 | QVQLVQSGAEVKKPGASVKVSCKASGYTFT GYYMHWVRQAPGQGLEWMGIIDPSDGYTSY A-QKFQGRVTMTRDTSTSTVYMELSSLRSE DTAVYYCARDGFTGDIAYWGQGTLVTVSS | 452 |
| 51 | QVQLVQSGAEVKKPGSSVKVSCKASGYTFT GYYMHWVRQAPGQGLEWMGWINPNSGGTNY A-QKFQGRVTITADESTSTAYMELSSLRSE DTAVYYCARVDDSSSPDYWGQGTLVTVSS | 453 |
| 52 | QVQLVQSGAEVKKPGSSVKVSCKASGYTFT GYYLHWVRQAPGQGLEWMGGIMPISGTTIY A-QKFQGRVTITADESTSTAYMELSSLRSE DTAVYYCTTGPDGTEVDYWGQGTLVTVSS | 454 |
| 52 | QVQLVQSGAEVKKPGASVKVSCKASGYTFT NHYMHWVRQAPGQGLEW-MGWMNPNSGNTG YA-QKFQGRVTMTRDTSTSTVYMELSSLRS EDTAVYYCASSESGSDLDYWGQGTLVTVSS | 455 |
| 54 | QVQLVQSGAEVKKPGASVKVSCKASGYTFT NYYIHWVRQAPGQGLEWMGWMSPTSGDTGY A-QKFQGRVTMTRDTSTSTVYMELSSLRSE DTAVYYCAREVEIEGYMDVWGQGTTVTVSS | 456 |
| 55 | QVQLVQSGAEVKKPGASVKVSCKASGYTFT SYYMHWVRQAPGQGLEWMGWINPNSGDTSY A-QKFQGRVTMTRDTSTSTVYMELSSLRSE DTAVYYCAKDLDDDWYMDVWGKGTTVTVSS | 457 |
| 56 | QVQLVQSGAEVKKPGASVKVSCKASGYTFT SYYMHWVRQAPGQGLEWMGIIDPSGDITSY A-QKFQGRVTMTRDTSTSTVYMELSSLRSE DTAVYYCTTDSTTWDAFDIWGQGTMVTVSS | 458 |

TABLE 5-continued

VH Sequences

| CD8 Binder | VH Sequence | SEQ ID NO: |
|---|---|---|
| 57 | QVQLVQSGAEVKKPGASVKVSCKASGYTFT DYYMHWVRQAPGQGLEWMGWINPNSGGTNY A-QKFQGRVTMTRDTSTSTVYMELSSLRSE DTAVYYCARVLVGSGSPDYWGQGTLVTVSS | 459 |
| 58 | QVQLVQSGAEVKKPGASVKVSCKASGYTFT ENEMHWVRQAPGQGLEWMGIIETSGGSTDY A-QKFQGRVTMTRDTSTSTVYMELSSLRSE DTAVYYCAREAAAGLDFQHWGQGTLVTVSS | 460 |
| 59 | QVQLVQSGAEVKKPGASVKVSCKASGYTFA SYDMHWVRQAPGQGLEWMGIINPNSGGTNY A-QKLQGRVTMTRDTSTSTVYMELSSLRSE DTAVYYCARANSWDAMVIDYWGQGTLVTVS S | 461 |
| 60 | EVQLLESGGGLVQPGGSLRLSCAASGFTFS NSDMHWVRQAPGKGLEWVSVISGSGVTTY- YADSVKGRFTISRDNSKNTLYLQMNSLRAE DTAVYYCAREHSSSWYTFDYWGQGTLVTVS S | 462 |
| 61 | QVQLVQSGAEVKKPGASVKVSCKASGYTFT AYYMHWVRQAPGQGLEWLGWINPNSGGTDY A-QKFQGRVTMTRDTSTSTVYMELSSLRSE DTAVYYCARDDDSSGYYLDYWGQGTLVTVS S | 463 |
| 62 | QVQLVQSGAEVKKPGASVKVSCKASGYTFT NYYIHWVRQAPGQGLEWMGMINPSGGSTTY A-QKFQGRVTMTRDTSTSTVYMELSSLRSE DTAVYYCARASGDYMDLIDYWGQGTLVTVS S | 464 |
| 63 | QVQLVQSGAEVKKPGASVKVSCKASGYTFT DYHMHWVRQAPGQGLEWL-GWINPDSGGTN YEQKFQGRVTMTRDTSTSTVYMELSSLRSE DTAVYYCALVGSSGYLAPTHWGQGTLVTVS S | 465 |
| 64 | QVQLVQSGAEVKKPGSSVKVSCKASGYPFT DYYMHWVRQAPGQGLEW-MGWMNPNSGNTG YA-QKFQGRVTITADESTSTAYMELSSLRS EDTAVYYCARVRGDGYNLGDYWGQGTLVTV SS | 466 |
| 65 | QVQLVQSGAEVKKPGASVKVSCKASGYTFS DYYMHWVRQAPGQGLEW-MGWINPNSGGTN SAQKFQGRVTMTRDTSTSTVYMELSSLRSE DTAVYYCARDVDTAMGAGDYWGQGTLVTVS S | 467 |
| 66 | QVQLVQSGAEVKKPGASVKVSCKASGYTFT DYYIHWVRQAPGQGLEWIGIINPSGGSASY A-QKFQGRVTMTRDTSTSTVYMELSSLRSE DTAVYYCARVARWGYGDYPDYWGQGTLVTV SS | 468 |
| 67 | QVQLVQSGAEVKKPGASVKVSCKASGDTFT THDINWVRQAPGQGLEWMGIISPSDGSTSY A-QKLQGRVTMTRDTSTSTVYMELSSLRSE DTAVYYCARDRNGDYYYGMDVWGQGTTVTV SS | 469 |
| 68 | QVQLVQSGAEVKKPGASVKVSCKASGDTFT NYYIHWVRQAPGQGLEWMGWINPISGGTHY A-QKFQGRVTMTRDTSTSTVYMELSSLRSE DTAVYYCAREGLGSSWYVLDYWGQGTLVTV SS | 470 |

TABLE 5-continued

| | VH Sequences | | |
|---|---|---|---|
| CD8 Binder | VH Sequence | | SEQ ID NO: |
| 69 | QVQLVQSGAEVKKPGASVKVSCKASGYTFT SYDINWVRQAPGQGLEWMGWISADNGDTSF A-QKFQGRVTMTRDTSTSTVYMELSSLRSE DTAVYYCARDGSHYGYYGMDVWGQGTTVTV SS | | 471 |
| 70 | QVQLVQSGAEVKKPGSSVKVSCKASGYTFT SYDINWVRQAPGQGLEWMGGISPIYGTPAY A-QKFQGRVTITADESTSTAYMELSSLRSE DTAVYYCASPGPEGYYYGMDVWGQGTTVT SS | | 472 |
| 71 | QVQLVQSGAEVKKPGASVKVSCKASGYTFT DNYMHWVRQAPGQGLEWM-MGWMNPNSGNTG YA-QKFQGRVTMTRDTSTSTVYMELSSLRS EDTAVYYCASHWDYGDYRFDYWGQGTLVT VSS | | 473 |
| 72 | QVQLVQSGAEVKKPGASVKVSCKASGYTFT SYYIHWVRQAPGQGLEWMGWMNPNSGNTGY A-QKFQGRVTMTRDTSTSTVYMELSSLRSE DTAVYYCARVEIDYGDSPPDYWGQGTLVTV SS | | 474 |
| 73 | QVQLVQSGAEVKKPGASVKVSCKASGGTSS SYAISWVRQAPGQGLEWMGIINPSDGDTSY A-QKFQGRVTMTRDTSTSTVYMELSSLRSE DTAVYYCARGAEWELRYAFDIWGQGTMVTV SS | | 475 |
| 74 | QVQLVQSGAEVKKPGASVKVSCKASGYTFT TYDISWVRQAPGQGLEWMGTINPSGGTTTY A-QKFQGRVTMTRDTSTSTVYMELSSLRSE DTAVYYCARETYYGLYYYGMDVWGKGTTVT VSS | | 476 |
| 75 | QVQLVQSGAEVKKPGASVKVSCKASGYTFT SYDINWVRQAPGQGLEWMGWMNPKSGNTGY A-QKFQGRVTMTRDTSTSTVYMELSSLRSE DTAVYYCARAPSLRGYSYGPDYWGQGTLVT VSS | | 477 |
| 76 | QVQLVQSGAEVKKPGASVKVSCKASGGTFT SYDINWVRQAPGQGLEWMGIINPSGGSTSY A-QKFQGRVTMTRDTSTSTVYMELSSLRSE DTAVYYCAKDRQERYYYYYMDVWGKGTLVT VSS | | 478 |
| 77 | QVQLVQSGAEVKKPGASVKVSCKASGYTFT SYDINWVRQAPGQGLEWMGIINPSDGSTDY A-QKFQGRVTMTRDTSTSTVYMELSSLRSE DTAVYYCAKDRSYGDYYYGMDVWGQGTTVT VSS | | 479 |
| 78 | QVQLVQSGAEVKKPGASVKVSCKASGGTFT SYDINWVRQAPGQGLEWMGIINPGGG-NAR HTQKFQGRVTMTRDTSTSTVYMELSSLRSE DTAVYYCAREVFSENYYYYMDVWGKGTTVT VSS | | 480 |
| 79 | QVQLVQSGAEVKKPGASVKVSCKASGYTFT SYYMHWVRQAPGQGLEWMGIINPSDGSTTY A-QKFQGRVTMTRDTSTSTVYMELSSLRSE DTAVYYCAREWDYTHYYYGMDVWGQGTTVT VSS | | 481 |
| 80 | QVQLVQSGAEVKKPGASVKVSCKASGNTFT SHWIHWVRQAPGQGLEWMGGFDPEDG-ETV YAQNFQGRVTMTRDTSTSTVYMELSSLRSE DTAVYYCARGDSSGYYQYYFDYWGQGTLVT VSS | | 482 |

TABLE 5-continued

| | VH Sequences | | |
|---|---|---|---|
| CD8 Binder | VH Sequence | | SEQ ID NO: |
| 81 | QVQLVQSGAEVKKPGSSVKVSCKASGYTFT SYDINWVRQAPGQGLEWMGGITPVFGIANY A-QKFQGRVTITADESTSTAYMELSSLRSE DTAVYYCARGSWDSSSWYIPEYWGQGTLVT VSS | | 483 |
| 82 | QVQLVQSGAEVKKPGASVKVSCKASGFTFS DYDIVWVRQAPGQGLEWMGIINPRGGSTNY A-QKFQGRVTMTRDTSTSTVYMELSSLRSE DTAVYYCASLVWGGAYYYMDVWGQGTTVT VSS | | 484 |
| 83 | QVQLVQSGAEVKKPGASVKVSCKASGYTFT SYGISWVRQAPGQGLEWMGWMNPNNGDTDY A-QKFQGRVTMTRDTSTSTVYMELSSLRSE DTAVYYCTTPVFSGSYYWYFDPWGQGTLVT VSS | | 485 |
| 84 | QVQLVQSGAEVKKPGASVKVSCKASGYTFT SYDINWVRQAPGQGLEWMGIINPSGGGTSY A-QKFQGRVTMTRDTSTSTVYMELSSLRSE DTAVYYCTTDQAVAGPYYYGMDVWGQGTLV TVSS | | 486 |
| 85 | QVQLVQSGAEVKKPGASVKVSCKASGGTFS SYAISWVRQAPGQGLEWMGIINPGSGNTNY A-QKFQGRVTMTRDTSTSTVYMELSSLRSE DTAVYYCARDRWLAGPYYYGMDVWGQGTTV TVSS | | 487 |
| 86 | QVQLVQSGAEVKKPGSSVKVSCKASGYMFT GHDMHWVRQAPGQGLEWMGGIIPIFGTPNY A-QKFQGRVTITADESTSTAYMELSSLRSE DTAVYYCARVMGPVDYYYYGMDVWGQGTTV TVSS | | 488 |
| 87 | QVQLVQSGAEVKKPGASVKVSCKASGYIFS NYDMHWVRQAPGQGLEWMGIINPSDGSTTY A-QKFQGRVTMTRDTSTSTVYMELSSLRSE DTAVYYCARDLGPFGSYYYYMDVWGKGTTV TVSS | | 489 |
| 88 | EVQLVESGGGLVKPGGSLRLSCAASGFTFS SYAMTWVRQAPGKGLEWVSTINGDGDDTDY -ADSVKGRFTISRDDSKNTLYLQMNSLKTE DTAVYYCAREGVVVPPYYYYMDVWGKGTTV TVSS | | 490 |
| 89 | QVQLVQSGAEVKKPGASVKVSCKASGYTFT TYYMHWVRQAPGQGLEWMGQIDPNSGD-TI YPQKFQGRVTMTRDTSTSTVYMELSSLRSE DTAVYYCARSSGWSRYYYYYMDVWGKGTTV TVSS | | 491 |
| 90 | QVQLVQSGAEVKKPGASVKVSCKASGSTFT NYQIHWVRQAPGQGLEWMGIINPSGGSTSY A-QKFQGRVTMTRDTSTSTVYMELSSLRSE DTAVYYCARDNGMTTGYYYYMDVWGKGTTV TVSS | | 492 |
| 91 | QVQLVQSGAEVKKPGASVKVSCKASGYTFT SYDIVWVRQAPGQGLEWMGIINPSGGSTSY A-QKFQGRVTMTRDTSTSTVYMELSSLRSE DTAVYYCARDRAMVTGYYYGMDVWGQGTTV TVSS | | 493 |
| 92 | QVQLVQSGAEVKKPGASVKVSCKASGYTFT SYDINWVRQAPGQGLEWMGIVNPSDGNTNY A-QKFQGRVTMTRDTSTSTVYMELSSLRSE DTAVYYCARDRGYGDRGYYYGMDVWGQGTT VTVSS | | 494 |

TABLE 5-continued

| | VH Sequences | |
|---|---|---|
| CD8 Binder | VH Sequence | SEQ ID NO: |
| 93 | QVQLVQSGAEVKKPGASVKVSCKASGGTLS SYDINWVRQAPGQGLEWMGWINTYNGNTYY A-QKLQGRVTMTRDTSTSTVYMELSSLRSE DTAVYYCATSPKATADYYYYYMDVWGKGTT VTVSS | 495 |
| 94 | QVQLVQSGAEVKKPGASVKVSCKASGYTFT SYDINWVRQAPGQGLEWMGIINPSDGITDY A-QRFQGRVTMTRDTSTSTVYMELSSLRSE DTAVYYCTTSTVTPSYYYYYGMDVWGQGTT VTVSS | 496 |
| 95 | QVQLVQSGAEVKKPGASVKVSCKASGYTFT SHAIHWVRQAPGQGLEWMGI-INPRDGDTV YAQKFQGRVTMTRDTSTSTVYMELSSLRSE DTAVYYCAREPVAGTGYYYYYGMDVWGQGT LVTVSS | 497 |
| 96 | QVQLVQSGAEVKKPGASVKVSCKASGGTFNS SYGINWVRQAPGQGLEW-MGWMNPNSGNTGY A-QKFQGRVTMTRDTSTSTVYMELSSLRSED TAVYYCARDNLAGFWSDYYYYGMDVWGQGTT VTVS | 498 |
| 97 | | |

TABLE 6

| | VL Sequences | |
|---|---|---|
| CD8 Binder | VL Sequence | SEQ ID NO: |
| 1 | DIQMTQSPSSLSASVGDRVTITCRASQ SISSYLNWYQQKPGKAPKLLIYAAS- SLQSGVPSRFSGSGSGTDFTLTISSLQ PEDFATYYCQQSYSTPLTFGGGTKVEI KR | 499 |
| 2 | DIQMTQSPSSLSASVGDRVTITCQASQ DISNYLNWYQQKPGKAPKLLIYAAS- SLQSGVPSRFSGSGSGTDFTLTISSLQ PEDFATYYCQQSYSNLVSFGQGTKVEI KR | 500 |
| 3 | DIQMTQSPSSLSASVGDRVTITCRASQ SISSYLNWYQQKPGKAPKLLIYAAS- SLQSGVPSRFSGSGSGTDFTLTISSLQ PEDFATYYCQQSYSTPLTFGQGTKVEI KR | 501 |
| 4 | DIVMTQSPLSLPVTPGEPASISCRSSQ SLLHSNGYNYLDWYLQKPGQSPQLLIY L- GSNRASGVPDRFSGSGSGTDFTLKISR VEAEDVGVYYCMQALQTPFTFGPGTKV DIKR | 502 |
| 5 | DIVMTQSPLSLPVTPGEPASISCRSSQ SLLHSNGYNYLDWYLQKPGQSPQLLIY L- GSNRASGVPDRFSGSGSGTDFTLKISR VEAEDVGVYYCMQGLQTPHTFGQGTKV EIKR | 503 |
| 6 | DIQMTQSPSSLSASVGDRVTITCRASQ SISRNLNWYQQKPGKAPKLLI- YKASNLKGGVPSRFSGSGSGTDFTLTI SSLQPEDFATYYCQQTYSAPLFGQGTK LEIKR | 504 |

TABLE 6-continued

| | VL Sequences | |
|---|---|---|
| CD8 Binder | VL Sequence | SEQ ID NO: |
| 7 | DIVMTQSPLSLPVTPGEPASISCRSSQ SLLHSNGYNYLDWYLQKPGQSPQLLIY L- GSNRASGVPDRFSGSGSGTDFTLKISR VEAEDVGVYYCMQTLQTPLTFGQGTKV EIKR | 505 |
| 8 | EIVMTQSPATLSVSPGERATLSCRASQ SVSASDLAWYQQKPGQAPRLLIYGAST RAT- GIPARFSGSGSGTEFTLTISSLQSEDF AVYYCQQYGDSPGSFGQGTKLEIKR | 506 |
| 9 | DIQMTQSPSSLSASVGDRVTITCQASQ DIGNYLNWYQQKPGKAPKLLI- YAASTLQRGVPSRFSGSGSGTDFTLTI SSLQPEDFATYYCQQANSFPPTFGGGT KVEIKR | 507 |
| 10 | EIVMTQSPATLSVSPGERATLSCRASQ SISTHLAWYQQKPGQAPRLLIYGASTR AT- GIPARFSGSGSGTEFTLTISSLQSEDF AVYYCQQYGNSRTFGQGTKVEIKR | 508 |
| 11 | DIQMTQSPSSLSASVGDRVTITCRASQ TISNYLNWYQQKPGKAPKLLI- YAASTLQSGVPSRFSGSGSGTDFTLTI SSLQPEDFATYYCQQSYSTPPTFGQGT KLEIKR | 509 |
| 12 | DIQMTQSPSSLSASVGDRVTITCRASQ GIRNDLGWYQQKPGKAPKLLI- YDASTLQSGVPSRFSGSGSGTDFTLTI SSLQPEDFATYYCQQSYSSPYTFGQGT KLEIKR | 510 |
| 13 | DIQMTQSPSSLSASVGDRVTITCRASQ SISNYLNWYQQKPGKAPKLLIYAAS- SLQSGVPSRFSGSGSGTDFTLTISSLQ PEDFATYYCQQSYSTPYTFGQGTKLEI KR | 511 |
| 14 | DIVMTQSPLSLPVTPGEPASISCRSSQ SLLHSNGYNYLDWYLQKPGQSPQLLIY L- GSNRASGVPDRFSGSGSGTDFTLKISR VEAEDVGVYYCMQGAHWPPTFGQGTKL EIKR | 512 |
| 15 | DIQMTQSPSSLSASVGDRVTITCRASQ GISDSLAWYQQKPGKAPKLLI- YGASSLRSGVPSRFSGSGSGTDFTLTI SSLQPEDFATYYCQQSYRTPYTFGQGT KLEIKR | 513 |
| 16 | DIQMTQSPSSLSASVGDRVTITCRASQ SISNYLNWYQQKPGKAPKLLIYAAS- SLQSGVPSRFSGSGSGTDFTLTISSLQ PEDFATYYCQESFTTQWTFGQGTKVEI KR | 514 |
| 17 | DIQMTQSPSSLSASVGDRVTITCQASQ DIHNYLNWYQQKPGKAPKLLIYDASN- LETGVPSRFSGSGSGTDFTLTISSLQP EDFATYYCQQANSFPPTFGQGTKVDIK R | 515 |
| 18 | DIQMTQSPSSLSASVGDRVTITCQASQ DISNYLNWYQQKPGKAP- KLLIYSASSLQSGVPSRFSGSGSGTDF TLTISSLQPEDFATYYCQQRSNWPLYT FGQGTKVEIKR | 516 |

TABLE 6-continued

VL Sequences

| CD8 Binder | VL Sequence | SEQ ID NO: |
|---|---|---|
| 19 | DIQMTQSPSSLSASVGDRVTITCRASQ SISDWLAWYQQKPGKAPKLLIYAAS- SLQTGVPSRFSGSGSGTDFTLTISSLQ PEDFATYYCQQAISFPITFGQGTKVEI KR | 517 |
| 20 | DIQMTQSPSSLSASVGDRVTITCQASQ DISNYLNWYQQKPGKAP- KLLIYSASTLQSGVPSRFSGSGSGTDF TLTISSLQPEDFATYYCQQSYSSPFTF GPGTKVDIKR | 518 |
| 21 | DIQMTQSPSSLSASVGDRVTITCRASQ SISTWLAWYQQKPGKAPKLLI- YAASTLQSGVPSRFSGSGSGTDFTLTI SSLQPEDFATYYCQQAISFPLTFGGGT KVEIKR | 519 |
| 22 | DIQMTQSPSSLSASVGDRVTITCRASQ SISNYLNWYQQKPGKAPKLLI- YAASTLQSGVPSRFSGSGSGTDFTLTI SSLQPEDFATYYCQQSYTFPITFGQGT RLEIKR | 520 |
| 23 | DIVMTQSPLSLPVTPGEPASISCRSSQ SLLHSNGYNYLDWYLQKPGQSPQLLIY DASH- LETGVPDRFSGSGSGTDFTLKISRVEA EDVGVYYCQQYYSYPPTFGQGTKVEIK R | 521 |
| 24 | DIQMTQSPSSLSASVGDRVTITCQASQ DISNYLNWYQQKPGKAPKLLI- YAASTLHSGVPSRFSGSGSGTDFTLTI SSLQPEDFATYYCQQSYSAPLTFGPGT KVDIKR | 522 |
| 25 | DIQMTQSPSSLSASVGDRVTITCQASQ DISNYLNWYQQKPGKAPKLLI- YAASTLQSGVPSRFSGSGSGTDFTLTI SSLQPEDFATYYCQQSFSTFYTFGQGT KVEIKR | 523 |
| 26 | DIQMTQSPSSLSASVGDRVTITCQASQ DISNYLNWYQQKPGKAPKLLI- YAASTLQSGVPSRFSGSGSGTDFTLTI SSLQPEDFATYYCQQSYSIPFTFGPGT KVDIKR | 524 |
| 27 | DIQMTQSPSSLSASVGDRVTITCRASQ SINRFLNWYQQKPGKAPKLLIYAAS- SLQNGVPSRFSGSGSGTDFTLTISSLQ PEDFATYYCQQSYSTPYTFGQGTKVEI KR | 525 |
| 28 | DIQMTQSPSSLSASVGDRVTITCRASQ SISSYLNWYQQKPGKAPKLLIYAAS- SLQSGVPSRFSGSGSGTDFTLTISSLQ PEDFATYYCQQSYSTPLTFGGGTKVEI KR | 499 |
| 29 | DIQMTQSPSSLSASVGDRVTITCQASQ DISNYLNWYQQKPGKAPKLLI- YAASTLQSGVPSRFSGSGSGTDFTLTI SSLQPEDFATYYCQQSYSTPITFGQGT RLEIKR | 526 |
| 30 | DIQMTQSPSSLSASVGDRVTITCRASQ SVSTYLNWYQQKPGKAPKLLIYAAS- SLQSGVPSRFSGSGSGTDFTLTISSLQ PEDFATYYCQQSYTIPSTFGQGTKVEI KR | 527 |

TABLE 6-continued

VL Sequences

| CD8 Binder | VL Sequence | SEQ ID NO: |
|---|---|---|
| 31 | DIQMTQSPSSLSASVGDRVTITCQASQ DIAKYLNWYQQKPGKAPKLLIYAAS- SLQSGVPSRFSGSGSGTDFTLTISSLQ PEDFATYYCQQSYSAPPTFGGGTKVEI KR | 528 |
| 32 | DIQMTQSPSSLSASVGDRVTITCQASQ GITNYLNWYQQKPGKAPKLLI- YGASSLQSGVPSRFSGSGSGTDFTLTI SSLQPEDFATYYCQQSYSTPWTFGPGT KVDIKR | 529 |
| 33 | DIQMTQSPSSLSASVGDRVTITCRASQ SISSYLNWYQQKPGKAPKLLIYAAS- SLQSGVPSRFSGSGSGTDFTLTISSLQ PEDFATYYCQQSYSTPLTFGGGTKVEI KR | 499 |
| 34 | DIQMTQSPSSLSASVGDRVTITCQASQ DIHNYLNWYQQKPGKAPKLLI- YAASTLQSGVPSRFSGSGSGTDFTLTI SSLQPEDFATYYCQQSYTTPLTFGQGT KVEIKR | 530 |
| 35 | DIQMTQSPSSLSASVGDRVTITCQASQ DISNYLNWYQQKPGKAP- KLLIYSAFSLQSGVPSRFSGSGSGTDF TLTISSLQPEDFATYYCQQSYSAPITF GQGTRLEIKR | 531 |
| 36 | DIQMTQSPSSLSASVGDRVTITCRASQ SISSYLNWYQQKPGKAP- KLLIYSASNLQSGVPSRFSGSGSGTDF TLTISSLQPEDFATYYCQQRSNWPPVT FGQGTKVEIKR | 532 |
| 37 | DIQMTQSPSSLSASVGDRVTITCQANQ DISNFLEWYQQKPGKAPKLLIYDAS- SLESGVPSRFSGSGSGTDFTLTISSLQ PEDFATYYCQQSYSIPITFGQGTRLEI KR | 533 |
| 38 | DIQMTQSPSSLSASVGDRVTITCRASQ GISNNLNWYQQKPGKAPKLLIYEAST- LESGVPSRFSGSGSGTDFTLTISSLQP EDFATYYCQQSYSTPLTFGGGTKVEIK R | 534 |
| 39 | DIVMTQSPLSLPVTPGEPASISCRSSQ SLLHSNGYNYLDWYLQKPGQSPQLLI- YGASTLETGVPDRFSGSGSGTDFTLKI SRVEAEDVGVYYCMQGLQPPGTFGQGT KVEIKR | 535 |
| 40 | DIQMTQSPSSLSASVGDRVTITCRASQ SISRSLVWYQQKPGKAPKLLI- YAASTLQTGVPSRFSGSGSGTDFTLTI SSLQPEDFATYYCQQSYNHFRTFGPGT KVDIKR | 536 |
| 41 | DIQMTQSPSSLSASVGDRVTITCQASQ DISNYLNWYQQKPGKAPKLLIYDASN- LETGVPSRFSGSGSGTDFTLTISSLQP EDFATYYCQRSDSTPLTFGGGTKVEIK R | 537 |
| 42 | DIQMTQSPSSLSASVGDRVTITCQASH DISKSLNWYQQKPGKAPKLLI- YGASTLQSGVPSRFSGSGSGTDFTLTI SSLQPEDFATYYCQQLNSYPRTFGGGT KVEIKR | 538 |

TABLE 6-continued | TABLE 6-continued

| CD8 Binder | VL Sequence | SEQ ID NO: |
|---|---|---|
| 43 | DIQMTQSPSSLSASVGDRVTITCRASQ DIGAYLAWYQQKPGKAPKLLIYAAS- SLQSGVPSRFSGSGSGTDFTLTISSLQ PEDFATYYCQQSYSIPYTFGQGTKLEI KR | 539 |
| 44 | DIQMTQSPSSLSASVGDRVTITCRASQ SISSYLAWYQQKPGKAPKLLIYAAS- SLQSGVPSRFSGSGSGTDFTLTISSLQ PEDFATYYCQQSYSTPYTFGQGTKLEI KR | 540 |
| 45 | DIQMTQSPSSLSASVGDRVTITCRASQ GIRSYLAWYQQKPGKAPKLLIYGASN- LETGVPSRFSGSGSGTDFTLTISSLQP EDFATYYCQQSYSTPYTFGQGTKLEIK R | 541 |
| 46 | DIQMTQSPSSLSASVGDRVTITCRASQ SISSYLNWYQQKPGKAPKLLIYAAS- SLQSGVPSRFSGSGSGTDFTLTISSLQ PEDFATYYCQQTYSTPYTFGQGTKLEI KR | 542 |
| 47 | DIQMTQSPSSLSASVGDRVTITCRASQ NIGTWLAWYQQKPGKAPKLLI- YAASTLQSGVPSRFSGSGSGTDFTLTI SSLQPEDFATYYCQQSYSTPQTFGPGT KVDIKR | 543 |
| 48 | DIQMTQSPSSLSASVGDRVTITCRASQ TISYYLNWYQQKPGKAPKLLI- YAASTLQSGVPSRFSGSGSGTDFTLTI SSLQPEDFATYYCQQSYRTPYTFGQGT KLEIKR | 544 |
| 49 | DIVMTQSPLSLPVTPGEPASISCRSSQ SLLHSNGYNYLDWYLQKPGQSPQLLI- YMGSNRASGVPDRFSGSGSGTDFTLKI SRVEAEDVGVYYCMQGTHWPTFGQGTR LEIKR | 545 |
| 50 | DIQMTQSPSSLSASVGDRVTITCRASQ NINNYLNWYQQKPGKAPKLLI- YGASSLQSGVPSRFSGSGSGTDFTLTI SSLQPEDFATYYCQQTFSLPYTFGQGT KVEIKR | 546 |
| 51 | DIQMTQSPSSLSASVGDRVTITCRASQ TISTYLNWYQQKPGKAPKLLIYDASN- LETGVPSRFSGSGSGTDFTLTISSLQP EDFATYYCQQSYSTPYTFGQGTKLEIK R | 547 |
| 52 | DIQMTQSPSSLSASVGDRVTITCRASR GIGNDLAWYQQKPGKAPKLLI- YDASTLETGVPSRFSGSGSGTDFTLTI SSLQPEDFATYYCQQGYNIVIPLTFGG GTKVEIKR | 548 |
| 52 | DIQMTQSPSSLSASVGDRVTITCRASQ TIGNYVNWYQQKPGKAPKLLI- YGASNLHTGVPSRFSGSGSGTDFTLTI SSLQPEDFATYYCQQTYSAPLTFGGGT KVEIKR | 549 |
| 54 | DIQMTQSPSSLSASVGDRVTITCRASQ FIGSWLAWYQQKPGKAPKLLI- YAASTLQSGVPSRFSGSGSGTDFTLTI SSLQPEDFATYYCQQSYSFPWTFGQGT KVEIKR | 550 |

| CD8 Binder | VL Sequence | SEQ ID NO: |
|---|---|---|
| 55 | DIQMTQSPSSLSASVGDRVTITCRASQ SISSWMAWYQQKPGKAPKLLIYDASN- LETGVPSRFSGSGSGTDFTLTISSLQP EDFATYYCQQTYSTPYIFGQGTKVEIK R | 551 |
| 56 | DIQMTQSPSSLSASVGDRVTITCRASQ GISNNLNWYQQKPGKAPKLLIYDASN- LETGVPSRFSGSGSGTDFTLTISSLQP EDFATYYCQQSYSSPWTFGQGTKVEIK R | 552 |
| 57 | DIVMTQSPDSLAVSLGERATINCKSSQ SVLYSSNNKNYLAWYQQKPGQPPKLLI - YWASTRESGVPDRFSGSGSGTDFTLTI SSLQAEDVAVYYCQQYASAPRTFGQGT KLEIKR | 553 |
| 58 | DIQMTQSPSSLSASVGDRVTITCRASQ SISSYLNWYQQKPGKAPKLLI- YKTSSLESGVPSRFSGSGSGTDFTLTI SSLQPEDFATYYCQQSFTIPYTFGQGT KVEIKR | 554 |
| 59 | DIQMTQSPSSLSASVGDRVTITCRVSQ GISSYLNWYQQKPGKAPKLLI- YGASSLQSGVPSRFSGSGSGTDFTLTI SSLQPEDFATYYCQQSYSTPLTFGGGT KVEIKR | 555 |
| 60 | DIQMTQSPSSLSASVGDRVTITCRASQ SISDWLAWYQQKPGKAPKLLIYDASN- LETGVPSRFSGSGSGTDFTLTISSLQP EDFATYYCQQSYSTPLTFGGGTKVEIK R | 556 |
| 61 | DIQMTQSPSSLSASVGDRVTITCRASQ GISNYLAWYQQKPGKAP- KLLIYSASNLQSGVPSRFSGSGSGTDF TLTISSLQPEDFATYYCQQTYRTPPTF GPGTKVDIKR | 557 |
| 62 | DIQMTQSPSSLSASVGDRVTITCRASQ SIRNYLTWYQQKPGKAP- KLLIYSASNLQSGVPSRFSGSGSGTDF TLTISSLQPEDFATYYCQQSYSTPLTF GQGTKVEIKR | 558 |
| 63 | DIQMTQSPSSLSASVGDRVTITCRASQ NIRLYLNWYQQKPGKAPKLLI- YAASTLQSGVPSRFSGSGSGTDFTLTI SSLQPEDFATYYCQQSLTTPFTFGPGT KVDIKR | 559 |
| 64 | DIQMTQSPSSLSASVGDRVTITCQASQ DIRKFLNWYQQKPGKAPKLLIYAAS- SLQSGVPSRFSGSGSGTDFTLTISSLQ PEDFATYYCQQLNGYPGTFGQGTRLEI KR | 560 |
| 65 | DIQMTQSPSSLSASVGDRVTITCRASQ SISSYLNWYQQKPGKAPKLLIYTAS- NLQSGVPSRFSGSGSGTDFTLTISSLQ PEDFATYYCQQSYSLPLTFGGGTKVEI KR | 561 |
| 66 | DIQMTQSPSSLSASVGDRVTITCQASQ DISNYLSWYQQKPGKAPKLLI- YDASNLQSGVPSRFSGSGSGTDFTLTI SSLQPEDFATYYCQQTYTTPRTFGPGT KVDIKR | 562 |

TABLE 6-continued

| CD8 Binder | VL Sequence | SEQ ID NO: |
|---|---|---|
| | VL Sequences | |
| 67 | DIQMTQSPSSLSASVGDRVTITCRASQ NVRSWLAWYQQKPGKAPKLLIYAAS- SLQSGVPSRFSGSGSGTDFTLTISSLQ PEDFATYYCQQSYNTPYTFGQGTKLEI KR | 563 |
| 68 | DIQMTQSPSSLSASVGDRVTITCRASQ GIGNDLGWYQQKPGKAPKLLIYAAS- SLQSGVPSRFSGSGSGTDFTLTISSLQ PEDFATYYCQQSYAPPPTFGQGTKVEI KR | 564 |
| 69 | DIQMTQSPSSLSASVGDRVTITCRASQ SISNWLAWYQQKPGKAPKLLIYGASN- LETGVPSRFSGSGSGTDFTLTISSLQP EDFATYYCQQSYSTPPPTFGQGTKLEIK R | 565 |
| 70 | DIVMTQSPLSLPVTPGEPASISCRSSQ SLLHSNGYNYLDWYLQKPGQSPQLLIY L- GSNRASGVPDRFSGSGSGTDFTLKISR VEAEDVGVYYCMQGLQTPLTFGQGTKV EIKR | 566 |
| 71 | DIQMTQSPSSLSASVGDRVTITCRASQ SISSYLNWYQQKPGKAPKLLI- YLASSLQSGVPSRFSGSGSGTDFTLTI SSLQPEDFATYYCQQSDSIPVTFGQGT KVEIKR | 567 |
| 72 | DIQMTQSPSSLSASVGDRVTITCQASQ DISNYLNWYQQKPGKAP- KLLIYSTSSLQSGVPSRFSGSGSGTDF TLTISSLQPEDFATYYCQQSYSTPYNF GQGTKLEIKR | 568 |
| 73 | DIQMTQSPSSLSASVGDRVTITCRASE SIGSWLAWYQQKPGKAPKLLIYAAS- SLQSGVPSRFSGSGSGTDFTLTISSLQ PEDFATYYCQQSYSTPYTFGQGTKLEI KR | 569 |
| 74 | DIQMTQSPSSLSASVGDRVTITCRASQ SISNYLNWYQQKPGKAPKLLIYAAS- SLQRGVPSRFSGSGSGTDFTLTISSLQ PEDFATYYCQQSYSTPLTFGQGTKVEI KR | 570 |
| 75 | EIVMTQSPATLSVSPGERATLSCRASQ SVTSNYLAWYQQKPGQAPRLLIYGAST RAT- GIPARFSGSGSGTEFTLTISSLQSEDF AVYYCQHYGSSPAFGQGTRLEIKR | 571 |
| 76 | DIQMTQSPSSLSASVGDRVTITCRASQ SISSYLNWYQQKPGKAPKLLIYAAS- SLQSGVPSRFSGSGSGTDFTLTISSLQ PEDFATYYCQQSYSTPLTFGGGTKVEI KR | 499 |
| 77 | DIQMTQSPSSLSASVGDRVTITCRASQ GISSYLAWYQQKPGKAPKLLI- YAASTLQSGVPSRFSGSGSGTDFTLTI SSLQPEDFATYYCQQSYSTPPTFGPGT KVDIKR | 572 |
| 78 | DIQMTQSPSSLSASVGDRVTITCRASQ DIGNYLNWYQQKPGKAPKLLIYAAS- SLQSGVPSRFSGSGSGTDFTLTISSLQ PEDFATYYCQQAYTYPYTFGQGTKLEI KR | 573 |

TABLE 6-continued

| CD8 Binder | VL Sequence | SEQ ID NO: |
|---|---|---|
| | VL Sequences | |
| 79 | DIQMTQSPSSLSASVGDRVTITCQASQ DISNYLNWYQQKPGKAPKLLI- YGASSLQSGVPSRFSGSGSGTDFTLTI SSLQPEDFATYYCQQSYTTPNTFGPGT KVDIKR | 574 |
| 80 | DIQMTQSPSSLSASVGDRVTITCRASQ GISNYLAWYQQKPGKAPKLLI- YAASTLQSGVPSRFSGSGSGTDFTLTI SSLQPEDFATYYCQQSYSTPYTFGQGT KVEIKR | 575 |
| 81 | DIQMTQSPSSLSASVGDRVTITCRASQ GISNGLSWYQQKPGKAPKLLIYDASN- LETGVPSRFSGSGSGTDFTLTISSLQP EDFATYYCQQSYSTPFTFGPGTKVDIK R | 576 |
| 82 | DIQMTQSPSSLSASVGDRVTITCRASQ NIRNYLNWYQQKPGKAPKLLI- YGASSLQSGVPSRFSGSGSGTDFTLTI SSLQPEDFATYYCQQSYSTPLTFGGGT KVEIKR | 577 |
| 83 | DIQMTQSPSSLSASVGDRVTITCQASL DINNYLNWYQQKPGKAPKLLI- YKASSLESGVPSRFSGSGSGTDFTLTI SSLQPEDFATYYCQQSYSMPLTFGPGT KVDIKR | 578 |
| 84 | DIQMTQSPSSLSASVGDRVTITCQASQ DISNYLNWYQQKPGKAPKLLIYAAS- SLQGGVPSRFSGSGSGTDFTLTISSLQ PEDFATYYCQQSYTTPWTFGQGTKLEI KR | 579 |
| 85 | DIQMTQSPSSLSASVGDRVTITCQASQ DISNYLNWYQQKPGKAPKLLIYAAS- SLQSGVPSRFSGSGSGTDFTLTISSLQ PEDFATYYCQQSYSSPLTFGGGTKVEI KR | 580 |
| 86 | DIQMTQSPSSLSASVGDRVTITCQASQ DISNYLNWYQQKPGKAPKLLI- YKASSLESGVPSRFSGSGSGTDFTLTI SSLQPEDFATYYCQQSYSDPLTFGQGT KVEIKR | 581 |
| 87 | DIQMTQSPSSLSASVGDRVTITCQASQ DISNYLNWYQQKPGKAPKLLI- YGASTLQSGVPSRFSGSGSGTDFTLTI SSLQPEDFATYYCQQSYSAPITFGQGT RLEIKR | 582 |
| 88 | DIQMTQSPSSLSASVGDRVTITCRASQ SISNYLNWYQQKPGKAPKLLI- YAASNLQSGVPSRFSGSGSGTDFTLTI SSLQPEDFATYYCQQSYTTPLTFGPGT KVDIKR | 583 |
| 89 | DIQMTQSPSSLSASVGDRVTITCRASQ NIGNYLNWYQQKPGKAPKLLI- YAASTLQSGVPSRFSGSGSGTDFTLTI SSLQPEDFATYYCQQSYSTPPWTFGQG TKVEIKR | 584 |
| 90 | DIQMTQSPSSLSASVGDRVTITCQASQ DISNYLNWYQQKPGKAPKLLI- YAASTLRSGVPSRFSGSGSGTDFTLTI SSLQPEDFATYYCQQSYQTPLTFGGGT KVEIKR | 585 |

TABLE 6-continued

| VL Sequences | | |
|---|---|---|
| CD8 Binder | VL Sequence | SEQ ID NO: |
| 91 | DIQMTQSPSSLSASVGDRVTITCQASQ DISNYLNWYQQKPGKAPKLLI- YAASTLQSGVPSRFSGSGSGTDFTLTI SSLQPEDFATYYCQQSYTTPPTFGQGT KVEIKR | 586 |
| 92 | DIQMTQSPSSLSASVGDRVTITCQASQ DISNYLNWYQQKPGKAPKLLIYAAS- SLHSGVPSRFSGSGSGTDFTLTISSLQ PEDFATYYCQQSYSTPQTFGQGTKVEI KR | 587 |
| 93 | DIQMTQSPSSLSASVGDRVTITCRASQ GIRNDLNWYQQKPGKAPKLLI- YAASNLQSGVPSRFSGSGSGTDFTLTI SSLQPEDFATYYCQQANSFPITFGQGT KLEIKR | 588 |

TABLE 6-continued

| VL Sequences | | |
|---|---|---|
| CD8 Binder | VL Sequence | SEQ ID NO: |
| 94 | DIQMTQSPSSLSASVGDRVTITCRASQ GINTWLAWYQQKPGKAPKLLIYAAS- SLQSGVPSRFSGSGSGTDFTLTISSLQ PEDFATYYCQQSYSTPYTFGQGTRLEI KR | 589 |
| 95 | DIQMTQSPSSLSASVGDRVTITCQASQ DISNYLNWYQQKPGKAPKLLI- YAASTLQSGVPSRFSGSGSGTDFTLTI SSLQPEDFATYYCQQSYTVPPTFGQGT KVEIKR | 590 |
| 96 | DIQMTQSPSSLSASVGDRVTITCQASQ DIRYFLNWYQQKPGKAPKLLI- YAASTLQSGVPSRFSGSGSGTDFTLTI SSLQPEDFATYYCQQDDSFPLTFGGGT KVEIKR | 591 |

TABLE 7

| SEQ ID NO: | SEQUENCE | ANNOTATION |
|---|---|---|
| 592 | MVVILDKRCY CNLLILILMI SECSVGILHY EKLSKIGLVK GVTRKYKIKS NPLTKDIVIK MIPNVSNMSQ CTGSVMENYK TRLNGILTPI KGALEIYKNN THDLVGDVRL AGVIMAGVAI GIATAAQITA GVALYEAMKN ADNINKLKSS IESTNEAVVK LQETAEKTVY VLTALQDYIN TNLVPTIDKI SCKQTELSLD LALSKYLSDL LFVFGPNLQD PVSNSMTIQA ISQAFGGNYE TLLRTLGYAT EDFDDLLESD SITGQIIYVD LSSYYIIVRV YFPILTEIQQ AYIQELLPVS FNNDNSEWIS IVPNFILVRN TLISNIEIGF CLITKRSVIC NQDYATPMTN NMRECLTGST EKCPRELVVS SHVPRFALSN GVLFANCISV TCQCQTTGRA ISQSGEQTLL MIDNTTCPTA VLGNVIISLG KYLGSVNYNS EGIAIGPPVF TDKVDISSQI SSMNQSLQQS KDYIKEAQRL LDTVNPSLIS MLSMIILYVL SIASLCIGLI TFISFIIVEK KRNTYSRLED RRVRPTSSGD LYYIGT | Nipah virus NiV-F with signal sequence (aa 1-546) Uniprot Q9IH63 |
| 593 | ILHY EKLSKIGLVK GVTRKYKIKS NPLTKDIVIK MIP-NVSNMSQ CTGSVMENYK TRLNGILTPI KGALEIYKNN THDLVGDVRL AGVIMAGVAI GIATAAQITA GVALYEAMKN ADNINKLKSS IESTNEAVVK LQETAEKTVY VLTALQDYIN TNLVPTIDKI SCKQTELSLD LALSKYLSDL LFVFGPNLQD PVSNSMTIQA ISQAFGGNYE TLLRTLGYAT EDFDDLLESD SITGQIIYVD LSSYYIIVRV YFPILTEIQQ AYIQELLPVS FNNDNSEWIS IVPNFILVRN TLISNIEIGF CLITKRSVIC NQDYATPMTN NMRECLTGST EKCPRELVVS SHVPRFALSN GVLFANCISV TCQCQTTGRA ISQSGEQTLL MIDNTTCPTA VLGNVIISLG KYLGSVNYNS EGIAIGPPVF TDKVDISSQI SSMNQSLQQS KDYIKEAQRL LDTVNPSLIS MLSMIILYVL SIASLCIGLI TFISFIIVEK KRNTYSRLED RRVRPTSSGD LYYIGT | Nipah virus NiV-F F0 (aa 27-546) |
| 594 | ILHYEKLSKIGLVKGVTRKYKIKSNPLTKDIVIKMIP-NVSNMSQCTGSVMENYKTRLNGILT-PIKGALEIYKNNTHDLVGDVR | Nipah virus NiV-F F2 (aa 27-109) |
| 595 | LAGVIMAGVAIGIATAAQITAGVALYEAMKNADNINKLKSSI-ESTNEAV-VKLQETAEKTVYVLTALQDYINTNLVPTIDKISCKQTELSLDLA LSKYLSDLLFVFGPNLQDPVSNSMTIQAISQAFGG-NYETLLRTLGYATEDFDDLLESDSITGQIIYVDLSSYYIIVRVY FPILTEIQQAYIQELLPVSFNNDNSEWISIVPN-FILVRNTLISNIEIGFCLITKRSVIC-NQDYATPMTNNMRECLTGSTEKCPRELVVSSHVPRFALSNGVLF ANCISVTCQCQTTGRAISQSGEQTLLMID-NTTCPTAVLGNVIISLGKYLGSVNYNSEGIAIG-PPVFTDKVDISSQISSMNQSLQQSKDYIKEAQRLLDTVNPSLIS MLSMIILYVLSIASLCIGLITFISFII-VEKKRNTYSRLEDRRVRPTSSGDLYYIGT | Nipah virus NiV F F1 (aa 110-546) |

TABLE 7-continued

| SEQ ID NO: | SEQUENCE | ANNOTATION |
|---|---|---|
| 596 | ILHY EKLSKIGLVK GVTRKYKIKS NPLTKDIVIK MIP-<br>NVSNMSQ CTGSVMENYK TRLNGILTPI KGALEIYKNN<br>THDLVGDVRL AGVIMAGVAI GIATAAQITA GVALYEAMKN<br>ADNINKLKSS IESTNEAVVK LQETAEKTVY VLTALQDYIN<br>TNLVPTIDKI SCKQTELSLD LALSKYLSDL LFVFGPNLQD<br>PVSNSMTIQA ISQAFGGNYE TLLRTLGYAT EDFDDLLESD<br>SITGQIIYVD LSSYYIIVRV YFPILTEIQQ AYIQELLPVS<br>FNNDNSEWIS IVPNFILVRN TLISNIEIGF CLITKRSVIC<br>NQDYATPMTN NMRECLTGST EKCPRELVVS SHVPRFALSN<br>GVLFANCISV TCQCQTTGRA ISQSGEQTLL MIDNTTCPTA<br>VLGNVIISLG KYLGSVNYNS EGIAIGPPVF TDKVDISSQI<br>SSMNQSLQQS KDYIKEAQRL LDTVNPSLIS MLSMIILYVL<br>SIASLCIGLI TFISFIIVEK KRNTGT | Nipah virus NiV-F F0<br>truncation (aa 525-544) |
| 597 | LAGVIMAGVAIGIATAAQITAGVALYEAMKNADNINKLKSSI-<br>ESTNEAV-<br>VKLQETAEKTVYVLTALQDYINTNLVPTIDKISCKQTELSLDLA<br>LSKYLSDLLFVFGPNLQDPVSNSMTIQAISQAFGG-<br>NYETLLRTLGYATEDFDDLLESDSITGQIIYVDLSSYYIIVRVY<br>FPILTEIQQAYIQELLPVSFNNDNSEWISIVPN-<br>FILVRNTLISNIEIGFCLITKRSVIC-<br>NQDYATPMTNNMRECLTGSTEKCPRELVVSSHVPRFALSNGVLF<br>ANCISVTCQCQTTGRAISQSGEQTLLMID-<br>NTTCPTAVLGNVIISLGKYLGSVNYNSEGIAIG-<br>PPVFTDKVDISSQISSMNQSLQQSKDYIKEAQRLLDTVNPSLIS<br>MLSMIILYVLSIASLCIGLITFISFIIVEKKRNTGT | Nipah virus NiV F F1 (aa<br>110-546) truncation (aa<br>525-544) |
| 598 | ILHY EKLSKIGLVK GVTRKYKIKS NPLTKDIVIK MIP-<br>NVSNMSQ CTGSVMENYK TRLNGILTPI KGALEIYKNQ<br>THDLVGDVRL AGVIMAGVAI GIATAAQITA GVALYEAMKN<br>ADNINKLKSS IESTNEAVVK LQETAEKTVY VLTALQDYIN<br>TNLVPTIDKI SCKQTELSLD LALSKYLSDL LFVFGPNLQD<br>PVSNSMTIQA ISQAFGGNYE TLLRTLGYAT EDFDDLLESD<br>SITGQIIYVD LSSYYIIVRV YFPILTEIQQ AYIQELLPVS<br>FNNDNSEWIS IVPNFILVRN TLISNIEIGF CLITKRSVIC<br>NQDYATPMTN NMRECLTGST EKCPRELVVS SHVPRFALSN<br>GVLFANCISV TCQCQTTGRA ISQSGEQTLL MIDNTTCPTA<br>VLGNVIISLG KYLGSVNYNS EGIAIGPPVF TDKVDISSQI<br>SSMNQSLQQS KDYIKEAQRL LDTVNPSLIS MLSMIILYVL<br>SIASLCIGLI TFISFIIVEK KRNTGT | Nipah virus NiV-F F0<br>truncation (aa 525-544)<br>AND mutation on N-<br>linked glycosylation site |
| 599 | MVVILDKRCY CNLLILILMI SECSVGILHY EKLSKIGLVK<br>GVTRKYKIKS NPLTKDIVIK MIPNVSNMSQ CTGSVMENYK<br>TRLNGILTPI KGALEIYKNN THDLVGDVRL AGVIMAGVAI<br>GIATAAQITA GVALYEAMKN ADNINKLKSS IESTNEAVVK<br>LQETAEKTVY VLTALQDYIN TNLVPTIDKI SCKQTELSLD<br>LALSKYLSDL LFVFGPNLQD PVSNSMTIQA ISQAFGGNYE<br>TLLRTLGYAT EDFDDLLESD SITGQIIYVD LSSYYIIVRV<br>YFPILTEIQQ AYIQELLPVS FNNDNSEWIS IVPNFILVRN<br>TLISNIEIGF CLITKRSVIC NQDYATPMTN NMRECLTGST<br>EKCPRELVVS SHVPRFALSN GVLFANCISV TCQCQTTGRA<br>ISQSGEQTLL MIDNTTCPTA VLGNVIISLG KYLGSVNYNS<br>EGIAIGPPVF TDKVDISSQI SSMNQSLQQS KDYIKEAQRL<br>LDTVNPSLIS MLSMIILYVL SIASLCIGLI TFISFIIVEK<br>KRNT | Truncated NiV fusion<br>glycoprotein<br>(FcDelta22) at<br>cytoplasmic tail<br>(with signal sequence) |
| 1092 | ILHY EKLSKIGLVK GVTRKYKIKS NPLTKDIVIK<br>MIPNVSNMSQ CTGSVMENYK TRLNGILTPI KGALEIYKNN<br>THDLVGDVRL AGVIMAGVAI GIATAAQITA GVALYEAMKN<br>ADNINKLKSS IESTNEAVVK LQETAEKTVY VLTALQDYIN<br>TNLVPTIDKI SCKQTELSLD LALSKYLSDL LFVFGPNLQD<br>PVSNSMTIQA ISQAFGGNYE TLLRTLGYAT EDFDDLLESD<br>SITGQIIYVD LSSYYIIVRV YFPILTEIQQ AYIQELLPVS<br>FNNDNSEWIS IVPNFILVRN TLISNIEIGF CLITKRSVIC<br>NQDYATPMTN NMRECLTGST EKCPRELVVS SHVPRFALSN<br>GVLFANCISV TCQCQTTGRA ISQSGEQTLL MIDNTTCPTA<br>VLGNVIISLG KYLGSVNYNS EGIAIGPPVF TDKVDISSQI<br>SSMNQSLQQS KDYIKEAQRL LDTVNPSLIS MLSMIILYVL<br>SIASLCIGLI TFISFIIVEK KRNT | Truncated NiV fusion<br>glycoprotein<br>(FcDelta22) F0 |
| 1093 | LAGVIMAGVAI GIATAAQITA GVALYEAMKN ADNINKLKSS<br>IESTNEAVVK LQETAEKTVY VLTALQDYIN TNLVPTIDKI<br>SCKQTELSLD LALSKYLSDL LFVFGPNLQD PVSNSMTIQA<br>ISQAFGGNYE TLLRTLGYAT EDFDDLLESD SITGQIIYVD<br>LSSYYIIVRV YFPILTEIQQ AYIQELLPVS FNNDNSEWIS | Truncated NiV fusion<br>glycoprotein<br>(FcDelta22) F1 |

TABLE 7-continued

| SEQ ID NO: | SEQUENCE | ANNOTATION |
|---|---|---|

```
     IVPNFILVRN  TLISNIEIGF  CLITKRSVIC  NQDYATPMTN
     NMRECLTGST  EKCPRELVVS  SHVPRFALSN  GVLFANCISV
     TCQCQTTGRA  ISQSGEQTLL  MIDNTTCPTA  VLGNVIISLG
     KYLGSVNYNS  EGIAIGPPVF  TDKVDISSQI  SSMNQSLQQS
     KDYIKEAQRL  LDTVNPSLIS  MLSMIILYVL  SIASLCIGLI
     TFISFIIVEK  KRNT

600  MGPAENKKVR  FENTTSDKGK  IPSKVIKSYY  GTMDIKKINE    NiVG protein attach-
     GLLDSKILSA  FNTVIALLGS  IVIIVMNIMI  IQNYTRSTDN    ment glycoprotein (602
     QAVIKDALQG  IQQQIKGLAD  KIGTEIGPKV  SLIDTSSTIT    aa)
     IPANIGLLGS  KISQSTASIN  ENVNEKCKFT  LPPLKIHECN
     ISCPNPLPFR  EYRPQTEGVS  NLVGLPNNIC  LQKTSNQILK
     PKLISYTLPV  VGQSGTCITD  PLLAMDEGYF  AYSHLERIGS
     CSRGVSKQRI  IGVGEVLDRG  DEVPSLFMTN  VWTPPNPNTV
     YHCSAVYNNE  FYYVLCAVST  VGDPILNSTY  WSGSLMMTRL
     AVKPKSNGGG  YNQHQLALRS  IEKGRYDKVM  PYGPSGIKQG
     DTLYFPAVGF  LVRTEFKYND  SNCPITKCQY  SKPENCRLSM
     GIRPNSHYIL  RSGLLKYNLS  DGENPKVVFI  EISDQRLSIG
     SPSKIYDSLG  QPVFYQASFS  WDTMIKFGDV  LTVNPLVVNW
     RNNTVISRPG  QSQCPRFNTC  PEICWEGVYN  DAFLIDRINW
     ISAGVFLDSN  QTAENPVFTV  FKDNEILYRA  QLASEDTNAQ
     KTITNCFLLK  NKIWCISLVE  IYDTGDNVIR  PKLFAVKIPE
     QC 601  MGKVR  FENTTSDKGK  IPSKVIKSYY  GTMDIKKINE         NiVG protein attach-
     GLLDSKILSA  FNTVIALLGS  IVIIVMNIMI  IQNYTRSTDN    ment glycoprotein
     QAVIKDALQG  IQQQIKGLAD  KIGTEIGPKV  SLIDTSSTIT    Truncated Δ5
     IPANIGLLGS  KISQSTASIN  ENVNEKCKFT  LPPLKIHECN
     ISCPNPLPFR  EYRPQTEGVS  NLVGLPNNIC  LQKTSNQILK
     PKLISYTLPV  VGQSGTCITD  PLLAMDEGYF  AYSHLERIGS
     CSRGVSKQRI  IGVGEVLDRG  DEVPSLFMTN  VWTPPNPNTV
     YHCSAVYNNE  FYYVLCAVST  VGDPILNSTY  WSGSLMMTRL
     AVKPKSNGGG  YNQHQLALRS  IEKGRYDKVM  PYGPSGIKQG
     DTLYFPAVGF  LVRTEFKYND  SNCPITKCQY  SKPENCRLSM
     GIRPNSHYIL  RSGLLKYNLS  DGENPKVVFI  EISDQRLSIG
     SPSKIYDSLG  QPVFYQASFS  WDTMIKFGDV  LTVNPLVVNW
     RNNTVISRPG  QSQCPRFNTC  PEICWEGVYN  DAFLIDRINW
     ISAGVFLDSN  QTAENPVFTV  FKDNEILYRA  QLASEDTNAQ
     KTITNCFLLK  NKIWCISLVE  IYDTGDNVIR  PKLFAVKIPE
     QC 602  MGNTTSDKGK  IPSKVIKSYY  GTMDIKKINE  GLLDSKILSA    NiVG protein attach-
     FNTVIALLGS  IVIIVMNIMI  IQNYTRSTDN  QAVIKDALQG    ment glycoprotein
     IQQQIKGLAD  KIGTEIGPKV  SLIDTSSTIT  IPANIGLLGS    Truncated Δ10
     KISQSTASIN  ENVNEKCKFT  LPPLKIHECN  ISCPNPLPFR
     EYRPQTEGVS  NLVGLPNNIC  LQKTSNQILK  PKLISYTLPV
     VGQSGTCITD  PLLAMDEGYF  AYSHLERIGS  CSRGVSKQRI
     IGVGEVLDRG  DEVPSLFMTN  VWTPPNPNTV  YHCSAVYNNE
     FYYVLCAVST  VGDPILNSTY  WSGSLMMTRL  AVKPKSNGGG
     YNQHQLALRS  IEKGRYDKVM  PYGPSGIKQG  DTLYFPAVGF
     LVRTEFKYND  SNCPITKCQY  SKPENCRLSM  GIRPNSHYIL
     RSGLLKYNLS  DGENPKVVFI  EISDQRLSIG  SPSKIYDSLG
     QPVFYQASFS  WDTMIKFGDV  LTVNPLVVNW  RNNTVISRPG
     QSQCPRFNTC  PEICWEGVYN  DAFLIDRINW  ISAGVFLDSN
     QTAENPVFTV  FKDNEILYRA  QLASEDTNAQ  KTITNCFLLK
     NKIWCISLVE  IYDTGDNVIR  PKLFAVKIPE  QC 603  MGKGK  IPSKVIKSYY  GTMDIKKINE  GLLDSKILSA          NiVG protein attach-
     FNTVIALLGS  IVIIVMNIMI  IQNYTRSTDN  QAVIKDALQG    ment glycoprotein
     IQQQIKGLAD  KIGTEIGPKV  SLIDTSSTIT  IPANIGLLGS    Truncated Δ15
     KISQSTASIN  ENVNEKCKFT  LPPLKIHECN  ISCPNPLPFR
     EYRPQTEGVS  NLVGLPNNIC  LQKTSNQILK  PKLISYTLPV
     VGQSGTCITD  PLLAMDEGYF  AYSHLERIGS  CSRGVSKQRI
     IGVGEVLDRG  DEVPSLFMTN  VWTPPNPNTV  YHCSAVYNNE
     FYYVLCAVST  VGDPILNSTY  WSGSLMMTRL  AVKPKSNGGG
     YNQHQLALRS  IEKGRYDKVM  PYGPSGIKQG  DTLYFPAVGF
     LVRTEFKYND  SNCPITKCQY  SKPENCRLSM  GIRPNSHYIL
     RSGLLKYNLS  DGENPKVVFI  EISDQRLSIG  SPSKIYDSLG
     QPVFYQASFS  WDTMIKFGDV  LTVNPLVVNW  RNNTVISRPG
     QSQCPRFNTC  PEICWEGVYN  DAFLIDRINW  ISAGVFLDSN
     QTAENPVFTV  FKDNEILYRA  QLASEDTNAQ  KTITNCFLLK
     NKIWCISLVE  IYDTGDNVIR  PKLFAVKIPE  QC 604  MGSKVIKSYY  GTMDIKKINE  GLLDSKILSA  FNTVIALLGS    NiVG protein attach-
     IVIIVMNIMI  IQNYTRSTDN  QAVIKDALQG  IQQQIKGLAD    ment glycoprotein
     KIGTEIGPKV  SLIDTSSTIT  IPANIGLLGS  KISQSTASIN    Truncated Δ20
```

TABLE 7-continued

| SEQ ID NO: | SEQUENCE | ANNOTATION |
|---|---|---|
| | ENVNEKCKFT LPPLKIHECN ISCPNPLPFR EYRPQTEGVS<br>NLVGLPNNIC LQKTSNQILK PKLISYTLPV VGQSGTCITD<br>PLLAMDEGYF AYSHLERIGS CSRGVSKQRI IGVGEVLDRG<br>DEVPSLFMTN VWTPPNPNTV YHCSAVYNNE FYYVLCAVST<br>VGDPILNSTY WSGSLMMTRL AVKPKSNGGG YNQHQLALRS<br>IEKGRYDKVM PYGPSGIKQG DTLYFPAVGF LVRTEFKYND<br>SNCPITKCQY SKPENCRLSM GIRPNSHYIL RSGLLKYNLS<br>DGENPKVVFI EISDQRLSIG SPSKIYDSLG QPVFYQASFS<br>WDTMIKFGDV LTVNPLVVNW RNNTVISRPG QSQCPRFNTC<br>PEICWEGVYN DAFLIDRINW ISAGVFLDSN QTAENPVFTV<br>FKDNEILYRA QLASEDTNAQ KTITNCFLLK NKIWCISLVE<br>IYDTGDNVIR PKLFAVKIPE QC | |
| 605 | MGSYY GTMDIKKINE GLLDSKILSA FNTVIALLGS<br>IVIIVMNIMI IQNYTRSTDN QAVIKDALQG IQQQIKGLAD<br>KIGTEIGPKV SLIDTSSTIT IPANIGLLGS KISQSTASIN<br>ENVNEKCKFT LPPLKIHECN ISCPNPLPFR EYRPQTEGVS<br>NLVGLPNNIC LQKTSNQILK PKLISYTLPV VGQSGTCITD<br>PLLAMDEGYF AYSHLERIGS CSRGVSKQRI IGVGEVLDRG<br>DEVPSLFMTN VWTPPNPNTV YHCSAVYNNE FYYVLCAVST<br>VGDPILNSTY WSGSLMMTRL AVKPKSNGGG YNQHQLALRS<br>IEKGRYDKVM PYGPSGIKQG DTLYFPAVGF LVRTEFKYND<br>SNCPITKCQY SKPENCRLSM GIRPNSHYIL RSGLLKYNLS<br>DGENPKVVFI EISDQRLSIG SPSKIYDSLG QPVFYQASFS<br>WDTMIKFGDV LTVNPLVVNW RNNTVISRPG QSQCPRFNTC<br>PEICWEGVYN DAFLIDRINW ISAGVFLDSN QTAENPVFTV<br>FKDNEILYRA QLASEDTNAQ KTITNCFLLK NKIWCISLVE<br>IYDTGDNVIR PKLFAVKIPE QC | NiVG protein attach-<br>ment glycoprotein<br>Truncated Δ25 |
| 606 | MGTMDIKKINE GLLDSKILSA FNTVIALLGS IVIIVMNIMI<br>IQNYTRSTDN QAVIKDALQG IQQQIKGLAD KIGTEIGPKV<br>SLIDTSSTIT IPANIGLLGS KISQSTASIN ENVNEKCKFT<br>LPPLKIHECN ISCPNPLPFR EYRPQTEGVS NLVGLPNNIC<br>LQKTSNQILK PKLISYTLPV VGQSGTCITD PLLAMDEGYF<br>AYSHLERIGS CSRGVSKQRI IGVGEVLDRG DEVPSLFMTN<br>VWTPPNPNTV YHCSAVYNNE FYYVLCAVST VGDPILNSTY<br>WSGSLMMTRL AVKPKSNGGG YNQHQLALRS IEKGRYDKVM<br>PYGPSGIKQG DTLYFPAVGF LVRTEFKYND SNCPITKCQY<br>SKPENCRLSM GIRPNSHYIL RSGLLKYNLS DGENPKVVFI<br>EISDQRLSIG SPSKIYDSLG QPVFYQASFS WDTMIKFGDV<br>LTVNPLVVNW RNNTVISRPG QSQCPRFNTC PEICWEGVYN<br>DAFLIDRINW ISAGVFLDSN QTAENPVFTV FKDNEILYRA<br>QLASEDTNAQ KTITNCFLLK NKIWCISLVE IYDTGDNVIR<br>PKLFAVKIPE QC | NiVG protein attach-<br>ment glycoprotein<br>Truncated Δ30 |
| 607 | MKKINEGLLDSKILSA FNTVIALLGS IVIIVMNIMI IQNY-<br>TRSTDN QAVIKDALQG IQQQIKGLAD KIGTEIGPKV<br>SLIDTSSTIT IPANIGLLGS KISQSTASIN ENVNEKCKFT<br>LPPLKIHECN ISCPNPLPFR EYRPQTEGVS NLVGLPNNIC<br>LQKTSNQILK PKLISYTLPV VGQSGTCITD PLLAMDEGYF<br>AYSHLERIGS CSRGVSKQRI IGVGEVLDRG DEVPSLFMTN<br>VWTPPNPNTV YHCSAVYNNE FYYVLCAVST VGDPILNSTY<br>WSGSLMMTRL AVKPKSNGGG YNQHQLALRS IEKGRYDKVM<br>PYGPSGIKQG DTLYFPAVGF LVRTEFKYND SNCPITKCQY<br>SKPENCRLSM GIRPNSHYIL RSGLLKYNLS DGENPKVVFI<br>EISDQRLSIG SPSKIYDSLG QPVFYQASFS WDTMIKFGDV<br>LTVNPLVVNW RNNTVISRPG QSQCPRFNTC PAICAEGVYN<br>DAFLIDRINW ISAGVFLDSN ATAANPVFTV FKDNEILYRA<br>QLASEDTNAQ KTITNCFLLK NKIWCISLVE IYDTGDNVIR<br>PKLFAVKIPE QCT | NiVG protein attach-<br>ment glycoprotein<br>Truncated and mutated<br>(E501A, W504A, Q530A,<br>E533A) NiV G protein<br>(Gc Δ 34) |
| 608 | MATQEVRLKC LLCGIIVLVL SLEGLGILHY EKLSKIGLVK<br>GITRKYKIKS<br>NPLTKDIVIK MIPNVSNVSK CTGTVMENYK SRLTGILSPI<br>KGAIELYNNN<br>THDLVGDVKL AGVVMAGIAI GIATAAQITA GVALYEAMKN<br>ADNINKLKSS<br>IESTNEAVVK LQETAEKTVY VLTALQDYIN TNLVPTIDQI<br>SCKQTELALD<br>LALSKYLSDL LFVFGPNLQD PVSNSMTIQA ISQAFGGNYE<br>TLLRTLGYAT EDFDDLLESD SIAGQIVYVD LSSYYIIVRV<br>YFPILTEIQQ AYVQELLPVS<br>FNNDNSEWIS IVPNFVLIRN TLISNIEVKY CLITKKSVIC<br>NQDYATPMTA | Hendra virus F protein<br>Uniprot O89342 (with<br>signal sequence) |

TABLE 7-continued

| SEQ ID NO: | SEQUENCE | ANNOTATION |
|---|---|---|
| | SVRECLTGST DKCPRELVVS SHVPRFALSG GVLFANCISV TCQCQTTGRA ISQSGEQTLL MIDNTTCTTV VLGNIIISLG KYLGSINYNS ESIAVGPPVY TDKVDISSQI SSMNQSLQQS KDYIKEAQKI LDTVNPSLIS MLSMIILYVL SIAALCIGLI TFISFVIVEK KRGNYSRLDD RQVRPVSNGD LYYIGT | |
| 609 | MMADSKLVSL NNNLSGKIKD QGKVIKNYYG TMDIKKINDG LLDSKILGAF NTVIALLGSI IIIVMNIMII QNYTRTTDNQ ALIKESLQSV QQQIKALTDK IGTEIGPKVS LIDTSSTITI PANIGLLGSK ISQSTSSINE NVNDKCKFTL PPLKIHECNI SCPNPLPFRE YRPISQGVSD LVGLPNQICL QKTTSTILKP RLISYTLPIN TREGVCITDP LLAVDNGFFA YSHLEKIGSC TRGIAKQRII GVGEVLDRGD KVPSMFMTNV WTPPNPSTIH HCSSTYHEDF YYTLCAVSHV GDPILNSTSW TESLSLIRLA VRPKSDSGDY NQKYIAITKV ERGKYDKVMP YGPSGIKQGD TLYFPAVGFL PRTEFQYNDS NCPIIHCKYS KAENCRLSMG VNSKSHYILR SGLLKYNLSL GGDIILQFIE IADNRLTIGS PSKIYNSLGQ PVFYQASYSW DTMIKLGDVD TVDPLRVQWR NNSVISRPGQ SQCPRFNVCP EVCWEGTYND AFLIDRLNWV SAGVYLNSNQ TAENPVFAVF KDNEILYQVP LAEDDTNAQK TITDCFLLEN VIWCISLVEI YDTGDSVIRP KLFAVKIPAQ CSES | Hendra virus G protein Uniprot O89343 |
| 610 | MVVILDKRCY CNLLILILMI SECSVGILHY EKLSKIGLVK GVTRKYKIKS NPLTKDIVIK MIPNVSNMSQ CTGSVMENYK TRLNGILTPI KGALEIYKNN THDLVGDVRL AGVIMAGVAI GIATAAQITA GVALYEAMKN ADNINKLKSS IESTNEAVVK LQETAEKTVY VLTALQDYIN TNLVPTIDKI SCKQTELSLD LALSKYLSDL LFVFGPNLQD PVSNSMTIQA ISQAFGGNYE TLLRTLGYAT EDFDDLLESD SITGQIIYVD LSSYYIIVRV YFPPILTEIQQ AYIQELLPVS FNNDNSEWIS IVPNFILVRN TLISNIEIGF CLITKRSVIC NQDYATPMTN NMRECLTGST EKCPRELVVS SHVPRFALSN GVLFANCISV TCQCQTTGRA ISQSGEQTLL MIDNTTCPTA VLGNVIISLG KYLGSVNYNS EGIAIGPPVF TDKVDISSQI SSMNQSLQQS KDYIKEAQRL LDTVNPSLIS MLSMIILYVL SIASLCIGLI TFISFIIVEK KRNTGT | Nipah virus NiV-F F0 truncation (aa 525-544) (with signal sequence) |
| 611 | MVVILDKRCY CNLLILILMI SECSVGILHY EKLSKIGLVK GVTRKYKIKS NPLTKDIVIK MIPNVSNMSQ CTGSVMENYK TRLNGILTPI KGALEIYKNQ THDLVGDVRL AGVIMAGVAI GIATAAQITA GVALYEAMKN ADNINKLKSS IESTNEAVVK LQETAEKTVY VLTALQDYIN TNLVPTIDKI SCKQTELSLD LALSKYLSDL LFVFGPNLQD PVSNSMTIQA ISQAFGGNYE TLLRTLGYAT EDFDDLLESD SITGQIIYVD LSSYYIIVRV YFPPILTEIQQ AYIQELLPVS FNNDNSEWIS IVPNFILVRN TLISNIEIGF CLITKRSVIC NQDYATPMTN NMRECLTGST EKCPRELVVS SHVPRFALSN GVLFANCISV TCQCQTTGRA ISQSGEQTLL MIDNTTCPTA VLGNVIISLG KYLGSVNYNS EGIAIGPPVF TDKVDISSQI SSMNQSLQQS KDYIKEAQRL LDTVNPSLIS MLSMIILYVL SIASLCIGLI TFISFIIVEK KRNTGT | Nipah virus NiV-F F0 truncation (aa 525-544) AND mutation on N-linked glycosylation site (with signal sequence) |
| 599 | MVVILDKRCY CNLLILILMI SECSVGILHY EKLSKIGLVK GVTRKYKIKS NPLTKDIVIK MIPNVSNMSQ CTGSVMENYK TRLNGILTPI KGALEIYKNN THDLVGDVRL AGVIMAGVAI GIATAAQITA GVALYEAMKN ADNINKLKSS IESTNEAVVK LQETAEKTVY VLTALQDYIN TNLVPTIDKI SCKQTELSLD LALSKYLSDL LFVFGPNLQD PVSNSMTIQA ISQAFGGNYE TLLRTLGYAT EDFDDLLESD SITGQIIYVD LSSYYIIVRV YFPPILTEIQQ AYIQELLPVS FNNDNSEWIS IVPNFILVRN TLISNIEIGF CLITKRSVIC NQDYATPMTN NMRECLTGST EKCPRELVVS SHVPRFALSN GVLFANCISV TCQCQTTGRA ISQSGEQTLL MIDNTTCPTA VLGNVIISLG KYLGSVNYNS EGIAIGPPVF TDKVDISSQI SSMNQSLQQS KDYIKEAQRL LDTVNPSLIS MLSMIILYVL SIASLCIGLI TFISFIIVEK KRNT | Truncated NiV fusion glycoprotein (FcDelta22) at cytoplasmic tail (with signal sequence) |

TABLE 7-continued

| SEQ ID NO: | SEQUENCE | ANNOTATION |
|---|---|---|
| 612 | MKKINEGLLDSKILSA FNTVIALLGS IVIIVMNIMI IQNY-<br>TRSTDN QAVIKDALQG IQQQIKGLAD KIGTEIGPKV<br>SLIDTSSTIT IPANIGLLGS KISQSTASIN ENVNEKCKFT<br>LPPLKIHECN ISCPNPLPFR EYRPQTEGVS NLVGLPNNIC<br>LQKTSNQILK PKLISYTLPV VGQSGTCITD PLLAMDEGYF<br>AYSHLERIGS CSRGVSKQRI IGVGEVLDRG DEVPSLFMTN<br>VWTPPNPNTV YHCSAVYNNE FYYVLCAVST VGDPILNSTY<br>WSGSLMMTRL AVKPKSNGGG YNQHQLALRS IEKGRYDKVM<br>PYGPSGIKQG DTLYFPAVGF LVRTEFKYND SNCPITKCQY<br>SKPENCRLSM GIRPNSHYIL RSGLLKYNLS DGENPKVVFI<br>EISDQRLSIG SPSKIYDSLG QPVFYQASFS WDTMIKFGDV<br>LTVNPLVVNW RNNTVISRPG QSQCPRFNTC PEICWEGVYN<br>DAFLIDRINW ISAGVFLDSN QTAENPVFTV FKDNEILYRA<br>QLASEDTNAQ KTITNCFLLK NKIWCISLVE IYDTGDNVIR<br>PKLFAVKIPE QCT | NiVG protein attach-<br>ment glycoprotein<br>Truncated (Gc Δ 34) |
| 613 | ILHY EKLSKIGLVK GVTRKYKIKS NPLTKDIVIK MIP-<br>NVSNMSQ CTGSVMENYK TRLNGILTPI KGALEIYKNN<br>THDLVGDVRL AGVIMAGVAI GIATAAQITA GVALYEAMKN<br>ADNINKLKSS IESTNEAVVK LQETAEKTVY VLTALQDYIN<br>TNLVPTIDKI SCKQTELSLD LALSKYLSDL LFVFGPNLQD<br>PVSNSMTIQA ISQAFGGNYE TLLRTLGYAT EDFDDLLESD<br>SITGQIIYVD LSSYYIIVRV YFPILTEIQQ AYIQELLPVS<br>FNNDNSEWIS IVPNFILVRN TLISNIEIGF CLITKRSVIC<br>NQDYATPMTN NMRECLTGST EKCPRELVVS SHVPRFALSN<br>GVLFANCISV TCQCQTTGRA ISQSGEQTLL MIDNTTCPTA<br>VLGNVIISLG KYLGSVNYNS EGIAIGPPVF TDKVDISSQI<br>SSMNQSLQQS KDYIKEAQRL LDTVNPSLIS MLSMIILYVL<br>SIASLCIGLI TFISFIIVEK KRNT | Truncated mature NiV<br>fusion glycoprotein<br>(FcDelta22) at<br>cytoplasmic tail |
| 614 | MSNKRTTVLIIISYTLFYLNNAAIVGFDFDKLNKIGWQGRVL-<br>NYKIKGDPMTKDLVLKFIP-<br>NIVNITECVREPLSRYNETVRRLLLPIHNMLGLYLNNTNAKMTG<br>LMIAGVIMGGIAIGIATAAQITAGFALYEAKKNTENIQKLT-<br>DSIMKTQDSIDKLT-<br>DSVGTSILILNKLQTYINNQLVPNLELLSCRQNKIEFDLMLTKY<br>LVDLMTVIGPNINNPVNKDMTIQSLSLLFDGNYDIMM-<br>SELGYTPQDFLD-<br>LIESKSITGQIIYVDMENLYVVIRTYLPTLIEVPDAQIYEFNKI<br>TMSSNGGEYLSTIPNFILIRGNYMSNIDVATCYMTKASVIC-<br>NQDYS-<br>LPMSQNLRSCYQGETEYCPVEAVIASHSPRFALTNGVIFANCIN<br>TICRCQDNGKTITQNINQFVSMIDNSTCNDVMVDKFTIK-<br>VGKYMGRKDINNINIQIG-<br>PQIIIDKVDLSNEINKMNQSLKDSIFYLREAKRILDSVNISLIS<br>PSVQLFLIIISVLSFIILLIIIVYLYCK-<br>SKHSYKYNKFIDDPDYYNDYKRERINGKASKSNNIYYVGD | gb: JQ001776: 6129-<br>8166|Organism: Cedar<br>virus|Strain<br>Name: CG1a|Protein<br>Name: fusion<br>glycoprotein|Gene Symbol:<br>F (with signal sequence) |
| 615 | MALNKNMFSSLFLGYLLVYATTVQSSIHYDSLS-<br>KVGVIKGLTYNYKIKGSPSTKLMVVKLIP-<br>NIDSVKNCTQKQYDEYKNLVRKALEPVKMAIDTMLNNVKSGNNK<br>YRFAGAIMAGVALGVATAATVTAGIALHRSNENA-<br>QAIANMKSAIQNTNEAV-<br>KQLQLANKQTLAVIDTIRGEINNNIIPVINQLSCDTIGLSVGIR<br>LTQYYSEIITAFGPALQNPVNTRITIQAISSVFNGNF-<br>DELLKIMGYTSGDLYEILHSELIR-<br>GNIIDVDVDAGYIALEIEFPNLTLVPNAVVQELMPISYNIDGDE<br>WVTLVPRFVLTRTTLLSNIDTSRCTITDSSVICDNDYALPM-<br>SHELIGCLQGDTSKCA-<br>REKWSSYVPKFALSDGLVYANCLNTICRCMDTDTPISQSLGAT<br>VSLLDNKRCSVYQVGDVLISVGSYL-<br>GDGEYNADNVELGPPIVIDKIDIGNQLAGINQTLQE-<br>AEDYIEKSEEFLKGVNPSIITLGSMVVLYIFMILIAIVSVIALV<br>LSIKLTVKGNVVRQQFTYTQHVPSMENINYVSH | gb: NC_025352: 5950-<br>8712|Organism: Mo-<br>jiang virus|Strain<br>Name: Tongguan1|Pro-<br>tein Name: fusion pro-<br>tein|Gene Symbol: F<br>(with signal sequence) |
| 616 | MKKKTDNPTISKRGHNHSRGIKSRALLRETDNYSNGLIVEN-<br>LVRNCHHPSKNNLNY-<br>TKTQKRDSTIPYRVEERKGHYPKIKHLIDKSYKHIKRGKRRNGH<br>NGNIITIILLLILILKTQMSEGAIHYETLSKIGLIKG-<br>ITREYKVKGTPSSKDIVIKLIP-<br>NVTGLNKCTNISMENYKEQLDKILIPINNIIELYANSTKSAPGN<br>ARFAGVIIAGVALGVAAAQITAGIALHEARQNAER-<br>INLLKDSISATNNAVAEL-<br>QEATGGIVNVITGMQDYINTNLVPQIDKLQCSQIKTALDISLSQ<br>YYSEILTVFGPNLQNPVTTSMSIQAISQSFGG- | gb: NC_025256: 6865-<br>8853|Organism: Bat<br>Paramyxovirus<br>Eid_hel/GH-<br>M74a/GHA/2009|Strain<br>Name: BatPV/Eid_hel/GH-<br>M74a/GHA/20091 Pro-<br>tein Name: fusion pro-<br>tein|Gene Symbol: F<br>(with signal sequence) |

TABLE 7-continued

| SEQ ID NO: | SEQUENCE | ANNOTATION |
|---|---|---|
| | NIDLLLNLLGYTANDLLDLLESKSITGQIT-<br>YINLEHYFMVIRVYYPIMTTISNAYVQELIKISFNVDGSEWVSL<br>VPSYILIRNSYLSNIDISECLITKNSVICRHDFAMPM-<br>SYTLKECLTGDTEKCPREAVVTSYV-<br>PRFAISGGVIYANCLSTTCQCYQTGKVIAQDGSQTLMMIDNQTC<br>SIVRIEEILISTGKYLGSQEYNTMHVSVGNPVFTDKL-<br>DITSQISNINQSIEQSKFYLDK-<br>SKAILDKINLNLIGSVPISILFIIAILSLILSIITFVIVMIIVR<br>RYNKYTPLINSDPSSRRSTIQDVYIIPNPGEHSIRSAAR-<br>SIDRDRD | |
| 27 | (GGGGGS)n wherein n is 1 to 6 | Peptide Linker |
| 618 | MPAENKKVRFENTTSDKGKIPSKVIKSYYGTMDIK-<br>KINEGLLDSKILSAFNTVIALLGSIV-<br>IIVMNIMIIQNYTRSTDNQAVIKDALQGIQQQIKGLADKIGTEI<br>GPKVSLIDTSSTITIPANIGLLGSKISQSTASINEN-<br>VNEKCKFTLPPLKIHECNISCPNPLP-<br>FREYRPQTEGVSNLVGLPNNICLQKTSNQILKPKLISYTLPVVG<br>QSGTCITDPLLAMDEGYFAYSHLERIGSCSRGVSKQRII-<br>GVGEVLDRGDEVPSLFMTNVWTPPNPNTVYHCSAVYNNEFYYVL<br>CAVSTVGDPILNSTYWSGSLMMTRLAVKPK-<br>SNGGGYNQHQLALRSIEKGRYDKVMPYGPSGIKQGDTLYFPAVG<br>FLVRTEFKYNDSNCPITKCQYSKPENCRLSMGIRPNSHYIL-<br>RSGLLKYNLSDGENPKVVFIEISDQRLSIGSPSKIYDSLGQPVF<br>YQASFSWDTMIKFGDVLTVNPLVVNWRN-<br>NTVISRPGQSQCPRFNTCPEICWEGVYN-<br>DAFLIDRINWISAGVFLDSNQTAENPVFTVFKDNEILYRAQLAS<br>EDTNAQKTITNCFLLKNKIWCISLVEIYDTGDNVIRPKLFAV-<br>KIPEQCT | gb: AF212302\|Organ-<br>ism: Nipah virus\|Strain<br>Name: UNKNOWN-<br>AF212302\|Protein<br>Name: attachment gly-<br>coprotein\|Gene Sym-<br>bol: G<br>(Uniprot Q9IH62) |
| 619 | MLSQLQKNYLDNSNQQGDKMNNPDKKLSVNFNPLELDKGQKDLN<br>KSYYVKNKNYNVSNLLNESLHDIKFCIYCIFSLLIIT-<br>IINIITISIVITRLKVHEEN-<br>NGMESPNLQSIQDSLSSLTNMINTEITPRIGILVTATSVTLSSS<br>INYVGTKTNQLVNELKDY-<br>ITKSCGFKVPELKLHECNISCADPKISKSAMYSTNAYAELAG-<br>PPKIFCKSVSKDPDFRLKQIDYVIPVQQDRSICMNNPLLDISDG<br>FFTYIHYEGINSCKKSDSFKVLL-<br>SHGEIVDRGDYRPSLYLLSSH-<br>YHPYSMQVINCVPVTCNQSSFVFCHISNNTKTLDNSDYSSDEYY<br>ITYFNGIDRPKTKKIPINNMTADNRYIHFTFSGGGGVCLGEEF-<br>IIPVTTVINTDVFTHDYCESFNCSVQTGKSLKEICSESLRSPTN<br>SSRYNLNGIMIISQNNMTDFKIQLNGITYNKLSFG-<br>SPGRLSKTLGQVLYYQSSMSWDTYLKAGFVEKWKPFTPNWMNNT<br>VISRPNQGNCPRY-<br>HKCPEICYGGTYNDIAPLDLGKDMYVSVILDSDQLAENPEITVF<br>NSTTILYKERVSKDELNTRSTTTSCFLFLDEPWCIS-<br>VLETNRFNGKSIRPEIYSYKIPKYC | gb: JQ001776: 8170-<br>10275\|Organism: Cedar<br>virus\|Strain<br>Name: CG1a\|Protein<br>Name: attachment gly-<br>coprotein\|Gene Sym-<br>bol: G |
| 620 | MPQKTVEFINMNSPLER-<br>GVSTLSDKKTLNQSKITKQGYFGLGSHSERNWKKQKNQNDHYMT<br>VSTMILEILVVLGIMFNLIVLTMVYYQND-<br>NINQRMAELTSNITVLNLNLNQLT-<br>NKIQREIIPRITLIDTATTITIPSAITYILATLTTRISELLPSI<br>NQKCEFKTPTLVLNDCRINCTP-<br>PLNPSDGVKMSSLATNLVAHGPSPCRNFSSVPTIY-<br>YYRIPGLYNRTALDERCILNPRLTISSTKFAYVHSEYDKNCTRG<br>FKYYELMTFGEILEGPEKEPRMFSRSFYSPTNAVNY-<br>HSCTPIVTVNEGYFLC-<br>LECTSSDPLYKANLSNSTFHLVILRHNKDEKIVSMPSFNLSTDQ<br>EYVQIIPAEGGGTAESGNLYFPCIGRLLHKRVTHPLCK-<br>KSNCSRTDDESCLKSYYNQG-<br>SPQHQVVNCLIRIRNAQRDNPTWDVITVDLTNTYPGSRSRIFGS<br>FSKPMLYQSSVSWHT-<br>LLQVAEITDLDKYQLDWLDTPYISRPGGSECPFGNYCPTVCWEG<br>TYNDVYSLTPNNDLFVTVYLKSEQVAENPY-<br>FAIFSRDQILKEFPLDAW-<br>ISSARTTTISCFMFNNEIWCIAALEITRLNDDIIRPIYYSFWLP<br>TDCRTPYPHTGKMTRVPLRSTYNY | gb: NC_025256: 9117-<br>11015\|Organism: Bat<br>Paramyxovirus<br>Eid_hel/GH-<br>M74a/GHA/2009\|Strain<br>Name: BatPV/Eid_hel/GH-<br>M74a/GHA/2009\|Pro-<br>tein Name: glycopro-<br>tein\|Gene Symbol: G |
| 621 | MATNRDNTITSAEVSQEDKVKKYYGVETAEKVADSIS-<br>GNKVFILM-<br>NTLLILTGAIITITLNITNLTAAKSQQNMLKIIQDDVNAKLEMF<br>VNLDQLVKGEIKPKVSLIN-<br>TAVSVSIPGQISNLQTKFLQKYVYLEESITKQCTCNPLSGIFPT | gb: NC_025352: 8716-<br>11257\|Organism: Mo-<br>jiang virus\|Strain<br>Name: Tongguan1\|Pro-<br>tein Name: attachment |

TABLE 7-continued

| SEQ ID NO: | SEQUENCE | ANNOTATION |
|---|---|---|
| | SGPTYPPTDKPDDDTTDDDKVDTTIKPIEYPKPDGCNRT-GDHFTMEPGANFYTVPNLGPASS-NSDECYTNPSFSIGSSIYMFSQEIRKTDCTAGEILSIQIVLGRIVDKGQQGPQASPLLVWAV-PNPKIINSCAVAAGDEMGWVLCSVTLTAASGEPIPHMFDGFWLYKLEPDTEVVSYRITGYAYLLDKQYDSVFIGKGG-GIQKGNDLYFQMYGLSRNRQSFKALCEHG-SCLGTGGGGYQVLCDRAVMSFGSEESLITNAYLKVNDLASGKPVIIGQTFPPSDSYKGSNGRMYTIGDKYGLYLAPSSWNRYLRFG-ITPDISVRSTTWLKSQDPIM-KILSTCTNTDRDMCPEICNTRGYQDIFPLSEDSEYYTYIGITPNNGGTKNFVAVRDSDGHIASIDILQNYYSITSATISCFMYKDEI-WCIAITEGKKQKDNPQRI-YAHSYKIRQMCYNMKSATVTVGNAKNITIRRY | glycoprotein\|Gene Symbol: G |
| 622 | FNTVIALLGS IVIIVMNIMI IQNYTRSTDN QAVIKDALQG IQQQIKGLAD KIGTEIGPKV SLIDTSSTIT IPANIGLLGS KISQSTASIN ENVNEKCKFT LPPLKIHECN ISCPNPLPFR EYRPQTEGVS NLVGLPNNIC LQKTSNQILK PKLISYTLPV VGQSGTCITD PLLAMDEGYF AYSHLERIGS CSRGVSKQRI IGVGEVLDRG DEVPSLFMTN VWTPPNPNTV YHCSAVYNNE FYYVLCAVST VGDPILNSTY WSGSLMMTRL AVKPKSNGGG YNQHQLALRS IEKGRYDKVM PYGPSGIKQG DTLYFPAVGF LVRTEFKYND SNCPITKCQY SKPENCRLSM GIRPNSHYIL RSGLLKYNLS DGENPKVVFI EISDQRLSIG SPSKIYDSLG QPVFYQASFS WDTMIKFGDV LTVNPLVVNW RNNTVISRPG QSQCPRFNTC PEICWEGVYN DAFLIDRINW ISAGVFLDSN QTAENPVFTV FKDNEILYRA QLASEDTNAQ KTITNCFLLK NKIWCISLVE IYDTGDNVIR PKLFAVKIPE QC | NivG protein attachment glycoprotein Without cytoplasmic tail Uniprot Q9IH62 |
| 623 | FNTVIALLGSI IIIVMNIMII QNYTRTTDNQ ALIKESLQSV QQQIKALTDK IGTEIGPKVS LIDTSSTITI PANIGLLGSK ISQSTSSINE NVNDKCKFTL PPLKIHECNI SCPNPLPFRE YRPISQGVSD LVGLPNQICL QKTTSTILKP RLISYTLPIN TREGVCITDP LLAVDNGFFA YSHLEKIGSC TRGIAKQRII GVGEVLDRGD KVPSMFMTNV WTPPNPSTIH HCSSTYHEDF YYTLCAVSHV GDPILNSTSW TESLSLIRLA VRPKSDSGDY NQKYIAITKV ERGKYDKVMP YGPSGIKQGD TLYFPAVGFL PRTEFQYNDS NCPIIHCKYS KAENCRLSMG VNSKSHYILR SGLLKYNLSL GGDIILQFIE IADNRLTIGS PSKIYNSLGQ PVFYQASYSW DTMIKLGDVD TVDPLRVQWR NNSVISRPGQ SQCPRFNVCP EVCWEGTYND AFLIDRLNWV SAGVYLNSNQ TAENPVFAVF KDNEILYQVP LAEDDTNAQK TITDCFLLEN VIWCISLVEI YDTGDSVIRP KLFAVKIPAQ CSES | Hendra virus G protein Uniprot O89343 Without cytoplasmic tail |
| 624 | MVVILDKRCY CNLLILILMI SECSVG | Signal sequence |
| 625 | GGGGGS | Peptide linker |
| 626 | (GGGGS)n wherein n is 1 to 10 | Peptide linker |
| 627 | GGGGS | Peptide linker |
| 628 | PAENKKVR FENTTSDKGK IPSKVIKSYY GTMDIKKINE GLLDSKILSA FNTVIALLGS IVIIVMNIMI IQNYTRSTDN QAVIKDALQG IQQQIKGLAD KIGTEIGPKV SLIDTSSTIT IPANIGLLGS KISQSTASIN ENVNEKCKFT LPPLKIHECN ISCPNPLPFR EYRPQTEGVS NLVGLPNNIC LQKTSNQILK PKLISYTLPV VGQSGTCITD PLLAMDEGYF AYSHLERIGS CSRGVSKQRI IGVGEVLDRG DEVPSLFMTN VWTPPNPNTV YHCSAVYNNE FYYVLCAVST VGDPILNSTY WSGSLMMTRL AVKPKSNGGG YNQHQLALRS IEKGRYDKVM PYGPSGIKQG DTLYFPAVGF LVRTEFKYND SNCPITKCQY SKPENCRLSM GIRPNSHYIL RSGLLKYNLS DGENPKVVFI EISDQRLSIG SPSKIYDSLG QPVFYQASFS WDTMIKFGDV LTVNPLVVNW RNNTVISRPG QSQCPRFNTC PEICWEGVYN DAFLIDRINW ISAGVFLDSN QTAENPVFTV FKDNEILYRA QLASEDTNAQ KTITNCFLLK NKIWCISLVE IYDTGDNVIR PKLFAVKIPE QC | NivG protein attachment glycoprotein (602 aa) Without N-terminal methionine |

TABLE 7-continued

| SEQ ID NO: | SEQUENCE | ANNOTATION |
|---|---|---|
| 629 | KVR FENTTSDKGK IPSKVIKSYY GTMDIKKINE GLLDSKILSA FNTVIALLGS IVIIVMNIMI IQNYTRSTDN QAVIKDALQG IQQQIKGLAD KIGTEIGPKV SLIDTSSTIT IPANIGLLGS KISQSTASIN ENVNEKCKFT LPPLKIHECN ISCPNPLPFR EYRPQTEGVS NLVGLPNNIC LQKTSNQILK PKLISYTLPV VGQSGTCITD PLLAMDEGYF AYSHLERIGS CSRGVSKQRI IGVGEVLDRG DEVPSLFMTN VWTPPNPNTV YHCSAVYNNE FYYVLCAVST VGDPILNSTY WSGSLMMTRL AVKPKSNGGG YNQHQLALRS IEKGRYDKVM PYGPSGIKQG DTLYFPAVGF LVRTEFKYND SNCPITKCQY SKPENCRLSM GIRPNSHYIL RSGLLKYNLS DGENPKVVFI EISDQRLSIG SPSKIYDSLG QPVFYQASFS WDTMIKFGDV LTVNPLVVNW RNNTVISRPG QSQCPRFNTC PEICWEGVYN DAFLIDRINW ISAGVFLDSN QTAENPVFTV FKDNEILYRA QLASEDTNAQ KTITNCFLLK NKIWCISLVE IYDTGDNVIR PKLFAVKIPE QC | NiVG protein attach-ment glycoprotein Truncated Δ5 Without N-terminal methionine |
| 630 | NTTSDKGK IPSKVIKSYY GTMDIKKINE GLLDSKILSA FNTVIALLGS IVIIVMNIMI IQNYTRSTDN QAVIKDALQG IQQQIKGLAD KIGTEIGPKV SLIDTSSTIT IPANIGLLGS KISQSTASIN ENVNEKCKFT LPPLKIHECN ISCPNPLPFR EYRPQTEGVS NLVGLPNNIC LQKTSNQILK PKLISYTLPV VGQSGTCITD PLLAMDEGYF AYSHLERIGS CSRGVSKQRI IGVGEVLDRG DEVPSLFMTN VWTPPNPNTV YHCSAVYNNE FYYVLCAVST VGDPILNSTY WSGSLMMTRL AVKPKSNGGG YNQHQLALRS IEKGRYDKVM PYGPSGIKQG DTLYFPAVGF LVRTEFKYND SNCPITKCQY SKPENCRLSM GIRPNSHYIL RSGLLKYNLS DGENPKVVFI EISDQRLSIG SPSKIYDSLG QPVFYQASFS WDTMIKFGDV LTVNPLVVNW RNNTVISRPG QSQCPRFNTC PEICWEGVYN DAFLIDRINW ISAGVFLDSN QTAENPVFTV FKDNEILYRA QLASEDTNAQ KTITNCFLLK NKIWCISLVE IYDTGDNVIR PKLFAVKIPE QC | NiVG protein attach-ment glycoprotein Truncated Δ10 Without N-terminal methionine |
| 631 | KGK IPSKVIKSYY GTMDIKKINE GLLDSKILSA FNTVI-ALLGS IVIIVMNIMI IQNYTRSTDN QAVIKDALQG IQQQIKGLAD KIGTEIGPKV SLIDTSSTIT IPANIGLLGS KISQSTASIN ENVNEKCKFT LPPLKIHECN ISCPNPLPFR EYRPQTEGVS NLVGLPNNIC LQKTSNQILK PKLISYTLPV VGQSGTCITD PLLAMDEGYF AYSHLERIGS CSRGVSKQRI IGVGEVLDRG DEVPSLFMTN VWTPPNPNTV YHCSAVYNNE FYYVLCAVST VGDPILNSTY WSGSLMMTRL AVKPKSNGGG YNQHQLALRS IEKGRYDKVM PYGPSGIKQG DTLYFPAVGF LVRTEFKYND SNCPITKCQY SKPENCRLSM GIRPNSHYIL RSGLLKYNLS DGENPKVVFI EISDQRLSIG SPSKIYDSLG QPVFYQASFS WDTMIKFGDV LTVNPLVVNW RNNTVISRPG QSQCPRFNTC PEICWEGVYN DAFLIDRINW ISAGVFLDSN QTAENPVFTV FKDNEILYRA QLASEDTNAQ KTITNCFLLK NKIWCISLVE IYDTGDNVIR PKLFAVKIPE QC | NiVG protein attach-ment glycoprotein Truncated Δ15 Without N-terminal methionine |
| 632 | SKVIKSYY GTMDIKKINE GLLDSKILSA FNTVIALLGS IVIIVMNIMI IQNYTRSTDN QAVIKDALQG IQQQIKGLAD KIGTEIGPKV SLIDTSSTIT IPANIGLLGS KISQSTASIN ENVNEKCKFT LPPLKIHECN ISCPNPLPFR EYRPQTEGVS NLVGLPNNIC LQKTSNQILK PKLISYTLPV VGQSGTCITD PLLAMDEGYF AYSHLERIGS CSRGVSKQRI IGVGEVLDRG DEVPSLFMTN VWTPPNPNTV YHCSAVYNNE FYYVLCAVST VGDPILNSTY WSGSLMMTRL AVKPKSNGGG YNQHQLALRS IEKGRYDKVM PYGPSGIKQG DTLYFPAVGF LVRTEFKYND SNCPITKCQY SKPENCRLSM GIRPNSHYIL RSGLLKYNLS DGENPKVVFI EISDQRLSIG SPSKIYDSLG QPVFYQASFS WDTMIKFGDV LTVNPLVVNW RNNTVISRPG QSQCPRFNTC PEICWEGVYN DAFLIDRINW ISAGVFLDSN QTAENPVFTV FKDNEILYRA QLASEDTNAQ KTITNCFLLK NKIWCISLVE IYDTGDNVIR PKLFAVKIPE QC | NiVG protein attach-ment glycoprotein Truncated Δ20 Without N-terminal methionine |
| 633 | SYY GTMDIKKINE GLLDSKILSA FNTVIALLGS IVIIVMNIMI IQNYTRSTDN QAVIKDALQG IQQQIKGLAD KIGTEIGPKV SLIDTSSTIT IPANIGLLGS KISQSTASIN ENVNEKCKFT LPPLKIHECN ISCPNPLPFR EYRPQTEGVS NLVGLPNNIC LQKTSNQILK PKLISYTLPV VGQSGTCITD PLLAMDEGYF AYSHLERIGS CSRGVSKQRI IGVGEVLDRG DEVPSLFMTN VWTPPNPNTV YHCSAVYNNE FYYVLCAVST VGDPILNSTY WSGSLMMTRL AVKPKSNGGG YNQHQLALRS IEKGRYDKVM PYGPSGIKQG DTLYFPAVGF LVRTEFKYND SNCPITKCQY SKPENCRLSM GIRPNSHYIL RSGLLKYNLS DGENPKVVFI EISDQRLSIG SPSKIYDSLG QPVFYQASFS | NiVG protein attach-ment glycoprotein Truncated Δ25 Without N-terminal methionine |

TABLE 7-continued

| SEQ ID NO: | SEQUENCE | ANNOTATION |
|---|---|---|
| | WDTMIKFGDV LTVNPLVVNW RNNTVISRPG QSQCPRFNTC PEICWEGVYN DAFLIDRINW ISAGVFLDSN QTAENPVFTV FKDNEILYRA QLASEDTNAQ KTITNCFLLK NKIWCISLVE IYDTGDNVIR PKLFAVKIPE QC | |
| 634 | TMDIKKINE GLLDSKILSA FNTVIALLGS IVIIVMNIMI IQNYTRSTDN QAVIKDALQG IQQQIKGLAD KIGTEIGPKV SLIDTSSTIT IPANIGLLGS KISQSTASIN ENVNEKCKFT LPPLKIHECN ISCPNPLPFR EYRPQTEGVS NLVGLPNNIC LQKTSNQILK PKLISYTLPV VGQSGTCITD PLLAMDEGYF AYSHLERIGS CSRGVSKQRI IGVGEVLDRG DEVPSLFMTN VWTPPNPNTV YHCSAVYNNE FYYVLCAVST VGDPILNSTY WSGSLMMTRL AVKPKSNGGG YNQHQLALRS IEKGRYDKVM PYGPSGIKQG DTLYFPAVGF LVRTEFKYND SNCPITKCQY SKPENCRLSM GIRPNSHYIL RSGLLKYNLS DGENPKVVFI EISDQRLSIG SPSKIYDSLG QPVFYQASFS WDTMIKFGDV LTVNPLVVNW RNNTVISRPG QSQCPRFNTC PEICWEGVYN DAFLIDRINW ISAGVFLDSN QTAENPVFTV FKDNEILYRA QLASEDTNAQ KTITNCFLLK NKIWCISLVE IYDTGDNVIR PKLFAVKIPE QC | NiVG protein attach- ment glycoprotein Truncated Δ30 Without N-terminal methionine |
| 635 | KKINEGLLDSKILSA FNTVIALLGS IVIIVMNIMI IQNY- TRSTDN QAVIKDALQG IQQQIKGLAD KIGTEIGPKV SLIDTSSTIT IPANIGLLGS KISQSTASIN ENVNEKCKFT LPPLKIHECN ISCPNPLPFR EYRPQTEGVS NLVGLPNNIC LQKTSNQILK PKLISYTLPV VGQSGTCITD PLLAMDEGYF AYSHLERIGS CSRGVSKQRI IGVGEVLDRG DEVPSLFMTN VWTPPNPNTV YHCSAVYNNE FYYVLCAVST VGDPILNSTY WSGSLMMTRL AVKPKSNGGG YNQHQLALRS IEKGRYDKVM PYGPSGIKQG DTLYFPAVGF LVRTEFKYND SNCPITKCQY SKPENCRLSM GIRPNSHYIL RSGLLKYNLS DGENPKVVFI EISDQRLSIG SPSKIYDSLG QPVFYQASFS WDTMIKFGDV LTVNPLVVNW RNNTVISRPG QSQCPRFNTC PAICAEGVYN DAFLIDRINW ISAGVFLDSN ATAANPVFTV FKDNEILYRA QLASEDTNAQ KTITNCFLLK NKIWCISLVE IYDTGDNVIR PKLFAVKIPE QCT | NiVG protein attach- ment glycoprotein Truncated and mutated (E501 A, W504A, Q530A, E533A) NiVG protein (Gc Δ 34) With- out N-terminal methio- nine |
| 636 | MADSKLVSL NNNLSGKIKD QGKVIKNYYG TMDIKKINDG LLDSKILGAF NTVIALLGSI IIIVMNIMII QNYTRTTDNQ ALIKESLQSV QQQIKALTDK IGTEIGPKVS LIDTSSTITI PANIGLLGSK ISQSTSSINE NVNDKCKFTL PPLKIHECNI SCPNPLPFRE YRPISQGVSD LVGLPNQICL QKTTSTILKP RLISYTLPIN TREGVCITDP LLAVDNGFFA YSHLEKIGSC TRGIAKQRII GVGEVLDRGD KVPSMFMTNV WTPPNPSTIH HCSSTYHEDF YYTLCAVSHV GDPILNSTSW TESLSLIRLA VRPKSDSGDY NQKYIAITKV ERGKYDKVMP YGPSGIKQGD TLYFPAVGFL PRTEFQYNDS NCPIIHCKYS KAENCRLSMG VNSKSHYILR SGLLKYNLSL GGDIILQFIE IADNRLTIGS PSKIYNSLGQ PVFYQASYSW DTMIKLGDVD TVDPLRVQWR NNSVISRPGQ SQCPRFNVCP EVCWEGTYND AFLIDRLNWV SAGVYLNSNQ TAENPVFAVF KDNEILYQVP LAEDDTNAQK TITDCFLLEN VIWCISLVEI YDTGDSVIRP KLFAVKIPAQ CSES | Hendra virus G protein Uniprot O89343 With- out N-terminal methio- nine |
| 637 | KKINEGLLDSKILSA FNTVIALLGS IVIIVMNIMI IQNY- TRSTDN QAVIKDALQG IQQQIKGLAD KIGTEIGPKV SLIDTSSTIT IPANIGLLGS KISQSTASIN ENVNEKCKFT LPPLKIHECN ISCPNPLPFR EYRPQTEGVS NLVGLPNNIC LQKTSNQILK PKLISYTLPV VGQSGTCITD PLLAMDEGYF AYSHLERIGS CSRGVSKQRI IGVGEVLDRG DEVPSLFMTN VWTPPNPNTV YHCSAVYNNE FYYVLCAVST VGDPILNSTY WSGSLMMTRL AVKPKSNGGG YNQHQLALRS IEKGRYDKVM PYGPSGIKQG DTLYFPAVGF LVRTEFKYND SNCPITKCQY SKPENCRLSM GIRPNSHYIL RSGLLKYNLS DGENPKVVFI EISDQRLSIG SPSKIYDSLG QPVFYQASFS WDTMIKFGDV LTVNPLVVNW RNNTVISRPG QSQCPRFNTC PEICWEGVYN DAFLIDRINW ISAGVFLDSN QTAENPVFTV FKDNEILYRA QLASEDTNAQ KTITNCFLLK NKIWCISLVE IYDTGDNVIR PKLFAVKIPE QCT | NiVG protein attach- ment glycoprotein Truncated (Gc Δ 34) Without N-terminal- methionine |
| 638 | LSQLQKNYLDNSNQQGDKMNNPDKKLSVNFNPLELDKGQKDLNK SYYVKNKNYNVSNLLNESLHDIKFCIYCIFSLLIIITIINIIT- ISIVITRLKVHEEN- | gb: JQ001776: 8170- 10275|Organism: Cedar virus|Strain |

TABLE 7-continued

| SEQ ID NO: | SEQUENCE | ANNOTATION |
|---|---|---|
| | NGMESPNLQSIQDSLSSLTNMINTEITPRIGILVTATSVTLSSS INYVGTKTNQLVNELKDY- ITKSCGFKVPELKLHECNISCADPKISKSAMYSTNAYAELAG- PPKIFCKSVSKDPDFRLKQIDYVIPVQQDRSICMNNPLLDISDG FFTYIHYEGINSCKKSDSFKVLL- SHGEIVDRGDYRPSLYLLSSH- YHPYSMQVINCVPVTCNQSSFVFCHISNNTKTLDNSDYSSDEYY ITYFNGIDRPKTKKIPINNMTADNRYIHFTFSGGGGVCLGEEF- IIPVTTVINTDVFTHDYCESFNCSVQTGKSLKEICSESLRSPTN SSRYNLNGIMIISQNNMTDFKIQLNGITYNKLSFG- SPGRLSKTLGQVLYYQSSMSWDTYLKAGFVEKWKPFTPNWMNNT VISRPNQGNCPRY- HKCPEICYGGTYNDIAPLDLGKDMYVSVILDSDQLAENPEITVF NSTTILYKERVSKDELNTRSTTTSCFLFLDEPWCIS- VLETNRFNGKSIRPEIYSYKIPKYC | Name: CG1a\|Protein Name: attachment gly-coprotein\|Gene-Symbol: G Without N-terminal methionine |
| 639 | PQKTVEFINMNSPLER- GVSTLSDKKTLNQSKITKQGYFGLGSHSERNWKKQKNQNDHYMT VSTMILEILVVLGIMFNLIVLTMVYYQND- NINQRMAELTSNITVLNLNLNQLT- NKIQREIIPRITLIDTATTITIPSAITYILATLTTRISELLPSI NQKCEFKTPTLVLNDCRINCTP- PLNPSDGVKMSSLATNLVAHGPSPCRNFSSVPTIY- YYRIPGLYNRTALDERCILNPRLTISSTKFAYVHSEYDKNCTRG FKYYELMTFGEILEGPEKEPRMFSRSFYSPTNAVNY- HSCTPIVTVNEGYFLC- LECTSSDPLYKANLSNSTFHLVILRHNKDEKIVSMPSFNLSTDQ EYVQIIPAEGGGTAESGNLYFPCIGRLLHKRVTHPLCK- KSNCSRTDDESCLKSYYNQG- SPQHQVVNCLIRIRNAQRDNPTWDVITVDLTNTYPGSRSRIFGS FSKPMLYQSSVSWHT- LLQVAEITDLDKYQLDWLDTPYISRPGGSECPFGNYCPTVCWEG TYNDVYSLTPNNDLFVTVYLKSEQVAENPY- FAIFSRDQILKEFPLDAW- ISSARTTTISCFMFNNEIWCIAALEITRLNDDIIRPIYYSFWLP TDCRTPYPHTGKMTRVPLRSTYNY | gb: NC_025256: 9117-11015\|Organism: Bat Paramyxovirus Eid_hel/GH-M74a/GHA/2009\|Strain Name: BatPV/ Eid_hel/GH-M74a/GHA/20091 Pro-tein Name: glycopro-tein\|Gene Symbol\|G Without N-terminal-methionine |
| 640 | ATNRDNTITSAEVSQEDKVKKYYGVETAEKVADSIS- GNKVFILMNTLLILTGAIITITLNIT- NLTAAKSQQNMLKIIQDDVNAKLEMFVNLDQLVKGEIKPKVSLI NTAVSVSIPGQISNLQTKFLQKYVYLEESITKQCTCNPLSGIFP TSGPTYPPTDKPDDDTTDDDKVDTTIKPIEYPKPDGCNRT- GDHFTMEP- GANFYTVPNLGPASSNSDECYTNPSFSIGSSIYMFSQEIRKTDC TAGEILSIQIVLGRIVDKGQQGPQASPLLVWAV- PNPKIINSCAVAAGDEMGWVLCSVTLTAASGEPIPHMFDGFWLY KLEPDTEVVSYRITGYAYLLDKQYDSVFIGKGG- GIQKGNDLYFQMYGLSRNRQSFKALCEHG- SCLGTGGGGYQVLCDRAVMSFGSEESLITNAYLKVNDLASGKPV IIGQTFPPSDSYKGSNGRMYTIGDKYGLYLAPSSWNRYLRFG- ITPDISVRSTTWLKSQDPIM- KILSTCTNTDRDMCPEICNTRGYQDIFPLSEDSEYYTYIGITPN NGGTKNFVAVRDSDGHIASIDILQNYYSITSATISCFMYKDEI- WCIAITEGKKQKDNPQRI- YAHSYKIRQMCYNMKSATVTVGNAKNITIRRY | gb: NC_025352: 8716-11257\|Organism: Mo-jiang virus\|Strain Name: Tongguan1\|Pro-tein Name: attachment glycoprotein\|Gene Symbol: G Without N-terminal methionine |
| 641 | DFDKLNKIGVVQGRVLNYKIKGDPMTKDLVLKFIP- NIVNITECVREPLSRYNETVRRLLLPIHNMLGLYLNNTNAKMTG LMIAGVIMGGIAIGIATAAQITAGFALYEAKKNTENIQKLT- DSIMKTQDSIDKLT- DSVGTSILILNKLQTYINNQLVPNLELLSCRQNKIEFDLMLTKY LVDLMTVIGPNINNPVNKDMTIQSLSLLFDGNYDIMM- SELGYTPQDFLD- LIESKSITGQIIYVDMENLYVVIRTYLPTLIEVPDAQIYEFNKI TMSSNGGEYLSTIPNFILIRGNYMSNIDVATCYMTKASVIC- NQDYS- LPMSQNLRSCYQGETEYCPVEAVIASHSPRFALTNGVIFANCIN TICRCQDNGKTITQNINQFVSMIDNSTCNDVMVDKFTIK- VGKYMGRKDINNINIQIG- PQIIIDKVDLSNEINKMNQSLKDSIFYLREAKRILDSVNISLIS PSVQLFLIIISVLSFIILLIIIVYLYCK- SKHSYKYNKFIDDPDYYNDYKRERINGKASKSNNIYYVGD | gb: JQ001776: 6129-8167\|Organism: Cedar virus\|Strain Name: CG1a\|Protein Name: fusion glycopro-tein\|Gene Symbol: F (without signal sequence) |

TABLE 7-continued

| SEQ ID NO: | SEQUENCE | ANNOTATION |
|---|---|---|
| 642 | SRALLRETDNYSNGLIVENLVRNCHHPSKNNLNYTKTQKRD-STIPY-RVEERKGHYPKIKHLIDKSYKHIKRGKRRNGHNGNIITIILLLI LILKTQMSEGAIHYETLSKIGLIKGITREYKVKGTPSSKDIVI-KLIPNVTGLNKCTNISME-NYKEQLDKILIPINNIIELYANSTKSAPGNARFAGVIIAGVALG VAAAAQITAGIALHEARQNAERINLLKDSISATNNAVAEL-QEATGGIVNVITGMQDYINT-NLVPQIDKLQCSQIKTALDISLSQYYSEILTVFGPNLQNPVTTS MSIQAISQSFGGNIDLLLNLLGYTANDLLDLLESKSITGQITY-INLEHYFM-VIRVYYPIMTTISNAYVQELIKISFNVDGSEWVSLVPSYILIRN SYLSNIDISECLITKNSVICRHDFAMPM-SYTLKECLTGDTEKCPREAVVTSYV-PRFAISGGVIYANCLSTTCQCYQTGKVIAQDGSQTLMMIDNQTC SIVRIEEILISTGKYLGSQEYNTMHVSVGNPVFTDKL-DITSQISNINQSIEQSKFYLDK-SKAILDKINLNLIGSVPISILFIIAILSLILSIITFVIVMIIVR RYNKYTPLINSDPSSRRSTIQDVYIIPNPGEHSIRSAAR-SIDRDRD | gb: NC_025256: 6865-8853\|Organism: Bat Paramyxovirus Eid_hel/GH-M74a/GHA/2009\|Strain Name: BatPV/Eid_hel/GH-M74a/GHA/2009\|Protein Name: fusion protein\|Gene Symbol: F (without signal sequence) |
| 643 | ILHY EKLSKIGLVK GITRKYKIKS NPLTKDIVIK MIPNVSNVSK CTGTVMENYK SRLTGILSPI KGAIELYNNN THDLVGDVKL AGVVMAGIAI GIATAAQITA GVALYEAMKN ADNINKLKSS IESTNEAVVK LQETAEKTVY VLTALQDYIN TNLVPTIDQI SCKQTELALD LALSKYLSDL LFVFGPNLQD PVSNSMTIQA ISQAFGGNYE TLLRTLGYAT EDFDDLLESD SIAGQIVYVD LSSYYIIVRV YFPPILTEIQQ AYVQELLPVS FNNDNSEWIS IVPNFVLIRN TLISNIEVKY CLITKKSVIC NQDYATPMTA SVRECLTGST DKCPRELVVS SHVPRFALSG GVLFANCISV TCQCQTTGRA ISQSGEQTLL MIDNTTCTTV VLGNIIISLG KYLGSINYNS ESIAVGPPVY TDKVDISSQI SSMNQSLQQS KDYIKEAQKI LDTVNPSLIS MLSMIILYVL SIAALCIGLI TFISFVIVEK KRGNYSRLDD RQVRPVSNGD LYYIGT | Hendra virus F protein Uniprot O89342 (without signal sequence) |
| 644 | IHYDSLSKVGVIKGLTYNYKIKGSPSTKLMWKLIP-NIDSVKNCTQKQYDEYKNLVRKALEPVKMAIDTMLNNVKSGNNK YRFAGAIMAGVALGVATAATVTAGIALHRSNENA-QAIANMKSAIQNTNEAV-KQLQLANKQTLAVIDTIRGEINNNIIPVINQLSCDTIGLSVGIR LTQYYSEIITAFGPALQNPVNTRITIQAISSVFNGNF-DELLKIMGYTSGDLYEILHSELIR-GNIIDVDVDAGYIALEIEFPNLTLVPNAVVQELMPISYNIDGDE WVTLVPRFVLTRTTLLSNIDTSRCTITDSSVICDNDYALPM-SHELIGCLQGDTSKCA-REKWSSYVPKFALSDGLVYANCLNTICRCMDTDTPISQSLGAT VSLLDNKRCSVYQVGDVLISVGSYL-GDGEYNADNVELGPPIVIDKIDIGNQLAGINQTLQE-AEDYIEKSEEFLKGVNPSIITLGSMVVLYIFMILIAIVSVIALV LSIKLTVKGNVVRQQFTYTQHVPSMENINYVSH | gb: NC_025352: 5950-8712\|Organism: Mojiang virus\|Strain Name: Tongguan1\|Protein Name: fusion protein\|Gene Symbol: F (without signal sequence) |
| 645 | (GGGS)n wherein n is 1 to 10 | Peptide linker |
| 646 | GGGGSGGGGSGGGGS | Peptide linker |
| 647 | TTAASGSSGGSSSGA | Peptide linker |
| 648 | GSTSGSGKPGSGEGSTKG | Peptide linker |

TABLE 8

| | HCDRs using the Chothia Numbering Scheme | | | | | |
|---|---|---|---|---|---|---|
| | H-CDR1 | | H-CDR2 | | H-CDR3 | |
| CD8 Binder | Sequence | SEQ ID NO: | Sequence | SEQ ID NO: | Sequence | SEQ ID NO: |
| 1 | GGTFSSY | 653 | DPSDGN | 701 | ERAAAGYYYYMDV | 148 |
| 2 | GGTFNTY | 654 | DPSSGG | 702 | EHAAGTYYYYMDV | 149 |
| 3 | GGTFSSY | 653 | DPSGGN | 703 | ERAAAGYYYYMDV | 148 |
| 4 | GYTFTGY | 655 | NPNNGD | 704 | EGYYYYGMDV | 649 |
| 5 | GYTFTDY | 656 | NPNSGG | 705 | EGDYYYGMDA | 150 |
| 6 | GYTFTRY | 657 | NPNDGS | 706 | ERGGMPDY | 151 |
| 7 | GYTFTSY | 658 | NPNSGG | 705 | GHGIPKY | 152 |
| 8 | GYTFTSY | 658 | NPNSGN | 707 | VRSGSPQH | 153 |
| 9 | GHTFSRH | 659 | NPNSGN | 707 | GGPWIVDAFDI | 154 |
| 10 | GYTFTSY | 658 | SAHNGV | 708 | GIAVAGTDY | 650 |
| 11 | GGTFSNT | 660 | NPSGGS | 709 | EATWGPYYYYMDV | 155 |
| 12 | GYTFTRS | 661 | SPYNGN | 710 | NKDGLQH | 156 |
| 13 | GDTFTGY | 662 | NPNSGD | 711 | DAKRVGYYYYMDV | 157 |
| 14 | GYTFTRY | 657 | NPNSGG | 705 | LVGGSPDY | 158 |
| 15 | GYTFTNY | 663 | NPNSGG | 705 | GAMVDY | 159 |
| 16 | GGTFSNT | 660 | NPSDGD | 712 | GNYVGSYYYGMDV | 160 |
| 17 | GYTFTNY | 663 | NPNSGD | 711 | DSRGDWYFDL | 161 |
| 18 | GYGFTRY | 664 | DPSGGS | 713 | HGGRGLADY | 162 |
| 19 | GYTFTSR | 665 | DPKSGD | 714 | LKELSSILDAFDI | 163 |
| 20 | GYTFTSY | 658 | NPGAGS | 715 | ERFGTGYYYYMDV | 164 |
| 21 | GFTFSNS | 666 | SGDGGT | 716 | VIGEMVDDAFDL | 165 |
| 22 | GYTFTGY | 655 | NPNSGD | 711 | ERLFGTYYYYMDV | 166 |
| 23 | GYTFTTY | 667 | IPIFGT | 717 | ADGELTDY | 167 |
| 24 | GFTFSSY | 668 | -GTGGG | 718 | HHLPAHYYYYMDV | 168 |
| 25 | GGTFSRY | 669 | NPNSGD | 711 | DVPAGRYYYYMDV | 169 |
| 26 | GNTFTSY | 670 | NPSDGS | 719 | DRGVGRYYYYMDV | 170 |
| 27 | GGTFSRY | 669 | NPSDGS | 719 | DSRYGRYYYYMDV | 171 |
| 28 | GGTFSNY | 671 | NPNGGS | 720 | EIVVGPYYYYMDV | 172 |
| 29 | GGTFTRY | 672 | NPNSGD | 711 | GMVRGPYYYYMDV | 173 |
| 30 | GGTFSSY | 653 | NPSGGS | 709 | EGVTGPYYYYMDV | 174 |
| 31 | GGTFSRF | 673 | NPSDGS | 719 | DAAAGTRYYYYYGMDV | 175 |
| 32 | GGTFSSH | 674 | NPSGGS | 709 | ELYSSTYYYYMDV | 176 |
| 33 | GGTFSSY | 653 | NPNTGG | 721 | ALYSGPYYYYMDV | 177 |
| 34 | GFTFSNS | 666 | SGSGGS | 722 | EHAAGTYYYYMDV | 149 |
| 35 | GGTFGSY | 675 | SGYNGD | 723 | DSLVGRYYYYMDV | 178 |
| 36 | GYIFTDY | 676 | SADNGN | 724 | RSELDY | 179 |
| 37 | GYTFTSY | 658 | SPNSGA | 725 | GDDNDY | 180 |

TABLE 8-continued

HCDRs using the Chothia Numbering Scheme

| CD8 Binder | H-CDR1 Sequence | SEQ ID NO: | H-CDR2 Sequence | SEQ ID NO: | H-CDR3 Sequence | SEQ ID NO: |
|---|---|---|---|---|---|---|
| 38 | GYTFTSY | 658 | NPNSGN | 707 | GEEVDY | 181 |
| 39 | GYTFTSY | 658 | NPSGGS | 709 | GRRVPDY | 182 |
| 40 | GYTFTDY | 656 | NPKSGA | 726 | GKVTTDY | 183 |
| 41 | GFTFSSF | 677 | SESGDS | 727 | GRELIEY | 184 |
| 42 | GFTFDDY | 678 | -GTGGG | 718 | VYDFPDV | 185 |
| 43 | GYTFTDS | 679 | NPSNGD | 728 | STYSHIDY | 186 |
| 44 | GYTFTNY | 663 | SPSDGS | 729 | EDSSGFDY | 187 |
| 45 | GYTFMNY | 680 | NPSGGS | 709 | DQGGGFDY | 188 |
| 46 | GYTFTSY | 658 | DPEDGE | 730 | DQGWGMDV | 189 |
| 47 | GYTFTSY | 658 | NPKSGR | 731 | LTEGIPDY | 190 |
| 48 | GYTLNDY | 681 | NPGGGS | 732 | DRYGPFDY | 191 |
| 49 | GYTFTSY | 658 | NPKTGD | 733 | LVAGGAPDY | 192 |
| 50 | GYTFTGY | 655 | DPSDGY | 734 | DGFTGDIAY | 193 |
| 51 | GYTFTGY | 655 | NPNSGG | 705 | VDDSSSPDY | 194 |
| 52 | GYTFTGY | 655 | MPISGT | 735 | GPDGTEVDY | 195 |
| 52 | GYTFTNH | 682 | NPNSGN | 707 | SESGSDLDY | 196 |
| 54 | GYTFTNY | 663 | SPTSGD | 736 | EVEIEGYMDV | 197 |
| 55 | GYTFTSY | 658 | NPNSGD | 711 | DLDDDWYMDV | 198 |
| 56 | GYTFTSY | 658 | DPSGDI | 737 | DSTTWDAFDI | 199 |
| 57 | GYTFTDY | 656 | NPNSGG | 705 | VLVGSGSPDY | 200 |
| 58 | GYTFTEN | 683 | ETSGGS | 738 | EAAAGLDFQH | 201 |
| 59 | GYTFASY | 684 | NPNSGG | 705 | ANSWDADY | 202 |
| 60 | GFTFSNS | 666 | SGSGVT | 739 | EHSSSWYTFDY | 203 |
| 61 | GYTFTAY | 685 | NPNSGG | 705 | DDDSSGYYLDY | 204 |
| 62 | GYTFTNY | 663 | NPSGGS | 709 | ASGDYMDLIDYMDY | 205 |
| 63 | GYTFTDY | 656 | NPDSGG | 740 | VGSSGYLAPTH | 206 |
| 64 | GYPFTDY | 686 | NPNSGN | 707 | VRGDGYNLGDY | 207 |
| 65 | GYTFSDY | 687 | NPNSGG | 705 | DVDTAMGAGDY | 208 |
| 66 | GYTFTDY | 656 | NPSGGS | 709 | VARWGYGDYPDY | 209 |
| 67 | GDTFTTH | 688 | SPSDGS | 729 | DRNGDYYYGMDV | 210 |
| 68 | GDTFTNY | 689 | NPISGG | 741 | EGLGSSWYVLDY | 211 |
| 69 | GYTFTSY | 658 | SADNGD | 742 | DGSHYGYYGMDV | 212 |
| 70 | GYTFTSY | 658 | SPIYGT | 743 | PGPEGYYYGMDV | 213 |
| 71 | GYTFTDN | 690 | NPNSGN | 707 | YHWDYGDYRFDY | 214 |
| 72 | GYTFTSY | 658 | NPNSGN | 707 | VEIDYGDSPPDY | 215 |
| 73 | GGTSSSY | 691 | NPSDGD | 712 | GAEWELRYAFDI | 216 |

TABLE 8-continued

| | HCDRs using the Chothia Numbering Scheme | | | | | |
|---|---|---|---|---|---|---|
| | H-CDR1 | | H-CDR2 | | H-CDR3 | |
| CD8 Binder | Sequence | SEQ ID NO: | Sequence | SEQ ID NO: | Sequence | SEQ ID NO: |
| 74 | GYTFTTY | 667 | NPSGGT | 744 | ETYYGLYYYGMDV | 217 |
| 75 | GYTFTSY | 658 | NPKSGN | 745 | APSLRGYSYGPDY | 218 |
| 76 | GGTFTSY | 692 | NPSGGS | 709 | DRQERYYYYMDV | 219 |
| 77 | GYTFTSY | 658 | NPSDGS | 719 | DRSYGDYYYGMDV | 220 |
| 78 | GGTFTSY | 692 | NPGGGN | 746 | EVFSENYYYYMDV | 221 |
| 79 | GYTFTSY | 658 | NPSDGS | 719 | EWDYTHYYYGMDV | 222 |
| 80 | GNTFTSH | 693 | DPEDGE | 730 | GDSSGYYQYYFDY | 223 |
| 81 | GYTFTSY | 658 | TPVFGI | 747 | GSWDSSSWYIPEY | 224 |
| 82 | GFTFSDY | 694 | NPRGGS | 748 | LVWGGAYYYYMDV | 225 |
| 83 | GYTFTSY | 658 | NPNNGD | 704 | PVFSGSYYWYFDP | 226 |
| 84 | GYTFTSY | 658 | NPSGGG | 749 | DQAVAGPYYYGMDV | 227 |
| 85 | GGTFSSY | 653 | NPGSGN | 750 | DRWLAGPYYYGMDV | 228 |
| 86 | GYMFTGH | 695 | IPIFGT | 717 | VMGPVDYYYYGMDV | 229 |
| 87 | GYIFSNY | 696 | NPSDGS | 719 | DLGPFGSYYYYMDV | 230 |
| 88 | GFTFSSY | 668 | NGDGDD | 751 | EGVVVPPYYYYMDV | 231 |
| 89 | GYTFTTY | 667 | DPNSGD | 752 | SSGWSRYYYYYMDV | 232 |
| 90 | GSTFTNY | 697 | NPSGGS | 709 | DNGMTTGYYYYMDV | 233 |
| 91 | GYTFTSY | 658 | NPSGGS | 709 | DRAMVTGYYYGMDV | 234 |
| 92 | GYTFTSY | 658 | NPSDGN | 753 | DRGYGDRGYYYGMDV | 235 |
| 93 | GGTLSSY | 698 | NTYNGN | 754 | SPKATADYYYYMDV | 236 |
| 94 | GYTFTSY | 658 | NPSDGI | 755 | STVTPSYYYYGMDV | 237 |
| 95 | GYTFTSH | 699 | NPRDGD | 756 | EPVAGTGYYYYGMDV | 238 |
| 96 | GGTFNSY | 700 | NPNSGN | 707 | DNLAGFWSDYYYGMDV | 239 |
| 97 | GRTFSGY | 1064 | SRGGLS | 1065 | DRSDLYEITAASNIDS | 1063 |

TABLE 9

| | LCDRs using the Chothia Numbering Scheme | | | | | |
|---|---|---|---|---|---|---|
| | L-CDR1 | | L-CDR2 | | L-CDR3 | |
| CD8 Binder | Sequence | SEQ ID NO: | Sequence | SEQ ID NO: | Sequence | SEQ ID NO: |
| 1 | RASQSISSYLN | 240 | AASSLQS | 294 | QQSYSTPLT | 333 |
| 2 | QASQDISNYLN | 241 | AASSLQS | 294 | QQSYSNLVS | 334 |
| 3 | RASQSISSYLN | 240 | AASSLQS | 294 | QQSYSTPLT | 333 |
| 4 | RSSQSLLHSNGYNYLD | 242 | LGSNRAS | 295 | MQALQTPFT | 335 |
| 5 | RSSQSLLHSNGYNYLD | 242 | LGSNRAS | 295 | MQGLQTPHT | 336 |
| 6 | RASQSISRNLN | 243 | KASNLKG | 296 | QQTYSAPL | 337 |
| 7 | RSSQSLLHSNGYNYLD | 242 | LGSNRAS | 295 | MQTLQTPLT | 338 |

TABLE 9-continued

LCDRs using the Chothia Numbering Scheme

| CD8 Binder | L-CDR1 Sequence | SEQ ID NO: | L-CDR2 Sequence | SEQ ID NO: | L-CDR3 Sequence | SEQ ID NO: |
|---|---|---|---|---|---|---|
| 8 | RASQSVSASDLA | 244 | GASTRAT | 297 | QQYGDSPGS | 339 |
| 9 | QASQDIGNYLN | 245 | AASTLQR | 298 | QQANSFPPT | 340 |
| 10 | RASQSISTHLA | 246 | GASTRAT | 297 | QQYGNSRT | 341 |
| 11 | RASQTISNYLN | 247 | AASTLQS | 299 | QQSYSTPPT | 342 |
| 12 | RASQGIRNDLG | 248 | DASTLQS | 300 | QQSYSSPYT | 343 |
| 13 | RASQSISNYLN | 249 | AASSLQS | 294 | QQSYSTPYT | 344 |
| 14 | RSSQSLLHSNGYNYLD | 242 | LGSNRAS | 295 | MQGAHWPPT | 345 |
| 15 | RASQGISDSLA | 250 | GASSLRS | 301 | QQSYRTPYT | 346 |
| 16 | RASQSISNYLN | 249 | AASSLQS | 294 | QESFTTQWT | 347 |
| 17 | QASQDIHNYLN | 251 | DASNLET | 302 | QQANSFPPT | 340 |
| 18 | QASQDISNYLN | 241 | SASSLQS | 303 | QQRSNWPLYT | 348 |
| 19 | RASQSISDWLA | 252 | AASSLQT | 304 | QQAISFPIT | 349 |
| 20 | QASQDISNYLN | 241 | SASTLQS | 305 | QQSYSSPFT | 350 |
| 21 | RASQSISTWLA | 253 | AASTLQS | 299 | QQAISFPLT | 351 |
| 22 | RASQSISNYLN | 249 | AASTLQS | 299 | QQSYTFPIT | 352 |
| 23 | RSSQSLLHSNGYNYLD | 242 | DASHLET | 306 | QQYYSYPPT | 353 |
| 24 | QASQDISNYLN | 241 | AASTLHS | 307 | QQSYSAPLT | 354 |
| 25 | QASQDISNYLN | 241 | AASTLQS | 299 | QQSFSTFYT | 355 |
| 26 | QASQDISNYLN | 241 | AASTLQS | 299 | QQSYSIPFT | 356 |
| 27 | RASQSINRFLN | 254 | AASSLQN | 308 | QQSYSTPYT | 344 |
| 28 | RASQSISSYLN | 240 | AASSLQS | 294 | QQSYSTPLT | 333 |
| 29 | QASQDISNYLN | 241 | AASTLQS | 299 | QQSYSTPIT | 357 |
| 30 | RASQSVSTYLN | 255 | AASSLQS | 294 | QQSYTIPST | 358 |
| 31 | QASQDIAKYLN | 256 | AASSLQS | 294 | QQSYSAPPT | 359 |
| 32 | QASQGITNYLN | 257 | GASSLQS | 309 | QQSYSTPWT | 360 |
| 33 | RASQSISSYLN | 240 | AASSLQS | 294 | QQSYSTPLT | 333 |
| 34 | QASQDIHNYLN | 251 | AASTLQS | 299 | QQSYTTPLT | 361 |
| 35 | QASQDISNYLN | 241 | SAFSLQS | 310 | QQSYSAPIT | 362 |
| 36 | RASQSISSYLN | 240 | SASNLQS | 311 | QQRSNWPPVT | 363 |
| 37 | QANQDISNFLE | 258 | DASSLES | 312 | QQSYSIPIT | 364 |
| 38 | RASQGISNNLN | 259 | EASTLES | 313 | QQSYSTPLT | 333 |
| 39 | RSSQSLLHSNGYNYLD | 242 | GASTLET | 314 | MQGLQPPGT | 365 |
| 40 | RASQSISRSLV | 260 | AASTLQT | 315 | QQSYNHFRT | 366 |
| 41 | QASQDISNYLN | 241 | DASNLET | 302 | QRSDSTPLT | 367 |
| 42 | QASHDISKSLN | 261 | GASTLQS | 316 | QQLNSYPRT | 368 |
| 43 | RASQDIGAYLA | 262 | AASSLQS | 294 | QQSYSIPYT | 369 |

TABLE 9-continued

LCDRs using the Chothia Numbering Scheme

| | L-CDR1 | | L-CDR2 | | L-CDR3 | |
|---|---|---|---|---|---|---|
| CD8 Binder | Sequence | SEQ ID NO: | Sequence | SEQ ID NO: | Sequence | SEQ ID NO: |
| 44 | RASQSISSYLA | 263 | AASSLQS | 294 | QQSYSTPYT | 344 |
| 45 | RASQGIRSYLA | 264 | GASNLET | 317 | QQSYSTPYT | 344 |
| 46 | RASQSISSYLN | 240 | AASSLQS | 294 | QQTYSTPYT | 370 |
| 47 | RASQNIGTWLA | 265 | AASTLQS | 299 | QQSYSTPQT | 371 |
| 48 | RASQTISYYLN | 266 | AASTLQS | 299 | QQSYRTPYT | 346 |
| 49 | RSSQSLLHSNGYNYLD | 242 | MGSNRAS | 318 | MQGTHWPT | 372 |
| 50 | RASQNINNYLN | 267 | GASSLQS | 309 | QQTFSLPYT | 373 |
| 51 | RASQTISTYLN | 268 | DASNLET | 302 | QQSYSTPYT | 344 |
| 52 | RASRGIGNDLA | 269 | DASTLET | 319 | QQGYNMPLT | 374 |
| 52 | RASQTIGNYVN | 270 | GASNLHT | 320 | QQTYSAPLT | 375 |
| 54 | RASQFIGSWLA | 271 | AASTLQS | 299 | QQSYSFPWT | 376 |
| 55 | RASQSISSWMA | 272 | DASNLET | 302 | QQTYSTPYI | 377 |
| 56 | RASQGISNNLN | 259 | DASNLET | 302 | QQSYSSPWT | 378 |
| 57 | KSSQSVLYSSNNKNYLA | 273 | WASTRES | 321 | QQYASAPRT | 379 |
| 58 | RASQSISSYLN | 240 | KTSSLES | 322 | QQSFTIPYT | 380 |
| 59 | RVSQGISSYLN | 274 | GASSLQS | 309 | QQSYSTPLT | 333 |
| 60 | RASQSISDWLA | 252 | DASNLET | 302 | QQSYSTPLT | 333 |
| 61 | RASQGISNYLA | 275 | SASNLQS | 311 | QQTYRTPPT | 381 |
| 62 | RASQSIRNYLT | 276 | SASNLQS | 311 | QQSYSTPLT | 333 |
| 63 | RASQNIRLYLN | 277 | AASTLQS | 299 | QQSLTTPFT | 382 |
| 64 | QASQDIRKFLN | 278 | AASSLQS | 294 | QQLNGYPGT | 383 |
| 65 | RASQSISSYLN | 240 | TASNLQS | 323 | QQSYSLPLT | 384 |
| 66 | QASQDISNYLS | 279 | DASNLQS | 324 | QQTYTTPRT | 385 |
| 67 | RASQNVRSWLA | 280 | AASSLQS | 294 | QQSYNTPYT | 386 |
| 68 | RASQGIGNDLG | 281 | AASSLQS | 294 | QQSYAPPPT | 387 |
| 69 | RASQSISNWLA | 282 | GASNLET | 317 | QQSYSTPPT | 342 |
| 70 | RSSQSLLHSNGYNYLD | 242 | LGSNRAS | 295 | MQGLQTPLT | 388 |
| 71 | RASQSISSYLN | 240 | LASSLQS | 325 | QQSDSIPVT | 389 |
| 72 | QASQDISNYLN | 241 | STSSLQS | 326 | QQSYSTPYN | 390 |
| 73 | RASESIGSWLA | 283 | AASSLQS | 294 | QQSYSTPYT | 344 |
| 74 | RASQSISNYLN | 249 | AASSLQR | 327 | QQSYSTPLT | 333 |
| 75 | RASQSVTSNYLA | 284 | GASTRAT | 297 | QHYGSSPA | 391 |
| 76 | RASQSISSYLN | 240 | AASSLQS | 294 | QQSYSTPLT | 333 |
| 77 | RASQGISSYLA | 285 | AASTLQS | 299 | QQSYSTPPT | 342 |
| 78 | RASQDIGNYLN | 286 | AASSLQS | 294 | QQAYTYPYT | 392 |
| 79 | QASQDISNYLN | 241 | GASSLQS | 309 | QQSYTTPNT | 393 |
| 80 | RASQGISNYLA | 275 | AASTLQS | 299 | QQSYSTPYT | 344 |

TABLE 9-continued

| | LCDRs using the Chothia Numbering Scheme | | | | | |
|---|---|---|---|---|---|---|
| | L-CDR1 | | L-CDR2 | | L-CDR3 | |
| CD8 Binder | Sequence | SEQ ID NO: | Sequence | SEQ ID NO: | Sequence | SEQ ID NO: |
| 81 | RASQGISNGLS | 287 | DASNLET | 302 | QQSYSTPFT | 394 |
| 82 | RASQNIRNYLN | 288 | GASSLQS | 309 | QQSYSTPLT | 333 |
| 83 | QASLDINNYLN | 289 | KASSLES | 328 | QQSYSMPLT | 395 |
| 84 | QASQDISNYLN | 241 | AASSLQG | 329 | QQSYTTPWT | 396 |
| 85 | QASQDISNYLN | 241 | AASSLQS | 294 | QQSYSSPLT | 397 |
| 86 | QASQDISNYLN | 241 | KASSLES | 328 | QQSYSDPLT | 398 |
| 87 | QASQDISNYLN | 241 | GASTLQS | 316 | QQSYSAPIT | 362 |
| 88 | RASQSISNYLN | 249 | AASNLQS | 330 | QQSYTTPLT | 361 |
| 89 | RASQNIGNYLN | 290 | AASTLQS | 299 | QQSYSTPPWT | 399 |
| 90 | QASQDISNYLN | 241 | AASTLRS | 331 | QQSYQTPLT | 400 |
| 91 | QASQDISNYLN | 241 | AASTLQS | 299 | QQSYTTPPT | 401 |
| 92 | QASQDISNYLN | 241 | AASSLHS | 332 | QQSYSTPQT | 371 |
| 93 | RASQGIRNDLN | 291 | AASNLQS | 330 | QQANSFPIT | 402 |
| 94 | RASQGINTWLA | 292 | AASSLQS | 294 | QQSYSTPYT | 344 |
| 95 | QASQDISNYLN | 241 | AASTLQS | 299 | QQSYTVPPT | 403 |
| 96 | QASQDIRYFLN | 757 | AASTLQS | 299 | QQDDSFPLT | 404 |

TABLE 10

| | HCDRs using the IMGT Numbering Scheme | | | | | |
|---|---|---|---|---|---|---|
| | H-CDR1 | | H-CDR2 | | H-CDR3 | |
| CD8 Binder | Sequence | SEQ ID NO: | Sequence | SEQ ID NO: | Sequence | SEQ ID NO: |
| 1 | GGTFSSYA | 758 | IDPSDGNT | 817 | AKERAAAGYYYYMDV | 878 |
| 2 | GGTFNTYA | 759 | IDPSSGGT | 818 | AKEHAAGTYYYYMDV | 879 |
| 3 | GGTFSSYA | 758 | IDPSGGNT | 819 | AKERAAAGYYYYMDV | 878 |
| 4 | GYTFTGYY | 760 | INPNNGDT | 820 | AKEGYYYYGMDV | 880 |
| 5 | GYTFTDYY | 761 | INPNSGGT | 821 | AKEGDYYYGMDA | 881 |
| 6 | GYTFTRYD | 762 | INPNDGST | 822 | ARERGGMPDY | 882 |
| 7 | GYTFTSYA | 763 | INPNSGGT | 821 | ARGHGIPKY | 883 |
| 8 | GYTFTSYY | 764 | MNPNSGNT | 823 | ARVRSGSPQH | 884 |
| 9 | GHTFSRHY | 765 | MNPNSGNT | 823 | ARGGPWIVDAFDI | 885 |
| 10 | GYTFTSYG | 766 | ISAHNGVT | 824 | ARGIAVAGTDY | 886 |
| 11 | GGTFSNTD | 767 | INPSGGST | 825 | AREATWGPYYYYMDV | 887 |
| 12 | GYTFTRSY | 768 | ISPYNGNT | 826 | VRNKDGLQH | 888 |
| 13 | GDTFTGYY | 769 | INPNSGDT | 827 | AKDAKRVGYYYYMDV | 889 |
| 14 | GYTFTRYY | 770 | INPNSGGT | 821 | ARLVGGSPDY | 890 |

TABLE 10-continued

HCDRs using the IMGT Numbering Scheme

| CD8 Binder | H-CDR1 Sequence | SEQ ID NO: | H-CDR2 Sequence | SEQ ID NO: | H-CDR3 Sequence | SEQ ID NO: |
|---|---|---|---|---|---|---|
| 15 | GYTFTNYD | 771 | INPNSGGT | 821 | ARGAMVDY | 891 |
| 16 | GGTFSNTD | 767 | INPSDGDT | 828 | ARGNYVGSYYYGMDV | 892 |
| 17 | GYTFTNYY | 772 | INPNSGDT | 827 | ARDSRGDWYFDL | 893 |
| 18 | GYGFTRYS | 773 | IDPSGGST | 829 | TRHGGRGLADY | 894 |
| 19 | GYTFTSRD | 774 | IDPKSGDT | 830 | ARLKELSSILDAFDI | 895 |
| 20 | GYTFTSYD | 775 | INPGAGSS | 831 | ARERFGTGYYYYMDV | 896 |
| 21 | GFTFSNSD | 776 | ISGDGGTT | 832 | ARVIGEMVDDAFDL | 897 |
| 22 | GYTFTGYY | 760 | INPNSGDT | 827 | ARERLFGTYYYYMDV | 898 |
| 23 | GYTFTTYD | 777 | HPIFGTA | 833 | ARADGELTDY | 899 |
| 24 | GFTFSSYT | 778 | I-GTGGGI | 834 | ARHHLPAHYYYYMDV | 900 |
| 25 | GGTFSRYD | 779 | INPNSGDT | 827 | ARDVPAGRYYYYMDV | 901 |
| 26 | GNTFTSYY | 780 | INPSDGST | 835 | AKDRGVGRYYYYMDV | 902 |
| 27 | GGTFSRYA | 781 | INPSDGST | 835 | AKDSRYGRYYYYMDV | 903 |
| 28 | GGTFSNYA | 782 | INPNGGSP | 836 | AKEIVVGPYYYYMDV | 904 |
| 29 | GGTFTRYA | 783 | INPNSGDT | 827 | ARGMVRGPYYYYMDV | 905 |
| 30 | GGTFSSYA | 758 | INPSGGST | 825 | AREGVTGPYYYYMDV | 906 |
| 31 | GGTFSRFD | 784 | INPSDGST | 835 | ARDAAAGTRYYYYYG-MDV | 907 |
| 32 | GGTFSSHA | 785 | INPSGGST | 825 | ARELYSSTYYYYMDV | 908 |
| 33 | GGTFSSYA | 758 | INPNTGGT | 837 | ARALYSGPYYYYMDV | 909 |
| 34 | GFTFSNSD | 776 | ISGSGGST | 838 | AKEHAAGTYYYYMDV | 879 |
| 35 | GGTFGSYG | 786 | ISGYNGDT | 839 | ARDSLVGRYYYYMDV | 910 |
| 36 | GYIFTDYD | 787 | ISADNGNT | 840 | ARRSELDY | 911 |
| 37 | GYTFTSYH | 788 | ISPNSGAT | 841 | ARGDDNDY | 912 |
| 38 | GYTFTSYD | 775 | INPNSGNT | 842 | ARGEEVDY | 913 |
| 39 | GYTFTSYP | 789 | INPSGGST | 825 | ARGRRVPDY | 914 |
| 40 | GYTFTDYY | 761 | INPKSGAT | 843 | ARGKVTTDY | 915 |
| 41 | GFTFSSFE | 790 | ISESGDSS | 844 | ASGRELIEY | 916 |
| 42 | GFTFDDYA | 791 | I-GTGGGT | 845 | ARVYDFPDV | 917 |
| 43 | GYTFTDSY | 792 | MNPSNGDT | 846 | ARSTYSHIDY | 918 |
| 44 | GYTFTNYY | 772 | ISPSDGST | 847 | AREDSSGFDY | 919 |
| 45 | GYTFMNYY | 793 | INPSGGST | 825 | ARDQGGGFDY | 920 |
| 46 | GYTFTSYY | 764 | FDPEDGET | 848 | ARDQGWGMDV | 921 |
| 47 | GYTFTSYY | 764 | INPKSGRT | 849 | ARLTEGIPDY | 922 |
| 48 | GYTLNDYY | 794 | INPGGGST | 850 | ARDRYGPFDY | 923 |
| 49 | GYTFTSYD | 775 | MNPKTGDT | 851 | TRLVAGGAPDY | 924 |
| 50 | GYTFTGYY | 760 | IDPSDGYT | 852 | ARDGFTGDIAY | 925 |

TABLE 10-continued

| HCDRs using the IMGT Numbering Scheme | | | | | |
|---|---|---|---|---|---|
| | H-CDR1 | | H-CDR2 | | H-CDR3 |
| CD8 Binder | Sequence | SEQ ID NO: | Sequence | SEQ ID NO: | Sequence | SEQ ID NO: |
| 51 | GYTFTGYY | 760 | INPNSGGT | 821 | ARVDDSSSPDY | 926 |
| 52 | GYTFTGYY | 760 | IMPISGTT | 853 | TTGPDGTEVDY | 927 |
| 52 | GYTFTNHY | 795 | MNPNSGNT | 823 | ASSESGSDLDY | 928 |
| 54 | GYTFTNYY | 772 | MSPTSGDT | 854 | AREVEIEGYMDV | 929 |
| 55 | GYTFTSYY | 764 | INPNSGDT | 827 | AKDLDDDWYMDV | 930 |
| 56 | GYTFTSYY | 764 | IDPSGDIT | 855 | TTDSTTWDAFDI | 931 |
| 57 | GYTFTDYY | 761 | INPNSGGT | 821 | ARVLVGSGSPDY | 932 |
| 58 | GYTFTENE | 796 | IETSGGST | 856 | AREAAAGLDFQH | 933 |
| 59 | GYTFASYD | 797 | INPNSGGT | 821 | ARANSWDAMVIDY | 934 |
| 60 | GFTFSNSD | 776 | ISGSGVTT | 857 | AREHSSSWYTFDY | 935 |
| 61 | GYTFTAYY | 798 | INPNSGGT | 821 | ARDDDSSGYYLDY | 936 |
| 62 | GYTFTNYY | 772 | INPSGGST | 825 | ARASGDYMDLIDY | 937 |
| 63 | GYTFTDYH | 799 | INPDSGGT | 858 | ALVGSSGYLAPTH | 938 |
| 64 | GYPFTDYY | 800 | MNPNSGNT | 823 | ARVRGDGYNLGDY | 939 |
| 65 | GYTFSDYY | 801 | INPNSGGT | 821 | ARDVDTAMGAGDY | 940 |
| 66 | GYTFTDYY | 761 | INPSGGSA | 859 | ARVARWGYGDYPDY | 941 |
| 67 | GDTFTTHD | 802 | ISPSDGST | 847 | ARDRNGDYYYGMDV | 942 |
| 68 | GDTFTNYY | 803 | INPISGGT | 860 | AREGLGSSWYVLDY | 943 |
| 69 | GYTFTSYD | 775 | ISADNGDT | 861 | ARDGSHYGYYGMDV | 944 |
| 70 | GYTFTSYD | 775 | ISPIYGTP | 862 | ASPGPEGYYYGMDV | 945 |
| 71 | GYTFTDNY | 804 | MNPNSGNT | 823 | ASYHWDYGDYRFDY | 946 |
| 72 | GYTFTSYY | 764 | MNPNSGNT | 823 | ARVEIDYGDSPPDY | 947 |
| 73 | GGTSSSYA | 805 | INPSDGDT | 828 | ARGAEWELRYAFDI | 948 |
| 74 | GYTFTTYD | 777 | INPSGGTT | 863 | ARETYYGLYYYGMDV | 949 |
| 75 | GYTFTSYD | 775 | MNPKSGNT | 864 | ARAPSLRGYSYGPDY | 950 |
| 76 | GGTFTSYD | 806 | INPSGGST | 825 | AKDRQERYYYYYMDV | 951 |
| 77 | GYTFTSYD | 775 | INPSDGST | 835 | AKDRSYGDYYYGMDV | 952 |
| 78 | GGTFTSYD | 806 | INPGGGNA | 865 | AREVFSENYYYYMDV | 953 |
| 79 | GYTFTSYY | 764 | INPSDGST | 835 | AREWDYTHYYYGMDV | 954 |
| 80 | GNTFTSHW | 807 | FDPEDGET | 848 | ARGDSSGYYQYYFDY | 955 |
| 81 | GYTFTSYD | 775 | ITPVFGIA | 866 | ARGSWDSSSWYIPEY | 956 |
| 82 | GFTFSDYD | 808 | INPRGGST | 867 | ASLVWGGAYYYYMDV | 957 |
| 83 | GYTFTSYG | 766 | MNPNNGDT | 868 | TTPVFSGSYYWYFDP | 958 |
| 84 | GYTFTSYD | 775 | INPSGGGT | 869 | TTDQAVAGPYYYGMDV | 959 |
| 85 | GGTFSSYA | 758 | INPGSGNT | 870 | ARDRWLAGPYYYGMDV | 960 |
| 86 | GYMFTGHD | 809 | HPIFGTP | 871 | ARVMGPVDYYYYGMDV | 961 |
| 87 | GYIFSNYD | 810 | INPSDGST | 835 | ARDLGPFGSYYYYMDV | 962 |

TABLE 10-continued

HCDRs using the IMGT Numbering Scheme

| CD8 Binder | H-CDR1 Sequence | SEQ ID NO: | H-CDR2 Sequence | SEQ ID NO: | H-CDR3 Sequence | SEQ ID NO: |
|---|---|---|---|---|---|---|
| 88 | GFTFSSYA | 811 | INGDGDDT | 872 | AREGVVVPPYYYYMDV | 963 |
| 89 | GYTFTTYY | 812 | IDPNSGDT | 873 | ARSSGWSRYYYYYMDV | 964 |
| 90 | GSTFTNYQ | 813 | INPSGGST | 825 | ARDNGMTTGYYYYMDV | 965 |
| 91 | GYTFTSYD | 775 | INPSGGST | 825 | ARDRAMVTGYYYGMDV | 966 |
| 92 | GYTFTSYD | 775 | VNPSDGNT | 874 | ARDRGYGDRGYYYGMDV | 967 |
| 93 | GGTLSSYD | 814 | INTYNGNT | 875 | ATSPKATADYYYYMDV | 968 |
| 94 | GYTFTSYD | 775 | INPSDGIT | 876 | TTSTVTPSYYYYYGMDV | 969 |
| 95 | GYTFTSHA | 815 | INPRDGDT | 877 | AREPVAGTGYYYYYGMDV | 970 |
| 96 | GGTFNSYG | 816 | MNPNSGNT | 823 | ARDNLAGFWSDYYYYGMDV | 971 |
| 97 | GRTFSGYV | 1066 | ISRGGLST | 1067 | AADRSDLYEITAASNIDS | 1068 |

TABLE 11

LCDRs using the IMGT Numbering Scheme

| CD8 Binder | L-CDR1 Sequence | SEQ ID NO: | L-CDR2 Sequence | SEQ ID NO: | L-CDR3 Sequence | SEQ ID NO: |
|---|---|---|---|---|---|---|
| 1 | QSISSY | 972 | AAS | 1021 | QQSYSTPLT | 333 |
| 2 | QDISNY | 973 | AAS | 1021 | QQSYSNLVS | 334 |
| 3 | QSISSY | 972 | AAS | 1021 | QQSYSTPLT | 333 |
| 4 | QSLLHSNGYNY | 974 | LGS | 1022 | MQALQTPFT | 335 |
| 5 | QSLLHSNGYNY | 974 | LGS | 1022 | MQGLQTPHT | 336 |
| 6 | QSISRN | 975 | KAS | 1023 | QQTYSAPL | 337 |
| 7 | QSLLHSNGYNY | 974 | LGS | 1022 | MQTLQTPLT | 338 |
| 8 | QSVSASD | 976 | GAS | 1024 | QQYGDSPGS | 339 |
| 9 | QDIGNY | 977 | AAS | 1021 | QQANSFPPT | 340 |
| 10 | QSISTH | 978 | GAS | 1024 | QQYGNSRT | 341 |
| 11 | QTISNY | 979 | AAS | 1021 | QQSYSTPPT | 342 |
| 12 | QGIRND | 980 | DAS | 1025 | QQSYSSPYT | 343 |
| 13 | QSISNY | 981 | AAS | 1021 | QQSYSTPYT | 344 |
| 14 | QSLLHSNGYNY | 974 | LGS | 1022 | MQGAHWPPT | 345 |
| 15 | QGISDS | 982 | GAS | 1024 | QQSYRTPYT | 346 |
| 16 | QSISNY | 981 | AAS | 1021 | QESFTTQWT | 347 |
| 17 | QDIHNY | 983 | DAS | 1025 | QQANSFPPT | 340 |
| 18 | QDISNY | 973 | SAS | 1026 | QQRSNWPLYT | 348 |
| 19 | QSISDW | 984 | AAS | 1021 | QQAISFPIT | 349 |
| 20 | QDISNY | 973 | SAS | 1026 | QQSYSSPFT | 350 |

TABLE 11-continued

LCDRs using the IMGT Numbering Scheme

| CD8 Binder | L-CDR1 Sequence | SEQ ID NO: | L-CDR2 Sequence | SEQ ID NO: | L-CDR3 Sequence | SEQ ID NO: |
|---|---|---|---|---|---|---|
| 21 | QSISTW | 985 | AAS | 1021 | QQAISFPLT | 351 |
| 22 | QSISNY | 981 | AAS | 1021 | QQSYTFPIT | 352 |
| 23 | QSLLHSNGYNY | 974 | DAS | 1025 | QQYYSYPPT | 353 |
| 24 | QDISNY | 973 | AAS | 1021 | QQSYSAPLT | 354 |
| 25 | QDISNY | 973 | AAS | 1021 | QQSFSTFYT | 355 |
| 26 | QDISNY | 973 | AAS | 1021 | QQSYSIPFT | 356 |
| 27 | QSINRF | 986 | AAS | 1021 | QQSYSTPYT | 344 |
| 28 | QSISSY | 972 | AAS | 1021 | QQSYSTPLT | 333 |
| 29 | QDISNY | 973 | AAS | 1021 | QQSYSTPIT | 357 |
| 30 | QSVSTY | 987 | AAS | 1021 | QQSYTIPST | 358 |
| 31 | QDIAKY | 988 | AAS | 1021 | QQSYSAPPT | 359 |
| 32 | QGITNY | 989 | GAS | 1024 | QQSYSTPWT | 360 |
| 33 | QSISSY | 972 | AAS | 1021 | QQSYSTPLT | 333 |
| 34 | QDIHNY | 983 | AAS | 1021 | QQSYTTPLT | 361 |
| 35 | QDISNY | 973 | SAF | 1027 | QQSYSAPIT | 362 |
| 36 | QSISSY | 972 | SAS | 1026 | QQRSNWPPVT | 363 |
| 37 | QDISNF | 990 | DAS | 1025 | QQSYSIPIT | 364 |
| 38 | QGISNN | 991 | EAS | 1028 | QQSYSTPLT | 333 |
| 39 | QSLLHSNGYNY | 974 | GAS | 1024 | MQGLQPPGT | 365 |
| 40 | QSISRS | 992 | AAS | 1021 | QQSYNHFRT | 366 |
| 41 | QDISNY | 973 | DAS | 1025 | QRSDSTPLT | 367 |
| 42 | HDISKS | 993 | GAS | 1024 | QQLNSYPRT | 368 |
| 43 | QDIGAY | 994 | AAS | 1021 | QQSYSIPYT | 369 |
| 44 | QSISSY | 972 | AAS | 1021 | QQSYSTPYT | 344 |
| 45 | QGIRSY | 995 | GAS | 1024 | QQSYSTPYT | 344 |
| 46 | QSISSY | 972 | AAS | 1021 | QQTYSTPYT | 370 |
| 47 | QNIGTW | 996 | AAS | 1021 | QQSYSTPQT | 371 |
| 48 | QTISYY | 997 | AAS | 1021 | QQSYRTPYT | 346 |
| 49 | QSLLHSNGYNY | 974 | MGS | 1029 | MQGTHWPT | 372 |
| 50 | QNINNY | 998 | GAS | 1024 | QQTFSLPYT | 373 |
| 51 | QTISTY | 999 | DAS | 1025 | QQSYSTPYT | 344 |
| 52 | RGIGND | 1000 | DAS | 1025 | QQGYNMPLT | 374 |
| 52 | QTIGNY | 1001 | GAS | 1024 | QQTYSAPLT | 375 |
| 54 | QFIGSW | 1002 | AAS | 1021 | QQSYSFPWT | 376 |
| 55 | QSISSW | 1003 | DAS | 1025 | QQTYSTPYI | 377 |
| 56 | QGISNN | 991 | DAS | 1025 | QQSYSSPWT | 378 |
| 57 | QSVLYSSNNKNY | 1004 | WAS | 1030 | QQYASAPRT | 379 |

TABLE 11-continued

LCDRs using the IMGT Numbering Scheme

| CD8 Binder | L-CDR1 Sequence | SEQ ID NO: | L-CDR2 Sequence | SEQ ID NO: | L-CDR3 Sequence | SEQ ID NO: |
|---|---|---|---|---|---|---|
| 58 | QSISSY | 972 | KTS | 1031 | QQSFTIPYT | 380 |
| 59 | QGISSY | 1005 | GAS | 1024 | QQSYSTPLT | 333 |
| 60 | QSISDW | 984 | DAS | 1025 | QQSYSTPLT | 333 |
| 61 | QGISNY | 1006 | SAS | 1026 | QQTYRTPPT | 381 |
| 62 | QSIRNY | 1007 | SAS | 1026 | QQSYSTPLT | 333 |
| 63 | QNIRLY | 1008 | AAS | 1021 | QQSLTTPFT | 382 |
| 64 | QDIRKF | 1009 | AAS | 1021 | QQLNGYPGT | 383 |
| 65 | QSISSY | 972 | TAS | 1032 | QQSYSLPLT | 384 |
| 66 | QDISNY | 973 | DAS | 1025 | QQTYTTPRT | 385 |
| 67 | QNVRSW | 1010 | AAS | 1021 | QQSYNTPYT | 386 |
| 68 | QGIGND | 1011 | AAS | 1021 | QQSYAPPPT | 387 |
| 69 | QSISNW | 1012 | GAS | 1024 | QQSYSTPPT | 342 |
| 70 | QSLLHSNGYNY | 974 | LGS | 1022 | MQGLQTPLT | 388 |
| 71 | QSISSY | 972 | LAS | 1033 | QQSDSIPVT | 389 |
| 72 | QDISNY | 973 | STS | 1034 | QQSYSTPYN | 390 |
| 73 | ESIGSW | 1013 | AAS | 1021 | QQSYSTPYT | 344 |
| 74 | QSISNY | 981 | AAS | 1021 | QQSYSTPLT | 333 |
| 75 | QSVTSNY | 1014 | GAS | 1024 | QHYGSSPA | 391 |
| 76 | QSISSY | 972 | AAS | 1021 | QQSYSTPLT | 333 |
| 77 | QGISSY | 1005 | AAS | 1021 | QQSYSTPPT | 342 |
| 78 | QDIGNY | 977 | AAS | 1021 | QQAYTYPYT | 392 |
| 79 | QDISNY | 973 | GAS | 1024 | QQSYTTPNT | 393 |
| 80 | QGISNY | 1006 | AAS | 1021 | QQSYSTPYT | 344 |
| 81 | QGISNG | 1015 | DAS | 1025 | QQSYSTPFT | 394 |
| 82 | QNIRNY | 1016 | GAS | 1024 | QQSYSTPLT | 333 |
| 83 | LDINNY | 1017 | KAS | 1023 | QQSYSMPLT | 395 |
| 84 | QDISNY | 973 | AAS | 1021 | QQSYTTPWT | 396 |
| 85 | QDISNY | 973 | AAS | 1021 | QQSYSSPLT | 397 |
| 86 | QDISNY | 973 | KAS | 1023 | QQSYSDPLT | 398 |
| 87 | QDISNY | 973 | GAS | 1024 | QQSYSAPIT | 362 |
| 88 | QSISNY | 981 | AAS | 1021 | QQSYTTPLT | 361 |
| 89 | QNIGNY | 1018 | AAS | 1021 | QQSYSTPPWT | 399 |
| 90 | QDISNY | 973 | AAS | 1021 | QQSYQTPLT | 400 |
| 91 | QDISNY | 973 | AAS | 1021 | QQSYTTPPT | 401 |
| 92 | QDISNY | 973 | AAS | 1021 | QQSYSTPQT | 371 |
| 93 | QGIRND | 980 | AAS | 1021 | QQANSFPIT | 402 |

TABLE 11-continued

LCDRs using the IMGT Numbering Scheme

| | L-CDR1 | | L-CDR2 | | L-CDR3 | |
|---|---|---|---|---|---|---|
| CD8 Binder | Sequence | SEQ ID NO: | Sequence | SEQ ID NO: | Sequence | SEQ ID NO: |
| 94 | QGINTW | 1019 | AAS | 1021 | QQSYSTPYT | 344 |
| 95 | QDISNY | 973 | AAS | 1021 | QQSYTVPPT | 403 |
| 96 | QDIRYF | 1020 | AAS | 1021 | QQDDSFPLT | 404 |

TABLE 12

| CD8 Binder Variant | Full Binder Sequence | SEQ ID NO: |
|---|---|---|
| 98 | QVQLVQSGAEVKKPGASVKVSCKASGGTFS SYAISWVRQAPGQGLEWMGIIDPSDGNTNY A-QNFQGRVTMTRDTSTSTVYMELSSLRSE DTAVYYCAKERAAAGYYYYMDVWGQGTTVT VSSGGGGSGGGGSGGGGSDIQMTQSPSSLS ASVGDRVTITCRASQSISSYLNWYQQKPGK APKLLIYAAS-SLQSGVPSRFSGSGSGTDF TLTISSLQPEDFATYYCQQSYSTPLTFGGG TKVEIKR | 1035 |
| 99 | DIQMTQSPSSLSASVGDRVTITCRASQSIS SYLNWYQQKPGKAPKLLIYAAS-SLQSGVP SRFSGSGSGTDFTLTISSLQPEDFATYYCQ QSYSTPLTFGGGTKVEIKRGGGGSGGGGSG GGGSQVQLVQSGAEVKKPGASVKVSCKASG GTFSSYAISWVRQAPGQGLEWMGI-IDPSD GNTNYAQNFQGRVTMTRDTSTSTVYMELSS LRSEDTAVYYCAKERAAAGYYYYMDVWGQG TTVTVSS | 1036 |
| 100 | QVQLVQSGAEVKKPGASVKVSCKASGGTFS SYAISWVRQAPGQCLEWMGIIDPSDGNTNY A-QNFQGRVTMTRDTSTSTVYMELSSLRSE DTAVYYCAKERAAAGYYYYMDVWGQGTTVT VSSGGGGSGGGGSGGGGSDIQMTQSPSSLS ASVGDRVTITCRASQSISSYLNWYQQKPGK APKLLIYAAS-SLQSGVPSRFSGSGSGTDF TLTISSLQPEDFATYYCQQSYSTPLTFGCG TKVEIKR | 1037 |
| 101 | DIQMTQSPSSLSASVGDRVTITCRASQSIS SYLNWYQQKPGKAPKLLIYAAS-SLQSGVP SRFSGSGSGTDFTLTISSLQPEDFATYYCQ QSYSTPLTFGCGTKVEIKRGGGGSGGGGSG GGGSQVQLVQSGAEVKKPGASVKVSCKASG GTFSSYAISWVRQAPGQCLEWMGIIDPSDG NTNYA-QNFQGRVTMTRDTSTSTVYMELSS LRSEDTAVYYCAKERAAAGYYYYMDVWGQG TTVTVSS | 1038 |
| 102 | QVQLVQSGAEVKKPGASVKVSCKASGGTFS SYAISWVRQAPGQCLEWMGIIDPSDGNTNY A-QNFQGRVTMTRDTSTSTVYMELSSLRSE DTAVYYCAKERAAAGYYYYMDVWGQGTTVT VSSGGGGSGGGGSGGGGSDIQMTQSPSSLS ASVGDRVTITCRASQSISSYLNWYQQKPGK APKLLIYAAS-SLQSGVPSRFSGSGSGTDF TLTISSLQPEDFATYYCQQSYSTPLTFGCG TKVEIKR | 1037 |
| 103 | DIQMTQSPSSLSASVGDRVTITCRASQSIS SYLNWYQQKPGKAPKLLIYAAS-SLQSGVP SRFSGSGSGTDFTLTISSLQPEDFATYYCQ QSYSTPLTFGCGTKVEIKRGGGGSGGGGSG GGGSQVQLVQSGAEVKKPGASVKVSCKASG GTFSSYAISWVRQAPGQCLEWMGIIDPSDG NTNYA-QNFQGRVTMTRDTSTSTVYMELSS LRSEDTAVYYCAKERAAAGYYYYMDVWGQG TTVTVSS | |
| 104 | DIVMTQSPLSLPVTPGEPASISCRSSQSLL HSNGYNYLDWYLQKPGQSPQLLIYL-GSNR ASGVPDRFSGSGSGTDFTLKISRVEAEDVG VYYCMQGLQTPHTFGQGTKVEIKRGGGGSG GGGSGGGGSQVQLVQSGAEVKKPGASVKVS CKASGYTFTDYYIQWVRQAPGQGLEW-MGW INPNSGGTSYAQKFQGRVTMTRDTSTSTVY MELSSLRSEDTAVYYCAKEGDYYYGMDAWG QGTMVTVSS | 1039 |
| 105 | QVQLVQSGAEVKKPGASVKVSCKASGYTFT DYYIQWVRQAPGQGLEWMGWINPNSGGTSY A-QKFQGRVTMTRDTSTSTVYMELSSLRSE DTAVYYCAKEGDYYYGMDAWGQGTMVTVSS GGGGSGGGGSGGGGSDIVMTQSPLSLPVTP GEPASISCRSSQSLLHSNGYNYLDWYLQKP GQSPQLLI-YLGSNRASGVPDRFSGSGSGT DFTLKISRVEAEDVGVYYCMQGLQTPHTFG QGTKVEIKR | 1040 |
| 106 | DIVMTQSPLSLPVTPGEPASISCRSSQSLL HSNGYNYLDWYLQKPGQSPQLLIYL-GSNR ASGVPDRFSGSGSGTDFTLKISRVEAEDVG VYYCMQGLQTPHTFGQGTKVEIKRGGGGSG GGGSGGGGSQVQLVQSGAEVKKPGASVKVS CKASGYTFTDYYIQWVRQAPGQGLEW-MGW INPNSGGTSYAQKFQGRVTMTRDTSTSTVY MELSSLRSEDTAVYYCAKEGDYYYGMDAWG QGTMVTVSS | 1039 |
| 107 | QVQLVQSGAEVKKPGASVKVSCKASGYTFT DYYIQWVRQAPGQCLEWMGWINPNSGGTSY A-QKFQGRVTMTRDTSTSTVYMELSSLRSE DTAVYYCAKEGDYYYGMDAWGQGTMVTVSS GGGGSGGGGSGGGGSDIVMTQSPLSLPVTP GEPASISCRSSQSLLHSNGYNYLDWYLQKP GQSPQLLI-YLGSNRASGVPDRFSGSGSGT DFTLKISRVEAEDVGVYYCMQGLQTPHTFG CGTKVEIKR | 1041 |
| 108 | DIVMTQSPLSLPVTPGEPASISCRSSQSLL HSNGYNYLDWYLQKPGQSPQLLIYL-GSNR ASGVPDRFSGSGSGTDFTLKISRVEAEDVG VYYCMQGLQTPHTFGCGTKVEIKRGGGGSG GGGSGGGGSQVQLVQSGAEVKKPGASVKVS CKASGYTFTDYYIQWVRQAPGQCLEW-MGW INPNSGGTSYAQKFQGRVTMTRDTSTSTVY MELSSLRSEDTAVYYCAKEGDYYYGMDAWG QGTMVTVSS | 1042 |
| 109 | QVQLVQSGAEVKKPGASVKVSCKASGYTFT DYYIQWVRQAPGQCLEWMGWINPNSGGTSY A-QKFQGRVTMTRDTSTSTVYMELSSLRSE DTAVYYCAKEGDYYYGMDAWGQGTMVTVSS | 1041 |

TABLE 12-continued

| CD8 Binder Variant | Full Binder Sequence | SEQ ID NO: |
|---|---|---|
| | GGGGSGGGGSGGGGSDIVMTQSPLSLPVTP GEPASISCRSSQSLLHSNGYNYLDWYLQKP GQSPQLLI-YLGSNRASGVPDRFSGSGSGT DFTLKISRVEAEDVGVYYCMQGLQTPHTFG CGTKVEIKR | |
| 110 | DIVMTQSPLSLPVTPGEPASISCRSSQSLL HSNGYNYLDWYLQKPGQSPQLLIYL-GSNR ASGVPDRFSGSGSGTDFTLKISRVEAEDVG VYYCMQGLQTPHTFGCGTKVEIKRGGGGSG GGGSGGGGSQVQLVQSGAEVKKPGASVKVS CKASGYTFTDYYIQWVRQAPGQCLEW-MGW INPNSGGTSYAQKFQGRVTMTRDTSTSTVY MELSSLRSEDTAVYYCAKEGDYYYGMDAWG QGTMVTVSS | 1042 |
| 111 | QVQLVQSGAEVKKPGASVKVSCKASGYTFT SYYMHWVRQAPGQCLEWMGGFDPEDGETIY A-QKFQGRVTMTRDTSTSTVYMELSSLRSE DTAVYYCARDQGWGMDVWGQGTTVTVSSGG GGSGGGGSGGGGSDIQMTQSPSSLSASVGD RVTITCRASQSISSYLNWYQQKPGKAPKLL IYAAS-SLQSGVPSRFSGSGSGTDFTLTIS SLQPEDFATYYCQQTYSTPYTFGCGTKLEI KR | 1043 |
| 112 | QVQLVQSGAEVKKPGASVKVSCKASGYTFT SYYMHWVRQAPGQCLEWMGGFDPEDGETIY A-QKFQGRVTMTRDTSTSTVYMELSSLRSE DTAVYYCARDQGWGMDVWGQGTTVTVSSGG GGSGGGGSGGGGSDIQMTQSPSSLSASVGD RVTITCRASQSISSYLNWYQQKPGKAPKLL IYAAS-SLQSGVPSRFSGSGSGTDFTLTIS SLQPEDFATYYCQQTYSTPYTFGCGTKLEI KR | 1043 |
| 113 | QVQLVQSGAEVKKPGASVKVSCKASGYTFT SYYMHWVRQAPGQCLEWMGGFDPEDGETIY A-QKFQGRVTMTRDTSTSTVYMELSSLRSE DTAVYYCARDQGWGMDVWGQGTTVTVSSGG GGSGGGGSGGGGSDIQMTQSPSSLSASVGD RVTITCRASQSISSYLNWYQQKPGKAPKLL IYAAS-SLQSGVPSRFSGSGSGTDFTLTIS SLQPEDFATYYCQQTYSTPYTFGQGTKLEI KR | 1044 |
| 114 | DIQMTQSPSSLSASVGDRVTITCRASQSIS SYLNWYQQKPGKAPKLLIYAAS-SLQSGVP SRFSGSGSGTDFTLTISSLQPEDFATYYCQ QTYSTPYTFGCGTKLEIKRGGGGSGGGGSG GGGSQVQLVQSGAEVKKPGASVKVSCKASG YTFTSYYMHWVRQAPGQCLEWMGGFDPEDG ETIYA-QKFQGRVTMTRDTSTSTVYMELSS LRSEDTAVYYCARDQGWGMDVWGQGTTVTV SS | 1045 |
| 115 | DIQMTQSPSSLSASVGDRVTITCRASQSIS SYLNWYQQKPGKAPKLLIYAAS-SLQSGVP SRFSGSGSGTDFTLTISSLQPEDFATYYCQ QTYSTPYTFGCGTKLEIKRGGGGSGGGGSG GGGSQVQLVQSGAEVKKPGASVKVSCKASG YTFTSYYMHWVRQAPGQCLEWMGGFDPEDG ETIYA-QKFQGRVTMTRDTSTSTVYMELSS LRSEDTAVYYCARDQGWGMDVWGQGTTVTV SS | 1045 |
| 116 | DIQMTQSPSSLSASVGDRVTITCRASQSIS SYLNWYQQKPGKAPKLLIYAAS-SLQSGVP SRFSGSGSGTDFTLTISSLQPEDFATYYCQ QTYSTPYTFGQGTKLEIKRGGGGSGGGGSG GGGSQVQLVQSGAEVKKPGASVKVSCKASG YTFTSYYMHWVRQAPGQGLEWMGGFDPEDG -ETIYAQKFQGRVTMTRDTSTSVYMELSSL RSEDTAVYYCARDQGWGMDVWGQGTTVTVS S | 1046 |

TABLE 12-continued

| CD8 Binder Variant | Full Binder Sequence | SEQ ID NO: |
|---|---|---|
| 117 | DIQMTQSPSSLSASVGDRVTITCRASQTIG NYVNWYQQKPGKAPKLLI-YGASNLHTGVP SRFSGSGSGTDFTLTISSLQPEDFATYYCQ QTYSAPLTFGGGTKVEIKRGGGGSGGGGSG GGGSQVQLVQSGAEVKKPGASVKVSCKASG YTFTNHYMHWVRQAPGQGLEW-MGWMNPNS GNTGYAQKFQGRVTMTRDTSTSTVYMELSS LRSEDTAVYYCASSESGSDLDYWGQGTLVT VSS | 1047 |
| 118 | QVQLVQSGAEVKKPGASVKVSCKASGYTFT NHYMHWVRQAPGQGLEWMGWMNPNSGNTGY A-QKFQGRVTMTRDTSTSTVYMELSSLRSE DTAVYYCASSESGSDLDYWGQGTLVTVSSG GGGSGGGGSGGGGSDIQMTQSPSSLSASVG DRVTITCRASQTIGNYVNWYQQKPGKAPKL LI-YGASNLHTGVPSRFSGSGSGTDFTLTI SSLQPEDFATYYCQQTYSAPLTFGGGTKVE IKR | 1048 |
| 119 | DIQMTQSPSSLSASVGDRVTITCRASQTIG NYVNWYQQKPGKAPKLLI-YGASNLHTGVP SRFSGSGSGTDFTLTISSLQPEDFATYYCQ QTYSAPLTFGGGTKVEIKRGGGGSGGGGSG GGGSQVQLVQSGAEVKKPGASVKVSCKASG YTFTNHYMHWVRQAPGQGLEW-MGWMNPNS GNTGYAQKFQGRVTMTRDTSTSTVYMELSS LRSEDTAVYYCASSESGSDLDYWGQGTLVT VSS | 1047 |
| 120 | QVQLVQSGAEVKKPGASVKVSCKASGYTFT NHYMHWVRQAPGQCLEWMGWMNPNSGNTGY A-QKFQGRVTMTRDTSTSTVYMELSSLRSE DTAVYYCASSESGSDLDYWGQGTLVTVSSG GGGSGGGGSGGGGSDIQMTQSPSSLSASVG DRVTITCRASQTIGNYVNWYQQKPGKAPKL LI-YGASNLHTGVPSRFSGSGSGTDFTLTI SSLQPEDFATYYCQQTYSAPLTFGCGTKVE IKR | 1049 |
| 121 | DIQMTQSPSSLSASVGDRVTITCRASQTIG NYVNWYQQKPGKAPKLLI-YGASNLHTGVP SRFSGSGSGTDFTLTISSLQPEDFATYYCQ QTYSAPLTFGCGTKVEIKRGGGGSGGGGSG GGGSQVQLVQSGAEVKKPGASVKVSCKASG YTFTNHYMHWVRQAPGQCLEW-MGWMNPNS GNTGYAQKFQGRVTMTRDTSTSTVYMELSS LRSEDTAVYYCASSESGSDLDYWGQGTLVT VSS | 1050 |
| 122 | QVQLVQSGAEVKKPGASVKVSCKASGYTFT NHYMHWVRQAPGQCLEWMGWMNPNSGNTGY A-QKFQGRVTMTRDTSTSTVYMELSSLRSE DTAVYYCASSESGSDLDYWGQGTLVTVSSG GGGSGGGGSGGGGSDIQMTQSPSSLSASVG DRVTITCRASQTIGNYVNWYQQKPGKAPKL LI-YGASNLHTGVPSRFSGSGSGTDFTLTI SSLQPEDFATYYCQQTYSAPLTFGCGTKVE IKR | 1049 |
| 123 | DIQMTQSPSSLSASVGDRVTITCRASQTIG NYVNWYQQKPGKAPKLLI-YGASNLHTGVP SRFSGSGSGTDFTLTISSLQPEDFATYYCQ QTYSAPLTFGCGTKVEIKRGGGGSGGGGSG GGGSQVQLVQSGAEVKKPGASVKVSCKASG YTFTNHYMHWVRQAPGQCLEW-MGWMNPNS GNTGYAQKFQGRVTMTRDTSTSTVYMELSS LRSEDTAVYYCASSESGSDLDYWGQGTLVT VSS | 1050 |
| 124 | QVQLVQSGAEVKKPGASVKVSCKASGYTFT NHYMFIWVRQAPGQGLEWMGIINPNSGNTG YA-QKFQGRVTMTRDTSTSTVYMELSSLRS EDTAVYYCASSESGSDLDYWGQGTLVTVSS GGGGSGGGGSGGGGSDIQMTQSPSSLSASV GDRVTITCRASQTIGNYVNWYQQKPGKAPK | 1051 |

TABLE 12-continued

| CD8 Binder Variant | Full Binder Sequence | SEQ ID NO: |
|---|---|---|
| | LLI-YGASNLHTGVPSRFSGSGSGTDFTLT ISSLQPEDFATYYCQQTYSAPLTFGGGTKV EIKR | |
| 125 | DIQMTQSPSSLSASVGDRVTITCRASQTIG NYVNWYQQKPGKAPKLLI-YGASNLHTGVP SRFSGSGSGTDFTLTISSLQPEDFATYYCQ QTYSAPLTFGGGTKVEIKRGGGGSGGGGSG GGGSQVQLVQSGAEVKKPGASVKVSCKASG YTFTNHYMHWVRQAPGQGLEWMGI-INPNS GNTGYAQKFQGRVTMTRDTSTSTVYMELSS LRSEDTAVYYCASSESGSDLDYWGQGTLVT VSS | 1052 |
| 126 | QVQLVQSGAEVKKPGASVKVSCKASGYTFT NHYMHWVRQAPGQGLEWMGIINPNSGNTGY A-QKFQGRVTMTRDTSTSTVYMELSSLRSE DTAVYYCASSESGSDLDYWGQGTLVTVSSG GGGSGGGGSGGGGSDIQMTQSPSSLSASVG DRVTITCRASQTIGNYVNWYQQKPGKAPKL LI-YGASNLHTGVPSRFSGSGSGTDFTLTI SSLQPEDFATYYCQQTYSAPLTFGGGTKVE IKR | 1051 |
| 127 | DIQMTQSPSSLSASVGDRVTITCRASQTIG NYVNWYQQKPGKAPKLLI-YGASNLHTGVP SRFSGSGSGTDFTLTISSLQPEDFATYYCQ QTYSAPLTFGGGTKVEIKRGGGGSGGGGSG GGGSQVQLVQSGAEVKKPGASVKVSCKASG YTFTNHYMHWVRQAPGQGLEWMGI-INPNS GNTGYAQKFQGRVTMTRDTSTSTVYMELSS LRSEDTAVYYCASSESGSDLDYWGQGTLVT VSS | 1052 |
| 128 | QVQLVESGGGLVQAGGSLRLSCAASGRTFS GYVMGWFRQAPGKQRKFVAAISRG-GLSTS YADSVKGRFTISRDNAKNTVFLQMNTLKPE DTAVYYCAADRSDLYEITAASNIDSWGQGT LVTVSS | 1060 |

TABLE 13

| CD8 Fusion Proteins | Full Fusion Protein Sequence | SEQ ID NO: |
|---|---|---|
| NivG.002_1 | MKKINEGLLDSKILSAFNTVIALLGSIVII VMNIMIIQNYTRSTDNQAVIKDAL-QGIQQ QIKGLADKIGTEIGPKVSLIDTSSTITIPA NIGLLGSKISQSTASINENVNEKCKFTLPP LKIHECNISCPNPLPFREYRPQTEGVSNLV GLPNNICLQKTSNQILKPK-LISYTLPWGQ SGTCITDPLLAMDEGYFAYSHLERIGSCSR GVSKQRIIGVGEVLDRGDEVPSLFMTNVWT PPNPNTVYHCSAVYNNEFYYVLCAVSTVGD PILNSTYWSGSLMMTRLAVKPK-SNGGGYN QHQLALRSIEKGRYDKVMPYGPSGIKQGDT LYFPAVGFLVRTEFKYNDSNCPITKCQYSK PENCRLSMGIRPNSHYILRSGLLKYNLSDG ENPKWFIEISDQRLSIG-SPSKIYDSLGQP VFYQASFSWDTMIKFGDVLTVNPLVVNWRN NTVISRPGQSQCPRFNTCPAICAEGVYNDA FLIDRINWISAGVFLDSNATAANPVFTVFK DNEILYRAQLASEDTNAQKTITNCFLLK-N KIWCISLVEIYDTGDNVIRPKLFAVKIPEQ CTGGGGSGGGGSGGGGSQVQLVQSGAEVKK PGASVKVSCKASGGTFSSYAISWVRQAPGQ GLEWMGIIDPSDGNTNYA-QNFQGRVTMTR DTSTSTVYMELSSLRSEDTAVYYCAKERAA AGYYYYMDVWGQGTTVTVSSGGGGSGGGGS GGGGSDIQMTQSPSSLSASVGDRVTITCRA | 1053 |

TABLE 13-continued

| CD8 Fusion Proteins | Full Fusion Protein Sequence | SEQ ID NO: |
|---|---|---|
| | SQSISSYLNWYQQKPGKAPKLLIYAAS-SL QSGVPSRFSGSGSGTDFTLTISSLQPEDFA TYYCQQSYSTPLTFGGGTKVEIKR | |
| NivG.002_5 | MKKINEGLLDSKILSAFNTVIALLGSIVII VMNIMIIQNYTRSTDNQAVIKDAL-QGIQQ QIKGLADKIGTEIGPKVSLIDTSSTITIPA NIGLLGSKISQSTASINENVNEKCKFTLPP LKIHECNISCPNPLPFREYRPQTEGVSNLV GLPNNICLQKTSNQILKPK-LISYTLPVVG QSGTCITDPLLAMDEGYFAYSHLERIGSCS RGVSKQRIIGVGEVLDRGDEVPSLFMTNVW TPPNPNTVYHCSAVYNNEFYYVLCAVSTVG DPIINSTYWSGSLMMTRLAVKPK-SNGGGY NQHQLALRSIEKGRYDKVMPYGPSGIKQGD TLYFPAVGFLVRTEFKYNDSNCPITKCQYS KPENCRLSMGIRPNSHYILRSGLLKYNLSD GENPKWFIEISDQRLSIG-SPSKIYDSLGQ PVFYQASFSWDTMIKFGDVLTVNPLVVNWR NNTVISRPGQSQCPRFNTCPAICAEGVYND AFLIDRINWISAGVFLDSNATAANPVFTVF KDNEILYRAQLASEDTNAQKTITNCFLLK- NKIWCISLVEIYDTGDNVIRPKLFAVKIPE QCTGGGGSGGGGSGGGGSQVQLVQSGAEVK KPGASVKVSCKASGYTFTDYYIQWVRQAPG QGLEWMGWINPNSGGTSYA-QKFQGRVTMT RDTSTSTVYMELSSLRSEDTAVYYCAKEGD YYYGMDAWGQGTMVTVSSGGGGSGGGGSGG GGSDIQMTQSPLSLPVTPGEPASISCRSSQ SLLHSNGYNYLDWYLQKPGQSPQLLIYL-G SNRASGVPDRFSGSGSGTDFTLKISRVEAE DVGVYYCMQGLQTPHTFGQGTKVEIKR | 1054 |
| NivG.002_46 | MKKINEGLLDSKILSAFNTVIALLGSIVII VMNIMIIQNYTRSTDNQAVIKDAL-QGIQQ QIKGLADKIGTEIGPKVSLIDTSSTITIPA NIGLLGSKISQSTASINENVNEKCKFTLPP LKIHECNISCPNPLPFREYRPQTEGVSNLV GLPNNICLQKTSNQILKPK-LISYTLPVVG QSGTCITDPLLAMDEGYFAYSHLERIGSCS RGVSKQRIIGVGEVLDRGDEVPSLFMTNVW TPPNPNTVYHCSAVYNNEFYYVLCAVSTVG DPILNSTYWSGSLMMTRLAVKPK-SNGGGY NQHQLALRSIEKGRYDKVMPYGPSGIKQGD TLYFPAVGFLVRTEFKYNDSNCPITKCQYS KPENCRLSMGIRPNSHYILRSGLLKYNLSD GENPKWFIEISDQRLSIG-SPSKIYDSLGQ PVFYQASFSWDTMIKFGDVLTVNPLVVNWR NNTVISRPGQSQCPRFNTCPAICAEGVYND AFLIDRINWISAGVFLDSNATAANPVFTVF KDNEILYRAQLASEDTNAQKTITNCFLLK- NKIWCISLVEIYDTGDNVIRPKLFAVKIPE QCTGGGGSGGGGSGGGGSQVQLVQSGAEVK KPGASVKVSCKASGYTFTSYYMHWVRQAPG QGLEWMGGFDPEDGETIYA-QKFQGRVTMT RDTSTSTVYMELSSLRSEDTAVYYCARDQG WGMDVWGQGTTVTVSSGGGGSGGGGSGGGG SDIQMTQSPSSLSASVGDRVTITCRASQSI SSYLNWYQQKPGKAPKLLIYAAS-SLQSGV PSRFSGSGSGTDFTLTISSLQPEDFATYYC QQTYSTPYTFGQGTKLEIKR | 1055 |
| NivG.002_52 | MKKINEGLLDSKILSAFNTVIALLGSIVII VMNIMIIQNYTRSTDNQAVIKDAL-QGIQQ QIKGLADKIGTEIGPKVSLIDTSSTITIPA NIGLLGSKISQSTASINENVNEKCKFTLPP LKIHECNISCPNPLPFREYRPQTEGVSNLV GLPNNICLQKTSNQILKPK-LISYTLPVVG QSGTCITDPLLAMDEGYFAYSHLERIGSCS RGVSKQRIIGVGEVLDRGDEVPSLFMTNVW TPPNPNTVYHCSAVYNNEFYYVLCAVSTVG DPILNSTYWSGSLMMTRLAVKPK-SNGGGY NQHQLALRSIEKGRYDKVMPYGPSGIKQGD TLYFPAVGFLVRTEFKYNDSNCPITKCQYS KPENCRLSMGIRPNSHYILRSGLLKYNLSD GENPKWFIEISDQRLSIG-SPSKIYDSLGQ | 1056 |

TABLE 13-continued

| CD8 Fusion Proteins | Full Fusion Protein Sequence | SEQ ID NO: |
|---|---|---|
| | PVFYQASFSWDTMIKFGDVLTVNPLVVNWR NNTVISRPGQSQCPRFNTCPAICAEGVYND AFLIDRINWISAGVFLDSNATAANPVFTVF KDNEILYRAQLASEDTNAQKTITNCFLLK- NKIWCISLVEIYDTGDNVIRPKLFAVKIPE QCTGGGGSGGGGSGGGGSQVQLVQSGAEVK KPGASVKVSCKASGYTFTNHYMHWVRQAPG QGLEWMGWMNPNSGNTGYA-QKFQGRVTMT RDTSTSTVYMELSSLRSEDTAVYYCASSES GSDLDYWGQGTLVTVSSGGGGSGGGGSGGG GSDIQMTQSPSSLSASVGDRVTITCRASQT IGNYVNWYQQKPGKAPKLLI-YGASNLHTG VPSRFSGSGSGTDFTLTISSLQPEDFATYY CQQTYSAPLTFGGGTKVEIKR | |
| NivG.002_97 | MKKINEGLLDSKILSAFNTVIALLGSIVII VMNIMIIQNYTRSTDNQAVIKDAL-QGIQQ QIKGLADKIGTEIGPKVSLIDTSSTITIPA NIGLLGSKISQSTASINENVNEKCKFTLPP LKIHECNISCPNPLPFREYRPQTEGVSNLV GLPNNICLQKTSNQILKPK-LISYTLPVVG QSGTCITDPLLAMDEGYFAYSHLERIGSCS RGVSKQRIIGVGEVLDRGDEVPSLFMTNVW TPPNPNTVYHCSAVYNNEFYYVLCAVSTVG DPILNSTYWSGSLMMTRLAVKPK-SNGGGY NQHQLALRSIEKGRYDKVMPYGPSGIKQGD TLYFPAVGFLVRTEFKYNDSNCPITKCQYS KPENCRLSMGIRPNSHYILRSGLLKYNLSD GENPKWFIEISDQRLSIG-SPSKIYDSLGQ PVFYQASFSWDTMIKFGDVLTVNPLVVNWR NNTVISRPGQSQCPRFNTCPAICAEGVYND AFLIDRINWISAGVFLDSNATAANPVFTVF KDNEILYRAQLASEDTNAQKTITNCFLLK- NKIWCISLVEIYDTGDNVIRPKLFAVKIPE QCTGGGGSGGGGSGGGGSQVQLVESGGGLV QAGGSLRLSCAASGRTFSGYVMGWFRQAPG KQRKFVAAISRGGLSTSYADSVKGRFTISR DNAK-NTVFLQMNTLKPEDTAVYYCAADRS DLYEITAASNIDSWGQGTLVTVSS | 1069 |
| NivG.002_1_2 | KKINEGLLDSKILSAFNTVIALLGSIVIIV MNIMIIQNYTRSTDNQAVIKDAL-QGIQQQ IKGLADKIGTEIGPKVSLIDTSSTITIPAN IGLLGSKISQSTASINENVNEKCKFTLPPL KIHECNISCPNPLPFREYRPQTEGVSNLVG LPNNICLQKTSNQILKPK-LISYTLPVVGQ SGTCITDPLLAMDEGYFAYSHLERIGSCSR GVSKQRIIGVGEVLDRGDEVPSLFMTNVWT PPNPNTVYHCSAVYNNEFYYVLCAVSTVGD PILNSTYWSGSLMMTRLAVKPK-SNGGGYN QHQLALRSIEKGRYDKVMPYGPSGIKQGDT LYFPAVGFLVRTEFKYNDSNCPITKCQYSK PENCRLSMGIRPNSHYILRSGLLKYNLSDG ENPKWFIEISDQRLSIG-SPSKIYDSLGQP VFYQASFSWDTMIKFGDVLTVNPLWNWRNN TVISRPGQSQCPRFNTCPAICAEGVYNDAF LIDRINWISAGVFLDSNATAANPVFTVFKD NEILYRAQLASEDTNAQKTITNCFLLK-NK IWCISLVEIYDTGDNVIRPKLFAVKIPEQC TGGGGSGGGGSGGGGSQVQLVQSGAEVKKP GASVKVSCKASGGTFSSYAISWVRQAPGQG LEWMGIIDPSDGNTNYA-QNFQGRVTMTRD TSTSTVYMELSSLRSEDTAVYYCAKERAAA GYYYYMDVWGQGTTVTVSSGGGGSGGGGSG GGSDIQMTQSPSSLSASVGDRVTITCRAS QSISSYLNWYQQKPGKAPKLLIYAAS-SLQ SGVPSRFSGSGSGTDFTLTISSLQPEDFAT YYCQQSYSTPLTFGGGTKVEIKR | 1070 |
| NivG.002_5_2 | KKINEGLLDSKILSAFNTVIALLGSIVIIV MNIMIIQNYTRSTDNQAVIKDAL-QGIQQQ IKGLADKIGTEIGPKVSLIDTSSTITIPAN IGLLGSKISQSTASINENVNEKCKFTLPPL KIHECNISCPNPLPFREYRPQTEGVSNLVG LPNNICLQKTSNQILKPK-LISYTLPVVGQ SGTCITDPLLAMDEGYFAYSHLERIGSCSR | 1071 |

TABLE 13-continued

| CD8 Fusion Proteins | Full Fusion Protein Sequence | SEQ ID NO: |
|---|---|---|
| | GVSKQRIIGVGEVLDRGDEVPSLFMTNVWT PPNPNTVYHCSAVYNNEFYYVLCAVSTVGD PILNSTYWSGSLMMTRLAVKPK-SNGGGYN QHQLALRSIEKGRYDKVMPYGPSGIKQGDT LYFPAVGFLVRTEFKYNDSNCPITKCQYSK PENCRLSMGIRPNSHYILRSGLLKYNLSDG ENPKWFIEISDQRLSIG-SPSKIYDSLGQP VFYQASFSWDTMIKFGDVLTVNPLVVNWRN NTVISRPGQSQCPRFNTCPAICAEGVYNDA FLIDRINWISAGVFLDSNATAANPVFTVFK DNEILYRAQLASEDTNAQKTITNCFLLK-N KIWCISLVEIYDTGDNVIRPKLFAVKIPEQ CTGGGGSGGGGSGGGGSQVQLVQSGAEVKK PGASVKVSCKASGYTFTDYYIQWVRQAPGQ GLEWMGWINPNSGGTSYA-QKFQGRVTMTR DTSTSTVYMELSSLRSEDTAVYYCAKEGDY YYGMDAWGQGTMVTVSSGGGGSGGGGSGGG GSDIVMTQSPLSLPVTPGEPASISCRSSQS LLHSNGYNYLDWYLQKPGQSPQLLIYL-GS NRASGVPDRFSGSGSGTDFTLKISRVEAED VGVYYCMQGLQTPHTFGQGTKVEIKR | |
| NivG.002_46_2 | KKINEGLLDSKILSAFNTVIALLGSIVIIV MNIMIIQNYTRSTDNQAVIKDAL-QGIQQQ IKGLADKIGTEIGPKVSLIDTSSTITIPAN IGLLGSKISQSTASINENVNEKCKFTLPPL KIHECNISCPNPLPFREYRPQTEGVSNLVG LPNNICLQKTSNQILKPK-LISYTLPVVGQ SGTCITDPLLAMDEGYFAYSFILERIGSCS RGVSKQRIIGVGEVLDRGDEVPSLFMTNVW TPPNPNTVYHCSAVYNNEFYYVLCAVSTVG DPILNSTYWSGSLMMTRLAVKPK-SNGGGY NQHQLALRSIEKGRYDKVMPYGPSGIKQGD TLYFPAVGFLVRTEFKYNDSNCPITKCQYS KPENCRLSMGIRPNSHYILRSGLLKYNLSD GENPKWFIEISDQRLSIG-SPSKIYDSLGQ PVFYQASFSWDTMIKFGDVLTVNPLVVNWR NNTVISRPGQSQCPRFNTCPAICAEGVYND AFLIDRINWISAGVFLDSNATAANPVFTVF KDNEILYRAQLASEDTNAQKTITNCFLLK- NKIWCISLVEIYDTGDNVIRPKLFAVKIPE QCTGGGGSGGGGSGGGGSQVQLVQSGAEVK KPGASVKVSCKASGYTFTSYYMFIWVRQAP GQGLEWMGGFDPEDGETIYA-QKFQGRVTM TRDTSTSTVYMELSSLRSEDTAVYYCARDQ GWGMDVWGQGTTVTVSSGGGGSGGGGSGGG GSDIQMTQSPSSLSASVGDRVTITCRASQS ISSYLNWYQQKPGKAPKLLIYAAS-SLQSG VPSRFSGSGSGTDFTLTISSLQPEDFATYY CQQTYSTPYTFGQGTKLEIKR | 1072 |
| NivG.002_52_2 | KKINEGLLDSKILSAFNTVIALLGSIVIIV MNIMIIQNYTRSTDNQAVIKDAL-QGIQQQ IKGLADKIGTEIGPKVSLIDTSSTITIPAN IGLLGSKISQSTASINENVNEKCKFTLPPL KIHECNISCPNPLPFREYRPQTEGVSNLVG LPNNICLQKTSNQILKPK-LISYTLPVVGQ SGTCITDPLLAMDEGYFAYSHLERIGSCSR GVSKQRIIGVGEVLDRGDEVPSLFMTNVWT PPNPNTVYHCSAVYNNEFYYVLCAVSTVGD PILNSTYWSGSLMMTRLAVKPK-SNGGGYN QHQLALRSIEKGRYDKVMPYGPSGIKQGDT LYFPAVGFLVRTEFKYNDSNCPITKCQYSK PENCRLSMGIRPNSHYILRSGLLKYNLSDG ENPKWFIEISDQRLSIG-SPSKIYDSLGQP VFYQASFSWDTMIKFGDVLTVNPLVVNWRN NTVISRPGQSQCPRFNTCPAICAEGVYNDA FLIDRINWISAGVFLDSNATAANPVFTVFK DNEILYRAQLASEDTNAQKTITNCFLLK-N KIWCISLVEIYDTGDNVIRPKLFAVKIPEQ CTGGGGSGGGGSGGGGSQVQLVQSGAEVKK PGASVKVSCKASGYTFTNHYMHWVRQAPGQ GLEWMGWMNPNSGNTGYA-QKFQGRVTMTR DTSTSTVYMELSSLRSEDTAVYYCASSESG SDLDYWGQGTLVTVSSGGGGSGGGGSGGGG SDIQMTQSPSSLSASVGDRVTITCRASQTI | 1073 |

TABLE 13-continued

| CD8 Fusion Proteins | Full Fusion Protein Sequence | SEQ ID NO: |
|---|---|---|
| | GNYVNWYQQKPGKAPKLLI-YGASNLHTGV PSRFSGSGSGTDFTLTISSLQPEDFATYYC QQTYSAPLTFGGGTKVEIKR | |
| NIvG.002_97_2 | KKINEGLLDSKILSAFNTVIALLGSIVIIV MNIMIIQNYTRSTDNQAVIKDAL-QGIQQQ IKGLADKIGTEIGPKVSLIDTSSTITIPAN IGLLGSKISQSTASINENVNEKCKFTLPPL KIHECNISCPNPLPFREYRPQTEGVSNLVG LPNNICLQKTSNQILKPK-LISYTLPWGQS GTCITDPLLAMDEGYFAYSHLERIGSCSRG VSKQRIIGVGEVLDRGDEVPSLFMTNVWTP PNPNTVYHCSAVYNNEFYYVLCAVSTVGDP ILNSTYWSGSLMMTRLAVKPK-SNGGGYNQ HQLALRSIEKGRYDKVMPYGPSGIKQGDTL | 1074 |

TABLE 13-continued

| CD8 Fusion Proteins | Full Fusion Protein Sequence | SEQ ID NO: |
|---|---|---|
| | YFPAVGFLVRTEFKYNDSNCPITKCQYSKP ENCRLSMGIRPNSHYILRSGLLKYNLSDGE NPKWFIEISDQRLSIG-SPSKIYDSLGQPV FYQASFSWDTMIKFGDVLTVNPLVVNWRNN TVISRPGQSQCPRFNTCPAICAEGVYNDAF LIDRINWISAGVFLDSNATAANPVFTVFKD NEILYRAQLASEDTNAQKTITNCFLLK-NK IWCISLVEIYDTGDNVIRPKLFAVKIPEQC TGGGGSGGGGSGGGGSQVQLVESGGGLVQA GGSLRLSCAASGRTFSGYVMGWFRQAPGKQ RKFVAAISRGGLSTSYADSVKGRFTISRDN AK-NTVFLQMNTLKPEDTAVYYCAADRSDL YEITAASNIDSWGQGTLVTVSS | |

The invention claimed is:

1. An antibody or antigen binding fragment thereof that binds CD8, comprising a heavy chain variable region (V$_H$), and a light chain variable region (V$_L$), wherein the heavy chain variable region comprises three heavy chain complementarity determining regions (HCDR1, HCDR2, and HCDR3), and the light chain variable region comprises three light chain complementarity determining regions (LCDR1, LCDR2, and LCDR3), wherein the HCDR1, HCDR2, HCDR3, LCDR1, LCDR2, and LCDR3, respectively, comprise:

a) SEQ ID NOs: 1, 70, 148, 240, 294, and 333, respectively;

b) SEQ ID NOs: 2, 71, 149, 241, 294, and 334, respectively;

c) SEQ ID NOs: 3, 72, 148, 240, 294, and 333, respectively;

d) SEQ ID NOs: 4, 73, 649, 242, 295, and 335, respectively;

e) SEQ ID NOs: 5, 74, 150, 242, 295, and 336, respectively;

f) SEQ ID NOs: 6, 75, 151, 243, 296, and 337, respectively;

g) SEQ ID NOs: 7, 76, 152, 244, 295, and 338, respectively;

h) SEQ ID NOs: 8, 77, 153, 244, 297, and 339, respectively;

i) SEQ ID NOs: 9, 77, 154, 245, 298, and 340, respectively;

j) SEQ ID NOs: 10, 78, 650, 246, 297, and 341, respectively;

k) SEQ ID NOs: 11, 79, 155, 247, 299, and 342, respectively;

l) SEQ ID NOs: 12, 80, 156, 248, 300, and 343, respectively;

m) SEQ ID NOs: 13, 81, 157, 249, 294, and 344, respectively;

n) SEQ ID NOs: 14, 76, 158, 242, 295, and 345, respectively;

o) SEQ ID NOs: 15, 76, 159, 250, 301, and 346, respectively;

p) SEQ ID NOs: 11, 82, 160, 249, 294, and 347, respectively;

q) SEQ ID NOs: 16, 83, 161, 251, 302, and 340, respectively;

r) SEQ ID NOs: 17, 84, 162, 241, 303, and 348, respectively;

s) SEQ ID NOs: 18, 85, 163, 252, 304, and 349, respectively;

t) SEQ ID NOs: 19, 86, 164, 241, 305, and 350, respectively;

u) SEQ ID NOs: 20, 87, 165, 253, 299, and 351, respectively;

v) SEQ ID NOs: 4, 88, 166, 249, 299, and 352, respectively;

w) SEQ ID NOs: 21, 89, 167, 242, 306, and 353, respectively;

x) SEQ ID NOs: 22, 90, 168, 241, 307, and 354, respectively;

y) SEQ ID NOs: 23, 91, 169, 241, 299, and 355, respectively;

z) SEQ ID NOs: 24, 92, 170, 241, 299, and 356, respectively;

aa) SEQ ID NOs: 25, 93, 171, 254, 308, and 344, respectively;

bb) SEQ ID NOs: 26, 94, 172, 240, 294, and 333, respectively;

cc) SEQ ID NOs: 26, 94, 172, 240, 294, and 333, respectively;

dd) SEQ ID NOs: 1, 79, 174, 255, 294, and 358, respectively;

ee) SEQ ID NOs: 28, 95, 175, 256, 294, and 359, respectively;

ff) SEQ ID NOs: 29, 79, 176, 257, 309, and 360, respectively;

gg) SEQ ID NOs: 1, 96, 177, 240, 294, and 333, respectively;

hh) SEQ ID NOs: 20, 97, 149, 251, 299, and 361, respectively;

ii) SEQ ID NOs: 30, 98, 178, 241, 310, and 362, respectively;

jj) SEQ ID NOs: 31, 99, 179, 240, 311, and 363, respectively;

kk) SEQ ID NOs: 32, 100, 180, 258, 312, and 364, respectively;

ll) SEQ ID NOs: 19, 101, 181, 259, 313, and 333, respectively;

mm) SEQ ID NOs: 33, 102, 182, 242, 314, and 365, respectively;

nn) SEQ ID NOs: 34, 103, 183, 260, 315, and 366, respectively;

oo) SEQ ID NOs: 35, 104, 184, 241, 302, and 367, respectively;

pp) SEQ ID NOs: 36, 105, 185, 261, 316, and 368, respectively;

qq) SEQ ID NOs: 37, 106, 186, 262, 294, and 369, respectively;

rr) SEQ ID NOs: 38, 107, 187, 263, 294, and 344, respectively;

ss) SEQ ID NOs: 39, 108, 188, 264, 317, and 344, respectively;

tt) SEQ ID NOs: 40, 109, 189, 240, 294, and 370, respectively;

uu) SEQ ID NOs: 8, 110, 190, 265, 299, and 371, respectively;

vv) SEQ ID NOs: 41, 111, 191, 266, 299, and 346, respectively;

ww) SEQ ID NOs: 19, 112, 192, 242, 318, and 372, respectively;

XX) SEQ ID NOs: 4, 113, 193, 267, 309, and 373, respectively;

yy) SEQ ID NOs: 4, 114, 194, 268, 302, 344, and 453, respectively;

zz) SEQ ID NOs: 42, 115, 195, 269, 319, 374, and 454, respectively;

aaa) SEQ ID NOs: 43, 77, 196, 270, 320, and 375, respectively;

bbb) SEQ ID NOs: 44, 116, 197, 271, 299, and 376, respectively;

ccc) SEQ ID NOs: 40, 117, 198, 272, 302, and 377, respectively;

ddd) SEQ ID NOs: 40, 118, 199, 259, 302, and 378, respectively;

eee) SEQ ID NOs: 45, 114, 200, 273, 321, and 379, respectively;

fff) SEQ ID NOs: 46, 119, 201, 240, 322, and 380, respectively;

ggg) SEQ ID NOs: 47, 120, 202, 274, 309, and 333, respectively;

hhh) SEQ ID NOs: 48, 121, 203, 252, 302, and 333, respectively;

iii) SEQ ID NOs: 49, 122, 204, 275, 311, and 381, respectively;

jjj) SEQ ID NOs: 44, 123, 205, 276, 311, and 333, respectively;

kkk) SEQ ID NOs: 50, 124, 206, 277, 299, and 382, respectively;

lll) SEQ ID NOs: 51, 77, 207, 278, 294, and 383, respectively;

mmm) SEQ ID NOs: 52, 125, 208, 240, 323, and 384, respectively;

nnn) SEQ ID NOs: 34, 126, 209, 279, 324, and 385, respectively;

ooo) SEQ ID NOs: 53, 127, 210, 280, 294, and 386, respectively;

ppp) SEQ ID NOs: 54, 128, 211, 281, 294, and 387, respectively;

qqq) SEQ ID NOs: 19, 129, 212, 282, 317, and 342, respectively;

rrr) SEQ ID NOs: 19, 130, 213, 242, 295, and 388, respectively;

sss) SEQ ID NOs: 55, 77, 214, 240, 325, and 389, respectively;

ttt) SEQ ID NOs: 8, 77, 215, 241, 326, and 390, respectively;

uuu) SEQ ID NOs: 56, 131, 216, 283, 294, and 344, respectively;

vvv) SEQ ID NOs: 57, 132, 217, 249, 327, and 333, respectively;

www) SEQ ID NOs: 19, 133, 218, 284, 297, and 391, respectively;

XXX) SEQ ID NOs: 58, 79, 219, 240, 294, and 333, respectively;

yyy) SEQ ID NOs: 19, 95, 220, 285, 299, and 342, respectively;

zzz) SEQ ID NOs: 58, 134, 221, 286, 294, and 392, respectively;

aaaa) SEQ ID NOs: 40, 93, 222, 241, 309, and 393, respectively;

bbbb) SEQ ID NOs: 59, 135, 223, 275, 299, and 344, respectively;

cccc) SEQ ID NOs: 19, 136, 224, 287, 302, and 394, respectively;

dddd) SEQ ID NOs: 60, 137, 225, 288, 309, and 333, respectively;

eeee) SEQ ID NOs: 10, 138, 226, 289, 328, and 395, respectively;

ffff) SEQ ID NOs: 19, 139, 227, 241, 329, and 396, respectively;

gggg) SEQ ID NOs: 1, 140, 228, 241, 294, and 397, respectively;

hhhh) SEQ ID NOs: 61, 141, 229, 241, 328, and 395, respectively;

iiii) SEQ ID NOs: 62, 93, 230, 241, 316, and 362, respectively;

jjjj) SEQ ID NOs: 63, 142, 231, 249, 330, 361, and 490, respectively;

kkkk) SEQ ID NOs: 64, 143, 232, 290, 299, and 399, respectively;

llll) SEQ ID NOs: 65, 79, 233, 241, 331, and 400, respectively;

mmmm) SEQ ID NOs: 66, 79, 234, 241, 299, and 401, respectively;

nnnn) SEQ ID NOs: 19, 144, 235, 241, 332, and 371, respectively;

oooo) SEQ ID NOs: 67, 145, 236, 291, 330, and 402, respectively;

pppp) SEQ ID NOs: 19, 146, 237, 292, 294, and 344, respectively;

qqqq) SEQ ID NOs: 68, 147, 238, 241, 299, and 403, respectively; or rrrr) SEQ ID NOs: 69, 77, 239, 293, 299, and 404, respectively.

2. The antibody or antigen binding fragment thereof of claim 1, comprising a heavy chain variable region ($V_H$) having an amino acid sequence with at least 90% identity to a sequence selected from SEQ ID NOs: 405-498.

3. The antibody or antigen binding fragment thereof of claim 1, comprising a light chain variable region ($V_L$) having an amino acid sequence with at least 90% identity to a sequence selected from SEQ ID NOs: 499-591.

4. The antibody or antigen binding fragment thereof of claim 2, comprising a $V_H$ having an amino acid sequence with at least 90% identity to a sequence selected from SEQ ID NOs: 405-498 and a $V_L$ having an amino acid sequence with at least 90% identity to a sequence selected from SEQ ID NOs: 499-591.

5. The antibody or antigen binding fragment thereof of claim 2, wherein the $V_H$ is selected from SEQ ID NOs: 405, 408, 448, and 455, and the $V_L$ is selected from 499, 503, 542, and 549.

6. The antibody or antigen binding fragment thereof of claim 1, wherein the HCDR1, HCDR2, HCDR3, LCDR1, LCDR2, and LCDR3, respectively, comprise:

a) SEQ ID NOs: 1, 70, 148, 240, 294, 333, respectively;

b) SEQ ID NOs: 5, 74, 150, 242, 295, 336, respectively;

c) SEQ ID NOs: 40, 109, 189, 240, 294, 370, respectively; or d) SEQ ID NOs: 43, 77, 196, 270, 320, 375, respectively.

7. The antibody or antigen binding fragment thereof of claim 1, which binds to human CD8α or CD8β.

8. The antibody or antigen binding fragment thereof of claim 1, which binds to a human CD8α homodimer composed of two α chains.

9. The antibody or antigen binding fragment thereof of claim 1, which binds to a human CD8 heterodimer composed of one α chain and one β chain.

10. The antibody or antigen binding fragment thereof of claim 1, wherein the antigen binding fragment is a Fab, Fab', F(ab')2, scFv, (scFv)2, scFv-Fc, or Fv fragment.

11. The antibody or antigen binding fragment thereof of claim 10, wherein the antigen binding fragment is a scFv.

12. The antibody or antigen binding fragment thereof of claim 11, wherein the $V_H$ is on the N-terminal side of the $V_L$.

13. The antibody or antigen binding fragment thereof of claim 11, wherein the $V_L$ is on the N-terminal side of the $V_H$.

14. The antibody or antigen binding fragment thereof of claim 11, wherein the scFv comprises a linker connecting the $V_H$ and $V_L$.

15. The antibody or antigen binding fragment thereof of claim 14, wherein the linker comprises the amino acid sequence set forth in SEQ ID NOs: 625-627 and 645-648.

16. The antibody or antigen binding fragment thereof of claim 1, which binds to human CD8α or human CD8β with a $K_D$ of about 400 nM or lower.

17. The antibody or antigen binding fragment thereof of claim 1, which binds to *M. nemestrina* CD8α or *M. nemestrina* CD8β with a $K_D$ of about 5 nM to about 500 nM.

18. The antibody or antigen binding fragment thereof of claim 1, which binds to human CD8α or CD8β with a $K_D$ of about 5 nM to about 500 nM.

19. An isolated polynucleotide encoding the antibody or antigen binding fragment thereof of claim 1.

20. An isolated vector comprising the polynucleotide of claim 19.

21. An isolated host cell comprising the polynucleotide of claim 19.

\* \* \* \* \*